(12) United States Patent
Xia et al.

(10) Patent No.: US 8,343,944 B2
(45) Date of Patent: Jan. 1, 2013

(54) TRISUBSTITUTED BORON-CONTAINING MOLECULES

(75) Inventors: Yi Xia, Palo Alto, CA (US); Michael Richard Kevin Alley, Santa Clara, CA (US); Yasheen Zhou, Moraga, CA (US); Rajeshwar Singh, Edmonton (CA); Charles Ding, San Mateo, CA (US); Kathy Cao, Sunnyvale, CA (US); Jacob J. Plattner, Orinda, CA (US); Ligong Ou, Edmonton (CA); Guofeng Jia, Edmonton (CA); Neerja Saraswat, Edmonton, CA (US); Sreekanth Ramachandran, Edmonton (CA); Ding Zhou, Shanghai (CN)

(73) Assignee: Anacor Pharmaceuticals, Inc., Palo Alto, CA (US)

( * ) Notice: Subject to any disclaimer, the term of this patent is extended or adjusted under 35 U.S.C. 154(b) by 153 days.

(21) Appl. No.: 12/844,748

(22) Filed: Jul. 27, 2010

(65) Prior Publication Data

US 2011/0136763 A1    Jun. 9, 2011

Related U.S. Application Data

(60) Provisional application No. 61/229,230, filed on Jul. 28, 2009, provisional application No. 61/260,360, filed on Nov. 11, 2009.

(51) Int. Cl.
*A61K 31/69*    (2006.01)
*C07F 5/04*    (2006.01)

(52) U.S. Cl. .......................................... 514/64; 558/288
(58) Field of Classification Search .................. 558/288; 514/64
See application file for complete search history.

(56) References Cited

U.S. PATENT DOCUMENTS

| | | | |
|---|---|---|---|
| 2,260,336 A | 10/1941 | Prescott et al. |
| 3,873,279 A | 3/1975 | Singer |
| 4,602,011 A | 7/1986 | West et al. |
| 4,716,035 A | 12/1987 | Sampathkamar |
| 4,766,113 A | 8/1988 | West et al. |
| 4,894,220 A | 1/1990 | Nabi et al. |
| 5,348,947 A | 9/1994 | Patel et al. |
| 5,348,948 A | 9/1994 | Patel et al. |
| 5,591,731 A | 1/1997 | Kennedy et al. |
| 5,668,258 A | 9/1997 | Stolowitz |
| 5,688,928 A | 11/1997 | Stolowitz |
| 5,831,045 A | 11/1998 | Stolowitz et al. |
| 5,880,188 A | 3/1999 | Austin et al. |
| 5,962,498 A | 10/1999 | Driedger et al. |
| 6,083,903 A | 7/2000 | Adams et al. |
| 6,306,628 B1 | 10/2001 | Rothschild et al. |
| 6,369,098 B1 | 4/2002 | Pershadsingh et al. |
| 6,521,619 B2 | 2/2003 | Link et al. |
| 6,800,645 B1 | 10/2004 | Cox et al. |
| 6,855,848 B2 | 2/2005 | Scherer et al. |
| 7,169,603 B2 | 1/2007 | Hedley et al. |
| 7,217,701 B2 | 5/2007 | Mikoshiba et al. |
| 7,390,806 B2 | 6/2008 | Lee et al. |
| 7,465,836 B2 | 12/2008 | Lee et al. |
| 7,582,621 B2 | 9/2009 | Baker et al. |
| 7,767,657 B2 | 8/2010 | Baker et al. |
| 7,816,344 B2 | 10/2010 | Baker et al. |
| 2002/0028831 A1 | 3/2002 | Manley |
| 2002/0161230 A1 | 10/2002 | Meudt et al. |
| 2003/0032673 A1 | 2/2003 | Nagy |
| 2004/0077601 A1 | 4/2004 | Adams et al. |
| 2004/0224923 A1 | 11/2004 | Lee et al. |
| 2005/0054644 A1 | 3/2005 | Lee et al. |
| 2005/0125852 A1 | 6/2005 | Caenepeel et al. |
| 2006/0009386 A1 | 1/2006 | Stossel et al. |
| 2006/0222671 A1 | 10/2006 | Weidner |
| 2006/0234981 A1 | 10/2006 | Baker et al. |
| 2007/0155699 A1 | 7/2007 | Baker et al. |
| 2007/0286822 A1 | 12/2007 | Sanders et al. |
| 2007/0293457 A1 | 12/2007 | Baker et al. |
| 2009/0227541 A1 | 9/2009 | Baker et al. |
| 2010/0256092 A1 | 10/2010 | Xia et al. |

FOREIGN PATENT DOCUMENTS

| | | |
|---|---|---|
| EP | 0969531 | 1/2000 |
| EP | 1155698 A1 | 11/2001 |
| EP | 1 444 981 A1 | 8/2004 |
| WO | WO 9533754 | 5/1995 |
| WO | WO 9812206 A1 | 3/1998 |
| WO | WO 0044387 A1 | 8/2000 |
| WO | WO 0075142 A2 | 12/2000 |
| WO | WO 0244184 | 6/2002 |
| WO | WO 03033002 A1 | 4/2003 |
| WO | WO 03059916 A2 | 7/2003 |
| WO | WO 2004056322 A2 | 7/2004 |
| WO | WO 2005013892 A3 | 2/2005 |
| WO | WO 2006007384 | 1/2006 |
| WO | WO 2006062731 A1 | 6/2006 |
| WO | WO 2006079843 A1 | 8/2006 |
| WO | WO 2006089067 A2 | 8/2006 |
| WO | WO 2007022437 A2 | 2/2007 |
| WO | WO 2007078340 A2 | 7/2007 |
| WO | WO 2007095638 A2 | 8/2007 |
| WO | WO 2007146965 A2 | 12/2007 |
| WO | WO 2008157726 A1 | 12/2008 |
| WO | WO 2009111676 A2 | 9/2009 |

(Continued)

OTHER PUBLICATIONS

Austin, et al., "Oxaboroles and Salts and their Use of Biocides for Plastics", CAS, vol. 124, pp. 234-024, (1996).

(Continued)

*Primary Examiner* — Bernard Dentz

(74) *Attorney, Agent, or Firm* — Morgan, Lewis & Bockius LLP

(57) ABSTRACT

This invention largely relates to 3,4,6-trisubstituted benzoxaborole compounds, and their use for treating bacterial infections.

59 Claims, 21 Drawing Sheets

FOREIGN PATENT DOCUMENTS

| | | |
|---|---|---|
| WO | WO 2009014309 A2 | 11/2009 |
| WO | WO 2010028005 A1 | 3/2010 |
| WO | WO 2010045503 A | 4/2010 |
| WO | WO 2010045505 A1 | 4/2010 |

OTHER PUBLICATIONS

Bailey, et al., "Boron-Containing Antibacterial Agents: Effects on Growth and Morphology of Bacteria Under Various Culture Conditions," Antimicrobial Agents and Chemotherapy, 17(04):549-553, (Apr. 1980).

Baker, et al., "Discovery of New Boron-Containing Antifungal Agent, 5-Fluoro-1,3-dihydro-1-hydroxy-2, 1-benzoxaborole (AN2690) for Potential Treatment of Onychomoycosis", Journal of Medicinal Chemistry, vol. 49, No. 15; pp. 4447-4450, (Jul. 27, 2006).

Baker, et al., "Progress on New Therapeutics for Fungal Nail Infections", Annual Reports in Medicinal Chemistry, vol. 40: pp. 323-335, (2005).

Bessis, N., "Gene Therapy for Rheumatoid Arthritis," J. Gene Med, vol. 4; pp. 581-591 (2002).

Brown, et al., "Chiral Synthesis Via Organoboranes. 35. Simple Procedures for the Efficient Recycling of the Terpenyl Chiral Auxiliaries and Convenient Isolation of the Homoallylic Alcohols in Asymmetric Allyl- and Crotylboration of Aldehydes," J. Org. Chem., vol. 57, No. 24; pp. 6608-6614, (1992).

Cairns, et al., "Derivatives of 1,4-Xylene-2,5-diboronic acid and 1,4-xylene-2-boronic acid", J. Org. Chem. vol. 29; pp. 2810-2812, (1964).

Chander, et al. "Prevalence of Fungal Corneal Ulcers in Northern India", Infections, vol. 22, No. 3; pp. 207-209, (1994).

Chemical Abstracts Registry No. 845302-09-2, Entered STN Mar. 11, 2005.

Cui, et al., "Organoboron Compounds with an 8-Hydroxyquinolato Chelate and Its Derivatives: Substituent Effects on Structures and Luminescence," Inorganic Chemistry, vol. 44, No. 03; pp. 601-609, (Feb. 7, 2005).

Dale, et al., "Substituted Styrenes VIII Syntheses and some Reactions of the Vinylbenzeneboronic Acids" J. Org. Chem. vol. 27; pp. 2598-2603, (1962).

Denis, "Pharmacology 1104 Lecture: Drug Classifications & Characteristics of Antimicrobials" (2003).

Farfan, et al., "Through-Bond Modulation on N-B Ring Formation Shown by NMR and X-Ray Diffraction Studies of Borate Derivatives of Pyridyl Alcohols," J. Chem. Soc. Perkin Trans., vol. 2; pp. 527-532 (1992).

Ferrer, Targeting Aminocytl-tRNA Synthetases for the Treatment of Fungal Infections, Drug News Perspective, vol. 19, No. 6; pp. 347-348, (Jul./Aug. 2006).

Fungicide: Definition from Answer.com, (1998).

Grassberger, et al., "Degradation of 1,2-dihydro-1-hydroxy-2-(organosulfonyl)2,3,1-benzodiasaborines and -thieno[3,2-d][1,,3]diazaborines in Alkaline Aqueous Solutions", Liebigs Annalen Der Chemie, vol. 4; pp. 683-688, (1985).

Guo-Zheng, et al., "Single Site Transarylation of 2,2'-Dimetalized-1,1'-Binaphthyl to Aminochloroborates and Synthesis of 2-Binaphthyl Boron Compounds," Youji Huaxue/Organic Chemistry, Science Press, vol. 16, No. 02; pp. 139-144, (1996) (English Abstract).

Haynes, et al., "Arylboronic Acids VIII. Reactions of boronphthalide" J. Org. Chem. vol. 29, No. 11; pp. 3229-3233, (1964).

Hauck, et al., "Preparation and Anticonvulsant Activity of Some Arydialkkylsuccinimides" Research Lab of Parke Davis Co. (1967).

He, et al., "Small-Molecule Inhibition of TNF-alpha", Science, vol. 310, No. 5750; pp. 1022-1025, (Nov. 11, 2005).

Lampe, et al., "Synthesis and Protien Kinase Inhibitory Activity of Balanol Analogues with Modified Benzophenone Subunits", J. Med. Chem., vol. 45; pp. 2624-2643, (2002).

Lennarz, et al., "Arylboronic Acids. IV. Reactions of Boronophthalide" J. Am. Chem. Soc. vol. 82; pp. 2172-2175, (1960).

Li, et al., "An Improved Protocol for Preparation of 3-Pyridyl- and Some Arylboronic Acids", J. Org. Chem., vol. 67; pp. 5394-5397, (2002).

Koster, et al., "Cyclisierugen von Bor-Stickstoff-Verbindugen in der Hietz" Liebigs Ann. Chem., vol. 720; pp. 23-31, (1968).

Koster, et al., "Boron Compounds, XXXIX. Alkenoxy(diorgany)boranes Substituted at the Alkeonxy Group from 2-methylacrolein and triorganylboranes," Justus Liebigs Annalen Der Chemie, No. 06; pp. 1116-1134, (1976).

McMillin, et al., "Systemic Aspects of Psoriasis: An Intergrative Model Based on Intestinal Etiology", Int. Med. vol. 2, Issue 2/3, (1999).

Moeder, et al., "Kinetic Analysis of the Asymmetric Amplification exhibited by B-chlorodiisopinocampheylborane," Journal of Physical Organic Chemistry, vol. 17, No. 4; pp. 317-324, (Apr. 2004).

Morissette, et al., "High-throughput Crystallization: Polymorphs, Salts, Co-Crystals and Solvates of Pharmaceutical Solids", Advanced Drug Delivery Reviews, vol. 56; pp. 273-300, (2004).

Mudran, "Drug Delivery to the Nail Following Topical Application", International Journal of Pharmaceutics, vol. 236: pp. 1-26, (2002).

Patani, et al., "Bioterrorism: A Rational Approach to Drug Design", Chem. Rev., vol. 96; pp. 3147-3176 (1996).

Qin, et al., "Luminescent Organoboron Quinolate Polymers," Journal of the American Chemical Society, vol. 126, No. 22; pp. 7015-7018, (Jun. 9, 2004).

Rock, et al., "An Antifungal Agents Inhibits Aminoacyl-tRNA Synthetase by Trapping tRNA in the Editing Site", Science, vol. 316, No. 5832; pp. 1759-1761, (Jun. 22, 2007).

Snyder, et al. "Common Bacteria Whose Susceptibility to Antimicrobials in no longer Predictable" J. Med. Liban, vol. 48 No. 4; pp. 208-214, (2000).

Sugar, et al., "Comparison of Three Methods of Antifungal Susceptibility Testing with the Proposed NCCLS Stardard Broth Macrodilution Assay: Lack of Effect of Phenol Red" Diagn. Microbiol. Infect. Dis. vol. 21; pp. 129-133, (1995).

Tabuchi, et al., "Anticoccidial Activity of some Azacyclo Organoborinates," Heterocycles, vol. 60, No. 01; pp. 177-182, (2003).

Toporcer, et al., "Preparation and Properties of some Tetracoordinate Boron Compounds. The Pseudo-metal Ion Concept," Inorganic Chemistry, vol. 4, No. 11; pp. 649-1655, (Nov. 1965).

Trujillo, et al., "X-Ray Crystallographic Study of Boroxazolidones, Obtained from L-ornithine, L-methionine, Kainic acid and 2,6-pyridinedicarboxylic acid", Journal of Organometallic Chemistry, vol. 571; pp. 21-29, (1998).

Tschampel, et al., "Arylboronic Acids. VII. Some Reactions to o-Formybenzeneboronic Acids", J. Org. Chem. vol. 29, No. 8; pp. 2168-2172, (1964).

Turner, et al., Current Pharmaceutical Design, vol. 2; pp. 209-224 (1996).

Vippagunta, "Crystalline Solids", Advanced Drug Delivery Reviews, vol. 48; pp. 3-26, (2001).

Wang, et al., "Expression, Purification and Characterization of Human cAMP-Specific Phosphodiesterase (PDE4) Subtypes A, B, C, and D", Biochemical and Biophysical Research Communications, vol. 234; pp. 320-324, (1997).

Ye, et al., "Convenient and Versatile Synthesis of formyl-substituted Benzoxaboroles", Tetrahedron, vol. 65; pp. 8738-8744, (2009).

Zhdankin, et al., "Synthesis and Structure of Benzoboroxoles: Novel Organboron Heterocycles," Tetrahedron Letters, vol. 40; pp. 6705-6708, (1999).

Zhou, et al., "Hemodextrin: a Self-assembled Cyclodextrin-Porphyrin Construct That Binds Dioxygen," Biophysical Chemistry, 105:639-648 (2003).

Zhou, et al., "Structure-activity Studies on a Library of Potent Calix[4]arene-based PDGF Antagonists that Inhibit PDGF-stimulated PDGFR Tyrosine Phosphorylation," Org. Biomol. Chem., 4:2376-2386 (2006).

Zhou, et al., "Pattern Recognition of Proteins Based on an Array of Functionalized Porphyrins," J. Am. Chem. Soc., 128:2421-2425 (2006).

Zixing, et al., "Synthesis of Aromatic Nitrogen-containing Heterocyclic Derivatives of Asymmetric Diarylborinic Acids," Wuhan Daxue Xuebo-Wuhan University Journal, vol. 3; pp. 67-71, (1990), (English Abstract).

Figure 1A

| Compound ID | Ki CTX-M 9a uM | Ki KPC-2 uM | Ki SHV-18 uM | Ki TEM-1 uM | Ki TEM-64 uM | Ki AmpC uM | Ki CMY-2 uM | MIC ug/mL cefepime CTX-M 8 Enterobacter aerogenes Enb253 | MIC ug/mL cefepime KPC-2 Enterobacter cloacae 01MGH49 | MIC ug/mL cefepime KPC-3 like Escherichia coli EC236 | MIC ug/mL cefepime CTX-M 18 Escherichia coli EC257 | MIC ug/mL ceftazidime SHV-18 Escherichia coli K12 deltalacU169 pSHV18 | MIC ug/mL ceftazidime SHV-18 Escherichia coli K12 deltalacU169 tolC Tn10 mdfA Kan pSHV18 | MIC ug/mL cefepime CTX-M 14 Escherichia coli LPS_0076 | MIC ug/mL cefepime CTX-M 14 Escherichia coli LPS_0074 | MIC ug/mL cefepime CTX-M 15 Escherichia coli LPS_0034 | MIC ug/mL cefepime CTX-M 15 Escherichia coli LPS_0014 | MIC ug/mL cefepime CTX-M 9 Escherichia coli LPS_0073 | MIC ug/mL cefepime KPC-2 Escherichia coli LPS_0035 | MIC ug/mL ceftazidime KPC-2 Escherichia coli LPS_0015 |
|---|---|---|---|---|---|---|---|---|---|---|---|---|---|---|---|---|---|---|---|---|
| G1 | 3.11 | 0.375 | 1.72 | 0.966 | | 0.879 | 0.477 | >128 | | | >128 | | | | >128 | 32 | | | 16 | 64 |
| G2 | >32.3 | 40.8 | >6.69 | | | 32.2 | 48.1 | >128 | | | 4 | | | | | >128 | >128 | | >128 | |
| G5 | 1.42 | 0.198 | 1.22 | 0.602 | | 0.917 | 0.354 | 2 | | | | | | | | 4; 4 | 4 | | 1; 1 | 1 |
| G6 | 0.868 | 0.125 | 0.862 | 0.503 | | 0.353 | 0.163 | | | | | | | | 0.5; 4 | | | | | |
| G7 | 7.64 | 2.89 | >6.69 | 6.67 | | 56.2 | 23.4 | | | | | | | | | | | | | |
| G8 | 1.3 | 0.164 | 2.99 | 2.07 | | 32.4 | 37.1 | 8 | | | 32 | | | | 64 | 32 | | | 8 | 4 |
| G9 | 1.73 | 0.247 | 0.694 | 0.318 | | 0.878 | 0.466 | | | | >128 | | | | | 4; 8 | | | 1; 1 | |
| G10 | 0.192 | 0.0249 | 1.24 | 0.474 | | 0.233 | 0.107 | | 4 | | | | | | | | | | | |
| G11 | 0.902 | 0.118 | 0.333 | 0.134 | | 0.844 | 0.899 | 16 | | 8 | | | | | | 8 | | | 1; 2 | 2 |
| G12 | 0.719 | 0.116 | 0.752 | 0.358 | | 2.97 | 1.44 | 128 | 0.125 | 4 | >128 | | | | 4 | 4; 16 | | | | 8 |
| G13 | 1.01 | 0.364 | 0.46 | 0.221 | | 4.44 | 3.07 | 32 | 0.125 | 4 | 8 | | | | 4 | 32 | | | 8 | 1 |
| G14 | 9.09 | 0.576 | 2.1 | 0.271 | >41.2 | 51.7 | 13.6 | 128 | | 4 | 8; >128 | | | | 128 | 64 | | | 8 | 1 |
| G15 | 3.76 | | >5.01 | 0.31 | >41.2 | >123 | >104 | 16 | | 4 | 8; >128 | | | | 4 | 4 | >128 | | 16 | 16 |
| G16 | 0.924 | 0.0727 | 2.44 | 0.74 | | 10.9 | 13.3 | 16 | <=0.06 | 4 | 4; >128 | | | | 2; 4 | 4; 8 | | | 4; 8 | 4 |
| G17 | 0.377 | 0.0712 | 0.556 | 0.188 | | 0.21 | 0.107 | | | 4 | | | | | | | | | 4 | |
| G18 | 0.838 | 0.0381 | 0.445 | 0.114 | | 0.224 | 0.199 | | | 4 | >128 | | | | | | | | | |
| G19 | | | 0.362 | 0.0937 | | 0.489 | 0.294 | | | | | | | | | | | | | |
| G20 | >32.3 | >70.9 | >6.69 | >37.4 | | 9.18 | 10.9 | 32 | 2 | | 16 | | | | 1 | | | | | |
| G21 | 8.35 | 1.68 | 1.85 | 0.138 | | 7.46 | 17.4 | 8 | | | 4 | | | | | 64 | | | 16 | >128 |
| G22 | 11.3 | 0.0531 | >6.69 | 1.49 | >54.9 | 16.4 | >13.8 | | | | >128 | | | | 1 | 45.3 | | | 2 | |
| G23 | 0.608 | 0.0313 | 0.286 | 0.0974 | | 1.5 | 0.783 | | | | | | | | | 16 | | | 8 | |
| G24 | 0.627 | | 0.711 | 0.0766 | | 0.836 | 0.73 | | | | | | | | | 16; 16 | | | 8; 8 | |
| G25 | 1.64 | | 1.07 | 0.161 | | 0.0697 | 0.0614 | | | | | | | | | | | | | |

Figure 1B

| Compound ID | Ki CTX-M 9a uM | Ki KPC-2 uM | Ki SHV-18 uM | Ki TEM-1 uM | Ki TEM-64 uM | Ki AmpC uM | Ki CMY-2 uM | MIC ug_mL cefepime CTX-M 8 Enterobacter aerogenes Entb253 | MIC ug_mL cefepime KPC-2 Enterobacter cloacae 01MGH49 | MIC ug_mL cefepime KPC-3 like Escherichia coli EC236 | MIC ug_mL cefepime CTX-M 18 Escherichia coli EC257 | MIC ug_mL ceftazidime SHV-18 Escherichia coli K12 deltalacU169 pSHV18 | MIC ug_mL ceftazidime SHV-18 Escherichia coli K12 deltalacU169 tolC Tn10 mdfA Kan pSHV18 | MIC ug_mL cefepime CTX-M 14 Escherichia coli LPS_0076 | MIC ug_mL cefepime CTX-M 14 Escherichia coli LPS_0074 | MIC ug_mL cefepime CTX-M 15 Escherichia coli LPS_0034 | MIC ug_mL cefepime CTX-M 15 Escherichia coli LPS_0014 | MIC ug_mL cefepime CTX-M 9 Escherichia coli LPS_0073 | MIC ug_mL cefepime KPC-2 Escherichia coli LPS_0035 | MIC ug_mL ceftazidime KPC-2 Escherichia coli LPS_0015 |
|---|---|---|---|---|---|---|---|---|---|---|---|---|---|---|---|---|---|---|---|---|
| G26 | 0.592 | 0.0692 | 0.444 | | | 0.00861 | 0.00429 | 32 | 16 | 8 | 128 | | | | 8 | 64 | | 16 | 16 | |
| G27 | 0.616 | 0.0857 | 1.11 | 0.105 | | 0.0204 | 0.0181 | 8 | 4 | 4 | 32 | | | | 4; 4 | 32; 64 | | | 4; 16 | 4; 16 | |
| G28 | 0.405 | 0.044 | 0.27 | 0.307 | | 0.0585 | 0.0325 | 16 | 4 | 8 | 32 | | | | 4 | 64 | | 8 | 8 | 16 | |
| G29 | 8.05 | 2.49 | 2.35 | 0.234 | | 6.17 | 1.54 | 32; >128 | 0.5 | 8; 16 | 128; >128 | | | | 16; 64 | 32; 32 | | 8; 16 | 8; 64 | 8; 64 | |
| G30 | 1.17 | 0.143 | 0.3 | >12.5 | | 0.21 | 0.121 | 16 | 1 | 4; >128 | >128 | | | | | | | | | | |
| G31 | | | | | | | | 64 | 4 | 4; >128 | | | | | 4 | 16 | | | 8 | 4 | |
| G32 | | 13.4 | >6.69 | 1.7 | >54.9 | 15.4 | 13.7 | 8 | 4 | 2 | 32 | | | | 2 | 32 | | 4 | 4 | 16 | |
| G33 | 0.222 | | 1.26 | 7.06 | >54.9 | 0.0808 | 0.0414 | | 0.5 | 4 | 32 | | | | 4 | 16 | | | 8 | 32 | |
| G34 | 23.1 | 1.47 | >6.69 | 0.131 | | 3.59 | 2.01 | 32 | 1 | 16 | >128 | | | | >128 | 64 | | | 16 | 8 | |
| G35 | | | | 1.24 | | | | | 8 | 8; >128 | 8; >128 | | | | | 128 | | | 16 | 16 | |
| G36 | 0.822 | 0.229 | 1.1 | 0.268 | 24.6 | 0.0703 | 0.0713 | 8 | 1; 2 | 4 | 4; >128 | | | | 4 | 32 | | | 8; 4 | 8; 4 | |
| G37 | 0.938 | 0.437 | 0.74 | 0.555 | | 1.09 | 1.04 | 32 | | 4 | 128 | | | | 2 | 32 | | | 8 | 4 | |
| G38 | 0.484 | 0.131 | 0.566 | 0.327 | | 0.331 | 0.0747 | 16 | | 16 | 16 | | | | 2 | 32 | | | 8 | 8 | |
| G39 | 0.0358 | 0.013 | 0.133 | 0.0935 | | 0.0609 | 0.0593 | 4 | 16 | 4 | 32 | | | | 4 | 128 | | | 24; 8 | 24; 8 | |
| G40 | 10.4 | 1.91 | | 1.23 | | 0.386; >128 | 0.287; >128 | 8 | | 8; >128 | | | | | 16 | | >128 | | 16 | 16 | |
| G41 | 5.39 | 0.33 | 5.99 | 0.421 | | 0.287 | 0.283 | | 16 | 4 | | 32 | | | | | | | | | |
| G42 | 0.56 | 0.0694 | 1.07 | 0.502 | | 0.843 | 0.59 | | | 4 | | | | | 2 | 32 | | | 8 | 8 | |
| G43 | 0.106 | 0.0143 | 0.222 | 0.192 | | 0.537 | 0.206 | 8 | | 4 | 32 | | | | 1; 8 | | | | 4; 8 | 4; 8 | |
| G44 | 0.321 | 2.26 | 0.667 | 0.271 | | 1.01 | 0.607 | 2 | | 8 | 16 | | | | 0.5; 4 | | | | 4; 2 | 4; 2 | |
| G45 | >32.3 | >70.9 | >6.69 | | | | 0.685 | | | | | | | | | | | | | | |
| G46 | 0.0226 | 0.041 | 0.0749 | 0.0193 | | | 0.0269 | 4 | | 4 | 16 | | | | 1; >16; 32 | 32 | >128 | | 4; 8 | 4; 8 | >128 |
| G47 | 0.00154 | 0.0584 | 0.0362 | 0.00566 | | 0.0457 | 0.00981 | 1 | | 4 | 1 | 32 | | | 0.25; 32; 32 | | | | 2; 8 | 2; 8 | |
| G48 | | | 0.922 | | | | | 2 | | 4 | 4 | | 4 | | 0.25; 0.5; 0.5 | 16 | | | 1 | 4 | 4 |

Figure 1C

| Compound ID | Ki CTX-M 9a uM | Ki KPC-2 uM | Ki SHV-18 uM | Ki TEM-1 uM | Ki TEM-64 uM | Ki AmpC uM | Ki CMY-2 uM | MIC ug_mL cefepime CTX-M 8 Enterobacter aerogenes Entb253 | MIC ug_mL cefepime KPC-2 Enterobacter cloacae 01MGH49 | MIC ug_mL cefepime KPC-3 like Escherichia coli EC236 | MIC ug_mL cefepime CTX-M 18 Escherichia coli EC257 | MIC ug_mL ceftazidime SHV-18 Escherichia coli K12 deltalacU169 pSHV18 | MIC ug_mL ceftazidime SHV-18 Escherichia coli K12 deltalacU169 tolC Tn10 mfa Kan pSHV18 | MIC ug_mL cefepime CTX-M 14 Escherichia coli LPS_0076 | MIC ug_mL cefepime CTX-M 14 Escherichia coli LPS_0074 | MIC ug_mL cefepime CTX-M 15 Escherichia coli LPS_0034 | MIC ug_mL cefepime CTX-M 15 Escherichia coli LPS_0014 | MIC ug_mL cefepime CTX-M 9 Escherichia coli LPS_0073 | MIC ug_mL cefepime KPC-2 Escherichia coli LPS_0035 | MIC ug_mL ceftazidime KPC-2 Escherichia coli LPS_0015 |
|---|---|---|---|---|---|---|---|---|---|---|---|---|---|---|---|---|---|---|---|---|
| G49 | 0.135 | 0.0324 | 0.0443 | 0.0333 | 8.73 | 0.0251 | 0.0175 | 16 | 4 | 8 | 32 | | | | 4 | 32 | | 8 | 16 | |
| G50 | 0.0275 | 0.124 | 0.256 | 0.00716 | 4.8 | 0.0624 | 0.0362 | 4 | 1 | 4 | 16 | | | | 0.25 | 16 | | 4 | 64 | |
| G51 | 0.00921 | 0.114 | 0.442 | 0.169 | 46.6 | 0.033 | 0.0306 | 1 | 1 | 4 | 8 | | | | <=0.06 | 16 | | 1 | 16 | |
| G52 | 0.0177 | 0.131 | 0.201 | 0.145 | 27.4 | 0.0332 | 0.0163 | 2 | 2 | 4 | 16 | | | | 4 | 32 | | 4 | 32 | |
| G53 | 0.00502 | 0.186 | 0.343 | 0.0846 | 9.23 | 0.0382 | 0.0238 | 0.25 | 4 | 4 | 8 | | | | 0.25 | 8 | | 0.5 | 16 | |
| G54 | 0.00307 | 0.0512 | 0.157 | 0.0252 | 4.15 | 0.0117 | 0.00624 | 4 | 4 | 4 | 16 | | | | 1 | 64 | | 4 | 16 | |
| G55 | 0.0193 | 0.128 | 0.214 | 0.072 | 8.01 | 0.0268 | 0.019 | 8 | 4 | 8 | 16 | | | | 2 | 32 | | 8 | 16 | |
| G56 | 0.0285 | 0.0602 | 1.28 | 0.0943 | >54.9 | 0.149 | 0.0848 | 8 | 8 | 4 | 16 | | | | 0.5 | 16 | | 4 | 64 | |
| G57 | 0.0487 | 0.0752 | 0.329 | 0.297 | >54.9 | 0.0111 | 0.00635 | 8 | 4 | 8 | 16 | | | | 2 | 32 | | 8 | 22.6 | |
| G58 | 0.142 | 0.099 | 2.52 | 0.675 | >54.9 | 0.0652 | 0.0554 | 8 | 4 | 8 | 32 | | | | 4 | 16 | | 8 | 32 | |
| G59 | 0.0316 | 0.118 | 0.152 | 0.0568 | 14.3 | 0.0235 | 0.0131 | 8 | 4 | 8 | 16 | | | | 4 | 32 | | 8 | 32 | |
| G60 | 0.214 | 0.228 | 0.104 | 2.13 | >54.9 | 0.134 | 0.0396 | 2 | 8 | 16 | 64 | | | | 0.707 | 11.3 | | 2.83 | 16 | |
| G61 | 0.0117 | 0.115 | 0.367 | 0.108 | 15.4 | 0.0606 | 0.0449 | 4 | 11.3 | 5.66 | 22.6 | | | | 0.5 | 8 | | 4 | 8 | |
| G62 | 0.0218 | 0.356 | 0.45 | 0.259 | 35.8 | 0.0587 | 0.0623 | 0.354 | 1 | 4 | 16 | | | | <0.122 | 2 | | 0.5 | 32 | |
| G63 | 0.068 | 1.02 | 1.11 | 0.101 | >54.9 | 0.138 | 0.0794 | 0.125 | 0.354 | 1.41 | 0.707 | | | | <=0.06 | 2 | | 0.25 | 4 | |
| G64 | 0.0401 | 0.476 | 1.88 | 0.222 | >54.9 | 0.288 | 0.345 | 4 | <=0.06 | 1 | 0.25 | | | | 2 | 32 | | 4 | 64 | |
| G65 | 0.295 | 6.22 | >6.69 | 4.04 | >54.9 | 1.27 | 0.659 | 1 | 4 | 8 | 16 | | | | 0.25 | 64 | 8 >128; >128 | 4 | >128 | |
| G66 | 0.216 | 1.39 | >6.69 | 3.75 | >54.9 | 0.157 | 0.0867 | | 16 | 8 | 64 | 16; 128 | 32; 32 | | | | >128 | | | 16; >128 |
| G67 | 0.0553 | 0.138 | 1 | 0.233 | | 0.0452 | 0.0212 | | | | | | | | | | | | | 16; >128 |
| G68 | 0.107 | 0.161 | 1.39 | 0.384 | | 0.125 | 0.0455 | | | | 16 | | | | | | | | 16 | 16 |
| G69 | 0.05 | 0.0326 | 0.112 | 0.0812 | | 0.0662 | 0.0278 | | | 4 | 16 | | | | 1 | 32; 64 | | | 8 16; 16 | |
| G70 | 0.0532 | 0.22 | 0.508 | 0.652 | | 0.0483 | 0.0518 | 4 | 4 | | | | | | 2 | 32; 32 | | | 8 16; 16 | |
| G71 | 0.0552 | 0.129 | 0.542 | 0.529 | | 0.0716 | 0.0978 | | | | | | | | | | | | | |

Figure 1D

| Compound ID | Ki CTX-M 9a uM | Ki KPC-2 uM | Ki SHV-18 uM | Ki TEM-1 uM | Ki TEM-64 uM | Ki AmpC uM | Ki CMY-2 uM | MIC ug/mL cefepime CTX-M 8 Enterobacter aerogenes Enb253 | MIC ug/mL cefepime KPC-2 Enterobacter cloacae 01MGH49 | MIC ug/mL cefepime KPC-3 like Escherichia coli EC236 | MIC ug/mL cefepime CTX-M 18 Escherichia coli EC257 | MIC ug/mL ceftazidime SHV-18 Escherichia coli K12 deltalacU169 pSHV18 | MIC ug/mL ceftazidime SHV-18 Escherichia coli K12 deltalacU169 tolC Tn10 mdfA Kan pSHV18 | MIC ug/mL cefepime CTX-M 14 Escherichia coli LPS_0076 | MIC ug/mL cefepime CTX-M 14 Escherichia coli LPS_0074 | MIC ug/mL cefepime CTX-M 15 Escherichia coli LPS_0034 | MIC ug/mL cefepime CTX-M 15 Escherichia coli LPS_0014 | MIC ug/mL cefepime CTX-M 9 Escherichia coli LPS_0073 | MIC ug/mL cefepime KPC-2 Escherichia coli LPS_0035 | MIC ug/mL ceftazidime KPC-2 Escherichia coli LPS_0015 |
|---|---|---|---|---|---|---|---|---|---|---|---|---|---|---|---|---|---|---|---|---|
| G72 | 0.0303 | 0.039 | 0.293 | 0.054 | | 0.0936 | 0.0544 | 8 | 1 | 8 | 8 | | | | 2 | 32 | | 8 | 32 | |
| G73 | 16 | >128 | >128 | 11.6 | 7.78 | >400 | 4.53 | >400 | 1.79 | 2.05 | >128 | 1.38 | >6.69 | 0.423 | >54.9 | 0.736 | 0.707 | 2 | 1 | 2 |
| G74 | 0.0215 | 0.0424 | 0.312 | 0.28 | | 0.0849 | 0.0414 | 4 | 0.5 | 8 | 8 | | | 0.5; 1; 1 | 1; 1 | 4 | | 4 | 8 | |
| G75 | 11.6 | 0.0357 | 6.69 | | >54.9 | 16 | 21.2 | 8 | 8 | 4 | 16 | | | | | | | | | |
| G76 | 0.0769 | 1.07 | 0.295 | 0.146 | 28.9 | 0.0306 | 0.0118 | 11.3 | 4 | 8 | 32 | 16 | | | 2 | 64 | | 4 | 16 | |
| G77 | 0.00149 | 1.07 | 1.1 | 0.7 | >54.9 | 0.207 | 0.129 | 0.5 | 8 | 8 | 11.3 | | | | | 8 | 128 | 4 | 32 | >128 |
| G78 | 0.00145 | 0.0656 | 0.126 | 0.0205 | | 0.0206 | 0.0173 | 0.5 | | 4 | 1 | | | | 0.125 | 4; 4; 4 | | 0.707 | 1; 8; 8; 16 | |
| | | | | | | | | <=0.06; 0.125; 0.25; 0.25; 0.25; 0.5; 0.5; 0.5; 0.5; 1; 1 | | 2; 2; 2; 2; 4; 4; 4; 4; 8; 8 | 0.25; 0.25; 0.25; 0.25; 0.25; 0.5; 0.5; 0.5; 0.5; 1; 1; 1; 4 | | | | <=0.06; <=0.06; <=0.06; <=0.06; <=0.06; 0.125; 0.125; 0.125; 0.125; 0.25; 0.25; 0.25; 0.25 | 2; 2; 2; 2; 2; 2; 2; 2; 2; 2; 2; 4; 4; 4; 4 | | <=0.06; 0.5; 0.5; 0.5; 0.5; 1; 1; 1; 1; 2 | 4; 4; 4; 8; 8; 8; 8; 8; 8; 8; 8; 8 | |
| G81 | 0.00087 | 0.00754 | 0.0398 | 0.0252 | | 0.0154 | 0.00975 | | | | | | | 0.125 | 0.125 | | | | | |
| G82 | 0.347 | 0.0624 | 1.62 | 1.82 | | 1.72 | 2.3 | | | | | | | | | | | | >32 | |

Figure 1E

| Compound ID | Ki CTX-M 9a uM | Ki KPC-2 uM | Ki SHV-18 uM | Ki TEM-1 uM | Ki TEM-64 uM | Ki AmpC uM | Ki CMY-2 uM | MIC ug/mL cefepime CTX-M 8 Enterobacter aerogenes Entb253 | MIC ug/mL cefepime KPC-2 Enterobacter cloacae 01MGH49 | MIC ug/mL cefepime KPC-3 like Escherichia coli EC236 | MIC ug/mL cefepime CTX-M 18 Escherichia coli EC257 | MIC ug/mL ceftazidime SHV-18 Escherichia coli K12 deltaacrU169 deltaacrU169 pSHV18 | MIC ug/mL ceftazidime SHV-18 Escherichia coli K12 deltaacrU169 tolC Tn10 mdfA Kan pSHV18 | MIC ug/mL cefepime CTX-M 14 Escherichia coli LPS_0076 | MIC ug/mL cefepime CTX-M 14 Escherichia coli LPS_0074 | MIC ug/mL cefepime CTX-M 15 Escherichia coli LPS_0034 | MIC ug/mL cefepime CTX-M 15 Escherichia coli LPS_0014 | MIC ug/mL cefepime CTX-M 9 Escherichia coli LPS_0073 | MIC ug/mL cefepime KPC-2 Escherichia coli LPS_0035 | MIC ug/mL ceftazidime KPC-2 Escherichia coli LPS_0015 |
|---|---|---|---|---|---|---|---|---|---|---|---|---|---|---|---|---|---|---|---|---|
| G83 | 0.00403 | 0.0164 | 0.199 | 0.0507 | | 0.0224 | 0.0183 | | | | | | | | | | | | 8 | 8 |
| G84 | 0.00138 | 0.0867 | 0.064 | 0.0661 | 5.13 | 0.03 | 0.0442 | 4 | | 4 | 8 | | | | | 16 | | | 8 | |
| G85 | 8 | 64 | >128 | 0.00774 | 0.492 | 3.46 | 0.36 | 17.5 | 0.0207 | 4 | 0.00063 | 0.0872 | 0.0579 | 0.0336 | 2.4 | 32 | 0.00429 | 4 | 4 | 4 |
| G86 | 0.0167 | 0.369 | 0.52 | 0.972 | | 0.676 | 0.114 | 1 | 0.707 | 4 | 8 | | | | 0.5; 8; 16 | 0.00852 | | 2; 8; 16 | |
| G87 | 0.00714 | 0.037 | 0.344 | 0.183 | | 0.0405 | 0.0286 | | 8 | | 8 | | | | | | | | | |
| G88 | 0.0118 | 0.34 | 0.443 | 0.111 | >54.9 | 0.206 | 0.169 | 0.25 | 8 | 2.83 | 1.41 | | | | <0.0866 | 8 | | 1.41 | 16 | |
| G89 | 0.00191 | 0.104 | 0.296 | 0.0577 | 8.89 | 0.0217 | 0.0198 | 2 | 1 | 5.66 | 16 | | | | 0.354 | 32 | | 2 | 22.6 | |
| G90 | 0.0257 | 0.172 | 0.129 | 0.156 | >54.9 | 0.00676 | 0.0104 | 8 | 8 | 4 | 16 | | | | 1 | 64 | | 4 | 16 | |
| G91 | 9.58 | 0.915 | >6.69 | 9.28 | >54.9 | 0.0612 | 0.0317; >128 | >128 | 1 | 2; >128 | >128 | | | | 64 | 16 | | 64 | 128 | |
| G92 | 0.297 | 0.295 | 3.4 | 0.594 | >54.9 | 0.0443 | 0.0221 | 8 | 8 | 8 | 32 | | | | 4 | 64 | | 8 | 32 | |
| G93 | 0.0394 | 0.105 | 1.32 | 0.516 | >54.9 | 0.04 | 0.0244 | 4 | 8 | 8 | >128 | | | | 2 | 64 | | 8 | 32 | |
| G94 | 3.11 | 4.12 | >6.69 | 12 | >54.9 | 0.212 | 0.214; >128 | 8 | 128 | 64; >128 | 128 | | | >128 | | 128 | | 64; >128 | 2 | |
| G95 | 0.00331 | 0.141 | 3.01 | 0.0818 | >54.9 | 0.283 | 0.211 | 0.25 | 0.177 | 2 | 0.25 | | | <=0.06 | <=0.06 | 2 | | 0.25 | 16 | |
| G96 | 0.232 | 0.136 | 1.34 | 0.245 | >54.9 | 0.217 | 0.245 | 4 | <=0.06 | 8 | 32 | | | 0.125 | 0.125 | 32 | | 2 | 32 | |
| G97 | 0.0059 | 4.12 | 0.335 | 5.17 | >54.9 | 1.05 | 0.18 | 0.25 | 0.5 | 2 | 0.125 | | | | 0.25 | 2 | | 0.25 | 16 | |
| G98 | | | >6.69 | | | | | 4 | 0.25 | 4 | 16 | | | <=0.06 | <=0.06 | 1 | | 4 | 8 | |
| G99 | 0.00314 | 0.0434 | 0.109 | 0.156 | 13.5 | 0.0305 | 0.0173 | 0.25 | 0.25 | 4 | 1 | | | | 0.25 | 32 | | 0.5 | 8 | |
| G100 | >32.3 | >70.9 | >6.69 | >37.4 | >54.9 | >16.4 | >13.8 | 64 | 128 | 32; >128 | | | | 16 | 16 | 64 | | 8; >128 | 8; >128 | 8 |
| G101 | >10.8 | >70.9 | 5.39 | 14.6 | >54.9 | 0.808 | 1.71 | >128 | >128 | 32; >128 | | | | | 64 | 64 | | 8; >128 | 8; >128 | 8 |
| G102 | | 0.0079 | 0.0486 | 0.0306 | | 0.0745 | 0.0513 | 4 | | 4 | 32 | | | | 0.5; 0.5 | 8 | | 1; 16; 16 | | |
| G103 | 0.00464 | 0.0222 | 0.141 | 0.0442 | | 0.0855 | 0.0462 | | | | 8 | | | | | | | | 16 | |
| G104 | 0.0218 | 0.175 | 0.412 | 0.0768 | | 0.0883 | 0.0646 | 4 | | 4 | 16 | | | | 0.5 | 16 | | 2 | 16 | |
| G105 | | 0.0747 | 0.0454 | 0.0577 | | 0.0481 | 0.0397 | 4 | 8 | 4 | 32 | | | | 1 | 32 | | 8 | 32 | |
| G106 | 0.00957 | 0.028 | 0.0942 | 0.0284 | | 0.228 | 0.115 | 8 | | 4 | 16 | | | | 2 | 32 | | 8 | 16 | |

Figure 1F

| Compound ID | Ki CTX-M 9a uM | Ki KPC-2 uM | Ki SHV-18 uM | Ki TEM-1 uM | Ki TEM-64 uM | Ki AmpC uM | Ki CMY-2 uM | MIC ug_mL cefepime CTX-M 8 Enterobacter aerogenes Entb253 | MIC ug_mL cefepime KPC-2 Enterobacter cloacae 01MGH49 | MIC ug_mL cefepime KPC-3 like Escherichia coli EC236 | MIC ug_mL cefepime CTX-M 18 Escherichia coli EC257 | MIC ug_mL ceftazidime SHV-18 Escherichia coli K12 deltalacU169 pSHV18 | MIC ug_mL ceftazidime SHV-18 Escherichia coli K12 deltalacU169 ToIC Tn10 mdfA Kan pSHV18 | MIC ug_mL cefepime CTX-M 14 Escherichia coli LPS_0076 | MIC ug_mL cefepime CTX-M 14 Escherichia coli LPS_0074 | MIC ug_mL cefepime CTX-M 15 Escherichia coli LPS_0034 | MIC ug_mL cefepime CTX-M 15 Escherichia coli LPS_0014 | MIC ug_mL cefepime CTX-M 9 Escherichia coli LPS_0073 | MIC ug_mL cefepime KPC-2 Escherichia coli LPS_0035 | MIC ug_mL ceftazidime KPC-2 Escherichia coli LPS_0015 |
|---|---|---|---|---|---|---|---|---|---|---|---|---|---|---|---|---|---|---|---|---|
| G107 | 0.014 | 0.429 | 4.26 | 0.235 | >41.2 | 105 | 7.56 | 0.5 | <=0.06 | 4 | 1 |  |  |  | 0.125 | 32 |  | 0.5 | 2 |  |
| G108 | 0.0047 | 0.0293 | 0.0133 | 0.00362 | 2.71 | 0.328 | 0.0397 | 4 | 0.5 | 8 | 2 |  |  |  | 0.5 | 16 |  | 0.5 | 8 |  |
| G109 | 0.00266 | 0.0587 | 1.14 | 0.187 | 36.5 | 4.33 | 2.66 | 2 | 0.125 | 4 | 1 |  |  |  | 0.125 | 16 |  | 0.5 | 4 |  |
| G110 | 0.00057 | 0.0334 | 0.446 | 0.0466 | 12.8 | 1.39 | 0.708 | 1 | 0.25 | 16 | 0.5 |  |  |  | 2 | 2 |  | 0.5 | 2 |  |
| G111 | 0.00115 | 0.00859 | 0.055 | 0.0195 | 3.5 | 1.35 | 0.0792 | 16 | 4 | 16 | 16 |  |  |  | 2 | 32 |  | 4 | 16 |  |
| G112 |  | 0.00942 | 0.0427 | 0.0158 | 11.6 | 0.127 | 0.061 | 8 |  | 8 | 32 |  |  |  | 2 | 64 |  | 8 | 32 |  |
| G113 | 0.0287 | 0.0729 | 0.154 | 0.177 |  | 0.14 | 0.0904 | 4 |  | 8 | 32 |  |  |  | 2 | 16 |  | 4 | 16 |  |
| G115 | 0.0123 | 0.068 | 0.454 | 0.194 |  | 0.022 | 0.0221; 2 | 1 |  | 4; 4 | 16; 16 |  |  |  | 0.5; 0.5 | 16; 16 |  | 2; 8 | 16; 16 | 1.41 |
| G116 | 0.0157 | 0.11 | 0.703 | 0.145 | 21.5 | 0.0344 | 0.0455 |  |  | 1.8 | 4 |  |  | 0.355 | >54.9 | 0.948 | 0.622 | 0.354 | 0.25 | 4 |
| G117 | 1.41 | >64 | >128 | 1.95 | 3.91 |  | 3.81 >400 | 8 | 2.31 |  |  |  |  |  |  |  |  | 16 | 0.25 | 8 |
| G118 | 8 | >128 | >128 | 2.94 | 1.18 |  | >400 | 8 | 0.0436 | 0.0264 | 0.158 | 0.693 |  | 0.958 | >54.9 | 0.0179 | 0.00914 | 8 | 8 |  |
| G119 | 16 | >128 |  |  | 1.4 | 10.3 | 0.00615 | 2 | 0.25 | 4 | 0.237 | 0.209 |  |  | 0.125 | 16 |  | 4 | 4 |  |
| G120 | 0.00107 | 0.0112 | 0.0746 | 0.0494 | 1.48 | 0.0334 | 0.00067 | 8 | 1 | 4 | 0.5 |  |  |  | 0.25 | 16 |  | 4 | 2 |  |
| G121 | 0.0191 | 0.0618 | 0.0166 | 0.0263 | >54.9 | 0.00389 | 0.0544 |  |  | 8 | 16 |  |  |  |  |  |  |  |  |  |
| G122 | 0.00029 | 0.0762 | 0.908 | 0.157 | 14 | 0.128 | 0.505 | 8 | 2 | 8 | 8 |  |  |  | 0.25 | 8 |  | 1 | 8 |  |
| G123 | 0.0424 | 0.236 | 0.521 | 1.06 | >54.9 | 0.744 | 0.127 | 16 | 8 | 8 | 64 |  |  |  | 4 | 64 |  | 8 | 32 |  |
| G124 | 0.144 | 0.0717 | 0.31 | 3.86 | 4.44 | 0.209 | 0.005 | 2 | 0.707 | 1.41 | 4 |  |  |  | <0.122 | 8 |  | 4 | 16 | 1.41 |
| G125 | 0.000085 | 0.0297 | 0.0177 | 0.0428 | 0.0114 | 0.00762 | 0.00503 |  |  |  |  |  |  |  |  |  |  | 0.707 |  |  |
| G126 | 0.00024 | 0.022 | 0.0114 | 0.034 | 12.9 | 0.00921 | 0.252 | 8 | 0.5 | 4 | 16 |  |  |  | 1 | 32 |  | 4 | 16 |  |
| G127 |  | 0.3 | 0.213 | 0.277 | 2.6 | 0.289 | 0.149 | 0.5; 1 |  | 2; 4 | 2; 4 |  |  |  | 0.25 0.125; 0.2; 4; 4 |  |  | 2 | 2; 4; 4 |  |
| G128 | 0.028 | 0.088 | 0.272 | 0.0233 |  | 0.155 | 0.0383 | >128 |  | 16 >128 | >128 |  |  |  | 64 | 64 |  | 16 >128 | 2; 4 |  |
| G129 | 0.0129 |  | 0.161 | 0.061 |  | 0.125 | 5.16 >128 | 0.5 |  | 4 | 1 |  |  |  | 0.25 | 4 |  | 0.5; 2 | 2; 2 |  |
| G130 | 11.4 | >70.9 | >6.69 | 28.9 |  | 5.92 | 0.12 |  |  |  |  |  |  |  |  |  |  |  |  | 64 |
| G131 | 0.00149 |  | 0.0682 | 0.0457 |  | 0.214 |  |  |  |  |  |  |  |  | 0.25; 0.5 | 4; 4 | >128 |  |  |  |

Figure 1G

| Compound ID | Ki CTX-M 9a uM | Ki KPC-2 uM | Ki SHV-18 uM | Ki TEM-1 uM | Ki TEM-64 uM | Ki AmpC uM | Ki CMY-2 uM | MIC ug_mL cefepime CTX-M 8 Enterobacter aerogenes Entb253 | MIC ug_mL cefepime KPC-2 Enterobacter cloacae 01MGH49 | MIC ug_mL cefepime KPC-3 like Escherichia coli EC236 | MIC ug_mL cefepime CTX-M 18 Escherichia coli EC257 | MIC ug_mL ceftazidime SHV-18 Escherichia coli K12 deltalacU169 pSHV18 | MIC ug_mL ceftazidime SHV-18 Escherichia coli K12 deltalacU169 tolC Tn10 mdfA Kan pSHV18 | MIC ug_mL cefepime CTX-M 14 Escherichia coli LPS_0076 | MIC ug_mL cefepime CTX-M 14 Escherichia coli LPS_0074 | MIC ug_mL cefepime CTX-M 15 Escherichia coli LPS_0034 | MIC ug_mL cefepime CTX-M 15 Escherichia coli LPS_0014 | MIC ug_mL cefepime CTX-M 9 Escherichia coli LPS_0073 | MIC ug_mL cefepime KPC-2 Escherichia coli LPS_0035 | MIC ug_mL ceftazidime KPC-2 Escherichia coli LPS_0015 |
|---|---|---|---|---|---|---|---|---|---|---|---|---|---|---|---|---|---|---|---|---|
| G132 | 0.00061 | 0.00121 | 0.0428 | 0.022 | 2.79 | 0.0613 | 0.0517 | | 0.125 | 2 | <=0.06 | | | | <=0.06 | 1 | | 0.25 | 0.5 | |
| G133 | | 0.0384 | 1.39 | 0.62 | 1.2 | 3.39 | 2.84 | | 0.354 | 5.66 | 8 | | | | 0.354 | 45.3 | | 2 | 4 | |
| G134 | 0.0108 | 0.0179 | 0.0911 | 0.00568 | | 2.24 | 0.133 | | <=0.06 | 2.83 | 4 | | | | 0.177 | 32 | | 1.41 | 5.66 | 5.66 |
| G135 | 0.00364 | 0.0216 | 0.498 | 0.0793 | 24.6 | 0.398 | 0.338 | >5.66 | 2 | 4 | >22.6 | | | | <0.49 | 22.6 | | 4 | 4 >45.3 | |
| G136 | | | | | | | | | | | | | | | | | | | | |
| G145 | 0.00317 | 0.00207 | 0.0176 | 0.0165 | 1.56 | 0.0139 | 0.00752 | | 0.5 | 2 | 8 | | | | 0.125 | 8 | | 0.5 | 2 | |
| G146 | 0.00158 | 0.0361 | 0.0145 | 0.00794 | 1.65 | 0.0146 | 0.00773 | | 1 | 4 | 16 | | | | 0.5 | 32 | | 4 | 8 | |
| G147 | 0.0418 | 0.205 | 0.129 | 0.324 | 15.2 | 0.0491 | 0.0115 | | 0.125 | 4 | 16 | | | | 0.125 | 32 | | 2 | 16 | |
| G148 | 64 | >128 | >128 | 41.2 | 1.21 | 55.2 | 47 | >400 | 3.45 | 4.76 | 8 | | | | 2 | 16 | | 4 | 32 | 8 |
| G149 | 8 | 64 | >128 | 1.58 | 0.0701 | 2.74 | 2.83 | 15.2 | 0.243 | 0.26 | 3.33 | 0.215 | 0.922 | | >54.9 | 1.42 | 1.64 | >128 | 2 | 5.66 |
| G151 | 16 | >128 | >128 | 10.2 | 0.886 | 5.25 | 19.3 | 122 | 0.844 | 0.767 | 0.127 | 0.0124 | 0.0457 | | 2.09 | 0.0999 | 0.0898 | 8 | 2 | 8 |

Figure 1H

| Compound ID | MIC ug/mL cefepime KPC-3 Escherichia coli LPS_0036 | MIC ug/mL ceftazidime KPC-3 Escherichia coli LPS_0016 | MIC ug/mL cefepime SHV-5 Klebsiella oxytoca ATCC 51983 | MIC ug/mL ceftazidime SHV-5 Klebsiella oxytoca ATCC 51983 | MIC ug/mL cefepime KPC-2 Klebsiella pneumoniae | MIC ug/mL ceftazidime KPC-2 Klebsiella pneumoniae | MIC ug/mL cefepime TEM-26 Klebsiella pneumoniae | MIC ug/mL ceftazidime TEM-26 Klebsiella pneumoniae | MIC ug/mL cefepime TEM-10 TEM-12 Klebsiella pneumoniae ATCC 51503 | MIC ug/mL cefepime TEM-10 Klebsiella pneumoniae ATCC 51504 | MIC ug/mL ceftazidime TEM-10 Klebsiella pneumoniae ATCC 51504 | MIC ug/mL cefepime SHV-18 Klebsiella pneumoniae ATCC 700603 | MIC ug/mL ceftazidime SHV-18 Klebsiella pneumoniae ATCC 700603 | MIC ug/mL cefepime CTX-M 14 Klebsiella pneumoniae K283 | MIC ug/mL cefepime KPC-2 Klebsiella pneumoniae SYN 71 | MIC ug/mL ceftazidime KPC-2 Klebsiella pneumoniae SYN 71 | MIC ug/mL cefepime CTX-M 2 Klebsiella pneumoniae VII0982 | MIC ug/mL cefepime CTX-M 15 OXA-30 Escherichia coli CUMC247 | MIC ug/mL cefepime CTX-M 2 OXA-2 Escherichia coli | MIC ug/mL ceftazidime CTX-M 2 OXA-2 Escherichia coli |
|---|---|---|---|---|---|---|---|---|---|---|---|---|---|---|---|---|---|---|---|---|
| G1 | 2 | | 2 | | 8 | | >2 | | >128 | 32 | | | | | 4 | | | 128 | >32 | 8 |
| G2 | 0.5 | 2 | 0.5 | | >128 | | 2;>1 | | >128 | | >128 | 0.25 | | 32 | 4 | | 32 | >128 | >128 | |
| G5 | 0.5 | | 32 | | 0.5;0.5 | | | | 16;>128 | 4 | | | | 4 | 4 | | | 16 | >32 | |
| G6 | 1 | | | | 1 | | | | >128 | 16 | | | | 16 | 16 | | 8 | 32 | 2 16;16 | |
| G7 | 0.5;1 | | | | >128 | | | | 8;8 | 2;16 | | | | | | | 32 | 16 | >128 | |
| G8 | | | | | 0.25;1 | | | | 16 | | | 0.5;0.5 | | | 4,4 | | 8 | 64;128 | | |
| G9 | 0.25;0.5 | 0.5 | | | 0.5 | | >2;>2 | | 32 | 4 | | | | 32 | 4,4 | | 32 | 8 | 32;32 | |
| G10 | | | | | 2 | | | | | | >32 | | | 16 | 16 | | 32 | 16 | >128 | |
| G11 | | | | | 0.25 | | | | 16 | | | | | | 16 | | | | | |
| G12 | | | | | 0.5 | | | | | | | | | | 4 | | | | >128 | |
| G13 | | | | | 2 | | | | >128 | | | | | 16 | 4 | | 32 | 64 | >128 | |
| G14 | | | | | 0.25 | | | | >128 | | | | | 32 | | | 32 | | >128 | |
| G15 | | | | | 0.25 | | | | >128 | | | | | 32 | 4 | | 64 | 32 | 64 | |
| G16 | 1 | | | | 8 | | | | | 8 | 8 | | | | 4 | | 32 | | | |
| G17 | 1 | | 4;>1 | | 32 | | 2;>1 | | >128 | >128 | 8 | >1 | | | 8 | | 64 | 16 | 32;>128 | 32 |
| G18 | | | | | 16 | | | | | | | | | | | | 32 | 16 | 64;>128 | |
| G19 | 1 | | | | 1 | | | | | 4 | | | 1;1 | | | | 32 | 16 | 128 | |
| G20 | | | | | 32 | | | | | | | | | | | | | | | |
| G21 | | | | | | 16 | | | | | | | | | | | | | | |
| G22 | | | | | | | | | | | | | | | | | | | | |
| G23 | | | | | 2;2 | | 2;>2 | | | 8;8 | | | 1;2 | | | | | | 32;>32 | |
| G24 | 1;2 | | 1;1 | | | | | | | | | | | | | | | | | |
| G25 | | | | | | | | | | | | | | | | | | | >32;>32 | |

Figure 11

| Compound ID | MIC ug_mL cefepime KPC-3 Escherichia coli LPS_0036 | MIC ug_mL cefepime KPC-3 Escherichia coli LPS_0016 | MIC ug_mL cefepime SHV-5 Klebsiella oxytoca ATCC 51983 | MIC ug_mL ceftazidime SHV-5 Klebsiella oxytoca ATCC 51983 | MIC ug_mL cefepime KPC-2 Klebsiella pneumoniae | MIC ug_mL ceftazidime KPC-2 Klebsiella pneumoniae | MIC ug_mL cefepime TEM-26 Klebsiella pneumoniae | MIC ug_mL ceftazidime TEM-26 Klebsiella pneumoniae | MIC ug_mL cefepime TEM-10 TEM-12 Klebsiella pneumoniae ATCC 51503 | MIC ug_mL cefepime TEM-10 Klebsiella pneumoniae ATCC 51504 | MIC ug_mL ceftazidime TEM-10 Klebsiella pneumoniae ATCC 51504 | MIC ug_mL cefepime SHV-18 Klebsiella pneumoniae ATCC 700603 | MIC ug_mL ceftazidime SHV-18 Klebsiella pneumoniae ATCC 700603 | MIC ug_mL cefepime CTX-M 14 Klebsiella pneumoniae K283 | MIC ug_mL ceftazidime KPC-2 Klebsiella pneumoniae SYN 71 | MIC ug_mL cefepime KPC-2 Klebsiella pneumoniae SYN 71 | MIC ug_mL cefepime CTX-M 2 Klebsiella pneumoniae VII0982 | MIC ug_mL cefepime CTX-M 15 OXA-30 Escherichia coli CUMC247 | MIC ug_mL cefepime CTX-M 2 OXA-2 Escherichia coli | MIC ug_mL ceftazidime CTX-M 2 OXA-2 Escherichia coli |
|---|---|---|---|---|---|---|---|---|---|---|---|---|---|---|---|---|---|---|---|---|
| G26 | 4 | | >2 | | 2; 4 | | >2 | | 32 | | 16 | | | 32 | | | 64 | 32 | 128 | |
| G27 | | | | | 8 | | | | 16 | | | | | 32 | | 4 | 64 | 32; 128 | >32; 128 | |
| G28 | | | | | 2; 8 | | | | 16 | | | | | 16 | | | 64 | 16 | >128 | |
| G29 | | | | | | | | | >128; >128 | | | | | 32; 32 | | | 64; 128 | 64; 64 | >128; >128 | |
| G30 | | | | | 2 | | | | 64 | | | | | 16 | | | 32 | 16 | >128 | |
| G31 | | | | | 4 | | | | 32 | | | | | 32 | | | 64 | 4 | >128 | |
| G32 | 1 | | | | 1 | | | | | | | | | 4 | | | 64 | 64 | 128 | |
| G33 | | | | | 8 | | | | 32 | | 8 | | | 32 | | | 64 | 64 | 128 | |
| G34 | | | | | 2 | | | | >128 | | | | | 16 | | | 64 | 32; >128 | >128 | |
| G35 | 8 | | >2 | | 8 | | 2 | | >128 | | | | | 32 | | 8 | 32 | 64; >128 | >128 | |
| G36 | 16 | | | | 4 | | | | 64 | | 32 | | | 32 | | 4 | 32 | 128 | 128 | |
| G37 | 0.5 | | | | 2 | | | | 16; 32 | | | 1 | | 16 | | 16 | 128 | 32 | 16 128; >128 | |
| G38 | | | | | 8 | | | | 32 | | | 1 | | 16 | | 4 | 64 | 32 | 128 | |
| G39 | | | 1 | | 4 | | 2 | | 32 | | 16 | 1 | | 32 | | | 128 | 16 >32; 64 | 128 | |
| G40 | | | | | >32 | | >1 | | 16 | | | | | 32 | | | 64 | 128 >128 | | |
| G41 | | | | | 1; 1 | | | | 8; 16 | | 8 >16 | | | 8; 16 | | | | 1; 2 | >32 | |
| G42 | 2 | 32 | 4 | | 1; 1 | | 2 >128 | | | | | 0.5 | | | | | | | 128 | 32 |
| G43 | 4 | | | | 0.5; 1 | | | | 8; 8 | | 16 | | | 32 | | 2 | 32 | 16 | 128 | |
| G44 | | | | | 2; 2 | | | | 32 | | | | | | | 4 | 16 | 2 | 32; 128 | |
| G45 | | | | | 1; 2 | | | | | | | | | 8; 16 | | | 64 | | | |
| G46 | 2 | | | | | | 2 | | | | 16 | | | 32 | | 2 | 32 | 4; >16; 64 | 4 | |
| G47 | 4 | | | | | | | | | | | | | 8 | | 4 | 16 | 4; 32; 64 | | |
| G48 | | | | | | | | | | | | | | 2 | | | 64 | 4 | 16 | |

Figure 1J

| Compound ID | MIC ug_mL cefepime KPC-3 E. coli LPS_0036 | MIC ug_mL ceftazidime KPC-3 E. coli LPS_0016 | MIC ug_mL cefepime SHV-5 K. oxytoca ATCC 51983 | MIC ug_mL ceftazidime SHV-5 K. oxytoca ATCC 51983 | MIC ug_mL cefepime KPC-2 K. pneumoniae | MIC ug_mL ceftazidime KPC-2 K. pneumoniae | MIC ug_mL cefepime TEM-26 K. pneumoniae | MIC ug_mL ceftazidime TEM-26 K. pneumoniae | MIC ug_mL cefepime TEM-10 TEM-12 K. pneumoniae ATCC 51503 | MIC ug_mL cefepime TEM-10 K. pneumoniae ATCC 51504 | MIC ug_mL ceftazidime TEM-10 K. pneumoniae ATCC 51504 | MIC ug_mL cefepime SHV-18 K. pneumoniae ATCC 700603 | MIC ug_mL ceftazidime SHV-18 K. pneumoniae ATCC 700603 | MIC ug_mL cefepime CTX-M 14 K. pneumoniae K283 | MIC ug_mL ceftazidime KPC-2 K. pneumoniae SYN 71 | MIC ug_mL cefepime KPC-2 K. pneumoniae SYN 71 | MIC ug_mL cefepime CTX-M 2 K. pneumoniae VII0982 | MIC ug_mL cefepime CTX-M 15 OXA-30 E. coli CUMC247 | MIC ug_mL cefepime CTX-M 2 OXA-2 E. coli | MIC ug_mL ceftazidime CTX-M 2 OXA-2 E. coli |
|---|---|---|---|---|---|---|---|---|---|---|---|---|---|---|---|---|---|---|---|---|
| G49 | | | | | 4 | | | | 16 | | | | | 32 | | | 32 | 32 | 128 | |
| G50 | | | | | 8 | | | | 128 | | | | | 16 | | | 64 | 8 | 128 | |
| G51 | | | | | 2 | | | | 32 | | | | | 16 | | | 64 | 4 | 128 | |
| G52 | | | | | 4 | | | | 16 | | | | | 16 | | | 64 | 8 | 64 | |
| G53 | | | | | 8 | | | | 32 | | | | | 8 | | | 64 | 1 | 128 | |
| G54 | | | | | 16 | | | | 16 | | | | | 32 | | | 64 | 8 | 128 | |
| G55 | | | | | 32 | | | | 64 | | | | | 16 | | | 64 | 32 | 128 | |
| G56 | | | | | 22.6 | | | | 11.3 | | | | | 16 | | | 64 | 16 | 128 | |
| G57 | | | | | 16 | | | | 16 | >128 | | | | 16 | | | 32 | 8 | 128 | |
| G58 | | | | | 8 | | | | 16 | | | | | 16 | | | 64 | 8 | 128 | |
| G59 | | | | | 8 | | | | 64 | | | | | 16 | | | 64 | 8 | 128 | |
| G60 | | | | | 16 | | | | 16 | | | | | 16 | | | 64 | 8 | 128 | |
| G61 | | | | | 4 | | | | 32 | | | | | 32 | | | 32 | 8 | 64 | |
| G62 | | | | | 1.41 | | | | >90.5 | | | | | 16 | | | 45.3 | 2.83 | 32 | |
| G63 | | | | | 0.5 | | | | >128 | | | | | 5.66 | | | 64 | 2 | 16 | |
| G64 | | | | | 16 | | | | >128 | | | | | 0.5 | | | 32 | 64 | 128 | |
| G65 | | | | | 16 | | | | >128 | | | | | 16 | | | 64 | 16 | | |
| G66 | | | | | | | | | | | | | | 16 | | | | | 128 | |
| G67 | 2; 16;>128 | 16;>128 | >128;>12 | >2 | 8;8 | >2 | >2 | >128;>128 | | 16 | >128;>12 | 1 | 32;64 | | 4;8;8 | | >128 | | >32 | 64;64 |
| G68 | 8 | 64 | >128 | 32;>1 | 8 | 32;>1 | >1 | >128 | 16;32 | 32 | >128 | 1 | 32 | 8 | 8 | 16 | | | 8 64;64 | 32 |
| G69 | 8 | | | >1 | | >1 | >1 | | | 16 | | | | 16 | 16 | 8 | | | | |
| G70 | 4 | | | | 4;8 | | | | 16;16 | 16 | | | | 8 | 8 | 16 | 64 | 8 | 8 64;64 | |
| G71 | 4 | | | | 4;16 | | | | 16;16 | 8 | | | | 16 | 8 | 8 | 64 | 8 | 8 128;128 | |

Figure 1K

| Compound ID | MIC μg/mL cefepime KPC-3 Escherichia coli LPS_0036 | MIC μg/mL cefepime KPC-3 Escherichia coli LPS_0016 | MIC μg/mL cefepime SHV-5 Klebsiella oxytoca ATCC 51983 | MIC μg/mL ceftazidime SHV-5 Klebsiella oxytoca ATCC 51983 | MIC μg/mL cefepime KPC-2 Klebsiella pneumoniae | MIC μg/mL ceftazidime KPC-2 Klebsiella pneumoniae | MIC μg/mL cefepime TEM-26 Klebsiella pneumoniae | MIC μg/mL ceftazidime TEM-26 Klebsiella pneumoniae | MIC μg/mL cefepime TEM-10 TEM-12 Klebsiella pneumoniae ATCC 51503 | MIC μg/mL ceftazidime TEM-10 Klebsiella pneumoniae ATCC 51504 | MIC μg/mL cefepime TEM-10 Klebsiella pneumoniae ATCC 51504 | MIC μg/mL ceftazidime SHV-18 Klebsiella pneumoniae ATCC 700603 | MIC μg/mL cefepime SHV-18 Klebsiella pneumoniae ATCC 700603 | MIC μg/mL cefepime CTX-M 14 Klebsiella pneumoniae K283 | MIC μg/mL ceftazidime KPC-2 Klebsiella pneumoniae SYN 71 | MIC μg/mL cefepime KPC-2 Klebsiella pneumoniae SYN 71 | MIC μg/mL cefepime CTX-M 2 Klebsiella pneumoniae VII0982 | MIC μg/mL cefepime CTX-M 15 OXA-30 Escherichia coli CUMC247 | MIC μg/mL cefepime CTX-M 2 OXA-2 Escherichia coli | MIC μg/mL ceftazidime CTX-M 2 OXA-2 Escherichia coli |
|---|---|---|---|---|---|---|---|---|---|---|---|---|---|---|---|---|---|---|---|---|
| G72 | 16 | | | | 16 | 16 | | | >128 | | | | | 16 | | | 64 | 16 | 128 | |
| G73 | | 1 | | | 8 | | | | 2 | >128 | | | | 16 | | 128 | 16 | 128 | >128 | >128 |
| G74 | | | | | 2 | | | | 32 | | | | | 16 | | | 32 | 2 | 128 | |
| G75 | | | | | 4 | | | | 16 | | | | | 16 | | | 128 | | 128 | |
| G76 | | | | | 5.66 | | | | 16 | | | | | 22.6 | | | >64 | 22.6 | 128 | |
| G77 | | | | | 8 | | | | 22.6 | | | | | 11.3 | | | 45.3 | 5.66 | | 32 |
| G78 | 1; 2 | >128 | 0.5; 1 | >1; 1 | 1; 4; 4 | 4 | >1; 2 | >128 | 8; 8; 8; 8; 8; 8; 16; 16; 16; 16 | >16 | 4; 8; 8; 16 | 0.5; 0.5 | | 4; 4; 4; 4; 4; 4; 8; 8; 8; 8; 16 | 2; 2; 4; 4 | | 4; 8; 8; 8; 8; 8; 8; 8; 16; 16; 16 | 0.5; 1; 1; 1; 1; 1; 2; 2; 2; 2; 2; 2; 4 | 8; 8; 8; 16; 16; 16; 16; 16; 16; 16; 32; 32; 32; 32; 64; 64; 64; 64; 64 | 4; >16; >32; >32 |
| G81 | | | | >2 | | 32 | >2; >2 | | | | | | 1 | | 16 | | | | >32 | |
| G82 | 1; 1; 1; 1; 1 | | | 0.5; 1 | | | | | | | | | | | | | | | | |

Figure 1L

| Compound ID | MIC ug/mL cefepime KPC-3 E. coli LPS_0036 | MIC ug/mL ceftazidime KPC-3 E. coli LPS_0016 | MIC ug/mL cefepime SHV-5 Klebsiella oxytoca ATCC 51983 | MIC ug/mL ceftazidime SHV-5 Klebsiella oxytoca ATCC 51983 | MIC ug/mL cefepime KPC-2 Klebsiella pneumoniae | MIC ug/mL ceftazidime KPC-2 Klebsiella pneumoniae | MIC ug/mL cefepime TEM-26 Klebsiella pneumoniae | MIC ug/mL ceftazidime TEM-26 Klebsiella pneumoniae | MIC ug/mL cefepime TEM-10 TEM-12 Klebsiella pneumoniae ATCC 51503 | MIC ug/mL cefepime TEM-10 Klebsiella pneumoniae ATCC 51504 | MIC ug/mL ceftazidime TEM-10 Klebsiella pneumoniae ATCC 51504 | MIC ug/mL cefepime SHV-18 Klebsiella pneumoniae ATCC 700603 | MIC ug/mL ceftazidime SHV-18 Klebsiella pneumoniae ATCC 700603 | MIC ug/mL cefepime CTX-M 14 Klebsiella pneumoniae K283 | MIC ug/mL cefepime KPC-2 Klebsiella pneumoniae SYN 71 | MIC ug/mL ceftazidime KPC-2 Klebsiella pneumoniae SYN 71 | MIC ug/mL cefepime CTX-M 2 Klebsiella pneumoniae VII0982 | MIC ug/mL cefepime CTX-M 15 OXA-30 E. coli CUMC247 | MIC ug/mL cefepime CTX-M 2 OXA-2 E. coli | MIC ug/mL ceftazidime CTX-M 2 OXA-2 E. coli |
|---|---|---|---|---|---|---|---|---|---|---|---|---|---|---|---|---|---|---|---|---|
| G83 | 8 |  | >2 |  | 8 |  |  | >2 | 8 | 32 |  | 1 |  | 16 | 4 |  | 64 |  | >32 |  |
| G84 |  | 0.5 |  |  | 8 | 8 |  |  | 8 |  | 16 |  |  | 16 |  | 32 | 4 | 8 | 64 | >128 |
| G85 | 4 |  |  | 64 | 4 |  |  |  |  | 16 |  |  |  | 16 | 4 |  | 32 | 64 | 64; >128 |  |
| G86 | 4 |  | >2 |  | 1; 8 |  |  |  | 32; 32 | 16 |  | 1 |  | 16 | 4 |  |  | 8; 128; 128 |  |  |
| G87 | 2 |  |  |  | 2 |  | 2 |  | >45.3 |  |  |  |  | 8 |  |  |  | >32 |  |  |
| G88 |  |  |  |  | 5.66 |  |  |  | 11.3 |  |  |  |  | 16 |  |  | 32 | 2 | 128 |  |
| G89 |  |  |  |  | 8 |  |  |  | 16 |  |  |  |  | 16 |  |  | 45.3 | 11.3 | 128 |  |
| G90 |  |  |  |  | 8 |  |  |  |  |  |  |  |  | 64 |  |  | 32 | 8 | 128 |  |
| G91 |  |  |  |  | 128 |  |  |  | 32 |  |  |  |  | 16 |  |  | >128 | >128 | >128 |  |
| G92 |  |  |  |  | 32 |  |  |  | 32 |  |  |  |  | 16 |  |  | 32 | 16 | 128 |  |
| G93 |  |  |  |  | 16 |  |  |  |  |  |  |  |  | 128 |  |  | 64 | 16 | 4 |  |
| G94 |  |  |  |  |  |  |  |  | 16 |  |  |  |  | 0.25 |  |  | >128 | >128 | >128 |  |
| G95 |  |  |  |  | 1 |  |  |  | >128 |  |  |  |  | 16 |  |  | 32 | 0.25 | 64 |  |
| G96 |  |  |  |  | 8 |  |  |  | 64 |  |  |  |  | 0.5 |  |  | 64 | 16 | 128 |  |
| G97 |  |  |  |  | 0.5 |  |  |  | 32 |  |  |  |  | 16 |  |  | 32 | 0.5 | 16 |  |
| G98 |  |  |  |  | 2 |  |  |  | 32 |  |  |  |  | 16 |  |  | 16 | 4 | 64 |  |
| G99 |  |  | 1 |  | 1 |  |  |  | 128 |  |  |  |  | 32 |  |  | 16 | 8 | 64 |  |
| G100 |  |  |  |  | >128 |  |  |  | >128 |  |  |  |  | 32 |  |  | 64 | 64 | 64; >128 |  |
| G101 |  |  |  |  | >128 |  |  |  | 8 | 8 |  | 1 |  | 16 |  |  | 128 | 64 | 64; >128 |  |
| G102 | 4 |  |  |  | 2; 4 |  | >2 |  | 16 |  |  |  |  |  | 4 |  | 16 | 32; >128 | 32; >32; 128 |  |
| G103 | 4 |  |  |  |  |  |  |  | 16 |  |  |  |  | 16 | 4 |  | 16 |  | 128 |  |
| G104 |  |  |  |  | 4 |  |  |  | 8 |  |  |  |  | 16 |  |  | 32 | 8 | 64 |  |
| G105 |  |  |  |  | 16 |  |  |  |  |  |  |  |  | 16 |  |  | 64 | 16 | 128 |  |
| G106 |  |  |  |  | 8 |  |  |  | 16 |  |  |  |  |  |  |  |  | 16 | 128 |  |

Figure 1M

| Compound ID | cefepime KPC-3 E. coli LPS_0036 | ceftazidime KPC-3 E. coli LPS_0016 | cefepime SHV-5 K. oxytoca ATCC 51983 | ceftazidime SHV-5 K. oxytoca ATCC 51983 | cefepime KPC-2 K. pneumoniae | ceftazidime KPC-2 K. pneumoniae | cefepime TEM-26 K. pneumoniae | ceftazidime TEM-26 K. pneumoniae | cefepime TEM-10 TEM-12 K. pneumoniae ATCC 51503 | cefepime TEM-10 K. pneumoniae ATCC 51504 | ceftazidime TEM-10 K. pneumoniae ATCC 51504 | cefepime SHV-18 K. pneumoniae ATCC 700603 | ceftazidime SHV-18 K. pneumoniae ATCC 700603 | cefepime CTX-M 14 K. pneumoniae K283 | cefepime KPC-2 K. pneumoniae SYN 71 | ceftazidime KPC-2 K. pneumoniae SYN 71 | cefepime CTX-M 2 K. pneumoniae VII0982 | cefepime CTX-M 15 OXA-30 E. coli CUMC247 | cefepime CTX-M 2 OXA-2 E. coli | ceftazidime CTX-M 2 OXA-2 E. coli |
|---|---|---|---|---|---|---|---|---|---|---|---|---|---|---|---|---|---|---|---|---|
| G107 | | | | | 0.5 | | | | >128 | | | | | 2 | | | 32 | 8 | 16 | |
| G108 | | | | | 4 | | | | 16 | | | | | 16 | | | 8 | 16 | 64 | |
| G109 | | | | | 0.5 | | | | >128 | | | | | 4 | | | 32 | 8 | 64 | |
| G110 | | | | | 0.25 | | | | 64 | | | | | 2 | | | 16 | 1 | 64 | |
| G111 | 1 | <=0.06 | | | 16 | | | | 32 | | | | | 16 | | | 64 | 16 | 128 | |
| G112 | 16 | 1 | | | 32 | | | | 32 | | | | | 32 | | | 64 | 16 | 128 | |
| G113 | | 2 | | | 32 | 2; 4 | | | 16 | | | | | 16 | | | 32 | 32 | 64 | |
| G115 | | | | | | 5.66 | | | 16 | | | | | 16 | 32; 64 | | 32; 64 | 2, 4 | 64; 64 | >90.5 |
| G116 | | | 16 | | 4 | | | | 1.41 | >128 | | | | 2 | 64 | | 1.41 | | 64 | |
| G117 | | | 8 | | 0.5 | | 5.66 | | 4 | | 64 | | | 16 | | | 32 | 8 | 64; >64 | 8; >128 |
| G118 | | | | | 4 | | 16 | | 16 | | | | | 32 | | 32 | 32; >128 | 128 | 128; >128 | 128; >128 |
| G119 | >128 | 16 | 64 | | 8 | | 16 | | 4 | | | | | 4 | | 64 | 32 | 0.5 | 32 | |
| G120 | | | | | 1 | | | | 16 | | | | | 4 | | | 32 | 2 | 64 | |
| G121 | | | | | 0.5 | | | | 16 | | | | | 4 | | | 32 | 1 | 8 | |
| G122 | | | | | | | | | 64 | | | | | 8 | | | | | | |
| G123 | | | | | 8 | | | | 32 | 32 | | | | 16 | | | 32 | 2 | 64 | |
| G124 | | | | | 16 | | | | 16 | | | | | 16 | | | | 8 | 128 | |
| G125 | | | | | 5.66 | | | | 22.6 | 8 | | | | 11.3 | | 4 | | 1 | | |
| G126 | | | | | | | | | | | | | | | | | | | | |
| G127 | | | | | | | | | | | | | | | | | | | | |
| G128 | | | | | | | | | 32 | | | | | 16 | | | 32 | 8 | 128 | |
| G129 | 0.25 | | | | 16 | | | | 16; 16; 16 | | | | | 8; 16 | | | 16; 32 | 1; 1 | 64; 64; 128 | |
| G130 | | | 64 | 1 | 0.5; 1; 4 | | | | >128 | | >128 | 0.5 | | 32 | | 4 | 128 | 64 | 64; >128 | 128; >128 |
| G131 | 0.25 | 2 | | | >128 | 1; 2 | 2; >1 | | 8 | | | | 16 | 2 | | 4 | 8 | 1; 1 | 16; >32 | 16 |

Figure 1N

| Compound ID | MIC μg/mL cefepime KPC-3 Escherichia coli LPS_0036 | MIC μg/mL ceftazidime KPC-3 Escherichia coli LPS_0016 | MIC μg/mL cefepime SHV-5 Klebsiella oxytoca ATCC 51983 | MIC μg/mL ceftazidime SHV-5 Klebsiella oxytoca ATCC 51983 | MIC μg/mL cefepime KPC-2 Klebsiella pneumoniae | MIC μg/mL ceftazidime KPC-2 Klebsiella pneumoniae | MIC μg/mL cefepime TEM-26 Klebsiella pneumoniae | MIC μg/mL ceftazidime TEM-26 Klebsiella pneumoniae | MIC μg/mL cefepime TEM-10 TEM-12 Klebsiella pneumoniae ATCC 51503 | MIC μg/mL ceftazidime TEM-10 Klebsiella pneumoniae ATCC 51504 | MIC μg/mL cefepime TEM-10 Klebsiella pneumoniae ATCC 51504 | MIC μg/mL ceftazidime SHV-18 Klebsiella pneumoniae ATCC 700603 | MIC μg/mL cefepime SHV-18 Klebsiella pneumoniae ATCC 700603 | MIC μg/mL cefepime CTX-M 14 Klebsiella pneumoniae K283 | MIC μg/mL ceftazidime KPC-2 Klebsiella pneumoniae SYN 71 | MIC μg/mL cefepime KPC-2 Klebsiella pneumoniae SYN 71 | MIC μg/mL cefepime CTX-M 2 Klebsiella pneumoniae VII0982 | MIC μg/mL cefepime CTX-M 15 OXA-30 Escherichia coli CUMC247 | MIC μg/mL cefepime CTX-M 2 OXA-2 Escherichia coli | MIC μg/mL ceftazidime CTX-M 2 OXA-2 Escherichia coli |
|---|---|---|---|---|---|---|---|---|---|---|---|---|---|---|---|---|---|---|---|---|
| G132 | | | | | 0.25 | | | | 16 | 8 | | | | 0.25 | | | 4 | 0.25 | 0.5 | |
| G133 | | | | | 1.41 | | | | >90.5 | >128 | | | | 11.3 | | | 45.3 | 5.66 | 64 | 64 |
| G134 | | | | | 16 | | | | 32 | | | | | 8 | | | 45.3 | 1 | 64 | 64 |
| G135 | | | | | >22.6 | | | | >45.3 | | | | | 11.3 | | | 45.3 | 8 | >90.5 | |
| G136 | | | | | 2 | | | | 64 | | | | | 8 | | | 16 | 1 | 64 | 64 |
| G145 | | | 16 | | 2 | 32 | | | 128 | | | | | 16 | | | 32 | 2 | 128 | 128 |
| G146 | | 64 | 64 | | 8 | 8 | | | 16 | | | | | 16 | | | 8 | 16 | 64 | 64 |
| G147 | | 2.83 | 64 | | 1 | 16 | | | 16 | | | | | 8 | | | 32 | 2 | 64 | 64 |
| G148 | | 64 | | | 128 | 32 | | | 32 | >128 | | | | 32 | 128 | | 128 | >128 | 64 | >128 |
| G149 | >128 | | | | 8 | 8 | | | 5.66 | 8 | | | | 32 | 22.6 | | 11.3 | 90.5 | 32 | >128 |
| G151 | >128 | | | | 16 | | | | 16 | 128 | | | | 32 | 32 | | 16 | >128 | 32 | >128 |

Figure 10

| Compound ID | cefepime SHV-5 OXA-1 E. coli | cefazidime SHV-5 OXA-1 E. coli | cefepime TEM-1 OXA-2 E. coli | cefepime CTX-M 15 OXA-30 K. pneumoniae HUH44 | cefazidime AmpC E. aerogenes ATCC 29751 | cefepime AmpC E. cloacae BAA 1143 LPS_0037 | cefepime AmpC E. cloacae BAA 1143 LPS_0075 | cefepime AmpC E. cloacae BAA 1143 LPS_0017 | cefepime AmpC E. cloacae P99 | cefepime CMY-2 E. coli K12 deltaacU169 pCMY2 LPS_00031 | cefepime CMY-2 E. coli K12 deltaacU169 pCMY2 | cefepime CMY-2 E. coli K12 deltaacU169 tolC Tn10 mdfA Kan pCMY2 | cefazidime CMY-2 E. coli K12 deltaacU169 tolC Tn10 mdfA Kan pCMY2 | cefazidime FOX-5 E. coli LPS_0057 | cefazidime FOX-5 E. coli LPS_0056 | cefepime AmpC P. aeruginosa SYN 228 | cefazidime AmpC P. aeruginosa SYN 228 | cefepime CMY-2 CTX-M 14 K. pneumoniae CUMCK2 |
|---|---|---|---|---|---|---|---|---|---|---|---|---|---|---|---|---|---|---|
| G1 | >32 | | | | | 2 | | | 1 | 0.06 | | | | 16 | | | | |
| G2 | 128 | 8; >128 | >128 | 64 | | 8 | | | 0.5 | 0.03 | | 2 | 0.03 | 16 | 8 | 8 | | >128 |
| G5 | 8; 32 | | 4; 8 | 2 | | 0.5 | | | | | | | | >32 | | | | |
| G6 | 64 | | >128 | | | 0.25; 1 | | | | | | | | 8; 32 | | | | |
| G7 | 128 | | >128 | 32 | | 4 | | | | | | | | 32 | 8 | | | 8 |
| G8 | 8; 16 | | 32; 64 | 16 | | 8 | | | | | | | | 16 | | | | 1 |
| G9 | 8; 32 | | >128 | | | 2 | | | 0.5; 1 | 0.06; 0.125 | 2 | | 0.03; 0.06 | 8; 32 | 8 | | 8; 16 | |
| G10 | 16 | | 64 | 32 | | 1 | | | | | | | | 8 | | | | 4 |
| G11 | 32 | | >128 | 128 | | 4 | | | | | | | | 8 | | | | 2 |
| G12 | 16 | | >128 | 32 | >128 | 8 | | | | | | | | 32 | | | | 32 |
| G13 | 16 | | >128 | 32 | | 16 | | 32 | | | | | | 32 | | | | 8 |
| G14 | 16 | | >128 | 16 | | 4 | | | | | | | | 16 | | | | 2 |
| G15 | 64 | | | 16 | | 0.5 | | | 0.5 | 0.03 | | | 0.06 | | | | | 1 |
| G16 | 8 | | >128 | | | 1 | | | | | | | | 8 | | 16 | 16 | |
| G17 | 1; 32 | >128 | >128 | | | 1; 2 | | | | | | | | 2; 8; 16 | 32 | | | 8 |
| G18 | | | | | | | | | | | | | | | | | | 5.66 |
| G19 | | | | | | | | | | | | | | | | | | 2 |
| G20 | | | | | | | | | | | | | | | | | | |
| G21 | 32 | | >128 | 32 | | 2 | | 32 | | | | | | 32 | 32 | | | |
| G22 | 32 | | >128 | 8 | | 5.66 | | | | | | | | 64 | | | | |
| G23 | 32 | | 128 | 32 | | 4 | | | 1; 1 | 0.125; 0.5 | 8 | | 0.03; 0.06 | 16; >32 | | | 8; 16 | |
| G24 | 32; 32 | | | | | 4 | | | | | | | | | | | | |
| G25 | | | | | | | | | | | | | | | | | | |

Figure 1P

| Compound ID | MIC ug/mL ceftazidime SHV-5 OXA-1 E. coli | MIC ug/mL cefepime SHV-5 OXA-1 E. coli | MIC ug/mL cefepime TEM-1 OXA-2 E. coli | MIC ug/mL cefepime CTX-M 15 OXA-30 Klebsiella pneumoniae HUH44 | MIC ug/mL ceftazidime AmpC Enterobacter aerogenes ATCC 29751 | MIC ug/mL cefepime AmpC Enterobacter cloacae BAA_1143 LPS_0037 | MIC ug/mL cefepime AmpC Enterobacter cloacae BAA_1143 LPS_0075 | MIC ug/mL cefepime AmpC Enterobacter cloacae BAA_1143 LPS_0017 | MIC ug/mL cefepime AmpC Enterobacter cloacae P99 | MIC ug/mL cefepime CMY-2 E. coli K12 deltacU169 pCMY2 LPS_0031 | MIC ug/mL ceftazidime CMY-2 E. coli K12 deltacU169 pCMY2 | MIC ug/mL cefepime CMY-2 E. coli K12 deltacU169 tolC Tn10 mdfA Kan pCMY2 | MIC ug/mL ceftazidime CMY-2 E. coli K12 deltacU169 tolC Tn10 mdfA Kan pCMY2 | MIC ug/mL cefepime FOX-5 E. coli LPS_0057 | MIC ug/mL ceftazidime FOX-5 E. coli LPS_0056 | MIC ug/mL cefepime AmpC Pseudomonas aeruginosa SYN 228 | MIC ug/mL ceftazidime AmpC Pseudomonas aeruginosa SYN 228 | MIC ug/mL cefepime CMY-2 CTX-M 14 Klebsiella pneumoniae CUMCK2 |
|---|---|---|---|---|---|---|---|---|---|---|---|---|---|---|---|---|---|---|
| G26 | 64 | | | | | | | | | | | | | 8 | | | | 16 |
| G27 | 32; 32 | 64 | >128 | 16 | 0.5; 1, 4 | | | | 0.25 | | | 0.03 | | 8; 64 | | | | 4 |
| G28 | 64 | | 128 | 64 | 2 | | | | | | | | | 8 | | 16 | | 4 |
| G29 | 32; >128 | | >128 | 32; >12, 16; 16 | 4; 4 | | | | | | | | | 16; 64 | | | | 8; 16 |
| G30 | 16 | | 8 | 32 | 0.5 | | | | | | | | | | | | | 8 |
| G31 | | | 32 | 32 | 1 | | | | | | | | | 16 | | | | 8 |
| G32 | 32 | | 64 | 32 | 0.25 | | | | | | | | | 4 | | | | 2 |
| G33 | >128 | | >128 | 32 | 4 | | | | | | | | | 8 | | | | 8 |
| G34 | >128 | | >128 | 32 | 4 | | | | | | | | | 8; 64 | | | | 8 |
| G35 | >128 | | 64 | 32 | 0.5 | | | | | | | | | 16; 64 | | | | 16 |
| G36 | 64 | | 128 | 32 | 2 | | | | | | | | | 4 | | | | 8 |
| G37 | 32; 32 | | >128; >12 | 16 | 1; 2 | | | | | 0.06 | | | | 16 | | 8; 16 | | 8 |
| G38 | 32 | | >128 | 8 | | | | | 0.25 | | | | | 8; 64 | | | | 2 |
| G39 | 32; 32 | | >128 | 16 | 1; 1 | | | | 0.06 | | | 0.03 | | 8 | | 16 | | 2 |
| G40 | | | >128 | 64 | | | | | | | | | | | | | | 2 |
| G41 | | | >128 | 32 | | | | | | | | 0.03 | | 8 | | 16 | | 32 |
| G42 | >32 | | | 32 | 2; 4 | | | | | 0.0625 | | 0.25 | | 8; 8 | | | 8 | 4 |
| G43 | 1; 32 | | 16 | 16 | 1; 1 | | | 64 | | | | | | | | | | 1 |
| G44 | 8; 16 | | 16; 64 | 2; 4 | 0.5; 1 | | | | | | 16 | | | | | | | 0.5, 0.5 |
| G45 | | | | | | | | | | | | | | | | | | 4 |
| G46 | 16; 32 | | 128 | 32 | | | | | | | | 0.03 | | 8 | | | | 4 |
| G47 | 16; 32 | | 128; >128 | 16 | 2; 4 | | | | | | | 0.25 | | 8 | | | | 0.25 |
| G48 | 32 | | 128 | 8 | | | | | | | | | | 8 | | | | 0.5 |

Figure 1Q

| Compound ID | MIC ug_mL cefepime SHV-5 OXA-1 Escherichia coli | MIC ug_mL cefepime SHV-5 OXA-1 Escherichia coli | MIC ug_mL cefepime TEM-1 OXA-2 Escherichia coli | MIC ug_mL cefepime CTX-M 15 OXA-30 Klebsiella pneumoniae HUH44 | MIC ug_mL ceftazidime AmpC Enterobacter aerogenes ATCC 29751 | MIC ug_mL cefepime AmpC Enterobacter cloacae BAA 1143 LPS_0037 | MIC ug_mL cefepime AmpC Enterobacter cloacae BAA 1143 LPS_0075 | MIC ug_mL cefepime AmpC Enterobacter cloacae BAA 1143 LPS_0017 | MIC ug_mL cefepime AmpC Enterobacter cloacae P99 | MIC ug_mL ceftazidime CMY-2 Escherichia coli K12 deltalacU169 pCMY2 LPS_0031 | MIC ug_mL ceftazidime CMY-2 Escherichia coli K12 deltalacU169 pCMY2 | MIC ug_mL cefepime CMY-2 Escherichia coli K12 deltalacU169 tolC Tn10 mdfA Kan pCMY2 | MIC ug_mL ceftazidime CMY-2 Escherichia coli K12 deltalacU169 tolC Tn10 mdfA Kan pCMY2 | MIC ug_mL ceftazidime FOX-5 Escherichia coli LPS_0057 | MIC ug_mL ceftazidime FOX-5 Escherichia coli LPS_0056 | MIC ug_mL cefepime AmpC Pseudomonas aeruginosa SYN 228 | MIC ug_mL ceftazidime AmpC Pseudomonas aeruginosa SYN 228 | MIC ug_mL cefepime CMY-2 CTX-M 14 Klebsiella pneumoniae CUMCK2 |
|---|---|---|---|---|---|---|---|---|---|---|---|---|---|---|---|---|---|---|
| G49 | 16 | | 64 | 16 | | 2 | | | | | | | | 8 | | | | 4 |
| G50 | 128 | | >128 | 16 | | 2 | | | | | | | | 8 | | | | 0.5 |
| G51 | 64 | | >128 | 32 | | 4 | | | | | | | | 32 | | | | 0.25 |
| G52 | 32 | | >128 | 16 | | 2 | | | | | | | | 8 | | | | 4 |
| G53 | 32 | | 64 | 8 | | 1 | | | | | | | | 16 | | | | 1 |
| G54 | 32 | | >128 | 16 | | 1 | | | | | | | | 8 | | | | 1 |
| G55 | 64 | | >128 | 16 | | 1 | | | | | | | | 8 | | | | 1 |
| G56 | 45.3 | | >128 | 32 | | 2 | | | | | | | | 8 | | | | 5.66 |
| G57 | 32 | | >128 | 16 | | 5.66 | | | | | | | | 8 | | | | 1 |
| G58 | 32 | | >128 | 16 | | 4 | | | | | | | | 8 | | | | 4 |
| G59 | 32 | | >128 | 16 | | 4 | | | | | | | | 8 | | | | 4 |
| G60 | 32 | | 128 | 16 | | 1 | | | | | | | | 8 | | | | 4 |
| G61 | 32 | | 90.5 | 32 | | 2 | | | | | | | | 5.66 | | | | 8 |
| G62 | 16 | | 16 | 11.3 | | 2.83 | | | | | | | | 8 | | | | 2.83 |
| G63 | 32 | | >90.5 | 8 | | 4 | | | | | | | | 2.83 | | | | 8 |
| G64 | 16 | | 32 | 32 | | 0.354 | | | | | | | | 4 | | | | 0.707 |
| G65 | 32 | | >128 | 32 | | 2 | | | | | | | | 16 | | | | <=0.06 |
| G66 | | | >128 | | 32; 64 | 4 | | | 2 | 0.06 | 2; 4 | 0.03 | 4; 4 | 8 | 32 | 8; 16 | | 16 |
| G67 | >128 | >128; >128 | | 16 | | 4 | | 128; 128 | 1 | 0.06 | | 0.25 | 16 | 8 | | 16 | 8; 16 | 4 |
| G68 | >32 | >128 | | 16 | | 4 | | >128 | 2 | 0.03 | | 0.5 | | 8 | | | 16 | |
| G69 | >1 | | | | | 0.5; 1 | | | | | | | | | | | | 1 |
| G70 | >128; 128 | | >128; >12 | 16 | | 1; 2 | | | | | | | | 4; 8 | | | | 1 |
| G71 | 64; >128 | | >128; >12 | 16 | | | | | | | | | | 4; 8 | | | | 2 |

Figure 1R

| Compound ID | MIC ug_mL cefepime SHV-5 OXA-1 Escherichia coli | MIC ug_mL cefepime SHV-5 OXA-1 Escherichia coli | MIC ug_mL cefepime TEM-1 OXA-2 Escherichia coli | MIC ug_mL cefepime CTX-M 15 OXA-30 Klebsiella pneumoniae HUH44 | MIC ug_mL cefepime AmpC Enterobacter aerogenes ATCC 27751 | MIC ug_mL cefepime AmpC Enterobacter cloacae BAA_1143 LPS_0037 | MIC ug_mL cefepime AmpC Enterobacter cloacae BAA_1143 LPS_0075 | MIC ug_mL cefepime AmpC Enterobacter cloacae BAA_1143 LPS_0017 | MIC ug_mL cefepime AmpC Enterobacter cloacae P99 | MIC ug_mL cefepime CMY-2 Escherichia coli K12 deltalacU169 pCMY2 LPS_0031 | MIC ug_mL cefepime CMY-2 Escherichia coli K12 deltalacU169 pCMY2 | MIC ug_mL cefepime CMY-2 Escherichia coli K12 deltalacU169 tolC Tn10 mdfA Kan pCMY2 | MIC ug_mL cefepime CMY-2 Escherichia coli K12 deltalacU169 tolC Tn10 mdfA Kan pCMY2 | MIC ug_mL cefepime FOX-5 Escherichia coli LPS_0057 | MIC ug_mL cefepime FOX-5 Escherichia coli LPS_0056 | MIC ug_mL cefepime AmpC Pseudomonas aeruginosa SYN 228 | MIC ug_mL ceftazidime AmpC Pseudomonas aeruginosa SYN 228 | MIC ug_mL cefepime CMY-2 CTX-M 14 Klebsiella pneumoniae CUMCK2 |
|---|---|---|---|---|---|---|---|---|---|---|---|---|---|---|---|---|---|---|
| G72 | >128 | | | 128 | 16 | 8 | | | | | | | | | | | | 4 |
| G73 | 16 | | 1 | 8 | | 2; 4 | 8 | | 1 | | | | | 4 | | | | 4 |
| G74 | 32 | | | >128 | 16 | | 2 | | | | | | | 8 | | | | 2 |
| G75 | >64 | | | >128 | 16 | 2 | | | | | | | | 8 | | | | 2.83 |
| G76 | 64 | | | >128 | 32 | 2.83 | | | | | | | | 11.3 | | | | 1 |
| G77 | 64 | >128 | | 16 | 16 | 5.66 | | | | | | | | | | 8; 16 | 8 | 0.25 |
| G78 | 8; 16; 16 | | | | | 16; 0.25; 1; 2 | | 64 | 1 | 0.5; 0.03; 0.06 | 2 | 0.03; 0.06 | 1 | 8; 32 | | | | |
| | 8; 8; 8; 8; 8; 16; 16; 16; 16; 16 | | 2; 4; 4; 4; 4; 4; 4; 8; 8; 8; 16 | 8; 8; 8; 8; 8; 16; 16; 16; 32 | | 0.25; 0.25; 0.25; 0.25; 0.5; 0.5; 0.5; 0.5; 0.5; 0.5; 0.5; 1; 1; 1; 1; 1; 2; 2; 2 | | | 0.25; 0.25 | 0.03; 0.03 | | 0.015; 0.03 | | 4; 4; 4; 4; 8; 8; 8; 8; 8; 8; 16 | | | | <=0.06; <=0.06; 0.125; 0.125; 0.25; 0.5; 0.5; 0.5; 0.5; 0.5; 0.5; 0.5; 0.5; 1; 1; 1 |
| G81 | >32 | | | 16; 32 | | | | | | 0.5 | | 0.06 | | 8 | | 16 | 16 | |
| G82 | | | | | | | | | | | | | | | | | | |

Figure 1S

| Compound ID | MIC µg/mL cefepime SHV-5 OXA-1 Escherichia coli | MIC µg/mL cefepime SHV-5 OXA-1 Escherichia coli | MIC µg/mL cefepime TEM-1 OXA-2 Escherichia coli | MIC µg/mL cefepime CTX-M 15 OXA-30 Klebsiella pneumoniae HUH44 | MIC µg/mL cefepime AmpC Enterobacter aerogenes ATCC 29751 | MIC µg/mL cefepime AmpC Enterobacter cloacae BAA_1143 LPS_0037 | MIC µg/mL cefepime AmpC Enterobacter cloacae BAA_1143 LPS_0075 | MIC µg/mL cefepime AmpC Enterobacter cloacae BAA_1143 LPS_0017 | MIC µg/mL cefepime AmpC Enterobacter cloacae P99 | MIC µg/mL cefepime CMY-2 Escherichia coli K12 deltacU169 pCMY2 LPS_0031 | MIC µg/mL cefepime CMY-2 Escherichia coli K12 deltacU169 pCMY2 | MIC µg/mL cefepime CMY-2 Escherichia coli K12 deltacU169 tolC Tn10 mdfA Kan pCMY2 | MIC µg/mL cefepime CMY-2 Escherichia coli K12 deltacU169 tolC Tn10 mdfA Kan pCMY2 | MIC µg/mL cefepime FOX-5 Escherichia coli LPS_0057 | MIC µg/mL cefepime FOX-5 Escherichia coli LPS_0056 | MIC µg/mL cefepime AmpC Pseudomonas aeruginosa SYN 228 | MIC µg/mL cefepime AmpC Pseudomonas aeruginosa SYN 228 | MIC µg/mL cefepime CMY-2 CTX-M 14 Klebsiella pneumoniae CUMCK2 |
|---|---|---|---|---|---|---|---|---|---|---|---|---|---|---|---|---|---|---|
| G83 | 32 | | | | | 2 | | | | | | | | 8 | | 16 | | 4 |
| G84 | 32 | | 128 | 16 | | 1 | | | 1 | 0.25 | 0.03 | | | 8 | | | | |
| G85 | 16 | 2 | >12 | | | | | | 0.5 | | | | | | | | | 0.25 |
| G86 | 16; 32 | | >128 | 11.3 | | 2 | | | 1 | 0.125 | 0.03 | | | 8; 8 | | 16 | | <0.122 |
| G87 | 32 | | >128 | 32 | | 4; 4 | 8 | | | | | | | 4 | | | | 2 |
| G88 | 45.3 | | >128 | 16 | | 1.41 | | | | | | | | 22.6 | | | | 8 |
| G89 | 32 | | >128 | 32 | | 4 | | | | | | | | 32 | | | | 4 |
| G90 | >128 | | >128 | 32 | >128 | 4 | | | | | | | | 32 | | | | 2 |
| G91 | 64 | | >128 | 32 | | 4 | | | | | | | | 8 | | | | 4 |
| G92 | 32 | | >128 | 128 | | 2 | | | | | | | | 8 | | | | 4 |
| G93 | 32 | | >128 | 4 | | 4 | | | | | | | | 128 | | | | 2 |
| G94 | 16 | | 128 | 16 | | 2 | | | | | | | | 4 | | | | 4 |
| G95 | 8 | | 128 | 1 | | 4 | | | | | | | | 16 | | | | 0.125 |
| G96 | 16 | | >128 | 4 | | 2 | | | | | | | | 4 | | | | 16 |
| G97 | 64 | | 128 | 8 | | 2 | | | | | | | | 8 | | | | 0.5 |
| G98 | 64 | | 128 | 64 | | 4 | | | | | | | | 32 | | | | 32 |
| G99 | >128 | | 64 | 64 | | 2 | | | | | | | | 16 | | 16 | | 4 |
| G100 | 16; 32 | | 64 | 16 | | 2; 4; 4 | 4 | | 1 | 0.5 | 0.25 | | | 64 | | | | >128 |
| G101 | | | | | | | | | | | | | | | | | | 4 |
| G102 | 16 | | >128 | 16 | | 2 | | | | | | | | 8; 16 | | | | 1 |
| G103 | 16 | | | 32 | | 2 | | | | | | | | 8 | | | | 4 |
| G104 | 16 | | 128 | 32 | | 4 | | | | | | | | 8 | | | | 4 |
| G105 | | | | | | | | | | | | | | 8 | | | | |
| G106 | | | | | | | | | | | | | | 8 | | | | |

Figure 1T

| Compound ID | MIC ug/mL cefepime SHV-5 OXA-1 Escherichia coli | MIC ug/mL ceftazidime SHV-5 OXA-1 Escherichia coli | MIC ug/mL cefepime TEM-1 OXA-2 Escherichia coli | MIC ug/mL cefepime CTX-M 15 OXA-30 Klebsiella pneumoniae HUH44 | MIC ug/mL ceftazidime AmpC Enterobacter aerogenes ATCC 29751 | MIC ug/mL cefepime AmpC Enterobacter cloacae BAA_1143 LPS_0037 | MIC ug/mL cefepime AmpC Enterobacter cloacae BAA_1143 LPS_0075 | MIC ug/mL ceftazidime AmpC Enterobacter cloacae BAA_1143 LPS_0017 | MIC ug/mL cefepime AmpC Enterobacter cloacae P99 | MIC ug/mL cefepime CMY-2 Escherichia coli K12 deltalacU169 pCMY2 LPS_0031 | MIC ug/mL cefepime CMY-2 Escherichia coli K12 deltalacU169 pCMY2 | MIC ug/mL cefepime CMY-2 Escherichia coli K12 deltalacU169 tolC Tn10 mdfA Kan pCMY2 | MIC ug/mL ceftazidime CMY-2 Escherichia coli K12 deltalacU169 tolC Tn10 mdfA Kan pCMY2 | MIC ug/mL cefepime FOX-5 Escherichia coli LPS_0057 | MIC ug/mL ceftazidime FOX-5 Escherichia coli LPS_0056 | MIC ug/mL cefepime AmpC Pseudomonas aeruginosa SYN 228 | MIC ug/mL ceftazidime AmpC Pseudomonas aeruginosa SYN 228 | MIC ug/mL cefepime CMY-2 CTX-M 14 Klebsiella pneumoniae CUMCK2 |
|---|---|---|---|---|---|---|---|---|---|---|---|---|---|---|---|---|---|---|
| G107 | 32 | | >128 | 128 | | 2 | | | | | | | | 16 | | | | 0.25 |
| G108 | 16 | | 64 | 32 | | 4 | | | | | | | | 4 | | | | 2 |
| G109 | 16 | | | 8 | | 4 | | | | | | | | 64 | | | | 0.5 |
| G110 | 16 | | >128 | 4 | | 2 | | | | | | | | 32 | | | | 0.25 |
| G111 | 32 | | >128 | 32 | | 4 | | | | | | | | 4 | | | | 4 |
| G112 | 64 | | >128 | 32 | | 8 | | | | | | | | 8 | | | | 4 |
| G113 | 32 | | >128 | 16 | | 2 | | | | | | | | 8 | | | | 4 |
| G114 | 16; 32 | 1.41 | 32; 64 | 16; 32 | | 1; 2 | | | <=0.06 | | | | | 4; 8 | | | | 2 |
| G115 | 32 | | 128 | | | 1 | | | 16 | | | | | 8 | | | | 0.5 |
| G116 | 2.83 | 4 | | | | | | | 4 | | | | | | | | | |
| G117 | 8 | 4 | | 16 | | | 8 | | | | | | | 4; 8 | | | | |
| G118 | 32 | | | | | | 8 | | | | | | | 4 | | | | 4 |
| G119 | 16 | | >128 | 2 | | 2 | 16 | | | | | | | 8 | | | | 2 |
| G120 | 8 | | >128 | 8 | | 2 | | | | | | | | 8 | | | | 4 |
| G121 | 16 | | | | | 4 | | | | | | | | 4 | | | | 1.41 |
| G122 | 32 | | >128 | 4 | | 4 | | | | | | | | 8 | | | | |
| G123 | 8 | | >128 | 32 | | 2 | | | | | | | | 8 | | | | |
| G124 | | | >128 | 11.3 | | | | | | | | | | 2 | | | | |
| G125 | | | | | | | | | | | | | | | | | | |
| G126 | | | | | | | | | | | | | | | | | | |
| G127 | 16 | | | 16 | | | | | | | | | | | | | | 4 |
| G128 | 16; 16; 32 | >128 | 8; 16; 32 | 4; 16 | | 0.5; 1; 1 | 4 | | | | | | | 4; 8; 8 | | | | 0.5; 0.5 |
| G129 | >128 | | 128 | 64 | | | | | | | | | | 8 | | | | 32 |
| G130 | 8; 8 | | 32 | 2 | | 1; 2 | | | 1 | 0.03 | 16 | 0.03 | 4; >32 | >32 | 32 | 16 | 16 | 1 |
| G131 | | | | | | | | 128 | | | | | | | | | | |

Figure 1U

| Compound ID | G132 | G133 | G134 | G135 | G136 | G145 | G146 | G147 | G148 | G149 | G151 |
|---|---|---|---|---|---|---|---|---|---|---|---|
| MIC ug_mL cefepime SHV-5 OXA-1 Escherichia coli | 2 | 16 | 32 | >64 | 16 | 16 | 16 | 8 | 32 | 22.6 | 16 |
| MIC ug_mL ceftazidime SHV-5 OXA-1 Escherichia coli |  |  |  |  |  |  |  | 4 | 4 | 2 |  |
| MIC ug_mL cefepime TEM-1 OXA-2 Escherichia coli | 4 | >128 | 128 | >128 | 64 | 128 | 128 | 64 |  |  |  |
| MIC ug_mL cefepime CTX-M 15 OXA-30 Klebsiella pneumoniae HUH44 | 0.5 | 5.66 | 11.3 | 11.3 | 8 | 16 | 16 | 4 |  |  |  |
| MIC ug_mL ceftazidime AmpC Enterobacter aerogenes ATCC 29751 |  |  |  |  |  |  |  |  |  |  |  |
| MIC ug_mL cefepime AmpC Enterobacter cloacae BAA_1143 LPS_0037 | 0.5 | 8 | 2.83 | 5.66 | 4 | 2 | 2 | 0.5 |  |  |  |
| MIC ug_mL cefepime AmpC Enterobacter cloacae BAA_1143 LPS_0075 |  |  |  |  |  |  |  |  | 8 | 11.3 | 8 |
| MIC ug_mL ceftazidime AmpC Enterobacter cloacae BAA_1143 LPS_0017 |  |  |  |  |  |  |  |  |  |  |  |
| MIC ug_mL cefepime AmpC Enterobacter cloacae P99 |  |  |  |  |  |  |  | >128 |  | 4 | 16 |
| MIC ug_mL cefepime CMY-2 Escherichia coli K12 deltalacU169 pCMY2 LPS_0031 |  |  |  |  |  |  |  |  |  |  |  |
| MIC ug_mL ceftazidime CMY-2 Escherichia coli K12 deltalacU169 pCMY2 |  |  |  |  |  |  |  |  |  |  |  |
| MIC ug_mL cefepime CMY-2 Escherichia coli K12 deltalacU169 tolC Tn10 mdfA Kan pCMY2 |  |  |  |  |  |  |  |  |  |  |  |
| MIC ug_mL ceftazidime CMY-2 Escherichia coli K12 deltalacU169 tolC Tn10 mdfA Kan pCMY2 |  |  |  |  |  |  |  |  |  |  |  |
| MIC ug_mL cefepime FOX-5 Escherichia coli LPS_0057 | 4 | 22.6 | 5.66 | 5.66 | 8 | 8 | 8 | 16 |  |  |  |
| MIC ug_mL ceftazidime FOX-5 Escherichia coli LPS_0056 |  |  |  |  |  |  |  |  |  |  |  |
| MIC ug_mL cefepime AmpC Pseudomonas aeruginosa SYN 228 |  |  |  |  |  |  |  |  |  |  |  |
| MIC ug_mL ceftazidime AmpC Pseudomonas aeruginosa SYN 228 |  |  |  |  |  |  |  |  |  |  |  |
| MIC ug_mL cefepime CMY-2 CTX-M 14 Klebsiella pneumoniae CUMCK2 | <=0.06 | 2 | 1 |  | 5.66 | 0.5 | 1 | 0.25 | 2 |  |  |

TRISUBSTITUTED BORON-CONTAINING MOLECULES

CROSS-REFERENCE TO RELATED APPLICATIONS

This application claims the benefit of U.S. Provisional Pat. App. No. 61/229,230, filed Jul. 28, 2009, and U.S. Provisional Pat. App. No. 61/260,360, filed Nov. 11, 2009, each of which is incorporated by reference in its entirety for all purposes.

REFERENCE TO SEQUENCE LISTING SUBMITTED ELECTRONICALLY

The sequence listing contained in the file named "0645075052USST25.txt", created on Feb. 14, 2011 and having a size of 6 kilobytes, has been submitted electronically herewith via EFS-Web, and the contents of the txt file are hereby incorporated by reference in their entirety.

BACKGROUND OF THE INVENTION

The global rise of bacteria and other microorganisms resistant to antibiotics and antimicrobials in general, poses a major threat. Deployment of massive quantities of antimicrobial agents into the ecosphere during the past 60 years has introduced a powerful selective pressure for the emergence and spread of antimicrobial-resistant pathogens. Thus, there is a need to discover new broad spectrum antimicrobials, such as antibiotics, useful in combating microorganisms, especially those with multidrug-resistance. There is also a need to discover compounds which are useful in inhibiting or deactivating the resistance mechanisms of microorganisms, such as beta-lactamase enzymes.

Boron-containing molecules, such as 1-hydroxy-1,3-dihydro-benzo[c][1,2]oxaborole (also sometimes known as 1-hydroxy-benzo[c][1,2]oxaborole or oxaboroles or cyclic boronic esters), useful as antimicrobials have been described previously, such as in U.S. patent application Ser. Nos. 12/142,692; 11/505,591 and 11/357,687. Generally speaking, a 1-hydroxy-1,3-dihydro-benzo[c][1,2]oxaborole has the following structure and substituent numbering system:

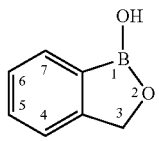

It has been discovered that certain classes of 1-hydroxy-1,3-dihydro-benzo[c][1,2]oxaboroles which are substituted at the 6-position, and are also substituted at the 3-position, and are also substituted at the 4-position, are surprisingly effective beta-lactamase inhibitors. This, and other uses of these 1-hydroxy-1,3-dihydro-benzo[c][1,2]oxaboroles are described herein.

SUMMARY OF THE INVENTION

In a first aspect, the invention provides a compound having a structure according to the formula:

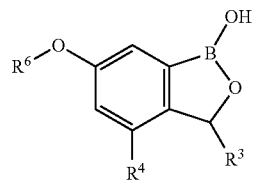

wherein $R^3$ is $-(CH_2)_m C(O)OR^{3a}$ wherein m is an integer selected from 1, 2, 3, 4, 5, or 6. $R^{3a}$ is selected from the group consisting of H, unsubstituted alkyl, and phenyl substituted alkyl. $R^4$ is selected from the group consisting of unsubstituted alkyl, $-OR^{4b}$, $-(CH_2)_n-O-(CH_2)_p CH_3$ and halogen. n is an integer selected from 1, 2, 3, 4, 5, or 6. p is an integer selected from 0, 1, 2, 3, 4, 5, or 6. $R^{4b}$ is H or substituted or unsubstituted alkyl. $R^6$ is selected from the group consisting of H, substituted or unsubstituted alkyl, $-C(O)OR^{6a}$, $-C(O)NR^{6a}R^{6b}$, $-S(O_2)R^{6c}$, and A. $R^{6a}$ is H or unsubstituted alkyl. $R^{6b}$ is unsubstituted alkyl. $R^{6c}$ is selected from the group consisting of unsubstituted alkyl, $NH_2$ and heteroaryl, optionally substituted with unsubstituted alkyl. A is selected from the group consisting of substituted or unsubstituted cycloalkyl, substituted or unsubstituted heterocycloalkyl, substituted or unsubstituted aryl and substituted or unsubstituted heteroaryl, or a salt thereof.

In a second aspect, the invention provides a combination comprising: a) a compound described herein, or a pharmaceutically acceptable salt thereof; and b) at least one therapeutic agent.

In a third aspect, the invention provides a pharmaceutical formulation comprising: a) a compound described herein or a combination described herein, or a pharmaceutically acceptable salt thereof and b) a pharmaceutically acceptable excipient.

In a fourth aspect, the invention provides a method of treating a bacterial infection comprising: administering to an animal suffering from said infection an effective amount of a compound described herein, or a pharmaceutically-acceptable salt thereof, and an effective amount of an antibiotic, or a pharmaceutically acceptable salt thereof, wherein said antibiotic comprises a β-lactam moiety, thereby treating the bacterial infection.

In a fifth aspect, the invention provides a method of killing or inhibiting the growth of a bacteria, said method comprising: contacting the bacteria with an effective amount of a compound described herein or a combination described herein, or a pharmaceutically acceptable salt thereof, thereby killing or inhibiting the growth of the bacteria.

In a sixth aspect, the invention provides a method of inhibiting a β-lactamase, comprising contacting the β-lactamase with an effective amount of the compound described herein, or a pharmaceutically acceptable salt thereof, thereby inhibiting the β-lactamase.

BRIEF DESCRIPTION OF THE DRAWINGS

FIG. 1 displays biological data for exemplary compounds of the invention.

DETAILED DESCRIPTION OF THE INVENTION

I. Definitions and Abbreviations

As used herein, the singular forms "a," "an", and "the" include plural references unless the context clearly dictates otherwise. For example, reference to "an active agent" includes a single active agent as well as two or more different active agents in combination. It is to be understood that present teaching is not limited to the specific dosage forms, carriers, or the like, disclosed herein and as such may vary.

The abbreviations used herein generally have their conventional meaning within the chemical and biological arts.

The following abbreviations have been used: Ac is acetyl; AcOH is acetic acid; ACTBr is cetyltrimethylammonium bromide; AIBN is azobisisobutyronitrile or 2,2 azobisisobutyronitrile; aq. is aqueous; Ar is aryl; $B_2pin_2$ is bis(pinacolato) diboron; Bn is, in general, benzyl [see Cbz for one example of an exception]; $(BnS)_2$ is benzyl disulfide; BnSH is benzyl thiol or benzyl mercaptan; BnBr is benzyl bromide; Boc is tert-butoxy carbonyl; $Boc_2O$ is di-tert-butyl dicarbonate; Bz is, is general, benzoyl; BzOOH is benzoyl peroxide; Cbz or Z is benzyloxycarbonyl or carboxybenzyl; $Cs_2CO_3$ is cesium carbonate; CSA is camphor sulfonic acid; CTAB is cetyltrimethylammonium bromide; Cy is cyclohexyl; DABCO is 1,4-diazabicyclo[2.2.2]octane; DCM is dichloromethane or methylene chloride; DHP is dihydropyran; DIAD is diisopropyl azodicarboxylate; DIEA or DIPEA is N,N-diisopropylethylamine; DMAP is 4-(dimethylamino)pyridine; DME is 1,2-dimethoxyethane; DMF is N,N-dimethylformamide; DMSO is dimethylsulfoxide; equiv or eq. is equivalent; EtOAc is ethyl acetate; EtOH is ethanol; $Et_2O$ is diethyl ether; EDCI is N-(3-dimethylaminopropyl)-N'-ethylcarbodiimide hydrochloride; m-CPBA is 3-chloroperoxybenzoic acid; equiv is equivalent; h is hours; HATU is O-(7-azabenzotriazol-1-yl)-N,N,N',N'-tetramethyluronium hexafluorophosphate; HCl is hydrochloric acid; HPLC is high pressure liquid chromatography; ISCO Companion is automated flash chromatography equipment with fraction analysis by UV absorption available from Presearch; KOAc or AcOK is potassium acetate; $K_2CO_3$ is potassium carbonate; $LiAlH_4$ or LAH is lithium aluminum hydride; LDA is lithium diisopropylamide; LHMDS is lithium bis(trimethylsilyl) amide; KHMDS is potassium bis(trimethylsilyl) amide; LiOH is lithium hydroxide; m-CPBA is 3-chloroperoxybenzoic acid; MeCN or ACN is methyl cyanide or cyanomethane or ethanenitrile or acetonitrile which are all names for the same compound; MeOH is methanol; $MgSO_4$ is magnesium sulfate; mins or min is minutes; Mp or MP is melting point; $NaCNBH_3$ is sodium cyanoborohydride; NaOH is sodium hydroxide; $Na_2SO_4$ is sodium sulfate; NBS is N-bromosuccinimide; $NH_4Cl$ is ammonium chloride; NIS is N-iodosuccinimide; $N_2$ is nitrogen; NMM is N-methylmorpholine; n-BuLi is n-butyllithium; overnight is O/N; $PdCl_2(pddf)$ is 1,1'-Bis(diphenylphosphino) ferrocene]dichloropalladium(II); Pd/C is the catalyst known as palladium on carbon; $Pd_2(dba)_3$ is an organometallic catalyst known as tris(dibenzylideneacetone) dipalladium(0); Ra Ni or Raney Ni is Raney nickel; Ph is phenyl; PMB is p-methoxybenzyl; PrOH is 1-propanol; iPrOH is 2-propanol; $POCl_3$ is phosphorus chloride oxide; PTSA is para-toluene sulfonic acid; Pyr. or Pyr or Py as used herein means Pyridine; RT or rt or r.t. is room temperature; sat. is saturated; Si-amine or Si—$NH_2$ is amino-functionalized silica, available from SiliCycle; Si-pyr is pyridyl-functionalized silica, available from SiliCycle; TEA or $Et_3N$ is triethylamine; TFA is trifluoroacetic acid; $Tf_2O$ is trifluoromethanesulfonic anhydride; THF is tetrahydrofuran; TFAA is trifluoroacetic anhydride; THP is tetrahydropyranyl; TMSI is trimethylsilyl iodide; $H_2O$ is water; $diNO_2PhSO_2Cl$ is dinitrophenyl sulfonyl chloride; 3-F-4-$NO_2$—$PhSO_2Cl$ is 3-fluoro-4-nitrophenylsulfonyl chloride; 2-MeO-4-$NO_2$—$PhSO_2Cl$ is 2-methoxy-4-nitrophenylsulfonyl chloride; and $(EtO)_2POCH_2COOEt$ is a triethylester of phosphonoacetic acid known as triethyl phosphonoacetate.

"Compound of the invention," as used herein refers to the compounds discussed herein, salts (e.g. pharmaceutically acceptable salts), prodrugs, solvates and hydrates of these compounds.

"Combination of the invention," as used herein refers to the compounds and antibiotics discussed herein as well as acids, bases, salt forms (such as pharmaceutically acceptable salts), prodrugs, solvates and hydrates of these compounds and antibiotics.

"Boron containing compounds", as used herein, refers to the compounds of the invention that contain boron as part of their chemical formula.

Where substituent groups are specified by their conventional chemical formulae, written from left to right, they equally encompass the chemically identical substituents, which would result from writing the structure from right to left, e.g., —$CH_2O$— is intended to also recite —$OCH_2$—.

The term "poly" as used herein means at least 2. For example, a polyvalent metal ion is a metal ion having a valency of at least 2.

"Moiety" refers to a radical of a molecule that is attached to the remainder of the molecule.

The symbol ∿, whether utilized as a bond or displayed perpendicular to a bond, indicates the point at which the displayed moiety is attached to the remainder of the molecule.

The term "alkyl," by itself or as part of another substituent, means, unless otherwise stated, a straight or branched chain, or cyclic hydrocarbon radical, or combination thereof, which may be fully saturated, mono-or polyunsaturated and can include di-and multivalent radicals, having the number of carbon atoms designated (i.e. $C_1$-$C_{10}$ means one to ten carbons). In some embodiments, the term "alkyl" means a straight or branched chain, or combinations thereof, which may be fully saturated, mono-or polyunsaturated and can include di-and multivalent radicals. Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1-and 3-propynyl, 3-butynyl, and the higher homologs and isomers.

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the invention. A "lower alkyl" or "lower alkylene" is a shorter chain alkyl or alkylene group, generally having eight or fewer carbon atoms.

The term "alkenylene" by itself or as part of another substituent means a divalent radical derived from an alkene.

The term "cycloalkylene" by itself or as part of another substituent means a divalent radical derived from a cycloalkyl.

The term "heteroalkylene" by itself or as part of another substituent means a divalent radical derived from an heteroalkane.

The term "heterocycloalkylene" by itself or as part of another substituent means a divalent radical derived from an heterocycloalkane.

The term "arylene" by itself or as part of another substituent means a divalent radical derived from an aryl.

The term "heteroarylene" by itself or as part of another substituent means a divalent radical derived from heteroaryl.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom. In some embodiments, the term "heteroalkyl," by itself or in combination with another term, means a stable straight or branched chain, or combinations thereof, consisting of the stated number of carbon atoms and at least one heteroatom. In an exemplary embodiment, the heteroatoms can be selected from the group consisting of B, O, N and S, and wherein the nitrogen and sulfur atoms may optionally be oxidized and the nitrogen heteroatom may optionally be quaternized. The heteroatom(s) B, O, N and S may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl," by themselves or in combination with other terms, represent, unless otherwise stated, cyclic versions of "alkyl" and "heteroalkyl," respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms. In an exemplary embodiment, the heteroatom is selected from B, N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —R', —OR', =O, =NR', =N—OR', —NR'R", —SR', -halogen, —SiR'R"R''', —OC(O)R', —C(O)R', —$CO_2$R', —CONR'R", —OC(O)NR'R", —NR"C(O)R', —NR'—C(O)NR"R''', —NR"C(O)$_2$R', —NR''''—C(NR'R"R''')=NR'''', —NR''''—C(NR'R")=NR''', —S(O)R', —S(O)$_2$R', —S(O)$_2$NR'R", —NR"$SO_2$R', —CN, —$NO_2$, —$N_3$, —CH(Ph)$_2$, fluoro($C_1$-$C_4$)alkoxy, and fluoro($C_1$-$C_4$)alkyl, in a number ranging from zero to (2 m'+1), where m' is the total number of carbon atoms in such radical. R', R", R''', R'''' and R'''' each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R''', R'''' and R'''' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are generically referred to as "aryl group substituents." The substituents are selected from, for example: —R', —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR''''—C(NR'R"R''')=NR'''', —NR''''—C(NR'R")=NR''', —S(O)R', —S(O)$_2$R', —S(O)$_2$NR'R", —NR"SO$_2$R', —CN, —NO$_2$, —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'", R'''' and R''''' are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'", R'''' and R''''' groups when more than one of these groups is present.

Two of the substituents on adjacent atoms of the aryl or heteroaryl ring may optionally be replaced with a substituent of the formula —T—C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula —A—(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted (C$_1$-C$_6$)alkyl.

"Ring" as used herein, means a substituted or unsubstituted cycloalkyl, substituted or unsubstituted heterocycloalkyl, substituted or unsubstituted aryl, or substituted or unsubstituted heteroaryl. A ring includes fused ring moieties. The number of atoms in a ring is typically defined by the number of members in the ring. For example, a "5-to 7-membered ring" means there are 5 to 7 atoms in the encircling arrangement. Unless otherwise specified, the ring optionally includes a heteroatom. Thus, the term "5-to 7-membered ring" includes, for example phenyl, pyridinyl and piperidinyl. The term "5-to 7-membered heterocycloalkyl ring", on the other hand, would include pyridinyl and piperidinyl, but not phenyl. The term "ring" further includes a ring system comprising more than one "ring", wherein each "ring" is independently defined as above.

As used herein, the term "heteroatom" includes atoms other than carbon (C) and hydrogen (H). Examples include oxygen (O), nitrogen (N) sulfur (S), silicon (Si), germanium (Ge), aluminum (Al) and boron (B).

The term "leaving group" means a functional group or atom which can be displaced by another functional group or atom in a substitution reaction, such as a nucleophilic substitution reaction. By way of example, representative leaving groups include triflate, chloro, bromo and iodo groups; sulfonic ester groups, such as mesylate, tosylate, brosylate, nosylate and the like; and acyloxy groups, such as acetoxy, trifluoroacetoxy and the like.

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, substituted or unsubstituted cycloalkyl and substituted or unsubstituted heterocycloalkyl groups.

By "effective" amount of a drug, formulation, or permeant is meant a sufficient amount of an active agent to provide the desired local or systemic effect. A "Topically effective," "pharmaceutically effective," or "therapeutically effective" amount refers to the amount of drug needed to effect the desired therapeutic result.

The term "pharmaceutically acceptable salt" is meant to include a salt of a compound of the invention which is prepared with relatively nontoxic acids or bases, depending on the particular substituents found on the compounds described herein. When compounds of the invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science 66: 1-19 (1977)). Certain specific compounds of the invention contain both basic and acidic functionalities that allow the compounds to be converted into either base or acid addition salts.

The neutral forms of the compounds are preferably regenerated by contacting the salt with a base or acid and isolating the parent compounds in the conventional manner. The parent form of the compound differs from the various salt forms in certain physical properties, such as solubility in polar solvents.

In addition to salt forms, the invention provides compounds which are in a prodrug form. Prodrugs of the compounds described herein readily undergo chemical changes under physiological conditions to provide the compounds of the invention. Additionally, prodrugs can be converted to the compounds of the invention by chemical or biochemical methods in an ex vivo environment.

Certain compounds of the invention can exist in unsolvated forms as well as solvated forms, including hydrated forms. In general, the solvated forms are equivalent to unsolvated forms and are encompassed within the scope of the invention. Certain compounds of the invention may exist in multiple crystalline or amorphous forms.

Certain compounds of the invention possess asymmetric carbon atoms (optical centers) or double bonds; the racemates, diastereomers, geometric isomers and individual isomers are encompassed within the scope of the invention. The graphic representations of racemic, ambiscalemic and scalemic or enantiomerically pure compounds used herein are taken from Maehr, *J. Chem. Ed.* 1985, 62: 114-120. Solid and broken wedges are used to denote the absolute configuration of a stereocenter unless otherwise noted. When the compounds described herein contain olefinic double bonds or other centers of geometric asymmetry, and unless specified otherwise, it is intended that the compounds include both E and Z geometric isomers. Likewise, all tautomeric forms are included.

Compounds of the invention can exist in particular geometric or stereoisomeric forms. The invention contemplates all such compounds, including cis-and trans-isomers, (−)-and (+)-enantiomers, (R)-and (S)-enantiomers, diastereomers, (D)-isomers, (L)-isomers, the racemic mixtures thereof, and other mixtures thereof, such as enantiomerically or diastereomerically enriched mixtures, as falling within the scope of the invention. Additional asymmetric carbon atoms can be present in a substituent such as an alkyl group. All such isomers, as well as mixtures thereof, are intended to be included in this invention.

Optically active (R)-and (S)-isomers and d and/isomers can be prepared using chiral synthons or chiral reagents, or resolved using conventional techniques. If, for instance, a particular enantiomer of a compound of the invention is desired, it can be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as an amino group, or an acidic functional group, such as a carboxyl group, diastereomeric salts can be formed with an appropriate optically active acid or base, followed by resolution of the diastereomers thus formed by fractional crystallization or chromatographic means known in the art, and subsequent recovery of the pure enantiomers. In addition, separation of enantiomers and diastereomers is frequently accomplished using chromatography employing chiral, stationary phases, optionally in combination with chemical derivatization (e.g., formation of carbamates from amines).

The compounds of the invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). The compounds may also be labeled with stable isotopes such as deuterium. All isotopic variations of the compounds of the invention, whether radioactive or not, are intended to be encompassed within the scope of the invention.

The term "pharmaceutically acceptable carrier" or "pharmaceutically acceptable vehicle" refers to any formulation or carrier medium that provides the appropriate delivery of an effective amount of an active agent as defined herein, does not interfere with the effectiveness of the biological activity of the active agent, and that is sufficiently non-toxic to the host or patient. Representative carriers include water, oils, both vegetable and mineral, cream bases, lotion bases, ointment bases and the like. These bases include suspending agents, thickeners, penetration enhancers, and the like. Their formulation is well known to those in the art of cosmetics and topical pharmaceuticals. Additional information concerning carriers can be found in *Remington: The Science and Practice of Pharmacy*, 21st Ed., Lippincott, Williams & Wilkins (2005) which is incorporated herein by reference.

The term "excipients" is conventionally known to mean carriers, diluents and/or vehicles used in formulating drug compositions effective for the desired use.

The term "topical administration" refers to the application of a pharmaceutical agent to the external surface of the skin, nail, hair, claw or hoof, such that the agent crosses the external surface of the skin, nail, hair, claw or hoof and enters the underlying tissues. Topical administration includes application of the composition to intact skin, nail, hair, claw or hoof, or to a broken, raw or open wound of skin, nail, hair, claw or hoof. Topical administration of a pharmaceutical agent can result in a limited distribution of the agent to the skin and surrounding tissues or, when the agent is removed from the treatment area by the bloodstream, can result in systemic distribution of the agent.

The terms "effective amount" or a "therapeutically effective amount" of a drug or pharmacologically active agent refers to a nontoxic but sufficient amount of the drug or agent to provide the desired effect. In the oral dosage forms of the present disclosure, an "effective amount" of one active of the combination is the amount of that active that is effective to provide the desired effect when used in combination with the other active of the combination. The amount that is "effective" will vary from subject to subject, depending on the age and general condition of the individual, the particular active agent or agents, and the appropriate "effective" amount in any individual case may be determined by one of ordinary skill in the art using routine experimentation.

The phrases "active ingredient", "therapeutic agent", "active", or "active agent" mean a chemical entity which can be effective in treating a targeted disorder, disease or condition.

The phrase "pharmaceutically acceptable" means moieties or compounds that are, within the scope of medical judgment, suitable for use in humans without causing undesirable biological effects such as undue toxicity, irritation, allergic response, and the like, for example.

The phrase "oral dosage form" means any pharmaceutical composition administered to a subject via the oral cavity. Exemplary oral dosage forms include tablets, capsules, films, powders, sachets, granules, solutions, solids, suspensions or as more than one distinct unit (e.g., granules, tablets, and/or capsules containing different actives) packaged together for co-administration, and other formulations known in the art. An oral dosage form can be one, two, three, four, five or six units. When the oral dosage form has multiple units, all of the units are contained within a single package, (e.g. a bottle or other form of packaging such as a blister pack). When the oral dosage form is a single unit, it may or may not be in a single package. In a preferred embodiment, the oral dosage form is one, two or three units. In a particularly preferred embodiment, the oral dosage form is one unit.

The phrase "unit", as used herein, refers to the number of discrete objects to be administered which comprise the dosage form. In some embodiments, the dosage form includes a compound of the invention in one capsule. This is a single unit. In some embodiments, the dosage form includes a compound of the invention as part of a therapeutically effective dosage of a cream or ointment. This is also a single unit. In some embodiments, the dosage form includes a compound of the invention and another active ingredient contained within one capsule, or as part of a therapeutically effective dosage of a cream or ointment. This is a single unit, whether or not the interior of the capsule includes multiple discrete granules of the active ingredient. In some embodiments, the dosage form includes a compound of the invention in one capsule, and the active ingredient in a second capsule. This is a two unit dosage form, such as two capsules or tablets, and so such units are contained in a single package. Thus the term 'unit' refers to the object which is administered to the animal, not to the interior components of the object.

The term, "prodrug", as defined herein, is a derivative of a parent drug molecule that exerts its pharmacological effect only after chemical and/or enzymatic conversion to its active form in vivo. Prodrugs include those designed to circumvent problems associated with delivery of the parent drug. This may be due to poor physicochemical properties, such as poor chemical stability or low aqueous solubility, and may also be due to poor pharmacokinetic properties, such as poor bioavailability or poor half-life. Thus, certain advantages of prodrugs may include improved chemical stability, absorption, and/or PK properties of the parent carboxylic acids. Prodrugs may also be used to make drugs more "patient friendly," by minimizing the frequency (e.g., once daily) or route of dosing (e.g., oral), or to improve the taste or odor if given orally, or to minimize pain if given parenterally.

In some embodiments, the prodrugs are chemically more stable than the active drug, thereby improving formulation and delivery of the parent drug, compared to the drug alone.

Prodrugs for carboxylic acid analogs of the invention may include a variety of esters. In an exemplary embodiment, the pharmaceutical compositions of the invention include a carboxylic acid ester. In an exemplary embodiment, the prodrug is suitable for treatment/prevention of those diseases and conditions that require the drug molecule to cross the blood brain barrier. In an exemplary embodiment, the prodrug enters the brain, where it is converted into the active form of the drug molecule. In one embodiment, a prodrug is used to enable an active drug molecule to reach the inside of the eye after topical application of the prodrug to the eye. Additionally, a prodrug can be converted to its parent compound by chemical or biochemical methods in an ex vivo environment. For example, a prodrug can be slowly converted to its parent compound when placed in a transdermal patch reservoir with a suitable enzyme or chemical reagent.

"Antibiotic", as used herein, is a compound which can kill or inhibit the growth of bacteria. The term antibiotic is broad enough to encompass acids, bases, salt forms (such as pharmaceutically acceptable salts), prodrugs, solvates and hydrates of the antibiotic compound.

The term "microbial infection" or "infection by a microorganism" refers to any infection of a host by an infectious agent including, but not limited to, bacteria (see, e.g., Harrison's Principles of Internal Medicine, pp. 93-98 (Wilson et al., eds., 12th ed. 1991); Williams et al., *J. of Medicinal Chem.* 42:1481-1485 (1999), herein each incorporated by reference in their entirety).

"Biological medium," as used herein refers to both in vitro and in vivo biological milieus. Exemplary in vitro "biological media" include, but are not limited to, cell culture, tissue culture, homogenates, plasma and blood. In vivo applications are generally performed in mammals, preferably humans.

"Inhibiting" and "blocking," are used interchangeably herein to refer to the partial or full blockade of an enzyme, such as a beta-lactamase.

Boron is able to form additional covalent or dative bonds with oxygen, sulfur or nitrogen under some circumstances in this invention.

Embodiments of the invention also encompass compounds that are poly- or multi-valent species, including, for example, species such as dimers, trimers, tetramers and higher homologs of the compounds of use in the invention or reactive analogues thereof.

"Salt counterion", as used herein, refers to positively charged ions that associate with a compound of the invention when the boron is fully negatively or partially negatively charged. Examples of salt counterions include $H^+$, $H_3O^+$, ammonium, potassium, calcium, magnesium and sodium.

The compounds comprising a boron bonded to a carbon and three heteroatoms (such as three oxygens described in this section) can optionally contain a fully negatively charged boron or partially negatively charged boron. Due to the negative charge, a positively charged counterion may associate with this compound, thus forming a salt. Examples of positively charged counterions include $H^+$, $H_3O^+$, calcium, sodium, ammonium and potassium. The salts of these compounds are implicitly contained in descriptions of these compounds.

II. Introduction

The invention provides novel boron compounds and methods for the preparation of these molecules. The invention provides combinations of novel boron compounds and an additional therapeutic agent, such as an antibiotic. The invention further provides methods of treating bacterial infections, killing or inhibiting the growth of bacteria, and/or inhibiting β-lactamase in part or wholly through the use of the compounds described herein. In another aspect, the invention is a pharmaceutical formulation comprising a pharmaceutically acceptable excipient and a compound of the invention.

II. a.) The Compounds

In one aspect the invention provides a compound of the invention. In an exemplary embodiment, the invention provides a compound described herein, or a salt thereof. In an exemplary embodiment, the salt of a compound described herein is a pharmaceutically acceptable salt. In an exemplary embodiment, the invention provides a compound described herein, or a pharmaceutically acceptable salt thereof. In an exemplary embodiment, the invention provides a compound described in a formula provided herein. In an exemplary embodiment, the invention provides a compound described herein.

In an exemplary embodiment, the invention provides a compound having a structure according to the formula:

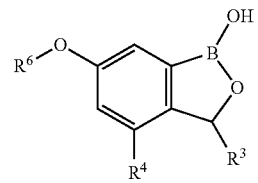

wherein $R^3$ is —$(CHR^{3b})_m C(O)OR^{3a}$ or —$(CHR^{3b})_m S(O)_2 OR^{3a}$, wherein m is an integer selected from 1, 2, 3, 4, 5, or 6; $R^{3a}$ is H or unsubstituted alkyl; $R^{3b}$ is H or $C_1$-$C_3$ unsubstituted alkyl; $R^4$ is selected from the group consisting of unsubstituted alkyl, (substituted or unsubstituted amino)alkylene, azido, —$OR^{4b}$, —$(CH_2)_n$—O—$(CH_2)_p CH_3$ and halogen, wherein n is an integer selected from 1, 2, 3, 4, 5, or 6; and p is an integer selected from 0, 1, 2, 3, 4, 5, or 6. $R^{4b}$ is H or substituted or unsubstituted alkyl or (substituted or unsubstituted amino)alkylene. $R^6$ is selected from the group consisting of H, substituted or unsubstituted alkyl, —$C(O)OR^{6a}$, —$C(O)NR^{6a}R^{6b}$, —$S(O_2)R^{6c}$ and A, wherein $R^{6a}$ is H or unsubstituted alkyl; $R^{6b}$ is H or unsubstituted alkyl; $R^{6c}$ is selected from the group consisting of unsubstituted alkyl, $NH_2$ and heteroaryl, optionally substituted with unsubstituted alkyl; A is selected from the group consisting of substituted or unsubstituted cycloalkyl, substituted or unsubstituted heterocycloalkyl, substituted or unsubstituted aryl and substituted or unsubstituted heteroaryl, and salts thereof. In an exemplary embodiment, $R^3$ is —$(CH_2)_m C(O)OR^{3a}$, wherein m is an integer selected from 1, 2, 3, 4, 5, or 6; wherein $R^4$, $R^6$ and $R^{3a}$ are as described herein. In an exemplary embodiment, $R^3$ is —$(CHR^{3b})_mC(O)OR^{3a}$, wherein m is an integer selected from 1, 2, 3, 4, 5, or 6; $R^{3b}$ is $C_1$ or $C_2$ or $C_3$ unsubstituted alkyl; wherein $R^4$, $R^6$ and $R^{3a}$ are as described herein. In an exemplary embodiment, $R^3$ is —$(CH(CH_3))_mC(O)OR^{3a}$, wherein m is an integer selected from 1, 2, 3, 4, 5, or 6; wherein $R^4$, $R^6$ and $R^{3a}$ are as described herein. In an exemplary embodiment, $R^3$ is —$(CH(CH_3))C(O)OR^{3a}$, wherein $R^4$, $R^6$ and $R^{3a}$ are as described herein. In an exemplary embodiment, $R^3$ is —$(CH(CH_3))C(O)OCH_2CH_3$, wherein $R^4$ and $R^6$ are as described herein. In an exemplary embodiment, $R^4$ and $R^3$ are as described herein, and $R^6$ is —$C(O)OR^{6a}$, wherein $R^{6a}$ is unsubstituted alkyl. In an exemplary embodiment, $R^3$ is —$(CH_2)_mS(O)_2OR^{3a}$, wherein m is an integer selected from 1 or 2 or 3; $R^{3a}$ is $C_1$ or $C_2$ or $C_3$ unsubstituted alkyl; wherein $R^4$, $R^6$ and $R^{3a}$ are as described herein. In an exemplary embodiment, $R^3$ is —$CH_2S(O)_2OR^{3a}$, $R^{3a}$ is $C_1$ or $C_2$ or $C_3$ unsubstituted alkyl; wherein $R^4$ and $R^6$ are as described herein. In an exemplary embodiment, $R^3$ is —$CH_2S(O)_2OH$, wherein $R^4$ and $R^6$ are as described herein. In an exemplary embodiment, $R^3$ is —$CH_2S(O)_2OH$, $R^4$ is unsubstituted alkyl and $R^6$ are as described herein. In an exemplary embodiment, $R^3$ is —$CH_2S(O)_2OH$, $R^4$ is methyl and $R^6$ are as described herein.

In an exemplary embodiment, the compound has a structure according to the formula:

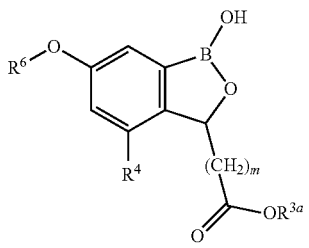

wherein $R^4$ and $R^6$ are as described herein.

In an exemplary embodiment, the compound has a structure according to the formula:

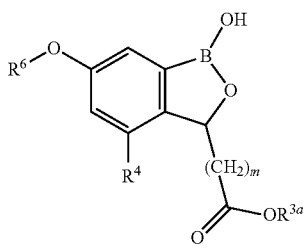

wherein $R^6$ is as described herein, $R^4$ is unsubstituted alkyl, m is an integer selected from 1, 2, 3, 4, 5, or 6; and $R^{3a}$ is H or unsubstituted alkyl. In an exemplary embodiment, m is an integer selected from 1, 2, or 3. In an exemplary embodiment, m is 1 or 2. In an exemplary embodiment, m is 1.

In an exemplary embodiment, the compound has a structure according to the formula:

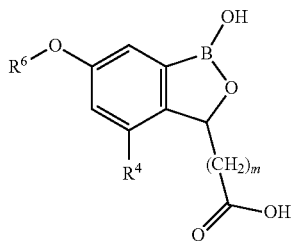

wherein $R^6$, $R^4$, and m are as described herein.

In an exemplary embodiment, the compound has a structure according to the formula:

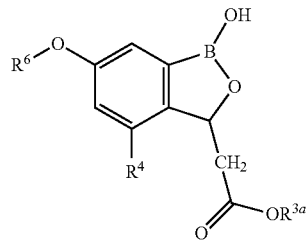

wherein $R^6$ and $R^{3a}$ are as described herein and $R^4$ is unsubstituted alkyl. In an exemplary embodiment, $R^4$ is methyl. In an exemplary embodiment, the compound has a structure according to the formula:

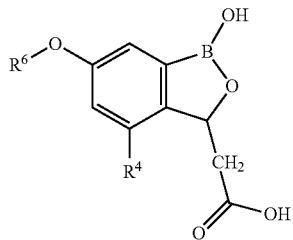

wherein $R^6$ and $R^4$ are as described herein. In an exemplary embodiment, the compound has a structure according to the formula:

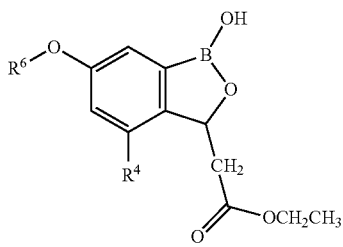

wherein $R^6$ and $R^4$ are as described herein.

In an exemplary embodiment, the compound has a structure according to the formula:

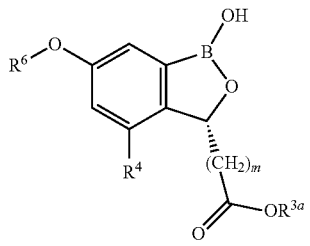

wherein $R^6$, $R^4$, m and $R^{3a}$ are as defined herein. In an exemplary embodiment, $R^4$ is unsubstituted alkyl. In an exemplary embodiment, $R^4$ is methyl.

In an exemplary embodiment, the compound has a structure according to the formula:

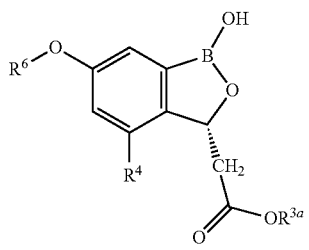

wherein $R^6$ and $R^{3a}$ are as defined herein, and $R^4$ is unsubstituted alkyl. In an exemplary embodiment, $R^{3a}$ is H. In an exemplary embodiment, $R^4$ is methyl.

In an exemplary embodiment, $R^{3a}$ is H. In an exemplary embodiment, $R^{3a}$ is methyl. In an exemplary embodiment, $R^{3a}$ is ethyl. In an exemplary embodiment, $R^{3a}$ is unsubstituted $C_3$ alkyl. In an exemplary embodiment, $R^{3a}$ is unsubstituted $C_4$ alkyl. In an exemplary embodiment, $R^{3a}$ is tert-butyl. In an exemplary embodiment, $R^{3a}$ is unsubstituted $C_5$ alkyl. In an exemplary embodiment, $R^{3a}$ is unsubstituted $C_6$ alkyl. In an exemplary embodiment, $R^{3a}$ is selected from the group consisting of methyl, ethyl, tert-butyl, and unsubstituted benzyl.

In an exemplary embodiment, $R^{3a}$ is $C_1$ or $C_2$ or $C_3$ or $C_4$ or $C_5$ or $C_6$ alkyl, substituted with phenyl. In an exemplary embodiment, $R^{3a}$ is benzyl.

In an exemplary embodiment, $R^3$ is —$CH_2C(O)OH$ or —$CH_2C(O)OCH_2CH_3$.

In an exemplary embodiment, $R^3$ and $R^6$ are as described herein, $R^4$ is methyl. In an exemplary embodiment, $R^3$ and $R^6$ are as described herein, $R^4$ is ethyl. In an exemplary embodiment, $R^3$ and $R^6$ are as described herein, $R^4$ is unsubstituted $C_3$ alkyl. In an exemplary embodiment, $R^3$ and $R^6$ are as described herein, $R^4$ is unsubstituted $C_4$ alkyl. In an exemplary embodiment, $R^3$ and $R^6$ are as described herein, $R^4$ is unsubstituted $C_5$ alkyl. In an exemplary embodiment, $R^3$ and $R^6$ are as described herein, $R^4$ is unsubstituted $C_6$ alkyl. In one aspect, the invention provides a compound having a structure according to the formula:

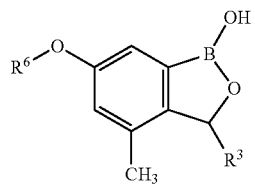

wherein $R^3$ and $R^6$ are as described herein. In one aspect, the invention provides a compound having a structure according to the formula:

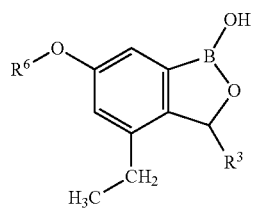

wherein $R^3$ and $R^6$ are as described herein.

In an exemplary embodiment, $R^3$ and $R^6$ are as described herein, $R^4$ is (substituted or unsubstituted amino) alkylene. In an exemplary embodiment, $R^3$ and $R^6$ are as described herein, $R^4$ is —$(CH_2)_nNR^{4a}R^{4b}$, n is an integer selected from 1, 2, 3, 4, 5 or 6, $R^{4a}$ is H or unsubstituted alkyl and $R^{4b}$ is H or unsubstituted alkyl. In an exemplary embodiment, $R^3$ and $R^6$ are as described herein, $R^4$ is —$(CH_2)_nNR^{4a}R^{4b}$, n is an integer selected from 1, 2, or 3, $R^{4a}$ is H or unsubstituted alkyl and $R^{4b}$ is H or unsubstituted alkyl. In an exemplary embodiment, $R^3$ and $R^6$ are as described herein, $R^4$ is —$CH_2NR^{4a}R^{4b}$, $R^{4a}$ is H or unsubstituted alkyl and $R^{4b}$ is H or unsubstituted alkyl. In an exemplary embodiment, $R^3$ and $R^6$ are as described herein, $R^4$ is —$(CH_2)_nNHR^{4b}$, n is an integer selected from 1, 2, 3, 4, 5, 6, and $R^{4b}$ is unsubstituted alkyl. In an exemplary embodiment, $R^3$ and $R^6$ are as described herein, $R^4$ is —$CH_2NHR^{4b}$, and $R^{4b}$ is unsubstituted alkyl. In an exemplary embodiment, $R^3$ and $R^6$ are as described herein, $R^4$ is —$(CH_2)_nNH_2$, n is an integer selected from 1, 2, or 3. In an exemplary embodiment, $R^3$ and $R^6$ are as described herein, $R^4$ is —$CH_2NH_2$.

In an exemplary embodiment, $R^3$ and $R^6$ are as described herein, $R^4$ is —$(CH_2)_nNR^{4a}R^{4b}$, n is an integer selected from 1, 2, or 3, $R^{4a}$ is $C_1$ or $C_2$ or $C_3$ unsubstituted alkyl and $R^{4b}$ is $C_1$ or $C_2$ or $C_3$ unsubstituted alkyl. In an exemplary embodiment, $R^3$ and $R^6$ are as described herein, $R^4$ is —$CH_2NR^{4a}R^{4b}$, $R^{4a}$ is $C_1$ or $C_2$ or $C_3$ unsubstituted alkyl and $R^{4b}$ is $C_1$ or $C_2$ or $C_3$ unsubstituted alkyl. In an exemplary embodiment, $R^3$ and $R^6$ are as described herein, $R^4$ is —$CH_2N(CH_2CH_3)R^{4b}$, and $R^{4b}$ is $C_1$ or $C_2$ or $C_3$ unsubstituted alkyl. In an exemplary embodiment, $R^3$ and $R^6$ are as described herein, $R^4$ is —$CH_2N(CH_2CH_3)_2$.

In an exemplary embodiment, $R^3$ and $R^6$ are as described herein, $R^4$ is —$OR^{4b}$, and $R^{4b}$ is methyl. In an exemplary embodiment, $R^3$ and $R^6$ are as described herein, $R^4$ is —$OR^{4b}$, and $R^{4b}$ is ethyl. In an exemplary embodiment, $R^3$ and $R^6$ are as described herein, $R^4$ is —$OR^{4b}$, and $R^{4b}$ is unsubstituted $C_3$ alkyl. In an exemplary embodiment, $R^3$ and $R^6$ are as described herein, $R^4$ is —$OR^{4b}$, and $R^{4b}$ is isopropyl. In an exemplary embodiment, $R^3$ and $R^6$ are as described herein, $R^4$ is —$OR^{4b}$, and $R^{4b}$ is unsubstituted $C_4$ alkyl. In an exemplary embodiment, $R^3$ and $R^6$ are as described herein, $R^4$ is —$OR^{4b}$, and $R^{4b}$ is unsubstituted $C_5$ alkyl. In an exemplary embodiment, $R^3$ and $R^6$ are as described herein, $R^4$ is —$OR^{4b}$, and $R^{4b}$ is unsubstituted $C_6$ alkyl.

In an exemplary embodiment, $R^3$ and $R^6$ are as described herein, $R^4$ is —OH. In an exemplary embodiment, $R^3$ and $R^6$ are as described herein, $R^4$ is —$OR^{4b}$, and $R^{4b}$ is unsubstituted alkyl. In an exemplary embodiment, $R^3$ and $R^6$ are as described herein, $R^4$ is —$OR^{4b}$, and $R^{4b}$ is methyl. In an exemplary embodiment, $R^3$ and $R^6$ are as described herein, $R^4$ is —$OR^{4b}$, and $R^{4b}$ is ethyl. In an exemplary embodiment, $R^3$ and $R^6$ are as described herein, $R^4$ is —$OR^{4b}$, and $R^{4b}$ is unsubstituted $C_3$ alkyl. In an exemplary embodiment, $R^3$ and $R^6$ are as described herein, $R^4$ is —$OR^{4b}$, and $R^{4b}$ is isopropyl. In an exemplary embodiment, $R^3$ and $R^6$ are as described herein, $R^4$ is —$OR^{4b}$, and $R^{4b}$ is unsubstituted $C_4$ alkyl. In an exemplary embodiment, $R^3$ and $R^6$ are as described herein, $R^4$ is —$OR^{4b}$, and $R^{4b}$ is unsubstituted $C_5$ alkyl. In an exemplary embodiment, $R^3$ and $R^6$ are as described herein, $R^4$ is —$OR^{4b}$, and $R^{4b}$ is unsubstituted $C_6$ alkyl.

In an exemplary embodiment, $R^3$ and $R^6$ are as described herein, $R^4$ is —$OR^{4b}$, and $R^{4b}$ is selected from $C_1$, $C_2$, $C_3$, $C_4$, $C_5$ or $C_6$ alkyl, optionally mono-substituted with phenyl or cyano or $C(O)OR^{4c}$, wherein $R^{4c}$ is H or unsubstituted $C_1$-$C_6$ alkyl. In an exemplary embodiment, $R^3$ and $R^6$ are as described herein, $R^4$ is selected from the group consisting of —OH, —$OCH_3$, —$OCH(CH_3)_2$, —$OCH_2CN$, —$OCH_2Ph$, —$OCH_2C(O)OH$ and —$OCH_2C(O)OCH_2CH_3$.

In an exemplary embodiment, $R^3$ and $R^6$ are as described herein, $R^4$ is —$OR^{4b}$, and $R^{4b}$ is alkyl, substituted with an ester moiety. In an exemplary embodiment, $R^3$ and $R^6$ are as described herein, $R^4$ is —$O(CH_2)$—$C(O)OR^{4c}$, wherein n is an integer selected from 1, 2, 3, 4, 5, or 6 and $R^{4c}$ is H or unsubstituted $C_1$-$C_6$ alkyl. In an exemplary embodiment, $R^3$ and $R^6$ are as described herein, $R^4$ is —$OCH_2C(O)OR^{4c}$, $R^{4c}$ is H or unsubstituted $C_1$-$C_6$ alkyl. In an exemplary embodiment, $R^3$ and $R^6$ are as described herein, $R^4$ is —$O(CH_2)_nC(O)OH$, wherein n is an integer selected from 1, 2, 3, 4, 5, or 6. In an exemplary embodiment, $R^3$ and $R^6$ are as described herein, $R^4$ is —$O(CH_2)_nC(O)OCH_2CH_3$, wherein n is an integer selected from 1, 2, 3, 4, 5, or 6. In an exemplary embodiment, $R^3$ and $R^6$ are as described herein, $R^4$ is —$OCH_2C(O)OH$. In an exemplary embodiment, $R^4$ is —$OCH_2C(O)OCH_2CH_3$.

In an exemplary embodiment, $R^3$ and $R^6$ are as described herein, $R^4$ is —$O(CH_2)_nNR^{4b}R^{4c}$, wherein n is an integer selected from 1, 2, 3, 4, 5, or 6 and $R^{4b}$ and $R^{4c}$ are independently selected from H or unsubstituted $C_1$ or $C_2$ or $C_3$ or $C_4$ or $C_5$ or $C_6$ alkyl. In an exemplary embodiment, $R^3$ and $R^6$ are as described herein, $R^4$ is —$OCH_2NR^{4b}R^{4c}$, and $R^{4b}$ and $R^{4c}$ are independently selected from H or unsubstituted $C_1$ or $C_2$ or $C_3$ or $C_4$ or $C_5$ or $C_6$ alkyl. In an exemplary embodiment, $R^3$ and $R^6$ are as described herein, $R^4$ is —$O(CH_2)_nNH_2$, wherein n is an integer selected from 1, 2, 3, 4, 5, or 6. In an exemplary embodiment, $R^3$ and $R^6$ are as described herein, $R^4$ is —$O(CH_2)_nNHR^{4c}$, wherein n is an integer selected from 1, 2, 3, 4, 5, or 6 and $R^{4c}$ is as described herein. In an exemplary embodiment, $R^3$ and $R^6$ are as described herein, $R^4$ is —$O(CH_2)_nNH_2$, wherein n is 3 or 4 or 5 or 6. In an exemplary embodiment, $R^3$ and $R^6$ are as described herein, $R^4$ is —$O(CH_2)_4NH_2$.

In an exemplary embodiment, $R^3$ and $R^6$ are as described herein, $R^4$ is —$OR^{4b}$, and $R^{4b}$ is alkyl, substituted with an unsubstituted phenyl. In an exemplary embodiment, $R^3$ and $R^6$ are as described herein, $R^4$ is —$O(CH_2)_nPh$, wherein n is an integer selected from 1, 2, 3, 4, 5, or 6. In an exemplary embodiment, $R^3$ and $R^6$ are as described herein, $R^4$ is —$OCH_2Ph$.

In an exemplary embodiment, $R^3$ and $R^6$ are as described herein, $R^4$ is —$CH_2$—O—$(CH_2)_pCH_3$, wherein p is as described herein. In an exemplary embodiment, $R^3$ and $R^6$ are as described herein, $R^4$ is —$(CH_2)_n$—O—$CH_2CH_3$, wherein n is as described herein. In an exemplary embodiment, $R^3$ and $R^6$ are as described herein, $R^4$ is —$CH_2$—O—$CH_2CH_3$. In an exemplary embodiment, $R^3$ and $R^6$ are as described herein, $R^4$ is —$(CH_2)_2$—O—$CH_2CH_3$. In an exemplary embodiment, $R^3$ and $R^6$ are as described herein, $R^4$ is —$(CH_2)_3$—O—$CH_2CH_3$. In an exemplary embodiment, $R^3$ and $R^6$ are as described herein, $R^4$ is —$CH_2$—O—$(CH_2)_3CH_3$. In an exemplary embodiment, $R^3$ and $R^6$ are as described herein, $R^4$ is —$CH_2$—O—$(CH_2)_3CH_3$. In an exemplary embodiment, $R^3$ and $R^6$ are as described herein, $R^4$ is —$(CH_2)_2$—O—$(CH_2)_2CH_3$. In an exemplary embodiment, $R^3$ and $R^6$ are as described herein, $R^4$ is —$(CH_2)_n$—O—$(CH_2)_3CH_3$.

In an exemplary embodiment, $R^3$ and $R^6$ are as described herein, $R^4$ is —$(CH_2)_n$—O—$CH_3$, wherein n is selected from 1, 2, 3, 4, 5, or 6. In an exemplary embodiment, $R^3$ and $R^6$ are as described herein, $R^4$ is —$(CH_2)_n$—O—$CH_3$, wherein n is selected from 1 or 2 or 3. In an exemplary embodiment, $R^3$ and $R^6$ are as described herein, $R^4$ is —$CH_2$—O—$CH_3$.

In an exemplary embodiment, $R^3$ and $R^6$ are as described herein, $R^4$ is F. In an exemplary embodiment, $R^3$ and $R^6$ are as described herein, $R^4$ is Cl. In an exemplary embodiment, $R^3$ and $R^6$ are as described herein, $R^4$ is Br. In an exemplary embodiment, $R^3$ and $R^6$ are as described herein, $R^4$ is I.

In an exemplary embodiment, $R^3$ and $R^4$ are as described herein, $R^6$ is H. In an exemplary embodiment, $R^3$ and $R^4$ are as described herein, $R^6$ is methyl. In an exemplary embodiment, $R^3$ and $R^4$ are as described herein, $R^6$ is ethyl. In an exemplary embodiment, $R^3$ and $R^4$ are as described herein, $R^6$ is unsubstituted $C_3$ alkyl. In an exemplary embodiment, $R^3$ and $R^4$ are as described herein, $R^6$ is isopropyl. In an exemplary embodiment, $R^3$ and $R^4$ are as described herein, $R^6$ is unsubstituted $C_4$ alkyl. In an exemplary embodiment, $R^3$ and $R^4$ are as described herein, $R^6$ is unsubstituted $C_5$ alkyl. In an exemplary embodiment, $R^3$ and $R^4$ are as described herein, $R^6$ is unsubstituted $C_6$ alkyl.

In an exemplary embodiment, $R^3$ and $R^4$ are as described herein, $R^6$ is H. In an exemplary embodiment, $R^3$ is as described herein, $R^4$ is unsubstituted alkyl, and $R^6$ is H. In an exemplary embodiment, $R^3$ is as described herein, $R^4$ is methyl, and $R^6$ is H. In an exemplary embodiment, $R^4$ is as described herein, $R^3$ is —$CH_2C(O)OH$, and $R^6$ is H.

In an exemplary embodiment, $R^3$ and $R^4$ are as described herein, $R^6$ is —$(CH_2)_uR^{6d}$, wherein $R^{6d}$ is selected from the group consisting of phenyl, cyano, —$C(O)OR^{6e}$, —$C(O)NR^{6e}R^{6f}$, —$OR^{6e}$, —$NR^{6e}R^{6f}$, wherein u is an integer selected from 1, 2, 3, 4, 5, or 6, $R^{6e}$ is selected from the group consisting of H, unsubstituted alkyl, t-butoxycarbonyl, and tri(unsubstituted alkyl) silyl; and $R^{6f}$ is H or unsubstituted alkyl. In an exemplary embodiment, u is selected from the group consisting of 1, 2, or 3.

In an exemplary embodiment, $R^3$ and $R^4$ are as described herein, $R^6$ is —$(CH_2)_uR^{6d}$, wherein $R^{6d}$ is unsubstituted phenyl, and u is an integer selected from 1, 2, 3, 4, 5, or 6. In an exemplary embodiment, $R^3$ and $R^4$ are as described herein, $R^6$ is —$(CH_2)_uR^{6d}$, wherein $R^{6d}$ is unsubstituted phenyl, and u is an integer selected from 1, 2 or 3. In an exemplary embodiment, $R^3$ and $R^4$ are as described herein, $R^6$ is —$CH_2R^{6d}$, wherein $R^{6d}$ is unsubstituted phenyl. In an exemplary embodiment, $R^3$ and $R^4$ are as described herein, $R^6$ is —$CH_2R^{6d}$, wherein $R^{6d}$ is selected from the group consisting of phenyl, cyano, —$C(O)OH$, and —$C(O)NH_2$.

In an exemplary embodiment, $R^3$ and $R^4$ are as described herein, $R^6$ is —$(CH_2)_u R^{6d}$, wherein $R^{6d}$ is cyano, and u is an integer selected from 1, 2, 3, 4, 5, or 6.

In an exemplary embodiment, $R^3$ and $R^4$ are as described herein, $R^6$ is —$(CH_2)_u R^{6d}$, wherein $R^{6d}$ is cyano, and u is an integer selected from 1, 2, or 3. In an exemplary embodiment, $R^3$ and $R^4$ are as described herein, $R^6$ is —$CH_2 R^{6d}$, wherein $R^{6d}$ is cyano.

In an exemplary embodiment, $R^3$ and $R^4$ are as described herein, $R^6$ is —$(CH_2)_u C(O)OR^{6e}$, wherein $R^{6e}$ is selected from the group consisting of H, unsubstituted alkyl, t-butoxycarbonyl, tri(unsubstituted alkyl) silyl, and u is an integer selected from 1, 2, 3, 4, 5, or 6. In an exemplary embodiment, $R^3$ and $R^4$ are as described herein, $R^6$ is —$(CH_2)_u C(O)OR^{6e}$, wherein $R^{6e}$ is described herein, and u is an integer selected from 1, 2, 3, or 4. In an exemplary embodiment, $R^3$ and $R^4$ are as described herein, $R^6$ is —$(CH_2)_u C(O)OH$. In an exemplary embodiment, $R^6$ is —$CH_2 C(O)OH$.

In an exemplary embodiment, $R^3$ and $R^4$ are as described herein, $R^6$ is —$(CH_2)_u C(O)NR^{6e} R^{6f}$, wherein $R^{6e}$ is H or unsubstituted alkyl or $R^{6f}$ is H or unsubstituted alkyl, and u is an integer selected from 1, 2, 3, 4, 5, or 6. In an exemplary embodiment, $R^3$ and $R^4$ are as described herein, $R^6$ is —$(CH_2)_u C(O)NR^{6e} R^{6f}$, wherein $R^{6e}$ and $R^{6f}$ is as described herein, and u is an integer selected from 1, 2 or 3. In an exemplary embodiment, $R^3$ and $R^4$ are as described herein, $R^6$ is —$CH_2 C(O)NR^{6e} R^{6f}$, wherein $R^{6e}$ and $R^{6f}$ is as described herein. In an exemplary embodiment, $R^3$ and $R^4$ are as described herein, $R^6$ is —$(CH_2)_u C(O)NH_2$. In an exemplary embodiment, $R^6$ is —$CH_2 C(O)NH_2$.

In an exemplary embodiment, $R^3$ and $R^4$ are as described herein, $R^6$ is —$(CH_2)_u OR^{6e}$, wherein $R^{6e}$ is selected from the group consisting of H, unsubstituted alkyl and tri(unsubstituted alkyl) silyl, and u is an integer selected from 1, 2, 3, 4, 5, or 6. In an exemplary embodiment, $R^3$ and $R^4$ are as described herein, $R^6$ is —$(CH_2)_u OH$, and u is an integer selected from 1, 2, 3, 4, 5, or 6. In an exemplary embodiment, $R^3$ and $R^4$ are as described herein, $R^6$ is —$(CH_2)_u OH$, and u is 1 or 2 or 3. In an exemplary embodiment, $R^3$ and $R^4$ are as described herein, $R^6$ is —$(CH_2)_u OH$, and u is an integer selected from 2, 3, or 4. In an exemplary embodiment, $R^3$ and $R^4$ are as described herein, $R^6$ is —$(CH_2)_3 OH$.

In an exemplary embodiment, $R^3$ and $R^4$ are as described herein, $R^6$ is —$(CH_2)_u OR^{6e}$, wherein $R^{6e}$ is $Si(R^{6f})(R^{6g})(R^{6h})$, wherein $R^{6f}$ and $R^{6g}$ and $R^{6h}$ are each independently selected unsubstituted $C_1$-$C_6$ alkyl and u is an integer selected from 1, 2, 3, 4, 5, or 6. In an exemplary embodiment, $R^3$ and $R^4$ are as described herein, $R^6$ is —$(CH_2)_u OR^{6e}$, wherein $R^{6e}$ is $Si(R^{6f})(R^{6g})(R^{6h})$, wherein $R^{6f}$ and $R^{6g}$ and $R^{6h}$ are each independently selected unsubstituted $C_1$-$C_6$ alkyl and u is an integer selected from 2, 3, or 4. In an exemplary embodiment, $R^3$ and $R^4$ are as described herein, $R^6$ is —$(CH_2)_u OR^{6e}$, wherein $R^{6e}$ is $Si(R^{6f})(R^{6g})(R^{6h})$, wherein $R^{6f}$ is methyl, $R^{6g}$ is methyl and $R^{6h}$ is unsubstituted $C_1$-$C_6$ alkyl and u is an integer selected from 1, 2, 3, 4, 5, or 6. In an exemplary embodiment, $R^3$ and $R^4$ are as described herein, $R^6$ is —$(CH_2)_u OR^{6e}$, wherein $R^{6e}$ is $Si(R^{6f})(R^{6g})(R^{6h})$, wherein $R^{6f}$ and $R^{6g}$ are each independently selected unsubstituted $C_1$-$C_6$ alkyl and $R^{6h}$ is tert-butyl and u is an integer selected from 1, 2, 3, 4, 5, or 6. In an exemplary embodiment, $R^3$ and $R^4$ are as described herein, $R^6$ is —$(CH_2)_u OR^{6e}$, wherein $R^{6e}$ is $Si(CH_3)_2(C(CH_3)_3)$, wherein u is an integer selected from 1, 2, 3, 4, 5, or 6. In an exemplary embodiment, $R^3$ and $R^4$ are as described herein, $R^6$ is —$(CH_2)_u OR^{6e}$, wherein $R^{6e}$ is $Si(CH_3)_2(C(CH_3)_3)$, wherein u is an integer selected from 2, 3, or 4. In an exemplary embodiment, $R^3$ and $R^4$ are as described herein, $R^6$ is —$(CH_2)_3 OSi(CH_3)_2(C(CH_3)_3)$.

In an exemplary embodiment, $R^3$ and $R^4$ are as described herein, $R^6$ is —$(CH_2)_u NR^{6e} R^{6f}$, wherein u is an integer selected from 1, 2, 3, 4, 5, or 6, $R^{6e}$ is selected from the group consisting of H, unsubstituted alkyl and t-butoxycarbonyl, $R^{6f}$ is H or unsubstituted alkyl. In an exemplary embodiment, $R^3$ and $R^4$ are as described herein, $R^6$ is —$(CH_2)_u NR^{6e} R^{6f}$, wherein u is an integer selected from 1, 2, or 3, $R^{6e}$ is selected from the group consisting of H, unsubstituted alkyl and t-butoxycarbonyl, $R^{6f}$ is H or unsubstituted alkyl. In an exemplary embodiment, $R^3$ and $R^4$ are as described herein, $R^6$ is —$(CH_2)_u NH_2$, wherein u is an integer selected from 1, 2, 3, 4, 5, or 6. In an exemplary embodiment, $R^3$ and $R^4$ are as described herein, $R^6$ is —$(CH_2)_u N(CH_3)_2$, wherein u is an integer selected from 1, 2, 3, 4, 5, or 6. In an exemplary embodiment, $R^3$ and $R^4$ are as described herein, $R^6$ is —$(CH_2)_u N(CH_3)_2$, wherein u is an integer selected from 1, 2, or 3. In an exemplary embodiment, $R^3$ and $R^4$ are as described herein, $R^6$ is —$(CH_2)_2 N(CH_3)_2$. In an exemplary embodiment, $R^3$ and $R^4$ are as described herein, $R^6$ is —$(CH_2)_u NHR^{6e}$, wherein u is an integer selected from 1, 2, 3, 4, 5, or 6, $R^{6e}$ is unsubstituted alkyl or t-butoxycarbonyl. In an exemplary embodiment, $R^3$ and $R^4$ are as described herein, $R^6$ is —$(CH_2)_u NHR^{6e}$, wherein u is an integer selected from 2, 3, or 4, $R^{6e}$ is unsubstituted alkyl or t-butoxycarbonyl. In an exemplary embodiment, $R^3$ and $R^4$ are as described herein, $R^6$ is —$(CH_2)_u NHR^{6e}$, wherein u is an integer selected from 2, 3, or 4, $R^{6e}$ is t-butoxycarbonyl. In an exemplary embodiment, $R^3$ and $R^4$ are as described herein, $R^6$ is —$(CH_2)_2 NHR^{6e}$, $R^{6e}$ is t-butoxycarbonyl. In an exemplary embodiment, $R^3$ and $R^4$ are as described herein, $R^6$ is —$(CH_2)_3 NHR^{6e}$, $R^{6e}$ is t-butoxycarbonyl.

In an exemplary embodiment, $R^3$ and $R^4$ are as described herein, $R^6$ is —$C(O)OR^{6a}$, wherein $R^{6a}$ is H or unsubstituted alkyl. In an exemplary embodiment, $R^3$ and $R^4$ are as described herein, $R^6$ is —$C(O)OH$. In an exemplary embodiment, $R^3$ and $R^4$ are as described herein, $R^6$ is —$C(O)OR^{6a}$, wherein $R^{6a}$ is $C_1$ or $C_2$ or $C_3$ or $C_4$ or $C_5$ or $C_6$ unsubstituted alkyl. In an exemplary embodiment, $R^3$ and $R^4$ are as described herein, $R^6$ is —$C(O)OR^{6a}$, wherein $R^{6a}$ is $C_1$ or $C_2$ or $C_3$ unsubstituted alkyl. In an exemplary embodiment, $R^3$ and $R^4$ are as described herein, $R^6$ is —$C(O)OCH_2 CH_3$.

In an exemplary embodiment, $R^3$ and $R^4$ are as described herein, $R^6$ is —$C(O)NR^{6a} R^{6b}$, $R^{6a}$ is H or unsubstituted alkyl, $R^{6b}$ is H or unsubstituted alkyl. In an exemplary embodiment, $R^3$ and $R^4$ are as described herein, $R^6$ is —$C(O)NH_2$. In an exemplary embodiment, $R^3$ and $R^4$ are as described herein, $R^6$ is —$C(O)$, $R^{6b}$ is unsubstituted alkyl. In an exemplary embodiment, $R^3$ and $R^4$ are as described herein, $R^6$ is —$C(O)NR^{6a} R^{6b}$, $R^{6a}$ is unsubstituted alkyl, $R^{6b}$ is unsubstituted alkyl. In an exemplary embodiment, $R^3$ and $R^4$ are as described herein, $R^6$ is —$C(O)N(CH_3)_2$.

In an exemplary embodiment, $R^3$ and $R^4$ are as described herein, $R^6$ is —$S(O_2)R^{6c}$, wherein $R^{6c}$ is unsubstituted alkyl or $NH_2$. In an exemplary embodiment, $R^6$ is —$S(O_2)NH_2$. In an exemplary embodiment, $R^3$ and $R^4$ are as described herein, $R^6$ is —$S(O_2)R^{6c}$, wherein $R^{6c}$ is $C_1$ or $C_2$ or $C_3$ or $C_4$ or $C_5$ or $C_6$ unsubstituted alkyl. In an exemplary embodiment, $R^3$ and $R^4$ are as described herein, $R^6$ is —$S(O_2)R^{6c}$, wherein $R^{6c}$ is $C_1$ or $C_2$ or $C_3$ unsubstituted alkyl. In an exemplary embodiment, $R^3$ and $R^4$ are as described herein, $R^6$ is —$S(O_2)CH_3$.

In an exemplary embodiment, wherein $R^6$ is as described herein, $R^4$ is ethyl, and $R^3$ is selected from the group consisting of —$CH_2 C(O)OH$, —$CH_2 C(O)OCH_3$, —$CH_2 C(O)OCH_2 CH_3$, —$CH_2 CH_2 C(O)OH$, and —$CH_2 CH_2 C(O)OCH_2 CH_3$. In an exemplary embodiment, wherein $R^6$ is as described herein, $R^4$ is F or Cl, and $R^3$ is —$CH_2 C(O)OH$ or —$CH_2 C(O)OCH_2 CH_3$.

In one aspect, the invention provides a compound having a structure according to the formula:

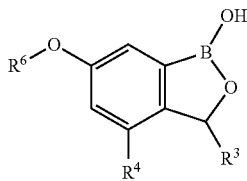

wherein $R^4$ is halogen, and $R^3$ and $R^6$ are as described herein. In an exemplary embodiment, the compound has a structure according to the formula

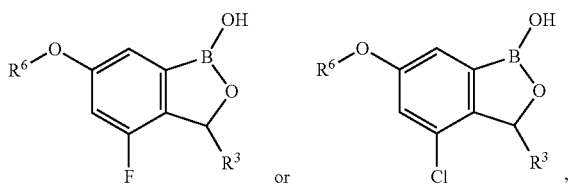

wherein $R^3$ and $R^6$ are as described herein.

In one aspect, the invention provides a compound having a structure according to the formula:

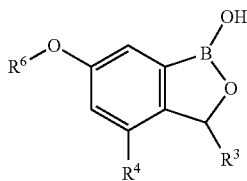

wherein $R^4$ is $-(CH_2)_n-O-(CH_2)_pCH_3$ wherein n is an integer selected from 1, 2, 3, 4, 5, or 6, and p is an integer selected from 0, 1, 2, 3, 4, 5, or 6, and $R^3$ and $R^6$ are as described herein. In an exemplary embodiment, $R^4$ is $-(CH_2)_n-O-(CH_2)_pCH_3$, wherein n is an integer selected from 1, 2 or 3, and p is an integer selected from 0, 1 or 2, and $R^3$ and $R^6$ are as described herein. In an exemplary embodiment, $R^4$ is $-(CH_2)_n-O-CH_3$, wherein n is an integer selected from 1, 2 or 3, and $R^3$ and $R^6$ are as described herein. In an exemplary embodiment, $R^4$ is $-CH_2-O-CH_3$, and $R^3$ and $R^6$ are as described herein.

In one aspect, the invention provides a compound having a structure according to the formula:

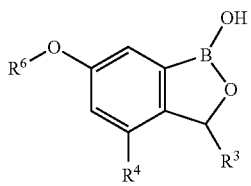

wherein $R^4$ is alkyl substituted with amino or azido, and $R^3$ and $R^6$ are as described herein. In an exemplary embodiment, $R^4$ is $-(CH_2)_n-NR^{10}R^{11}$, wherein n is an integer selected from 1, 2, 3, 4, 5 or 6, $R^{10}$ and $R^{11}$ are each independently selected from H or unsubstituted $C_1$, $C_2$, $C_3$, $C_4$, $C_5$ or $C_6$ alkyl, and $R^3$ and $R^6$ are as described herein. In an exemplary embodiment, $R^4$ is $-(CH_2)_nN(CH_3)_2$, wherein n is an integer selected from 1, 2 or 3, and $R^3$ and $R^6$ are as described herein. In an exemplary embodiment, $R^4$ is $-CH_2N(CH_3)_2$, and $R^3$ and $R^6$ are as described herein. In an exemplary embodiment, $R^4$ is $-(CH_2)_nNH_2$, wherein n is an integer selected from 1, 2 or 3, and $R^3$ and $R^6$ are as described herein. In an exemplary embodiment, $R^4$ is $-CH_2NH_2$, and $R^3$ and $R^6$ are as described herein.

In one aspect, the invention provides a compound having a structure according to the formula:

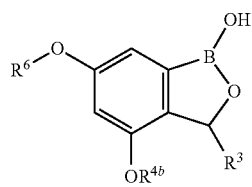

wherein $R^{4b}$ is H or unsubstituted $C_1$ or $C_2$ or $C_3$ or $C_4$ or $C_5$ or $C_6$ alkyl and $R^3$ and $R^6$ are as described herein. In an exemplary embodiment, $R^{4b}$ is unsubstituted $C_1$ or $C_2$ or $C_3$ alkyl and $R^3$ and $R^6$ are as described herein. In an exemplary embodiment, $R^{4b}$ is methyl and $R^3$ and $R^6$ are as described herein. In an exemplary embodiment, $R^{4b}$ is isopropyl and $R^3$ and $R^6$ are as described herein. In an exemplary embodiment, $R^{4b}$ is H and $R^3$ and $R^6$ are as described herein.

In one aspect, the invention provides a compound having a structure according to the formula:

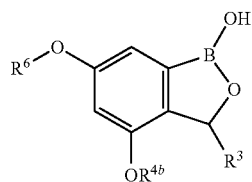

wherein $R^{4b}$ is $C_1$ or $C_2$ or $C_3$ or $C_4$ or $C_5$ or $C_6$ alkyl, substituted with phenyl or carboxyl or unsubstituted alkyl ester, and $R^3$ and $R^6$ are as described herein. In an exemplary embodiment, $R^{4b}$ is $C_1$ or $C_2$ or $C_3$ alkyl, substituted with phenyl and $R^3$ and $R^6$ are as described herein. In an exemplary embodiment, $R^{4b}$ is benzyl and $R^3$ and $R^6$ are as described herein. In an exemplary embodiment, $R^{4b}$ is carboxymethyl and $R^3$ and $R^6$ are as described herein. In an exemplary embodiment, $R^{4b}$ is ethylcarboxymethyl and $R^3$ and $R^6$ are as described herein.

In one aspect, the invention provides a compound having a structure according to the formula:

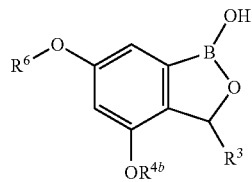

wherein $R^{4b}$ is $C_1$ or $C_2$ or $C_3$ or $C_4$ or $C_5$ or $C_6$ alkyl, substituted with amino or alkylsubstitutedcarbonylamino, and $R^3$ and $R^6$ are as described herein. In an exemplary embodiment, $R^{4b}$ is $C_2$ or $C_3$ or $C_4$ alkyl, substituted with amino and $R^3$ and $R^6$ are as described herein. In an exemplary embodiment, $R^{4b}$ is aminopropyl and $R^3$ and $R^6$ are as described herein. In an exemplary embodiment, $R^{4b}$ is aminoethyl and $R^3$ and $R^6$ are as described herein.

In one aspect, the invention provides a compound having a structure according to the formula:

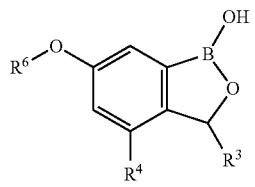

wherein $R^6$ is unsubstituted $C_1$ or $C_2$ or $C_3$ or $C_4$ or $C_5$ or $C_6$ alkyl, and $R^3$ and $R^4$ are as described herein. In an exemplary embodiment, $R^6$ is unsubstituted $C_1$ or $C_2$ or $C_3$ or $C_4$ alkyl, and $R^3$ and $R^4$ are as described herein. In an exemplary embodiment, $R^6$ is methyl or isopropyl, and $R^3$ and $R^4$ is as described herein. In an exemplary embodiment, $R^3$ is as described herein, $R^4$ is unsubstituted alkyl, and $R^6$ is methyl. In an exemplary embodiment, $R^3$ is as described herein, $R^4$ is methyl, and $R^6$ is methyl. In an exemplary embodiment, $R^4$ is as described herein, $R^3$ is —CH$_2$C(O)OH, and $R^6$ is methyl.

In one aspect, the invention provides a compound having a structure according to the formula:

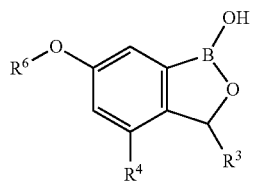

wherein $R^6$ is $C_1$ or $C_2$ or $C_3$ or $C_4$ or $C_5$ or $C_6$ alkyl, substituted with a member selected from the group consisting of phenyl, cyano, carboxyl, unsubstituted alkoxycarbonyl, OR$^{6m}$, NR$^{6m}$R$^{6n}$, wherein R$^{6m}$ is H or unsubstituted alkyl and R$^{6n}$ is selected from the group consisting of H, unsubstituted alkyl and C(O)O—R$^{6o}$, wherein R$^{6o}$ is unsubstituted alkyl, and $R^3$ and $R^4$ are as described herein. In an exemplary embodiment, $R^6$ is unsubstituted $C_1$ or $C_2$ or $C_3$ alkyl, substituted with a member selected from the group consisting of phenyl, cyano, carboxyl, unsubstituted alkoxycarbonyl, OR$^{6m}$, NR$^{6m}$R$^{6n}$, wherein R$^{6m}$ is H or unsubstituted alkyl and R$^{6n}$ is H or unsubstituted alkyl or C(O)O—R$^{6o}$, wherein R$^{6o}$ is unsubstituted alkyl, and $R^3$ and $R^4$ are as described herein. In an exemplary embodiment, $R^6$ is benzyl, and $R^3$ and $R^4$ are as described herein. In an exemplary embodiment, $R^6$ is carboxymethyl, and $R^3$ and $R^4$ are as described herein. In an exemplary embodiment, $R^6$ is selected from the group consisting of methoxycarbonylmethyl, ethoxycarbonylmethyl, and propoxycarbonylmethyl, and $R^3$ and $R^4$ are as described herein. In an exemplary embodiment, $R^6$ is cyanomethyl, and $R^3$ and $R^4$ are as described herein. In an exemplary embodiment, $R^6$ is —(CH$_2$)$_q$OH, and q is an integer selected from 1, 2, 3, 4, 5, or 6, and $R^3$ and $R^4$ are as described herein. In an exemplary embodiment, $R^6$ is —(CH$_2$)$_q$OH, and q is an integer selected from 2, 3, or 4, and $R^3$ and $R^4$ are as described herein. In an exemplary embodiment, $R^6$ is —(CH$_2$)$_3$OH, and q is an integer selected from 2, 3 or 4, and $R^3$ and $R^4$ are as described herein. In an exemplary embodiment, $R^6$ is —(CH$_2$)$_q$NR$^{6m}$R$^{6n}$, and q is an integer selected from 1, 2, 3, 4, 5, or 6, and R$^{6m}$, R$^{6n}$, $R^3$ and $R^4$ are as described herein. In an exemplary embodiment, $R^6$ is —(CH$_2$)$_q$N(CH$_3$)$_2$, and q is an integer selected from 1, 2, 3, or 4, and $R^3$ and $R^4$ are as described herein. In an exemplary embodiment, $R^6$ is —(CH$_2$)$_q$NH$_2$, and q is an integer selected from 1, 2, 3, or 4, and $R^3$ and $R^4$ are as described herein. In an exemplary embodiment, $R^6$ is —(CH$_2$)$_q$NH(C(O)O-t-Bu), and q is an integer selected from 1, 2, 3, or 4, and $R^3$ and $R^4$ are as described herein. In an exemplary embodiment, $R^6$ is —(CH$_2$)$_3$NR$^{6m}$R$^{6n}$, and R$^{6m}$, R$^{6n}$, $R^3$ and $R^4$ are as described herein. In an exemplary embodiment, $R^6$ is —(CH$_2$)$_2$N(CH$_3$)$_2$, and $R^3$ and $R^4$ are as described herein. In an exemplary embodiment, $R^6$ is —(CH$_2$)$_3$NH$_2$, and q is an integer selected from 1, 2, 3, or 4, and $R^3$ and $R^4$ are as described herein. In an exemplary embodiment, $R^6$ is —(CH$_2$)$_2$NH(C(O)O-t-Bu), and q is an integer selected from 1, 2, 3, or 4, and $R^3$ and $R^4$ are as described herein.

In one aspect, the invention provides a compound having a structure according to the formula:

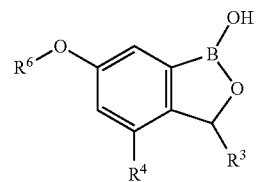

wherein $R^6$ is unsubstituted $C_1$ or $C_2$ or $C_3$ or $C_4$ or $C_5$ or $C_6$ alkoxycarbonyl, and $R^3$ and $R^4$ are as described herein. In an exemplary embodiment, $R^6$ is unsubstituted $C_1$ or $C_2$ or $C_3$ alkoxycarbonyl, and $R^3$ and $R^4$ are as described herein. In an exemplary embodiment, $R^6$ is ethoxycarbonyl, and $R^3$ and $R^4$ are as described herein.

In one aspect, the invention provides a compound having a structure according to the formula:

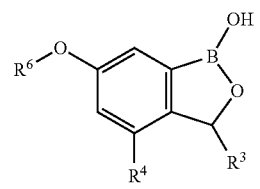

wherein $R^6$ is monoalkylaminocarbonyl or dialkylaminocarbonyl, and $R^3$ and $R^4$ are as described herein. In an exemplary embodiment, $R^6$ is —C(O)N(CH$_3$)$_2$, and $R^3$ and $R^4$ are as described herein.

In one aspect, the invention provides a compound having a structure according to the formula:

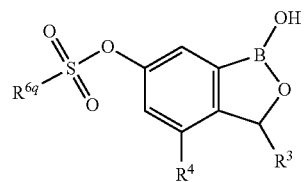

wherein R$^{6q}$ is selected from the group consisting of unsubstituted $C_1$, $C_2$, $C_3$, $C_4$, $C_5$, or $C_6$ alkyl, amino, alkyl substituted and unsubstituted heteroaryl, and $R^3$ and $R^4$ are as described herein. In an exemplary embodiment, $R^{6q}$ is methyl, and $R^3$ and $R^4$ are as described herein. In an exemplary embodiment, $R^{6q}$ is $NH_2$, and $R^3$ and $R^4$ are as described herein. In an exemplary embodiment, $R^{6q}$ is methyl, and $R^3$ and $R^4$ are as described herein. In an exemplary embodiment, $R^{6q}$ is pyrazolyl, and $R^3$ and $R^4$ are as described herein. In an exemplary embodiment, $R^{6q}$ is pyrazol-5-yl, and $R^3$ and $R^4$ are as described herein. In an exemplary embodiment, $R^{6q}$ is unsubstituted $C_1$ or $C_2$ or $C_3$ or $C_4$ or $C_5$ or $C_6$ alkyl-pyrazolyl, and $R^3$ and $R^4$ are as described herein. In an exemplary embodiment, $R^{6q}$ is 1-(unsubstituted $C_1$ or $C_2$ or $C_3$ or $C_4$ or $C_5$ or $C_6$ alkyl)-pyrazol-5-yl, and $R^3$ and $R^4$ are as described herein. In an exemplary embodiment, $R^{6q}$ is 1-methyl-pyrazol-5-yl, and $R^3$ and $R^4$ are as described herein. In an exemplary embodiment, $R^{6q}$ is 1,2,4-triazolyl, and $R^3$ and $R^4$ are as described herein. In an exemplary embodiment, $R^{6q}$ is 1,2,4-triazol-5-yl, and $R^3$ and $R^4$ are as described herein.

In an exemplary embodiment, $R^6$ is H and $R^3$ and $R^4$ are as described herein. In an exemplary embodiment, $R^6$ is H, $R^4$ is unsubstituted $C_1$ or $C_2$ or $C_3$ or $C_4$ or $C_5$ or $C_6$ alkyl, and $R^3$ is as described herein. In an exemplary embodiment, $R^6$ is H, $R^4$ is unsubstituted $C_1$ or $C_2$ or $C_3$ alkyl, and $R^3$ is as described herein. In an exemplary embodiment, $R^6$ is H, $R^4$ is methyl, and $R^3$ is as described herein. In an exemplary embodiment, $R^6$ is H, $R^3$ is —$(CH_2)_mC(O)OH$, wherein m is an integer selected from 1, 2, 3, 4, 5, or 6, and $R^4$ is as described herein. In an exemplary embodiment, $R^6$ is H, $R^3$ is —$(CH_2)_mC(O)OH$, wherein m is an integer selected from 1, 2 or 3, and $R^4$ is as described herein. In an exemplary embodiment, $R^6$ is H, $R^3$ is —$CH_2C(O)OH$, and $R^4$ is as described herein. In an exemplary embodiment, $R^6$ is H, $R^3$ is —$(CH_2)_mC(O)OR^{3a}$, wherein m is an integer selected from 1, 2 or 3, $R^{3a}$ is unsubstituted $C_1$ or $C_2$ or $C_3$ or $C_4$ or $C_5$ or $C_6$ alkyl, and $R^4$ is as described herein. In an exemplary embodiment, $R^6$ is H, $R^3$ is —$(CH_2)_mC(O)OR^{3a}$, wherein m is as described herein, $R^{3a}$ is unsubstituted $C_1$ or $C_2$ or $C_3$ alkyl, and $R^4$ is as described herein. In an exemplary embodiment, $R^6$ is H, $R^3$ is —$(CH_2)_mC(O)OR^{3a}$, $R^{3a}$ is unsubstituted ethyl, m is as described herein, and $R^4$ is as described herein. In an exemplary embodiment, $R^6$ is H, $R^3$ is —$CH_2C(O)OCH_2CH_3$, and $R^4$ is as described herein. In an exemplary embodiment, $R^6$ is H, $R^3$ is in a R configuration. In an exemplary embodiment, $R^6$ is H, $R^3$ is —$(CH_2)_mC(O)OR^{3a}$, wherein m is an integer selected from 1, 2, 3, 4, 5, or 6, $R^{3a}$ is as described herein, and $R^4$ is halogen. In an exemplary embodiment, $R^6$ is H, $R^3$ is —$(CH_2)_mC(O)OR^{3a}$, wherein m is an integer selected from 1, 2, 3, 4, 5, or 6, $R^{3a}$ is as described herein, and $R^4$ is F or Cl. In an exemplary embodiment, $R^6$ is H, $R^3$ is —$(CH_2)_mC(O)OH$, wherein m is an integer selected from 1, 2, 3, 4, 5, or 6, $R^{3a}$ is as described herein, and $R^4$ is halogen. In an exemplary embodiment, $R^6$ is H, $R^3$ is —$(CH_2)_mC(O)OR^{3a}$, wherein $R^{3a}$ is unsubstituted $C_1$ or $C_2$ or $C_3$ or $C_4$ or $C_5$ or $C_6$ alkyl wherein m is an integer selected from 1, 2 or 3, $R^{3a}$ is as described herein, and $R^4$ is halogen. In an exemplary embodiment, $R^6$ is H, $R^3$ is —$CH_2C(O)OR^{3a}$, wherein $R^{3a}$ is as described herein, and $R^4$ is F or Cl.

In an exemplary embodiment, the compound has a structure according to the formula:

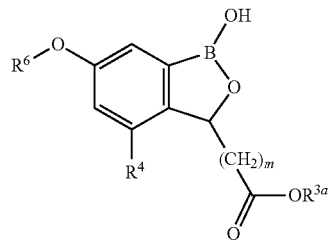

wherein $R^6$, $R^4$, m and $R^{3a}$ are as described herein. In an exemplary embodiment, $R^6$ is unsubstituted alkyl, and $R^4$, m and $R^{3a}$ are as described herein. In an exemplary embodiment, $R^6$ is —$S(O)_2R^{6q}$ wherein $R^{6q}$ is unsubstituted alkyl, and $R^4$, m and $R^{3a}$ are as described herein. In an exemplary embodiment, $R^6$ is A, and $R^4$, m and $R^{3a}$ are as described herein. In an exemplary embodiment, $R^6$ is substituted or unsubstituted phenyl, and $R^4$, m and $R^{3a}$ are as described herein. In an exemplary embodiment, $R^6$ is substituted or unsubstituted pyridin-2-yl, and $R^4$, m and $R^{3a}$ are as described herein. In an exemplary embodiment, $R^6$ is substituted or unsubstituted pyridin-4-yl, and $R^4$, m and $R^{3a}$ are as described herein. In an exemplary embodiment, $R^6$ is substituted or unsubstituted pyrazinyl, and $R^4$, m and $R^{3a}$ are as described herein. In an exemplary embodiment, $R^6$ is substituted or unsubstituted thiazolyl, and $R^4$, m and $R^{3a}$ are as described herein. In an exemplary embodiment, $R^6$ is substituted or unsubstituted 1,2,4-thiadiazolyl, and $R^4$, m and $R^{3a}$ are as described herein. In an exemplary embodiment, $R^6$ is substituted or unsubstituted 1,3,4-thiadiazolyl, and $R^4$, m and $R^{3a}$ are as described herein.

In an exemplary embodiment, the compound has a structure according to the formula:

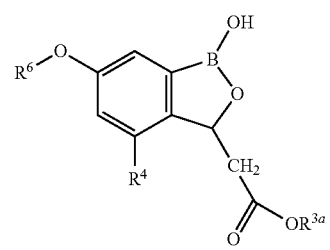

wherein $R^6$, $R^4$, and $R^{3a}$ are as described herein. In an exemplary embodiment, $R^{3a}$ is H. In an exemplary embodiment, $R^6$ is unsubstituted alkyl, and $R^4$ and $R^{3a}$ are as described herein. In an exemplary embodiment, $R^6$ is —$S(O)_2R^{6q}$ wherein $R^{6q}$ is unsubstituted alkyl, and $R^4$ and $R^{3a}$ are as described herein. In an exemplary embodiment, $R^6$ is A, and $R^4$ and $R^{3a}$ are as described herein. In an exemplary embodiment, $R^6$ is substituted or unsubstituted phenyl, and $R^4$ and $R^{3a}$ are as described herein. In an exemplary embodiment, $R^6$ is substituted or unsubstituted pyridin-2-yl, and $R^4$ and $R^{3a}$ are as described herein. In an exemplary embodiment, $R^6$ is substituted or unsubstituted pyridin-4-yl, and $R^4$ and $R^{3a}$ are as described herein. In an exemplary embodiment, $R^6$ is substituted or unsubstituted pyrazinyl, and $R^4$ and $R^{3a}$ are as described herein. In an exemplary embodiment, $R^6$ is substituted or unsubstituted thiazolyl, and $R^4$ and $R^{3a}$ are as described herein. In an exemplary embodiment, $R^6$ is substituted or unsubstituted 1,2,4-thiadiazolyl, and $R^4$ and $R^{3a}$ are as described herein. In an exemplary embodiment, $R^6$ is substituted or unsubstituted 1,3,4-thiadiazolyl, and $R^4$ and $R^{3a}$ are as described herein.

In an exemplary embodiment, the compound has a structure according to the formula:

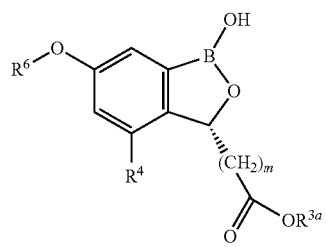

wherein $R^6$, $R^4$, m and $R^{3a}$ are as described herein. In an exemplary embodiment, $R^6$ is unsubstituted alkyl, and $R^4$, m and $R^{3a}$ are as described herein. In an exemplary embodiment, $R^6$ is —S(O)$_2$R$^{6q}$ wherein $R^{6q}$ is unsubstituted alkyl, and $R^4$, m and $R^{3a}$ are as described herein. In an exemplary embodiment, $R^6$ is A, and $R^4$, m and $R^{3a}$ are as described herein. In an exemplary embodiment, $R^6$ is substituted or unsubstituted phenyl, and $R^4$, m and $R^{3a}$ are as described herein. In an exemplary embodiment, $R^6$ is substituted or unsubstituted pyridin-2-yl, and $R^4$, m and $R^{3a}$ are as described herein. In an exemplary embodiment, $R^6$ is substituted or unsubstituted pyridin-4-yl, and $R^4$, m and $R^{3a}$ are as described herein. In an exemplary embodiment, $R^6$ is substituted or unsubstituted pyrazinyl, and $R^4$, m and $R^{3a}$ are as described herein. In an exemplary embodiment, $R^6$ is substituted or unsubstituted thiazolyl, and $R^4$, m and $R^{3a}$ are as described herein. In an exemplary embodiment, $R^6$ is substituted or unsubstituted 1,2,4-thiadiazolyl, and $R^4$, m and $R^{3a}$ are as described herein. In an exemplary embodiment, $R^6$ is substituted or unsubstituted 1,3,4-thiadiazolyl, and $R^4$, m and $R^{3a}$ are as described herein.

In an exemplary embodiment, the compound has a structure according to the formula:

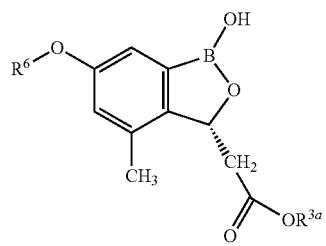

wherein $R^6$, $R^4$, and $R^{3a}$ are as described herein. In an exemplary embodiment, $R^{3a}$ is H. In an exemplary embodiment, $R^6$ is unsubstituted alkyl, and $R^4$ and $R^{3a}$ are as described herein. In an exemplary embodiment, $R^6$ is —S(O)$_2$R$^{6q}$ wherein $R^{6q}$ is unsubstituted alkyl, and $R^4$ and $R^{3a}$ are as described herein. In an exemplary embodiment, $R^6$ is A, and $R^4$ and $R^{3a}$ are as described herein. In an exemplary embodiment, $R^6$ is substituted or unsubstituted phenyl, and $R^4$ and $R^{3a}$ are as described herein. In an exemplary embodiment, $R^6$ is substituted or unsubstituted pyridin-2-yl, and $R^4$ and $R^{3a}$ are as described herein. In an exemplary embodiment, $R^6$ is substituted or unsubstituted pyridin-4-yl, and $R^4$ and $R^{3a}$ are as described herein. In an exemplary embodiment, $R^6$ is substituted or unsubstituted pyrazinyl, and $R^4$ and $R^{3a}$ are as described herein. In an exemplary embodiment, $R^6$ is substituted or unsubstituted thiazolyl, and $R^4$ and $R^{3a}$ are as described herein. In an exemplary embodiment, $R^6$ is substituted or unsubstituted 1,2,4-thiadiazolyl, and $R^4$ and $R^{3a}$ are as described herein. In an exemplary embodiment, $R^6$ is substituted or unsubstituted 1,3,4-thiadiazolyl, and $R^4$ and $R^{3a}$ are as described herein.

In an exemplary embodiment, the compound has a structure according to the formula:

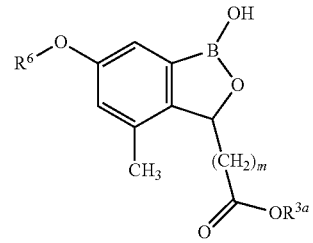

wherein $R^6$, m and $R^{3a}$ are as described herein. In an exemplary embodiment, $R^6$ is unsubstituted alkyl, and m and $R^{3a}$ are as described herein. In an exemplary embodiment, $R^6$ is —S(O)$_2$R$^{6q}$ wherein $R^{6q}$ is unsubstituted alkyl, and m and $R^{3a}$ are as described herein. In an exemplary embodiment, $R^6$ is A, and m and $R^{3a}$ are as described herein. In an exemplary embodiment, $R^6$ is substituted or unsubstituted phenyl, and m and $R^{3a}$ are as described herein. In an exemplary embodiment, $R^6$ is substituted or unsubstituted pyridin-2-yl, and m and $R^{3a}$ are as described herein. In an exemplary embodiment, $R^6$ is substituted or unsubstituted pyridin-4-yl, and m and $R^{3a}$ are as described herein. In an exemplary embodiment, $R^6$ is substituted or unsubstituted pyrazinyl, and m and $R^{3a}$ are as described herein. In an exemplary embodiment, $R^6$ is substituted or unsubstituted thiazolyl, and m and $R^{3a}$ are as described herein. In an exemplary embodiment, $R^6$ is substituted or unsubstituted 1,2,4-thiadiazolyl, and m and $R^{3a}$ are as described herein. In an exemplary embodiment, $R^6$ is substituted or unsubstituted 1,3,4-thiadiazolyl, and m and $R^{3a}$ are as described herein.

In an exemplary embodiment, the compound has a structure according to the formula:

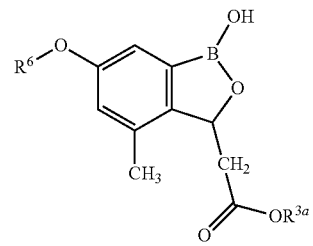

wherein $R^6$ and $R^{3a}$ are as described herein. In an exemplary embodiment, $R^{3a}$ is H. In an exemplary embodiment, $R^6$ is unsubstituted alkyl, and $R^{3a}$ are as described herein. In an exemplary embodiment, $R^6$ is —S(O)$_2$R$^{6q}$ wherein $R^{6q}$ is unsubstituted alkyl, and $R^{3a}$ are as described herein. In an exemplary embodiment, $R^6$ is A, and $R^{3a}$ are as described herein. In an exemplary embodiment, $R^6$ is substituted or unsubstituted phenyl, and $R^{3a}$ are as described herein. In an exemplary embodiment, $R^6$ is substituted or unsubstituted pyridin-2-yl, and $R^{3a}$ are as described herein. In an exemplary embodiment, $R^6$ is substituted or unsubstituted pyridin-4-yl, and $R^{3a}$ are as described herein. In an exemplary embodiment, $R^6$ is substituted or unsubstituted pyrazinyl, and $R^{3a}$ are as described herein. In an exemplary embodiment, $R^6$ is substituted or unsubstituted thiazolyl, and $R^{3a}$ are as described herein. In an exemplary embodiment, $R^6$ is substituted or unsubstituted 1,2,4-thiadiazolyl, and $R^{3a}$ are as described herein. In an exemplary embodiment, $R^6$ is substituted or unsubstituted 1,3,4-thiadiazolyl, and $R^{3a}$ are as described herein.

In an exemplary embodiment, the compound has a structure according to the formula:

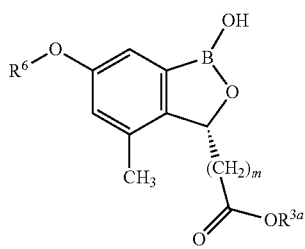

wherein $R^6$, m and $R^{3a}$ are as described herein. In an exemplary embodiment, $R^6$ is unsubstituted alkyl, and m and $R^{3a}$ are as described herein. In an exemplary embodiment, $R^6$ is $-S(O)_2 R^{6q}$ wherein $R^{6q}$ is unsubstituted alkyl, and m and $R^{3a}$ are as described herein. In an exemplary embodiment, $R^6$ is A, and m and $R^{3a}$ are as described herein. In an exemplary embodiment, $R^6$ is substituted or unsubstituted phenyl, and m and $R^{3a}$ are as described herein. In an exemplary embodiment, $R^6$ is substituted or unsubstituted pyridin-2-yl, and m and $R^{3a}$ are as described herein. In an exemplary embodiment, $R^6$ is substituted or unsubstituted pyridin-4-yl, and m and $R^{3a}$ are as described herein. In an exemplary embodiment, $R^6$ is substituted or unsubstituted pyrazinyl, and m and $R^{3a}$ are as described herein. In an exemplary embodiment, $R^6$ is substituted or unsubstituted thiazolyl, and m and $R^{3a}$ are as described herein. In an exemplary embodiment, $R^6$ is substituted or unsubstituted 1,2,4-thiadiazolyl, and m and $R^{3a}$ are as described herein. In an exemplary embodiment, $R^6$ is substituted or unsubstituted 1,3,4-thiadiazolyl, and m and $R^{3a}$ are as described herein.

In an exemplary embodiment, the compound has a structure according to the formula:

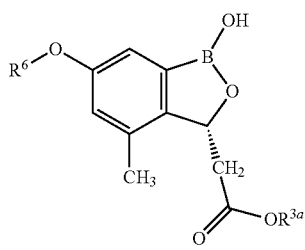

wherein $R^6$ and $R^{3a}$ are as described herein. In an exemplary embodiment, $R^{3a}$ is H. In an exemplary embodiment, $R^6$ is unsubstituted alkyl, and $R^{3a}$ are as described herein. In an exemplary embodiment, $R^6$ is $-S(O)_2 R^{6q}$ wherein $R^{6q}$ is unsubstituted alkyl, and $R^{3a}$ are as described herein. In an exemplary embodiment, $R^6$ is A, and $R^{3a}$ are as described herein. In an exemplary embodiment, $R^6$ is substituted or unsubstituted phenyl, and $R^{3a}$ are as described herein. In an exemplary embodiment, $R^6$ is substituted or unsubstituted pyridin-2-yl, and $R^{3a}$ are as described herein. In an exemplary embodiment, $R^6$ is substituted or unsubstituted pyridin-4-yl, and $R^{3a}$ are as described herein. In an exemplary embodiment, $R^6$ is substituted or unsubstituted pyrazinyl, and $R^{3a}$ are as described herein. In an exemplary embodiment, $R^6$ is substituted or unsubstituted thiazolyl, and $R^{3a}$ are as described herein. In an exemplary embodiment, $R^6$ is substituted or unsubstituted 1,2,4-thiadiazolyl, and $R^{3a}$ are as described herein. In an exemplary embodiment, $R^6$ is substituted or unsubstituted 1,3,4-thiadiazolyl, and $R^{3a}$ are as described herein.

In an exemplary embodiment, A is phenyl, substituted either with hydroxyl or $X-(CH_2)_q O-$, wherein q is an integer selected from 1, 2, 3, 4, 5, or 6; X is selected from the group consisting of benzyl, $NH_2$, and NH(Boc). In an exemplary embodiment, q is an integer is selected from 1, 2, or 3.

In an exemplary embodiment, A is selected from the group consisting of substituted or unsubstituted 2-pyrimidinyl or substituted or unsubstituted 4-pyrimidinyl. In an exemplary embodiment, A is unsubstituted pyrimidinyl. In an exemplary embodiment, A is pyrimidinyl, substituted with a member selected from the group consisting of halogen, cyano, amino substituted alkyl, $OR^{10}$, $NR^{10}R^{11}$, wherein $R^{10}$ or $R^{11}$ is independently selected from H or alkyl, optionally substituted with substituted or unsubstituted alkyl. In an exemplary embodiment, said $R^{10}$ or said $R^{11}$ is selected from the group consisting of $-NH_2$, $-NH(Boc)$, dimethoxybenzyl, $-(CH_2)_r NH_2$, and $-(CH_2)_r NH(Boc)$. In an exemplary embodiment, r is an integer selected from 1, 2, 3, 4, 5, or 6. In an exemplary embodiment, r is 2 or 3. In an exemplary embodiment, A is pyrimidinyl, substituted with a member selected from the group consisting of Cl, cyano, $-CH_2 NH_2$, $-NH(CH_2)_2 NH_2$, $-NH(CH_2)_3 NH_2$, $-NH(CH_2)_2 NH$ (Boc), $-NH(CH_2)_3 NH(Boc)$, $-NH_2$, $-N(CH_3)_2$, $-O(CH_2)_3 NH_2$, $-O(CH_2)_3 NH(Boc)$, and 2,5-dimethoxybenzyl.

In an exemplary embodiment, wherein said A is unsubstituted pyrazinyl. In an exemplary embodiment, said A is pyrazinyl, substituted with a member selected from halogen, cyano, and $-(CH_2)_s NR^{10}R^{11}$, wherein $R^{10}$ and $R^{11}$ are each independently selected from H or unsubstituted alkyl; and s is an integer selected from 1, 2, 3, 4, 5, or 6. In an exemplary embodiment, A is pyrazinyl, substituted with a member selected from the group consisting of chloro, cyano, and aminomethyl.

In an exemplary embodiment, said A is unsubstituted pyridazinyl. In an exemplary embodiment, A is pyridazinyl, substituted with a member selected from the group consisting of halogen, cyano, carbamoyl, $-(CH_2)_t NR^{10}R^{11}$, wherein $R^{10}$ or $R^{11}$ are each independently selected from H or unsubstituted alkyl, wherein t is an integer selected from 1, 2, 3, 4, 5, or 6. In an exemplary embodiment, wherein A is pyridazinyl, substituted with a member selected from the group consisting of chloro, cyano, aminomethyl, and $-C(O)NH_2$.

In an exemplary embodiment, said A is unsubstituted thiadiazolyl. In an exemplary embodiment, A is thiadiazolyl, substituted with a member selected from the group consisting of nitro, amino, and halogen. In an exemplary embodiment, A is thiadiazolyl, substituted with a member selected from the group consisting of nitro, amino, and bromine. In an exemplary embodiment, A is unsubstituted tetrahydropyranyl.

In an exemplary embodiment, the invention provides a compound having a structure according to the following formula:

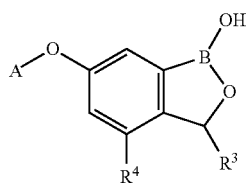

wherein R³, R⁴ and A are as described herein.

In an exemplary embodiment, A is selected from the group consisting of

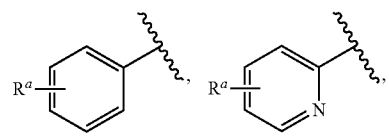

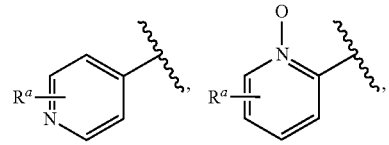

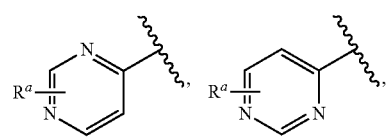

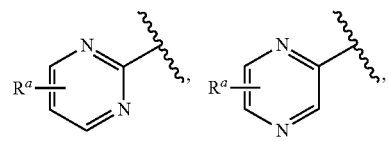

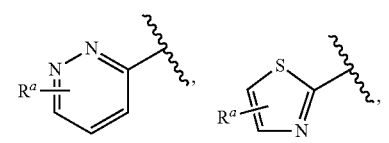

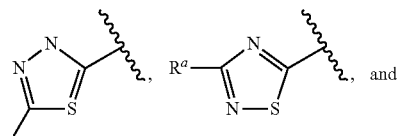

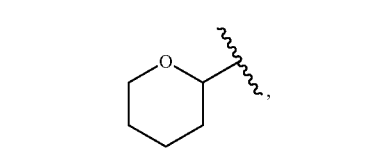

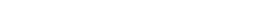

wherein $R^a$ is selected from the group consisting of halogen, cyano, nitro, $OR^{a1}$, $NR^{a1}R^{a2}$, alkyl substituted with $OR^{a1}$ and $NR^{a1}R^{a2}$, $C(O)NR^{a1}R^{a2}$, $OC(O)NR^{a1}R^{a2}$, $C(O)OR^{a1}$, $NHC(O)OR^{a1}$, $NHC(O)R^{a1}$, $C(NH)NHR^{a3}$, $C(NH)OR^{a4}$, wherein each $R^{a1}$ and $R^{a2}$ is independently selected from H or substituted or unsubstituted alkyl, wherein $R^{a3}$ is H or $OR^{a4}$ or substituted or unsubstituted alkyl, wherein $R^{a4}$ is H or unsubstituted alkyl. In an exemplary embodiment, A is selected from the group consisting of

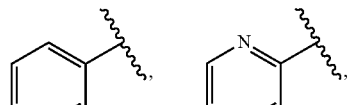

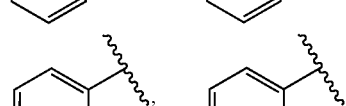

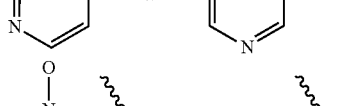

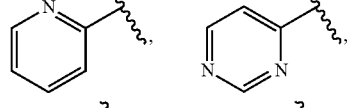

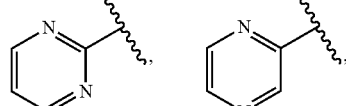

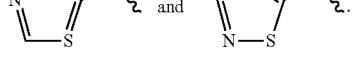

In an exemplary embodiment, the compound is selected from the group consisting of

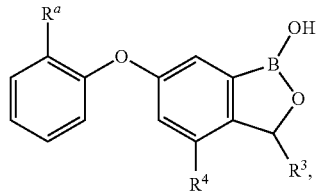

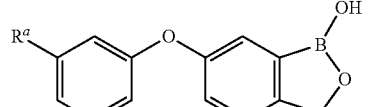

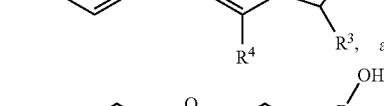

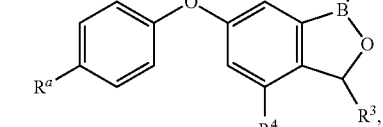

wherein R³, R⁴ and $R^a$ are as described herein. In an exemplary embodiment, $R^a$ is $OR^{a1}$, wherein $R^{a1}$ is H or substituted or unsubstituted alkyl. In an exemplary embodiment, $R^{a1}$ is aminosubstituted alkyl. In an exemplary embodiment, $R^{a1}$ is X—$(CH_2)_q$—, wherein q is an integer selected from 1, 2, 3, 4, 5, or 6; and X is selected from the group consisting of phenyl, $NH_2$ and $NHR^b$, wherein $R^b$ is $C(O)OR^c$, wherein $R^c$ is unsubstituted $C_1$ or $C_2$ or $C_3$ or $C_4$ or $C_5$ or $C_6$ alkyl. In an exemplary embodiment, q is an integer selected from 1, 2, or 3. In an exemplary embodiment, $R^a$ is selected from the group consisting of OH, benzyloxy, and —O(CH$_2$)$_3$NH$_2$, —O(CH$_2$)$_3$NHC(O)C(CH$_3$)$_3$, and $R^4$ or $R^3$ is as described herein.

In an exemplary embodiment, the compound is selected from the group consisting of

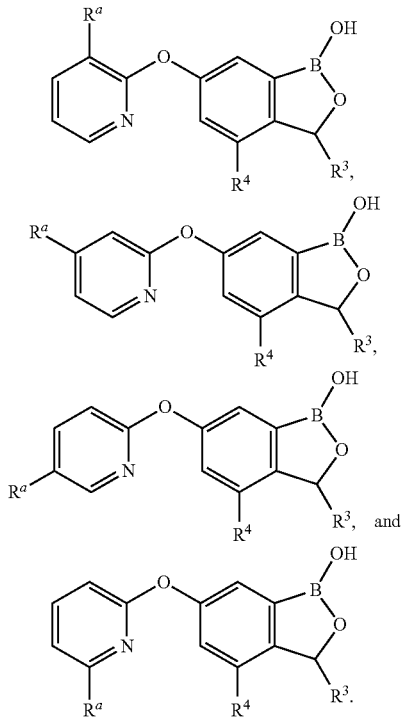

wherein $R^4$ and $R^3$ are as described herein and $R^a$ is selected from the group consisting of halogen, cyano, C(O)NH$_2$, C(NH)NH$_2$, C(NH)NHOH, NO$_2$, NH$_2$, C(O)OR$^{a1}$, amino-substituted alkyl, NHC(O)OR$^{a1}$, wherein $R^{a1}$ is H or substituted or unsubstituted alkyl. In an exemplary embodiment, $R^{a1}$ is methyl. In an exemplary embodiment, $R^{a1}$ is ethyl. In an exemplary embodiment, $R^{a1}$ is unsubstituted C$_3$ alkyl. In an exemplary embodiment, $R^{a1}$ is unsubstituted C$_4$ alkyl. In an exemplary embodiment, $R^{a1}$ is t-butyl. In an exemplary embodiment, $R^{a1}$ is unsubstituted C$_5$ alkyl. In an exemplary embodiment, $R^{a1}$ is unsubstituted C$_6$ alkyl. In an exemplary embodiment, $R^4$ and $R^3$ are as described herein and $R^a$ is $R^d$NH$_2$, wherein $R^d$ is unsubstituted alkylene. In an exemplary embodiment, $R^d$ is methylene. In an exemplary embodiment, $R^d$ is ethylene. In an exemplary embodiment, $R^d$ is unsubstituted C$_3$ alkylene. In an exemplary embodiment, $R^d$ is unsubstituted C$_4$ alkylene. In an exemplary embodiment, $R^d$ is unsubstituted C$_5$ alkylene. In an exemplary embodiment, $R^d$ is unsubstituted C$_6$ alkylene.

In an exemplary embodiment, the compound is

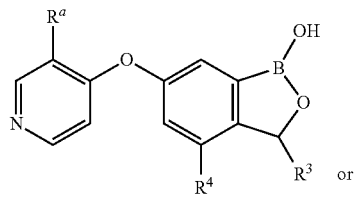

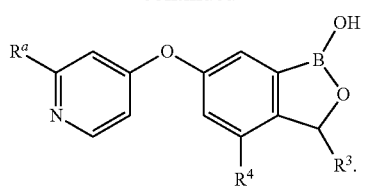

wherein $R^4$ and $R^3$ are as described herein and $R^a$ is selected from the group consisting of H, halogen, cyano, C(O)NH$_2$, C(NH)NH$_2$, C(NH)NHOH, NO$_2$, NH$_2$, C(O)OR$^{a1}$, amino-substituted alkylene, NHC(O)OR$^{a1}$, wherein $R^{a1}$ is H or substituted or unsubstituted alkyl. In an exemplary embodiment, $R^{a1}$ is methyl. In an exemplary embodiment, $R^{a1}$ is ethyl. In an exemplary embodiment, $R^{a1}$ is unsubstituted C$_3$ alkyl. In an exemplary embodiment, $R^{a1}$ is unsubstituted C$_4$ alkyl. In an exemplary embodiment, $R^{a1}$ is t-butyl. In an exemplary embodiment, $R^{a1}$ is unsubstituted C$_5$ alkyl. In an exemplary embodiment, $R^{a1}$ is unsubstituted C$_6$ alkyl. In an exemplary embodiment, $R^4$ and $R^3$ are as described herein and $R^a$ is $R^d$NH$_2$, wherein $R^d$ is unsubstituted alkylene. In an exemplary embodiment, $R^d$ is methylene. In an exemplary embodiment, $R^d$ is ethylene. In an exemplary embodiment, $R^d$ is unsubstituted C$_3$ alkylene. In an exemplary embodiment, $R^d$ is unsubstituted C$_4$ alkylene. In an exemplary embodiment, $R^d$ is unsubstituted C$_5$ alkylene. In an exemplary embodiment, $R^d$ is unsubstituted C$_6$ alkylene.

In an exemplary embodiment, the compound is

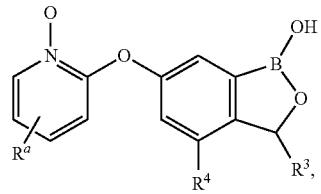

wherein $R^4$ and $R^3$ are as described herein and $R^a$ is selected from the group consisting of H, NO$_2$, and NH$_2$. In an exemplary embodiment, $R^4$ is methyl, $R^3$ is —CH$_2$COOH, and $R^a$ is as described herein.

In an exemplary embodiment, the compound is

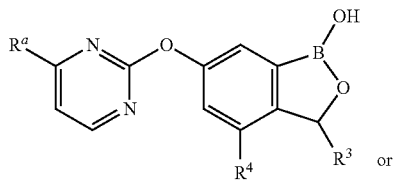

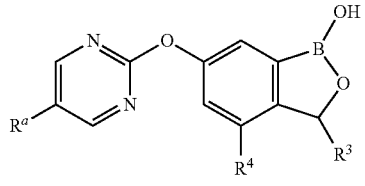

wherein $R^a$, $R^4$ and $R^3$ are as described herein.

In an exemplary embodiment, the compound is selected from the group consisting of

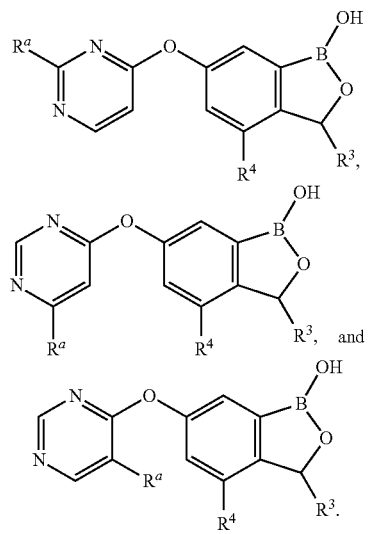

In an exemplary embodiment, $R^a$ is selected from the group consisting of cyano, aminosubstituted alkyl, $OR^{a1}$, and $NR^{a1}R^{a2}$, wherein each $R^{a1}$ and $R^{a2}$ is independently selected from H or substituted or unsubstituted alkyl. In an exemplary embodiment, $R^{a1}$ is aminosubstituted alkyl. In an exemplary embodiment, $R^{a1}$ is X—$(CH_2)_q$—, wherein q is an integer selected from 1, 2, 3, 4, 5, or 6; and X is selected from the group consisting of phenyl, $NH_2$ and $NHR^e$, wherein $R^e$ is $C(O)OR^f$, wherein $R^f$ is unsubstituted $C_1$ or $C_2$ or $C_3$ or $C_4$ or $C_5$ or $C_6$ alkyl. In an exemplary embodiment, $R^a$ is selected from the group consisting of $Ph(CH_2)$—, $NH_2CH_2$—, $NH_2$—$(CH_2)_3$—, $NH_2$, $NH_2$—$(CH_2)_3NH$—, $NH_2$—$(CH_2)_2NH$— and —$N(CH_3)_2$.

In an exemplary embodiment, the compound is selected from the group consisting of

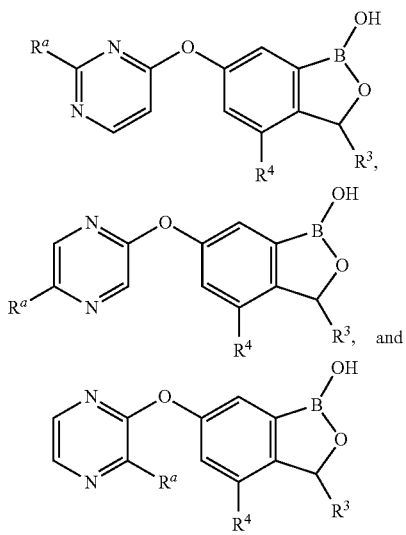

wherein $R^4$ and $R^3$ are as described herein and $R^a$ is selected from the group consisting of H, halogen, cyano, $C(O)NH_2$, $C(NH)NHR^{a1}$, $C(NH)OR^{a4}$, $C(NH)NHOH$, $NO_2$, $C(O)OR^{a1}$, aminosubstituted alkylene, $NHC(O)OR^{a1}$, $NR^{a1}R^{a2}$, wherein $R^{a1}$ and $R^{a2}$ is independently selected from H or substituted or unsubstituted alkyl, and wherein $R^{a4}$ is selected from the group consisting of H or unsubstituted alkyl. In an exemplary embodiment, $R^4$ and $R^3$ are as described herein, and $R^a$ is selected from the group consisting of F, Cl and $N(CH_3)_2$. In an exemplary embodiment, $R^4$ is methyl, $R^3$ is —$CH_2COOH$, and $R^a$ is selected from the group consisting of F, Cl and $N(CH_3)_2$. In an exemplary embodiment, $R^4$ and $R^3$ are as described herein and $R^a$ is $R^dNH_2$, wherein $R^d$ is unsubstituted alkylene. In an exemplary embodiment, $R^d$ is methylene. In an exemplary embodiment, $R^d$ is ethylene. In an exemplary embodiment, $R^d$ is unsubstituted $C_3$ alkylene. In an exemplary embodiment, $R^d$ is unsubstituted $C_4$ alkylene. In an exemplary embodiment, $R^d$ is unsubstituted $C_5$ alkylene. In an exemplary embodiment, $R^d$ is unsubstituted $C_6$ alkylene. In an exemplary embodiment, $R^a$ is $NH_2$.

In an exemplary embodiment, the compound is selected from the group consisting of

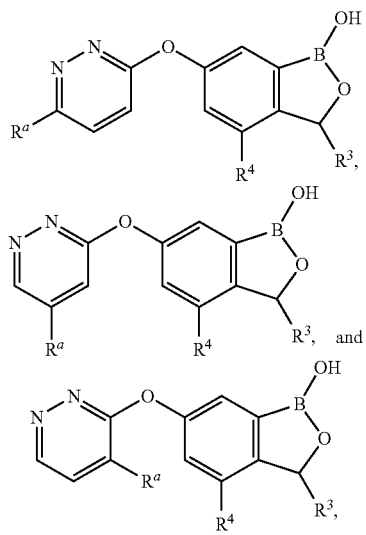

wherein $R^4$ and $R^3$ are as described herein and $R^a$ is selected from the group consisting of cyano, halogen, carbamoyl, and aminoalkyl. In an exemplary embodiment, $R^4$ and $R^3$ are as described herein, and $R^a$ is selected from the group consisting of F, Cl, cyano, —$C(O)NH_2$ and —$(CH_2)_nNH_2$, wherein n is an integer selected from 1, 2, 3, 4, 5, or 6. In an exemplary embodiment, $R^4$ is methyl, $R^3$ is —$CH_2COOH$, and $R^a$ is selected from the group consisting of F, Cl, cyano, —$C(O)NH_2$ and —$CH_2NH_2$. In an exemplary embodiment, $R^4$ is F or Cl, $R^3$ is —$CH_2COOH$, and $R^a$ is selected from the group consisting of F, Cl, cyano, —$C(O)NH_2$ and —$CH_2NH_2$.

In an exemplary embodiment, the compound is

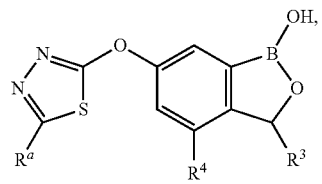

wherein $R^4$ and $R^3$ are as described herein and $R^a$ is selected from the group consisting of nitro, unsubstituted amino, —$C(O)NH_2$, —$C(=NH)NH(OH)$, —$NHC(O)R^f$ and aminosubstituted alkylene, wherein $R^f$ is aminosubstituted alkyl or unsubstituted alkyl. In an exemplary embodiment, $R^a$ are as described herein, and $R^a$ is nitro or amino. In an exemplary embodiment, $R^4$ and $R^3$ are as described herein, and $R^a$ is nitro or amino. In an exemplary embodiment, $R^a$ is aminomethylene. In an exemplary embodiment, $R^a$ is aminoethylene. In an exemplary embodiment, $R^a$ is aminopropylene. In an exemplary embodiment, $R^a$ is —NHC(O)CH$_3$. In an exemplary embodiment, $R^a$ is —NHC(O)CH$_2$CH$_3$. In an exemplary embodiment, $R^a$ is $R^d$NHR$^b$, wherein $R^b$ is H or a protecting group, and $R^d$ is unsubstituted alkylene. In an exemplary embodiment, $R^a$ is $R^d$NHC(O)OR$^c$, wherein $R^c$ is unsubstituted $C_1$ or $C_2$ or $C_3$ or $C_4$ or $C_5$ or $C_6$ alkyl. In an exemplary embodiment, $R^a$ is $R^d$NH$_2$, wherein $R^d$ is unsubstituted alkylene. In an exemplary embodiment, $R^d$ is methylene or ethylene or unsubstituted $C_3$ alkylene or unsubstituted $C_4$ alkylene or unsubstituted $C_5$ alkylene or unsubstituted $C_6$ alkylene. In an exemplary embodiment, $R^a$ is NHC(O)CH$_2$NH$_2$. In an exemplary embodiment, $R^a$ is aminoethylene. In an exemplary embodiment, $R^a$ is aminopropylene. In an exemplary embodiment, $R^4$ is methyl, $R^3$ is —CH$_2$COOH, and $R^a$ is nitro or amino. In an exemplary embodiment, $R^4$ is F or Cl, $R^3$ is —CH$_2$COOH, and $R^a$ is nitro or amino.

In an exemplary embodiment, the compound is

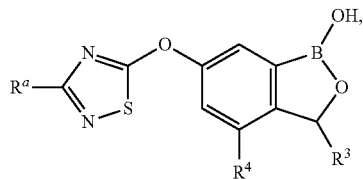

wherein $R^4$ and $R^3$ are as described herein and $R^a$ is H or halogen or amino. In an exemplary embodiment, $R^4$ and $R^3$ are as described herein and $R^a$ is F or Cl. In an exemplary embodiment, $R^4$ and $R^3$ is —CH$_2$COOH, and $R^a$ is as described herein. In an exemplary embodiment, $R^4$ is methyl, $R^3$ is —CH$_2$COOH, and $R^a$ is as described herein. In an exemplary embodiment, $R^4$ is F or Cl, $R^3$ is —CH$_2$COOH, and $R^a$ is as described herein.

In an exemplary embodiment, the compound is

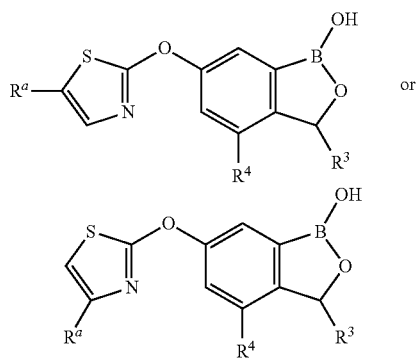

wherein $R^4$ and $R^3$ are as described herein and $R^a$ is selected from the group consisting of C(O)NH$_2$, C(NH)NH$_2$, C(NH)NHOH, NO$_2$, C(O)OR$^{a1}$, NHC(O)OR$^{a1}$, wherein $R^{a1}$ is H or substituted or unsubstituted alkyl. In an exemplary embodiment, $R^{a1}$ is methyl. In an exemplary embodiment, $R^{a1}$ is ethyl. In an exemplary embodiment, $R^{a1}$ is unsubstituted $C_3$ alkyl. In an exemplary embodiment, $R^{a1}$ is unsubstituted $C_4$ alkyl. In an exemplary embodiment, $R^{a1}$ is t-butyl. In an exemplary embodiment, $R^{a1}$ is unsubstituted $C_5$ alkyl. In an exemplary embodiment, $R^{a1}$ is unsubstituted $C_6$ alkyl.

In an exemplary embodiment, the compound is G6 or a salt thereof. In an exemplary embodiment, the compound is G6 or a pharmaceutically acceptable salt thereof. In an exemplary embodiment, the compound is G81 or a salt thereof. In an exemplary embodiment, the compound is G81 or a pharmaceutically acceptable salt thereof. In an exemplary embodiment, the compound is G131 or a salt thereof. In an exemplary embodiment, the compound is G131 or a pharmaceutically acceptable salt thereof. In an exemplary embodiment, the compound is G18 or a salt thereof. In an exemplary embodiment, the compound is G18 or a pharmaceutically acceptable salt thereof. In an exemplary embodiment, the compound is G78 or a salt thereof. In an exemplary embodiment, the compound is G78 or a pharmaceutically acceptable salt thereof. In an exemplary embodiment, the compound is G43 or a salt thereof. In an exemplary embodiment, the compound is G43 or a pharmaceutically acceptable salt thereof. In an exemplary embodiment, the compound is G104 or a salt thereof. In an exemplary embodiment, the compound is G104 or a pharmaceutically acceptable salt thereof. In an exemplary embodiment, the compound is G129 or a salt thereof. In an exemplary embodiment, the compound is G129 or a pharmaceutically acceptable salt thereof. In an exemplary embodiment, the compound is G17 or a salt thereof. In an exemplary embodiment, the compound is G17 or a pharmaceutically acceptable salt thereof. In an exemplary embodiment, the compound is G48 or a salt thereof. In an exemplary embodiment, the compound is G48 or a pharmaceutically acceptable salt thereof.

In another exemplary embodiment, the invention provides poly-or multi-valent species of the compounds of the invention. In an exemplary embodiment, the invention provides a dimer of the compounds described herein. In an exemplary embodiment, the invention provides a dimer of the compounds described herein.

In an exemplary embodiment, the invention provides an anhydride of the compounds described herein. In an exemplary embodiment, the invention provides an anhydride of the compounds described herein.

In an exemplary embodiment, the invention provides a trimer of the compounds described herein. In an exemplary embodiment, the invention provides a trimer of the compounds described herein.

The compounds of the invention can form a hydrate with water, solvates with alcohols such as methanol, ethanol, propanol, and the like; adducts with amino compounds, such as ammonia, methylamine, ethylamine, and the like; adducts with acids, such as formic acid, acetic acid and the like; complexes with ethanolamine, quinoline, amino acids, and the like.

In an exemplary embodiment, alkyl is linear alkyl. In another exemplary embodiment, alkyl is branched alkyl.

In an exemplary embodiment, heteroalkyl is linear heteroalkyl. In another exemplary embodiment, heteroalkyl is branched heteroalkyl.

III. b) Compositions Involving Stereoisomers

As used herein, the term "chiral", "enantiomerically enriched" or "diastereomerically enriched" refers to a composition having an enantiomeric excess (ee) or a diastereomeric excess (de) of greater than about 50%, preferably greater than about 70% and more preferably greater than about 90%. In general, higher than about 90% enantiomeric or diastereomeric excess is particularly preferred, e.g., those compositions with greater than about 95%, greater than about 97% and greater than about 99% ee or de.

When a first compound and a second compound are present in a composition, and the first compound is a non-superimposable mirror image of the second compound, and the first compound is present in the composition in a greater amount than the second compound, then the first compound is referred to herein as being present in "enantiomeric excess".

The term "enantiomeric excess" of a compound z, as used herein, is defined as:

$$ee_z = \left(\frac{\text{conc. of } z - \text{conc. of } y}{\text{conc. of } z + \text{conc. of } y}\right) \times 100$$

wherein z is a first compound in a composition, y is a second compound in the composition, and the first compound is a non-superimposable mirror image of the second compound.

The term "enantiomeric excess" is related to the older term "optical purity" in that both are measures of the same phenomenon. The value of ee will be a number from 0 to 100, zero being racemic and 100 being enantiomerically pure. A composition which in the past might have been called 98% optically pure is now more precisely characterized by 96% ee. A 90% ee reflects the presence of 95% of one enantiomer and 5% of the other(s) in the material in question.

When a first compound and at least one additional compound are present in a composition, and the first compound and each of the additional compounds are stereoisomers, but not mirror images, of one another, and the first compound is present in the composition in a greater amount than each of the additional compounds, then the first compound is referred to herein as being present in "diastereomeric excess".

When dealing with mixtures of diastereomers, the term "diastereomeric excess" or "de" is defined analogously to enantiomeric excess. Thus:

$$de_w = \left(\frac{\text{conc. of major diastereomer} - \text{conc. of minor diastereomer(s)}}{\text{conc. of major diastereomer} + \text{conc. of minor diastereomer(s)}}\right) \times 100$$

wherein the major diastereomer is a first compound in a composition, and the minor diastereomer(s) is at least one additional compound in the composition, and the major diastereomer and minor diastereomer(s) are stereoisomers, but not mirror images, of one another.

The value of de will likewise be a number from 0 to 100, zero being an equal mixture of a first diastereomer and the remaining diastereomer(s), and 100 being 100% of a single diastereomer and zero % of the other(s)—i.e. diastereomerically pure. Thus, 90% de reflects the presence of 95% of one diastereomer and 5% of the other diastereomer(s) in the material in question.

Hence, in one embodiment, the invention provides a composition including a first compound of the invention, wherein the first compound of the invention has at least one stereocenter, and at least one stereoisomer of the first compound of the invention. In another embodiment, the invention provides a composition including a first compound of the invention, wherein the first compound of the invention has at least one stereocenter, and a second compound of the invention, wherein the first compound of the invention is a stereoisomer of the second compound of the invention. In another embodiment, the invention provides a composition including a first compound of the invention, wherein the first compound of the invention has at least one stereocenter, and only one stereoisomer of the first compound of the invention.

In another embodiment, the invention provides a composition including a first compound of the invention, wherein the first compound of the invention has only one stereocenter, and an enantiomer of the first compound of the invention. In another embodiment, the invention provides a composition including a first compound of the invention, wherein the first compound of the invention has two stereocenters, and an enantiomer of the first compound of the invention. In another embodiment, the invention provides a composition including a first compound of the invention, wherein the first compound of the invention has two stereocenters, and at least one diastereomer of the first compound of the invention. In another embodiment, the invention provides a composition including a first compound of the invention, wherein the first compound of the invention has two stereocenters, and only one diastereomer of the first compound of the invention.

In situations where the first compound of the invention and its enantiomer are present in a composition, the first compound of the invention can be present in an enantiomeric excess of at least about 80%, or at least about 90%, or at least about 92% or at least about 95%. In another embodiment, where the first compound of the invention and its enantiomer are present in a composition, the first compound of the invention can be present in an enantiomeric excess of at least about 96%, at least about 97%, at least about 98%, at least about 99% or at least about 99.5%. In another embodiment, the first compound of the invention has at least one stereocenter and is enantiomerically pure (enantiomeric excess is about 100%).

In situations where the first compound of the invention and at least one diastereomer of the first compound of the invention are present in a composition, the first compound of the invention can be present in a diastereomeric excess of at least about 80%, or at least about 90%, or at least about 92% or at least about 95%. In situations where the first compound of the invention and at least one diastereomer of the first compound of the invention are present in a composition, the first compound of the invention can be present in a diastereomeric excess of at least about 96%, at least about 97%, at least about 98%, at least about 99% or at least about 99.5%. In another embodiment, the first compound of the invention has at least two stereocenters and is diastereomerically pure (diastereomeric excess is about 100%).

Enantiomeric or diastereomeric excess can be determined relative to exactly one other stereoisomer, or can be determined relative to the sum of at least two other stereoisomers. In an exemplary embodiment, enantiomeric or diastereomeric excess is determined relative to all other detectable stereoisomers, which are present in the mixture. Stereoisomers are detectable if a concentration of such stereoisomer in the analyzed mixture can be determined using common analytical methods, such as chiral HPLC.

As used herein, and unless otherwise indicated, a composition that is "substantially free" of a compound means that the composition contains less than about 20% by weight, or less than about 15% by weight, or less than about 10% by weight, or less than about 5% by weight, or less than about 3% by weight, or less than about 2% by weight, or less than about 1% by weight of the compound.

As used herein, the term "substantially free of the (or its) enantiomer" means that a composition contains a significantly greater proportion of a first compound of the invention than a second compound of the invention, wherein the first compound is a non-superimposable mirror image of the second compound. In one embodiment of the invention, the term "substantially free of the enantiomer" means that the composition is made up of at least about 90% by weight of a first compound of the invention, and about 10% by weight or less of a second compound of the invention, wherein the first compound is a non-superimposable mirror image of the second compound. In one embodiment of the invention, the term "substantially free of the (R) enantiomer" means that the composition is made up of at least about 90% by weight of a first compound of the invention which has only one stereocenter and the stereocenter is in an (S) configuration, and about 10% by weight or less of a second compound of the invention, wherein the second compound is the enantiomer of the first compound. In one embodiment of the invention, the term "substantially free of the enantiomer" means that the composition is made up of at least about 95% by weight of a first compound of the invention, and about 5% by weight or less of a second compound of the invention, wherein the first compound is a non-superimposable mirror image of the second compound. In one embodiment of the invention, the term "substantially free of the (R) enantiomer" means that the composition is made up of at least about 95% by weight of a first compound of the invention which has only one stereocenter and the stereocenter is in an (S) configuration, and about 5% by weight or less of a second compound of the invention, wherein the second compound is the enantiomer of the first compound. In one embodiment of the invention, the term "substantially free of the enantiomer" means that the composition is made up of at least about 98% by weight of a first compound of the invention, and about 2% by weight or less of a second compound of the invention, wherein the first compound is a non-superimposable mirror image of the second compound. In one embodiment of the invention, the term "substantially free of the (R) enantiomer" means that the composition is made up of at least about 98% by weight of a first compound of the invention which has only one stereocenter and the stereocenter is in an (S) configuration, and about 2% by weight or less of a second compound of the invention, wherein the second compound is the enantiomer of the first compound. In one embodiment of the invention, the term "substantially free of the enantiomer" means that the composition is made up of at least about 99% by weight of a first compound of the invention, and about 1% by weight or less of a second compound of the invention, wherein the first compound is a non-superimposable mirror image of the second compound. In one embodiment of the invention, the term "substantially free of the (R) enantiomer" means that the composition is made up of at least about 99% by weight of a first compound of the invention which has only one stereocenter and the stereocenter is in an (S) configuration, and about 1% by weight or less of a second compound of the invention, wherein the second compound is the enantiomer of the first compound.

In an exemplary embodiment, the invention provides a composition comprising a) a first stereoisomer of a compound described herein; b) at least one additional stereoisomer of the first stereoisomer, wherein the first stereoisomer is present in an enantiomeric excess of at least 80% relative to said at least one additional stereoisomer. In an exemplary embodiment, the enantiomeric excess is at least 92%. In an exemplary embodiment, the C* stereocenter of the first stereoisomer is in a (R) configuration. In an exemplary embodiment, the C* stereocenter of the first stereoisomer is in a (R) configuration, and $R^3$ is as described herein. In an exemplary embodiment, the C* stereocenter of the first stereoisomer is in a (R) configuration, and $R^3$ is —CH$_2$COOH or —CH$_2$COOCH$_2$CH$_3$.

In an exemplary embodiment, the invention provides a composition comprising a compound of the invention, wherein $R^3$ is as described herein and the C* stereocenter is in a (R) configuration, and said composition is substantially free of the enantiomer of the compound. In an exemplary embodiment, the composition comprises G6 or G81, wherein the composition is substantially free of the enantiomer of G6 or G81. In an exemplary embodiment, the invention provides a composition comprising a compound described herein, and the C* stereocenter is in a (S) configuration.

II. c) Combinations Comprising Additional Therapeutic Agents

The compounds of the invention may also be used in combination with additional therapeutic agents. The invention thus provides, in a further aspect, a combination comprising a compound of the invention together with at least one additional therapeutic agent, or a salt, prodrug, hydrate or solvate thereof. In an exemplary embodiment, the compound of the invention is a compound described herein, or a salt thereof. In an exemplary embodiment, the additional therapeutic agent is a compound of the invention. In an exemplary embodiment, the additional therapeutic agent includes a boron atom. In an exemplary embodiment, the additional therapeutic agent does not contain a boron atom. In an exemplary embodiment, the additional therapeutic agent is a compound described herein. In an exemplary embodiment, the additional therapeutic agent is a compound described in section II a) or b).

When a compound of the invention is used in combination with a second therapeutic agent active against the same disease state, the dose of each compound may differ from that when the compound is used alone. Appropriate doses will be readily appreciated by those skilled in the art. It will be appreciated that the amount of a compound of the invention required for use in treatment will vary with the nature of the condition being treated and the age and the condition of the patient and will be ultimately at the discretion of the attendant physician or veterinarian.

In another aspect, the invention provides a combination which includes a compound of the invention; and an antibiotic. In an exemplary embodiment, the compound is described herein, or is a pharmaceutically acceptable salt thereof. In an exemplary embodiment, the antibiotic comprises a β-lactam moiety. In an exemplary embodiment, the antibiotic is described herein.

In an exemplary embodiment, the antibiotic is a penicillin. In an exemplary embodiment, the antibiotic comprises a penam moiety. In an exemplary embodiment, the antibiotic comprises a moiety which has a structure according to the following formula:

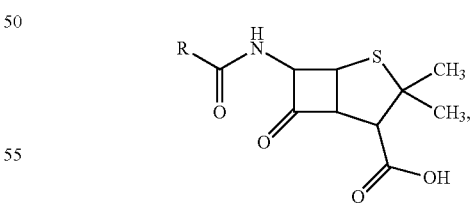

wherein R is selected from the group consisting of substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. In an exemplary embodiment, the antibiotic is an aminopenicillin. In an exemplary embodiment, the penicillin is selected from the group consisting of amoxicillin, ampicillin and epicillin. In an exemplary embodiment, the antibiotic is a carboxypenicillin. In an exemplary embodiment, the penicillin is selected from the group consisting of carbenicillin, ticarcillin and temocillin. In an exemplary embodiment, the antibiotic is an ureidopenicillin. In an exemplary embodiment, the penicillin is selected from the group consisting of azlocillin, piperacillin and mezlocillin. In an exemplary embodiment, the penicillin is mecillinam or sulbenicillin. In an exemplary embodiment, the penicillin is selected from the group consisting of penicillin G, phenoxymethylpenicillin, azidocillin, penamecillin, clometocillin, benzathine benzylpenicillin, procaine benzylpenicillin, propicillin, benzathine phenoxymethylpenicillin, and pheneticillin. In an exemplary embodiment, the penicillin is selected from the group consisting of oxacillin, cloxacillin, dicloxacillin, flucloxacillin, meticillin, and nafcillin.

In an exemplary embodiment, the antibiotic is a cephalosporin. In an exemplary embodiment, the antibiotic comprises a moiety which has a structure according to the following formula:

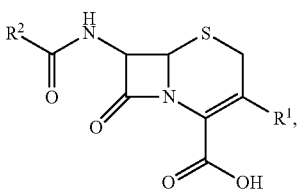

wherein $R^1$ and $R^2$ are each independently selected from the group consisting of substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, the antibiotic is a cephamycin. In an exemplary embodiment, the antibiotic comprises a moiety which has a structure according to the following formula:

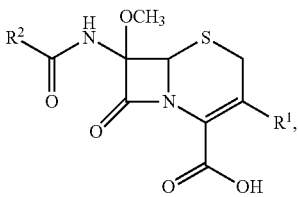

wherein $R^1$ and $R^2$ are each members independently selected from substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl.

In an exemplary embodiment, the antibiotic is a carbacephem. In an exemplary embodiment, the carbacephem is loracarbef. In an exemplary embodiment, the antibiotic is a cephamycin. In an exemplary embodiment, the cephamycin is selected from the group consisting of cefbuperazone, cefmetazole, cefminox, cefotetan, and cefoxitin.

In an exemplary embodiment, the antibiotic is a first-generation cephalosporin. In an exemplary embodiment, the cephalosporin is selected from the group consisting of cefacetrile, cefadroxil, cefalexin, cefaloglycin, cefalonium, cefaloridine, cefalotin, cefapirin, cefatrizine, cefazaflur, cefazedone, cefazolin, cefradine, cefroxadine, and ceftezole.

In an exemplary embodiment, the antibiotic is a second-generation cephalosporin. In an exemplary embodiment, the antibiotic is selected from the group consisting of cefonicid, ceforanide, cefotiam, cefprozil, cefaclor, cefuroxime, cefuzonam, and cefamandole.

In an exemplary embodiment, the antibiotic is a third-generation cephalosporin. In an exemplary embodiment, the antibiotic is selected from the group consisting of cefcapene, cefdaloxime, cefdinir, cefditoren, cefetamet, cefixime, cefmenoxime, cefodizime, cefotaxime, cefpimizole, cefpodoxime, cefteram, ceftibuten, ceftiofur, ceftiolene, ceftizoxime, and ceftriaxone. In an exemplary embodiment, the antibiotic is cefoperazone or ceftazidime. In an exemplary embodiment, the antibiotic is cefpiramide or cefsulodin. In an exemplary embodiment, the antibiotic is latamoxef or flomoxef.

In an exemplary embodiment, the antibiotic is a fourth-generation cephalosporin. In an exemplary embodiment, the antibiotic is selected from the group consisting of cefclidine, cefepime, cefluprenam, cefoselis, cefozopran, cefpirome, and cefquinome.

In an exemplary embodiment, the antibiotic is a fifth-generation cephalosporin. In an exemplary embodiment, the antibiotic is ceftobiprole. In an exemplary embodiment, the antibiotic is medocaril.

In an exemplary embodiment, the antibiotic is selected from the group consisting of cefaclomexine, cefaloram, cefaparole, cefcanel, cefedrolor, cefempidone, cefetrizole, cefivitril, cefmatilen, cefmepidium, cefovecin, cefoxazole, cefrotil, cefsumide, ceftaroline, ceftioxide, and cefuracetime.

In an exemplary embodiment, the antibiotic is a monobactam. In an exemplary embodiment, the antibiotic is aztreonam or tigemonam.

In an exemplary embodiment, the antibiotic is a carbapenem. In an exemplary embodiment, the antibiotic is selected from the group consisting of thienamycin, imipenem, meropenem, ertapenem, doripenem, panipenem, biapenem, and PZ-601.

In an exemplary embodiment, the antibiotic is a penem. In an exemplary embodiment, the antibiotic is faropenem.

In an exemplary embodiment, the antibiotic is selected from the group consisting of benzathine penicillin, benzylpenicillin (penicillin G), phenoxymethylpenicillin (penicillin V), and procaine penicillin.

In an exemplary embodiment, the antibiotic is selected from the group consisting of penicillin G, amoxicillin, ampicillin, azlocillin, carbenicillin, cloxacillin, dicloxacillin, flucloxacillin, mezlocillin, nafcillin, pipericillin, ticarcillin, ceftazidime, cephalothin, cefotaxime, cefpirome, cefepime, and cefoxitin. In an exemplary embodiment, the antibiotic is selected from the group consisting of ceftazidime, cephalothin, cefotaxime, cefpirome or cefepime, cefoxitin, penicillin G, amoxicillin, ampicillin, azlocillin, carbenicillin, cloxacillin, dicloxacillin, flucloxacillin, mezlocillin, nafcillin, pipericillin, ticarcillin, methicillin, and temocillin.

In an exemplary embodiment, the antibiotic is CXA-101.

In an exemplary embodiment, the combination of the invention is a boron-containing compound described herein or a salt thereof, and cefepime. In an exemplary embodiment, the combination of the invention is a boron-containing compound described herein or a salt thereof, and cefepime.

In an exemplary embodiment, the combination of the invention is a boron-containing compound described herein or a salt thereof, and imipenem. In an exemplary embodiment, the combination of the invention is a boron-containing compound described herein or a salt thereof, and imipenem.

In an exemplary embodiment, the combination of the invention is a boron-containing compound described herein or a salt thereof, and meropenem. In an exemplary embodiment, the combination of the invention is a boron-containing compound described herein or a salt thereof, and meropenem.

In an exemplary embodiment, the combination of the invention is a boron-containing compound described herein or a salt thereof and ceftraroline.

In an exemplary embodiment, the combination of the invention is a boron-containing compound described herein or a salt thereof, and at least one additional beta-lactamase inhibitor. In an exemplary embodiment, the combination of the invention is a boron-containing compound described herein or a salt thereof, and an additional beta-lactamase inhibitor. In an exemplary embodiment, the beta-lactamase inhibitor is a clavam. In an exemplary embodiment, the beta-lactamase inhibitor is selected from the group consisting of tazobactam, sulbactam, and NXL-104. In an exemplary embodiment, the beta-lactamase inhibitor is clavulanic acid.

In an exemplary embodiment, the combination of the invention is a boron-containing compound described herein or a salt thereof, an antibiotic, and at least one additional beta-lactamase inhibitor. In an exemplary embodiment, the combination of the invention is a boron-containing compound described herein or a salt thereof, an antibiotic described herein, and at least one additional beta-lactamase inhibitor described herein. In an exemplary embodiment, the combination of the invention is a boron-containing compound described herein or a salt thereof, ampicillin, and sulbactam. In an exemplary embodiment, the combination of the invention is a boron-containing compound described herein or a salt thereof, piperacillin, and tazobactam. In an exemplary embodiment, the combination of the invention is a boron-containing compound described herein or a salt thereof, amoxicillin, and clavulanic acid.

In an exemplary embodiment, the combination of the invention is a boron-containing compound described herein or a salt thereof, imipenem and a dihydropeptidase inhibitor. In an exemplary embodiment, the combination of the invention is a boron-containing compound described herein or a salt thereof, imipenem and cilastatin.

The individual components of such combinations may be administered either simultaneously or sequentially in a unit dosage form. The unit dosage form may be a single or multiple unit dosage forms. In an exemplary embodiment, the invention provides a combination in a single unit dosage form. An example of a single unit dosage form is a capsule wherein both the compound of the invention and the additional therapeutic agent are contained within the same capsule. In an exemplary embodiment, the invention provides a combination in a two unit dosage form. An example of a two unit dosage form is a first capsule which contains the compound of the invention and a second capsule which contains the additional therapeutic agent. Thus the term 'single unit' or 'two unit' or 'multiple unit' refers to the object which the animal (for example, a human) ingests, not to the interior components of the object. Appropriate doses of known therapeutic agents will be readily appreciated by those skilled in the art.

The combinations referred to herein may conveniently be presented for use in the form of a pharmaceutical formulation. Thus, an exemplary embodiment of the invention is a pharmaceutical formulation comprising a) a compound of the invention; b) an additional therapeutic agent and c) a pharmaceutically acceptable excipient. In an exemplary embodiment, the pharmaceutical formulation is a unit dosage form. In an exemplary embodiment, the pharmaceutical formulation is a single unit dosage form. In an exemplary embodiment, the pharmaceutical formulation is a single unit dosage form which includes a compound of the invention; an antibiotic and a pharmaceutically acceptable excipient. In an exemplary embodiment, the pharmaceutical formulation is a single unit dosage form which includes a compound of the invention; an antibiotic and at least one pharmaceutically acceptable excipient. In an exemplary embodiment, the pharmaceutical formulation is a two unit dosage form. In an exemplary embodiment, the pharmaceutical formulation is a two unit dosage form comprising a first unit dosage form and a second unit dosage form, wherein the first unit dosage form includes a) a compound of the invention and b) a first pharmaceutically acceptable excipient; and the second unit dosage form includes c) an additional therapeutic agent and d) a second pharmaceutically acceptable excipient. In an exemplary embodiment, the pharmaceutical formulation is a two unit dosage form comprising a first unit dosage form and a second unit dosage form, wherein the first unit dosage form includes a) a compound of the invention and b) a first pharmaceutically acceptable excipient; and the second unit dosage form includes c) an antibiotic and d) a second pharmaceutically acceptable excipient.

Methods of Making the Compounds

Compounds of use in the invention can be prepared using commercially available starting materials, known intermediates, or by using the synthetic methods published in references described and incorporated by reference herein, such as U.S. patent application Ser. No. 12/142,692 and U.S. Pat. Pubs. US20060234981, US20070155699 and US20070293457.

The following general procedures were used as indicated in generating the examples and can be applied, using the knowledge of one of skill in the art, to other appropriate compounds to obtain additional analogues.

General Procedure A:

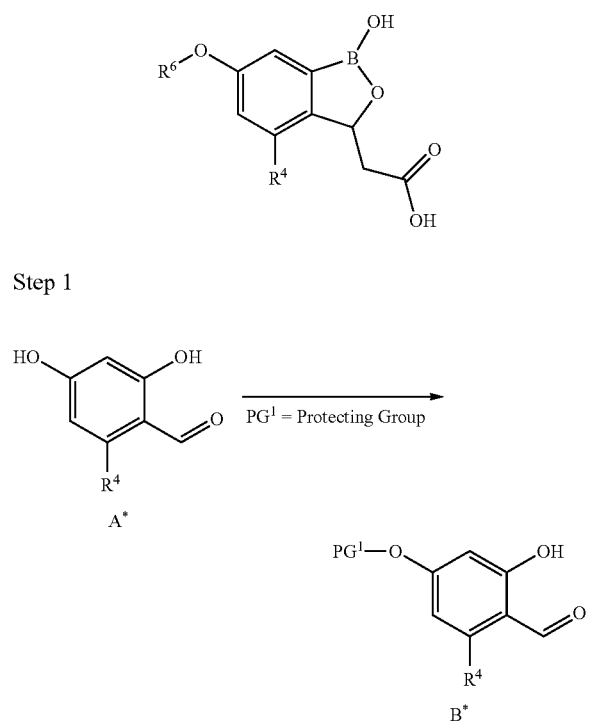

Step 1

The hydroxyl group of A* can be protected by subjecting the molecule to protecting group appropriate conditions, thereby producing B*.

Step 2

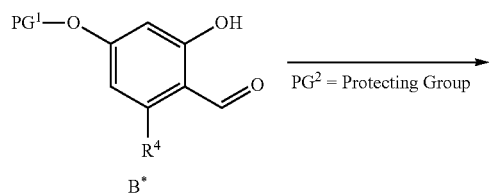

The hydroxyl group of B* can be protected by subjecting the molecule to protecting group appropriate conditions, thereby producing C*.

Step 3

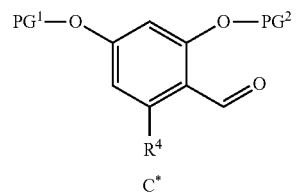

D* can be produced by subjecting C* to conditions that will selectively deprotect $PG^1$, but not $PG^2$.

Step 4

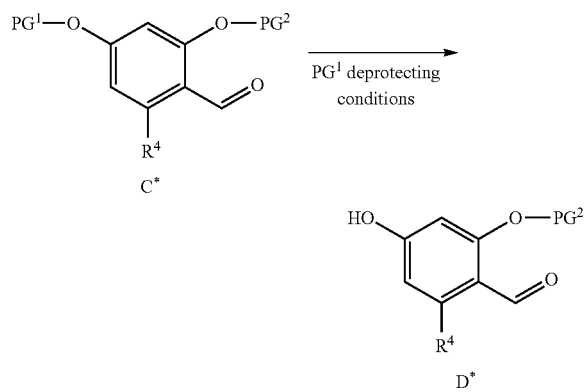

E* can be produced by subjecting D* to conditions that will add $R^a$-A. $R^a$-A can comprise a leaving group.

Step 5

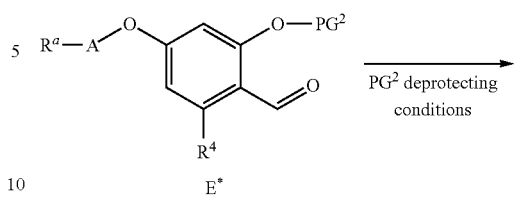

F* can be produced by subjecting E* to conditions that will selectively deprotect $PG^2$.

Step 6

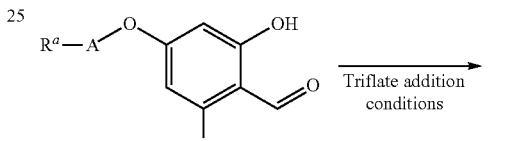

G* can be produced by subjecting F* to conditions that will selectively add a triflate, or a similar group.

Step 7

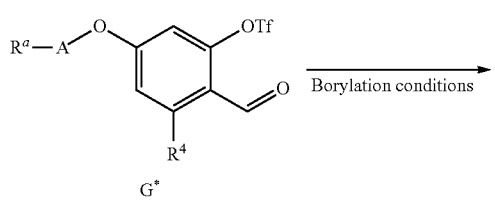

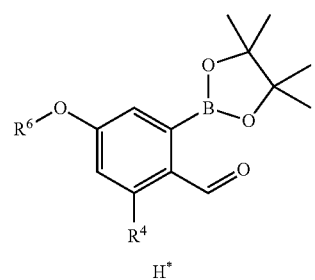

H* can be produced by subjecting G* to borylation conditions.

Step 8

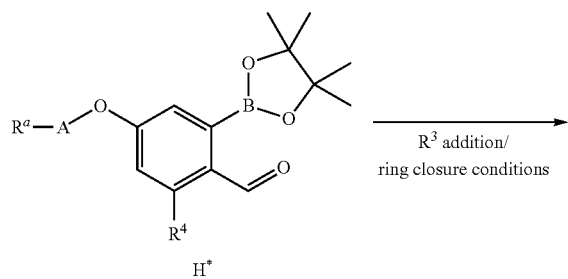

I* can be produced by subjecting H* to R³ addition/ring closure conditions.

Step 9

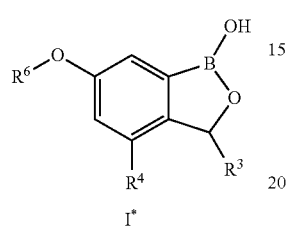

When R³ comprises an ester, for example, J*, the compound can be subjected to hydrolysis conditions to produce K*. The mixture can be purified via precipitation, silica gel column purification or preparative HPLC.

General Procedure B:

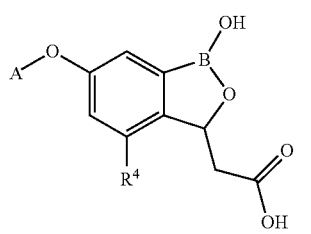

Step 1

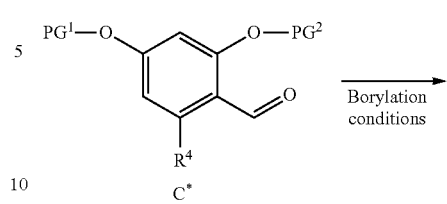

L* can be produced by subjecting C* to borylation conditions.

Step 2

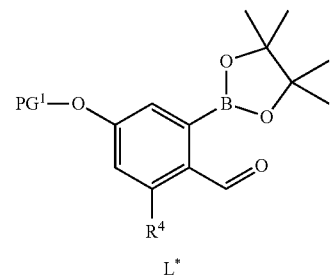

The reaction was carried out using a procedure similar to that described in Step 8 of General Strategy A.

Step 3

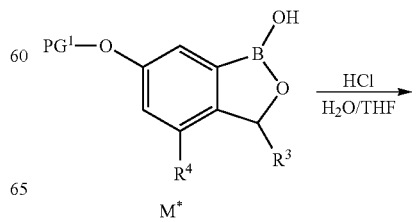

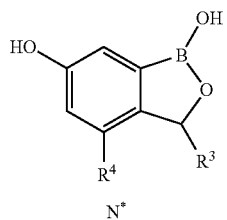

N* can be produced by subjecting M* to conditions that will deprotect $PG^1$.

Step 4

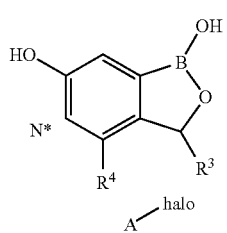

A = heteroaryl or aryl

O* can be produced by subjecting N* to appropriate coupling conditions.

General Procedure C:

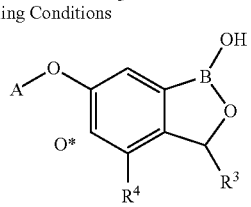

Step 1

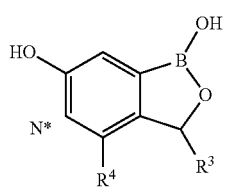

P* can be produced by subjecting N* to appropriate coupling conditions.

Step 2.

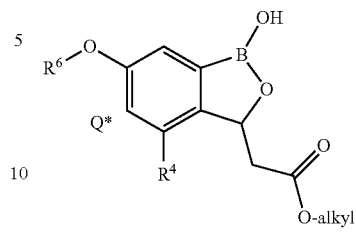

When $R^3$ comprises an ester, for example, Q*, the compound can be subjected to hydrolysis conditions to produce S*. The mixture can be purified via precipitation, silica gel column purification or preparative HPLC.

General Procedure D:

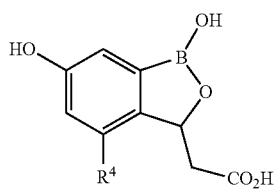 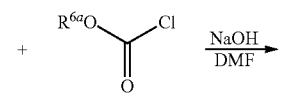

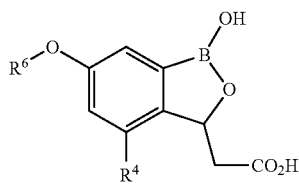

To a mixture of 2-(4-substituted-1,6-dihydroxy-1,3-dihydrobenzo[c][1,2]oxaborol-3-yl)-acetic acid (one equivalent) and sodium hydroxide (approximately three equivalents) in water (3 mL) can be added a chloroformate (approximately one equivalent). The reaction mixture can be stirred at room temperature for approximately 15 min and then acidified to approximately pH=2 with an acid, for example, 1N HCl.

General Procedure E:

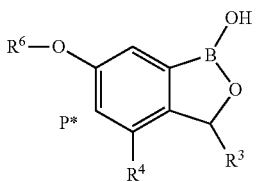 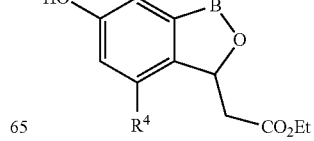 

-continued

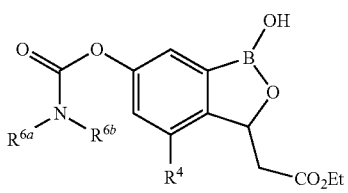

To a solution of ethyl 2-(4-substituted-1,6-dihydroxy-1,3-dihydrobenzo[c][1,2]oxaborol-3-yl)acetate (one equivalent) in a solvent such as DMF can be slowly added a compound such as NaH (about 3 equivalents) at a temperature such as 0° C. The mixture can be stirred for 20 min and a carbamoyl chloride can be added at 0° C. The reaction can be carried out at room temperature for 8-48 hours.

General Procedure F:

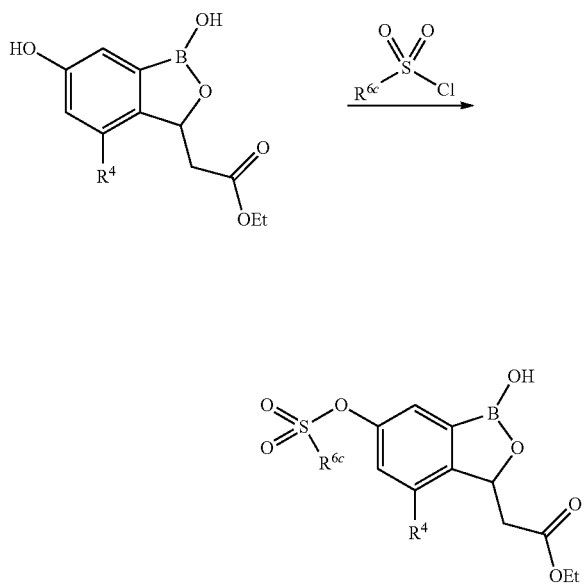

To a solution of ethyl 2-(4-substituted-1,6-dihydroxy-1,3-dihydrobenzo[c][1,2]oxaborol-3-yl)acetate (one equivalent) in a solvent such as DMF can be slowly added a compound such as NaH (about 3 equivalents) at a temperature such as 0° C. The reaction mixture can be stirred for 20 min and a sulfonyl chloride can be added. The reaction can be also carried out using $Et_3N$ (5 eq) in DCM.

General Procedure G:

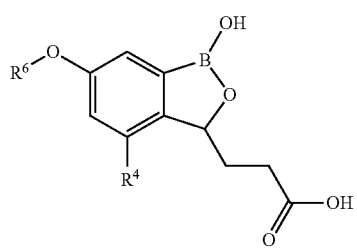

Step 1

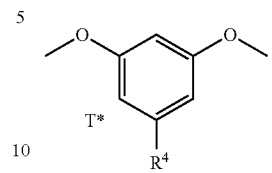 

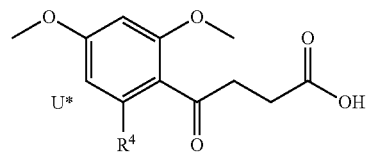

U* can be produced by subjecting T* to succinylation conditions.

Step 2

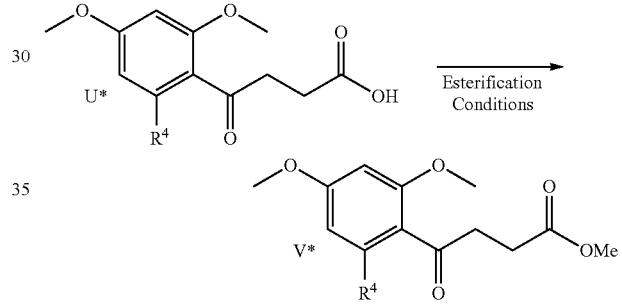

V* can be produced by subjecting U* to esterification conditions.

Step 3

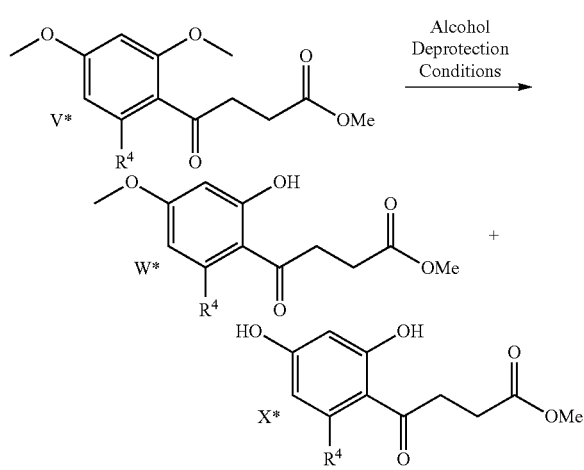

W* or X* can be produced by subjecting V* to alcohol deprotection conditions.

Step 4
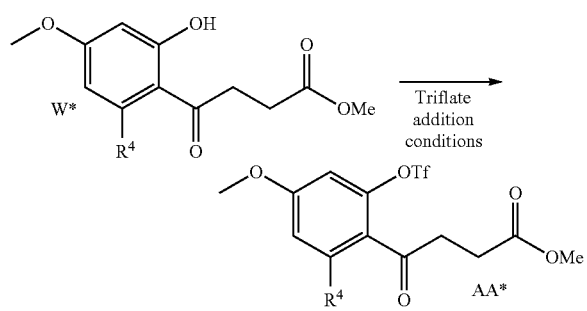
AA** can be produced by subjecting W* to conditions that will selectively add a triflate, or a similar group.
Step 5
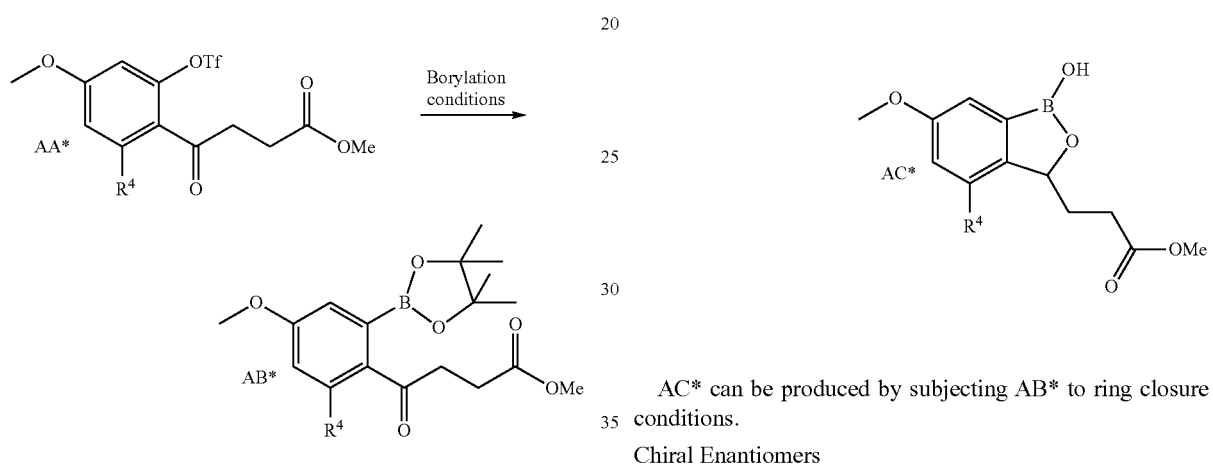
AB* can be produced by subjecting AA* to borylation conditions.
Step 6
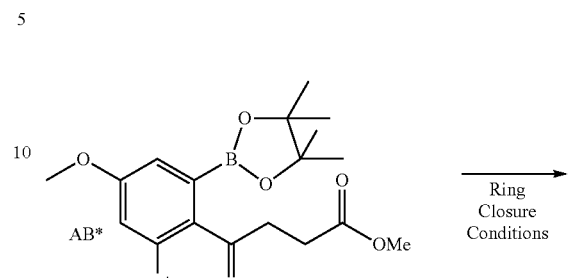
AC* can be produced by subjecting AB* to ring closure conditions.
Chiral Enantiomers
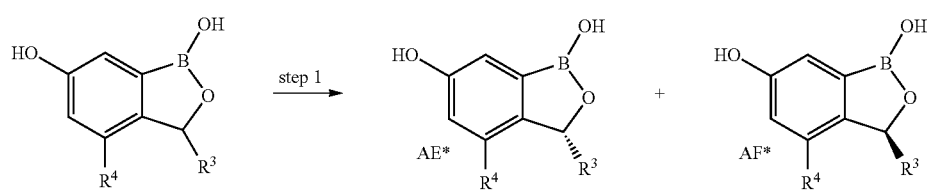
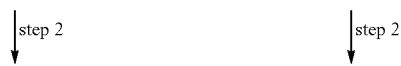
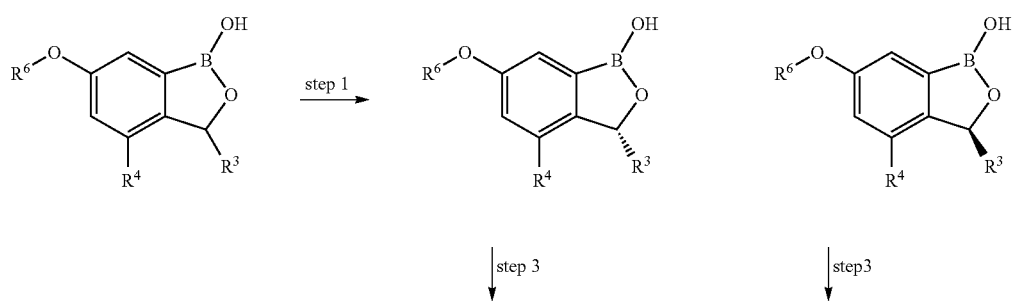

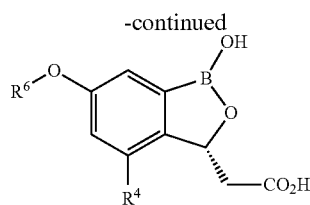
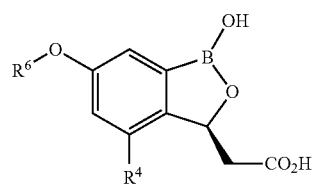

Step 1

Racemates of compounds described herein can be separated into pure enantiomers via preparative chiral HPLC or preparative supercritical fluid chromatography. Chiral columns which can be utilized to separate compounds of the invention are commercially available from companies such as Chiral Tech (West Chester, Pa.). Exemplary chiral columns which can be utilized include CHIRALPAK® IC, and CHIRALPAK® 405. Solvent systems of use in this purification include $CO_2$/MeOH (approx 85/15), Hexane/i-PrOH/TFA Hexane/EtOH/TFA as solvent. EtOH can be replaced with other alcohols.

Step 2 or Step 3

When $R^3$ comprises an ester, the compound can be subjected to hydrolysis conditions to produce compounds such as AE* or AF*. The mixture can be purified via precipitation, silica gel column purification or preparative HPLC.

In an exemplary embodiment, the invention provides a compound which is useful as an intermediate in making a compound described herein. In an exemplary embodiment, the compound has a structure according to the following formula:

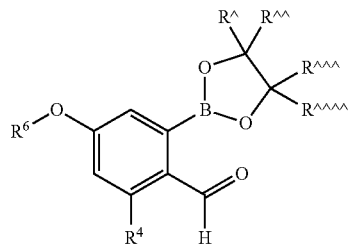

wherein $R^4$ and $R^6$ are described herein, and $R^\wedge$, $R^{\wedge\wedge}$, $R^{\wedge\wedge\wedge}$ and $R^{\wedge\wedge\wedge\wedge}$ are each independently selected unsubstituted $C_1$-$C_6$ alkyl. In an exemplary embodiment, the compound has a structure according to the following formula:

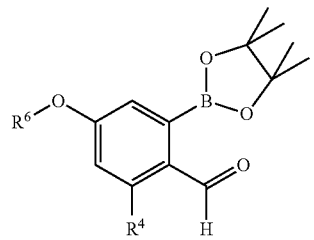

wherein $R^4$ and $R^6$ are described herein.

Compounds of the invention can be produced according to the strategies described herein.

III. Assays

Art-recognized techniques of genetics and molecular biology are of use to identify compounds that bind to and/or inhibit an enzyme, such as a beta-lactamase. Moreover, these techniques are of use to distinguish whether a compound binds to and/or inhibits a particular domain of the enzyme.

III. a) Beta-lactamase

In an exemplary assay, activity of a representative compound against a beta-lactamase was confirmed.

Assays to determine whether, and how effectively, a particular compound binds to and/or inhibits a beta-lactamase are also set forth herein, and additional assays are readily available to those of skill in the art.

Generally, the compounds to be tested are present in the assays in ranges from about 1 pM to about 100 mM, preferably from about 1 pM to about 1 μM. Other compounds range from about 1 nM to about 100 nM, preferably from about 1 nM to about 1 μM.

Utilizing the assays set forth herein and others readily available in the art, those of skill in the art will be able to readily and routinely determine other compounds and classes of compounds that operate to bind to and/or inhibit a beta-lactamase.

In another aspect, the invention provides a method for identifying a compound which binds a beta-lactamase comprising: a) contacting said beta-lactamase with a test compound under conditions suitable for binding; and b) detecting binding of said test compound to said beta-lactamase. In an exemplary embodiment, detecting binding of said compound comprises use of at least one detectable element, isotope, or chemical label attached to said compound. In an exemplary embodiment, the element, isotope or chemical label is detected by a fluorescent, luminescent, radioactive, or absorbance readout. In another exemplary embodiment, wherein said beta-lactamase comprises the amino acid sequence of a peptide sequence described herein.

In another aspect, the invention provides a method for identifying a compound which binds to a beta-lactamase, said assay comprising: a) contacting said beta-lactamase with said compound under conditions suitable for binding of said compound with said beta-lactamase; b) comparing a biological activity of said beta-lactamase contacting said compound to said biological activity when not contacting said compound; and c) identifying said compound as binding to said beta-lactamase if said biological activity of said beta-lactamase is reduced when contacting said compound.

IV. Methods

In another aspect, the compounds of the invention can be utilized to inhibit an enzyme, such as a beta-lactamase. In another aspect, the compounds of the invention and/or combinations of the invention exhibit potency against microorganisms, such as bacteria, and therefore have the potential to kill and/or inhibit the growth of microorganisms. In another aspect, the compounds of the invention and/or combinations of the invention exhibit potency against microorganisms, such as bacteria, and therefore have the potential to achieve therapeutic efficacy in the animals described herein.

IV. a) Beta-lactamase

In an exemplary embodiment, the compounds of the invention exhibit the ability to inhibit a beta-lactamase, and therefore have the potential to be used to treat bacterial infections in an animal which involve beta-lactamases. According to another aspect of the invention, a method for binding to and/or inhibiting a beta-lactamase is provided which comprises contacting the beta-lactamase with an effective amount of a compound of the invention. Such conditions are known to those skilled in the art. In an exemplary embodiment, the compound of use in the method is described herein, or a salt, hydrate or solvate thereof, or a combination thereof. In an exemplary embodiment, the compound of use in the method is described herein, or a salt, hydrate or solvate thereof. In an exemplary embodiment, the compound of use in the method is described herein, or a salt thereof. In an exemplary embodiment, the compound of use in the method is described herein, or a salt thereof. The beta-lactamase is contacted with an amount of a compound of the invention sufficient to result in a detectable amount of beta-lactamase inhibition. This method can be performed on a beta-lactamase that is contained within an organism or which is outside an organism. In an exemplary embodiment, the method is performed on a beta-lactamase that is contained within a microorganism that is in, or on the surface of, an animal. In an exemplary embodiment, the animal is a human. In an exemplary embodiment, the inhibition takes place in a cell, such as a microorganism cell. In another exemplary embodiment, the microorganism is a bacterium. In an exemplary embodiment, the method is performed on a beta-lactamase that is outside of a microorganism. In an exemplary embodiment, the method is performed on a beta-lactamase that is outside of a microorganism and is in an assay of the type described herein.

In an exemplary embodiment, the compound has a structure according to the following formula:

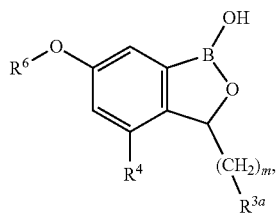

in which $R^4$, $R^6$, m and $R^{3a}$ is described herein. In an exemplary embodiment, the compound has a structure according to the following formula:

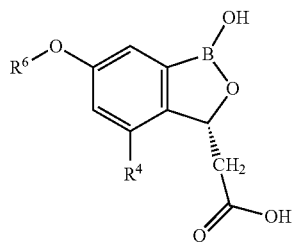

in which $R^4$ and $R^6$ are described herein.

In an exemplary embodiment, the β-lactamase is selected from the group consisting of a Group 1 β-lactamase, a Group 2 β-lactamase, and a Group 4 β-lactamase. In an exemplary embodiment, the Group 1 β-lactamase is a cephalosporinase. In an exemplary embodiment, said Group 2 β-lactamase is selected from the group consisting of a penicillinase, a Group 2b β-lactamase, Group 2be β-lactamase, Group 2br β-lactamase, carbenicillinase, cloxacilanase, cephalosporinase and carbapenamase. In an exemplary embodiment, said Group 4 β-lactamase is a penicillinase. In an exemplary embodiment, the β-lactamase is selected from the group consisting of a class A β-lactamase, a class B β-lactamase, a class C β-lactamase, and a class D β-lactamase. In an exemplary embodiment, the class A β-lactamase is selected from the group consisting of a TEM β-lactamase, SHV β-lactamase, CTX-M β-lactamase and a KPC β-lactamase. In an exemplary embodiment, β-lactamase is TEM β-lactamase. In an exemplary embodiment, the β-lactamase is TEM-1 β-lactamase. In an exemplary embodiment, the β-lactamase is TEM-3 β-lactamase. In an exemplary embodiment, the β-lactamase is KPC-2 β-lactamase. In an exemplary embodiment, the β-lactamase is CMY-2 β-lactamase. In an exemplary embodiment, the class C β-lactamase is selected from the group consisting of a CMY β-lactamase, a PER β-lactamase, and an AmpC β-lactamase. In an exemplary embodiment, the β-lactamase is AmpC β-lactamase. In an exemplary embodiment, the class D β-lactamase is an OXA β-lactamase. In an exemplary embodiment, the β-lactamase is a class A β-lactamase or a class C β-lactamase. In an exemplary embodiment, the contacting takes place in vitro. In an exemplary embodiment, the contacting takes place in vivo. In an exemplary embodiment, the contacting takes place in an animal, such as a human.

IV. b) Inhibiting Microorganism Growth or Killing Microorganisms

The compounds of the invention and/or combinations of the invention exhibit potency against microorganisms, such as bacteria, and therefore have the potential to kill and/or inhibit the growth of microorganisms. Testing for the presence of a beta-lactamase in a bacteria can be accomplished using methods known to one of skill in the art. See, for example, Sturenburg et al., *J. Antimic. Chemo.*, (2004) 54, 134-138 and Tan et al, *Antimicrob. Agents Chemother.*, (2009) 53(1): 146-149.

In a further aspect, the invention provides a method of killing and/or inhibiting the growth of a microorganism, said method comprising: contacting said microorganism with an effective amount of a compound of the invention, thereby killing and/or inhibiting the growth of the microorganism. In a further aspect, the invention provides a method of killing and/or inhibiting the growth of a microorganism, said method comprising: contacting said microorganism with an effective amount of a combination of the invention, thereby killing and/or inhibiting the growth of the microorganism. In an exemplary embodiment, the microorganism is a bacteria. In an exemplary embodiment, the compound is described herein, or a salt, prodrug, hydrate or solvate thereof, or a combination thereof. In an exemplary embodiment, the invention provides a compound described herein, or a salt, hydrate or solvate thereof. In an exemplary embodiment, the invention provides a compound described herein, or a prodrug thereof. In an exemplary embodiment, the invention provides a compound described herein, or a salt thereof. In another exemplary embodiment, the compound of the invention is a compound described herein, or a pharmaceutically acceptable salt thereof. In another exemplary embodiment, the compound is described by a formula listed herein, or a pharmaceutically acceptable salt thereof. In an exemplary embodiment, the compound is part of a combination described herein. In an exemplary embodiment, the compound is part of a pharmaceutical formulation described herein. In another exemplary embodiment, the contacting occurs under conditions which permit entry of the compound into the organism. Such conditions are known to one skilled in the art and are described herein.

In another aspect, the microorganism is inside, or on the surface of an animal. In an exemplary embodiment, the animal is selected from the group consisting of a human, cattle, deer, reindeer, goat, honey bee, pig, sheep, horse, cow, bull, dog, guinea pig, gerbil, rabbit, cat, camel, yak, elephant, ostrich, otter, chicken, duck, goose, guinea fowl, pigeon, swan, and turkey. In another exemplary embodiment, the animal is a human.

In an exemplary embodiment, the microorganism is killed or its growth is inhibited through oral administration of the compound of the invention and/or the combination of the invention. In an exemplary embodiment, the microorganism is killed or its growth is inhibited through intravenous administration of the compound of the invention and/or the combination of the invention. In an exemplary embodiment, the microorganism is killed or its growth is inhibited through topical administration of the compound of the invention and/or the combination of the invention.

In an exemplary embodiment, the microorganism is a bacterium. In an exemplary embodiment, the bacterium is a gram-positive bacteria. In another exemplary embodiment, the gram-positive bacterium is selected from the group consisting of *Staphylococcus* species, *Streptococcus* species, *Bacillus* species, *Corynebacterium* species (*Propionibacterium* species), *Clostridium* species, *Actinomyces* species, *Enterococcus* species, and *Streptomyces* species. In another exemplary embodiment, the gram-positive bacterium is selected from the group consisting of *Propionibacterium acnes, Staphylococcus aureus, Staphylococcus epidermidis, Staphylococcus saprophyticus, Staphylococcus haemolyticus, Streptococcus pyogenes, Streptococcus agalactiae, Streptococcus pneumoniae, Enterococcus faecalis, Enterococcus faecium, Bacillus anthracis, Corynebacterium diphtheria, Clostridium perfringens, Clostridium botulinum, Clostridium tetani,* and *Clostridium difficile*. In another exemplary embodiment, the gram-positive bacterium is selected from the group consisting of *Staphylococcus aureus, Staphylococcus epidermidis, Streptococcus pneumoniae, Streptococcus pyogenes, Enterococcus faecalis, Enterococcus faecium, Clostridium difficile,* and *Propionibacter acnes*. In another exemplary embodiment, the bacterium is a gram-negative bacterium. In another exemplary embodiment, the gram-negative bacterium is selected from the group consisting of *Acinetobacter* species, *Neisseria* species, *Pseudomonas* species, *Brucella* species, *Agrobacterium* species, *Bordetella* species, *Escherichia* species, *Shigelia* species, *Yersinia* species, *Salmonella* species, *Klebsiella* species, *Enterobacter* species, *Haemophilus* species, *Pasteurella* species, *Streptobacillus* species, spirochetal species, *Campylobacter* species, *Vibrio* species, *Helicobacter* species, *Bacteroides* species, *Citrobacter* species, *Proteus* species, *Providencia* species, *Serratia* species, *Stenotrophomonas* species, and *Burkholderia* species. In another exemplary embodiment, the gram-negative bacterium is selected from the group consisting of *Acinetobacter* species, *Pseudomonas* species, *Escherichia* species, *Klebsiella* species, *Enterobacter* species, *Bacteroides* species, *Citrobacter* species, *Proteus* species, *Providencia* species, *Serratia* species, *Stenotrophomonas* species, and *Burkholderia* species. In another exemplary embodiment, the gram-negative bacterium is selected from the group consisting of *Acinetobacter baumanii, Neisseria gonorrhoeae, Neisseria meningitidis, Pseudomonas aeruginosa, Legionella pneumophila, Escherichia coli, Yersinia pestis, Haemophilus influenzae, Helicobacter pylori, Campylobacter fetus, Campylobacter jejuni, Vibrio cholerae, Vibrio parahemolyticus, Trepomena pallidum, Actinomyces israelii, Rickettsia prowazekii, Rickettsia rickettsii, Chlamydia trachomatis, Chlamydia psittaci, Brucella abortus, Agrobacterium tumefaciens, Francisella tularensis, Klebsiella pneumoniae, Enterobacter cloacae, Acinetobacter baumannii, Bacteroides fragilis, Citrobacter freundii, Proteus mirabilis, Providencia stuartii, Serratia marcescens, Stenotrophomonas maltophilia,* and *Burkholderia cepacia*. In another exemplary embodiment, the gram-negative bacterium is selected from the group consisting of *Pseudomonas aeruginosa, Escherichia coli, Haemophilus influenzae, Klebsiella pneumoniae, Enterobacter cloacae, Acinetobacter baumannii, Bacteroides fragilis, Citrobacter freundii, Proteus mirabilis, Providencia stuartii, Serratia marcescens, Stenotrophomonas maltophilia,* and *Burkholderia cepacia*. In another exemplary embodiment, the gram-negative bacterium is selected from the group consisting of *Enterobacter aerogenes, Enterobacter cloacae, Enterobacter sakazakii, Escherichia coli, Klebsiella pneumoniae, Proteus mirabilis, Serratia marcescens,* and *Citrobacter freundii*. In another exemplary embodiment, the gram-negative bacterium is a *Providencia* spp. In another exemplary embodiment, the gram-negative bacterium is an *Enterobacter* spp.

In another exemplary embodiment, the bacterium is a *Pseudomonas* species. In another exemplary embodiment, the bacterium is *Pseudomonas aeruginosa*. In another exemplary embodiment, the bacterium is selected from the group consisting of *Pseudomonas aeruginosa, Acinetobacter baumannii, Stenotrophomonas maltophilia,* and *Burkholderia cepacia*. In another exemplary embodiment, the bacterium is *Acinetobacter baumannii*. In another exemplary embodiment, the bacterium is *Stenotrophomonas maltophilia*. In another exemplary embodiment, the bacterium is *Burkholderia cepacia*. In another exemplary embodiment, the bacterium is *Acinetobacter* species. In another exemplary embodiment, the bacterium is *Acinetobacter anitratus*. In another exemplary embodiment, the bacterium is selected from the group consisting of *Enterobacter aerogenes, Enterobacter cloacae, Enterobacter sakazakii, E. coli, K. pneumoniae, P. mirabilis, Serratia marcescens, Citrobacter freundii,* and *Providencia* spp. In another exemplary embodiment, the bacterium is selected from the group consisting of *Enterobacter aerogenes, Enterobacter cloacae, Enterobacter sakazakii, E. coli, K. pneumoniae, P. mirabilis, Serratia marcescens, Citrobacter freundii, Providencia* spp., *S. aureus, S. pneumonia, S. pyogenes, E. faecalis,* and *E. faecium*. In another exemplary embodiment, the bacterium is selected from the group consisting of *Pseudomonas aeruginosa, Acinetobacter baumannii, Stenotrophomonas maltophilia, Burkholderia cepacia*. In another exemplary embodiment, the bacterium is selected from the group consisting of *S. aureus, S. pneumonia, S. pyogenes, E. faecalis,* and *E. faecium*. In another exemplary embodiment, the bacterium is Viridans group Strep. In another exemplary embodiment, the bacterium is selected from the group consisting of *Strep. mitis, Strep. mutans, Strep. oxalis, Strep. sanguis, Strep. sobrinus,* and *Strep. millari*. In another exemplary embodiment, the bacterium is *S. pneumonia*. In another exemplary embodiment, the bacterium is *H. influenzae*. In another exemplary embodiment, the bacterium is *S. aureus*. In another exemplary embodiment, the bacterium is from the *Mycobacterium* species. In another exemplary embodiment, the bacterium is *M. catarrhalis*. In another exemplary embodiment, the bacterium is *M. pneumoniae*. In another exemplary embodiment, the bacterium is *L. pneumoniae*. In another exemplary embodiment, the bacterium is *C. pneumoniae*. In another exemplary embodiment, the bacterium is *S. pyogenes*. In another exemplary embodiment, the bacterium is an anaerobe. In another exemplary embodiment, the bacterium is an *Alcaligenes* species. In another exemplary embodiment, the bacterium is a *B. cepacia*. In another exemplary embodiment, the bacterium is selected from the group consisting of *Enterobacter cloacae, Escherichia coli, Klebsiella pneumoniae, Proteus mirabilis, Providencia stuartii, Serratia marcescens,* and *Citrobacter freundii*. In another exemplary embodiment, the bacterium is resistant to methicillin. In another exemplary embodiment, the bacterium is methicillin-resistant *staphylococcus aureus*. In another exemplary embodiment, the bacterium is selected from the group consisting of *Streptococcus pneumoniae, Haemophilus influenzae, Staphylococcus aureus, Mycobacterium catarrhalis, Mycobacterium pneumoniae, Legionella pneumophila,* and *Chlamydia pneumoniae*. In another exemplary embodiment, the bacterium is selected from the group consisting of *Enterobacter cloacae, Escherichia coli, Klebsiella pneumoniae, Proteus mirabilis, Serratia marcescens, Citrobacter freundii, Providencia stuartii, Pseudomonas aeruginosa, Acinetobacter baumannii, Stenotrophomonas maltophilia, Burkholderia cepacia, Staphylococcus aureus, Streptococcus pneumoniae, Streptococcus pyogenes, Enterococcus faecalis,* and *Enterococcus faecium*. In another exemplary embodiment, the bacterium is selected from the group consisting of *Staphylococcus aureus, Staphylococcus epidermidis, Staphylococcus haemolyticus, Streptococcus pyogenes, Streptococcus agalactiae,* and *Streptococcus pneumoniae*.

In an exemplary embodiment, the microorganism is a bacterium, which is selected from the group consisting of acid-fast bacteria, including *Mycobacterium* species, bacilli, including *Bacillus* species, *Corynebacterium* species (also *Propionibacterium*) and *Clostridium* species, filamentous bacteria, including *Actinomyces* species and *Streptomyces* species, bacilli, such as *Pseudomonas* species, *Brucella* species, *Agrobacterium* species, *Bordetella* species, *Escherichia* species, *Shigella* species, *Yersinia* species, *Salmonella* species, *Klebsiella* species, *Enterobacter* species, *Haemophilus* species, *Pasteurella* species, and *Streptobacillus* species, spirochetal species, *Campylobacter* species, *Vibrio* species, and intracellular bacteria including *Rickettsiae* species and *Chlamydia* species.

IV. c) Microorganism Infection

The compounds of the invention and/or combinations of the invention exhibit potency against microorganisms, such as bacteria, and therefore have the potential to be used to treat and/or prevent a microorganism infection, such as a bacterial infection.

In a further aspect, the invention provides a method of treating a bacterial infection comprising administering to an animal suffering from the infection an effective amount of a compound of the invention, or a pharmaceutically acceptable salt thereof, thereby treating the bacterial infection. In an exemplary embodiment, the invention provides a method of treating a bacterial infection comprising administering to an animal suffering from the infection an effective amount of a compound of the invention, or a pharmaceutically acceptable salt thereof, and an effective amount of an antibiotic, or a pharmaceutically acceptable salt thereof, thereby treating the bacterial infection.

In a further aspect, the invention provides a method of preventing a bacterial infection comprising administering to an animal a prophylactic amount of a compound of the invention, or a pharmaceutically acceptable salt thereof, thereby treating the bacterial infection. In an exemplary embodiment, the invention provides a method of preventing a bacterial infection comprising administering to an animal a prophylactic amount of a compound of the invention, or a pharmaceutically acceptable salt thereof, and an effective amount of an antibiotic, or a pharmaceutically acceptable salt thereof, thereby treating the bacterial infection.

In an exemplary embodiment, the compound used in the method is described herein, or a salt, prodrug, hydrate or solvate thereof, or a combination thereof. In an exemplary embodiment, the compound used in the method is described herein, or a salt, hydrate or solvate thereof. In an exemplary embodiment, compound used in the method is described herein, or a prodrug thereof. In an exemplary embodiment, the compound used in the method is described herein, or a salt thereof. In another exemplary embodiment, the compound of the invention is a compound described herein, or a pharmaceutically acceptable salt thereof. In another exemplary embodiment, the compound is described by a formula listed herein, or a pharmaceutically acceptable salt thereof. In an exemplary embodiment, the compound is part of a combination described herein. In an exemplary embodiment, the compound is part of a pharmaceutical formulation described herein. In another exemplary embodiment, the administering occurs under conditions which permit entry of the compound into the animal, and subsequently into the bacteria. Such conditions are known to one skilled in the art and specific conditions are set forth herein.

In another aspect, the microorganism is inside, or on the surface of an animal. In an exemplary embodiment, the animal is selected from the group consisting of human, cattle, deer, reindeer, goat, honey bee, pig, sheep, horse, cow, bull, dog, guinea pig, gerbil, rabbit, cat, camel, yak, elephant, ostrich, otter, chicken, duck, goose, guinea fowl, pigeon, swan, and turkey. In another exemplary embodiment, the animal is a human.

In an exemplary embodiment, the bacterial infection is treated and/or prevented through oral administration of the compound of the invention and/or the combination of the invention. In an exemplary embodiment, the bacterial infection is treated and/or prevented through intravenous administration of the compound of the invention and/or the combination of the invention. In an exemplary embodiment, the bacterial infection is treated and/or prevented through topical administration of the compound of the invention and/or the combination of the invention.

In an exemplary embodiment, the bacterial infection is caused by and/or associated with a gram-positive bacteria. In another exemplary embodiment, the gram-positive bacterium is selected from the group consisting of *Staphylococcus* species, *Streptococcus* species, *Bacillus* species, *Mycobacterium* species, *Corynebacterium* species (*Propionibacterium* species), *Clostridium* species, *Actinomyces* species, *Enterococcus* species and *Streptomyces* species. In another exemplary embodiment, the gram-positive bacterium is selected from the group consisting of *Propionibacterium acnes, Staphylococcus aureus, Staphylococcus epidermidis, Staphylococcus saprophyticus, Staphylococcus haemolyticus, Streptococcus pyogenes, Streptococcus agalactiae, Streptococcus pneumoniae, Enterococcus faecalis, Enterococcus faecium, Bacillus anthracis, Mycobacterium avium-intracellulare, Mycobacterium tuberculosis, Corynebacterium diphtheria, Clostridium perfringens, Clostridium botulinum, Clostridium tetani,* and *Clostridium difficile*. In another exemplary embodiment, the gram-positive bacterium is selected from the group consisting of *Staphylococcus aureus, Staphylococcus epidermidis, Streptococcus pneumoniae, Streptococcus pyogenes, Enterococcus faecalis, Enterococcus faecium, Clostridium difficile,* and *Propionibacter acnes*.

In an exemplary embodiment, the bacterial infection is caused by and/or associated with a gram-negative bacterium. In another exemplary embodiment, the gram-negative bacterium is selected from the group consisting of *Acinetobacter* species, *Neisseria* species, *Pseudomonas* species, *Brucella* species, *Agrobacterium* species, *Bordetella* species, *Escherichia* species, *Shigelia* species, *Yersinia* species, *Salmonella* species, *Klebsiella* species, *Enterobacter* species, *Haemophilus* species, *Pasteurella* species, *Streptobacillus* species, spirochetal species, *Campylobacter* species, *Vibrio* species, *Helicobacter* species, *Bacteroides* species, *Citrobacter* species, *Proteus* species, *Providencia* species, *Serratia* species, *Stenotrophomonas* species, and *Burkholderia* species. In another exemplary embodiment, the gram-negative bacterium is selected from the group consisting of *Acinetobacter* species, *Pseudomonas* species, *Escherichia* species, *Klebsiella* species, *Enterobacter* species, *Bacteroides* species, *Citrobacter* species, *Proteus* species, *Providencia* species, *Serratia* species, *Stenotrophomonas* species, and *Burkholderia* species. In another exemplary embodiment, the gram-negative bacterium is selected from the group consisting of *Neisseria gonorrhoeae, Neisseria meningitidis, Pseudomonas aeruginosa, Legionella pneumophila, Escherichia coli, Yersinia pestis, Haemophilus influenzae, Helicobacter pylori, Campylobacter fetus, Campylobacter jejuni, Vibrio cholerae, Vibrio parahemolyticus, Trepomena pallidum, Actinomyces israelii, Rickettsia prowazekii, Rickettsia rickettsii, Chlamydia trachomatis, Chlamydia psittaci, Brucella abortus, Agrobacterium tumefaciens, Francisella tularensis, Klebsiella pneumoniae, Enterobacter cloacae, Acinetobacter baumannii, Bacteroides fragilis, Citrobacter freundii, Proteus mirabilis, Providencia stuartii, Serratia marcescens, Stenotrophomonas maltophilia*, and *Burkholderia cepacia*. In another exemplary embodiment, the gram-negative bacterium is selected from the group consisting of *Pseudomonas aeruginosa, Escherichia coli, Haemophilus influenzae, Klebsiella pneumoniae, Enterobacter cloacae, Acinetobacter baumannii, Bacteroides fragilis, Citrobacter freundii, Proteus mirabilis, Providencia stuartii, Serratia marcescens, Stenotrophomonas maltophilia* and *Burkholderia cepacia*. In another exemplary embodiment, the gram-negative bacterium is selected from the group consisting of *Enterobacter aerogenes, Enterobacter cloacae, Enterobacter sakazakii, Escherichia coli, Klebsiella pneumoniae, Proteus mirabilis, Serratia marcescens* and *Citrobacter freundii*. In another exemplary embodiment, the gram-negative bacterium is a *Providencia* spp. In another exemplary embodiment, the gram-negative bacterium is an *Enterobacter* spp.

In another exemplary embodiment, the bacterial infection is caused by and/or associated with a *Pseudomonas* species. In another exemplary embodiment, the bacterial infection is caused by and/or associated with *Pseudomonas aeruginosa*. In another exemplary embodiment, the bacterial infection is caused by and/or associated with a member selected from the group consisting of *Pseudomonas aeruginosa, Acinetobacter baumannii, Stenotrophomonas maltophilia*, and *Burkholderia cepacia*. In another exemplary embodiment, the bacterial infection is caused by and/or associated with *Acinetobacter baumannii*. In another exemplary embodiment, the bacterial infection is caused by and/or associated with *Stenotrophomonas maltophilia*. In another exemplary embodiment, the bacterial infection is caused by and/or associated with *Burkholderia cepacia*. In another exemplary embodiment, the bacterial infection is caused by and/or associated with *Acinetobacter* species. In another exemplary embodiment, the bacterial infection is caused by and/or associated with *Acinetobacter anitratus*. In another exemplary embodiment, the bacterial infection is caused by and/or associated with a member selected from the group consisting of *Enterobacter aerogenes, Enterobacter cloacae, Enterobacter sakazakii, E. coli, K. pneumoniae, P. mirabilis, Serratia marcescens, Citrobacter freundii* and *Providencia* spp. In another exemplary embodiment, the bacterial infection is caused by and/or associated with a member selected from the group consisting of *Enterobacter aerogenes, Enterobacter cloacae, Enterobacter sakazakii, E. coli, K. pneumoniae, P. mirabilis, Serratia marcescens, Citrobacter freundii, Providencia* spp., *S. aureus, S. pneumonia, S. pyogenes, E. faecalis*, and *E. faecium*. In another exemplary embodiment, the bacterial infection is caused by and/or associated with a member selected from the group consisting of *Pseudomonas aeruginosa, Acinetobacter baumannii, Stenotrophomonas maltophilia, Burkholderia cepacia*. In another exemplary embodiment, the bacterial infection is caused by and/or associated with a member selected from the group consisting of *S. aureus, S. pneumonia, S. pyogenes, E. faecalis*, and *E. faecium*. In another exemplary embodiment, the bacterial infection is caused by and/or associated with Viridans group *Strep*. In another exemplary embodiment, the bacterial infection is caused by and/or associated with a member selected from the group consisting of *Strep. mitis, Strep. mutans, Strep. oxalis, Strep. sanguis, Strep. sobrinus* and *Strep. millari*. In another exemplary embodiment, the bacterial infection is caused by and/or associated with *S. pneumonia*. In another exemplary embodiment, the bacterial infection is caused by and/or associated with *H. influenzae*. In another exemplary embodiment, the bacterial infection is caused by and/or associated with *S. aureus*. In another exemplary embodiment, the bacterial infection is caused by and/or associated with *M catarrhalis*. In another exemplary embodiment, the bacterial infection is caused by and/or associated with *M. pneumoniae*. In another exemplary embodiment, the bacterial infection is caused by and/or associated with *L. pneumoniae*. In another exemplary embodiment, the bacterial infection is caused by and/or associated with *C. pneumoniae*. In another exemplary embodiment, the bacterial infection is caused by and/or associated with *S. pyogenes*. In another exemplary embodiment, the bacterial infection is caused by and/or associated with an anaerobe. In another exemplary embodiment, the bacterial infection is caused by and/or associated with *Alcaligenes* species. In another exemplary embodiment, the bacterial infection is caused by and/or associated with *B. cepacia*. In another exemplary embodiment, the bacterial infection is caused by and/or associated with a member selected from the group consisting of *Enterobacter cloacae, Escherichia coli, Klebsiella pneumoniae, Proteus mirabilis, Providencia stuartii, Serratia marcescens*, and *Citrobacter freundii*. In another exemplary embodiment, the bacterial infection is caused by and/or associated with a bacteria which is resistant to methicillin. In another exemplary embodiment, the bacterial infection is caused by and/or associated with methicillin-resistant *Staphylococcus aureus*. In another exemplary embodiment, the bacterial infection is caused by and/or associated with a member selected from the group consisting of *Streptococcus pneumoniae, Haemophilus influenzae, Staphylococcus aureus, Mycobacterium catarrhalis, Mycobacterium pneumoniae, Legionella pneumophila*, and *Chlamydia pneumoniae*. In another exemplary embodiment, the bacterial infection is caused by and/or associated with a member selected from the group consisting of *Enterobacter cloacae, Escherichia coli, Klebsiella pneumoniae, Proteus mirabilis, Serratia marcescens, Citrobacter freundii, Providencia stuartii, Pseudomonas aeruginosa, Acinetobacter baumannii, Stenotrophomonas maltophilia, Burkholderia cepacia, Sta-*

*phylococcus aureus, Streptococcus pneumoniae, Streptococcus pyogenes, Enterococcus faecalis,* and *Enterococcus faecium*. In another exemplary embodiment, the bacterial infection is caused by and/or associated with a member selected from the group consisting of *Staphylococcus aureus, Staphylococcus epidermidis, Staphylococcus haemolyticus, Streptococcus pyogenes, Streptococcus agalactiae,* and *Streptococcus pneumoniae*.

In an exemplary embodiment, the bacterial infection is caused by and/or associated with a member selected from the group consisting of acid-fast bacteria, including *Mycobacterium* species, bacilli, including *Bacillus* species, *Corynebacterium* species (also *Propionibacterium*) and *Clostridium* species, filamentous bacteria, including *Actinomyces* species and *Streptomyces* species, bacilli, such as *Pseudomonas* species, *Brucella* species, *Agrobacterium* species, *Bordetella* species, *Escherichia* species, *Shigella* species, *Yersinia* species, *Salmonella* species, *Klebsiella* species, *Enterobacter* species, *Haemophilus* species, *Pasteurella* species, and *Streptobacillus* species, spirochetal species, *Campylobacter* species, *Vibrio* species, and intracellular bacteria including *Rickettsiae* species and *Chlamydia* species.

IV. d) Diseases

The compounds of the invention and/or combinations of the invention exhibit potency against microorganisms, such as bacteria, and therefore have the potential to achieve therapeutic efficacy in the animals described herein.

In another aspect, the invention provides a method of treating and/or preventing a disease. In an exemplary embodiment, the method includes administering to the animal a therapeutically effective amount of a compound of the invention, sufficient to treat and/or prevent the disease. In an exemplary embodiment, the method includes administering to the animal a therapeutically effective amount of a combination of the invention, sufficient to treat and/or prevent the disease. In an exemplary embodiment, the compound of the invention or the combination of the invention can be used in human or veterinary medical therapy, particularly in the treatment or prophylaxis of bacterial-associated disease. In an exemplary embodiment, the compound is described herein, or a salt, prodrug, hydrate or solvate thereof, or a combination thereof. In an exemplary embodiment, the invention provides a compound described herein, or a prodrug thereof. In an exemplary embodiment, the invention provides a compound described herein, or a salt, hydrate or solvate thereof. In an exemplary embodiment, the invention provides a compound described herein, or a salt thereof. In another exemplary embodiment, the compound of the invention is a compound described herein, or a pharmaceutically acceptable salt thereof. In an exemplary embodiment, the compound is a compound described herein, or a pharmaceutically acceptable salt thereof. In an exemplary embodiment, the compound is according to a formula described herein, or a pharmaceutically acceptable salt thereof. In an exemplary embodiment, the compound is part of a combination described herein. In an exemplary embodiment, the compound is part of a pharmaceutical formulation described herein. In another exemplary embodiment, the animal is selected from the group consisting of human, cattle, deer, reindeer, goat, honey bee, pig, sheep, horse, cow, bull, dog, guinea pig, gerbil, rabbit, cat, camel, yak, elephant, ostrich, otter, chicken, duck, goose, guinea fowl, pigeon, swan, and turkey. In another exemplary embodiment, the animal is a human. In another exemplary embodiment, the animal is selected from the group consisting of a human, cattle, goat, pig, sheep, horse, cow, bull, dog, guinea pig, gerbil, rabbit, cat, chicken and turkey. In another exemplary embodiment, the disease is a systemic disease. In another exemplary embodiment, the disease is a topical disease.

In an exemplary embodiment, the disease is treated through oral administration of a compound of the invention and/or a combination of the invention. In an exemplary embodiment, the disease is treated through topical administration of a compound of the invention and/or a combination of the invention. In an exemplary embodiment, the disease is treated through intravenous administration of a compound of the invention and/or a combination of the invention.

Systemic Diseases

In another aspect, the invention provides a method of treating a systemic disease. The method involves contacting an animal with a compound of the invention and/or a combination of the invention.

In another exemplary embodiment, the disease is associated with infection by a Gram-positive bacteria. In an exemplary embodiment, the disease is associated with a *Staphylococcus* species. In another exemplary embodiment, the disease is selected from the group consisting of pneumonia, gastroenteritis, toxic shock syndrome, community acquired pneumonia (CAP), meningitis, septic arthritis, urinary tract infection, bacteremia, endocarditis, osteomylitis, skin and skin-structure infection. In an exemplary embodiment, the disease is associated with a *Streptococcus* species. In another exemplary embodiment, the disease is selected from the group consisting of strep throat, skin infections, necrotizing fasciitis, toxic shock syndrome, pneumonia, otitis media and sinusitis. In an exemplary embodiment, the disease is associated with an *Actinomyces* species. In another exemplary embodiment, the disease is actinomycosis. In an exemplary embodiment, the disease is associated with a *Norcardia* species. In another exemplary embodiment, the disease is pneumonia. In an exemplary embodiment, the disease is associated with a *Corynebacterium* species. In another exemplary embodiment, the disease is diptheria. In an exemplary embodiment, the disease is associated with a *Listeria* species. In another exemplary embodiment, the disease is meningitis. In an exemplary embodiment, the disease is associated with a *Bacillus* species. In another exemplary embodiment, the disease is anthrax or food poisoning. In an exemplary embodiment, the disease is associated with a *Clostridium* species. In another exemplary embodiment, the disease is selected from the group consisting of botulism, tetanus, gas gangrene, and diarrhea. In an exemplary embodiment, the disease is associated with a *Mycobacterium* species. In another exemplary embodiment, the disease is tuberculosis or leprosy.

In another exemplary embodiment, the disease is associated with infection by a Gram-negative bacteria. In an exemplary embodiment, the disease is associated with a *Neisseria* species. In another exemplary embodiment, the disease is selected from the group consisting of meningitis, gonorrhea, otitis extema, and folliculitis. In an exemplary embodiment, the disease is associated with an *Escherichia* species. In another exemplary embodiment, the disease is selected from the group consisting of diarrhea, urinary tract infections, meningitis, sepsis, and HAP. In an exemplary embodiment, the disease is associated with a *Shigella* species. In another exemplary embodiment, the disease is selected from the group consisting of diarrhea, bacteremia, endocarditis, meningitis, and gastroenteritis. In an exemplary embodiment, the disease is associated with a *Salmonella* species. In another exemplary embodiment, the disease is selected from the group consisting of Typhoid fever, supsis, gastroenteritis, endocarditis, sinusitis, and meningitis. In an exemplary embodiment, the disease is associated with a *Yersinia* species.

In another exemplary embodiment, the disease is selected from the group consisting of Typhoid fever, bubonic plague, enteric fever, and gastroenteritis. In an exemplary embodiment, the disease is associated with a *Klebsiella* species. In another exemplary embodiment, the disease is sepsis or urinary tract infection. In an exemplary embodiment, the disease is associated with a *Proteus* species. In another exemplary embodiment, the disease is an urinary tract infection. In an exemplary embodiment, the disease is associated with an *Enterobacter* species. In another exemplary embodiment, the disease is a hospital-acquired infection. In an exemplary embodiment, the disease is associated with a *Serratia* species. In another exemplary embodiment, the disease is selected from the group consisting of urinary tract infection, skin and skin-structure infection and pneumonia. In an exemplary embodiment, the disease is associated with a *Vibrio* species. In another exemplary embodiment, the disease is cholera or gastroenteritis. In an exemplary embodiment, the disease is associated with a *Campylobacter* species. In another exemplary embodiment, the disease is gastroenteritis. In an exemplary embodiment, the disease is associated with a *Helicobacter* species. In another exemplary embodiment, the disease is chronic gastritis. In an exemplary embodiment, the disease is associated with a *Pseudomonas* species. In another exemplary embodiment, the disease is selected from the group consisting of pneumonia, osteomylitis, burn-wound infections, sepsis, UTIs, endocarditis, otitis, and corneal infections. In an exemplary embodiment, the disease is associated with a *Bacteroides* species. In another exemplary embodiment, the disease is periodontal disease or aspriation pneumonia. In an exemplary embodiment, the disease is associated with a *Haemophilus* species. In another exemplary embodiment, the disease is selected from the group consisting of meningitis, epiglottitis, septic arthritis, sepsis, chancroid, and vaginitis. In an exemplary embodiment, the disease is associated with a *Bordetella* species. In another exemplary embodiment, the disease is whooping cough. In an exemplary embodiment, the disease is associated with a *Legionella* species. In another exemplary embodiment, the disease is pneumonia or pontiac fever. In an exemplary embodiment, the disease is associated with a *Francisella* species. In another exemplary embodiment, the disease is tularemia. In an exemplary embodiment, the disease is associated with a *Brucella* species. In another exemplary embodiment, the disease is brucellosis. In an exemplary embodiment, the disease is associated with a *Pasteurella* species. In another exemplary embodiment, the disease is a skin infection. In an exemplary embodiment, the disease is associated with a *Gardnerella* species. In another exemplary embodiment, the disease is vaginitis. In an exemplary embodiment, the disease is associated with a *Spirochetes* species. In another exemplary embodiment, the disease is syphilis or Lyme disease. In an exemplary embodiment, the disease is associated with a *Chlamydia* species. In another exemplary embodiment, the disease is chlamydia. In an exemplary embodiment, the disease is associated with a *Rickettsiae* species. In another exemplary embodiment, the disease is Rocky Mountain spotted fever or typhus.

In an exemplary embodiment, the disease is associated with *Mycoplasma pneumoniae*. In another exemplary embodiment, the disease is tracheobronchitis or walking pneumonia. In an exemplary embodiment, the disease is associated with *Ureaplasma urealyticum*. In another exemplary embodiment, the disease is urethritis. In another exemplary embodiment, the disease is pyelonephritis. In another exemplary embodiment, the disease is an intra-abdominal infection. In another exemplary embodiment, the disease is febrile neutropenia. In another exemplary embodiment, the disease is a pelvic infection. In another exemplary embodiment, the disease is bacteraemia. In another exemplary embodiment, the disease is septicaemia.

In an exemplary embodiment, the disease is an acute exacerbation of chronic obstructive pulmonary disease. In an exemplary embodiment, the disease is chronic obstructive pulmonary disease. In an exemplary embodiment, the disease is pharyngitis. In an exemplary embodiment, the disease is tonsillitis. In an exemplary embodiment, the disease is Acute Exacerbation of Chronic Bronchitis (AECB). In an exemplary embodiment, the disease is cervicitis. In an exemplary embodiment, the disease is genital ulcer disease.

In an exemplary embodiment, for any of the methods described herein, a compound of the invention, a combination of the invention, a compound described herein or a pharmaceutically acceptable salt thereof, or combination described herein, and/or a pharmaceutical formulation described herein can be used.

In an exemplary embodiment, for any of the methods described herein, a compound of the invention, a compound or formulation described herein or a pharmaceutically acceptable salt thereof and/or a pharmaceutical formulation described herein can be used.

In an exemplary embodiment, the disease is selected from the group consisting of febrile neutropenia, CNS infections due to susceptible pathogens, hospital acquired pneumonia, complicated/uncom UTI, pyelonephritis, Intra-abdominal infections, concurrent bacteraemia, cellulitis, febrile neutropenia—empirical therapy, 'Intra-abdominal' infections, bronchitis, lower respiratory tract infections, gynecologic infections, bacterial septicaemia, bone and joint infections, endocarditis, polymicrobic infections, and bacterial meningitis.

V. Pharmaceutical Formulation

In another aspect, the invention provides a pharmaceutical formulation comprising: a) a compound of the invention; and b) a pharmaceutically acceptable excipient. In another aspect, the invention provides a pharmaceutical formulation comprising: a) a combination of the invention; and b) a pharmaceutically acceptable excipient. In an exemplary embodiment, the compound is according to a formula described herein. In an exemplary embodiment, the compound is according to an example described herein. In an exemplary embodiment, the compound of the invention in the pharmaceutical formulation is a compound described herein. In an exemplary embodiment, the compound of the invention in the pharmaceutical formulation is a pharmaceutically acceptable salt of a compound described herein.

In an exemplary embodiment, the compound of the invention is present in the pharmaceutical formulation in an amount of between about 0.0001% to about 60% (w/w). In an exemplary embodiment, the amount is between about 0.01% to about 10% (w/w). In an exemplary embodiment, the amount is between about 0.1% to about 10% (w/w). In an exemplary embodiment, the amount is between about 0.25% to about 6% (w/w). In an exemplary embodiment, the amount is between about 0.5% to about 5% (w/w). In an exemplary embodiment, the amount is between about 0.1% and about 1.0% (w/w). In an exemplary embodiment, the amount is between about 1.0% and about 2.0% (w/w). In an exemplary embodiment, the amount is between about 2.0% and about 3.0% (w/w). In an exemplary embodiment, the amount is between about 3.0% and about 4.0% (w/w). In an exemplary embodiment, the amount is between about 4.0% and about 5.0% (w/w).

The pharmaceutical formulations of the invention can take a variety of forms adapted to the chosen route of administration. Those skilled in the art will recognize various synthetic methodologies that may be employed to prepare non-toxic pharmaceutical formulations incorporating the compounds described herein. Those skilled in the art will recognize a wide variety of non-toxic pharmaceutically acceptable solvents that may be used to prepare solvates of the compounds of the invention, such as water, ethanol, propylene glycol, mineral oil, vegetable oil and dimethylsulfoxide (DMSO).

The pharmaceutical formulation of the invention may be administered orally, topically, intraperitoneally, parenterally, by inhalation or spray or rectally in unit dosage forms containing conventional non-toxic pharmaceutically acceptable carriers, adjuvants and vehicles. It is further understood that the best method of administration may be a combination of methods. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques. In an exemplary embodiment, the pharmaceutical formulation is administered orally. In an exemplary embodiment, the pharmaceutical formulation is administered intravenously. In an exemplary embodiment, the pharmaceutical formulation is administered topically. In an exemplary embodiment, the pharmaceutical formulation is administered in a topically effective dose. In an exemplary embodiment, the pharmaceutical formulation is administered in a cosmetically effective dose. In an exemplary embodiment, the pharmaceutical formulation is administered in an orally effective dose.

The pharmaceutical formulations containing compounds of the invention are preferably in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known in the art for the manufacture of pharmaceutical formulations, and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; and dispersing or wetting agents, which may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical formulations of the invention may also be in the form of oil-in-water emulsions and water-in-oil emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth; naturally-occurring phosphatides, for example soy bean, lecithin, and esters or partial esters derived from fatty acids and hexitol; anhydrides, for example sorbitan monooleate; and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical formulations may be in the form of a sterile injectable aqueous or oleaginous suspension. This suspension may be formulated according to the known art using those suitable dispersing or wetting agents and suspending agents, which have been mentioned above. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The composition of the invention may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Alternatively, the compositions can be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For administration to non-human animals, the composition containing the therapeutic compound may be added to the animal's feed or drinking water. Also, it will be convenient to formulate animal feed and drinking water products so that the animal takes in an appropriate quantity of the compound in its diet. It will further be convenient to present the compound in a composition as a premix for addition to the feed or drinking water. The composition can also added as a food or drink supplement for humans.

Dosage levels of the order of from about 5 mg to about 250 mg per kilogram of body weight per day and more preferably from about 25 mg to about 150 mg per kilogram of body weight per day, are useful in the treatment of the above-indicated conditions. The amount of active ingredient that may be combined with the carrier materials to produce a unit dosage form will vary depending upon the condition being treated and the particular mode of administration. Unit dosage forms will generally contain between from about 1 mg to about 500 mg of an active ingredient.

Frequency of dosage may also vary depending on the compound used and the particular disease treated. However, for treatment of most disorders, a dosage regimen of 4 times daily or less is preferred. It will be understood, however, that the specific dose level for any particular patient will depend upon a variety of factors including the activity of the specific compound employed, the age, body weight, general health, sex, diet, time of administration, route of administration and rate of excretion, drug combination and the severity of the particular disease undergoing therapy.

In an exemplary embodiment, the unit dosage form contains from about 1 mg to about 800 mg of a compound of the invention. In an exemplary embodiment, the unit dosage form contains from about 1 mg to about 500 mg of an active ingredient. In an exemplary embodiment, the unit dosage form contains from about 100 mg to about 800 mg of a compound of the invention. In an exemplary embodiment, the unit dosage form contains from about 200 mg to about 500 mg of a compound of the invention. In an exemplary embodiment, the unit dosage form contains from about 500 mg to about 800 mg of a compound of the invention. In an exemplary embodiment, the unit dosage form contains from about 1 mg to about 100 mg of a compound of the invention. In an exemplary embodiment, the unit dosage form contains from about 10 mg to about 100 mg of a compound of the invention. In an exemplary embodiment, the unit dosage form contains from about 50 mg to about 100 mg of a compound of the invention. In an exemplary embodiment, the unit dosage form contains from about 25 mg to about 75 mg of a compound of the invention. In an exemplary embodiment, the unit dosage form contains from about 40 mg to about 60 mg of a compound of the invention. In an exemplary embodiment, the unit dosage form contains from about 75 mg to about 200 mg of a compound of the invention. In an exemplary embodiment, the unit dosage form contains from about 1 mg to about 5 mg of a compound of the invention. In an exemplary embodiment, the unit dosage form contains from about 10 mg to about 25 mg of a compound of the invention. In an exemplary embodiment, the unit dosage form contains from about 50 mg to about 350 mg of a compound of the invention. In an exemplary embodiment, the unit dosage form contains from about 200 mg to about 400 mg of a compound of the invention.

In an exemplary embodiment, the daily dosage contains from about 1 mg to about 800 mg of a compound of the invention. In an exemplary embodiment, the daily dosage contains from about 1 mg to about 500 mg of an active ingredient. In an exemplary embodiment, the daily dosage contains from about 100 mg to about 800 mg of a compound of the invention. In an exemplary embodiment, the daily dosage contains from about 200 mg to about 500 mg of a compound of the invention. In an exemplary embodiment, the daily dosage contains from about 500 mg to about 800 mg of a compound of the invention. In an exemplary embodiment, the daily dosage contains from about 1 mg to about 100 mg of a compound of the invention. In an exemplary embodiment, the daily dosage contains from about 10 mg to about 100 mg of a compound of the invention. In an exemplary embodiment, the daily dosage contains from about 50 mg to about 100 mg of a compound of the invention. In an exemplary embodiment, the daily dosage contains from about 75 mg to about 200 mg of a compound of the invention. In an exemplary embodiment, the daily dosage contains from about 1 mg to about 5 mg of a compound of the invention. In an exemplary embodiment, the daily dosage contains from about 10 mg to about 25 mg of a compound of the invention. In an exemplary embodiment, the daily dosage contains from about 50 mg to about 350 mg of a compound of the invention. In an exemplary embodiment, the daily dosage contains from about 200 mg to about 400 mg of a compound of the invention.

Preferred compounds of the invention will have desirable pharmacological properties that include, but are not limited to, oral bioavailability, low toxicity, low serum protein binding and desirable in vitro and in vivo half-lives. Penetration of the blood brain barrier for compounds used to treat CNS disorders is necessary, while low brain levels of compounds used to treat peripheral disorders are often preferred.

The amount of the composition required for use in treatment will vary not only with the particular compound selected but also with the route of administration, the nature of the condition being treated and the age and condition of the patient and will ultimately be at the discretion of the attendant physician or clinician.

V. a) Testing

Preferred compounds for use in the pharmaceutical formulations described herein will have certain pharmacological properties. Such properties include, but are not limited to, low toxicity, low serum protein binding and desirable in vitro and in vivo half-lives. Assays may be used to predict these desirable pharmacological properties. Assays used to predict bioavailability include transport across human intestinal cell monolayers, including Caco-2 cell monolayers. Serum protein binding may be predicted from albumin binding assays. Such assays are described in a review by Oravcova et al. (1996, *J. Chromat*. B677: 1-27).

Toxicity and therapeutic efficacy of such compounds can be determined by standard pharmaceutical procedures in cell cultures or experimental animals, e.g., for determining the LD50 (the dose lethal to 50% of the population) and the $ED_{50}$ (the dose therapeutically effective in 50% of the population).

The dose ratio between toxic and therapeutic effects is the therapeutic index and it can be expressed as the ratio between $LD_{50}$ and $ED_{50}$. Compounds that exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the unit dosage form employed and the route of administration utilized. The exact formulation, route of administration and dosage can be chosen by the individual physician in view of the patient's condition. (See, e.g. Fingl et al., 1975, in "The Pharmacological Basis of Therapeutics", Ch. 1, p. 1).

V. b) Administration

In general, the compounds prepared by the methods, and from the intermediates, described herein will be administered in a therapeutically or cosmetically effective amount by any of the accepted modes of administration for agents that serve similar utilities. It will be understood, however, that the specific dose level for any particular patient will depend upon a variety of factors including the activity of the specific compound employed, the age, body weight, general health, sex, diet, time of administration, route of administration, and rate of excretion, drug combination, the severity of the particular disease undergoing therapy and the judgment of the prescribing physician. The drug can be administered from once or twice a day, or up to 3 or 4 times a day.

Usual patient dosages for systemic administration range from 0.1 to 1000 mg/day, preferably, 1-500 mg/day, more preferably 10-200 mg/day, even more preferably 100-200 mg/day. Stated in terms of patient body surface areas, usual dosages range from 50-91 mg/m²/day.

The amount of the compound in a pharmaceutical formulation can vary within the full range employed by those skilled in the art. Typically, the pharmaceutical formulation will contain, on a weight percent (wt %) basis, from about 0.01-10 wt % of the drug based on the total formulation, with the balance being one or more suitable pharmaceutical excipients. Preferably, the compound is present at a level of about 0.1-3.0 wt %, more preferably, about 1.0 wt %.

Exemplary embodiments are summarized herein below.

In an exemplary embodiment, the invention is a compound having a structure according to the formula:

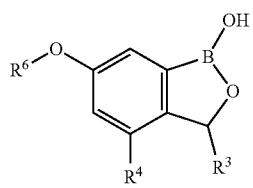

wherein $R^3$ is —$(CH_2)_mC(O)OR^{3a}$, wherein m is an integer selected from 1, 2, 3, 4, 5, or 6; $R^{3a}$ is selected from the group consisting of H, unsubstituted alkyl, and phenyl substituted alkyl; $R^4$ is selected from the group consisting of unsubstituted alkyl, —$OR^{4b}$, —$(CH_2)_n$—O—$(CH_2)_pCH_3$ and halogen, wherein n is an integer selected from 1, 2, 3, 4, 5, or 6, p is an integer selected from 0, 1, 2, 3, 4, 5, or 6; $R^{4b}$ is H or substituted or unsubstituted alkyl; $R^6$ is selected from the group consisting of H, substituted or unsubstituted alkyl, —$C(O)OR^{6a}$, —$C(O)NR^{6a}R^{6b}$, —$S(O_2)R^{6c}$, and A, wherein $R^{6a}$ is H or unsubstituted alkyl; $R^{6b}$ is H or unsubstituted alkyl; $R^{6c}$ is selected from the group consisting of unsubstituted alkyl, $NH_2$ and heteroaryl, optionally substituted with unsubstituted alkyl; A is selected from the group consisting of substituted or unsubstituted cycloalkyl, substituted or unsubstituted heterocycloalkyl, substituted or unsubstituted aryl and substituted or unsubstituted heteroaryl; or a salt thereof.

In an exemplary embodiment, according to the above paragraph, the compound has a having a structure according to the formula:

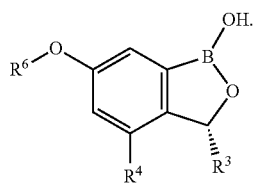

In an exemplary embodiment, according to any of the above paragraphs, $R^{3a}$ is H.

In an exemplary embodiment, according to any of the above paragraphs, $R^4$ is selected from unsubstituted $C_1$, $C_2$, $C_3$, $C_4$, $C_5$, or $C_6$ alkyl, or is selected from unsubstituted $C_1$, $C_2$, $C_3$, $C_4$, $C_5$, or $C_6$ alkoxy.

In an exemplary embodiment, according to any of the above paragraphs, $R^4$ is methyl.

In an exemplary embodiment, according to any of the above paragraphs, m is an integer selected from 1, 2, 3, or 4.

In an exemplary embodiment, according to any of the above paragraphs, $R^3$ is —$CH_2C(O)OH$.

In an exemplary embodiment, according to any of the above paragraphs, $R^4$ is methyl and $R^3$ is —$CH_2C(O)OH$.

In an exemplary embodiment, according to any of the above paragraphs, $R^6$ is H.

In an exemplary embodiment, according to any of the above paragraphs, $R^6$ is selected from unsubstituted $C_1$, $C_2$, or $C_3$ alkyl.

In an exemplary embodiment, according to any of the above paragraphs, $R^6$ is methyl.

In an exemplary embodiment, according to any of the above paragraphs, $R^6$ is —$S(O)_2CH_3$.

In an exemplary embodiment, according to any of the above paragraphs, $R^6$ is A and said A is selected from the group consisting of substituted or unsubstituted phenyl, substituted or unsubstituted tetrahydropyran, substituted or unsubstituted pyrimidinyl, substituted or unsubstituted pyrazinyl, substituted or unsubstituted pyridazinyl, substituted or unsubstituted thiazolyl, and substituted or unsubstituted thiadiazolyl.

In an exemplary embodiment, according to any of the above paragraphs, A is unsubstituted 1,3,4-thiadiazol-2-yl or amino substituted 1,3,4-thiadiazol-2-yl.

In an exemplary embodiment, according to any of the above paragraphs, A is thiazol-2-yl substituted with carbamoyl or carbamimidoyl.

In an exemplary embodiment, according to any of the above paragraphs, A is unsubstituted pyrazin-2-yl or pyrazin-2-yl substituted with aminomethyl or carbamimidoyl.

In an exemplary embodiment, according to any of the above paragraphs, A is pyridin-2-yl substituted with carbamimidoyl.

In an exemplary embodiment, according to any of the above paragraphs, A is 3-(3-aminopropoxy)phenyl.

In an exemplary embodiment, according to any of the above paragraphs, $R^6$ is unsubstituted pyrazin-2-yl and $R^4$ is OH or —$O(CH_2)_3NH_2$.

In an exemplary embodiment, the invention is a combination comprising a) a compound according to any of the above paragraphs, or a pharmaceutically acceptable salt thereof; and b) at least one therapeutic agent.

In an exemplary embodiment, the at least one therapeutic agent which is an antibiotic which comprises a beta-lactam moiety.

In an exemplary embodiment, according to any of the above paragraphs, the at least one therapeutic agent is selected from the group consisting of a penicillin, cephalosporin, cephamycin, monobactam, penem, and carbapenem.

In an exemplary embodiment, the invention is a pharmaceutical formulation comprising a) a compound according to any of the above paragraphs or a combination according to any of the above paragraphs, or a pharmaceutically acceptable salt thereof; and b) a pharmaceutically acceptable excipient.

In an exemplary embodiment, according to any of the above paragraphs, the formulation is a unit dosage form.

In an exemplary embodiment, according to any of the above paragraphs, the formulation is an oral unit dosage form or a topical unit dosage form.

In an exemplary embodiment, the invention is a method of treating a bacterial infection comprising: administering to an animal suffering from said infection an effective amount of a compound described herein, or a pharmaceutically-acceptable salt thereof, and an effective amount of an antibiotic, or a pharmaceutically acceptable salt thereof, wherein said antibiotic comprises a β-lactam moiety, thereby treating the bacterial infection.

In an exemplary embodiment, according to any of the above paragraphs, a bacteria involved with said infection is resistant to said antibiotic.

In an exemplary embodiment, according to any of the above paragraphs, the antibiotic is selected from the group consisting of a penicillin, cephalosporin, cephamycin, monobactam, penem, and carbapenem.

In an exemplary embodiment, according to any of the above paragraphs, the animal is a human.

In an exemplary embodiment, the invention is a use of a compound according to any of the above paragraphs or a combination according to any of the above paragraphs, or a pharmaceutically acceptable salt thereof, in the manufacture of a medicament for the treatment and/or prophylaxis of bacterial infection.

In an exemplary embodiment, the invention is a method of killing or inhibiting the growth of a bacteria, the method comprising: contacting said bacteria with an effective amount of a compound according to any of the above paragraphs or a combination according to any of the above paragraphs, or a pharmaceutically acceptable salt thereof, thereby killing or inhibiting the growth of the bacteria.

In an exemplary embodiment, according to any of the above paragraphs, the method further comprises contacting the bacteria with an effective amount of an antibiotic, or a pharmaceutically acceptable salt thereof, wherein said antibiotic comprises a β-lactam moiety.

In an exemplary embodiment, according to any of the above paragraphs, the bacteria is resistant to said antibiotic.

In an exemplary embodiment, the invention is a method of inhibiting a β-lactamase, comprising contacting the β-lactamase with an effective amount of the compound according to any of the above paragraphs, or a pharmaceutically acceptable salt thereof, thereby inhibiting the β-lactamase.

In an exemplary embodiment, according to any of the above paragraphs, the β-lactamase is selected from the group consisting of a Group 1 β-lactamase, a Group 2 β-lactamase, and a Group 4 β-lactamase.

In an exemplary embodiment, according to any of the above paragraphs, Group 1 β-lactamase is a cephalosporinase.

In an exemplary embodiment, according to any of the above paragraphs, Group 2 β-lactamase is selected from the group consisting of penicillinase, a Group 2b, Group 2be, Group 2br, carbenicillinase, cloxacilanase, cephalosporinase, and carbapenamase.

In an exemplary embodiment, according to any of the above paragraphs, Group 4 β-lactamase is a penicillinase.

In an exemplary embodiment, according to any of the above paragraphs, β-lactamase is selected from the group consisting of a class A β-lactamase, a class B β-lactamase, a class C β-lactamase, and a class D β-lactamase.

In an exemplary embodiment, according to any of the above paragraphs, the class A β-lactamase is selected from the group consisting of a TEM β-lactamase, SHV β-lactamase, CTX-M β-lactamase and a KPC β-lactamase.

In an exemplary embodiment, according to any of the above paragraphs, the class C β-lactamase is a CMY β-lactamase or a AmpC β-lactamase.

In an exemplary embodiment, according to any of the above paragraphs, the class D β-lactamase is an OXA β-lactamase.

In an exemplary embodiment, according to any of the above paragraphs, the contacting takes place in vitro.

The invention is further illustrated by the Examples that follow. The Examples are not intended to define or limit the scope of the invention.

EXAMPLES

Proton NMR are recorded on Varian AS 300 spectrometer and chemical shifts are reported as δ (ppm) down field from tetramethylsilane. Mass spectra are determined on Micromass Quattro II.

Example 1

G1: (4-Ethyl-1,6-dihydroxy-1,3-dihydro-benzo[c][1,2]oxaborol-3-yl)-acetic acid

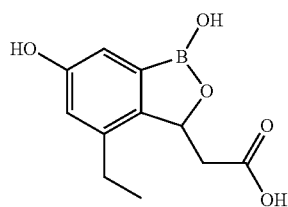 [SMILES: CCc1cc(O)cc2c1C(CC(=O)O)OB2O]

Step 1: 5-Ethyl-benzene-1,3-diol

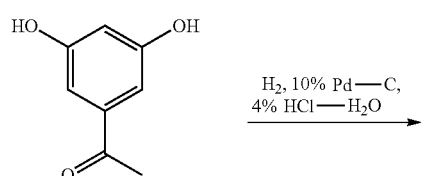

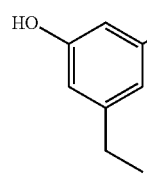

A mixture of 1-(3,5-dihydroxy-phenyl)-ethanone (5 g, 32.89 mmol), 10% Pd—C (1 g) in 4% HCl—H$_2$O (100 mL) was hydrogenated at 1 atmosphere for 16 hours. The mixture was extracted with EtOAc and the organic extracts was dried over anhydrous MgSO$_4$ and concentrated in vacuo. The residue was purified by silica gel flash column chromatography to give 5-ethyl-benzene-1,3-diol (2.37 g, 52%). $^1$H NMR (400 MHz, CDCl$_3$δ 6.26 (s, 2H), 6.20 (s, 1H), 4.78 (s, 2H), 2.55 (m, 2H), 1.20 (m, 3H).

Step 2: 2-Ethyl-4,6-dihydroxy-benzaldehyde

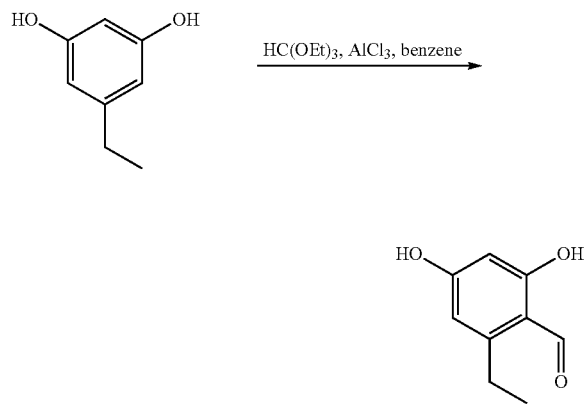

To a suspension of 5-ethyl-benzene-1,3-diol (2.17 g, 15.72 mmol) and triethyl orthoformate (23.26 g, 157 mmol) in benzene (40 mL) was added AlCl$_3$ (6.30 g, 47.16 mmol) at 0° C. The reaction mixture was stirred at room temperature for 30 minutes. After cooling to room temperature, the mixture was poured onto ice and acidified with HCl. The mixture was extracted with EtOAc and the organic extracts was dried over anhydrous MgSO$_4$ and concentrated in vacuo. The residue was purified by silica gel flash column chromatography to give 2-ethyl-4,6-dihydroxy-benzaldehyde (1.0 g, 38%). $^1$H NMR (400 MHz, CDCl$_3$δ 12.40 (s, 1H), 10.08 (s, 1H), 6.25 (s, 1H), 6.00 (s, 1H), 5.80 (s, 1H), 2.90 (m, 2H), 1.30 (m, 3H).

Step 3: 2-Ethyl-6-hydroxy-4-(tetrahydro-pyran-2-yloxy)-benzaldehyde

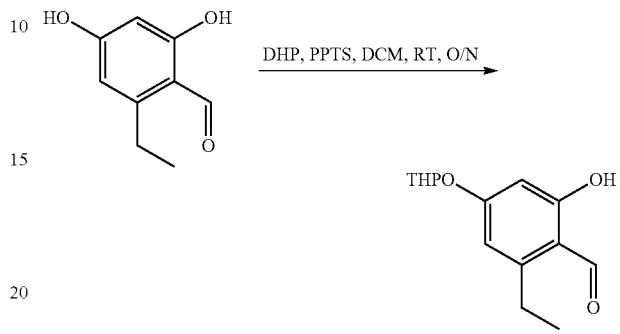

To a mixture of 2-ethyl-4,6-dihydroxy-benzaldehyde (1 g, 6.02 mmol) in dichloromethane (50 mL) was added 3,4-dihydro-2H-pyran (1.1 mL, 12.05 mmol) and pyridium p-toluenesulfonic acid (0.010 g) at room temperature. The resulting mixture was stirred at room temperature for 16 hours then concentrated in vacuo. The residue was purified by silica gel flash column chromatography to give 2-ethyl-6-hydroxy-4-(tetrahydro-pyran-2-yloxy)-benzaldehyde (1.56 g, 100%). $^1$H NMR (400 MHz, CDCl$_3$δ 12.40 (s, 1H), 10.08 (s, 1H), 6.48 (s, 1H), 6.40 (s, 1H), 5.50 (m, 1H), 3.84 (m, 1H), 3.60 (m, 1H), 2.90 (m, 2H), 2.00-1.50 (m, 6H), 1.30 (m, 3H).

Step 4: Trifluoro-methanesulfonic acid 3-ethyl-2-formyl-5-(tetrahydro-pyran-2-yloxy)-phenyl ester

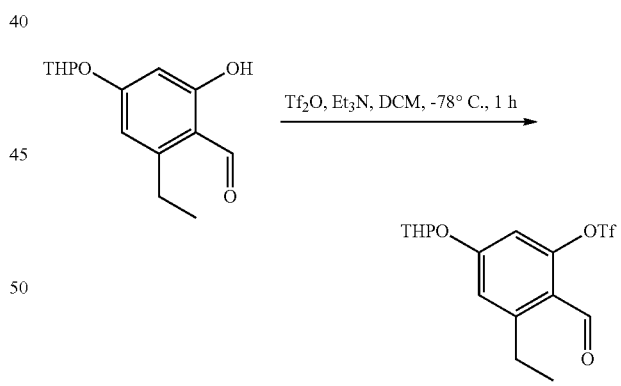

To a solution of 2-ethyl-6-hydroxy-4-(tetrahydro-pyran-2-yloxy)-benzaldehyde (1.56 g, 6.24 mmol) and Et$_3$N (2.61 mL, 18.72 mmol) in dichloromethane (20 mL) was slowly added Tf$_2$O (2.10 mL, 12.84 mmol) at −78° C. The mixture was stirred at −78° C. for 1 hour. The mixture was diluted with H$_2$O and extracted with dichloromethane. The organic extracts were washed with brine, dried and concentrated in vacuo. The residue was dissolved in Hexane-EtOAc(4:1), filtered through a plug of silica gel and filtrate was concentrated to give trifluoro-methanesulfonic acid 3-ethyl-2-formyl-5-(tetrahydro-pyran-2-yloxy)-phenyl ester (2.06 g, quant.). $^1$H NMR (400 MHz, CDCl$_3$δ 12.39 (s, 1H), 10.08 (s, 1H), 6.98 (s, 1H), 6.90 (s, 1H), 5.50 (s, 1H), 3.80 (m, 1H), 3.66 (m, 1H), 3.07 (m, 2H), 2.00-1.50 (m, 6H), 1.26 (m, 3H).

Step 5: 2-Ethyl-4-(tetrahydro-pyran-2-yloxy)-6-(4,4,5,5-tetramethyl-[1.3.2]dioxaborolan-2-yl)-benzaldehyde

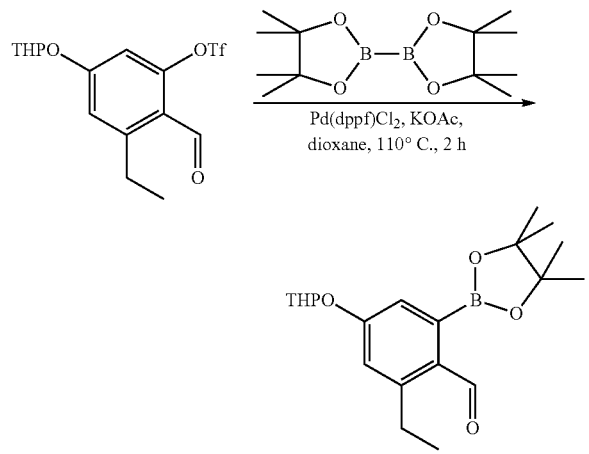

A mixture of trifluoro-methanesulfonic acid 3-ethyl-2-formyl-5-(tetrahydro-pyran-2-yloxy)-phenyl ester (2.06 g, 5.39 mmol), bis(pinacolato)diborane (2.74 g, 10.79 mmol) Pd(dppf)Cl$_2$ (0.39 g, 0.54 mmol) and KOAc (1.59 g, 16.17 mmol) in dioxane (20 mL) was degassed for 10 minutes with bubbling N$_2$. The reaction mixture was heated at 110° C. for 2 hours then diluted with EtOAc (100 mL). The mixture was filtered through a pad of celite and concentrated in vacuo. The residue was purified by silica gel flash column chromatography to give 2-ethyl-4-(tetrahydro-pyran-2-yloxy)-6-(4,4,5,5-tetramethyl-[1,3,2]dioxaborolan-2-yl)-benzaldehyde (2.07 g, quant) as an off-yellow oil. $^1$HNMR (400 MHz, CDCl$_3$): 10.27 (s, 1H), 7.00 (s, 1H), 6.90 (s, 1H), 5.60 (s, 1H), 3.80 (m, 1H), 3.60 (m, 1H), 3.00 (m, 2H), 2.00-1.50 (m, 6H), 1.40 (s, 12H).

Step 6: (4-Ethyl-1,6-dihydroxy-1,3-dihydro-benzo[c][1,2]oxaborol-3-yl)-acetic acid ethyl ester

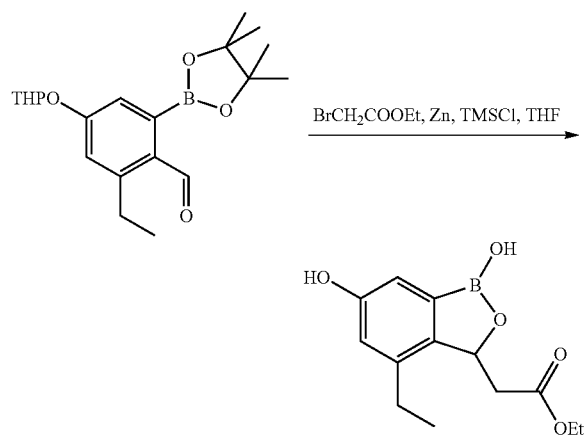

To a suspension of zinc dust (5.35 g, 82.3 mmol) in THF (10 mL) was added trimethylsilyl chloride (1.1 g, 10.15 mmol) at 40° C. The mixture was heated to 55° C. and stirred for 45 minutes. After cooling down to 37° C., ethyl bromoacetate (7.58 mL, 74.87 mmol) was slowly added to the reaction mixture at 37-40° C. After addition, the resulting mixture was allowed to cool to room temperature over 30 minutes. This solution was added to a solution of 2-ethyl-4-(tetrahydro-pyran-2-yloxy)-6-(4,4,5,5-tetramethyl-[1,3,2]dioxaborolan-2-yl)-benzaldehyde (2.07 g, 5.39 mmol) in THF (6 mL) at 0° C. The mixture was stirred for 10 minutes before treating with 3 N HCl and extracted with EtOAc (2×25 mL). The organic extracts were washed with brine, dried over anhydrous MgSO$_4$ and concentrated in vacuo. The residue was purified by silica gel flash column chromatography and lyophilized to give (4-ethyl-1,6-dihydroxy-1,3-dihydro-benzo[c][1,2]oxaborol-3-yl)-acetic acid ethyl ester(0.380 g, 27%). $^1$H NMR (400 MHz, DMSO-d$_6$ δ 9.30 (s, 1H), 9.02 (s, 1H), 6.88 (s, 1H), 6.68 (s, 1H), 5.40 (m, 1H), 4.00 (m, 2H), 3.00 (m, 1H), 2.50 (m, 2H), 2.20 (m, 1H), 1.20 (m, 3H).

Step 7: (4-Ethyl-1,6-dihydroxy-1,3-dihydro-benzo[c][1,2]oxaborol-3-yl)-acetic acid

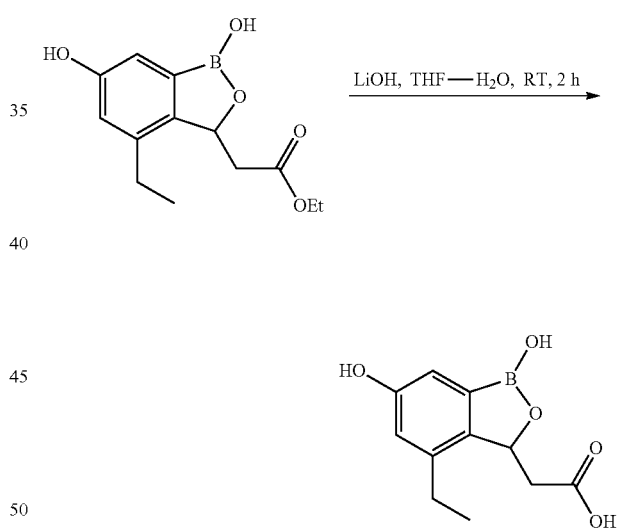

To a solution of (4-ethyl-1,6-dihydroxy-1,3-dihydro-benzo[c][1,2]oxaborol-3-yl)-acetic acid ethyl ester (0.19 g, 0.70 mmol) in THF (8 mL) and H$_2$O (2 mL) was added LiOH (0.178 g) at 0° C. The resulting mixture was stirred at room temperature for 2 hours then cooled to 0° C. and acidified to pH 3 with 6N HCl. The mixture was concentrated in vacuo and the residue purified by preparative HPLC to give (4-ethyl-1,6-dihydroxy-1,3-dihydro-benzo[c][1,2]oxaborol-3-yl)-acetic acid (0.080 g, 50%). $^1$H NMR (400 MHz, DMSO-d$_6$ δ 9.26 (s, 1H), 6.87 (s, 1H), 6.69 (s, 1H), 5.40 (m, 1H), 2.92 (m, 1H), 2.55 (m, 2H), 2.00 (m, 1H), 1.16 (m, 3H). MS (ESI) m/z: 235 [M−1]$^-$. HPLC purity: 92.64% (220 nm), 95.63% (Max-plot).

G2: (1,6-dihydroxy-4-methyl-1,3-dihydro-benzo[c][1,2]oxaborol-3-yl)-acetic acid ethyl ester

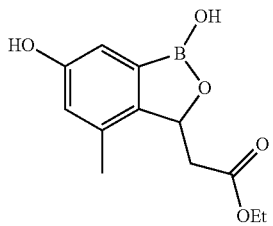

Step 1: 2-Hydroxy-6-methyl-4-(tetrahydro-pyran-2-yloxy)-benzaldehyde

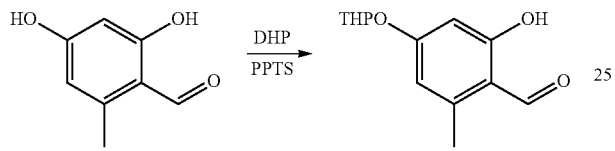

To a mixture of 2,4-dihydroxy-6-methyl-benzaldehyde (6.37 g, 37.88 mmol) in dichloromethane (150 mL) was added 3,4-dihydro-2H-pyran (4.78 g, 56.82 mmol) and pyridium p-toluenesulfonic acid (1.90 g, 7.58 mmol) at room temperature. The resulting mixture was stirred at room temperature for 18 hours then quenched by adding saturated NaHCO$_3$ at 0° C. The organic layer was washed with brine, dried over Na$_2$SO$_4$ and concentrated in vacuo. The residue was purified by silica gel flash column chromatography (EtOAc/hexane=1:3) to give pure product (8.78 g, 98.1%). $^1$H NMR (400 MHz, CDCl$_3$) δ ppm 12.33 (s, 1H), 10.11 (s, 1H), 6.47 (s, 1H), 6.39 (s, 1H), 5.49 (t, J=3.13 Hz, 1H), 3.78-3.90 (m, 1H), 3.52-3.72 (m, 1H), 2.54 (s, 3H), 1.77-2.03 (m, 3H), 1.53-1.70 (m, 3H); MS (ESI) m/z=285 [M+H]$^+$.

Step 2: Trifluoro-methanesulfonic acid 2-formyl-3-methyl-5-(tetrahydro-pyran-2-yloxy)-phenyl ester

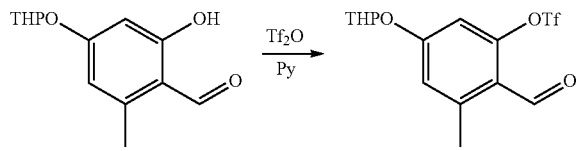

To a solution of 2-hydroxy-6-methyl-4-(tetrahydro-pyran-2-yloxy)-benzaldehyde (8.70 g, 36.8 mmol) and pyridine (14.56 g, 184.1 mmol) in dichloromethane (40 mL) was slowly added Tf$_2$O (15.58 g, 55.2 mol) at −10 to 0° C. The mixture was stirred at 0° C. for 3 hours. The mixture was diluted with cold brine and extracted with 50% EtOAc/hexane. The organic extracts were washed with brine, dried and concentrated in vacuo. The residue was purified by silica gel flash column chromatography (EtOAc/hexane=1:4) to give pure product (9.48 g, 69.3%). $^1$H NMR (400 MHz, CDCl$_3$) δ ppm 10.35 (s, 1H), 6.86-7.03 (m, 2H), 5.53 (t, J=2.93 Hz, 1H), 3.79 (m, 1 H), 3.55-3.71 (m, 1H), 2.65 (s, 3H), 1.84-2.05 (m, 3 H), 1.51-1.78 (m, 3 H). MS (ESI) m/z=369 [M+H]$^+$.

Step 3: 2-Methyl-4-(tetrahydro-pyran-2-yloxy)-6-(4,4,5,5-tetramethyl-[1,3,2]dioxaborolan-2-yl)-benzaldehyde

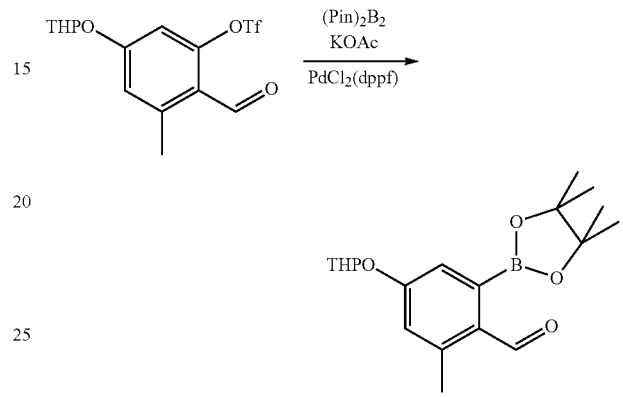

To a solution of bis(pinacolato)diborane (9.72 g, 38.3 mmol) in dioxane (95 mL) was added KOAc (7.52 g, 76.6 mmol). After degassing for 10 minutes with bubbling N$_2$, PdCl$_2$(dppf) (1.87 g, 2.55 mmol) and trifluoro-methanesulfonic acid 2-formyl-3-methyl-5-(tetrahydro-pyran-2-yloxy)-phenyl ester (9.40 g, 25.5 mmol) were added to the reaction mixture. The mixture was stirred at 80° C. for 1 hour then quenched by the addition of ice-water and extracted with 50% EtOAc/hexanes. The organic extracts were washed with brine, dried and concentrated in vacuo. The residue was purified by silica gel flash column chromatography (EtOAc/hexane=1:4) to give pure product (4.5 g, 51%). $^1$H NMR (400 MHz, CDCl$_3$) δ ppm 10.33 (s, 1H), 7.09 (d, J=2.34 Hz, 1H), 6.89 (d, J=2.34 Hz, 1H), 5.56 (t, J=2.93 Hz, 1H), 3.82 (m, 1H), 3.38-3.66 (m, 1H), 2.60 (s, 3H), 1.93-2.08 (m, 1H), 1.86 (m, 2H), 1.54-1.74 (m, 3H), 1.41 (s, 8H)

Step 4: [1-Hydroxy-4-methyl-6-(tetrahydro-pyran-2-yloxy)-1,3-dihydro-benzo[c][1,2]oxaborol-3-yl]-acetic acid ethyl ester

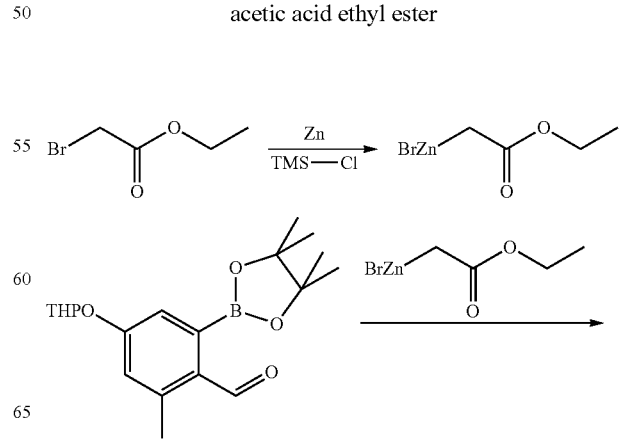

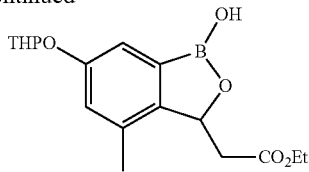

To a suspension of zinc dust (4.41 g, 67.4 mmol) in THF (30 mL) was added trimethylsilyl chloride (1.46 g, 13.5 mmol) at 40° C. The mixture was heated to 55° C. and stirred for 15 minutes. After cooling down to 37° C., ethyl bromoacetate (9.01 g, 53.9 mmol) was slowly added to the reaction mixture at 37-40° C. After addition, the resulting mixture was allowed to cool to room temperature over 30 minutes. This solution was added to a solution of 4-[4-formyl-3-(4,4,5,5-tetramethyl-[1,3,2]dioxaborolan-2-yl)-phenoxy]-piperidine-1-carboxylic acid tert-butyl ester (1.4 g, 3.2 mmol) in THF (10 mL) at −78° C. The mixture was allowed to warm to room temperature over 1.5 hours before treating with saturated NH$_4$Cl (10 mL) and extracting with EtOAc (2×25 mL). The organic extracts were washed with brine, dried and concentrated in vacuo to give the product which was used without further purification.

Step 5: (1,6-Dihydroxy-4-methyl-1,3-dihydro-benzo[c][1,2]oxaborol-3-yl)-acetic acid ethyl ester

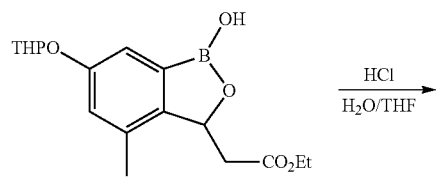

To a solution of crude [1-hydroxy-4-methyl-6-(tetrahydro-pyran-2-yloxy)-1,3-dihydro-benzo[c][1,2]oxaborol-3-yl]-acetic acid ethyl ester in THF (30 mL), was added dilute hydrochloric acid (6M, 3 mL) at 0° C. The mixture was allowed to warm to room temperature over 1 hour then concentrated in vacuo. The residue was purified by silica gel flash column chromatography (EtOAc/hexane=1:1) to give the product as a light brown gum (2.1 g, 62%, 2 steps). $^1$H NMR (400 MHz, DMSO-d) δ ppm 9.21 (s, 1H), 9.01 (s, 1H), 6.86 (d, J=2.4 Hz, 1H), 6.64 (d, J=2.4 Hz, 1H), 5.40-5.37 (m, 1H), 4.02 (q, J=7.2 Hz, 2H), 3.35-3.01 (m, 1H), 2.19-2.13 (m, 4H), 1.10 (t, 3H). MS (ESI) m/z=251 [M+H]$^+$.

G3: (3R)-(1,6-dihydroxy-4-methyl-1,3-dihydro-benzo[c][1,2]oxaborol-3-yl)-acetic acid ethyl ester

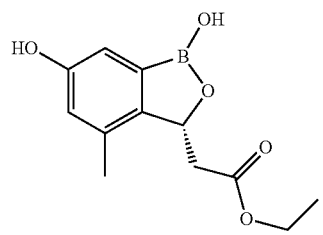 [SMILES: CCOC(=O)C[C@H]1OB(O)c2cc(O)cc(C)c21]

G4: (3S)-(1,6-dihydroxy-4-methyl-1,3-dihydro-benzo[c][1,2]oxaborol-3-yl)-acetic acid ethyl ester

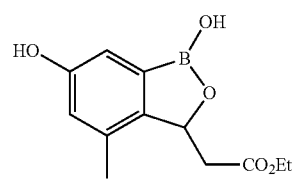

14.4 g of (1,6-dihydroxy-4-methyl-1,3-dihydro-benzo[c][1,2]oxaborol-3-yl)-acetic acid ethyl ester were separated by preparative HPLC using a CHIRALCEL® OZ column (250× 30 mm) using a mobile phase composition of 20% 2-propanol in hexane containing 0.1% trifluoroacetic acid at a flow rate of 40 ml/min at ambient temperature. The sample size was 11 ml at a concentration of 16.4 g/l, giving a production rate of 0.94 g/hour. The purity of the products was 98.8% ee ($1^{st}$ peak, [3R]) and 99.9% ee ($2^{nd}$ peak, [3S]).

G5: (1,6-Dihydroxy-4-methyl-1,3-dihydro-benzo[c][1,2]oxaborol-3-yl)-acetic acid

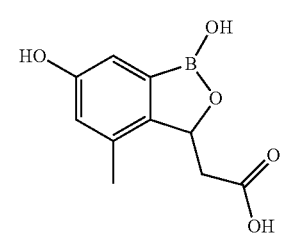

A solution of (1,6-dihydroxy-4-methyl-1,3-dihydro-benzo[c][1,2]oxaborol-3-yl)-acetic acid ethyl ester (0.835 g, 3.34 mmol) in THF (10 mL) was treated with lithium hydroxide (0.383 g, 16.70 mmol) in water (10 mL) at 0° C. The solution was stirred at 0° C. for 1 hour then quenched with 2N HCl to pH 2. The mixture was concentrated to approximately half of the entire volume. The solid that precipitated was collected by vacuum filtration, then rinsed with cold water and dried to give (1,6-dihydroxy-4-methyl-1,3-dihydro-benzo[c][1,2]oxaborol-3-yl)-acetic acid as a light yellow solid (0.65 g, 88%). mp 165-166° C. $^1$H NMR (400 MHz, DMSO-$d_6$) δ 12.31 (s, 1H), 9.30 (s, 1H), 9.08 (s, 1H), 6.88 (s, 1H), 6.66 (s, 1H), 5.38 (d, J=9.38 Hz, 1H), 3.00 (d, J=15.24 Hz, 1H), 2.20 (s, 3H), 2.00 (dd, J=15.24, 10.16 Hz, 1H). MS (ESI) m/z: 221 [M−1].

G6: (3R)-(1,6-Dihydroxy-4-methyl-1,3-dihydro-benzo[c][1,2]oxaborol-3-yl)-acetic acid

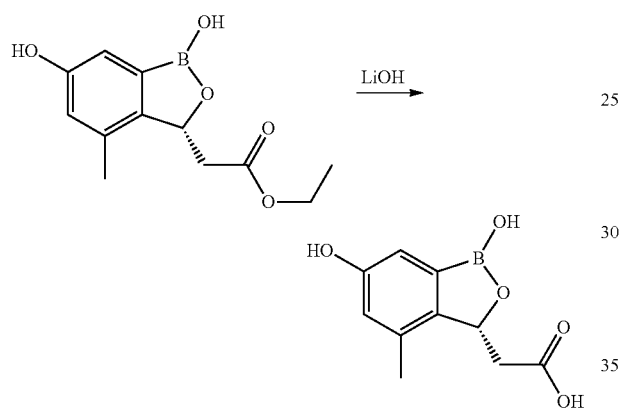

To a solution of (3R)-(1,6-dihydroxy-4-methyl-1,3-dihydro-benzo[c][1,2]oxaborol-3-yl)-acetic acid ethyl ester (1.00 g, 4.00 mmol) in THF (9 mL) was added a solution of LiOH (0.479 g, 20.0 mmol) in water (8 mL) at 0° C. The resulting mixture was stirred at room temperature for 1.5 hours then acidified to pH=2 with dilute hydrochloric acid and concentrated in vacuo. The residue was purified by silica gel flash column chromatography (DCM/MeOH/AcOH=20:1:trace) to give pure product as a white powder after lyophilization (0.579 g, 64.9%). $^1$HNMR (400 MHz, DMSO-d) δ12.26 (s, 1H), 9.25 (s, 1H), 9.04 (s, 1H), 6.86 (d, J=1.95 Hz, 1H), 6.64 (d, J=1.95 Hz, 1H), 5.36 (dd, J=9.76, 2.34 Hz, 1H), 2.98 (dd, J=15.22, 2.34 Hz, 1H), 2.17 (s, 3H), 1.98 (dd, 1H). MS (ESI) m/z=221 [M−H]$^−$.

G7: (3S)-(1,6-Dihydroxy-4-methyl-1,3-dihydro-benzo[c][1,2]oxaborol-3-yl)-acetic acid

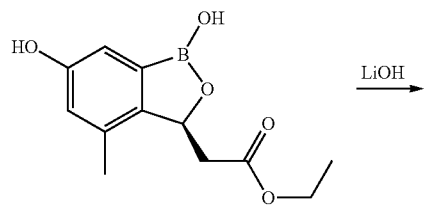

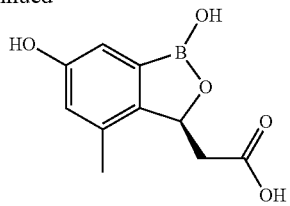

A solution of (3S)-(1,6-dihydroxy-4-methyl-1,3-dihydro-benzo[c][1,2]oxaborol-3-yl)-acetic acid ethyl ester (1.04 g, 4.16 mmol) in THF (5 mL) was treated with lithium hydroxide (0.478 g, 2.08 mmol) in water (5 mL) at 0° C. The solution was stirred at 0° C. for 1 hour then quenched with 2N HCl to pH 2 and concentrated to approximately half of the entire volume. The precipitated solid was collected by vacuum filtration, then rinsed with cold water and dried to give (1,6-dihydroxy-4-methyl-1,3-dihydro-benzo[c][1,2]oxaborol-3-yl)-acetic acid. The filtrate was neutralized with NaHCO$_3$ and lyophilized. The residue was suspended in water (5-10 mL) and stirred for 10 minutes. The solid was collected by vacuum filtration to give a second portion of (1,6-dihydroxy-4-methyl-1,3-dihydro-benzo[c][1,2]oxaborol-3-yl)-acetic acid as a yellow solid (total product; 0.49 g, 53%). $^1$H NMR (400 MHz, DMSO-$d_6$) δ 12.31 (s, 1H), 9.30 (s, 1H), 9.08 (s, 1H), 6.88 (s, 1H), 6.66 (s, 1H), 5.38 (d, J=9.38 Hz, 1H), 3.00 (d, J=15.24 Hz, 1H), 2.20 (s, 3H), 2.00 (dd, J=15.24, 10.16 Hz, 1H). MS (ESI) m/z: 221 [M−1].

G8: 3-(1,6-Dihydroxy-4-methyl-1,3-dihydro-benzo[c][1,2]oxaborol-3-yl)-propionic acid

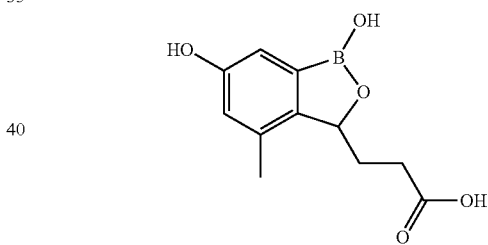

Step 1: 4-[2-Hydroxy-6-methyl-4-(tetrahydro-pyran-2-yloxy)-phenyl]-4-oxo-butyric acid methyl ester

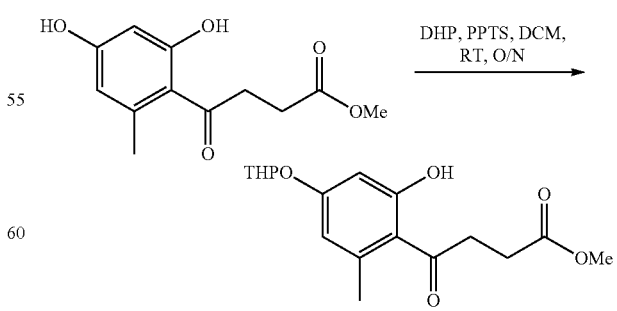

To a mixture of 4-(2,4-dihydroxy-6-methyl-phenyl)-4-oxo-butyric acid methyl ester (1.0 g, 4.20 mmol) in dichloromethane (50 mL) was added 3,4-dihydro-2H-pyran (0.38 mL, 8.40 mmol) and pyridium p-toluenesulfonic acid (0.010 g) at room temperature. The resulting mixture was stirred at room temperature for 16 hours then concentrated in vacuo. The residue was purified by silica gel flash column chromatography to give 4-[2-hydroxy-4-(tetrahydro-pyran-2-yloxy)-phenyl]-4-oxo-butyric acid methyl ester (1.1 g, 81%). $^1$HNMR (400 MHz, CDCl$_3$): 12.40 (s, 1H), 6.95 (s, 1H), 6.90 (s, 1H), 5.90 (br s, 1H), 3.27 (t, J=7.8 Hz, 2H), 2.78 (t, J=7.8 Hz, 2H), 2.30 (s, 3H).

Step 2: 4-[2-Methyl-4-(tetrahydro-pyran-2-yloxy)-6-trifluoromethanesulfonyloxy-phenyl]-4-oxo-butyric acid methyl ester

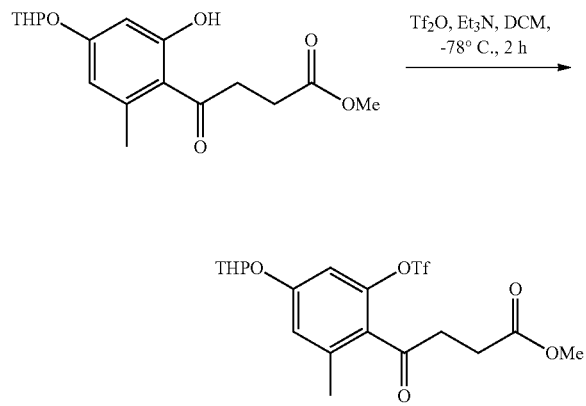

To a solution of 4-[2-hydroxy-4-(tetrahydro-pyran-2-yloxy)-phenyl]-4-oxo-butyric acid methyl ester (2.87 g, 8.91 mmol) and Et$_3$N (3.71 mL, 26.73 mmol) in dichloromethane (30 mL) was added Tf$_2$O (2.30 mL, 13.37 mmol) at −78° C. The mixture was stirred at −78° C. for 2 hours, diluted with H$_2$O and extracted with dichloromethane. The organic extracts were washed with brine, dried and concentrated in vacuo. The residue was dissolved in Hexane-EtOAc(4:1), filtered through a plug of silica gel and filtrate was concentrated to give 4-[2-methyl-4-(tetrahydro-pyran-2-yloxy)-6-trifluoromethanesulfonyloxy-phenyl]-4-oxo-butyric acid methyl ester (2.56 g, 63%). $^1$HNMR (400 MHz, CDCl$_3$): 6.95 (s, 1H), 6.90 (s, 1H), 5.45 (s, 1H), 3.82 (m, 1H), 3.77 (s, 3H), 3.65 (m, 1H), 3.10 (t, J=6.5 Hz, 2H), 2.75 (t, J=6.5 Hz, 2H), 2.30 (s, 3H), 2.05-1.50 (m, 6H).

Step 3: 4-[2-Methyl-4-(tetrahydro-pyran-2-yloxy)-6-(4,4,5,5-tetramethyl-[1,3,2]dioxaborolan-2-yl)-phenyl]-4-oxo-butyric acid methyl ester

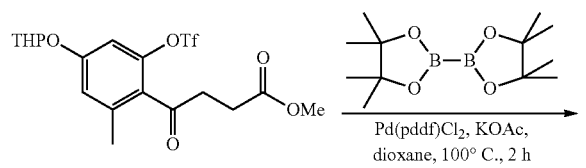

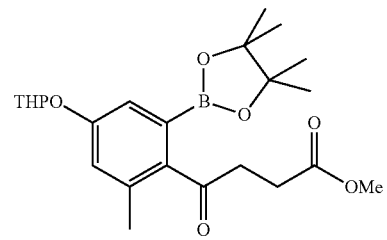

A mixture of 4-[2-methyl-4-(tetrahydro-pyran-2-yloxy)-6-trifluoromethanesulfonyloxy-phenyl]-4-oxo-butyric acid methyl ester (2.56 g, 5.64 mmol), bis(pinacolato)diborane (2.86 g, 11.28 mmol), Pd(dppf)Cl$_2$ (0.42 g, 0.57 mmol) and KOAc (1.66 g, 16.92 mmol) in dioxane (30 mL) was degassed for 10 minutes with bubbling N$_2$. The reaction mixture was heated at 100° C. for 2 hours then diluted with EtOAc (100 mL). The mixture was filtered through a pad of celite and concentrated in vacuo. The residue was purified by silica gel flash column chromatography to give 4-[2-methyl-4-(tetrahydro-pyran-2-yloxy)-6-(4,4,5,5-tetramethyl-[1,3,2]dioxaborolan-2-yl)-phenyl]-4-oxo-butyric acid methyl ester (1.15 g, 47%). $^1$HNMR (400 MHz, CDCl$_3$): 6.95 (s, 1H), 6.90 (s, 1H), 5.52 (m, 1H), 3.82 (m, 1H), 3.77 (s, 3H), 3.65 (m, 1H), 3.10 (t, J=6.5 Hz, 2H), 2.75 (t, J=6.5 Hz, 2H), 2.30 (s, 3H), 2.05-1.50 (m, 6H), 1.30 (s, 12H).

Step 4: 3-(1,6-Dihydroxy-4-methyl-1,3-dihydro-benzo[c][1,2]oxaborol-3-yl)-propionic acid methyl ester

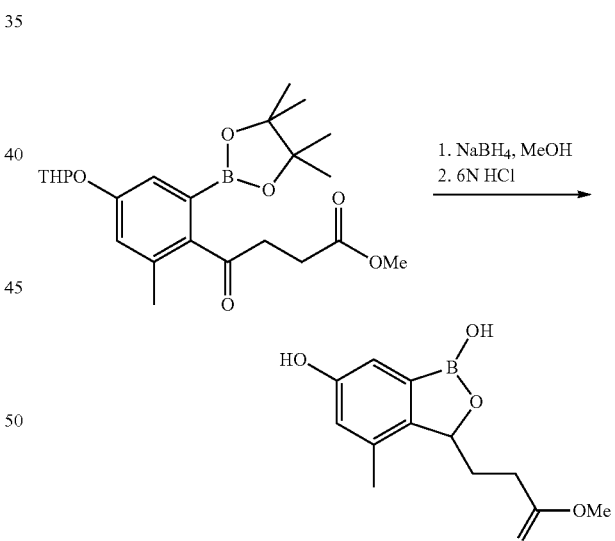

To a solution of 4-[2-Methyl-4-(tetrahydro-pyran-2-yloxy)-6-(4,4,5,5-tetramethyl-[1,3,2]dioxaborolan-2-yl)-phenyl]-4-oxo-butyric acid methyl ester (1.15 g, 2.57 mmol) in MeOH (50 mL) was added NaBH$_4$ (0.244 g, 6.42 mmol) at 0° C. The reaction mixture was stirred at 0° C. for 30 minutes, quenched with 6 N HCl and concentrated in vacuo. The residue was purified by silica gel flash column chromatography followed by lyophilization to give 3-(1,6-dihydroxy-4-methyl-1,3-dihydro-benzo[c][1,2]oxaborol-3-yl)-propionic acid methyl ester (0.19 g, 30%). $^1$H NMR (400 MHz, Actoned$_6$) δ 8.20 (s, 1H), 7.96 (s, 1H), 7.00 (s, 1H), 6.80 (s, 1H), 5.20 (m, 1H), 3.60 (s, 3H), 2.40 (m, 2H), 2.30 (m, 3H), 1.65 (m, 1H).

Step 5: 3-(1,6-Dihydroxy-4-methyl-1,3-dihydrobenzo[c][1,2]oxaborol-3-yl)-propionic acid

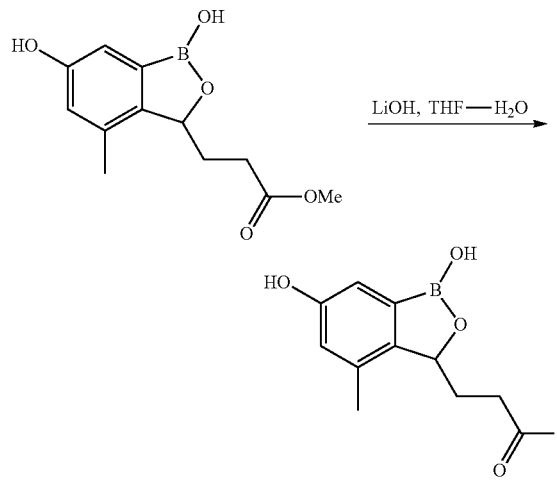

To a solution of 3-(1,6-dihydroxy-4-methyl-1,3-dihydrobenzo[c][1,2]oxaborol-3-yl)propionic acid methyl ester (0.190 g, 0.76 mmol) in THF (4 mL) and H$_2$O (2 mL) was added LiOH (0.146 g, 6.08 mmol) at 0° C. The resulting mixture was stirred at room temperature for 2 hours then cooled to 0° C. and acidified to pH 3 with 6N HCl. The mixture was concentrated and purified by silica gel flash column chromatography to give 3-(1,6-dihydroxy-4-methyl-1,3-dihydrobenzo[c][1,2]oxaborol-3-yl)propionic acid (0.110 g, 61%). $^1$H NMR (400 MHz, DMSO-d$_6$) δ 9.20 (s, 1H), 9.00 (s, 1H), 6.88 (s, 1H), 6.66 (s, 1H), 2.30-2.10 (m, 6H), 1.50 (m, 1H). MS (ESI) m/z: 235 [M−1]$^−$. HPLC purity: 99.06% (220 nm), 98.87% (Maxplot).

G9: (1-Hydroxy-6-hydroxy-4-fluoro-1,3-dihydrobenzo[c][1,2]oxaborol-3-yl)-acetic acid

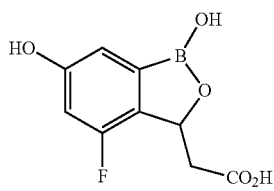 [SMILES: O=C(O)CC1OB(O)c2cc(O)cc(F)c21]

Step 1: 1-Fluoro-3,5-dimethoxybenzene

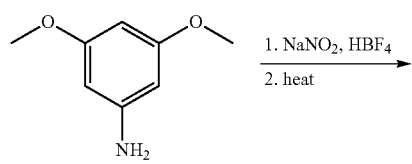

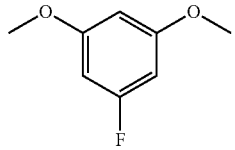

To a mixture of 3,5-dimethoxybenzenamine (6.12 g, 40.0 mmol) and tetrafluoroboric acid (8% solution, 70 mL) was added dropwise a solution of sodium nitrite (2.84 g, 41.2 mmol) in water (10 mL). After stirring at room temperature for 30 min, the reaction mixture was filtered. The solid was collected and washed with water (2×10 mL) and dried under high vacuum. The resulting red solid was suspended in dry hexane (50 mL) and heated to reflux for 2 hr. The mixture was filtered and the filtrate was concentrated to give the crude product as a yellow oil (3.03 g, Yield: 48.5%). MS (ESI) m/z=157 [M+H]$^+$.

Step 2: 2-Fluoro-4,6-dimethoxybenzaldehyde

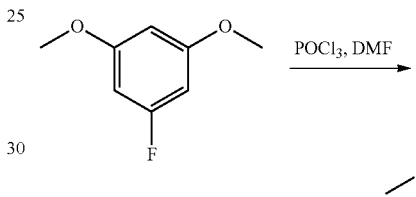

To a solution of 1-fluoro-3,5-dimethoxybenzene (3.12 g, 20.0 mmol) in DMF (15 mL) was added dropwise phosphoryl trichloride (1.55 mL) at 0° C. The reaction mixture was stirred at room temperature overnight and poured onto ice. The resulting mixture was extracted with ethyl acetate (2×50 mL) and the combined organic layers were dried over anhydrous Na$_2$SO$_4$, concentrated in vacuo. The residue was purified by column chromatography on silica gel (EtOAc/PE=1/8) to give the title compound as a yellow solid (2.75 g, Yield: 74.6%). $^1$H NMR (400 MHz, DMSO-d) δ 10.15 (s, 1H), 6.52-6.56 (m, 2H), 3.91 (s, 3H), 3.88 (s, 3H). MS (ESI) m/z=185 [M+H]$^+$.

Step 3: 2-Fluoro-4,6-dihydroxybenzaldehyde

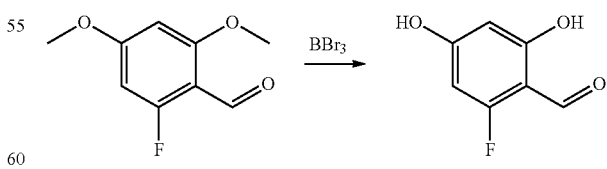

To a solution of 2-fluoro-4,6-dimethoxybenzaldehyde (3.68 g, 20.0 mmol) in dichloromethane (50 mL) was added dropwise boron tribromide (12.50 g, 50.0 mmol) at −78° C. The reaction was stirred at room temperature overnight and poured into ice. The resulting mixture was extracted with ethyl acetate (3×60 mL) and the combined organic layers were dried over anhydrous Na$_2$SO$_4$, concentrated in vacuo. The residue was purified by column chromatography (EtOAc/PE=1/6) on silica gel to give the title compound as a white solid. (2.31 g, Yield: 76.4%). $^1$H NMR (400 MHz, DMSO-d) δ 11.53 (s, 1H), 11.22 (s, 1H), 9.99 (s, 1H), 6.16-6.24 (m, 2H). MS (ESI) m/z=157 [M+H]$^+$.

Step 4: 2-Fluoro-6-hydroxy-4-(tetrahydro-2H-pyran-2-yloxy)benzaldehyde

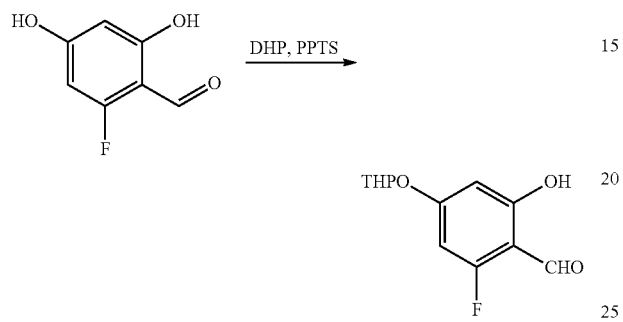

To a mixture of 2-fluoro-4,6-dihydroxybenzaldehyde (3.12 g, 20.0 mmol) and PPTS (0.51 g, 2.0 mmol) in dichloromethane (100 mL) was added dropwise DHP (3.02 g, 36.0 mmol). The mixture was stirred at room temperature overnight and concentrated under reduced pressure. The residue was purified by column chromatography (EtOAc/PE=1/15) on silica gel to give the title compounds as a colorless oil (3.99 g, Yield: 83.2%). MS (ESI) m/z=241 [M+H]$^+$.

Step 5: 3-Fluoro-2-formyl-5-(tetrahydro-2H-pyran-2-yloxy)phenyl trifluoromethanesulfonate

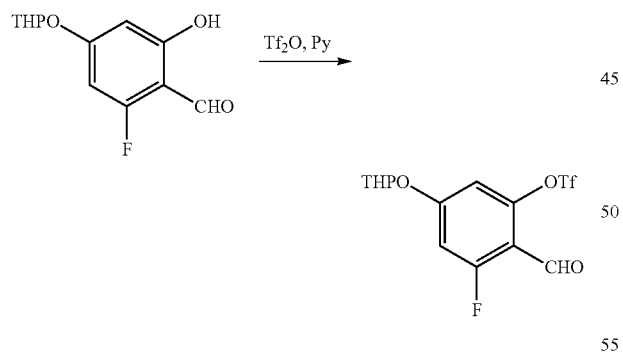

To a mixture of 2-fluoro-6-hydroxy-4-(tetrahydro-2H-pyran-2-yloxy)benzaldehyde (3.60 g, 15.0 mmol) and pyridine (5.93 g, 75.0 mmol) in dichloromethane (50 mL) was added dropwise Tf$_2$O (6.35 g, 22.5 mmol) at −15° C. After stirring at room temperature for 3 h, the reaction was quenched by addition of iced-brine (50 mL) and extracted with dichloromethane (2×50 mL). The combined organic layers were dried over anhydrous Na$_2$SO$_4$ and concentrated in vacuo. The residue was purified by column chromatography (EtOAc/PE=1/8) on silica gel to give the title compound as a white solid (3.77 g, Yield: 67.5%). $^1$H NMR (400 MHz, DMSO-d) δ 10.12 (s, 1H), 7.26-7.30 (m, 1H), 7.04 (s, 1H), 5.78 (s, 1H), 3.62-3.71 (m, 2H), 1.80-1.87 (m, 3H), 1.56-1.64 (m, 3H). MS (ESI) m/z=373 [M+H]$^+$.

Step 6: 2-Fluoro-4-(tetrahydro-2H-pyran-2-yloxy)-6-(4,4,5,5-tetramethyl-1,3,2-dioxaborolan-2-yl)benzaldehyde

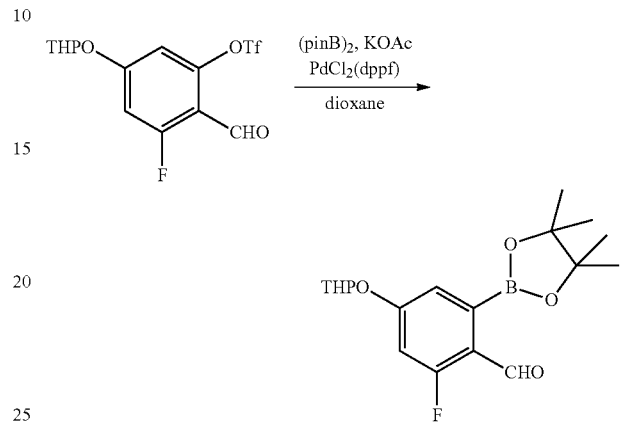

A mixture of 3-fluoro-2-formyl-5-(tetrahydro-2H-pyran-2-yloxy)phenyl trifluoro-methane sulfonate (3.72 g, 10.0 mmol), KOAc (2.94 g, 30.0 mmol), bis(pinacolato)diborane (3.81 g, 15.0 mmol) and PdCl$_2$(dppf) (0.73 g, 1.0 mmol) in dioxane (30 mL) was degassed by passing a stream of nitrogen for 15 min and heated to 80° C. for 45 min. The mixture was filtered and the filtrate was concentrated in vacuo. The residue was purified by column chromatography (EtOAc/PE=1/4) on silica gel to give the title compound as a yellow solid. (2.05 g, Yield: 58.7%). $^1$H NMR (400 MHz, DMSO-d) δ 10.14 (s, 1H), 7.04-7.07 (d, J=13.2 Hz, 1H), 6.94 (s, 1H), 5.73 (s, 1H), 3.60-3.72 (m, 2H), 1.79-1.89 (m, 3H), 1.57-1.63 (m, 3H), 1.34 (s, 12H). MS (ESI) m/z=351 [M+H]$^+$.

Step 7: Ethyl-2-(4-fluoro-1-hydroxy-6-(tetrahydro-2H-pyran-2-yloxy)-1,3-dihydrobenzo[c][1,2]oxaborol-3-yl)acetate

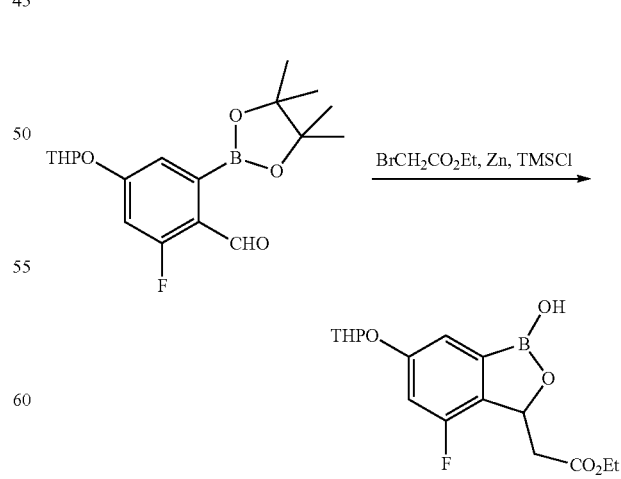

To a mixture of zinc powder (0.98 g, 15.0 mmol) in anhydrous THF (30 mL) was added TMSCl (0.39 mL, 3.0 mmol) at 40° C. The resulting mixture was stirred at 55° C. for 15 min and then cooled to 37° C. Ethyl 2-bromoacetate (1.35 mL, 12.0 mmol) was added at 37° C. and the reaction mixture was stirred at this temperature for 30 min. To a solution of 2-fluoro-4-(tetrahydro-2H-pyran-2-yloxy)-6-(4,4,5,5-tetramethyl-1,3,2-dioxaborolan-2-yl)benzaldehyde (1.05 g, 3.0 mmol) in anhydrous THF (40 mL) was added dropwise above prepared solution at −78° C. The reaction was allowed to stir at room temperature for 1.5 h and quenched by addition of aqueous ammonium chloride (20 mL). The resulting mixture was extracted with ethyl acetate (2×50 mL) and the combined organic layers were dried over anhydrous $Na_2SO_4$, concentrated in vacuo. The residue was purified by column chromatography (EtOAc/PE=1/3) on silica gel to give the title compound as a yellow solid. (0.89 g, Yield: 87.9%). MS (ESI) m/z=339 $[M+H]^+$.

Step 8: Ethyl-2-(4-fluoro-1,6-dihydroxy-1,3-dihydrobenzo[c][1,2]oxaborol-3-yl)acetate

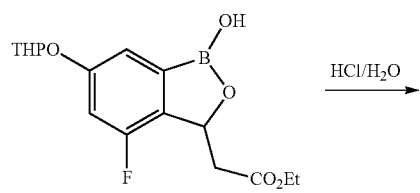

To a solution of ethyl-2-(4-fluoro-1-hydroxy-6-(tetrahydro-2H-pyran-2-yloxy)-1,3-dihydro benzo[c][1,2]oxaborol-3-yl)acetate (0.34 g, 1.0 mmol) in THF (10 mL) was added dropwise concentrated hydrochloride acid (0.2 mL) at 0° C. The reaction mixture was stirred at 0° C. for 1 h and quenched by addition of sat. aqueous $NaHCO_3$ (20 mL). The resulting mixture was extracted with EtOAc(2×30 mL). The combined extracts were dried over anhydrous $Na_2SO_4$ and concentrated in vacuo. The residue was purified by column chromatography on silica gel (EtOAc/PE=1/4) to give the title compound as a light yellow solid (180 mg, Yield: 70.9%). $^1$H NMR (400 MHz, DMSO-d) δ 9.93 (s, 1H), 9.40 (s, 1H), 6.94-6.94 (d, J=1.6 Hz, 1H), 6.65-6.68 (m, 1H), 5.49-5.52 (m, 1H), 4.00-4.08 (m, 2H), 2.94-2.99 (m, 1H), 2.38-2.44 (m, 1H), 1.13-1.20 (m, 3H). MS (ESI) m/z=255 $[M+H]^+$.

Step 9: 2-(4-fluoro-1,6-dihydroxy-1,3-dihydrobenzo[c][1,2]oxaborol-3-yl)acetic acid

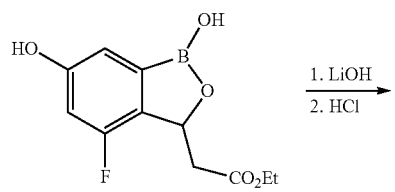

To a solution of ethyl-2-(4-fluoro-1,6-dihydroxy-1,3-dihydrobenzo[c][1,2]oxaborol-3-yl)acetate (127 mg, 0.50 mmol) in THF (2 mL) was added dropwise a solution of lithium hydroxide (102 mg, 2.5 mmol) in water (3 mL) at 0° C. The mixture was stirred at room temperature for 1.5 h and after cooling to 0° C., acidified to pH=2 by addition of diluted hydrochloride acid, extracted with ethyl acetate (2×15 mL). The combined extracts were dried over anhydrous $Na_2SO_4$ and concentrated in vacuo. The residue was purified by HPLC to give the title compound as a white solid (52 mg, Yield: 46%). $^1$H NMR (400 MHz, DMSO-d) δ 12.12 (s, 1H), 9.91 (s, 1H), 9.37 (s, 1H), 6.94-6.94 (d, J=1.6 Hz, 1H), 6.65-6.68 (m, 1H), 5.46-5.49 (m, 1H), 2.88-2.93 (m, 1H), 2.23-2.29 (m, 1H). MS (ESI) m/z=455 $[2M+H]^+$.

G10: 2-(4-Chloro-1,6-dihydroxy-1,3-dihydrobenzo[c][1,2]oxaborol-3-yl)-acetic acid

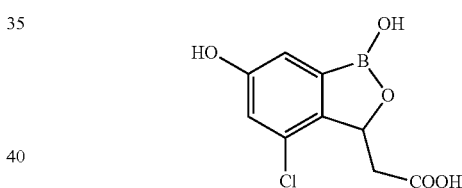

Step 1: 6-Chloro-2,4-dimethoxy-benzaldehyde

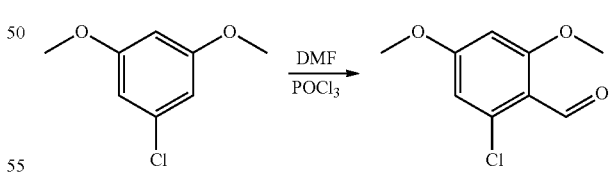

To a mixture of 5-chloro-1,3-dimethoxybenzene (25 g, 0.14 mol) in DMF (175 mL, 2.27 mol) at 0° C. was added $POCl_3$ (42.5 mL, 0.46 mol) dropwise. The mixture was stirred at room temperature for 30 min and heated to reflux at 100° C. for an additional 2 h. The reaction mixture was poured onto ice and the yellow precipitate was collected by filtration, rinsed with cold water and dried under high vacuum to give a light yellow solid (22.7 g. Yield 78.3%). $^1$H NMR (400 MHz, $CDCl_3$) δ10.43 (s, 1H), 6.59 (s, 1H), 6.42 (s, 1H), 3.92 (s, 3H), 3.89 (s, 3H); MS (ESI) m/z=201 $[M+H]^+$.

Step 2: 6-Chloro-2,4-dihydroxy-benzaldehyde

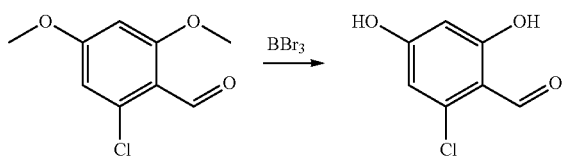

To the solution of 6-chloro-2,4-dimethoxy-benzaldehyde (8 g, 39.9 mmol) in dichloromethane (100 mL) was added boron tribromide (16 mL, 170 mmol) dropwise at −78° C. The reaction mixture was stirred overnight at room temperature and quenched by ice. The resulting mixture was extracted by EtOAc (2×50 mL). The combined organic layers were dried over anhydrous $Na_2SO_4$ and concentrated in vacuo. The residue was purified by column chromatography on silica gal (EtOAc/PE=1:5) to give the title compound as a yellow powder (4 g. Yield: 58%). $^1$H NMR (400 MHz, DMSO-$d_6$) δ12.11 (s, 1H), 11.33 (s, 1H), 10.08 (s, 1H), 6.52-6.53 (d, J=2.0 Hz, 1H), 6.27-6.28 (s, J=2.0 Hz, 1H) MS (ESI) m/z=173 [M+H]$^+$.

Step 3: 6-Chloro-2-hydroxy-4-(tetrahydro-pyran-2-yloxy)-benzaldehyde

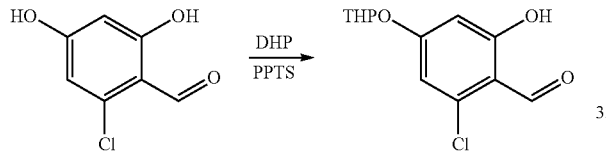

To a solution of 6-chloro-2,4-dihydroxybenzaldehyde (9.0 g, 52.2 mmol) in DCM (150 mL) was added 3,4-dihydro-2H-pyran (9 mL, 98.4 mmol), followed by PPTs (1.31 g, 5.2 mmol). The reaction mixture was stirred at room temperature for 1.5 h and quenched by saturated aqueous $NaHCO_3$ (50 mL) at 0° C. The organic layer was separated, washed with brine (40 mL) and dried over anhydrous $Na_2SO_4$. Concentration in vacuo followed by purification with column chromatography on silica gel (EtOAc/PE=1:100) gave the title compound as a colorless oil (10.5 g, Yield: 87.3%). $^1$H NMR (400 MHz, DMSO-$d_6$) δ12.00 (s, 1H), 10.17 (s, 1H), 6.72-6.78 (m, 1H), 6.57-6.64 (m, 1H), 5.50-5.70 (t, 1H), 3.60-3.73 (m, 2H), 1.55-1.87 (m, 6H) MS (ESI) m/z=257 [M+H]$^+$.

Step 4: 3-Chloro-2-formyl-5-(tetrahydro-2H-pyran-2-yloxy)phenyl trifluoromethanesulfonate

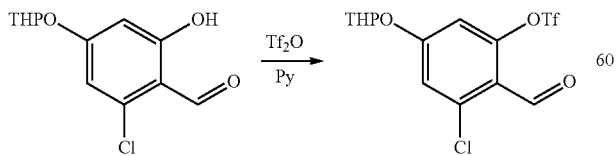

To a mixture of 6-chloro-2-hydroxy-4-(tetrahydro-pyran-2-yloxy)benzaldehyde (10.5 g, 40.9 mmol) and pyridine (14.6 mL, 0.20 mol) in DCM (150 mL) cooled at −10~0° C. was added $Tf_2O$ (10.3 mL, 61.2 mmol) dropwise. The reaction mixture was stirred at 0° C. for an additional 2 h and quenched with cold brine (40 mL). The resulting mixture was extracted with EtOAc (2×50 mL). The combined organic layers were dried over anhydrous $Na_2SO_4$ and concentrated in vacuo. The residue was purified by column chromatography on silica gel (EtOAc: PE=1:200) to give the title compound as a yellow oil (10.5 g. Yield: 66%).

Step 5: 2-Chloro-4-(tetrahydro-2H-pyran-2-yloxy)-6-(4,4,5,5-tetramethyl-1,3,2-dioxaborol-2-yl)-benzaldehyde

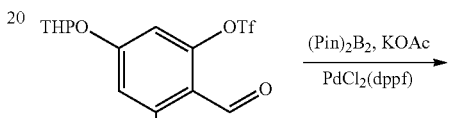

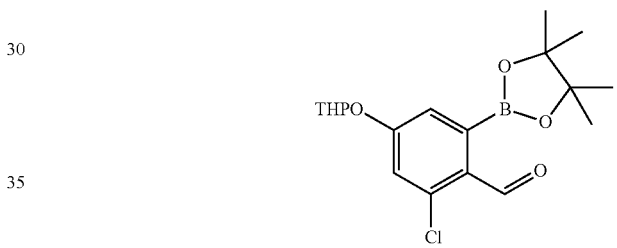

A mixture of bis(pinacolato)diborane (26.2 g, 10.3 mmol), KOAc (15.2 g, 15.5 mmol), $PdCl_2$(dppf) (3.8 g, 5.18 mmol) and 3-chloro-2-formyl-5-(tetrahydro-2H-pyran-2-yloxy) phenyl trifluoromethanesulfonate (20.5 g, 52.7 mmol) in anhydrous dioxane (300 mL) was degassed under a stream of nitrogen for 10 min and heated to 80° C. for 45 min. The reaction was quenched by addition of ice-water (15 mL). The resulting mixture was extracted with EtOAc (2×30 mL). The combined extracts were dried over anhydrous $Na_2SO_4$ and concentrated in vacuo. The residue was purified by column chromatography on silica gel (EtOAc/PE=1:8) to give the title compound as a yellow oil (6 g. Yield: 75.7%). $^1$H NMR (400 MHz, DMSO-d6) δ10.19 (s, 1H), 7.24 (d, J=2.0 Hz, 1H), 7.02-7.02 (d, J=2.0 Hz, 1H), 5.77 (s, 1H), 3.65 (m, 2H), 1.55-1.90 (m, 6H), 1.33 (d, J=6.4 Hz, 12H).

Step 6: Ethyl 2-(4-chloro-1-hydroxy-6-(tetrahydro-2H-pyran-2-yloxy)-1,3-dihydrobenzo[c][1,2]oxaborol-3-yl)acetate

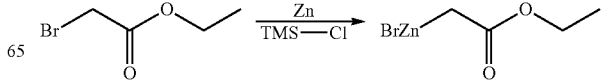

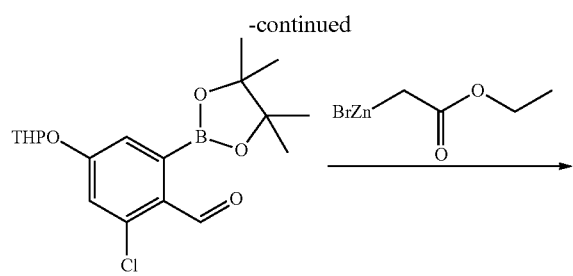
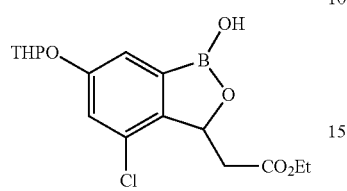

To a suspension of powdered zinc dust (1.0 g, 2.73 mmol) in THF (3 mL) was added trimethylsilyl chloride (0.21 mL, 2.73 mmol) at 40° C. The mixture was stirred at 55° C. for 15 min. After cooled to 37° C., ethyl bromoacetate (1.21 mL, 13.65 mmol) was added slowly while maintaining the temperature between 37~40° C. The resulting mixture was stirred at ambient temperature for an additional 30 min. To a solution of 2-chloro-4-(tetrahydro-2H-pyran-2-yloxy)-6-(4,4,5,5-tetramethyl-1,3,2-dioxa-borolan-2-yl)benzaldehyde (1 g, 2.73 mmol) in anhydrous THF (3 mL) cooled at −78° C., was added above freshly prepared zinc reagent. Upon completion of addition, the reaction mixture was warmed to room temperature and stirred for 30 min before quenched with saturated aqueous $NH_4Cl$. The resulting mixture was extracted with EtOAc (2×30 mL). The combined organic layers were washed with brine (20 mL), dried over anhydrous $Na_2SO_4$ and concentrated in vacuo. The crude product was used directly in the next step reaction without further purification. MS (ESI) m/z=355 [M+H]$^+$.

Step 7: Ethyl 2-(4-chloro-1,6-dihydroxy-1,3-dihydrobenzo[c][1,2]oxaborol-3-yl)acetate

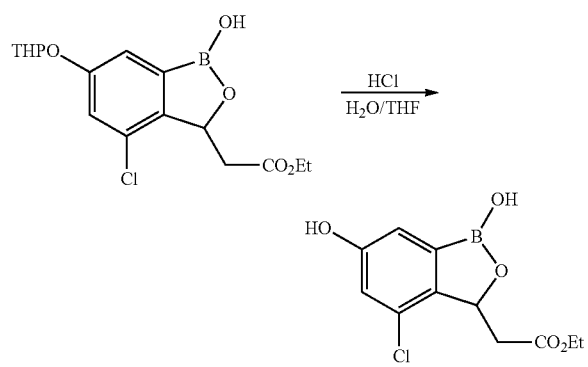

To a solution of the crude ethyl 2-(4-chloro-1-hydroxy-6-(tetrahydro-2H-pyran-2-yl-oxy)-1,3-dihydrobenzo[c][1,2]oxaborol-3-yl)acetate in THF (3 mL) was added concentrated HCl (1.5 mL) at 0° C. and the mixture was stirred at 0° C. for 30 min. The reaction mixture was concentrated under reduced pressure and the residue was purified by column chromatography on silica gel (EtOAc/PE=1:1) to give the title compound as a yellow oil (580 mg. Yield: 60.2%). $^1$H NMR (400 MHz, DMSO-d6) δ9.94 (d, J=2.8 Hz, 1H), 9.39 (s, 1H), 7.07-7.08 (d, J=2.0 Hz, 1H), 6.92-6.92 (d, J=2.0 Hz, 1H), 5.40-5.48 (m, 1H), 3.19-3.23 (m, 1H), 2.34-2.40 (m, 1H), 1.31-1.50 (m, 5H); MS (ESI) m/z=271 [M+H]$^+$.

Step 8: 2-(4-chloro-1,6-dihydroxy-1,3-dihydrobenzo[c][1,2]oxaborol-3-yl)acetic acid

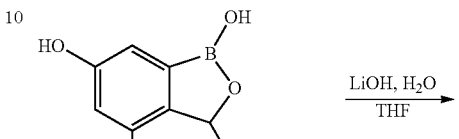
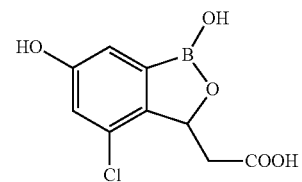

To a solution of ethyl 2-(4-chloro-1,6-dihydroxy-1,3-dihydrobenzo[c][1,2]oxaborol-3-yl)acetate (150 mg, 0.55 mmol) in THF (2 mL) was added an aqueous solution of lithium hydroxide (116 mg, 2.77 mmol) in water (1 mL) at 0° C. The resulting mixture was stirred at ambient temperature for 3 h and acidified with diluted hydrochloric acid at 0° C. to pH=1~2. The mixture was extracted with EtOAc (2×20 mL) and the combined organic layers were dried over anhydrous $Na_2SO_4$ and concentrated in vacuo. The residue was purified by prep HPLC to give the title compound as a white powder (78 mg. Yield: 69%). $^1$H NMR (400 MHz, DMSO-d6) δ 9.95 (s, 1H), 9.40 (s, 1H), 8.15 (s, 1H), 7.06 (d, J=1.6 Hz, 1H), 6.91 (d, J=1.6 Hz, 1H), 5.38-5.41 (m, 1H), 3.14-3.19 (m, 1H), 2.15-2.22 (m, 1H). MS (ESI) m/z=243 [M+H]$^+$.

G11: (1,6-Dihydroxy-4-methoxymethyl-1,3-dihydrobenzo[c][1,2]oxaborol-3-yl)-acetic acid

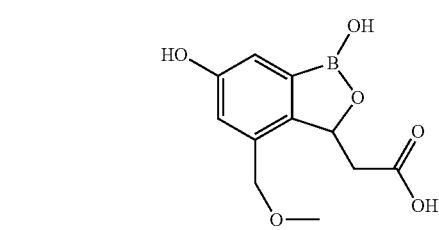 [SMILES: COCc1cc(O)cc2c1C(CC(=O)O)OB2O]

Step 1: 2-Bromo-1,5-bis-methoxymethoxy-3-methoxymethyl-benzene

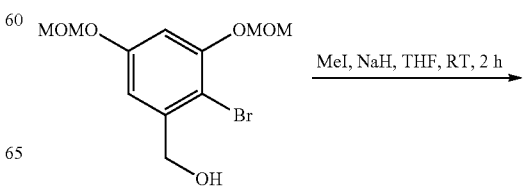

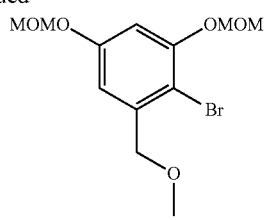

To a solution of (2-bromo-3,5-bis-methoxymethoxy-phenyl)-methanol (7.68 g, 24.94 mmol) in THF (50 mL) was added NaH at 0° C. The mixture was stirred at room temperature for 20 minutes then MeI (7.84 mL) was added and the resulting mixture was stirred at room temperature for 2 hours. The mixture was diluted with ether (50 mL), filtered through a pad of celite and concentrated in vacuo. The residue was purified by silica gel flash column chromatography to give 2-bromo-1,5-bis-methoxymethoxy-3-methoxymethyl-benzene (5.66 g, 70%). ¹H NMR (400 MHz, CDCl₃δ 6.90 (s, 1H), 6.80 (s, 1H), 6.77 (s, 1H), 5.25 (s, 2H), 5.20 (s, 2H), 4.50 (s, 23.77 (s, 3H), 3.40 (s, 6H).

Step 2: 2,4-Bis-methoxymethoxy-6-methoxymethyl-benzaldehyde

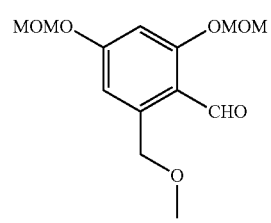

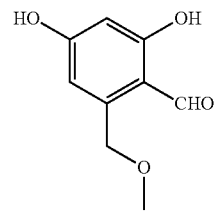

To a solution of 2-bromo-1,5-bis-methoxymethoxy-3-methoxymethyl-benzene (5.66 g, 17.59 mmol) in Et₂O (60 mL) was added n-BuLi (15.47 mL, 2.5 M in Hexane) at −78° C. After stirring for 1 hour at −78° C., DMF (13.6 mL, 175.8 mmol) was the added and reaction mixture was allowed to warm to room temperature over 3 hours. The reaction was quenched with saturated NH₄Cl and extracted with Et₂O. The organic extracts were dried and concentrated in vacuo. The residue was purified by silica gel flash column chromatography to give 2,4-bis-methoxymethoxy-6-methoxymethyl-benzaldehyde (3.93 g, 82%). ¹H NMR (400 MHz, CDCl₃δ 10.50 (s, 1H), 7.03 (s, 1H), 6.77 (s, 1H), 5.30 (s, 2H), 5.27 (s, 2H), 4.80 (s, 3H), 3.50 (s, 3H), 4.49 (s, 3H).

Step 3: 2,4-Dihydroxy-6-methoxymethyl-benzaldehyde

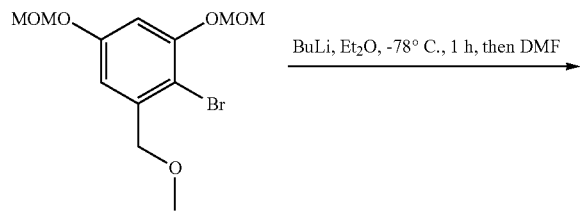

To a solution of 2,4-bis-methoxymethoxy-6-methoxymethyl-benzaldehyde (3.93 g, 14.45 mmol) in THF (30 mL) was added 6 N HCl (10 mL). The mixture was stirred at room temperature for 20 hours then diluted with EtOAc (200 mL). The mixture was washed with brine, dried and concentrated to give 2,4-dihydroxy-6-methoxymethyl-benzaldehyde (2.62 g, 100%). ¹H NMR (400 MHz, CDCl₃δ 12.40 (s, 1H), 10.10 (s, 1H), 6.41 (s, 1H), 6.30 (s, 1H), 5.60 (s, 1H), 4.61 (s, 2H), 3.40 (s, 3H).

Step 4: 2-Hydroxy-6-methoxymethyl-4-(tetrahydro-pyran-2-yloxy)-benzaldehyde

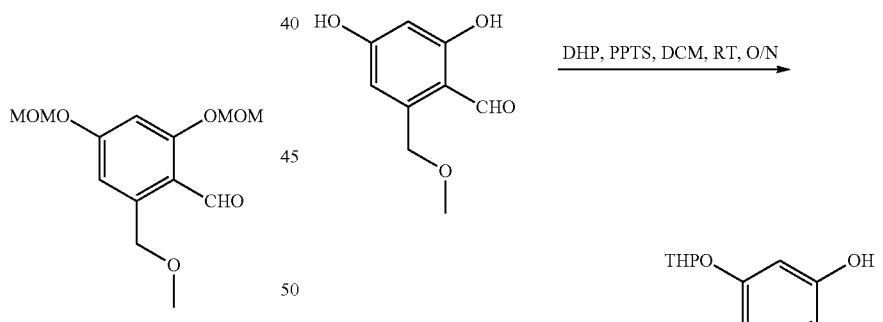

To a mixture of 2,4-dihydroxy-6-methoxymethyl-benzaldehyde (2.62 g, 14.45 mmol) in dichloromethane (50 mL) was added 3,4-dihydro-2H-pyran (2.42 g mL, 28.90 mmol) and pyridium p-toluenesulfonic acid (0.050 g) at room temperature. The resulting mixture was stirred at room temperature for 16 hours then concentrated in vacuo. The residue was purified by silica gel flash column chromatography to give 2-hydroxy-6-methoxymethyl-4-(tetrahydro-pyran-2-yloxy)-benzaldehyde (3.06 g, 80%). ¹H NMR (400 MHz, CDCl₃) δ

12.30 (s, 1H), 10.10 (s, 1H), 6.80 (s, 1H), 6.79 (s, 1H), 5.47 (s, 1H), 4.60 (s, 2H), 3.80 (m, 1H), 3.60 (m, 1H), 3.40 (s, 3H), 2.00-1.50 (m, 6H).

Step 5: Trifluoro-methanesulfonic acid 2-formyl-3-methoxymethyl-5-(tetrahydro-pyran-2-yloxy)-phenyl ester

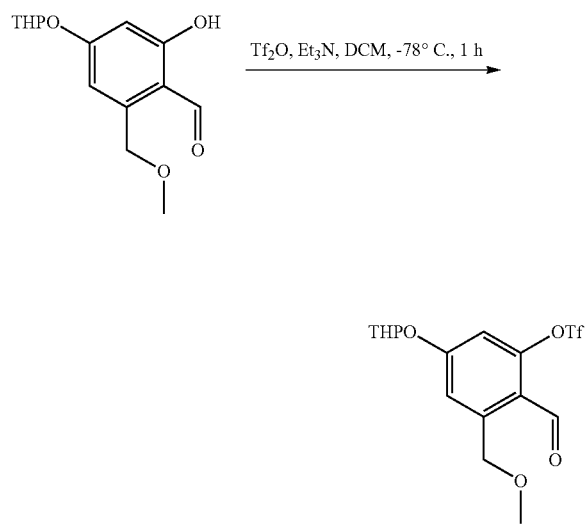

To a solution of 2-hydroxy-6-methoxymethyl-4-(tetrahydro-pyran-2-yloxy)-benzaldehyde (3.09 g, 11.62 mmol) and Et$_3$N (6.47 mL, 46.48 mmol) in dichloromethane (50 mL) was added Tf$_2$O (4.30 mL, 25.56 mmol) at −78° C. The mixture was stirred at −78° C. for 1 hour. The mixture was diluted with H$_2$O and extracted with dichloromethane. The organic extracts were washed with brine, dried and concentrated in vacuo. The residue was dissolved in Hexane-EtOAc (4:1), filtered through a plug of silica gel and filtrate was concentrated to give trifluoro-methanesulfonic acid 2-formyl-3-methoxymethyl-5-(tetrahydro-pyran-2-yloxy)-phenyl ester (2.60 g, 72%). $^1$H NMR (400 MHz, CDCl$_3$) δ 10.30 (s, 1H), 7.44 (s, 1H), 7.00 (s, 1H), 5.60 (s, 1H), 4.80 (s, 2H), 3.80 (m, 1H), 3.65 (m, 1H), 3.50 (s, 3H), 2.00-1.50 (m, 6H).

Step 6: 2-Methoxymethyl-4-(tetrahydro-pyran-2-yloxy)-6-(4,4,5,5-tetramethyl-[1,3,2]dioxaborolan-2-yl)-benzaldehyde

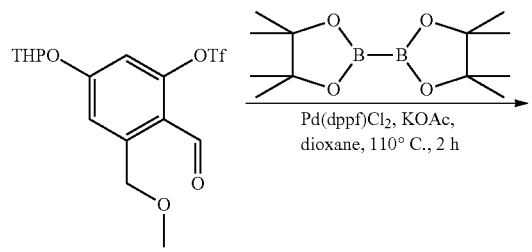

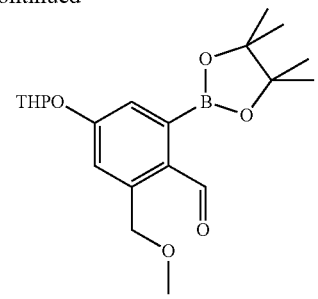

A mixture of trifluoro-methanesulfonic acid 2-formyl-3-methoxymethyl-5-(tetrahydro-pyran-2-yloxy)-phenyl ester (2.60 g, 6.53 mmol), bis(pinacolato)diborane (3.32 g, 13.07 mmol), Pd(dppf)Cl$_2$ (0.95 g, 1.31 mmol) and KOAc (1.92 g, 19.59 mmol) in dioxane (50 mL) was degassed for 10 minutes with bubbling N$_2$. The reaction mixture was heated at 110° C. for 2 hours then diluted with EtOAc (100 mL). The mixture was filtered through a pad of celite and concentrated in vacuo. The residue was purified by silica gel flash column chromatography to give 2-methoxymethyl-4-(tetrahydro-pyran-2-yloxy)-6-(4,4,5,5-tetramethyl-[1,3,2]dioxaborolan-2-yl)-benzaldehyde as a yellow oil (1.99 g, quant). $^1$HNMR (400 MHz, CDCl$_3$): 10.40 (s, 1H), 7.30 (s, 1H), 7.29 (s, 1H), 5.60 (s, 1H), 4.80 (m, 2H), 3.80 (m, 1H), 3.60 (m, 1H), 3.40 (s, 3H), 2.10-1.50 (m, 6H), 1.40 (s, 12H).

Step 7: (1,6-Dihydroxy-4-methoxymethyl-1,3-dihydro-benzo[c][1,2]oxaborol-3-yl)-acetic acid ethyl ester

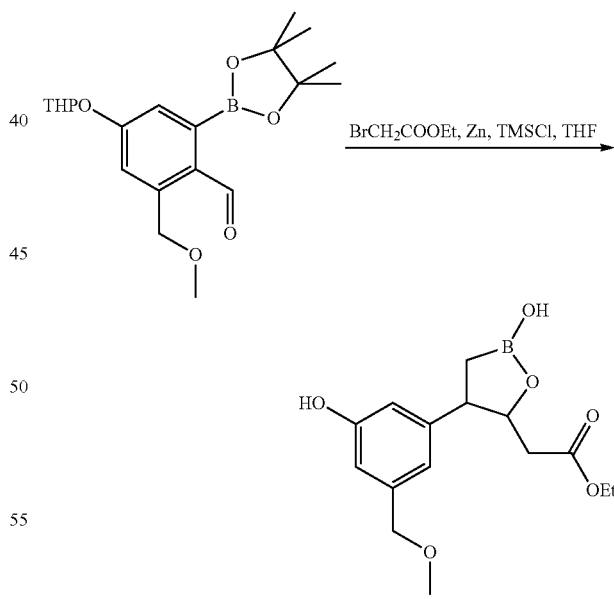

To a suspension of zinc dust (5.35 g, 82.3 mmol) in THF (10 mL) was added trimethylsilyl chloride (1.1 g, 10.15 mmol) at 40° C. The mixture was heated to 55° C. and stirred for 45 minutes. After cooling down to 37° C., ethyl bromoacetate (7.58 mL, 74.87 mmol) was slowly added to the reaction mixture at 37-40° C. After addition, the resulting mixture was allowed to cool to room temperature over 30 minutes. This solution was added to a solution of 2-methoxymethyl-4-(tetrahydro-pyran-2-yloxy)-6-(4,4,5,5-tetramethyl-[1,3,2]dioxaborolan-2-yl)-benzaldehyde (1.99 g, 5.29 mmol) in THF (6 mL) at 0° C. The mixture was stirred for 10 minutes before treating with 3 N HCl and extracting with EtOAc (2×25 mL). The organic extracts were washed with brine, dried and concentrated in vacuo. The residue was purified by silica gel flash column chromatography and lyophilized to give (1,6-dihydroxy-4-methoxymethyl-1,3-dihydro-benzo[c][1,2]oxaborol-3-yl)-acetic acid ethyl ester (1.0 g, 68%). $^1$H NMR (400 MHz, Acetone-d$_4$) δ 8.40 (s, 1H), 8.00 (s, 1H), 7.10 (s, 1H), 6.90 (s, 1H), 5.60 (m, 1H), 4.47 (m, 2H), 4.08 (m, 2H), 3.37 (s, 3H), 3.10 9m, 1H), 2.25 (m, 1H), 1.20 (m, 3H).

Step 8: (1,6-Dihydroxy-4-methoxymethyl-1,3-dihydro-benzo[c][1,2]oxaborol-3-yl)-acetic acid

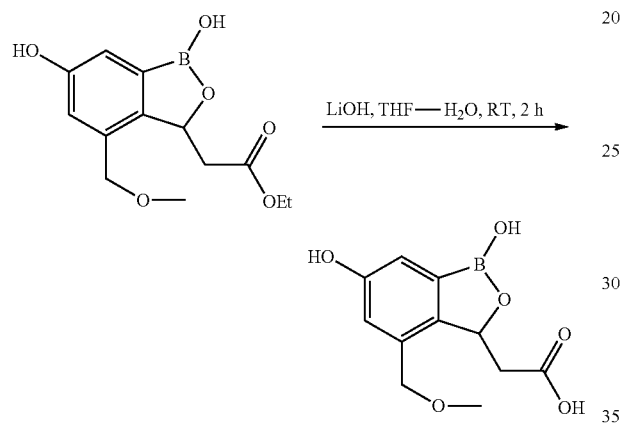

To a solution of (1,6-dihydroxy-4-methoxymethyl-1,3-dihydro-benzo[c][1,2]oxaborol-3-yl)-acetic acid ethyl ester (0.20 g, 0.67 mmol) in THF (6 mL) and H$_2$O (2 mL) was added LiOH (0.130 g) at 0° C. The resulting mixture was stirred at room temperature for 2 hours then cooled to 0° C. and acidified to pH 3 with 6N HCl. The mixture was concentrated in vacuo and the residue was purified by preparative HPLC to give (1,6-dihydroxy-4-methoxymethyl-1,3-dihydro-benzo[c][1,2]oxaborol-3-yl)-acetic acid (0.120 g, 71%). $^1$H NMR (400 MHz, DMSO-d$_6$) δ 12.24 (s, 1H), 9.42 (s, 1H), 9.10 (s, 1H), 6.99 (s, 1H), 6.82 (s, 1H), 5.46 (m, 1H), 3.28 (s, 3H), 3.03 (m, 1H), 2.02 (m, 1H). MS (ESI) m/z: 251 [M−1]$^-$. HPLC purity: 97.87% (220 nm), 98.47% (Maxplot).

G12: 2-(1,6-dihydroxy-4-methoxy-1,3-dihydrobenzo[c][1,2]oxaborol-3-yl)-acetic acid

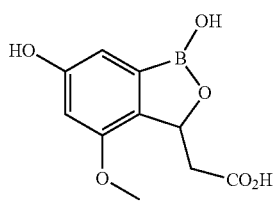 [SMILES: COc1cc(O)cc2c1C(CC(=O)O)OB2O]

Step 1: 2-bromo-4,6-dihydroxybenzaldehyde

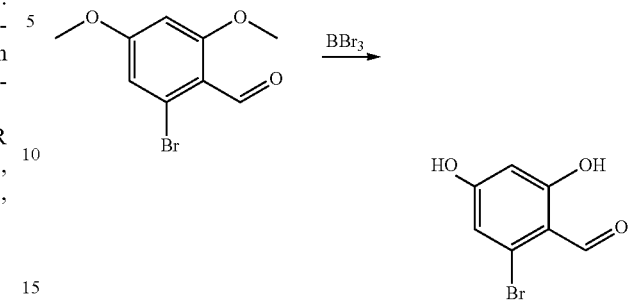

To a solution of 2-bromo-4,6-dimethoxybenzaldehyde (7.35 g, 30.0 mmol) in dichloromethane (50 mL) was added dropwise boron tribromide (18.75 g, 75.0 mmol) at −78° C. The reaction mixture was stirred at room temperature overnight, poured into ice and extracted with ethyl acetate (80 mL×3). The combined organic layers were dried over anhydrous Na$_2$SO$_4$ and concentrated in vacuo. The residue was purified by column chromatography (EtOAc/PE=1/3) on silica gel to give the title compound as a white solid. (5.09 g, Y: 78.2%). $^1$H NMR (400 MHz, DMSO-d) δ12.18 (s, 1H), 11.33 (s, 1H), 9.98 (s, 1H), 6.71-6.72 (d, J=2.4 Hz, 1H), 6.30-6.31 (d, J=2 Hz, 1H). MS (ESI) m/z=217 [M+H]$^+$.

Step 2: 2-bromo-6-hydroxy-4-(tetrahydro-2H-pyran-2-yloxy)benzaldehyde

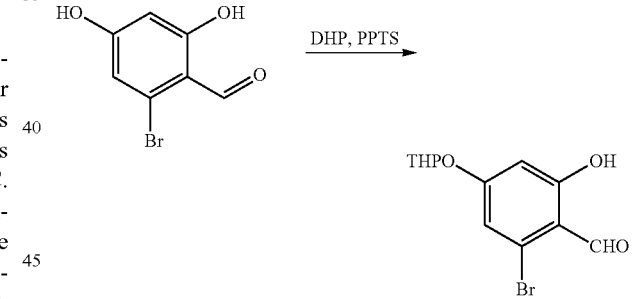

A mixture of 2-bromo-4,6-dihydroxybenzaldehyde (4.34 g, 20.0 mmol) and PPTS (0.51 g, 2.0 mmol) in dichloromethane (100 mL) was added DHP (3.02 g, 36.0 mmol). The reaction mixture was stirred at room temperature overnight and concentrated in vacuo. The residue was purified by column chromatography (EtOAc/PE=1/15) on silica gel to give the title compound as a colorless oil. (4.52 g, Y: 75.1%).

Step 3: 2-bromo-6-methoxy-4-(tetrahydro-2H-pyran-2-yloxy)benzaldehyde

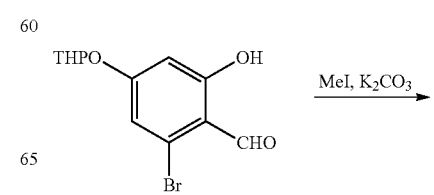

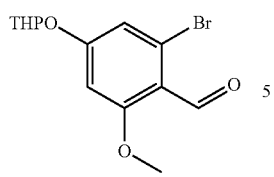

To a solution of 2-bromo-6-hydroxy-4-(tetrahydro-2H-pyran-2-yloxy)benzaldehyde (4.52 g, 15.0 mmol) in THF (50 mL) was added potassium carbonate (2.07 g, 15.0 mmol), followed by iodomethane (4.23 g, 30.0 mmol). The reaction mixture was stirred at room temperature overnight and quenched by saturated NaHCO$_3$ aqueous solution (20 mL). The resulting mixture was extracted with EtOAc (25 mL×2) and the combined extracts were dried over anhydrous Na$_2$SO$_4$ and concentrated in vacuo. The residue was purified by column chromatography (EtOAc/PE=1/8) on silica gel to give the title compound as a white solid. (4.53 g, Yield: 95.8%). $^1$H NMR (400 MHz, DMSO-d) δ0.19 (s, 1H), 6.98-6.98 (d, J=2.0 Hz, 1H), 6.81-6.82 (d, J=2.0 Hz, 1H), 6.73-6.74 (m, 1H), 3.88 (s, 3H), 3.60-3.75 (m, 2H), 1.75-1.89 (m, 3H), 1.53-1.67 (m, 3H). MS (ESI) m/z=315 [M+H]$^+$.

Step 4: 2-Methoxy-4-(tetrahydro-2H-pyran-2-yloxy)-6-(4,4,5,5-tetramethyl-1,3,2-dioxaborolan-2-yl)benzaldehyde

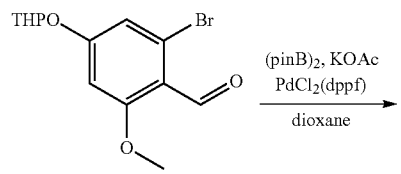

A mixture of 2-bromo-6-methoxy-4-(tetrahydro-2H-pyran-2-yloxy)benzaldehyde (3.15 g, 10.0 mmol), KOAc (2.94 g, 30.0 mmol), bis(pinacolato)diborane (3.81 g, 15.0 mmol) and PdCl$_2$(dppf) (0.733 g, 1.0 mmol) in dioxane (15 mL) was degassed with a stream of nitrogen and heated to 120° C. in a microwave reactor oven for 45 min. The reaction mixture was filtered and the filtrate was concentrated under reduced pressure. The residue was purified by column chromatography (EtOAc/PE=1/3) on silica gel to give the title compound as a yellow solid. (2.11 g, Y: 58.4%). $^1$H NMR (400 MHz, DMSO-d) δ 10.13 (s, 1H), 6.76 (s, 1H), 6.59 (s, 1H), 5.71 (s, 1H), 3.88 (s, 3H), 3.58-3.74 (m, 1H), 1.56-1.87 (m, 6H), 1.31 (s, 12H). MS (ESI) m/z=363 [M+H]$^+$.

Step 5: Ethyl-2-(1-hydroxy-4-methoxy-6-(tetrahydro-2H-pyran-2-yloxy)-1,3-dihydrobenzo[c][1,2]oxaborol-3-yl)acetate

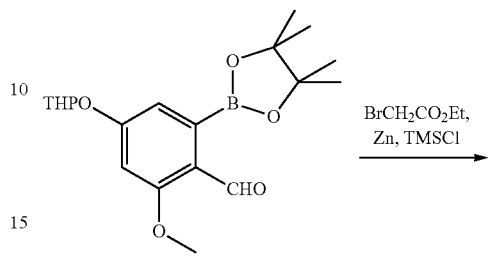

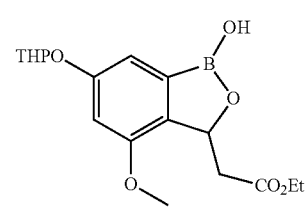

To a mixture of zinc powder (0.98 g, 15.0 mmol) in anhydrous THF (30 mL) was added TMSCl (0.39 mL, 3.0 mmol) at 40° C. The resulting mixture was stirred at 55° C. for 15 min and cooled to 37° C. After addition of ethyl 2-bromoacetate (1.35 mL, 12.0 mmol), the reaction mixture was stirred at this temperature for an additional 30 min. To a solution of 2-methoxy-4-(tetrahydro-2H-pyran-2-yloxy)-6-(4,4,5,5-tetramethyl-1,3,2-dioxaborolan-2-yl)benzaldehyde (1.09 g, 3.0 mmol) in anhydrous THF (40 mL) was added dropwise the above prepared solution at −78° C. The reaction mixture was allowed to warm to room temperature and stirred for 1.5 h before quenched by aqueous ammonium chloride (20 mL). The resulting mixture was extracted with ethyl acetate (50 mL×2) and the combined organic layers were dried over anhydrous Na$_2$SO$_4$ and concentrated in vacuo. The residue was purified by column chromatography (EtOAc/PE=1/4) on silica gel to give the title compound as a yellow solid. (0.86 g, Y: 82.3%). MS (ESI) m/z=267 [M+H]$^+$.

Step 6: Ethyl-2-(1,6-dihydroxy-4-methoxy-1,3-dihydrobenzo[c][1,2]oxaborol-3-yl)acetate

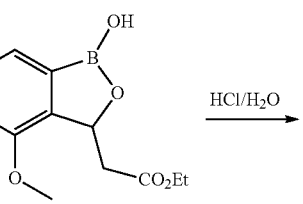

-continued

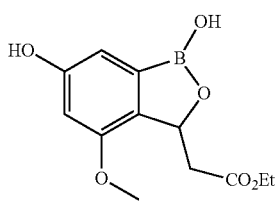

To a solution of ethyl-2-(1-hydroxy-4-methoxy-6-(tetrahydro-2H-pyran-2-yloxy)-1,3-dihydrobenzo[c][1,2]oxaborol-3-yl)acetate (0.35 g, 1.0 mmol) in THF (10 mL) was added dropwise concentrated hydrochloride acid (0.2 mL) at 0° C. The reaction mixture was stirred at 0° C. for 1 hr and concentrated in vacuo. The residue was purified by column chromatography on silica gel (EtOAc/PE=1/2) to give the title compound as a light yellow solid (180 mg, Y: 67.7%). $^1$H NMR (400 MHz, DMSO-d) δ 9.45 (s, 1H), 9.15 (s, 1H), 6.65-6.66 (d, J=1.2 Hz, 1H), 6.48-6.49 (d, J=1.2 Hz, 1H), 5.33-5.36 (m, 1H), 4.05-4.10 (m, 2H), 3.76 (s, 3H), 3.10-3.13 (m, 1H), 2.15-2.21 (m, 1H), 1.16-1.20 (m, 3H). MS (ESI) m/z=267 [M+H]$^+$.

Step 7: 2-(1,6-dihydroxy-4-methoxy-1,3-dihydrobenzo[c][1,2]oxaborol-3-yl)acetic acid

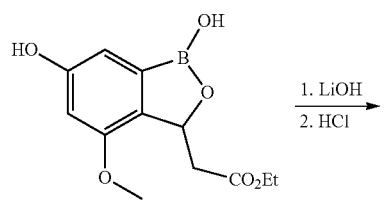

To a solution of ethyl-2-(1,6-dihydroxy-4-methoxy-1,3-dihydrobenzo[c][1,2]oxaborol-3-yl)acetate (133 mg, 0.50 mmol) in THF (2 mL) was added aqueous lithium hydroxide (102 mg, 2.5 mmol) in 3 mL of water at 0° C. The reaction mixture was stirred at room temperature for 1.5 hr and acidified to pH=2 using diluted hydrochloride acid. The resulting mixture was extracted with ethyl acetate (15 mL×2) and the combined organic layers were dried over anhydrous and concentrated in vacuo. The residue was purified by HPLC to give the title as a white solid (63 mg, Yield: 53%). $^1$H NMR (400 MHz, DMSO-d) δ 9.49 (s, 1H), 9.15 (s, 1H), 6.65 (s, 1H), 6.48 (s, 1H), 5.31-5.34 (m, 1H), 3.77 (s, 3H), 3.04-3.09 (m, 1H), 1.98-2.04 (m, 1H). MS (ESI) m/z=239 [M+H]$^+$.

G13: 2-(4-(Benzyloxy)-1,6-dihydroxy-1,3-dihydrobenzo[c][1,2]oxaborol-3-yl)acetic acid

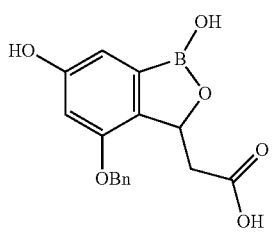 [SMILES: O=C(O)CC1OB(O)c2cc(O)cc(OCc3ccccc3)c21]

Step 1: 2-Bromo-4,6-dimethoxybenzaldehyde

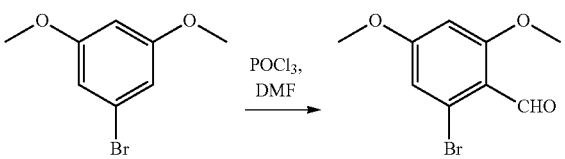

To a mixture of 1-bromo-3,5-dimethoxybenzene (21.7 g, 100.0 mmol) in DMF (80 mL) was added POCl$_3$ (15 mL, 150 mmol) at 0° C. The mixture was stirred at room temperature for 30 min and then heated at 100° C. for an additional 30 min. The reaction mixture was cooled to room temperature and poured onto ice. The precipitate was collected by filtration and dried under high vacuum to give the title compound as a yellow solid. (19.4 g, Yield: 79%). $^1$H NMR (400 MHz, DMSO-d) δ10.18 (s, 1H), 6.91-6.91 (d, J=2.0 Hz, 1H), 6.74-6.73 (d, J=2.0 Hz, 1H), 3.90 (s, 3H), 3.89 (s, 3H).

Step 2: 2-Bromo-4,6-dihydroxybenzaldehyde

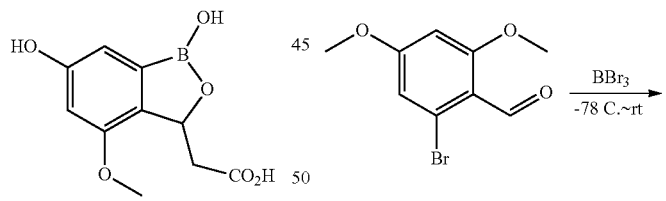

To a solution of 2-bromo-4,6-dimethoxybenzaldehyde (7.35 g, 30.0 mmol) in dichloromethane (50 mL) was added boron tribromide (18.7 g, 75.0 mmol) dropwise at −78° C. The reaction mixture was stirred at room temperature overnight and poured onto ice. The resulting mixture was extracted with ethyl acetate (3×80 mL) and the combined organic layers were dried over anhydrous Na$_2$SO$_4$, concentrated in vacuo. The residue was purified by column chromatography on silica gel (EtOAc:PE=1:1) to give the title compound as a white solid (5.10 g, Yield: 78.2%). $^1$H NMR (400

MHz, DMSO-d) δ 12.18 (s, 1H), 11.32 (s, 1H), 9.98 (s, 1H), 6.71-6.72 (d, J=2.4 Hz, 1H), 6.30-6.31 (d, J=2.0 Hz, 1H).

Step 3: 2-Bromo-6-hydroxy-4-(tetrahydro-2H-pyran-2-yloxy)benzaldehyde

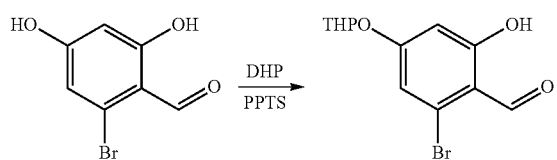

To a mixture of 2-bromo-4,6-dihydroxybenzaldehyde (2.50 g, 11.5 mmol) in dichloromethane was added 3,4-dihydro-2H-pyran (1.45 g, 17.3 mol) and PPTs (0.58 g, 2.3 mmol) at room temperature. The resulting mixture was stirred for 2 h and quenched by saturated aqueous $NaHCO_3$ (35 mL). The organic layer was washed with water (20 mL), brine (20 mL) and dried over anhydrous $Na_2SO_4$ and concentrated in vacuo. The residue was purified by column chromatography (PE:EtOAc=2:1) on silica gel to afford the title compound as a colorless oil (2.93 g, yield: 85%)

Step 4: 2-(Benzyloxy)-6-bromo-4-(tetrahydro-2H-pyran-2-yloxy)benzaldehyde

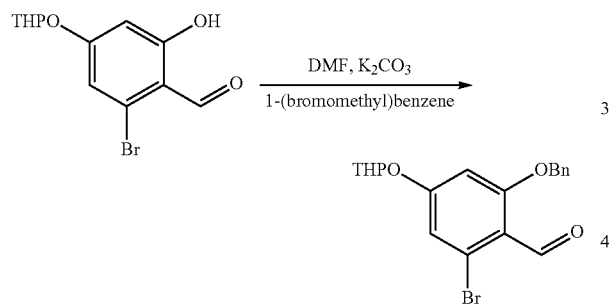

To a mixture of 2-bromo-6-hydroxy-4-(tetrahydro-2H-pyran-2-yloxy)benzaldehyde (1.8 g, 6.0 mmol) and anhydrous $K_2CO_3$ (1.66 g, 12.0 mmol) in DMF (10 mL) was slowly added 1-(bromomethyl)benzene (1.22 g, 7.2 mmol) at 0° C. The reaction mixture was allowed to warm to room temperature and stirred for 2 h before quenched by water (15 mL). The resulting mixture was further stirred for 20 min and white precipitate was collected by filtration. The solid was washed with ether and dried under high vacuum to give the title compound as a white powder (3.9 g, yield: 83%).

Step 5: 2-(Benzyloxy)-4-(tetrahydro-2H-pyran-2-yloxy)-6-(3,3,4,4-tetramethylborolan-1-yl)benzaldehyde

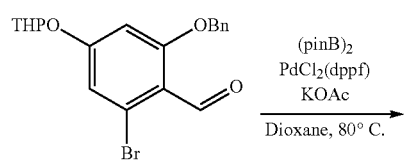

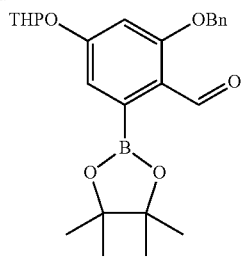

To a mixture of bis(pinacolato)diborane (3.05 g, 12.0 mmol), KOAc (2.94 g, 30.0 mmol). $PdCl_2(dppf)$ (0.73 g, 1.0 mmol) in dioxane (50 mL) was added 2-(benzyloxy)-6-bromo-4-(tetrahydro-2H-pyran-2-yloxy)benzaldehyde (3.91 g, 10.0 mmol). After degassed for 15 min with a stream of nitrogen, the mixture was heated to 80° C. for 1 h. The reaction was quenched by addition of ice-water (30 mL). The resulting mixture was extracted with $CH_2Cl_2$ (3×30 mL). The combined organic layers were washed with brine (25 mL), dried over anhydrous $Na_2SO_4$ and concentrated in vacuo. The residue was purified by column chromatography on silica gel (PE:EtOAc=1:2) to give the title compound as a light yellow solid (2.8 g, yield: 64%).

Step 6: Ethyl-(4-(benzyloxy)-1-hydroxy-6-(tetrahydro-2H-pyran-2-yloxy)-1,3-dihydrobenzo[c][1,2]oxaborol-3-yl)acetate

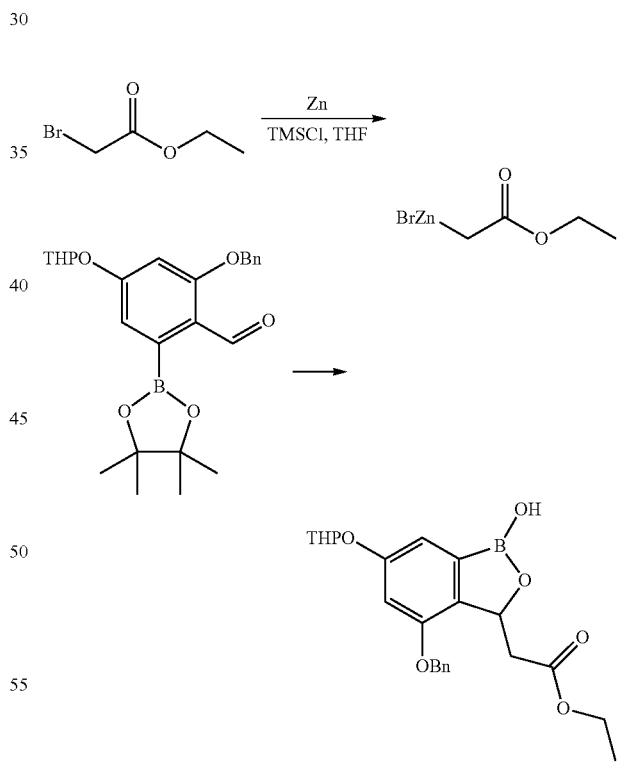

To a suspension of powdered zinc dust (3.3 g, 51 mmol) in THF (20 mL) was added trimethylsilyl chloride at room temperature. The reaction mixture was stirred at 40° C. for 20 min and ethyl bromoacetate (5.59 g, 33.0 mmol) was slowly added, the reaction mixture was stirred at 40° C. for an additional 30 min. To a solution of 2-(benzyloxy)-4-(tetrahydro-2H-pyran-2-yloxy)-6-(3,3,4,4-tetramethylborol-1-yl)benzaldehyde (2.8 g, 6.4 mmol) in THF (15 mL) was added dropwise the above prepared zinc reagent at −78° C. The reaction mixture was stirred at room temperature for 1 h and quenched by saturated aqueous NH₄Cl. The resulting mixture was extracted with EtOAc (3×25 mL). The combined organic layers were washed with brine (20 mL), dried over anhydrous Na₂SO₄ and concentrated in vacuo to give the title compound as a light yellow oil (1.3 g, yield: 48%).

Step 7: Ethyl 2-(4-(benzyloxy)-1,6-dihydroxy-1,3-dihydrobenzo[c][1,2]oxaborol-3-yl)acetate

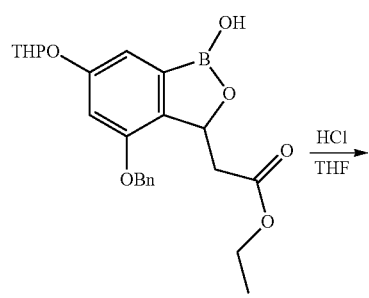

To a mixture of ethyl 2-(4-(benzyloxy)-1-hydroxy-6-(tetrahydro-2H-pyran-2-yloxy)-1,3-dihydrobenzo[c][1,2]oxaborol-3-yl)acetate (1.48 g, 3.1 mmol) in THF (10 mL) was slowly added conc. HCl (1.48 mL) at 0° C. The reaction mixture was stirred at room temperature for 1 h and neutralized by addition of Et₃N. The resulting mixture was extracted with EtOAc (3×25 mL), dried over anhydrous Na₂SO₄ and concentrated to give the title compound as a white powder (1.01 g, Yield: 95%).

Step 8: 2-(4-(Benzyloxy)-1,6-dihydroxy-1,3-dihydrobenzo[c][1,2]oxaborol-3-yl)acetic acid

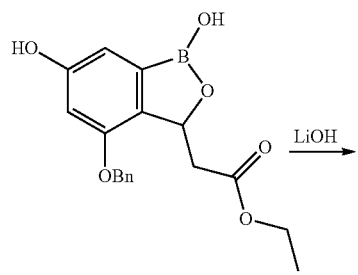

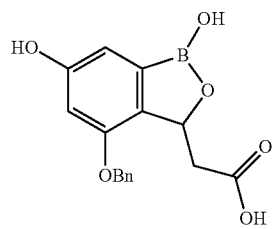

To a solution of ethyl 2-(4-(benzyloxy)-1,6-dihydroxy-1,3-dihydrobenzo[c][1,2]oxaborol-3-yl)acetate (195 mg, 0.57 mmol) in EtOH (4 mL) was added dropwise an aqueous solution of lithium hydroxide (47.9 mg, 1.14 mmol) in water (4 mL). The reaction mixture was stirred at room temperature overnight and acidified with 1N HCl to pH=3. The resulting mixture was extracted with EtOAc (2×20 mL). Combined organic layers were dried over anhydrous Na₂SO₄ and concentrated in vacuo. The residue was purified by prep HPLC to give the title compound as a white powder (41.2 mg, Yield: 23%). ¹H NMR (400 MHz, CDCl₃) δ 9.46 (s, 1H), 9.14 (s, 1H), 7.44-7.33 (m, 5H), 6.66 (d, J=1.2 Hz, 1H), 6.54 (s, 1H), 5.36 (m, 1H), 5.12 (s, 2H), 3.15 (m, 1H), 2.07 (m, 1H). MS (ESI) m/z=315 [M+H]⁺.

G14: (4-Aminomethyl-1,6-dihydroxy-1,3-dihydro-benzo[c][1,2]oxaborol-3-yl)-acetic acid

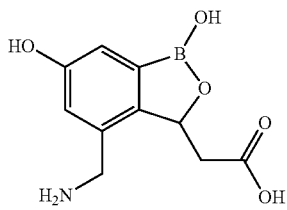 [SMILES: NCc1cc(O)cc2c1C(CC(=O)O)OB2O]

Step 1: 3,5-Bis-methoxymethoxy-benzoic acid methyl ester

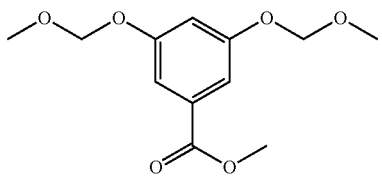

A solution of 3,5-dihydroxy-benzoic acid methyl ester (10.1 g, 60.0 mmol) in CH₂Cl₂ (100 mL) and DIPEA (40.0 mL, 240 mmol) was treated with chloromethyl methyl ether (13.7 mL, 180 mmol) at 0° C. for 30 min and the reaction was warmed to room temperature for 1 h. The reaction mixture was diluted with CH₂Cl₂ and washed with saturated NaHCO₃. The organic phase was separated, dried (Na₂SO₄),

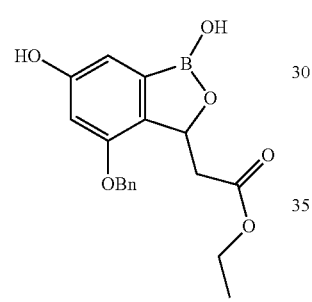

and concentrated. The residue was purified by flash column chromatography (silica, hexanes/ethyl acetate=3:1) to afford the title compound (11.1 g, 74%). ¹H NMR (300 MHz, CDCl₃) δ 7.36 (s, 2H), 6.91 (s, 1H), 5.19 (s, 4H), 3.90 (s, 3H), 3.48 (s, 6H).

Step 2: (3,5-Bis-methoxymethoxy-phenyl)-methanol

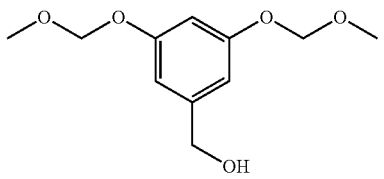

A solution of 3,5-bis-methoxymethoxybenzoic acid methyl ester (11.1 g, 43.3 mmol) in Et₂O (150 mL) was treated with LiAlH₄ (2.46 g, 65.0 mmol) at 0° C. The suspension was stirred at room temperature for 1 h. The reaction mixture was slowly quenched by water and extracted with ethyl acetate. The organic phase was separated, dried (Na₂SO₄), and concentrated. The residue was purified by flash column chromatography (silica, hexanes/ethyl acetate=2:3) to afford the title compound (9.16 g, 93%). ¹H NMR (300 MHz, CDCl₃) δ 6.71 (s, 1H), 6.70 (s, 1H), 6.64 (s, 1H), 5.15 (s, 4H), 4.62 (d, J=6.0 Hz, 2H), 3.47 (s, 6H), 1.93 (t, 1H).

Step 3: (2-Bromo-3,5-bis-methoxymethoxy-phenyl)-methanol

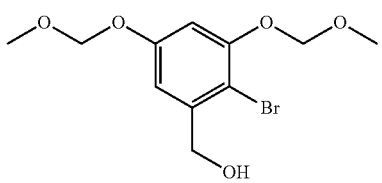

A solution of (3,5-bis-methoxymethoxy-phenyl)-methanol (9.16 g, 40.2 mmol) in DMF (40 mL) was treated with NBS (7.51 g, 42.2 mmol) at room temperature and the mixture was stirred at same temperature for 30 min. The residue was diluted with ethyl acetate and washed with brine. The organic phase was separated, dried (Na₂SO₄), and concentrated. The residue was purified by flash column chromatography (silica, hexanes/ethyl acetate=1:1) to afford the title compound (10.2 g, 83%). ¹H NMR (300 MHz, CDCl₃) δ 6.91 (s, 1H), 6.81 (s, 1H), 5.24 (s, 2H), 5.17 (s, 2H), 4.72 (d, J=6.3 Hz, 2H), 3.52 (s, 3H), 3.47 (s, 3H), 2.05 (t, 1H).

Step 4: 2-Bromo-1,5-bis-methoxymethoxy-3-methoxymethyl-benzene

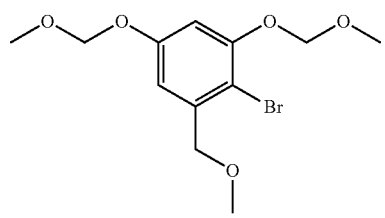

A solution of (2-bromo-3,5-bis-methoxymethoxy-phenyl)-methanol (10.2 g, 33.3 mmol) in THF (60 mL) was treated with NaH (2.67 g, 66.7 mmol) at 0° C. The resulting suspension was stirred at room temperature for 20 min. CH₃I was added to the mixture and the reaction was stirred at room temperature for 1 h. The reaction was quenched with water and extracted with ethyl acetate. The organic phase was separated, dried (Na₂SO₄), and concentrated. The residue was purified by flash column chromatography (silica, hexanes/ethyl acetate=5:1) to afford the title compound (10.5 g, 96%). ¹H NMR (300 MHz, CDCl₃) δ 6.88 (s, 1H), 6.80 (s, 1H), 5.23 (s, 2H), 5.17 (s, 2H), 4.50 (s, 2H), 3.51 (s, 3H), 3.47 (s, 6H).

Step 5: 2,4-Bis-methoxymethoxy-6-methoxymethyl-benzaldehyde

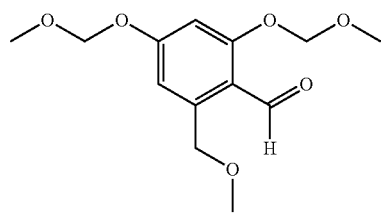

To a solution of 2-bromo-1,5-bis-methoxymethoxy-3-methoxymethyl-benzene (10.5 g, 32.8 mmol) in Et₂O (100 mL) was treated with n-BuLi (28.7 mL, 71.9 mmol) at −78° C. for 1 h. Then, DMF (27.7 mL, 359 mmol) was added to the reaction and the resulting mixture was warmed to room temperature for 3 h. The reaction was quenched with water and extracted with ethyl acetate. The organic phase was separated, dried (Na₂SO₄), and concentrated. The residue was purified by the flash column chromatography (silica, hexanes/ethyl acetate=2:1) affording the title compound (7.21 g). ¹H NMR (300 MHz, CD₃OD) δ 10.49 (s, 1H), 7.46 (s, 1H), 6.45 (s, 1H), 5.27 (s, 2H), 5.24 (s, 2H), 4.83 (s, 2H), 3.51 (s, 3H). 3.50 (s, 3H), 3.49 (s, 3H).

Step 6: 2,4-Dihydroxy-6-methoxymethyl-benzaldehyde

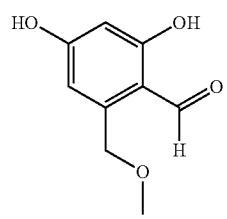

A solution of 2,4-bis-methoxymethoxy-6-methoxymethyl-benzaldehyde (7.21 g, 26.7 mmol) in THF (60 mL) was treated with 6N HCl (20 mL) at room temperature. The resulting mixture was heated to 60° C. for 1 h. The reaction was diluted with ethyl acetate and washed with water. The organic phase was separated, dried ($Na_2SO_4$), and concentrated. The residue was purified by flash column chromatography (silica, hexanes/ethyl acetate=1:1) to afford the title compound (4.08 g, 84%). $^1$H NMR (300 MHz, $CD_3OD$) δ 10.01 (s, 1H), 6.35 (s, 1H), 6.25 (s, 1H), 4.57 (s, 2H), 3.36 (s, 3H), 2.64 (s, 2H).

Step 7: 2-Hydroxy-6-methoxymethyl-4-(tetrahydro-pyran-2-yloxy)-benzaldehyde

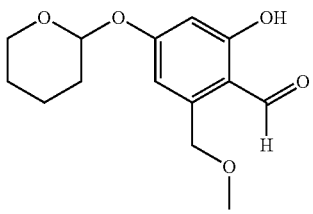 [SMILES: COCc1cc(OC2CCCCO2)cc(O)c1C=O]

A solution of 2,4-dihydroxy-6-methoxymethylbenzaldehyde (4.08 g, 22.4 mmol) in dichloromethane (100 mL) was treated with PPTS (100 mg) and DHP (4.06 mL, 44.8 mmol) at room temperature overnight. The reaction was concentrated to dryness. The residue was purified by the flash column chromatography (silica, hexanes/ethyl acetate=3:1) to afford the title compound (5.18 g, 87%). $^1$H NMR (300 MHz, $CD_3OD$) δ 12.34 (s, 1H), 10.12 (s, 1H), 6.58 (s, 1H), 6.56 (s, 1H), 5.58 (m, 1H), 4.63 (s, 2H), 3.84-3.81 (m, 1H), 3.66-3.62 (m, 1H), 3.40 (s, 3H), 1.95-1.86 (m, 2H), 1.75-1.62 (m, 4H).

Step 8: Trifluoromethanesulfonic acid 2-formyl-3-methoxymethyl-5-(tetrahydro-pyran-2-yloxy)-phenyl ester

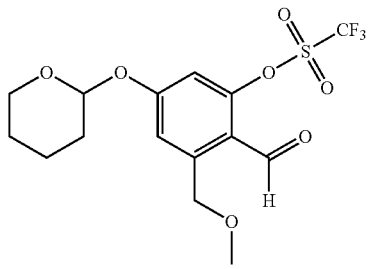 [SMILES: COCc1cc(OC2CCCCO2)cc(OS(=O)(=O)C(F)(F)F)c1C=O]

A solution of 2-hydroxy-6-methoxymethyl-4-(tetrahydro-pyran-2-yloxy)-benzaldehyde (5.18 g, 19.5 mmol) and TEA (10.9 mL, 78.0 mmol) in dichloromethane (100 mL) was treated with $Tf_2O$ (7.20 mL, 42.8 mmol) at −78° C. for 1 h. The mixture was diluted with water (150 mL) and extracted with dichloromethane. The organic phases were separated, dried ($Na_2SO_4$), and concentrated to dryness. The residue was purified by the flash column chromatography (silica, hexanes/ethyl acetate=4:1), affording the title compound (5.23 g, 67%). $^1$H NMR (300 MHz, $CDCl_3$) δ 10.29 (s, 1H), 7.44 (s, 1H), 6.99 (s, 1H), 5.60-5.58 (m, 1H), 4.84 (s, 2H), 3.78-3.74 (m, 1H), 3.68-3.62 (m, 1H), 3.51 (s, 3H), 1.91-1.88 (m, 2H), 1.74-1.68 (m, 4H).

Step 9: 2-Methoxymethyl-4-(tetrahydro-pyran-2-yloxy)-6-(4,4,5,5-tetramethyl-[1,3,2]dioxaborolan-2-yl)-benzaldehyde

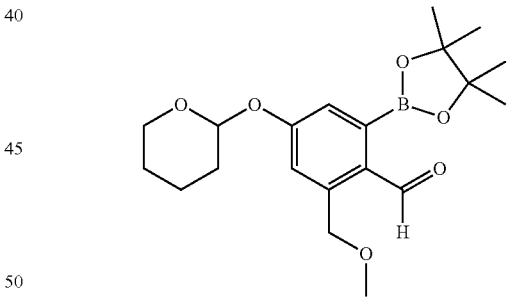

Trifluoromethanesulfonic acid 2-formyl-3-methoxymethyl-5-(tetrahydro-pyran-2-yloxy)-phenyl ester (5.23 g, 13.1 mmol), bis(pinacolato)diboron (5.00 g, 19.7 mmol), potassium acetate (3.86 g, 39.3 mmol), and $Pd(dppf)Cl_2$ (535 mg, 0.655 mmol) in a round bottle were degassed 3 times. Dioxane (80 mL) was added to the bottle and the suspension was heated to 110° C. for 2 h. The mixture was filtered through a pad of Celite and the filtrate was concentrated to dryness. The residue was purified by the flash column chromatography (silica, hexanes/ethyl acetate=5:1) to afford the title compound (3.56 g, 72%). $^1$H NMR (300 MHz, $CDCl_3$) δ 10.40 (s, 1H), 7.29 (s, 1H), 7.28 (s, 1H), 5.62-5.58 (m, 1H), 4.82-4.80 (m, 2H), 3.84-3.79 (m, 1H), 3.68-3.62 (m, 1H), 3.43 (s, 3H), 1.88-1.85 (m, 2H), 1.70-1.61 (m, 4H), 1.40 (s, 12H).

Step 10: [1-Hydroxy-4-methoxymethyl-6-(tetrahydro-pyran-2-yloxy)-1,3-dihydro-benzo[c][1,2]oxaborol-3-yl]-acetic acid ethyl ester

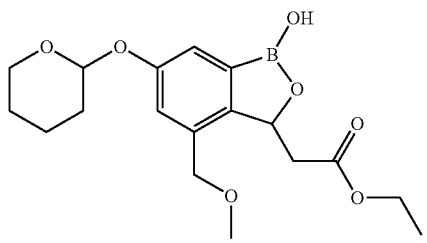 [SMILES: CCOC(=O)CC1OB(O)c2cc(OC3CCCCO3)cc(COC)c21]

A suspension of zinc (8.04 g, 123 mmol) in THF (80 mL) was added TMSCl (2.31 ml, 18.2 mmol) at 40° C. The temperature was increased to 55° C. over 30 min. Then, the temperature was lowered to 37° C. and ethyl 2-bromoacetate (12.6 mL, 114 mmol) was added slowly. The resulting solution was stirred for 30 min and cooled from 45° C. to room temperature and stood by for 1 h. The top clear layer (25 mL) was added to a solution of 2-methoxymethyl-4-(tetrahydro-pyran-2-yloxy)-6-(4,4,5,5-tetramethyl-[1,3,2]dioxaborolan-2-yl)-benzaldehyde (3.56 g, 9.46 mmol) in THF (50 ml) at −78° C. After the addition, the reaction was warmed to 0° C. using an ice bath and stirred at 0° C. 30 min. The reaction mixture was quenched with aqueous NH$_4$Cl and extracted with ethyl acetate. The organic phase was separated, dried (Na$_2$SO$_4$), and concentrated. The residue was purified by the flash column chromatography (silica, hexanes/ethyl acetate=2:1) to afford the title compound (2.30 g, 67%). $^1$H NMR (300 MHz, CDCl$_3$) δ 7.33 (s, 1H), 7.11 (s, 1H), 5.73-5.70 (m, 1H), 5.46-5.44 (m, 1H), 4.54-4.39 (m, 2H), 4.21-4.16 (q, 2H), 3.94-3.90 (m, 1H), 3.66-3.60 (m, 1H), 3.38 (s, 3H), 3.18-3.11 (m, 1H), 2.43-2.34 (m, 1H), 1.88-1.85 (m, 2H), 1.70-1.61 (m, 4H), 1.26 (t, 3H).

Step 11: (4-Bromomethyl-1,6-dihydroxy-1,3-dihydro-benzo[c][1,2]oxaborol-3-yl)-acetic acid ethyl ester

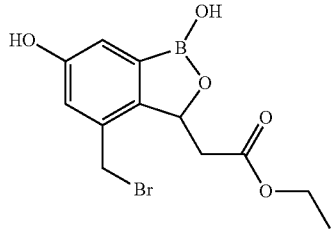

To a solution of [1-hydroxy-4-methoxymethyl-6-(tetrahydro-pyran-2-yloxy)-1,3-dihydro-benzo[c][1,2]oxaborol-3-yl]-acetic acid ethyl ester from step 1.10. (870 mg, 1.37 mmol) in DCM (10 mL) was added boron tribromide (0.46 mL, 3.02 mmol) slowly under −78° C. The reaction mixture was allowed to stir at room temperature for 1 h. Ethanol was added slowly and the solvent was removed under vacuum. The crude product was used for next step without further purification. $^1$H NMR (300 MHz, CD$_3$CN) δ 7.13 (s, 1H), 7.01 (s, 1H), 5.62 (dd, 1H), 4.42-4.63 (dd, 2H), 4.14 (q, 2H), 3.18-3.24 (dd, 1H), 2.40-2.51 (m, 1H), 1.22 (t, 3H).

Step 12: (4-Azidomethyl-1,6-dihydroxy-1,3-dihydro-benzo[c][1,2]oxaborol-3-yl)-acetic acid ethyl ester

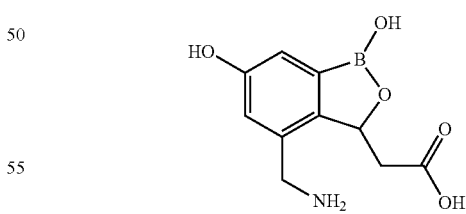

To a crude (4-bromomethyl-1,6-dihydroxy-1,3-dihydro-benzo[c][1,2]oxaborol-3-yl)-acetic acid ethyl ester in CH$_3$CN/H$_2$O (10/2 mL) was added sodium azide (3.1 g, 48 mmol). The solution was stirred overnight at r.t. The crude solution was purified by HPLC, yielded 450 mg of the title compound. $^1$H NMR (300 MHz, CD$_3$CN) δ 7.21 (s, 1H), 6.99 (s, 1H), 5.61 (dd, 1H), 4.31-4.56 (dd, 2H), 4.10 (q, 2H), 3.02-3.14 (dd, 1H), 2.37-2.43 (m, 1H), 1.21 (t, 3H).

Step 13: (4-Aminomethyl-1,6-dihydroxy-1,3-dihydro-benzo[c][1,2]oxaborol-3-yl)-acetic acid To a solution of (4-azidomethyl-1,6-dihydroxy-1,3-dihydro-benzo[c][1,2]oxaborol-3-yl)-acetic acid ethyl ester (15 mg) in THF/water (2:1, 1 mL) was added 10% Pd/C (5 mg), and a drop of 1N HCl. The reaction was degassed and stirred under hydrogen overnight and filtered off. The filtrate was purified by HPLC, yielded 2 mg of product. MS (ESI) m/z: 237.9 [M+1]$^+$; $^1$H NMR (300 MHz, CD$_3$OD) δ 8.25 (s, 3H), 7.06 (d, 1H), 6.98 (d, 1H), 8.20 (s, 1H), 5.68 (dd, 1H), 4.17 (s, 2H), 3.67 (s, 1H), 2.99-3.04 (m, 1H), 2.71-2.87 (m, 2H), 2.45-2.52 (m, 1H).

G15: (4-Diethylaminomethyl-1,6-dihydroxy-1,3-dihydro-benzo[c][1,2]oxaborol-3-yl)-acetic acid

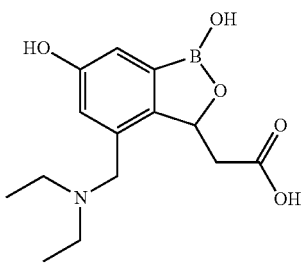 [SMILES: CCN(CC)Cc1cc(O)cc2c1C(CC(=O)O)OB2O]

To a mixture of (4-Bromomethyl-1,6-dihydroxy-1,3-dihydro-benzo[c][1,2]oxaborol-3-yl)-acetic acid ethyl ester (0.5 mmol) in DCM (5 mL) was added diethylamine (5 mmol) and the mixture was stirred overnight at r.t. The crude product was evaporated, LiOH (75 mg) in THF/water/methanol (2:1:1, 5 mL) was added and stirred at r.t. for 1 h. The solvent was evaporated to give a residue, which was purified by HPLC, yielded 5 mg of desire product. MS (ESI) m/z: 294 [M+1]$^+$; $^1$H NMR (300 MHz, CD$_3$OD) δ 7.18 (s, 2H), 5.72-5.76 (dd, 1H), 4.20-4.45 (dd, 2H), 3.05-3.22 (m, 3H), 2.36-2.44 (dd, 1H), 1.40-1.45 (t, 3H), 1.30-1.34 (t, 3H).

G16: 2-(1,6-dihydroxy-4-isopropoxy-1,3-dihydrobenzo[c][1,2]oxaborol-3-yl)acetic acid

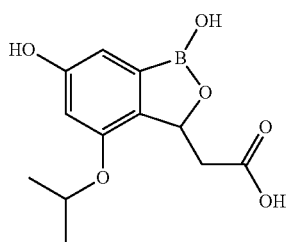 [SMILES: CC(C)Oc1cc(O)cc2c1C(CC(=O)O)OB2O]

Step 1: Ethyl 2-(1-hydroxy-4-isopropoxy-6-(tetrahydro-2H-pyran-2-yloxy)-1,3-dihydrobenzo[c][1,2]oxaborol-3-yl)acetate

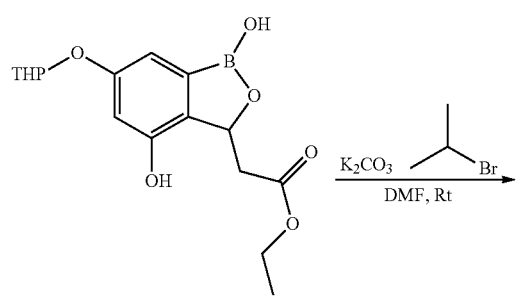

To a mixture of ethyl 2-(1,4-dihydroxy-6-(tetrahydro-2H-pyran-2-yloxy)-1,3-dihydrobenzo[c][1,2]oxaborol-3-yl)acetate (320 mg, 0.95 mmol) and anhydrous K$_2$CO$_3$ (480 mg, 3.48 mmol) in DMF (10 mL) at 0° C. under N$_2$ atmosphere was added 2-bromopropane (400 mg, 3.30 mmol). The reaction mixture was stirred at room temperature overnight and extracted with EtOAc (2×20 mL). The combined organic layers were dried over anhydrous Na$_2$SO$_4$ and concentrated in vacuo. The residue was purified by prep HPLC to give the title compound (110 mg. Yield: 30.6%)

Step 2: 2-(1,6-dihydroxy-4-isopropoxy-1,3-dihydrobenzo[c][1,2]oxaborol-3-yl)acetic acid

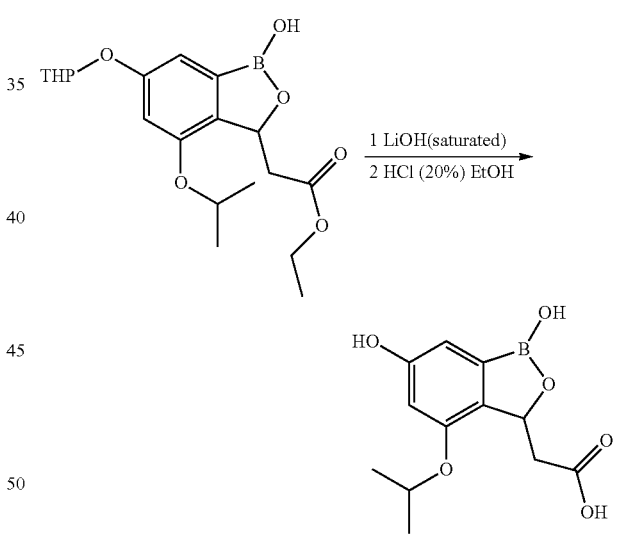

To a solution of ethyl 2-(1-hydroxy-4-isopropoxy-6-(tetrahydro-2H-pyran-2-yloxy)-1,3-dihydrobenzo[c][1,2]oxaborol-3-yl)acetate (110 mg, 0.29 mmol) in EtOH (4 mL) was added an aqueous solution of lithium hydroxide (25.2 mg, 0.60 mmol) in water (1 mL). The reaction mixture was stirred at room temperature for 30 min and acidified with 1N HCl to pH=4. The resulting mixture was extracted with EtOAc (2×20 mL). The combined organic layers were dried over anhydrous Na$_2$SO$_4$ and concentrated in vacuo. The residue was purified by prep HPLC to give the title compound as a white powder (40 mg. Yield: 51.8%). $^1$H NMR (400 MHz, CDCl$_3$) δ12.2 (s, 1H), 9.38 (s, 1H), 9.08 (s, 1H), 6.64 (3, 1H), 6.46 (s, 1H), 5.29-5.32 (m, 1H), 3.55 (m, 2H), 3.06-3.10 (m, 1H), 2.00-2.02 (m, 1H), 1.29-1.33 (m, 3H). MS (ESI) m/z=267 [M+H]⁺.

G17: (1-Hydroxy-6-methoxy-4-methyl-1,3-dihydro-benzo[c][1,2]oxaborol-3-yl)-acetic acid

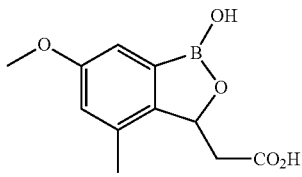 [SMILES: COc1cc(C)c2c(c1)B(O)OC2CC(=O)O]

Step 1: (1-Hydroxy-6-methoxy-4-methyl-1,3-dihydro-benzo[c][1,2]oxaborol-3-yl)-acetic acid ethyl ester

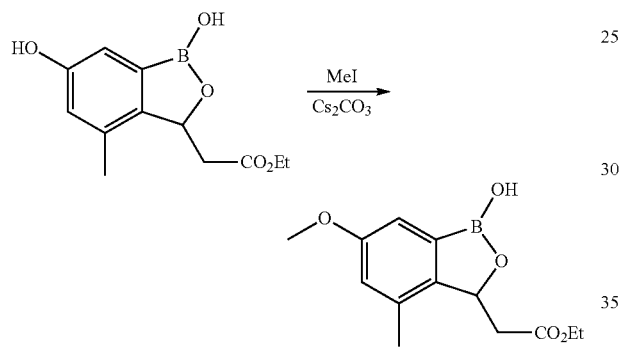

To a solution of (1,6-dihydroxy-4-methyl-1,3-dihydro-benzo[c][1,2]oxaborol-3-yl)-acetic acid ethyl ester (3.0 g, 12.0 mmol) in anhydrous DMF (20 mL) were added $Cs_2CO_3$ (23.45 g, 72 mmol) and methyl iodide (17.03 g, 120 mmol) at 0° C. After stirring at room temperature for 3 hours the reaction mixture was cooled to 0° C. and acidified to pH 2 with dilute hydrochloric acid. The mixture was extracted with ethyl acetate and the organic extracts were dried over sodium sulfate and concentrated in vacuo. The residue was purified by silica gel flash column chromatography (EtOAc/hexane/AcOH=1:1:1) to give the product (1.24 g, 39.1%). ¹HNMR (400 MHz, DMSO-d₆) δ9.12 (s, 1H), 7.02 (d, J=2.34 Hz, 1H), 6.83 (d, J=2.34 Hz, 1H), 5.44 (dd, J=9.23, 2.49 Hz, 1H), 3.93-4.08 (m, 2H), 3.73 (s, 3H), 3.08 (dd, J=15.24, 2.64 Hz, 1H), 2.10-2.31 (m, 4H), 1.05-1.19 (m, 3H).

Step 2: (1-Hydroxy-6-methoxy-4-methyl-1,3-dihydro-benzo[c][1,2]oxaborol-3-yl)-acetic acid

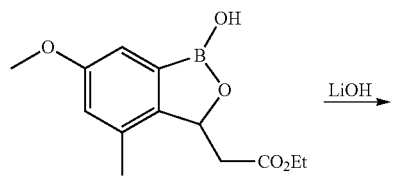

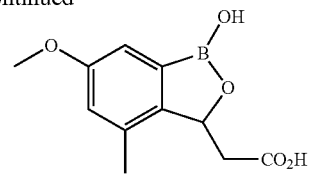

To a solution of (1-hydroxy-6-methoxy-4-methyl-1,3-dihydro-benzo[c][1,2]oxaborol-3-yl)-acetic acid ethyl ester (0.85 g, 3.22 mmol) in THF (7 mL) was added a solution of LiOH (0.385 g, 16.1 mmol) in water (7 mL) at 0° C. The resulting mixture was stirred at room temperature for 1.5 hours then acidified to pH 2 using dilute hydrochloric acid. The mixture was concentrated to remove THF and the white precipitate collected and washed with water to give pure product as a white powder (0.571 g, 75.1%); mp 157-158° C. ¹HNMR (400 MHz, DMSO-d δ 9.10 (s, 1H), 7.02 (d, J=2.34 Hz, 1H), 6.83 (d, J=1.76 Hz, 1H), 5.42 (dd, J=9.67, 2.64 Hz, 1H), 3.73 (s, 3H), 3.01 (dd, J=15.38, 2.49 Hz, 1H), 2.24 (s, 3H), 2.03 (dd, 1H). MS (ESI) m/z=235 [M−H]⁻.

G18: (3R)-(1-Hydroxy-6-methoxy-4-methyl-1,3-dihydro-benzo[c][1,2]oxaborol-3-yl)-acetic acid

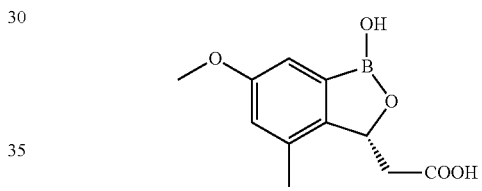

Step 1: (3R)-(1-Hydroxy-6-methoxy-4-methyl-1,3-dihydro-benzo[c][1,2]oxaborol-3-yl)-acetic acid ethyl ester

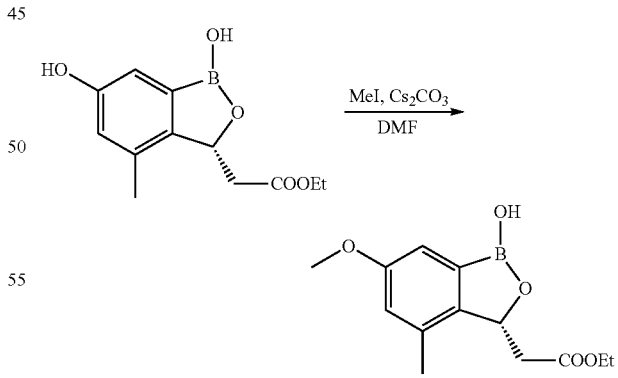

To a solution of (3R)-(1,6-dihydroxy-4-methyl-1,3-dihydro-benzo[c][1,2]oxaborol-3-yl)-acetic acid ethyl ester (2.0 g, 7.9 mmol) in anhydrous DMF (20 mL) were added $Cs_2CO_3$ (15.4 g, 47.4 mmol) and methyl iodide (1.43 g, 9.6 mmol) at 0° C. After stirring at room temperature for 4 hours the reaction mixture was cooled to 0° C. and acidified to pH 2 with concentrated HCl. The mixture was extracted with ethyl acetate and the organic extracts were washed with water, brine, dried over sodium sulfate and concentrated in vacuo. The residue was purified by silica gel flash column chromatography (30-100% EtOAc in hexane) to give (3R)-(1-hydroxy-6-methoxy-4-methyl-1,3-dihydro-benzo[c][1,2]oxaborol-3-yl)-acetic acid ethyl ester as a yellow foam (0.7 g, 35%). $^1$H NMR 400 MHz (DMSO-d$_6$) δ9.12 (s, 1H), 7.07 (d, J=2.0 Hz, 1H), 6.85 (d, J=2.0 Hz, 1H), 5.46 (dd, J=9.2, 2.4 Hz, 1H), 4.09-4.03 (m, 2H), 3.74 (s, 3H), 3.17-3.07 (m, 1H), 2.26 (s, 3H), 2.23-2.17 (m, 1H), 1.16-1.12 (m, 3H).

Step 2: (3R)-(1-Hydroxy-6-methoxy-4-methyl-1,3-dihydro-benzo[c][1,2]oxaborol-3-yl)-acetic acid

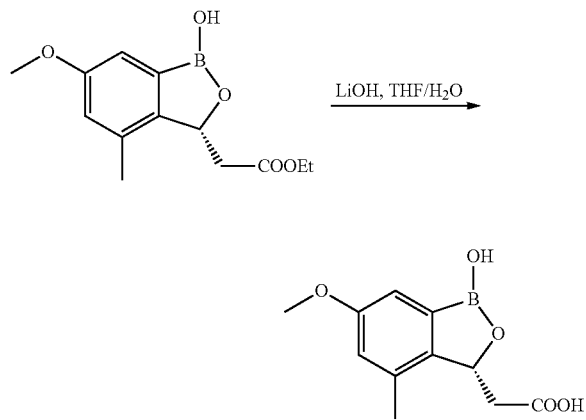

To a solution of (3R)-(1-hydroxy-6-methoxy-4-methyl-1,3-dihydro-benzo[c][1,2]oxaborol-3-yl)-acetic acid ethyl ester (0.68 g, 2.57 mmol) in THF (7 mL) was added a solution of LiOH (0.31 g, 12.87 mmol) in water (7 mL) at 0° C. The resulting mixture was stirred at room temperature for 3 hours then acidified to pH 2 using 6M hydrochloric acid and extracted with EtOAc. The organic extracts were washed with water, brine, dried over Na$_2$SO$_4$, and concentrated in vacuo. The residue was purified by silica gel flash column chromatography (0-5% MeOH in DCM) to give (3R)-(1-hydroxy-6-methoxy-4-methyl-1,3-dihydro-benzo[c][1,2]oxaborol-3-yl)-acetic acid as an off white solid (0.45 g, 74%). mp 48.2-50° C. $^1$HNMR (400 MHz, DMSO-d δ 9.10 (s, 1H), 7.02 (d, J=2.34 Hz, 1H), 6.83 (d, J=1.76 Hz, 1H), 5.42 (dd, J=9.67, 2.64 Hz, 1H), 3.73 (s, 3H), 3.01 (dd, J=15.38, 2.49 Hz, 1H), 2.24 (s, 3H), 2.03 (m, 1H). MS (ESI) m/z: 235 (M−1)$^-$. HPLC purity: 98.31% (Maxplot), 97.78% (220 nm).

G19: [1-Hydroxy-4-fluoro-6-methoxy-1,3-dihydro-benzo[c][1,2]oxaborol-3-yl]-acetic acid

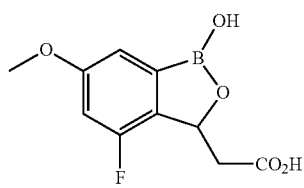 [SMILES: COc1cc(F)c2c(c1)B(O)OC2CC(=O)O]

Step 1: Ethyl 2-(4-fluoro-1-hydroxy-6-methoxy-1,3-dihydrobenzo[c][1,2]oxaborol-3-yl)acetate

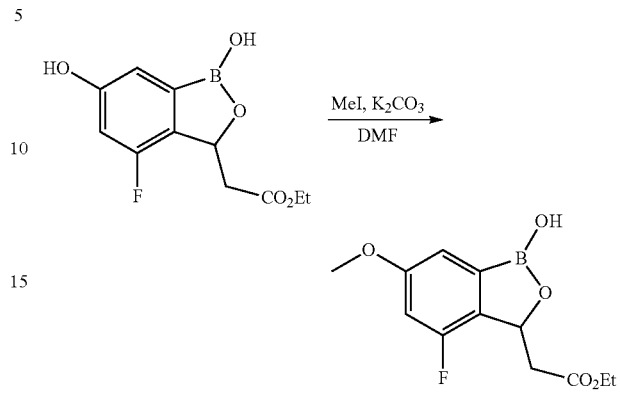

To a solution of ethyl-2-(4-fluoro-1,6-dihydroxy-1,3-dihydrobenzo[c][1,2]oxaborol-3-yl)acetate (0.25 g, 1.0 mmol) in DMF (5 mL) was added potassium carbonate (0.14 g, 1.0 mmol), followed by iodomethane (0.42 g, 3.0 mmol). The reaction mixture was stirred at room temperature overnight and quenched by addition of brine (20 mL). The resulting mixture was extracted with EtOAc (25 mL×2) and the combined organic layers were dried over anhydrous Na$_2$SO$_4$, concentrated in vacuo. The residue was purified by column chromatography (EtOAc/PE=1/4) on silica gel to give the title compound as a white solid. (253 mg, Yield: 94%). MS (ESI) m/z=269 [M+H]$^+$.

Step 2: 2-(4-fluoro-1-hydroxy-6-methoxy-1,3-dihydrobenzo[c][1,2]oxaborol-3-yl)acetic acid

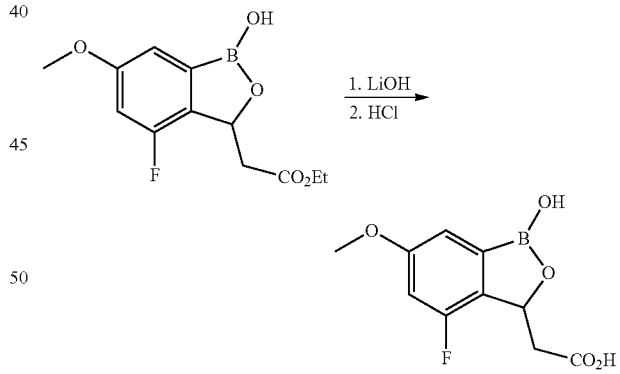

To a solution of ethyl 2-(4-fluoro-1-hydroxy-6-methoxy-1,3-dihydrobenzo[c][1,2]oxaborol-3-yl)acetate (134 mg, 0.50 mmol) in THF (2 mL) was added dropwise an aqueous solution of lithium hydroxide (102 mg, 2.5 mmol) in water (3 mL) at 0° C. The reaction mixture was stirred at room temperature for 1.5 h and acidified to pH=2 with diluted hydrochloride acid. The resulting mixture was extracted with ethyl acetate (2×15 mL). The combined organic layers were dried over anhydrous Na$_2$SO$_4$ and concentrated in vacuo. The residue was purified by HPLC to give the title compound as a white solid (43 mg, Yield: 36%). $^1$H NMR (400 MHz, DMSO-d) δ 12.20 (s, 1H), 9.45 (s, 1H), 7.09-7.09 (d, J=1.6

Hz, 1H), 6.91-6.95 (m, 1H), 5.51-5.55 (m, 1H), 3.80 (s, 3H), 2.91-2.97 (m, 1H), 2.27-2.33 (m, 1H). MS (ESI) m/z=481 [2M+H]$^+$.

G20: Ethyl 2-(4-chloro-1-hydroxy-6-methoxy-1,3-dihydrobenzo[c][1,2]oxaborol-3-yl)acetate

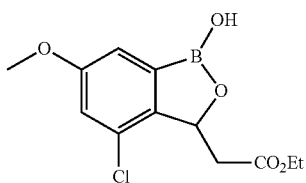 [SMILES: CCOC(=O)CC1OB(O)c2cc(OC)cc(Cl)c21]

Step 1: Ethyl 2-(4-chloro-1-hydroxy-6-methoxy-1,3-dihydrobenzo[c][1,2]oxaborol-3-yl)acetate

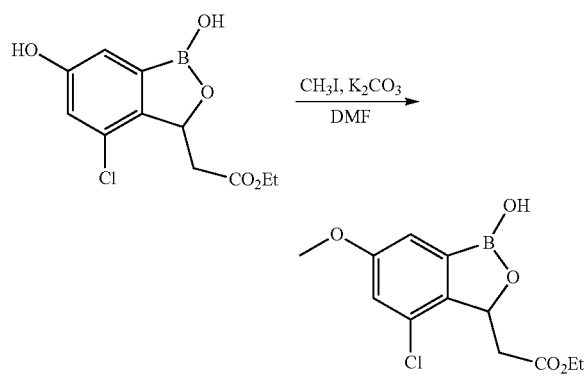

To a mixture of ethyl 2-(4-chloro-1,6-dihydroxy-1,3-dihydrobenzo[c][1,2]oxaborol-3-yl)acetate (150 mg, 0.55 mmol) and iodomethane (254 mg, 2.22 mL) in anhydrous DMF (2 mL) was added anhydrous $K_2CO_3$ (380 mg, 2.75 mmol). The reaction mixture was stirred for 10 h and concentrated under reduced pressure. The residue was purified by prep HPLC to give the title compound as a yellow oil (49.1 mg. Yield: 31%). $^1$H NMR (400 MHz, DMSO-d$_6$) δ 9.45 (s, 1H), 7.22-7.23 (d, J=4.0 Hz, 1H), 7.14-7.15 (d, J=4.0 Hz, 1H), 5.45-5.48 (m, 1H), 4.03-4.09 (m, 2H), 3.81 (s, 3H), 3.21-3.25 (m, 1H), 2.39-2.45 (m, 1H), 1.14-1.17 (m, 3H).

G21: 3-(1-Hydroxy-6-methoxy-4-methyl-1,3-dihydro-benzo[c][1,2]oxaborol-3-yl)-propionic acid

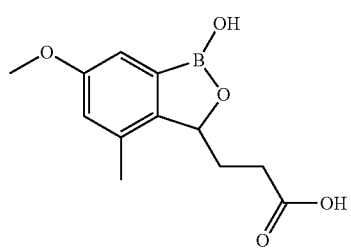 [SMILES: COc1cc(C)c2c(c1)B(O)OC2CCC(=O)O]

Step 1:
4-(2,4-Dimethoxy-6-methyl-phenyl)-4-oxo-butyric acid

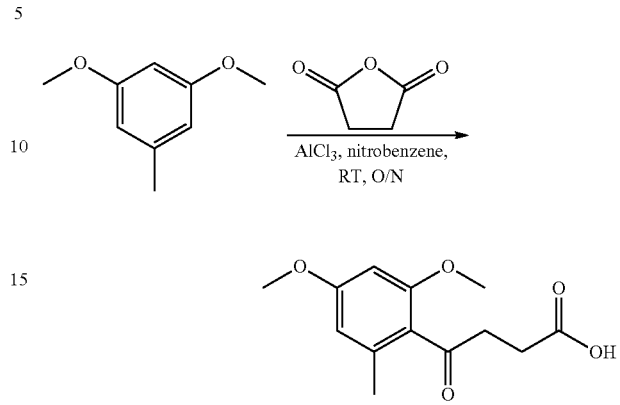

To a suspension of 1,3-dimethoxy-5-methyl-benzene (5.10 g, 33.55 mmol) and succinic anhydride (3.69 g, 36.91 mmol) in nitrobenzene (100 mL) was added AlCl$_3$ (8.9 g, 67.10 mmol). The reaction mixture was stirred at room temperature for 16 hours then carefully poured into aqueous NaOH. The pH was adjusted to 10 with solid NaOH and the aqueous solution washed with dichloromethane. The pH of the aqueous solution was adjusted to 3 with concentrated HCl and extracted with EtOAc. The organic extracts were dried and concentrated in vacuo. The residue was triturated dichloromethane to give 4-(2,4-dimethoxy-6-methyl-phenyl)-4-oxo-butyric acid as a pale yellow solid (3.7 g, 43%). $^1$H NMR (400 MHz, MeOD-d$_4$) δ 6.44 (s, 1H), 6.40 (s, 1H), 3.80 (s, 3H), 3.78 (s, 3H), 3.03 (t, J=8.1 Hz, 2H), 2.60 (t, J=8.1 Hz, 2H), 2.19 (s, 3H).

Step 2:
4-(2,4-Dimethoxy-6-methyl-phenyl)-4-oxo-butyric acid methyl ester

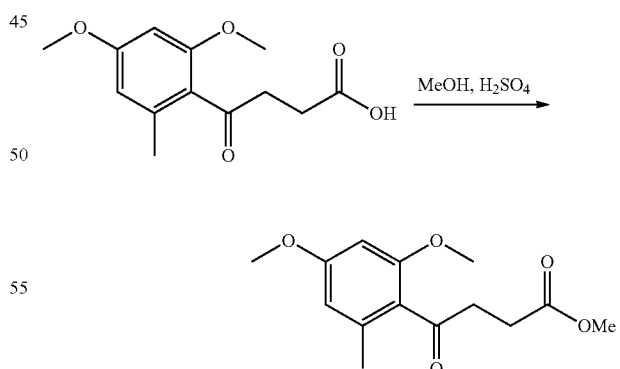

A mixture of 4-(2,4-dimethoxy-6-methyl-phenyl)-4-oxo-butyric acid (3.70 g, 14.68 mmol) and concentrated $H_2SO_4$ (0.2 mL) in MeOH (50 mL) was heated at 75° C. for 1 hour and concentrated in vacuo. The residue was purified by silica gel flash column chromatography to give 4-(2,4-dimethoxy-6-methyl-phenyl)-4-oxo-butyric acid methyl ester (3.86 g, quant.). $^1$H NMR (400 MHz, CDCl$_3$) δ 6.70 (s, 1H), 6.50 (s, 1H), 3.90 (s, 3H), 3.85 (s, 3H), 3.65 (s, 3H), 3.10 (t, J=8.1 Hz, 2H), 2.65 (t, J=8.1 Hz, 2H), 2.20 (s, 3H).

Step 3: 4-(2-Hydroxy-4-methoxy-6-methyl-phenyl)-4-oxo-butyric acid methyl ester and 4-(2,4-Dihydroxy-6-methyl-phenyl)-4-oxo-butyric acid methyl ester

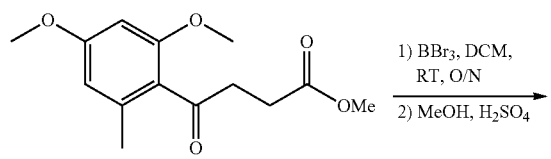

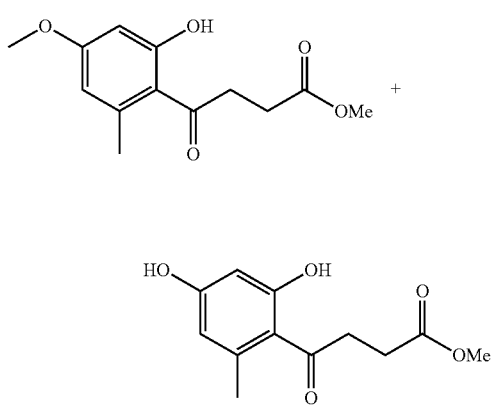

To a solution of 4-(2,4-dimethoxy-6-methyl-phenyl)-4-oxo-butyric acid methyl ester (1.0 g, 3.76 mmol) in dichloromethane (10 mL) was added 1 M BBr$_3$ in dichloromethane (15.04 mL). The reaction mixture was stirred at room temperature for 48 hours then poured onto ice and extracted with EtOAc. The organic extracts were dried and concentrated in vacuo. The residue was dissolved in concentrated H$_2$SO$_4$ (0.2 mL) and MeOH (10 mL) and the mixture was heated at 75° C. for 1 hour. The mixture was concentrated in vacuo and the residue was purified by silica gel flash column chromatography to give 4-(2-hydroxy-4-methoxy-6-methyl-phenyl)-4-oxo-butyric acid methyl ester (0.300 g, 31%) and 4-(2,4-dihydroxy-6-methyl-phenyl)-4-oxo-butyric acid methyl ester (0.300 g, 34%).

4-(2-Hydroxy-4-methoxy-6-methyl-phenyl)-4-oxo-butyric acid methyl ester $^1$H NMR (400 MHz, CDCl$_3$) δ 11.62 (s, 1H), 6.40 (s, 1H), 6.30 (s, 1H), 3.80 (s, 3H), 3.60 (s, 3H), 3.25 (t, J=8.2 Hz, 2H), 2.65 (t, J=8.2 Hz, 2H), 2.50 (s, 3H).

4-(2,4-Dihydroxy-6-methyl-phenyl)-4-oxo-butyric acid methyl ester $^1$H NMR (400 MHz, Acetone -d$_6$) δ11.80 (s, 1H), 9.02 (s, 1H), 6.30 (s, 1H), 6.20 (s, 1H), 3.60 (s, 3H), 3.25 (t, J=8.1 Hz, 2H), 2.68 (t, J=8.1 Hz, 2H), 2.44 (s, 3H).

Step 4: 4-(4-Methoxy-2-methyl-6-trifluoromethane-sulfonyloxy-phenyl)-4-oxo-butyric acid methyl ester

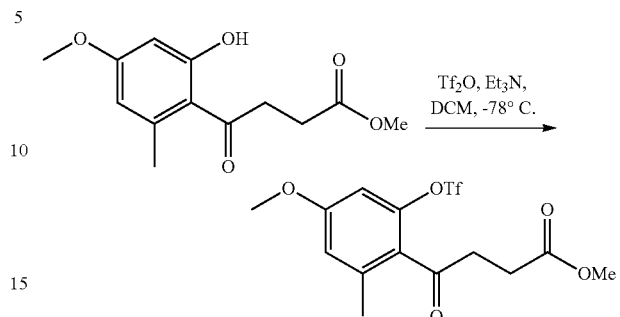

To a solution of 4-(2-hydroxy-4-methoxy-6-methyl-phenyl)-4-oxo-butyric acid methyl ester (0.350 g, 1.20 mmol) and Et$_3$N (0.58 mL, 4.14 mmol) in dichloromethane (10 mL) was added Tf$_2$O (0.35 mL, 2.08 mmol) at −78° C. The mixture was stirred at −78° C. for 1.5 hours. The mixture was diluted with H$_2$O and extracted with dichloromethane. The organic extracts were washed with brine, dried and concentrated in vacuo. The residue was dissolved in Hexane-EtOAc(4:1), filtered through a plug of silica gel and filtrate was concentrated to give trifluoro-methanesulfonic acid 2-formyl-3-methoxymethyl-5-(tetrahydro-pyran-2-yloxy)-phenyl ester (0.70 g, quant). $^1$H NMR (400 MHz, CDCl$_3$) δ 6.80 (s, 1H), 6.70 (s, 1H), 3.82 (s, 3H), 3.70 (s, 3H), 3.10 (t, J=8.2 Hz, 2H), 2.77 (t, J=8.2 Hz, 2H), 2.34 (s, 3H).

Step 5: 4-[4-Methoxy-2-methyl-6-(4,4,5,5-tetramethyl-[1,3,2]dioxaborolan-2-yl)-phenyl]-4-oxo-butyric acid methyl ester

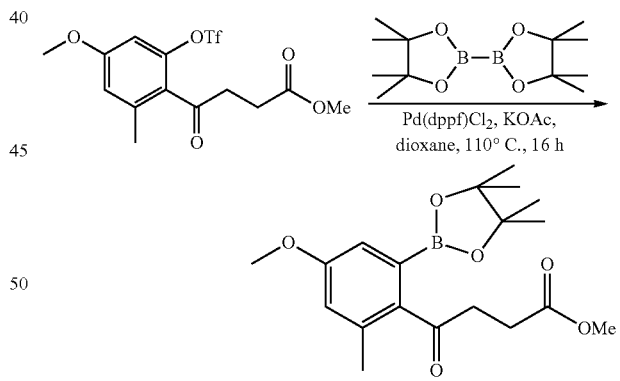

A mixture of trifluoro-methanesulfonic acid 2-formyl-3-methoxymethyl-5-(tetrahydro-pyran-2-yloxy)-phenyl ester (0.70 g, 1.83 mmol), bis(pinacolato)diborane (0.93 g, 3.65 mmol), Pd(dppf)Cl$_2$ (0.27 g, 0.37 mmol) and KOAc (0.54 g, 5.49 mmol) in dioxane (15 mL) was degassed for 10 minutes with bubbling N$_2$. The reaction mixture was heated at 110° C. for 2 hours then diluted with EtOAc (100 mL). The mixture was filtered through a pad of celite and concentrated in vacuo. The residue was purified by silica gel flash column chromatography to give 4-[4-methoxy-2-methyl-6-(4,4,5,5-tetramethyl-[1,3,2]dioxaborolan-2-yl)-phenyl]-4-oxo-butyric acid methyl ester (0.33 g, 63% over two steps). $^1$H NMR (400

MHz, CDCl₃) δ 7.10 (s, 1H), 6.75 (s, 1H), 3.80 (s, 3H), 3.70 (s, 3H), 3.10 (t, J=8.2 Hz, 2H), 2.77 (t, J=8.2 Hz, 2H), 2.34 (s, 3H), 1.30 (s, 12H).

Step 6: 3-(1-Hydroxy-6-methoxy-4-methyl-1,3-dihydro-benzo[c][1,2]oxaborol-3-yl)-propionic acid methyl ester

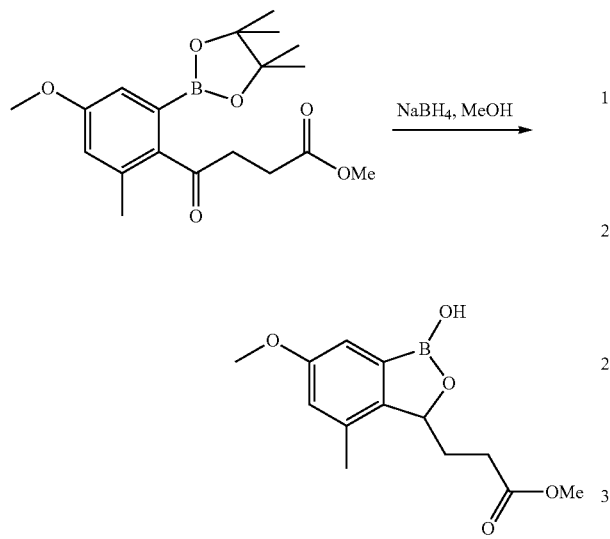

To a solution of 4-[4-methoxy-2-methyl-6-(4,4,5,5-tetramethyl-[1,3,2]dioxaborolan-2-yl)-phenyl]-4-oxo-butyric acid methyl ester (0.33 g, 0.87 mmol) in MeOH (3 mL) was added NaBH₄ (0.073 g, 1.92 mmol) at 0° C. The reaction mixture was stirred at 0° C. for 30 minutes, quenched with 6 N HCl and extracted with EtOAc. The organic extracts were dried and concentrated in vacuo. The residue was dissolved in CH₃CN and treated with polymer-bounded benzyl boric acid (2 equiv) for 2 hours. The mixture was filtered, concentrated and purified by silica gel flash column chromatography to give 3-(1-hydroxy-6-methoxy-4-methyl-1,3-dihydro-benzo[c][1,2]oxaborol-3-yl)-propionic acid methyl ester (0.160 g, 69%). ¹H NMR (400 MHz, MeOD-d₄) δ 6.98 (s, 1H), 6.80 (s, 1H), 5.25 (m, 1H), 3.80 (s, 3H), 3.60 (s, 3H), 2.50-2.30 (m, 6H), 1.77 (m, 1H).

Step 7: 3-(1-Hydroxy-6-methoxy-4-methyl-1,3-dihydro-benzo[c][1,2]oxaborol-3-yl)-propionic acid

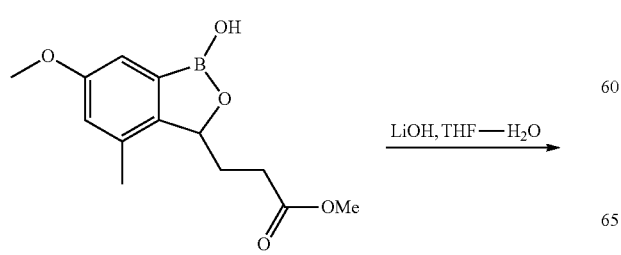

To a solution of 3-(1-hydroxy-6-methoxy-4-methyl-1,3-dihydro-benzo[c][1,2]oxaborol-3-yl)-propionic acid methyl ester (0.160 g, 0.60 mmol) in THF (4 mL) and H₂O (2 mL) was added LiOH (0.116 g) at 0° C. The resulting mixture was stirred at room temperature for 2 hours then cooled to 0° C. and acidified to pH 3 with 6N HCl. The mixture was concentrated to approximately half its volume and the precipitated solid was filtered, washed with water and dried to give 3-(1-hydroxy-6-methoxy-4-methyl-1,3-dihydro-benzo[c][1,2]oxaborol-3-yl)-propionic acid (0.140 g, 93%). ¹H NMR (400 MHz, DMSO-d₆) δ 9.06 (s, 1H), 7.02 (d, J=2 Hz, 1H), 6.81 (s, 1H), 5.12 (m, 1H), 3.72 (s, 3H), 2.30-2.20 (m, 5H), 2.10 (m, 1H), 1.50 (m, 1H). MS (ES) m/z: 249 (M−1)⁻. HPLC purity: 97.16% (220 nm), 96.94% (Maxplot).

G22: 2-(4-(Aminomethyl)-1-hydroxy-6-methoxy-1,3-dihydrobenzo[c][1,2]oxaborol-3-yl)acetic acid

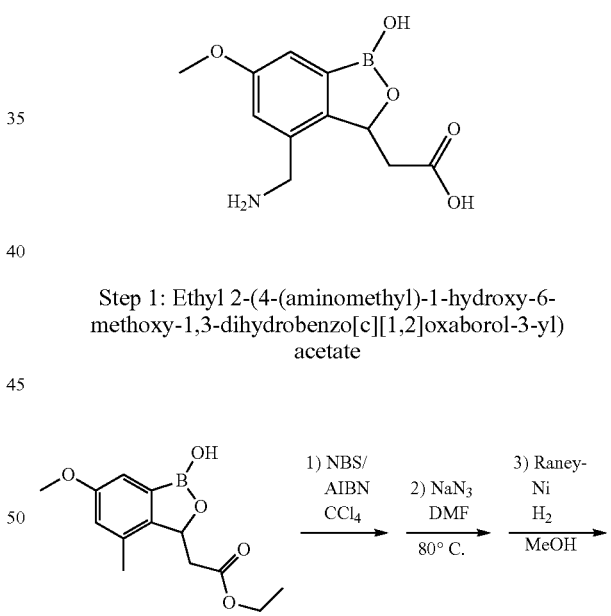

Step 1: Ethyl 2-(4-(aminomethyl)-1-hydroxy-6-methoxy-1,3-dihydrobenzo[c][1,2]oxaborol-3-yl)acetate

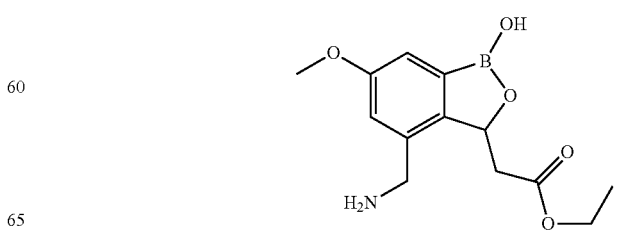

The mixture of ethyl 2-(1-hydroxy-6-methoxy-4-methyl-1,3-dihydrobenzo[c][1,2]oxaborol-3-yl)acetate (264 g, 1 mmol), NBS (196 mg, 1.1 mmol) and AIBN (50 mg, cat.) in anhydrous DMF (40 mL) was heated to 80° C. for 30 min. The reaction mixture was cooled to room temperature and diluted with DCM (100 ml), washed with H₂O, brine, dried over MgSO₄, concentrated in vacuum to dryness.

The above intermediate was dissolved in anhydrous DMF and NaN₃ (195 mg, 3 mmol) was added, heated to 80° C. for 3 h. The mixture was cooled to room temperature, diluted with ethyl acetate (70 ml), washed with H₂O, brine, dried and concentrated to dryness.

The above azide intermediate was dissolved in MeOH (10 ml) and Raney-Ni (100 mg) was added. The reaction mixture was hydrogenated for 2 h. Filtered to remove the catalyst and the filtrate was concentrated in reduced pressure to dryness. The crude product was purified by prep-HPLC to give the desired product (20 mg) as TFA salt. ¹H NMR (400 MHz, DMSO-d₆) δ 9.31 (s, 1H), 8.22 (brs, 3H), 7.23 (d, J=2.2 Hz, 1H), 7.17 (d, J=2.2 Hz, 1H), 5.63 (dd, J=9.2, 2.5 Hz, 1H), 4.04 (m, 4H), 3.78 (s, 3H), 3.07 (dd, J=15.6, 2.6 Hz, 1H), 2.26 (dd, J=9.2, 15.6 Hz, 1H) and 1.13 (t, J=7.0 Hz, 3H). MS (ESI) m/z=280 [M+H]⁺.

Step 2: 2-(4-(Aminomethyl)-1-hydroxy-6-methoxy-1,3-dihydrobenzo[c][1,2]oxaborol-3-yl)acetic acid

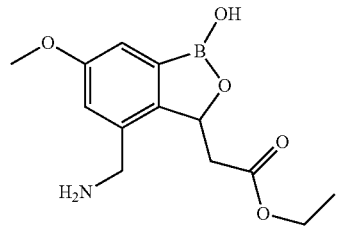

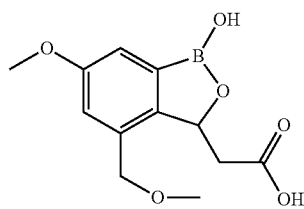 [SMILES: COCc1cc(OC)cc2c1C(CC(=O)O)OB2O]

The mixture of ethyl 2-(4-(aminomethyl)-1-hydroxy-6-methoxy-1,3-dihydrobenzo[c][1,2]oxaborol-3-yl)acetate (20 mg), LiOH (24 mg, 1 mmol) in THF/MeOH/H₂O (1.5 ml/1.5 ml/1.5 ml) was stirred at room temperature for 2 hrs. The solvent was removed in reduced pressure to dryness. The crude product was purified by Prep-HPLC to give desired product 5 mg as white powder (TFA salt). ¹H NMR (400 MHz, DMSO-d₆) δ 9.27 (s, 1H), 8.22 (brs, 3H), 7.19 (d, J=2.4 Hz, 1H), 7.16 (d, J=2.4 Hz, 1H), 5.60 (dd, J=9.4, 2.2 Hz, 1H), 4.04 (q, J=4.5 Hz, 2H), 3.78 (s, 3H), 2.99 (dd, J=15.8, 2.4 Hz, 1H), and 2.11 (dd, J=9.4, 15.8 Hz, 1H). MS (ESI) m/z=252 [M+H]⁺.

G23: (1-Hydroxy-6-methoxy-4-methoxymethyl-1,3-dihydro-benzo[c][1,2]oxaborol-3-yl)-acetic acid

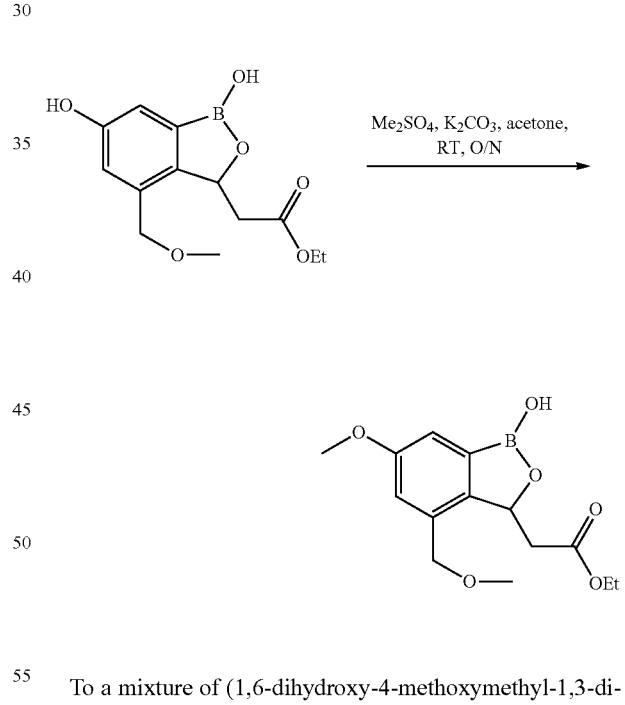

Step 1: (1-Hydroxy-6-methoxy-4-methoxymethyl-1,3-dihydro-benzo[c][1,2]oxaborol-3-yl)-acetic acid ethyl ester To a mixture of (1,6-dihydroxy-4-methoxymethyl-1,3-dihydro-benzo[c][1,2]oxaborol-3-yl)-acetic acid ethyl ester (0.18 g, 0.64 mmol) and K₂CO₃ (0.44 g, 3.2 mmol) in acetone was added Me₂SO₄ (0.16 g, 1.28 mmol). The mixture was stirred at room temperature for 16 hours then diluted with EtOAc. The organic extracts were washed with HCl (aq), dried and concentrated in vacuo. The residue was purified by silica gel flash column chromatography to give (1-hydroxy-6-methoxy-4-methoxymethyl-1,3-dihydro-benzo[c][1,2]oxaborol-3-yl)-acetic acid ethyl ester (0.060 g, 32%). ¹H NMR (400 MHz, MeOD-d₄) δ 7.08 (s, 1H), 6.99 (s, 1H), 5.62 (m, 1H), 5.50 (m, 2H), 4.08 (m, 2H), 3.80 (s, 3H), 3.37 (s, 3H), 3.12 (m, 1H), 2.17 (m, 1H), 1.20 (m, 3H).

Step 2: (1-Hydroxy-6-methoxy-4-methoxymethyl-1,3-dihydro-benzo[c][1,2]oxaborol-3-yl)-acetic acid

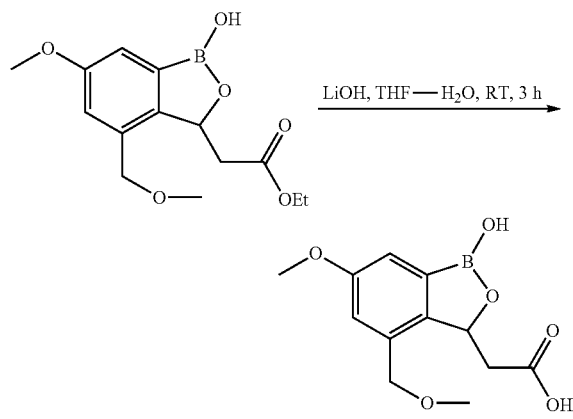

To a solution of (1-hydroxy-6-methoxy-4-methoxymethyl-1,3-dihydro-benzo[c][1,2]oxaborol-3-yl)-acetic acid ethyl ester (60 g, 0.20 mmol) in THF (3 mL) and H$_2$O (2 mL) was added LiOH (0.048 g) at 0° C. The resulting mixture was stirred at room temperature for 2 hours then cooled to 0° C. and acidified to pH 3 with 6N HCl. The mixture was concentrated in vacuo and the residue purified by silica gel flash column chromatography to give (1-hydroxy-6-methoxy-4-methoxymethyl-1,3-dihydro-benzo[c][1,2]oxaborol-3-yl)-acetic acid (0.050 g, 90%). $^1$H NMR (400 MHz, DMSO-d$_6$) δ 7.12 (s, 1H), 6.94 (s, 1H), 5.56 (m, 1H), 4.40 (m, 2H), 3.75 (s, 3H), 3.26 (s, 3H), 3.00 (m, 1H), 2.02 (m, 1H). MS (ESI) m/z: 235 [M−1]$^-$. HPLC purity: 86% (220 nm), 96% (Maxplot).

G24: 2-(1-Hydroxy-4,6-dimethoxy-1,3-dihydrobenzo[c][1,2]oxaborol-3-yl)acetic acid

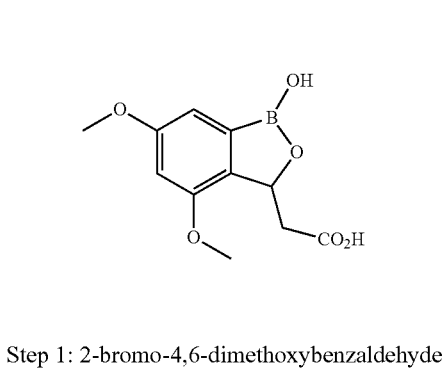

Step 1: 2-bromo-4,6-dimethoxybenzaldehyde

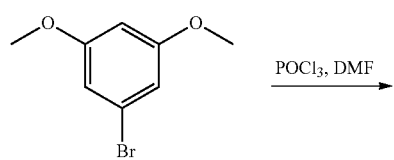

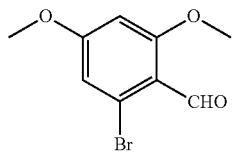

To a mixture of 1-bromo-3,5-dimethoxybenzene (21.7 g, 100.0 mmol) in DMF (80 mL) was added POCl$_3$ (15 mL, 150 mmol) at 0° C. The reaction mixture was stirred at room temperature for 30 min and then heated to 100° C. for an additional 30 min. After cooling to room temperature, the mixture was poured onto ice (200 g). The precipitate was collected by filtration and dried under high vacuum to give the title compound as a yellow solid (19.4 g, Yield: 79%). $^1$H NMR (400 MHz, CDCl$_3$) δ 12.33 (s, 1H), 10.11 (s, 1H), 6.47 (s, 1H), 6.39 (s, 1H), 5.49 (t, J=3.13 Hz, 1H), 3.78-3.90 (m, 1H), 3.52-3.72 (m, 1H), 2.54 (s, 3H), 1.77-2.03 (m, 3H), 1.53-1.70 (m, 3H); MS (ESI) m/z=285 [M+H]$^+$.

Step 2: 2,4-dimethoxy-6-(4,4,5,5-tetramethyl-1,3,2-dioxaborolan-2-yl)benzaldehyde

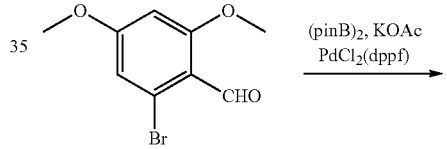

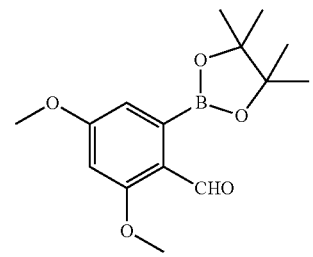

A mixture of 2-bromo-4,6-dimethoxybenzaldehyde (0.735 g, 3.0 mmol), KOAc (0.882 g, 9.0 mmol), bis(pinacolato)diborane (1.52 g, 6.0 mmol) and PdCl$_2$(dppf) (0.24 g, 0.3 mmol) in dioxane (9.0 mL) was degassed for 15 min with a stream of nitrogen flow and heated to 120° C. in a microwave reactor oven for 45 min. The reaction mixture was filtered and the filtrate was concentrated under reduced pressure. The residue was purified by column chromatography (EtOAc/PE=1/4) on silica gel to give the title compound as a yellow solid (0.45 g, Yield: 51.6%). MS (ESI) m/z=293 [M+H]$^+$.

Step 3: Ethyl 2-(1-hydroxy-4,6-dimethoxy-1,3-dihydrobenzo[c][1,2]oxaborol-3-yl)acetate

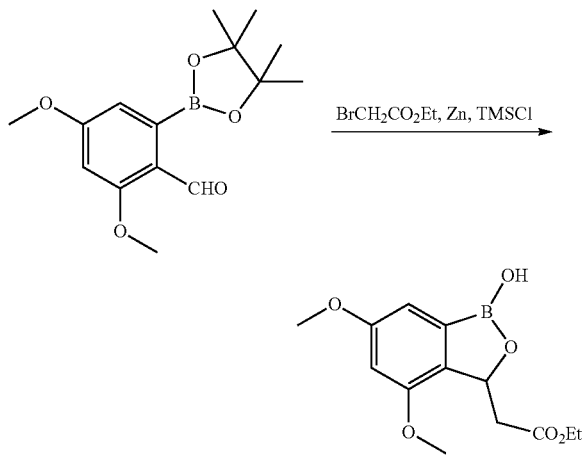

To a mixture of zinc powder (0.65 g, 10.0 mmol) in anhydrous THF (15 mL) was added TMSCl (0.13 mL, 1.0 mmol) at 40° C. The resulting mixture was stirred at 55° C. for 15 min and cooled to 37° C., followed by addition of ethyl 2-bromoacetate (0.45 mL, 4.0 mmol). The reaction mixture was stirred at this temperature for an additional 30 min. To the solution of 2,4-dimethoxy-6-(4,4,5,5-tetramethyl-1,3,2-dioxaborolan-2-yl)-benzaldehyde (0.29 g, 1.0 mmol) in anhydrous THF (20 mL) cooled at −78° C., was added above prepared solution dropwise. The reaction mixture was allowed to stir at room temperature for 1.5 hr and quenched by aqueous ammonium chloride (20 mL). The reaction mixture was extracted with ethyl acetate (2×15 mL), the combined organic layers were dried over anhydrous $Na_2SO_4$ and concentrated in vacuo. The residue was purified by column chromatography (EtOAc/PE=1/3) on silica gel to give the title compound as a white solid. (110 mg, Yield: 39.3%). MS (ESI) m/z=281 [M+H]$^+$.

Step 4: 2-(1-hydroxy-4,6-dimethoxy-1,3-dihydrobenzo[c][1,2]oxaborol-3-yl)acetic acid

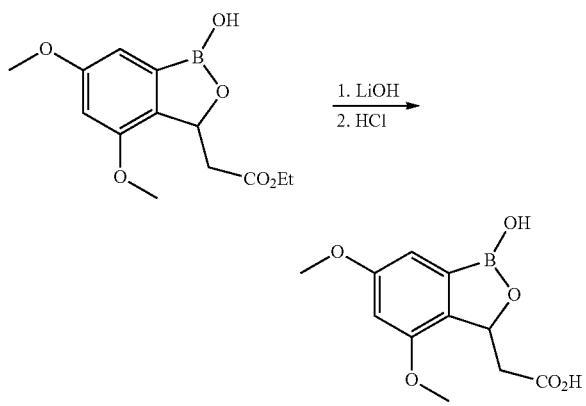

To a solution of ethyl 2-(1-hydroxy-4,6-dimethoxy-1,3-dihydrobenzo[c][1,2]oxaborol-3-yl)acetate (0.28 g, 1.0 mmol) in methanol (5 mL) was added dropwise an aqueous solution of lithium hydroxide (2N, 2.5 mL) at 0° C. The reaction mixture was stirred at room temperature for 3 hr and acidified to pH=2 with diluted hydrochloride acid. The resulting mixture was extracted with ethyl acetate (2×20 mL), the combined organic layers were dried over anhydrous $Na_2SO_4$ and concentrated in vacuo. The residue was purified by column chromatography on silica gel to give the title compound as a white solid (0.23 g, Yield: 92%). $^1$H NMR (400 Hz, $CDCl_3$) δ 12.27 (s, 1H), 9.18 (s, 1H), 6.80-6.81 (d, J=2.0 Hz, 1H), 6.63-6.64 (d, J=4.0 Hz, 1H), 5.35-5.38 (m, 1H), 3.81 (s, 3H), 3.78 (s, 3H), 3.07-3.11 (m, 1H), 2.04-2.10 (m, 1H); MS (ESI) m/z=253 [M+H]$^+$.

G25: 2-(4-Fluoro-1-hydroxy-6-isopropoxy-1,3-dihydrobenzo[c][1,2]oxaborol-3-yl)acetic acid

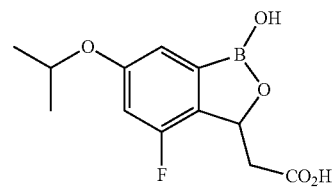 [SMILES: CC(C)Oc1cc(F)c2c(c1)B(O)OC2CC(=O)O]

Step 1: Ethyl 2-(4-fluoro-1-hydroxy-6-isopropoxy-1,3-dihydrobenzo[c][1,2]oxaborol-3-yl)acetate

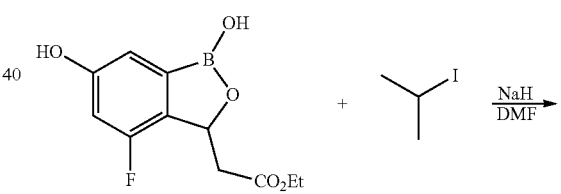

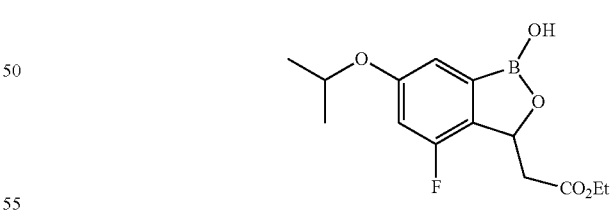

To a solution of ethyl-2-(4-fluoro-1,6-dihydroxy-1,3-dihydrobenzo[c][1,2]oxaborol-3-yl)acetate (0.254 g, 1.0 mmol) in DMF (4 mL) was added sodium hydride (0.12 g, 3.0 mmol). The reaction mixture was stirred for 30 min and then 2-iodopropane (0.19 g, 1.1 mmol) was added. After stirring for an additional 2 h, the reaction mixture was acidified to pH=2 using diluted hydrochloride acid and extracted with ethyl acetate (15 mL×3). The combined organic layers were dried over anhydrous $Na_2SO_4$ and concentrated to give the crude product as a yellow solid (0.25 g, Yield: 84%) which was used immediately without further purification. MS (ESI) m/z=297 [M+H]⁺.

Step 2: 2-(4-fluoro-1-hydroxy-6-isopropoxy-1,3-dihydrobenzo[c][1,2]oxaborol-3-yl)acetic acid

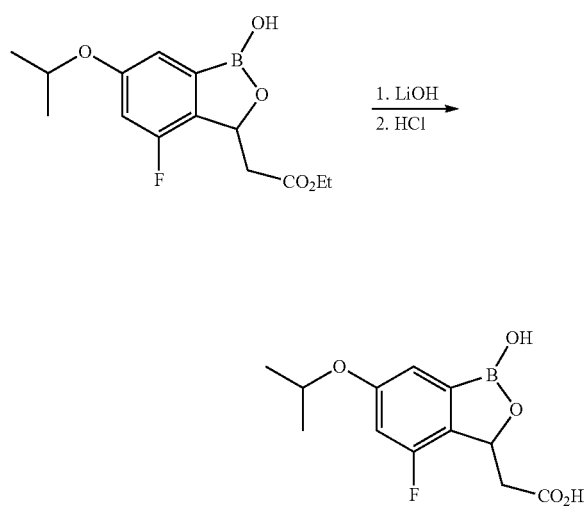

To a solution of ethyl 2-(4-fluoro-1-hydroxy-6-isopropoxy-1,3-dihydrobenzo[c][1,2]oxaborol-3-yl)acetate (148 mg, 0.50 mmol) in THF (2 mL) was added dropwise an solution of lithium hydroxide (102 mg, 2.5 mmol) in 3 mL of water at 0° C. The reaction mixture was stirred at room temperature for 1.5 h and then acidified to pH=2 using diluted hydrochloride acid. The reaction mixture was extracted with ethyl acetate (15 mL×2) and the combined organic layers were dried over anhydrous Na₂SO₄ and concentrated in vacuo. The residue was purified by HPLC to give the title compound as a white solid (24 mg, Yield: 18%). ¹H NMR (400 MHz, DMSO-d) δ 12.40 (s, 1H), 9.39 (s, 1H), 7.06-7.07 (d, J=2.0 Hz, 1H), 6.87-6.91 (m, 1H), 5.51-5.54 (m, 1H), 4.62-4.64 (m, 2H), 2.90-2.95 (m, 1H), 2.31-2.33 (m, 1H), 1.28 (s, 1H). MS (ESI) m/z=536 [2M]⁺.

G26: 2-(4-Chloro-1-hydroxy-6-isopropoxy-1,3-dihydrobenzo[c][1,2]oxaborol-3-yl)acetic acid

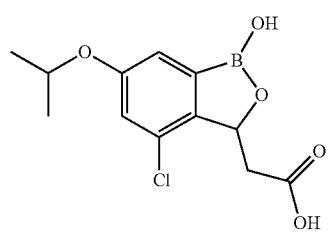 [SMILES: CC(C)Oc1cc(Cl)c2c(c1)B(O)OC2CC(=O)O]

Step 1: Ethyl 2-(4-chloro-1-hydroxy-6-isopropoxy-1,3-dihydrobenzo[c][1,2]oxaborol-3-yl)acetate

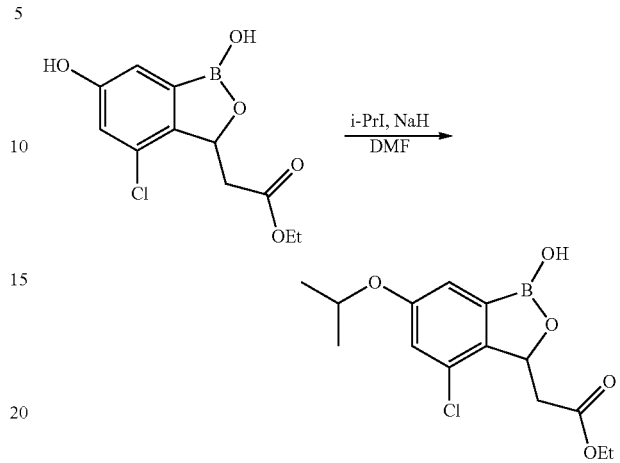

To a solution of ethyl 2-(4-chloro-1-hydroxy-6-isopropoxy-1,3-dihydrobenzo[c][1,2]oxaborol-3-yl)acetate (200 mg, 0.74 mmol) in DMF (3 mL) was slowly added NaH (89 mg, 2.22 mmol) at 0° C. The reaction mixture was stirred for 20 min, followed by addition of 2-iodopropane (151 mg, 0.89 mmol) and stirred overnight at room temperature before quenched with ice water. The resulting mixture was extracted with EtOAc (2×20 mL). The combined organic layers were dried over anhydrous Na₂SO₄ and concentrated in vacuo. The residue was used directly in the next step reaction without further purification. MS (ESI) m/z=313 [M+H]⁺.

Step 2: 2-(4-chloro-1-hydroxy-6-isopropoxy-1,3-dihydrobenzo[c][1,2]oxaborol-3-yl)acetic acid

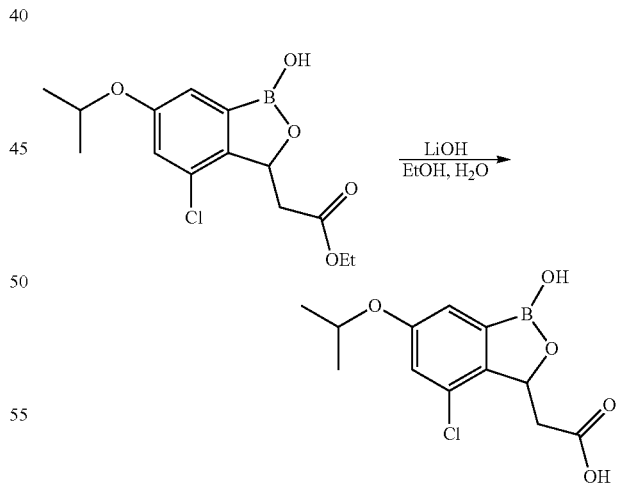

To the crude product from Step 5.1 in EtOH (10 ml) was added an aqueous LiOH (3 ml, 10%). The mixture was stirred at 0° C. for 3 h and acidified with 1N HCl to pH=2-4. The resulting mixture was extracted with EtOAc (2×20 mL). The combined organic layers were dried over anhydrous Na₂SO₄ and concentrated in vacuo. The residue was purified by prep HPLC to give the title compound as an off-white powder (18.9 mg, yield: 9%, two steps). ¹H NMR (400 MHz, DMSO)

12.35 (s, 1H), 9.39 (s, 1H), 7.20 (d, J=1.6 Hz, 1H), 7.09 (d, J=1.6 Hz, 1H), 5.44 (m, 1H), 4.64 (m, 1H), 3.18 (m, 1H), 2.23 (m, 1H).

G27: 2-(1-Hydroxy-6-isopropoxy-4-methyl-1,3-dihydrobenzo[c][1,2]oxaborol-3-yl)acetic acid

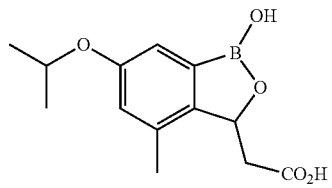 [SMILES: Cc1cc(OC(C)C)cc2c1C(CC(=O)O)OB2O]

Step 1: 2-(1-hydroxy-6-isopropoxy-4-methyl-1,3-dihydrobenzo[c][1,2]oxaborol-3-yl)acetic acid

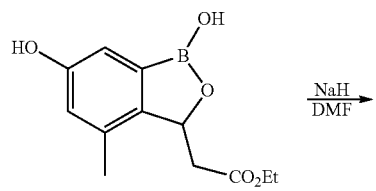

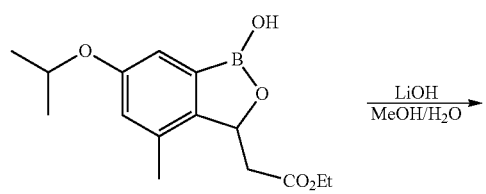

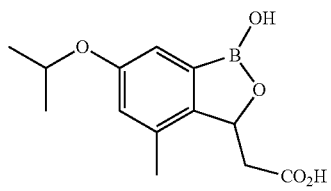

To a solution of ethyl 2-(1,6-dihydroxy-4-methyl-1,3-dihydrobenzo[c][1,2]oxaborol-3-yl)acetate (500 mg, 2 mmol) in 5 mL DMF was added 60% NaH (400 mg, 10 mmol) at 0° C. The reaction mixture was stirred at 0° C. for 1 h, followed by addition of 2-iodopropane (374 mg, 2.2 mmol). The reaction mixture was stirred at 0° C. for 7 h and quenched by ice water. The resulting mixture was extracted with EtOAc (2×15 mL) and the combined organic layers were dried over anhydrous Na$_2$SO$_4$ and concentrated in vacuo. The residue was dissolved in 2 mL MeCN and treated with lithium hydroxide (96 mg, 4 mmol) in 5 mL H$_2$O for 30 min. The reaction mixture was acidified by 1N HCl to pH=5 and extracted with EtOAc (3×20 mL). The combined organic layers were dried over anhydrous Na$_2$SO$_4$ and concentrated to dryness. The residue was purified by prep HPLC to give the title compound as a white powder (170 mg, Yield 32.2%, two steps). $^1$H NMR (400 MHz, DMSO) δ 12.25 (s, 1H), 9.09 (d, J=2.8 Hz, 1H), 7.03 (s, 1H), 6.81 (s, 1H), 5.44 (d, J=9.2 Hz, 1H), 4.58-4.55 (m, 1H), 3.15-3.00 (m, 1H), 2.24 (s, 3H), 2.08-2.02 (m, 1H), 1.27 (d, J=5.6 Hz, 6H). MS (ESI) m/z=529 [2M+H]$^+$.

G28: 2-(6-Benzyloxy-1-hydroxy-4-methyl-1,3-dihydro-benzo[c][1,2]oxaborol-3-yl)-acetic acid

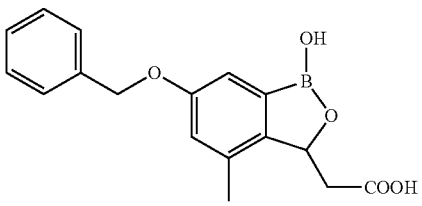 [SMILES: Cc1cc(OCc2ccccc2)cc2c1C(CC(=O)O)OB2O]

Step 1: (6-Benzyloxy-1-hydroxy-4-methyl-1,3-dihydro-benzo[c][1,2]oxaborol-3-yl)-acetic acid ethyl ester

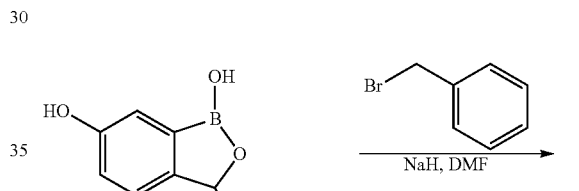

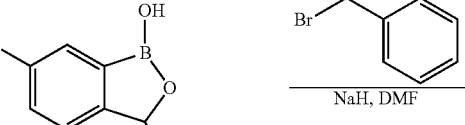

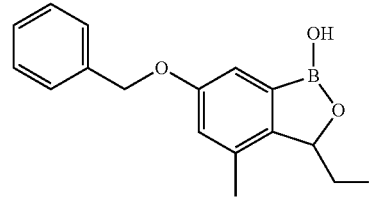

To a mixture of (1,6-dihydroxy-4-methyl-1,3-dihydro-benzo[c][1,2]oxaborol-3-yl)-acetic acid ethyl ester (0.2 g, 0.8 mmol) in anhydrous DMF (3 mL) was added sodium hydride (0.08 g, 1.6 mmol). After stirring for 15 minutes bromomethyl-benzene (0.274 g, 1.6 mmol) was added and the resulting mixture stirred at room temperature for 4 hours then quenched with crushed ice. The pH was adjusted to 4 with 6M HCl and the mixture extracted with EtOAc. The organic extracts were washed with water, brine, dried over Na$_2$SO$_4$, filtered, and concentrated in vacuo. The residue was purified by Biotage (5-60% EtOAc in hexane) to give 6-benzyloxy-1-hydroxy-4-methyl-1,3-dihydro-benzo[c][1,2]oxaborol-3-yl)-acetic acid ethyl ester (0.2 g, 73%). $^1$H NMR 400 MHz (DMSO-d$_6$) δ 9.15 (s, 1H), 7.45-7.31 (m, 5H), 7.11 (d, J=2.0 Hz, 1H), 6.94 (d, =2.0 Hz, 1H), 5.44 (dd, J=9.2, 2.4 Hz, 1H), 5.10 (s, 2H), 4.05 (q, J=7.2 Hz, 2H), 3.08 (dd, J=15.2, 2.4 Hz, 1H), 2.26 (s, 3H), 2.21 (m, 1H), 1.08 (t, 3H).

Step 2: (6-Benzyloxy-1-hydroxy-4-methyl-1,3-dihydro-benzo[c][1,2]oxaborol-3-yl)-acetic acid

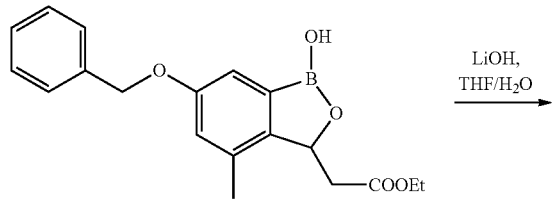

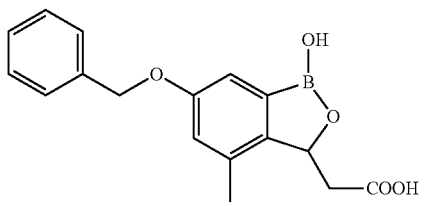

To a solution of 6-benzyloxy-1-hydroxy-1,3-dihydro-benzo[c][1,2]oxaborol-3-yl)-acetic acid ethyl ester (0.15 g, 0.44 mmol) in tetrahydrofuran (12 mL) at 0° C. was added a solution of LiOH (0.053 g, 2.2 mmol) in water (6 mL). The solution was allowed to warm to room temperature and stirred for 3 hours then acidified to pH 2 with 6M HCl. The solution was extracted with ethyl acetate (2×50 mL) and the organic extracts washed with water, brine, dried over sodium sulfate and concentrated in vacuo. The residue was purified by silica gel flash column chromatography (20-100% EtOAc in hexane) to give 6-benzyloxy-1-hydroxy-4-methyl-1,3-dihydro-benzo[c][1,2]oxaborol-3-yl)-acetic acid as a white solid (0.032 g, 23%). mp 190-191.2° C. $^1$H NMR 400 MHz (DMSO-d$_6$) δ 9.13 (s, 1H), 7.45-7.30 (m, 5H), 7.10 (s, 1H), 6.94 (s, 1H), 5.44 (dd, J=15.2, 2.4 Hz, 1H), 5.10 (s, 2H), 3.04 (dd, J=15.2, 2.4 Hz, 1H), 2.25 (s, 3H), 2.05 (m, 1H). MS (ESI) m/z: 311 (M−1)$^-$. HPLC purity: 98.64% (Maxplot), 97.92% (220 nm).

G29: (6-Carboxymethoxy-1-hydroxy-4-methyl-1,3-dihydro-benzo[c][1,2]oxaborol-3-yl)-acetic acid

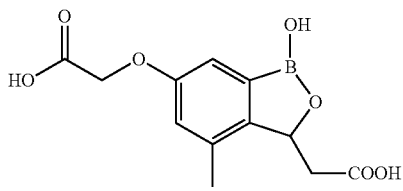 [SMILES: Cc1cc(OCC(=O)O)cc2c1C(CC(=O)O)OB2O]

Step 1: (6-Carbamoylmethoxy-1-hydroxy-4-methyl-1,3-dihydro-benzo[c][1,2]oxaborol-3-yl)-acetic acid ethyl ester

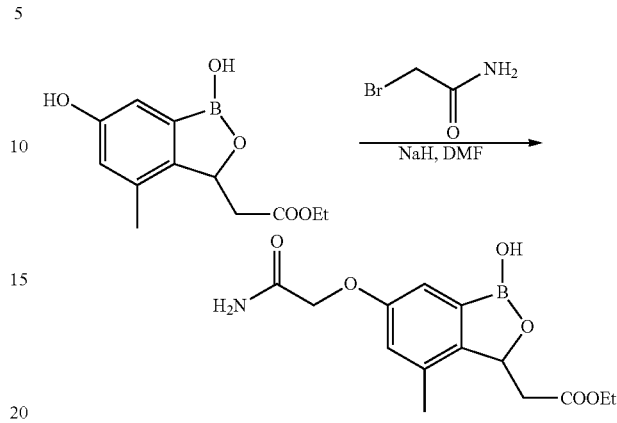

To a solution of (1,6-dihydroxy-4-methyl-1,3-dihydro-benzo[c][1,2]oxaborol-3-yl)-acetic acid ethyl ester (0.2 g, 0.8 mmol) in anhydrous DMF (3 mL) was added sodium hydride (0.08 g, 2.0 mmol). After stirring for 15 minutes 2-bromo-acetamide (0.166 g, 1.2 mmol) was added and the resulting mixture stirred at room temperature for 18 hours then quenched with crushed ice. The pH was adjusted to 3 with 6M HCl and the mixture extracted with EtOAc. The organic extracts were washed with water, brine, dried over Na$_2$SO$_4$, filtered, and concentrated in vacuo. The residue was purified by silica gel flash column chromatography (0-5% MeOH in DCM) to give 6-carbamoylmethoxy-1-hydroxy-4-methyl-1,3-dihydro-benzo[c][1,2]oxaborol-3-yl)-acetic acid ethyl ester (0.13 g, 53%). $^1$H NMR 400 MHz (DMSO-d$_6$) δ 9.17 (s, 1H), 7.47 (s, 1H), 7.36 (s, 1H), 7.02 (s, 1H), 6.89 (s, 1H), 5.45 (m, 1H), 4.40 (s, 2H), 4.09-4.02 (m, 2H), 3.10 (dd, J=15.2, 2.4 Hz, 1H), 2.26-2.17 (m, 4H), 1.17-1.04 (m, 3H).

Step 2: (6-Carboxymethoxy-1-hydroxy-4-methyl-1,3-dihydro-benzo[c][1,2]oxaborol-3-yl)-acetic acid

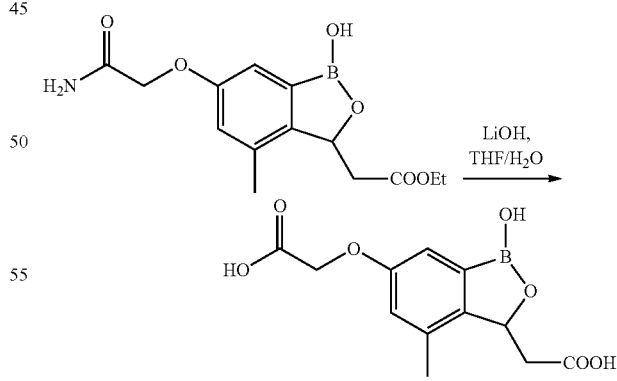

To a solution of 6-carbamoylmethoxy-1-hydroxy-4-methyl-1,3-dihydro-benzo[c][1,2]oxaborol-3-yl)-acetic acid ethyl ester (0.13 g, 0.44 mmol) in THF (3 mL) was added a solution of LiOH (0.051 g, 2.1 mmol) in water (1 mL) at 0° C. The resulting mixture was stirred at room temperature for 2 hours then acidified to pH 2 using 6M hydrochloric acid and extracted with EtOAc. The organic extracts were washed with water, brine, dried over $Na_2SO_4$, and concentrated in vacuo. The residue was purified by preparative HPLC to give (6-carboxymethoxy-1-hydroxy-4-methyl-1,3-dihydro-benzo[c][1,2]oxaborol-3-yl)-acetic acid as a white solid (0.035 g, 30%). mp 130.2-131° C. $^1$H NMR 400 MHz (DMSO-d$_6$) δ 9.15 (s, 1H), 6.97 (d, J=2.4 Hz, 1H), 6.83 (d, J=1.6 Hz, 1H), 5.43 (dd, J=10, 2.4 Hz, 1H), 4.61 (s, 2H), 3.04 (dd, J=15.2, 2.4 Hz, 1H), 2.25 (s, 3H), 2.07 (m, 1H). MS (ESI) m/z: 279 (M−1)$^−$. HPLC purity: 97.59% (Maxplot), 98.51% (220 nm).

G30: 2-(1-Hydroxy-4-methyl-6-(2-(methylamino)-2-oxoethoxy)-1,3-dihydrobenzo[c][1,2]oxaborol-3-yl)acetic acid

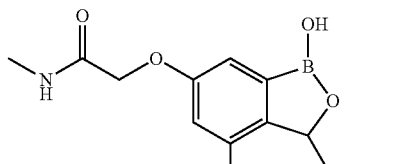

Step 1. Ethyl 2-(1-hydroxy-4-methyl-6-(2-(methylamino)-2-oxoethoxy)-1,3-dihydrobenzo[c][1,2]oxaborol-3-yl)acetate

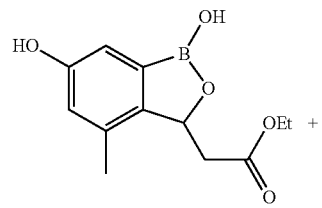

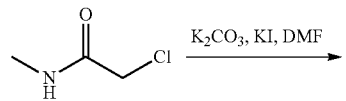

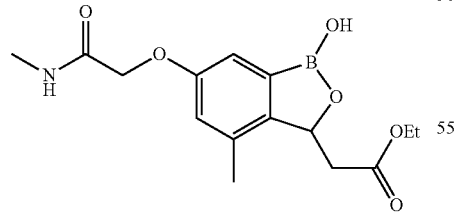

To a solution of ethyl 2-(1,6-dihydroxy-4-methyl-1,3-dihydrobenzo[c][1,2]oxaborol-3-yl)acetate (200 mg, 0.8 mmol) in anhydrous DMF (4 mL) was added $K_2CO_3$ (165 mg, 1.2 mmol), KI (199.2 mg, 1.2 mmol) and 2-chloro-N-methylacetamide (128.4 mg, 1.2 mmol) at rt. After stirring at room temperature overnight, the resulting mixture was quenched by adding water. The resulting mixture was extract with EtOAc. The extract was washed with brine, dried and concentrated to dryness. The residue was purified by recrystallization from mixture of ethyl acetate and hexane to give 80 mg of pure product as a white solid; $^1$H NMR (400 MHz, CDCl$_3$) δ 7.11 (s, 1H), 6.87 (s, 1H), 6.86 (br, 1H), 5.61 (d, J=9.2 Hz, 1H), 5.59 (s, 1H), 4.53 (s, 2H), 4.18 (q, 2H), 3.07 (d, 1H), 2.93 (t, 3H), 2.37 (m, 1H), 2.32 (s, 3H). 2.14 (s, 3H) ppm. MS (ESI) m/z=322 [M+H]$^+$.

Step 2. 2-(1-Hydroxy-4-methyl-6-(2-(methylamino)-2-oxoethoxy)-1,3-dihydrobenzo[c][1,2]oxaborol-3-yl)acetic acid

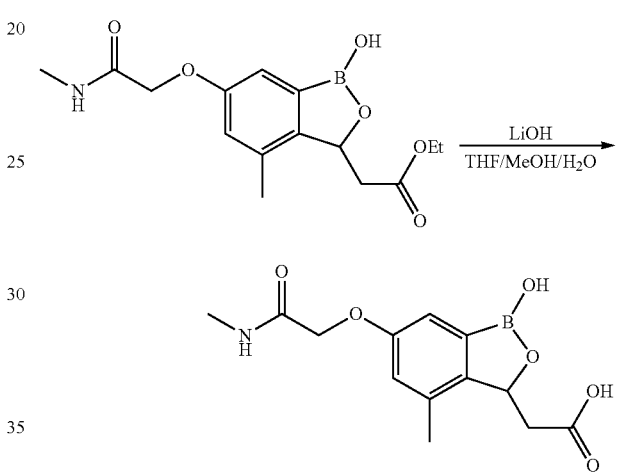

The mixture of ethyl 2-(1-hydroxy-4-methyl-6-(2-(methylamino)-2-oxoethoxy)-1,3-dihydrobenzo[c][1,2]oxaborol-3-yl)acetate (321 mg, 1 mmol), LiOH (119.5 mg, 5 mmol) in THF/MeOH/H$_2$O (5 ml/5 ml/10 ml) was stirred at room temperature for 4 hrs. The reaction mixture was quenched with 3N HCl. Filter the precipitate and washed with water. Dried to give desired product 150 mg as white powder. $^1$H NMR (400 MHz, DMSO-d6) δ 12.3 (s, 1H), 9.14 (s, 1H), 7.97 (s, 1H), 7.01 (s, 1H), 6.88 (s, 1H), 5.42 (d, J=9.6 Hz, 1H), 4.42 (s, 2H), 3.20 (dd, J=15.6, 2.4 Hz, 1H), 2.63 (d, J=3 Hz, 3H), 2.48 (s, 3H), 2.05 (dd, J=9.6, 15.6 Hz, 1H). MS (ESI) m/z=292 [M−H]$^−$.

G31: 2-(6-(Cyanomethoxy)-1-hydroxy-4-methyl-1,3-dihydrobenzo[c][1,2]oxaborol-3-yl)acetic acid

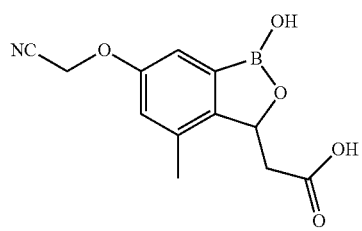 [SMILES: Cc1cc(OCC#N)cc2c1C(CC(=O)O)OB2O]

Step 1: tert-Butyl 2-(1-hydroxy-4-methyl-6-(tetrahydro-2H-pyran-2-yloxy)-1,3-dihydro-benzo[c][1,2]oxaborol-3-yl)acetate

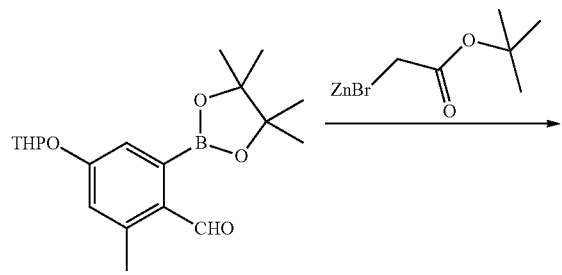

To a suspension of zinc powder (2.81 g, 43.35 mmol) in dry THF was added TMSCl (0.94 g, 8.67 mmol) at 40° C. The mixture was stirred at 55° C. for 15 min. The mixture was allowed to cooled to 30° C. and tert-butyl 2-bromoacetate (6.76 g, 34.68 mmol) was added slowly to the reaction mixture between 37-40° C. After completion of addition, the resulting mixture was stirred at room temperature for an additional 30 min. To a solution of 2-methyl-4-(tetrahydro-2H-pyran-2-yloxy)-6-(4,4,5,5-tetramethyl-1,3,2-dioxaborolan-2-yl)benzaldehyde (3 g, 8.67 mmol) in 20 mL dry THF at −78° C. was added dropwise the above prepared reaction mixture. The reaction mixture was stirred at room temperature for 1 h and quenched by ice-water at 0° C. The mixture was extracted with EtOAc (3×15 mL). The combined organic layers were dried over anhydrous Na₂SO₄ and concentrated in vacuo. The residue was purified by silica gel column (EA:PE=1:10) to give 2.2 g of desired product as a light yellow oil.

Step 2: tert-Butyl 2-(1,6-dihydroxy-4-methyl-1,3-dihydrobenzo[c][1,2]oxaborol-3-yl)acetate

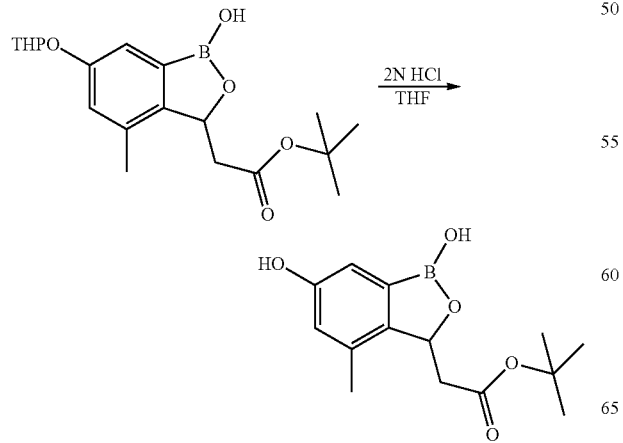

To a solution of tert-butyl 2-(1-hydroxy-4-methyl-6-(tetrahydro-2H-pyran-2-yloxy)-1,3-dihydrobenzo[c][1,2]oxaborol-3-yl)acetate (2.2 g, 6.07 mmol) in 15 mL THF was added 2N HCl (6 mL) at 0° C. The mixture was stirred overnight at room temperature and concentrated in vacuo. The residue was purified by column to give the desired product (1.2 g, yield: 71%).

Step 3: tert-Butyl 2-(6-(cyanomethoxy)-1-hydroxy-4-methyl-1,3-dihydrobenzo[c][1,2]oxaborol-3-yl)acetate

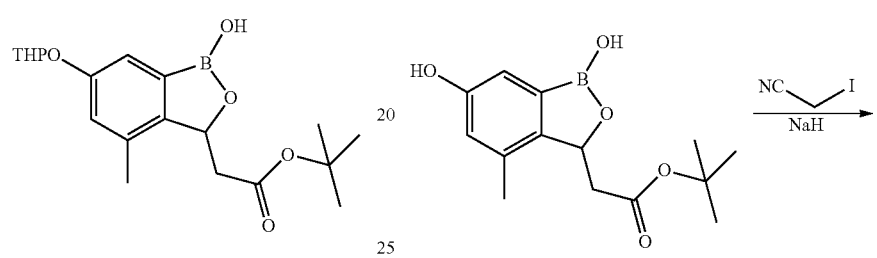

To a solution of tert-butyl 2-(1,6-dihydroxy-4-methyl-1,3-dihydrobenzo[c][1,2]oxaborol-3-yl)acetate (500 mg, 1.80 mmol) in DMF (10 mL) was added 60% NaH (215.8 mg, 5.40 mmol) in DMF (5 mL) at 0° C. The reaction mixture was stirred for 30 min, followed by addition of 2-iodoacetonitrile (450.5 mg, 2.70 mmol). The reaction mixture was stirred for an additional 5 h at room temperature, quenched by water (15 mL) at 0° C., and acidified by 1N HCl to pH=7. The resulting mixture was extracted by EtOAc (3×10 mL) and the combined organic layers were dried over anhydrous Na₂SO₄ and concentrated to dryness. The residue was purified by prep HPLC to give the title compound as a white solid (120 mg, yield: 21%).

Step 4: 2-(6-(cyanomethoxy)-1-hydroxy-4-methyl-1,3-dihydrobenzo[c][1,2]-oxaborol-3-yl)acetic acid

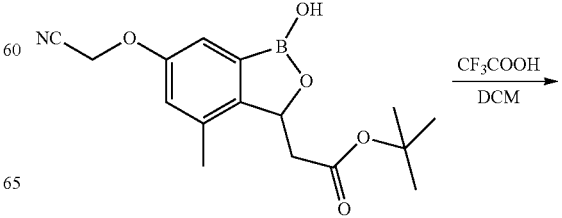

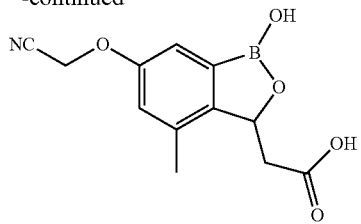

To a solution of tert-butyl 2-(6-(cyanomethoxy)-1-hydroxy-4-methyl-1,3-dihydrobenzo[c][1,2]oxaborol-3-yl)acetate (120 mg, 0.38 mmol) in 5 ml DCM was added TFA (5 mL) at 0° C. The reaction mixture was stirred for 30 min at room temperature and concentrated to dryness. The residue was purified by prep HPLC to give the title compound as a white solid (60 mg, yield: 60.8%). $^1$H NMR (400 MHz, DMSO-d) δ12.31 (s, 1H), 9.24 (s, 1H), 7.16 (d, J=2.4 Hz, 1H), 6.97 (d, J=2.4 Hz, 1H), 5.48-5.45 (m, 1H), 5.15 (s, 2H), 3.06-3.02 (m, 1H), 2.28 (s, 3H), 2.12-2.05 (m, 1H); MS (ESI) m/z=262 [M+H]$^+$.

G32: [6-(3-Amino-propoxy)-1-hydroxy-4-methyl-1,3-dihydro-benzo[c][1,2]oxaborol-3-yl]-acetic acid

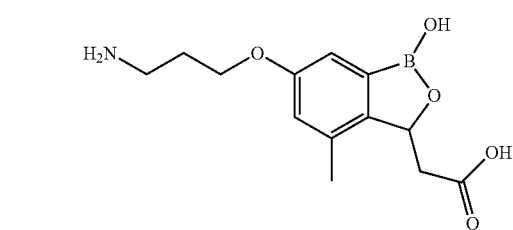 [SMILES: Cc1cc(OCCCN)cc2c1C(CC(=O)O)OB2O]

Step 1: [6-(3-tert-Butoxycarbonylamino-propoxy)-1-hydroxy-4-methyl-1,3-dihydro-benzo[c][1,2]oxaborol-3-yl]-acetic acid ethyl ester

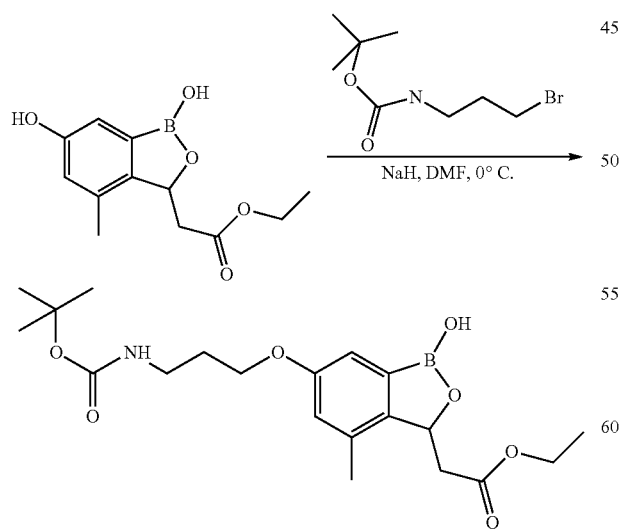

To a solution of (1,6-dihydroxy-1,3-dihydro-benzo[c][1,2]oxaborol-3-yl)-acetic acid ethyl ester (0.500 g, 1.99 mmol) in DMF (20 mL) was added NaH (0.176 g, 4.40 mmol) and the mixture was stirred at 0° C. for 45 minutes. A solution of (3-bromo-propyl)-carbamic acid tert-butyl ester (1.04 g, 4.38 mmol) in DMF (5 mL) was added and the mixture was stirred at room temperature for 18 hours. The reaction mixture was quenched with H$_2$O and extracted with EtOAc (3×50 mL). The organic extracts were washed with brine, dried over MgSO$_4$ and concentrated in vacuo. The residue was purified by silica gel flash column chromatography (33-66% EtOAc/Hexane) to give [6-(3-tert-butoxycarbonylamino-propoxy)-1-hydroxy-4-methyl-1,3-dihydro-benzo[c][1,2]oxaborol-3-yl]-acetic acid ethyl ester (0.325 g, 40%). $^1$H NMR (400 MHz, DMSO-d$_6$) δ ppm 7.00 (s, 1H), 6.87 (br. s., 1H), 6.81 (s, 1H), 5.43 (d, J=7.42 Hz, 1H), 3.97-4.10 (m, 2H), 3.93 (t, J=6.06 Hz, 2H), 2.99-3.08 (m, 3H), 2.23 (s, 3H), 2.14-2.22 (m, 1H), 1.72-1.85 (m, 2H), 1.35 (s, 9H), 1.08-1.19 (m, 3H).

Step 2: [6-(3-tert-Butoxycarbonylamino-propoxy)-1-hydroxy-4-methyl-1,3-dihydro-benzo[c][1,2]oxaborol-3-yl]-acetic acid To a solution [6-(3-tert-butoxycarbonylamino-propoxy)-1-hydroxy-4-methyl-1,3-dihydro-benzo[c][1,2]oxaborol-3-yl]-acetic acid ethyl ester (0.445 g, 1.09 mmol) in THF (14 mL) was added a solution of LiOH (0.229 g, 5.44 mmol) in water (5 mL) at 0° C. The resulting mixture was stirred at room temperature for 3 hours then acidified to pH=2 with 6M HCl and extracted with EtOAc (3×25 mL). The organic extracts were washed with brine, dried (MgSO$_4$), filtered and concentrated in vacuo. The residue was purified by silica gel flash column chromatography (20% EtOAc/hexane) to give [6-(3-tert-butoxycarbonylamino-propoxy)-1-hydroxy-4-methyl-1,3-dihydro-benzo[c][1,2]oxaborol-3-yl]-acetic acid (0.450 g, 80%). $^1$H NMR (400 MHz, DMSO-d$_6$) δ ppm 9.08 (s, 1H), 7.00 (d, J=1.90 Hz, 1H), 6.87 (br. s., 1H), 6.81 (s, 1H), 5.41 (dd, J=9.52, 2.22 Hz, 1H), 3.93 (t, J=6.19 Hz, 2H), 3.06

(t, J=6.34 Hz, 2H), 3.00 (dd, J=15.55, 2.54 Hz, 1H), 2.23 (s, 3H), 2.03 (dd, J=15.39, 9.68 Hz, 1H), 1.80 (t, J=6.66 Hz, 2H), 1.35 (s, 9H).

Step 3: [6-(3-Amino-propoxy)-1-hydroxy-4-methyl-1,3-dihydro-benzo[c][1,2]oxaborol-3-yl]-acetic acid

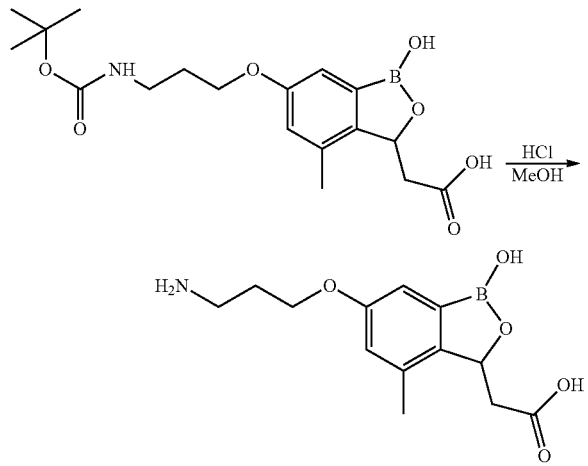

1.25M HCl in methanol (5 mL, 6.0 mmol) was added to [6-(3-tert-butoxycarbonylamino-propoxy)-1-hydroxy-4-methyl-1,3-dihydro-benzo[c][1,2]oxaborol-3-yl]-acetic acid (0.345 g, 0.80 mmol) at room temperature and stirred for 18 hours then concentrated in vacuo. The residue was dissolved in THF (14 mL) and a solution of LiOH (0.229 g, 5.44 mmol) in water (5 mL) at 0° C. was added. The resulting mixture was stirred at room temperature for 3 hours then acidified to pH=2 with 6M HCl and extracted with EtOAc (3×25 mL). The organic extracts were washed with brine, dried (MgSO$_4$), filtered and concentrated in vacuo. The residue was purified by preparative HPLC to give [6-(3-amino-propoxy)-1-hydroxy-4-methyl-1,3-dihydro-benzo[c][1,2]oxaborol-3-yl]-acetic acid as a white solid (0.035 g, 14%). $^1$H NMR (400 MHz, methanol-d$_4$) δ ppm 6.93 (br. s., 1H), 6.79 (br. s., 1H), 5.49 (d, J=5.86 Hz, 1H), 4.10 (t, J=5.47 Hz, 2H), 3.15 (t, J=7.03 Hz, 2H), 2.97 (d, J=14.85 Hz, 1H), 2.27 (s, 3H), 2.03-2.21 (m, 3H). MS (ESI) m/z: 280 [M+1]$^+$. HPLC purity: 96.23% (Maxplot), 95.78% (220 nm).

G33: 2-(6-(2-(tert-butoxycarbonyl)ethoxy)-1-hydroxy-4-methyl-1,3-dihydrobenzo[c][1,2]oxaborol-3-yl)acetic acid

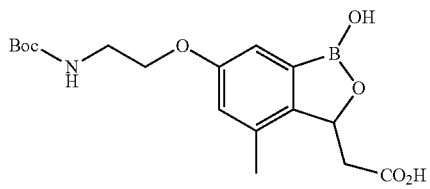 [SMILES: Cc1cc(OCCNC(=O)OC(C)(C)C)cc2c1C(CC(=O)O)OB2O]

Step 1: tert-Butyl 2-bromoethylcarbamate

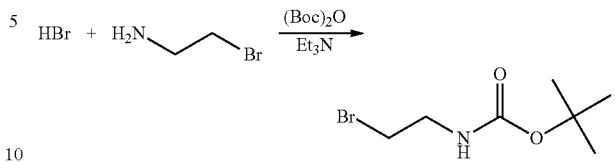

To the suspension of 2-bromoethanamine hydrobromide (1.0 g, 4.88 mmol) and Et$_3$N (0.98 g, 9.76 mmol) in 20 ml DCM was added Boc$_2$O (1.28 g, 5.85 mmol) at 0° C. The reaction mixture was stirred at room temperature for 2 h and quenched by saturated aqueous solution of NH$_4$Cl (10 mL). The resulting mixture was extracted with DCM (2×20 mL). The combined organic layers were dried over anhydrous Na$_2$SO$_4$ and concentrated to dryness. The residue was purified by column chromatography on silica gel (EtOAc/PE=1:5) to give the title compound as a colorless oil (0.7 g, yield: 64.1%).

Step 2: Ethyl 2-(6-(2-(tert-Butoxycarbonyl)ethoxy)-1-hydroxy-4-methyl-1,3-dihydro-benzo[c][1,2]oxaborol-3-yl)acetate To the mixture of ethyl 2-(1,6-dihydroxy-4-methyl-1,3-dihydrobenzo[c][1,2]oxaborol-3-yl)acetate (300 mg, 1.2 mmol) and tert-butyl 2-bromoethylcarbamate (322 mg, 1.44 mmol) in DMF (10 mL), was added Cs$_2$CO$_3$ (1.17 g, 3.6 mmol). The reaction mixture was stirred for 8 h at 80° C. and concentrated in vacuo. The residue was dissolved in 20 mL EtOAc and washed with H$_2$O (20 mL). The aqueous was extracted with EtOAc (3×20 mL). The combined organic layers were dried over anhydrous Na$_2$SO$_4$ and concentrated to dryness. The residue was purified by prep-TLC to give the title compound as a colorless oil (80 mg, yield: 17%).

Step 3: 2-(6-(2-(tert-Butoxycarbonyl)ethoxy)-1-hydroxy-4-methyl-1,3-dihydrobenzo[c][1,2]oxaborol-3-yl)acetic acid

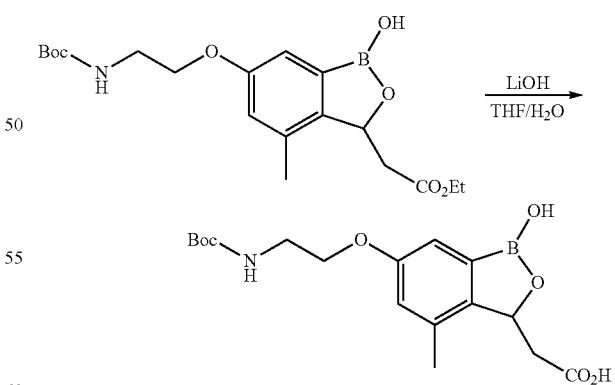

To a solution of ethyl 2-(6-(2-(tert-butoxycarbonyl)ethoxy)-1-hydroxy-4-methyl-1,3-dihydrobenzo[c][1,2]oxaborol-3-yl)acetate (80 mg, 0.2 mmol) in 16 mL of THF/H$_2$O (1/1) was added LiOH (42 mg, 1.0 mmol) in 5 mL of H$_2$O at 0° C. The reaction mixture was stirred at room temperature for 1.5 h and acidified by 1 N HCl to pH=5. The resulting mixture was extracted with EtOAc (3×20 ml). The combined organic layers were dried over anhydrous Na₂SO₄ and concentrated to dryness. The residue was purified by prep HPLC to give the title compound as an off-white powder (60 mg, yield: 82.2%). ¹H NMR (400 MHz, DMSO) δ12.23 (s, 1H), 9.09 (s, 1H), 7.03 (d, J=2.0 Hz, 1H), 7.01-6.98 (m, 1H), 6.85 (d, J=2.0 Hz, 1H), 5.45-5.42 (m, 1H), 3.96-3.93 (m, 2H), 3.27-3.31 (m, 2H), 3.00-3.04 (m, 1H), 2.25 (s, 3H), 2.08-2.02 (m, 1H), 1.39 (s, 9H); MS (ESI) m/z=366 [M+H]⁺.

G34: 2-(6-(2-Aminoethoxy)-1-hydroxy-4-methyl-1,3-dihydrobenzo[c][1,2]oxaborol-3-yl)acetic acid Trifluoroacetic acid

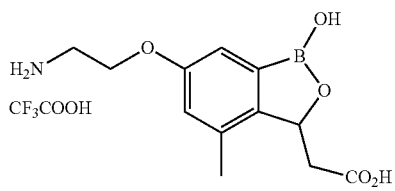 [SMILES: "CF3COOH" ; Cc1cc(OCCN)cc2c1C(CC(=O)O)OB2O]

Step 1: 2-(6-(2-Aminoethoxy)-1-hydroxy-4-methyl-1,3-dihydrobenzo[c][1,2]oxaborol-3-yl)acetic acid Trifluoroacetic acid

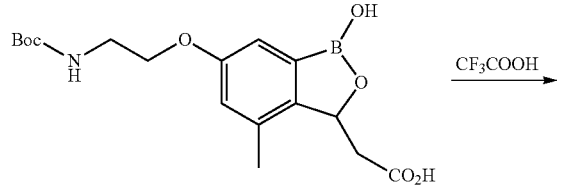

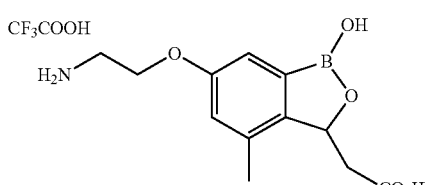

To a solution of 2-(6-(2-(tert-butoxycarbonyl)ethoxy)-1-hydroxy-4-methyl-1,3-dihydrobenzo[c][1,2]oxaborol-3-yl) acetic acid (40 mg, 0.101 mmol) in DCM (10 mL) was added TFA (5 mL) at 0° C. The reaction mixture was stirred for 30 min and concentrated in vacuo. The residue was re-crystallized from i-PrOH/H₂O (95/5) to give the title compound as a white solid (22 mg, yield: 53.1%). ¹H NMR (400 MHz, DMSO) δ 12.31 (s, 1H), 9.18 (s, 1H), 7.97 (d, J=8.0 Hz, 3H), 7.09 (d, J=2.0 Hz, 1H), 6.90 (d, J=2.0 Hz, 1H), 5.47-5.45 (m, 1H), 4.17-4.14 (t, J=2.0 Hz, 2H), 3.25-3.23 (m, 2H), 3.07-3.02 (m, 1H), 2.28 (s, 3H), 2.08-2.04 (m, 1H). MS (ESI) m/z=266 [M+H]⁺.

G35: 2-(6-(2-(Dimethylamino)ethoxy)-1-hydroxy-4-methyl-1,3-dihydrobenzo[c][1,2]-oxaborol-3-yl) acetic acid hydrochloride

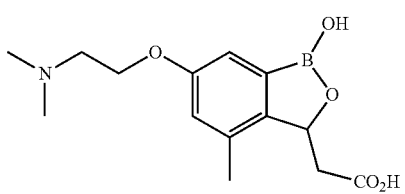 [SMILES: Cc1cc(OCCN(C)C)cc2c1C(CC(=O)O)OB2O]

Step 1: Ethyl 2-(6-(2-(dimethylamino)ethoxy)-1-hydroxy-4-methyl-1,3-dihydrobenzo[c][1,2]oxaborol-3-yl)acetate

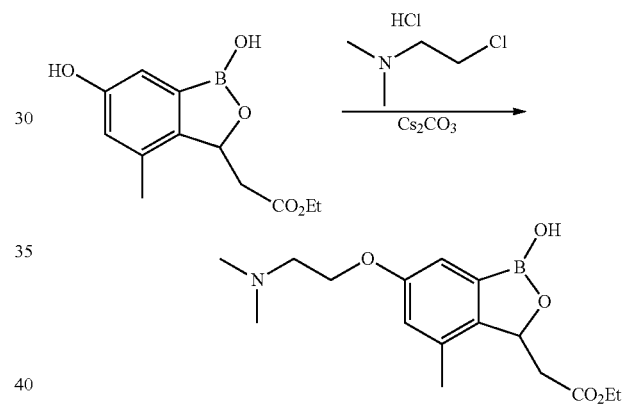

To the mixture of ethyl 2-(1,6-dihydroxy-4-methyl-1,3-dihydrobenzo[c][1,2]oxaborol-3-yl)acetate (200 mg, 0.8 mmol) in 15 ml DMF was added Cs₂CO₃ (782 mg, 2.4 mmol), followed by 2-chloro-N,N-dimethylethanamine hydrochloride (116 mg, 0.81 mmol). The mixture was heated to 90° C. for 6 h and quenched by ice water (20 mL). The resulting mixture was extracted with EtOAc (3×20 ml) and the combined organic layers were dried over anhydrous Na₂SO₄ and concentrated to dryness. The residue was used directly in next step reaction without further purification.

Step 2: 2-(6-(2-(Dimethylamino)ethoxy)-1-hydroxy-4-methyl-1,3-dihydrobenzo[c][1,2]oxaborol-3-yl) acetic acid hydrochloride

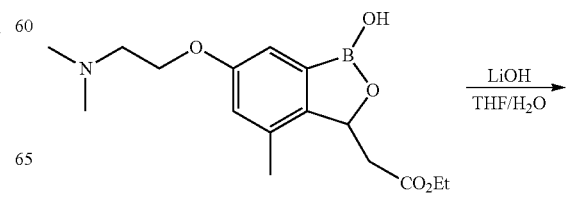

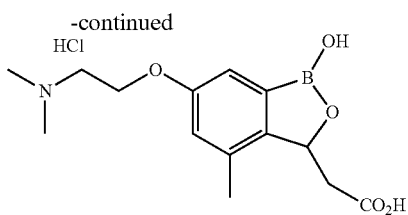

To a solution of ethyl 2-(6-(2-(dimethylamino)ethoxy)-1-hydroxy-4-methyl-1,3-dihydrobenzo[c][1,2]oxaborol-3-yl)acetate (crude) in 15 ml of THF/H$_2$O (2/1) was added LiOH (42 mg, 1.0 mmol) in 5 ml H$_2$O at 0° C. The reaction mixture was stirred at room temperature for 1.5 h and acidified by 1.0 N HCl to pH=6. The resulting mixture was extracted with EtOAc (3×20 mL) and the combined organic layers were dried over anhydrous Na$_2$SO$_4$ and concentrated in vacuo. The residue was purified by prep HPLC to give the title compound as a white solid (35 mg, yield: 15%, two steps). $^1$H NMR (400 MHz, DMSO-d) δ9.15 (s, 1H), 7.08 (d, J=1.6 Hz, 1H), 6.89 (d, J=1.6 Hz, 1H), 5.46-5.43 (m, 1H), 4.24-4.22 (m, 2H), 4.09 (m, 1H), 3.24 (m, 2H), 3.16 (s, 3H), 3.05-3.01 (m, 1H), 2.65 (s, 6H), 2.26 (s, 3H), 2.09-2.02 (m, 1H); MS (ESI) m/z=294 [M+H]$^+$.

G36: 2-(1-Hydroxy-6-(3-hydroxypropoxy)-4-methyl-1,3-dihydrobenzo[c][1,2]oxaborol-3-yl)acetic acid

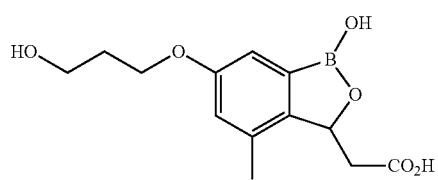 [SMILES: Cc1cc(OCCCO)cc2c1C(CC(=O)O)OB2O]

Step 1: Ethyl 2-(6-(3-(tert-butyldimethylsilyloxy)propoxy)-1-hydroxy-4-methyl-1,3-dihydrobenzo[c][1,2]oxaborol-3-yl)acetate

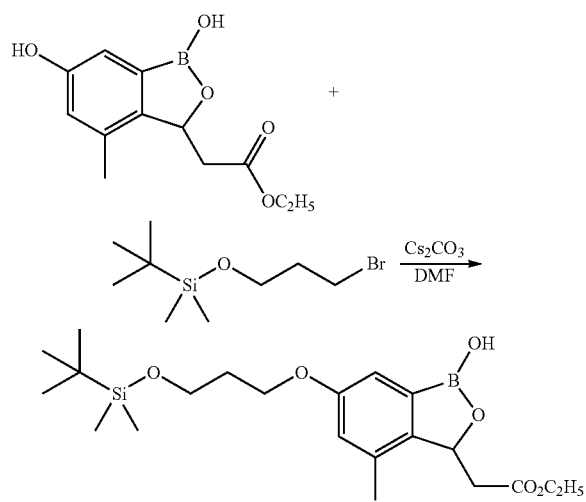

To a mixture of ethyl 2-(1,6-dihydroxy-4-methyl-1,3-dihydrobenzo[c][1,2]oxaborol-3-yl)acetate (0.5 g, 2 mmol) and cesium carbonate (1.95 g, 6 mmol) in 10 ml DMF was added (3-bromopropoxy)(tert-butyl)dimethylsilane (1.39 ml, 6 mmol). The reaction was heated at 60° C. for six hours. It was then quenched by water, extracted with EtOAc, washed with brine, dried over Na$_2$SO$_4$, and concentrated under reduced pressure. The crude was purified by column.

Step 2: Ethyl 2-(1-hydroxy-6-(3-hydroxypropoxy)-4-methyl-1,3-dihydrobenzo[c][1,2]oxaborol-3-yl)acetate

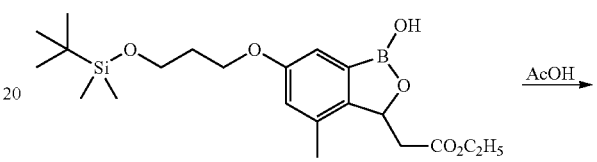

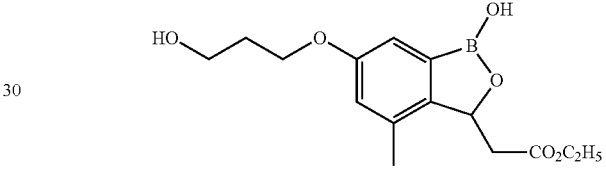

Ethyl 2-(6-(3-(tert-butyldimethylsilyloxy)propoxy)-1-hydroxy-4-methyl-1,3-dihydrobenzo[c][1,2]oxaborol-3-yl)acetate was treated with a mixture of THF:water:acetic acid (ratio 1:1:2) at 55° C. for 1.5 hours. The solvent was then removed under reduced pressure and the resulting residue was dried under vacuum overnight and used directly in next step without further purification.

Step 3: 2-(1-Hydroxy-6-(3-hydroxypropoxy)-4-methyl-1,3-dihydrobenzo[c][1,2]oxaborol-3-yl)acetic acid

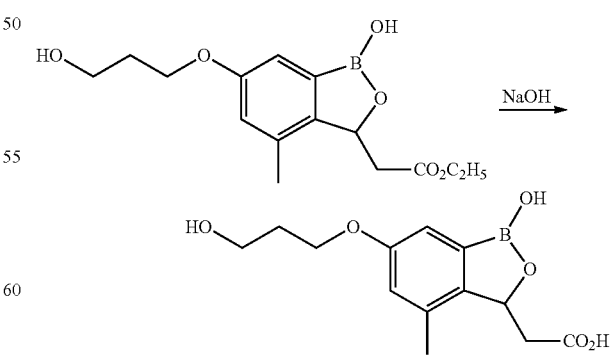

The product is a white solid. $^1$H NMR (400 MHz, DMSO-d$_6$) 12.2 (b, 1 H), 9.10 (s, 1H), 7.02 (d, J=2 Hz 1H), 6.82 (d, J=2 Hz, 1H), 5.41 (dd, J=9.6, 2.4 Hz, 1H), 4.00 (t, J=6.4 Hz, 2H), 3.54 (t, J=6 Hz, 2H), 3.01 (dd, J=15.2, 2.4 Hz, 2H), 2.23 (s, 3H), 2.04 (m, 2H), 1.84 (m, 1H). MS (ESI) m/z=279 [M−H]+.

G37: 2-(6-(Ethoxycarbonyloxy)-4-fluoro-1-hydroxy-1,3-dihydrobenzo[c][1,2]oxaborol-3-yl)acetic acid

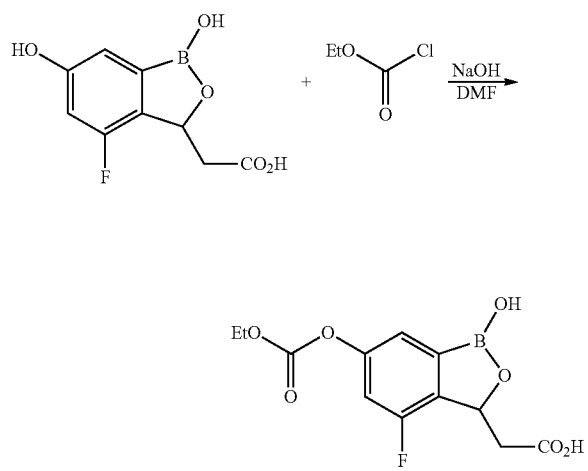

To a mixture of 2-(4-fluoro-1,6-dihydroxy-1,3-dihydrobenzo[c][1,2]oxaborol-3-yl)-acetic acid (113 mg, 0.5 mmol) and sodium hydroxide (0.06 g, 1.5 mmol) in water (3 mL) was added ethyl chloroformate (59 mg, 0.55 mmol). The reaction mixture was stirred at room temperature for 15 min and then acidified to pH=2 with 1N HCl. The mixture was extracted with ethyl acetate (2×15 mL) and the combined organic layers were dried over anhydrous Na$_2$SO$_4$ and concentrated in vacuo. The residue was purified by HPLC to give the title compound as a white solid (21 mg, Yield: 14%). $^1$H NMR (400 MHz, DMSO-d) δ9.57 (s, 1H), 7.32-7.37 (m, 2H), 5.59-5.62 (m, 1H), 4.25-4.30 (m, 2H), 2.95-3.00 (m, 1H), 2.36-2.42 (m, 1H), 1.29-1.32 (t, J=6.8 Hz, 3H). MS (ESI) m/z=299 [M+H]+.

G38: 2-(4-Chloro-6-(ethoxycarbonyloxy)-1-hydroxy-1,3-dihydrobenzo[c][1,2]oxaborol-3-yl)acetic acid

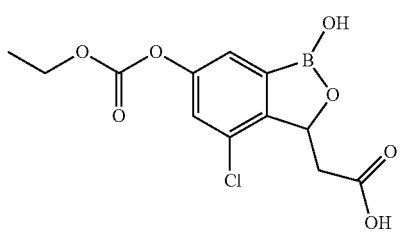 [SMILES: CCOC(=O)Oc1cc(Cl)c2c(c1)B(O)OC2CC(=O)O]

Step 1: 2-(4-chloro-1,6-dihydroxy-1,3-dihydrobenzo[c][1,2]oxaborol-3-yl)acetic acid

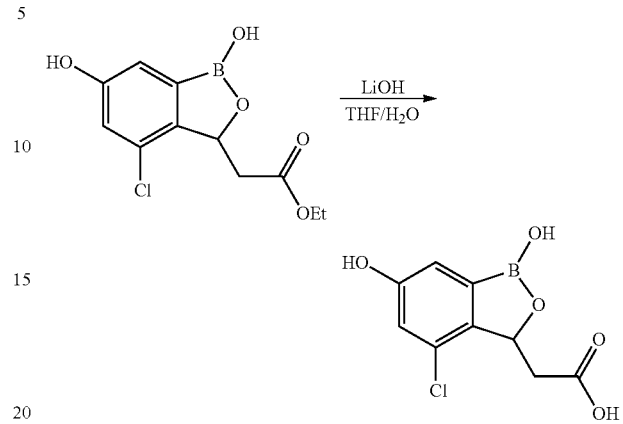

To a solution of ethyl 2-(4-chloro-1-hydroxy-6-isopropoxy-1,3-dihydrobenzo[c][1,2]oxaborol-3-yl)acetate (200 mg, 0.74 mmol) in 10 mL THF was added LiOH (100 mg, 2.22 mmol) in 5 mL H$_2$O dropwise at 0° C. The mixture was stirred at room temperature for 1.5 h and acidified to pH=5.0 using 1N HCl (8 mL). The resulting mixture was extracted with EtOAc (3×10 mL). The combined organic layers were dried over anhydrous Na$_2$SO$_4$ and concentrated in vacuo. The residue was use directly in next step reaction without further purification.

Step 2: 2-(4-Chloro-6-(ethoxycarbonyloxy)-1-hydroxy-1,3-dihydrobenzo[c][1,2]oxaborol-3-yl)acetic acid

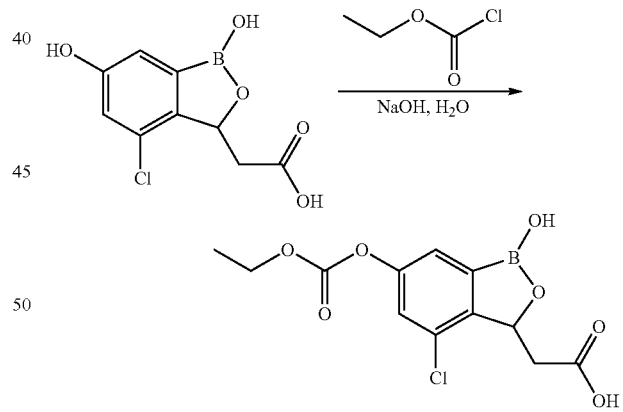

To the suspension of the crude 2-(4-chloro-1,6-dihydroxy-1,3-dihydrobenzo[c][1,2]oxaborol-3-yl)acetic acid (180 mg, 0.74 mmol) and NaOH (30 mg, 0.74 mmol) in 8 mL H$_2$O was added ethyl chloroformate (96 mg, 0.89 mol) dropwise at 0° C. The reaction mixture was stirred at room temperature for 30 min and acidified to pH=5.0 using 1N HCl. The resulting mixture was extracted with EtOAc (3×10 mL) and the combined organic layers were dried over anhydrous Na$_2$SO$_4$ and concentrated in vacuo. The residue was purified by prep HPLC to give the title compound as an off-white powder (50 mg, yield: 21.5%, two steps). $^1$H NMR (400 MHz, DMSO) δ12.43 (s, 1H), 9.50 (s, 1H), 7.55 (d, J=2.4 Hz, 1H), 7.50 (d, J=2.4 Hz, 1H), 5.52 (m, 1H), 4.28 (m, 2H), 3.19 (m, 1H), 2.36 (m, 1H), 1.31 (t, J=7.0 Hz, 1H).

G39: 2-(6-(Ethoxycarbonyloxy)-1-hydroxy-4-methyl-1,3-dihydrobenzo[c][1,2]oxaborol-3-yl) acetic acid

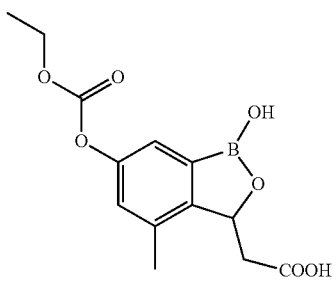 [SMILES: CCOC(=O)Oc1cc(C)c2c(c1)B(O)OC2CC(=O)O]

Step 1: 2-(1,6-dihydroxy-4-methyl-1,3-dihydrobenzo[c][1,2]oxaborol-3-yl)acetic acid

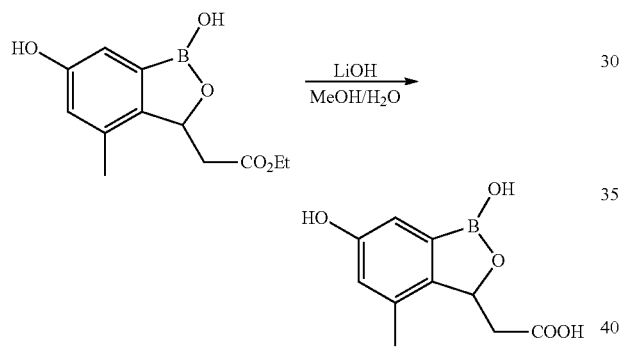

To a solution of ethyl 2-(1,6-dihydroxy-4-methyl-1,3-dihydrobenzo[c][1,2]oxaborol-3-yl)acetate (300 mg, 1.2 mmol) in MeOH (2 mL) was added LiOH (144 mg, 6 mmol) in 5 ml H$_2$O at 0° C. The reaction mixture was stirred at room temperature for 1.5 h and acidified by 1N HCl to pH=5.0. The resulting mixture was extracted with EtOAc (3×20 mL) and the combined organic layers were dried over anhydrous Na$_2$SO$_4$ and concentrated in vacuo to give a crude product, which was used directly in next step without further purification.

Step 2: 2-(6-(ethoxycarbonyloxy)-1-hydroxy-4-methyl-1,3-dihydrobenzo[c][1,2]oxaborol-3-yl) acetic acid

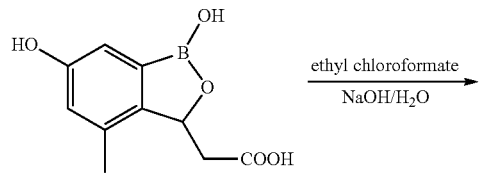

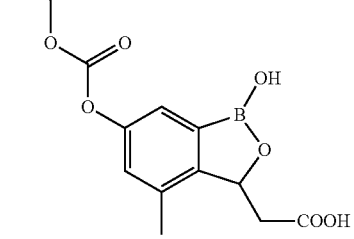

To the suspension of crude 2-(1,6-dihydroxy-4-methyl-1,3-dihydrobenzo[c][1,2]oxaborol-3-yl)acetic acid (250 mg, 1.126 mmol) in 2 ml H$_2$O was added NaOH (90 mg, 2.25 mmol) in 6 ml H$_2$O, followed by ethyl chloroformate (134.4 mg, 1.24 mmol) dropwise. The reaction mixture was stirred at room temperature for 20 min and acidified by 1N HCl to pH=5.0. The mixture was extracted with EtOAc (3×20 mL) and the combined organic layers were dried over anhydrous Na$_2$SO$_4$ and concentrated to dryness. The residue was purified by prep HPLC to give the title compound as an off-white powder (120.5 mg, yield: 34%, two steps). $^1$H NMR (400 MHz, DMSO) δ 12.37-12.36 (t, J=3.6 Hz, 1H), 9.29 (s, 1H), 7.30 (d, J=2.0 Hz, 1H), 7.14 (d, J=2.0 Hz, 1H), 5.53-5.50 (m, 1H), 4.28-4.22 (m, 2H), 3.10-3.05 (m, 1H), 2.31 (s, 3H), 2.11-2.17 (m, 1H), 1.32-1.27 (m, 3H); MS (ESI) m/z=285 [M+H]$^+$.

G40: 2-(4-Chloro-6-(dimethylcarbamoyloxy)-1-hydroxy-1,3-dihydrobenzo[c][1,2]oxaborol-3-yl)acetic acid

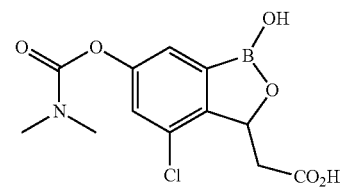 [SMILES: CN(C)C(=O)Oc1cc(Cl)c2c(c1)B(O)OC2CC(=O)O]

Step 1: Ethyl 2-(4-chloro-6-(dimethylcarbamoyloxy)-1-hydroxy-1,3-dihydrobenzo[c][1,2]oxaborol-3-yl)acetate

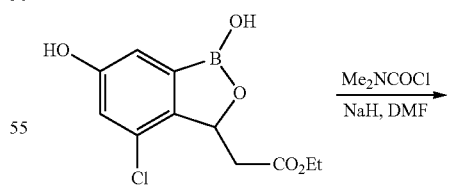

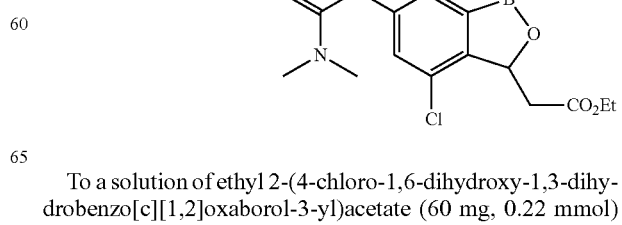

To a solution of ethyl 2-(4-chloro-1,6-dihydroxy-1,3-dihydrobenzo[c][1,2]oxaborol-3-yl)acetate (60 mg, 0.22 mmol)

in DMF (3 mL) was slowly added NaH (27 mg, 0.66 mmol) at 0° C. The mixture was stirred for 20 min and N,N-dimethylcarbamic chloride (29 mg, 0.27 mmol) was added at 0° C. The reaction mixture was stirred overnight at room temperature and quenched with ice water. The resulting mixture was extracted with EtOAc (2×15 mL) and the combined extracts were dried over anhydrous Na₂SO₄ and concentrated in vacuo. The residue was used directly in the next step reaction without further purification. MS (ESI) m/z=342 [M+H]⁺.

Step 2: 2-(4-Chloro-6-(dimethylcarbamoyloxy)-1-hydroxy-1,3-dihydrobenzo[c][1,2]oxaborol-3-yl)acetic acid

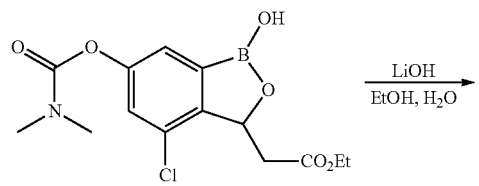

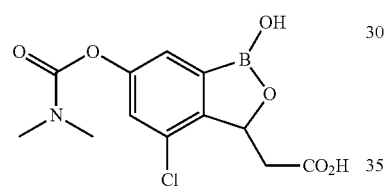

To the crude product from Step 3.1 in EtOH (10 mL was added an aqueous solution of LiOH (3 mL, 10%). The reaction mixture was stirred at 0° C. for 3 h and acidified with 1N HCl to pH=2-4. The resulting mixture was extracted with EtOAc (2×20 mL) and the combined organic layers were dried over anhydrous Na₂SO₄ and concentrated in vacuo. The residue was purified by prep HPLC to give the title compound as an off-white powder (15 mg, yield: 21.8%, two steps). ¹H NMR (400 MHz, DMSO) δ 12.43 (s, 1H), 9.51 (s, 1H), 7.40 (d, J=2.0 Hz, 1H), 7.39 (d, J=2.0 Hz, 1H), 5.49-5.52 (m, 1H), 3.19-3.23 (m, 1H), 3.05 (s, 1H), 2.93 (m, 1H), 2.29-2.35 (m, 1H); MS (ESI) m/z=314 [M+H]⁺.

G41: 2-(6-(Dimethylcarbamoyloxy)-1-hydroxy-4-methyl-1,3-dihydrobenzo[c][1,2]-oxaborol-3-yl)acetic acid

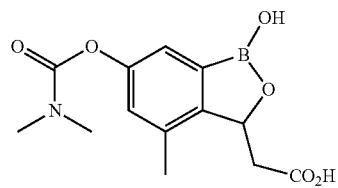 [SMILES: Cc1cc(OC(=O)N(C)C)cc2c1C(CC(=O)O)OB2O]

Step 1: Ethyl 2-(6-(dimethylcarbamoyloxy)-1-hydroxy-4-methyl-1,3-dihydrobenzo[c][1,2]oxaborol-3-yl)acetate

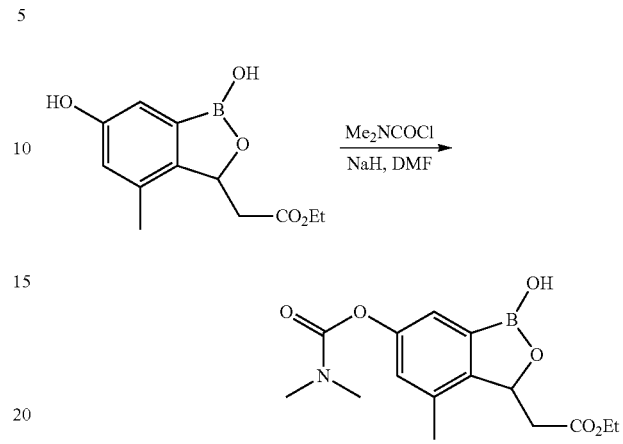

To a solution of ethyl 2-(1,6-dihydroxy-4-methyl-1,3-dihydrobenzo[c][1,2]oxaborol-3-yl)acetate (500 mg, 2 mmol) in DMF (5 mL) was slowly added NaH (360 mg, 6 mmol) at 0° C. The mixture was stirred for 20 min and N,N-dimethylcarbamic chloride (430 mg, 4 mmol) was added at 0° C. The mixture was stirred overnight at room temperature and quenched with ice water. The resulting mixture was extracted with EtOAc (2×25 mL) and the combined extracts were dried over anhydrous Na₂SO₄ and concentrated in vacuo. The residue was used directly in the next step reaction without further purification, MS (ESI) m/z=322 [M+H]⁺.

Step 2: 2-(6-(Dimethylcarbamoyloxy)-1-hydroxy-4-methyl-1,3-dihydrobenzo[c][1,2]oxaborol-3-yl)acetic acid To the crude product from Step 2.2 in EtOH (10 mL) was added an aqueous solution of LiOH (3 mL, 10%). The mixture was stirred at 0° C. for 3 h and acidified with 1N HCl to pH=2-4. The resulting mixture was extracted with EtOAc (2×20 ml) and combined extracts were washed with brine. The organic layer was dried over anhydrous Na₂SO₄ and concentrated in vacuo. The residue was purified by prep HPLC to give the title compound as a white powder (215 mg, yield: 36.7%, two steps). $^1$H NMR (400 MHz, DMSO) δ 12.33 (s, 1H), 9.21 (s, 1H), 7.21 (d, J=2.0 Hz, 1H), 7.01 (d, J=2.0 Hz, 1H), 5.49-5.52 (m, 1H), 3.09 (d, J=2.4 Hz, 3H), 3.91 (m, 3H), 2.39 (d, J=3.6 Hz, 3H), 2.09-2.16 (m, 3H); MS (ESI) m/z=294 [M+H]$^+$.

G42: 2-(4-Chloro-1-hydroxy-6-(methylsulfonyloxy)-1,3-dihydrobenzo[c][1,2]oxaborol-3-yl)acetic acid

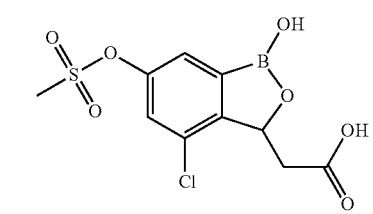

Step 1: Ethyl 2-(4-chloro-1-hydroxy-6-(methylsulfonyloxy)-1,3-dihydrobenzo[c][1,2]oxaborol-3-yl)acetate

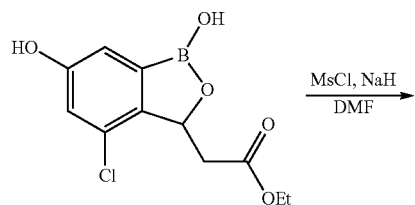

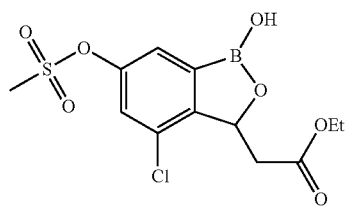

To a solution of ethyl 2-(4-chloro-1,6-dihydroxy-1,3-dihydrobenzo[c][1,2]oxaborol-3-yl)acetate (60 mg, 0.22 mmol) in DMF (3 mL) was slowly added NaH (27 mg, 0.66 mmol) at 0° C. The reaction mixture was stirred for 20 min and MsCl (29 mg, 0.27 mmol) was added. The reaction mixture was stirred overnight at room temperature and quenched with ice water. The resulting mixture was extracted with EtOAc (2×15 mL) and the combined organic layers were dried over anhydrous Na$_2$SO$_4$ and concentrated in vacuo. The residue was used directly in the next step reaction without further purification. MS (ESI) m/z=349 [M+H]$^+$.

Step 2: 2-(4-Chloro-1-hydroxy-6-(methylsulfonyloxy)-1,3-dihydrobenzo[c][1,2]oxaborol-3-yl)acetic acid

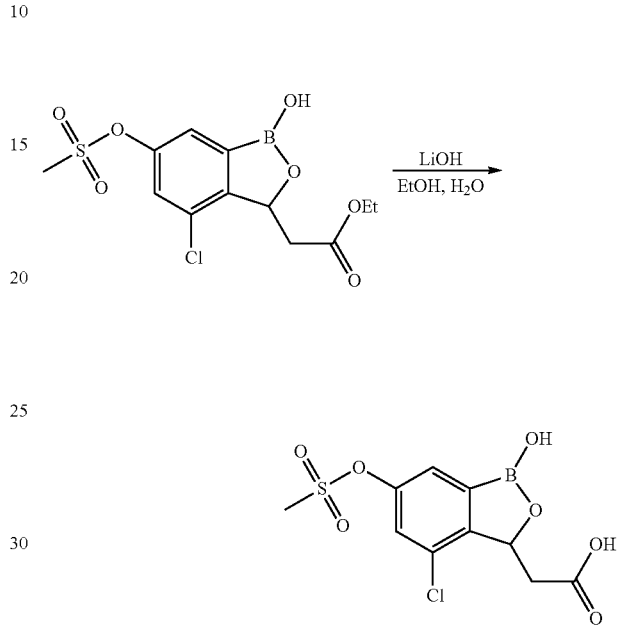

To the crude product from Step 4.1 in EtOH (10 mL) was added an aqueous solution of LiOH (3 mL, 10%). The reaction mixture was stirred at 0° C. for 3 h and acidified with 1N HCl to pH=2-4. The resulting mixture was extracted with EtOAc (2×20 mL). The combined organic layers were dried over anhydrous Na$_2$SO$_4$ and concentrated in vacuo. The residue was purified by prep HPLC to give the title compound as an off-white powder (15 mg, yield: 21.3%, two steps). $^1$H NMR (400 MHz, DMSO) δ 12.43 (s, 1H), 9.62 (s, 1H), 7.65 (d, J=2.0 Hz, 1H), 7.63 (d, J=2.0 Hz, 1H), 5.54 (m, 1H), 3.45 (s, 3H), 3.19 (m, 1H), 2.37 (m, 1H); MS (ESI) m/z=321 [M+H]$^+$.

G43: 2-(1-Hydroxy-4-methyl-6-(methylsulfonyloxy)-1,3-dihydrobenzo[c][1,2]oxaborol-3-yl)acetic acid

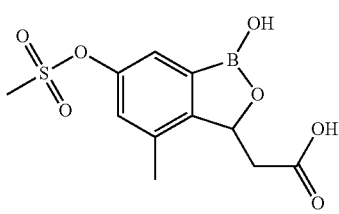 [SMILES: Cc1cc(OS(C)(=O)=O)cc2c1C(CC(=O)O)OB2O]

Step 1: Ethyl 2-(1-hydroxy-4-methyl-6-(methylsulfonyloxy)-1,3-dihydrobenzo[c][1,2]oxaborol-3-yl)acetate

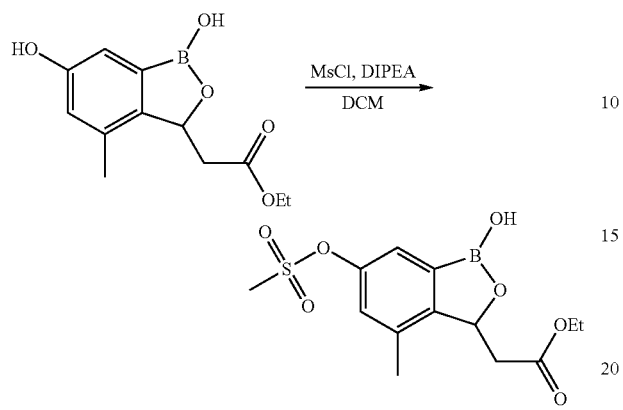

To a solution of ethyl 2-(1,6-dihydroxy-4-methyl-1,3-dihydrobenzo[c][1,2]oxaborol-3-yl)acetate (500 mg, 2 mmol), DIPEA (774 mg, 6 mmol) in DCM (10 mL) was slowly added MsCl (366 mg, 3.2 mmol) at −78° C. The reaction mixture was stirred overnight at room temperature, quenched with saturated NH$_4$Cl and washed with saturated NaHCO$_3$ and brine. The organic layer was dried over anhydrous Na$_2$SO$_4$ and concentrated in vacuo. The residue was used directly in next step reaction without further purification. MS (ESI) m/z=329 [M+H]$^+$ Step 2: 2-(1-Hydroxy-4-methyl-6-(methylsulfonyloxy)-1,3-dihydrobenzo[c][1,2]-oxaborol-3-yl)acetic acid

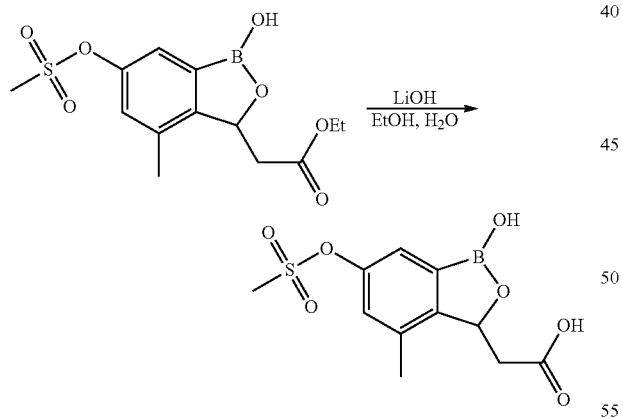

To a solution of 2-(1-hydroxy-4-methyl-6-(methylsulfonyloxy)-1,3-dihydrobenzo[c][1,2]oxaborol-3-yl)acetate in EtOH (10 mL) was added an aqueous solution of LiOH (3 mL, 10% aq.). The reaction mixture was stirred at 0° C. for 3 h. The reaction mixture was acidified with 1N HCl to pH=2 and extracted with EtOAc (2×20 mL). The combined organic layers were dried over anhydrous Na$_2$SO$_4$ and concentrated in vacuo. The residue was purified by prep HPLC to give the title compound as an off-white powder (64 mg, yield: 17.2%, two steps). $^1$H NMR (400 MHz, DMSO) δ 12.36 (s, 1H), 9.36 (s, 1H), 7.46 (d, J=2.0 Hz, 1H), 7.26 (d, J=2.0 Hz, 1H), 5.53-5.55 (m, 1H), 3.38 (s, 3H), 3.06-3.10 (m, 1H), 2.34 (s, 3H), 2.14-2.20 (m, 3H); MS (ESI) m/z=323 [M+Na]$^+$.

G44: 2-(1-Hydroxy-4-methyl-6-(sulfamoyloxy)-1,3-dihydrobenzo[c][1,2]oxaborol-3-yl)acetic acid

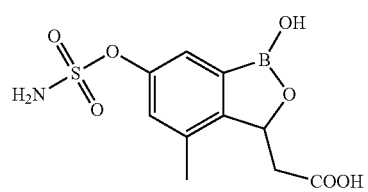 [SMILES: Cc1cc(OS(N)(=O)=O)cc2c1C(CC(=O)O)OB2O]

Step 1: 2-(1,6-Dihydroxy-4-methyl-1,3-dihydrobenzo[c][1,2]oxaborol-3-yl)acetic acid

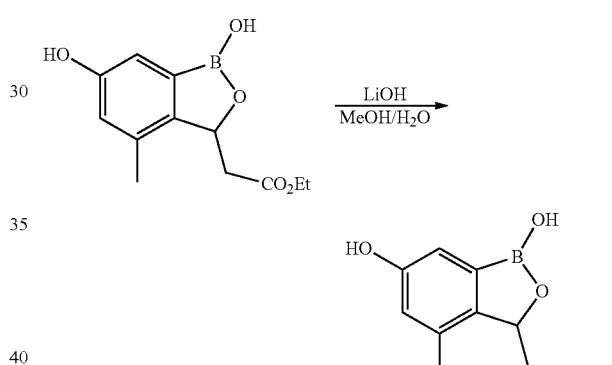

To a solution of ethyl 2-(1,6-dihydroxy-4-methyl-1,3-dihydrobenzo[c][1,2]oxaborol-3-yl)acetate (500 mg, 2.0 mmol) in 2 mL MeOH was added LiOH (240 mg, 10 mmol) in 5 ml H$_2$O dropwise at 0° C. The reaction mixture was stirred at room temperature for 1.5 h and acidified by 1 N HCl to pH=5.0. The mixture was extracted with EtOAc (3×20 mL) and the combined organic layers were dried over anhydrous Na$_2$SO$_4$ and concentrated to dryness. The residue was used directly in next step reaction without further purification.

Step 2: Benzyl 2-(1,6-dihydroxy-4-methyl-1,3-dihydrobenzo[c][1,2]oxaborol-3-yl)acetate

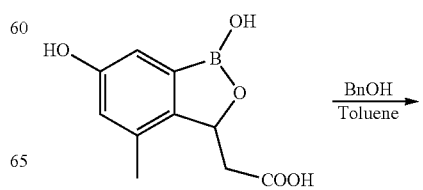

-continued

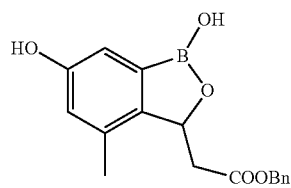

To a solution of 2-(1,6-dihydroxy-4-methyl-1,3-dihydrobenzo[c][1,2]oxaborol-3-yl)acetic acid (400 mg, 1.8 mmol) in 30 mL toluene was added 4-methylbenzenesulfonic acid (68.5 mg, 0.36 mmol) and BnOH (583.8 mg, 5.4 mmol). The reaction mixture was refluxed for 5 h and concentrated to dryness. The residue was dissolved in 20 mL EtOAc and washed with H$_2$O (15 mL). The aqueous layer was extracted with EtOAc (2×20 mL). The combined organic layers were dried with anhydrous Na$_2$SO$_4$ and concentrated to dryness. The residue was used directly in next step reaction without further purification.

Step 3: Benzyl 2-(6-(carbamoyloxy)-1-hydroxy-4-methyl-1,3-dihydrobenzo[c][1,2]oxaborol-3-yl)sulfamoyl

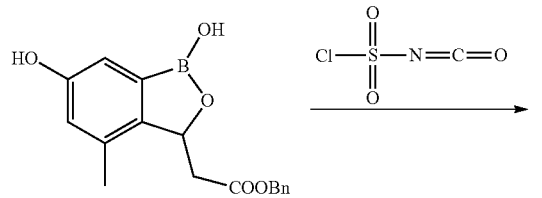

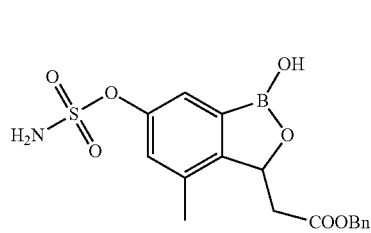

To a solution of chlorosulfonyl isocyanate (2 g, 14.0 mmol) in anhydrous CH$_3$CN (25 mL) was added H$_2$O (0.25 mL) at 0° C. The mixture was stirred for 30 min followed by addition of benzyl 2-(1,6-dihydroxy-4-methyl-1,3-dihydrobenzo[c][1, 2]oxaborol-3-yl)acetate (620 mg, 1.51 mmol purity 76%) in anhydrous CH$_3$CN (20 mL) at 0° C. The reaction mixture was stirred at room temperature for 1 h and concentrated in vacuo. The residue was dissolved in 20 mL of EtOAc and washed with 10 ml of H$_2$O. The aqueous layer was extracted with EtOAc (2×20 mL). The combined organic layers were dried with anhydrous Na$_2$SO$_4$ and concentrated in vacuo. The residue was use directly in next step reaction without further purification.

Step 4: 2-(1-hydroxy-4-methyl-6-(sulfamoyl)-1,3-dihydrobenzo[c][1,2]oxaborol-3-yl)acetic acid

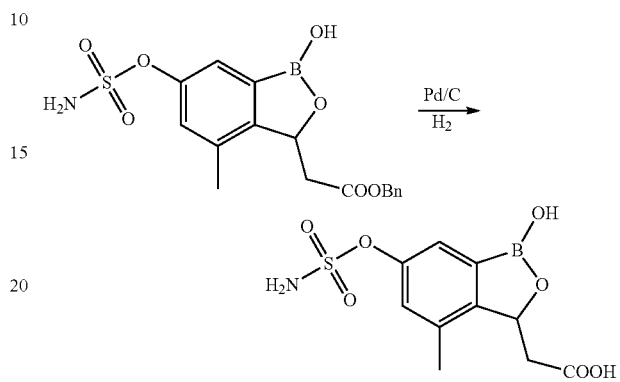

To a solution of Benzyl 2-(6-(carbamoyloxy)-1-hydroxy-4-methyl-1,3-dihydrobenzo[c][1,2]oxaborol-3-yl)sulfamoyl (560 mg, 1.00 mmol, purity 70%) in MeOH (5 mL) was added 10% Pd/C (50 mg). The mixture was hydrogenated using a balloon at room temperature for 2 h. The reaction mixture was filtrated to remove the catalyst and the filtrate was concentrated under reduced pressure. The residue was purified by prep HPLC to give the title compound as a white solid (30 mg, yield: 5%, four steps). $^1$H NMR (400 MHz, DMSO) δ 9.33 (s, 1H), 7.99 (s, 2H), 7.43 (s, 1H), 7.16 (s, 1H), 5.53 (d, J=8.8 Hz, 1H), 3.09-3.05 (m, 1H), 2.32 (s, 3H), 2.14-2.08 (m, 1H); MS (ESI) m/z=302 [M+H]$^+$.

G45: (1-Hydroxy-4-methyl-6-phenoxy-1,3-dihydrobenzo[c][1,2]oxaborol-3-yl)-acetic acid ethyl ester

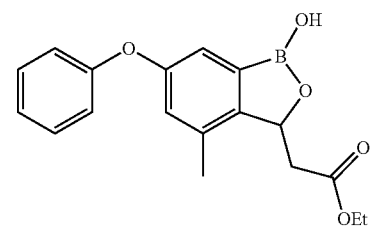 [SMILES: CCOC(=O)CC1OB(O)c2cc(Oc3ccccc3)cc(C)c21]

Step 1: 2-Hydroxy-6-methyl-4-(tetrahydro-pyran-2-yloxy)-benzaldehyde

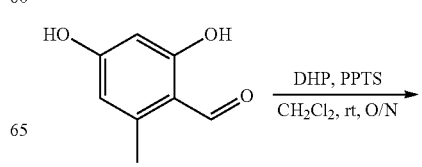

-continued

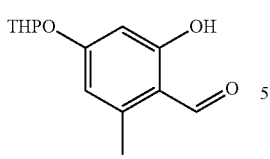

A light yellow suspension of 2,4-dihydroxy-6-methyl-benzaldehyde (4.90 g, 24.98 mmol) in DCM (400 mL) was treated with 3,4-dihydro-2H-pyran (3.5 mL, 38.61 mmol) followed by pyridinium-p-toluenesulfonate (0.20 g, 0.80 mmol). The suspension slowly cleared to a yellow solution. The solution was stirred at rt overnight then diluted with water and washed with saturated NaHCO$_3$. The organic layer was dried (Na$_2$SO$_4$), filtered and concentrated to a yellow oil. The residue was purified by column chromatography (SiO$_2$, EtOAc/hexanes; 1:9) to afford 2-hydroxy-6-methyl-4-(tetrahydro-pyran-2-yloxy)-benzaldehyde (4.60 g, 70%), as a light yellow liquid. $^1$H NMR (400 MHz, CDCl$_3$) δ 12.33 (s, 1H), 10.09 (s, 1H), 6.45 (d, J=2 Hz, 1H), 6.08 (d, J=2 Hz, 1H), 5.49-5.40 (m, 1H), 3.90-3.80 (m, 1H), 3.65-3.60 (m, 1H), 2.52 (s, 3H), 2.10-1.40 (m, 6H).

Step 2: 2-Methoxy-6-methyl-4-(tetrahydro-pyran-2-yloxy)-benzaldehyde

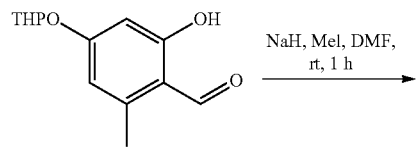

An ice-cold yellow solution of 2-hydroxy-6-methyl-4-(tetrahydro-pyran-2-yloxy)-benzaldehyde (7.60 g, 32.17 mmol) in DMF (150 mL), was treated with NaH (0.93 g, 38.63 mmol) in portions over 30 min. The suspension was stirred for 15 min, then methyl iodide (3.0 mL, 48.09 mmol) was added dropwise. The mixture was warmed to rt, stirred for 1 h, then quenched with water and extracted with EtOAc. The extracts were washed with brine, dried (Na$_2$SO$_4$), filtered and concentrated to a yellow liquid. The crude product of 2-methoxy-6-methyl-4-(tetrahydro-pyran-2-yloxy)-benzaldehyde was used in the next step without further purification. $^1$H NMR (400 MHz, CDCl$_3$) δ 10.49 (s, 1H), 6.50 (s, 1H), 6.49 (s, 1H), 5.54-5.52 (m, 1H), 3.87 (s, 1H), 3.88-3.80 (m, 1H), 3.67-3.61 (m, 1H), 2.57 (s, 3H), 2.10-1.95 (m, 1H), 1.95-1.82 (m, 2H), 1.80-1.58 (m, 3H).

Step 3: 4-Hydroxy-2-methoxy-6-methyl-benzaldehyde

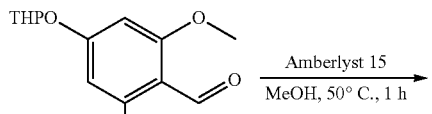

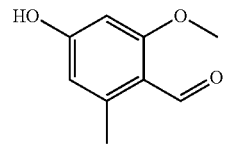

Crude 2-methoxy-6-methyl-4-(tetrahydro-pyran-2-yloxy)-benzaldehyde from the above step was diluted with MeOH (30 mL), then treated with Amberlyst® 15 (0.10 g). The suspension was heated at 50° C. for 1 h. The resin was removed by hot filtration and the filtrate was concentrated to a yellow semi-solid. The residue was recrystallized from MeOH and hexanes to give 4-hydroxy-2-methoxy-6-methyl-benzaldehyde (4.16 g, 78% over 2 steps), as a yellow solid. $^1$H NMR (400 MHz, CDCl$_3$) δ 10.47 (s, 1H), 6.32 (s, 1H), 6.25 (s, 1H), 5.49 (br s, 1H), 3.87 (s, 3H), 2.56 (s, 3H).

Step 4: 2-Methoxy-6-methyl-4-phenoxy-benzaldehyde

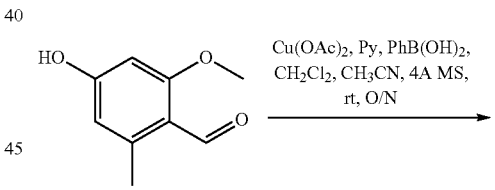

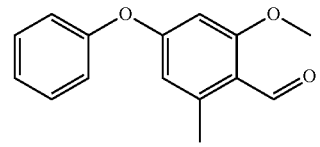

A suspension of 4-hydroxy-2-methoxy-6-methyl-benzaldehyde (1.00 g, 6.02 mmol), powdered 4A molecular sieves (4 g) in CH$_3$CN (40 mL) and DCM (40 mL) was treated with phenylboronic acid (1.47 g, 12.06 mmol), followed by copper (II) acetate (1.09 g, 6.00 mmol). Pyridine (2.40 mL, 29.70 mmol) was added to the green suspension and the resulting mixture was stirred at rt overnight in an open flask. The mixture was filtered through a pad of Celite and the filtrate was concentrated to a green oil. The residue was purified by column chromatography (SiO$_2$, EtOAc/hexanes; 1:9) to afford 2-methoxy-6-methyl-4-phenoxy-benzaldehyde (0.92 g, 63%), as a white solid. $^1$H NMR (400 MHz, CDCl$_3$) δ 10.52 (s, 1H), 7.41 (t, J=7.42 Hz, 2H), 7.22 (t, J=7.42 Hz, 1H), 7.08

(d, J=7.42 Hz, 2H), 6.43 (d, J=2.34 Hz, 1H), 6.31 (d, J=2.34 Hz, 1H), 3.83 (s, 3H), 2.53 (s, 3H).

Step 5: 2-Hydroxy-6-methyl-4-phenoxy-benzaldehyde

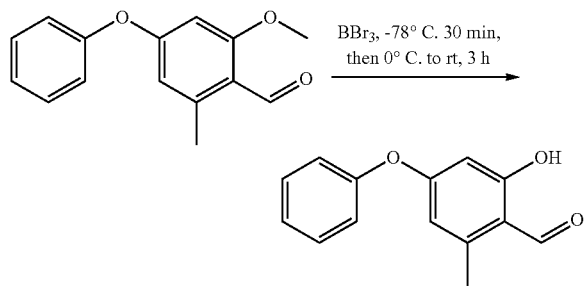

A light yellow solution of 2-methoxy-6-methyl-4-phenoxy-benzaldehyde (6.33 g, 26.13 mmol) in DCM (250 mL) was treated with boron tribromide (1.0 M solution in DCM, 76 mL, 76 mmol) dropwise at −78° C. (dry ice/acetone bath). The red/brown mixture was stirred at −78° C. for 30 minutes, 0° C. (ice-water bath) for 30 minutes, then rt for 3 h. The mixture was quenched with ice water, then extracted with EtOAc. The extracts were washed with brine, dried (Na$_2$SO$_4$), filtered, and concentrated to a brown residue. The residue was purified by column chromatography (SiO$_2$, EtOAc/hexanes; 1:9) to afford 2-hydroxy-6-methyl-4-phenoxy-benzaldehyde (5.06 g, 85%), as a white solid. $^1$H NMR (400 MHz, CDCl$_3$) δ 12.32 (s, 1H), 10.14 (s, 1H), 7.42 (t, J=7.42 Hz, 2H), 7.30-7.21 (m, 1H), 7.08 (d, J=7.42 Hz, 2H), 6.35 (s, 1H), 6.21 (s, 1H), 2.54 (s, 3H).

Step 6: Trifluoro-methanesulfonic acid 2-formyl-3-methyl-5-phenoxy-phenyl ester

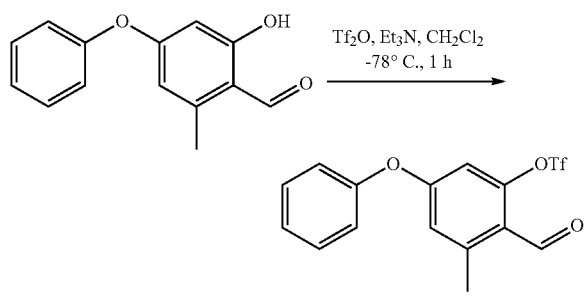

A light yellow solution of 2-hydroxy-6-methyl-4-phenoxy-benzaldehyde (5.87 g, 25.72 mmol), in DCM (100 mL) was treated with triethylamine (7.20 mL, 51.66 mmol) at −78° C. Trifluoromethanesulfonic anhydride (6.50 mL, 38.64 mmol)) was added dropwise and the orange solution was stirred at −78° C. for 1 h. The mixture was quenched with water, washed with 1 N HCl, extracted with DCM, dried (Na$_2$SO$_4$), filtered and concentrated to afford crude trifluoro-methanesulfonic acid 2-formyl-3-methyl-5-phenoxy-phenyl ester, as a brown liquid. The liquid was used in the next step without further purification. $^1$H NMR (400 MHz, CDCl$_3$) δ 10.36 (s, 1H), 7.51-7.40 (m, 2H), 7.33-7.25 (m, 1H), 7.12-7.08 (m, 2H), 6.81 (s, 1H), 6.77 (s, 1H), 2.62 (s, 3H).

Step 7: 2-Methyl-4-phenoxy-6-(4,4,5,5-tetramethyl-[1,3,2]dioxaborolan-2-yl)-benzaldehyde

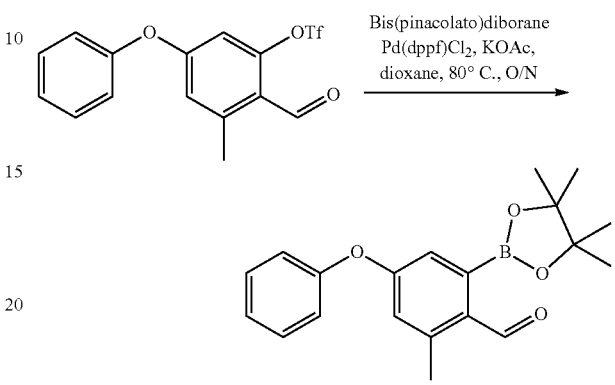

Crude trifluoro-methanesulfonic acid 2-formyl-3-methyl-5-phenoxy-phenyl ester in 1,4-dioxane (50 mL) from above was degassed for 15 minutes, then treated with bis(pinacolato)diborane (7.84 g, 30.87 mmol), potassium acetate (7.57 g, 77.15 mmol), and 1,1'-Bis(diphenylphosphino)ferrocene] dichloropalladium(II) (1.88 g, 2.57 mmol). The suspension was heated at 80° C. overnight. The mixture was cooled to rt, then filtered through Celite and the filtrate was concentrated to a brown oil. The residue was purified by column chromatography (SiO$_2$, EtOAc/hexanes; 1:9 to 1:7 gradient) to afford 2-methyl-4-phenoxy-6-(4,4,5,5-tetramethyl-[1,3,2]dioxaborolan-2-yl)-benzaldehyde (2.54 g, 29%), as a green waxy solid. $^1$H NMR (400 MHz, CDCl$_3$) δ 10.36 (s, 1H), 7.44-7.34 (m, 3H), 7.22-7.16 (m, 1H), 7.10-7.08 (m, 2H), 6.74 (s, 1H), 2.59 (s, 3H), 1.40 (s, 12H).

Step 8: (1-Hydroxy-4-methyl-6-phenoxy-1,3-dihydro-benzo[c][1,2]oxaborol-3-yl)-acetic acid ethyl ester

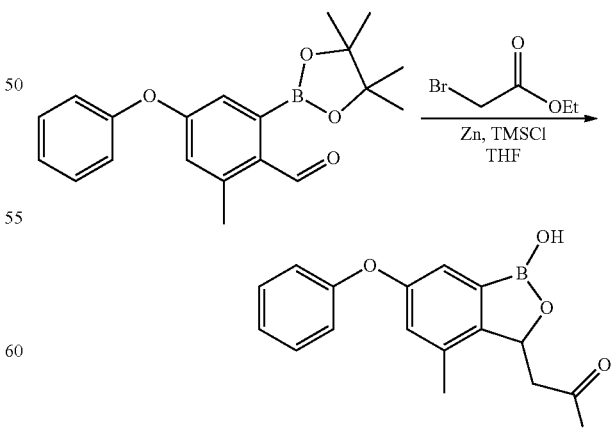

A suspension of zinc dust (1.26 g, 19.30 mmol) in THF (8 mL) was treated with chlorotrimethylsilane (0.30 mL, 2.40 mmol) at 40° C. The mixture was heated at 55° C. for 15 minutes, the cooled to 37° C. Ethyl bromoacetate (1.68 mL, 17.70 mmol) was added dropwise (refluxed gently upon addition), then stirred for 5 min. The suspension was allowed to settle at room temperature. The Reformasky reagent (approximately 1.7 M stock solution, 1.5 mL, 2.55 mmol) was transferred via syringe to a dry flask, then cooled to 0° C. 2-Methyl-4-phenoxy-6-(4,4,5,5-tetramethyl-[1,3,2]dioxaborolan-2-yl)-benzaldehyde (0.50 g, 1.48 mmol) in THF (5 mL) was added dropwise to the reagent, then stirred at 0° C. for 4 h. The mixture was quenched with saturated NH$_4$Cl, extracted with EtOAc, dried (Na$_2$SO$_4$), filtered and concentrated to a yellow oil. The oil was purified by column chromatography (SiO$_2$, EtOAc/hexanes; 1:5 to 1:1 gradient) to afford (1-hydroxy-4-methyl-6-phenoxy-1,3-dihydro-benzo[c][1,2]oxaborol-3-yl)-acetic acid ethyl ester (0.22 g, 46%), as a yellow oil. $^1$H NMR (400 MHz, DMSO-d$_6$) δ 9.18 (s, 1H), 7.40 (t, J=7.42 Hz, 2H), 7.16 (t, J=7.42 Hz, 1H), 7.07 (d, J=2.35 Hz, 1H), 7.02-6.97 (m, 3H), 5.51 (dd, J=9.33, 2.34 Hz, 1H), 4.05 (q, J=7.03 Hz, 2H), 3.14 (dd, J=15.63, 2.74 Hz, 1H), 2.89 (s, 3H), 2.33-2.26 (m, 1H), 1.14 (t, J=7.03 Hz, 3H); MS (ES) m/z: 325 (M−1).

G46: (1-Hydroxy-4-methyl-6-phenoxy-1,3-dihydro-benzo[c][1,2]oxaborol-3-yl)-acetic acid

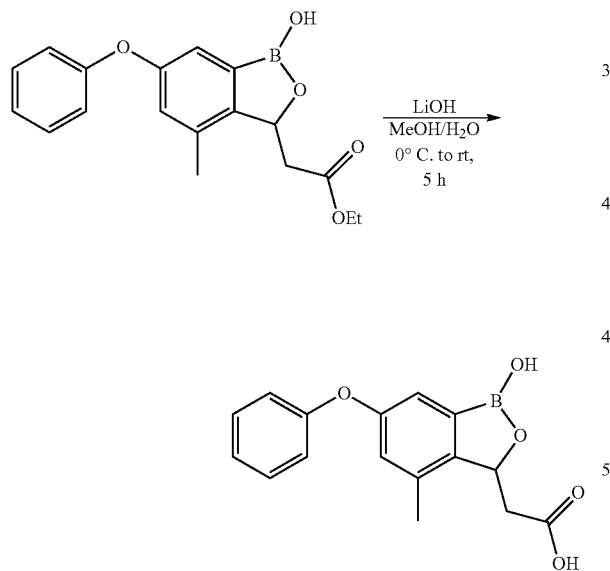

An ice-cold yellow solution of (1-hydroxy-4-methyl-6-phenoxy-1,3-dihydro-benzo[c][1,2]oxaborol-3-yl)-acetic acid ethyl ester G45 (0.19 g, 0.58 mmol) in MeOH (3 mL) was treated with lithium hydroxide (0.07 g, 2.92 mmol, in 2 mL of H$_2$O) dropwise. The mixture was stirred at 0° C. for 2 h, then rt for 3 h. The mixture was acidified with 2 N HCl to pH 3, then extracted with EtOAc, dried (Na$_2$SO$_4$), filtered and concentrated to a yellow oil. The oil was purified by column chromatography (SiO$_2$, AcOH/EtOAc/hexanes; 0.5:4:100) to afford 1-hydroxy-4-methyl-6-phenoxy-1,3-dihydro-benzo [c][1,2]oxaborol-3-yl)-acetic acid (0.14 g, 83%), as an off-white solid. $^1$H NMR (400 MHz, DMSO-d$_6$) δ 12.27 (br s, 1H), 9.16 (s, 1H), 7.40 (t, J=7.42 Hz, 2H), 7.14 (t, J=7.42 Hz, 1H), 7.07 (d, J=2.35 Hz, 1H), 7.06-6.97 (m, 3H), 5.48 (dd, J=9.38, 2.34 Hz, 1H), 3.05 (dd, J=15.44, 2.74 Hz, 1H), 2.29 (s, 3H), 2.16-2.06 (m, 1H); MS (ES) m/z: 297 (M−1).

G47: [1-Hydroxy-6-(3-hydroxy-phenoxy)-4-methyl-1,3-dihydro-benzo[c][1,2]oxaborol-3-yl]-acetic acid

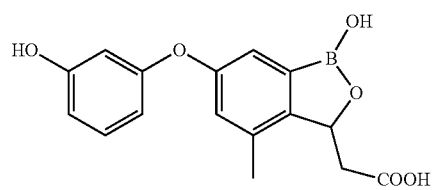 [SMILES: Cc1cc(Oc2cccc(O)c2)cc2c1C(CC(=O)O)OB2O]

Step 1: [6-(3-Benzyloxy-phenoxy)-1-hydroxy-4-methyl-1,3-dihydro-benzo[c][1,2]oxaborol-3-yl]-acetic acid

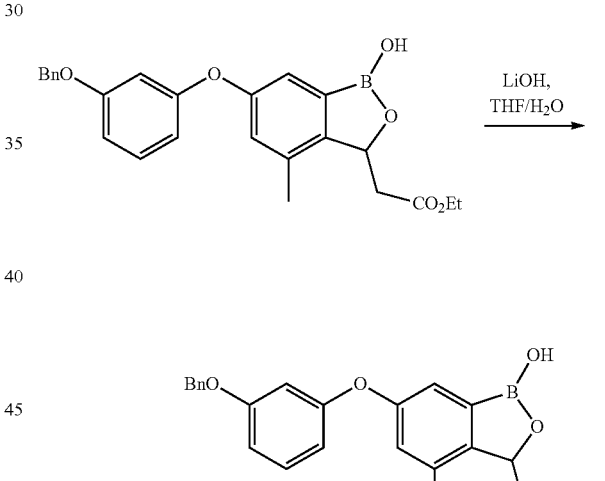

To a solution of [6-(3-benzyloxy-phenoxy)-1-hydroxy-4-methyl-1,3-dihydro-benzo[c][1,2]oxaborol-3-yl]-acetic acid ethyl ester (1.0 g, 2.3 mmol) in THF (20 mL) at 0° C. was added a solution of LiOH (0.278 g, 11.5 mmol) in water (10 mL). The solution was allowed to warm to room temperature and stirred for 3 hours then acidified to pH 2 with 6M HCl. The solution was extracted with ethyl acetate (2×50 mL) and the organic extracts washed with water, brine, dried over sodium sulfate and concentrated in vacuo to give [6-(3-benzyloxy-phenoxy)-1-hydroxy-4-methyl-1,3-dihydro-benzo [c][1,2]oxaborol-3-yl]-acetic acid as a clear oil (0.85 g, 91%) which was used without further purification. $^1$H NMR (400 MHz, DMSO): δ 9.13 (s, 1H), 7.42-7.25 (m, 6H), 7.08 (s, 1H), 6.96 (s, 1H), 6.79 (dd, J=8.4, 2.0 Hz, 1H), 6.64 (s, 1H), 6.51

(d, J=6.8 Hz, 1H), 5.48 (d, J=7.6 Hz, 1H), 5.07 (s, 2H), 3.10 (dd, J=15.6, 2.4 Hz, 1H), 2.26 (s, 3H), 2.13-2.07 (m, 1H).

Step 2: [1-Hydroxy-6-(3-hydroxy-phenoxy)-4-methyl-1,3-dihydro-benzo[c][1,2]oxaborol-3-yl]-acetic acid

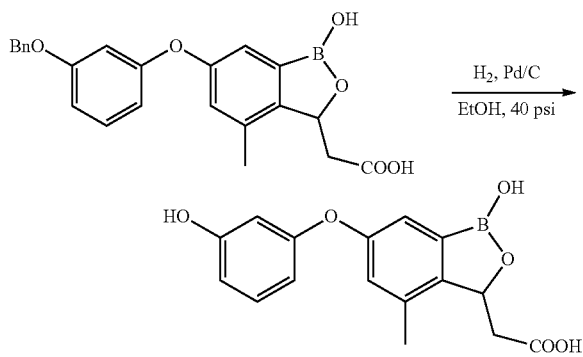

A solution of [6-(3-benzyloxy-phenoxy)-1-hydroxy-4-methyl-1,3-dihydro-benzo[c][1,2]oxaborol-3-yl]-acetic acid (0.55 g, 1.36 mmol) and 10% Pd/C (0.4 g) in EtOH (100 mL) was hydrogenated at 40 psi for 30 minutes. The mixture was filtered through a pad of celite and concentrated in vacuo. The residue was purified by silica gel flash column chromatography (MeOH:DCM 10:90) to give [1-hydroxy-6-(3-hydroxy-phenoxy)-4-methyl-1,3-dihydro-benzo[c][1,2]oxaborol-3-yl]-acetic acid (0.25 g, 58%). mp 138.2-140.1° C. $^1$H NMR (400 MHz, DMSO): δ 12.34 (s, 1H), 9.59 (s, 1H), 9.19 (s, 1H), 7.15 (t, J=8.0 Hz, 1H), 7.09 (d, J=2.0 Hz, 1H), 6.98 (d, J=1.6 Hz, 1H), 6.53 (dd, J=8.4, 2.0 Hz, 1H), 6.42 (dd, J=8.0, 2.0 Hz, 1H), 6.35 (t, J=2.4 Hz, 1H), 5.48 (dd, J=9.2, 2.4 Hz, 1H), 3.09 (dd, J=15.2, 2.4 Hz, 1H), 2.28 (s, 3H), 2.14-2.07 (m, 1H). MS (ESI) m/z: 315 (M+1)$^+$. HPLC purity: 98.56% (Maxplot), 98.87% (220 nm).

G48: {6-[3-(3-Amino-propoxy)-phenoxy]-1-hydroxy-4-methyl-1,3-dihydro-benzo[c][1,2]oxaborol-3-yl}-acetic acid

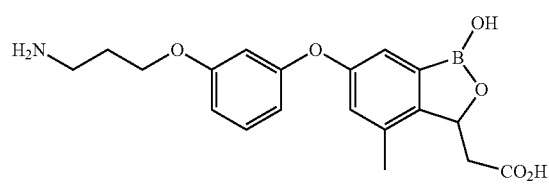 [SMILES: Cc1cc(Oc2cccc(OCCCN)c2)cc2c1C(CC(=O)O)OB2O]

Step 1: 2-Methoxymethoxy-6-methyl-4-(tetrahydro-pyran-2-yloxy)-benzaldehyde

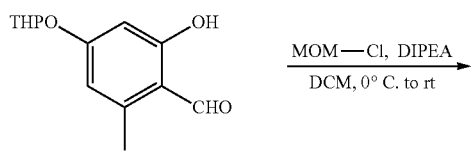

To a solution of 2-hydroxy-6-methyl-4-(tetrahydro-pyran-2-yloxy)-benzaldehyde (10.4 g, 44.0 mmol) in DCM (100 mL) at 0° C. was added DIPEA (11.5 mL, 66.0 mmol) followed by MOMCl (5.0 mL, 66.0 mmol). The reaction mixture was allowed to warm to room temperature and stirred for 6 hours. The mixture was concentrated in vacuo and the residue purified by silica gel flash column chromatography (hexane:EtOAc 70:30) to give 2-methoxymethoxy-6-methyl-4-(tetrahydro-pyran-2-yloxy)-benzaldehyde (10.0 g, 81%). $^1$H NMR (400 MHz, CDCl$_3$): δ 10.52 (s, 1H), 6.71 (d, J=2.4 Hz, 1H), 6.55 (d, J=1.6 Hz, 1H), 5.51 (t, J=3.2 Hz, 1H), 5.25 (q, J=6.8 Hz, 2H), 3.87-3.81 (m, 1H), 3.65-3.61 (m, 1H), 3.51 (s, 3H), 2.57 (s, 3H), 2.04-1.58 (m, 6H). MS (ESI) m/z=281 [M+H]$^+$.

Step 2: 4-Hydroxy-2-methoxymethoxy-6-methyl-benzaldehyde

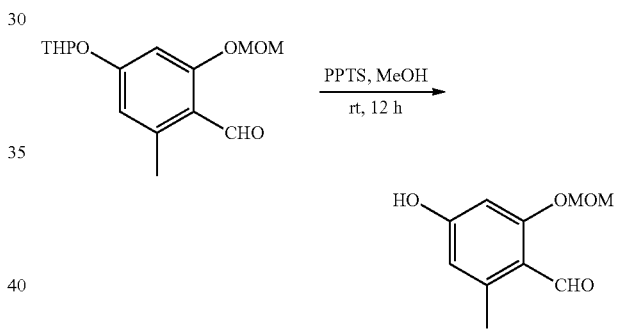

To a solution of 2-methoxymethoxy-6-methyl-4-(tetrahydro-pyran-2-yloxy)-benzaldehyde (9.8 g, 34.9 mmol) in MeOH (100 mL) was added PPTS (2.19 g, 8.7 mmol). The reaction mixture was stirred at room temperature for 12 hours then concentrated in vacuo. The residue was purified by silica gel flash column chromatography (hexane:EtOAc 80:20) to give 4-hydroxy-2-methoxymethoxy-6-methyl-benzaldehyde (5.4 g, 79%). $^1$H NMR (400 MHz, CDCl$_3$): δ 10.47 (s, 1H), 6.65 (s, 1H), 6.57 (d, J=2.0 Hz, 1H), 6.37 (s, 1H), 5.24 (s, 2H), 3.50 (s, 3H), 2.56 (s, 3H). MS (ESI) m/z=195 [M−H]$^-$.

Step 3: 4-(3-Benzyloxy-phenoxy)-2-methoxymethoxy-6-methyl-benzaldehyde

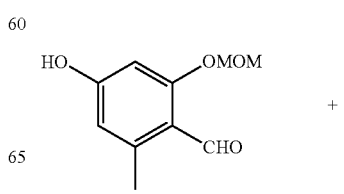 +

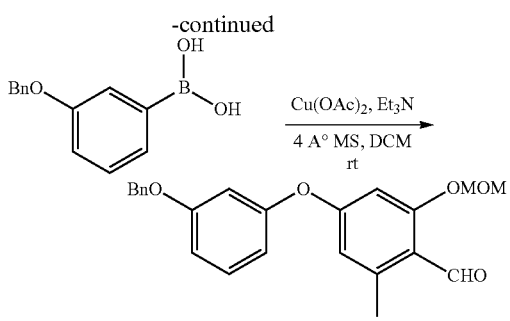

A mixture of 4-hydroxy-2-methoxymethoxy-6-methyl-benzaldehyde (5.3 g, 27.2 mmol), 3-benzyloxyphenylboronic acid (9.3 g, 40.8 mmol), Cu(OAc)$_2$ (4.9 g, 27.2 mmol), Et$_3$N (18.9 mL, 135.9 mmol) and 4 Å molecular sieves (26 g) in DCM (150 mL) was stirred at room temperature for 12 hours. The reaction mixture was filtered through a pad of celite and concentrated in vacuo. The residue was purified by silica gel flash column chromatography to give 4-(3-benzyloxy-phenoxy)-2-methoxymethoxy-6-methyl-benzaldehyde (3.5 g, 34%). $^1$H NMR (400 MHz, CDCl$_3$): δ 10.55 (s, 1H), 7.43-7.25 (m, 6H), 6.82 (dd, J=2.0, 8.4 Hz, 1H), 6.69-6.66 (m, 3H), 6.37 (s, 1H), 5.21 (s, 2H), 5.04 (s, 2H), 3.49 (s, 3H), 2.52 (s, 3H). MS (ESI) m/z=379 [M+H]$^+$.

Step 4: 4-(3-Benzyloxy-phenoxy)-2-hydroxy-6-methyl-benzaldehyde

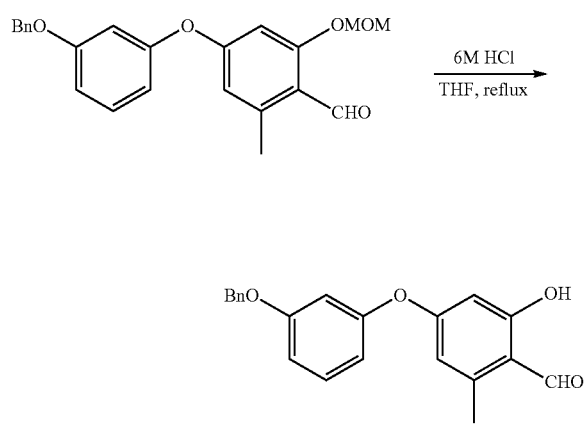

To a solution of 4-(3-benzyloxy-phenoxy)-2-methoxymethoxy-6-methyl-benzaldehyde (3.3 g, 8.8 mmol) in THF (50 mL) was added 6M HCl (6 mL) and the solution refluxed for 2 hours. The volatile organics were removed in vacuo and the aqueous residue extracted with EtOAc (2×25 mL). The organic extracts were dried and concentrated in vacuo. The residue was purified by silica gel flash column chromatography (hex:EtOAc 70:30) to give 4-(3-benzyloxy-phenoxy)-2-hydroxy-6-methyl-benzaldehyde (2.5 g, 85%). $^1$H NMR (400 MHz, CDCl$_3$): δ 10.13 (s, 1H), 7.43-7.25 (m, 6H), 6.85 (d, J=8.4 Hz, 1H), 6.68 (d, J=13.2 Hz, 2H), 6.34 (s, 1H), 6.24 (s, 1H), 5.04 (s, 2H), 2.52 (s, 3H). MS (ESI) m/z=335 [M+H]$^+$.

Step 5: Trifluoro-methanesulfonic acid 5-(3-benzyloxy-phenoxy)-2-formyl-3-methyl-phenyl ester

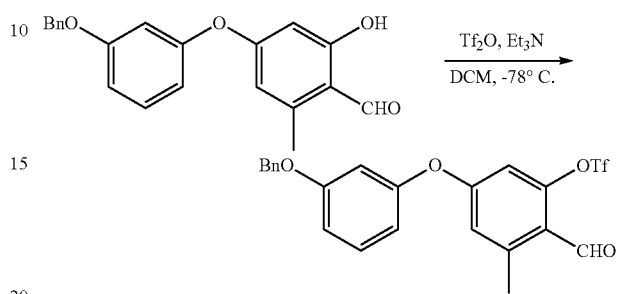

To a solution of 4-(3-benzyloxy-phenoxy)-2-hydroxy-6-methyl-benzaldehyde (2.5 g, 6.5 mmol) and Et$_3$N (2.72 mL, 19.5 mmol) in DCM (60 mL) at −78° C. was added Tf$_2$O (1.64 mL, 9.76 mmol). The reaction mixture was allowed to warm to room temperature and stirred for 3 hours. Water was added and the solution extracted with DCM (2×25 mL). The organic extracts were dried and concentrated in vacuo. The residue was purified by silica gel flash column chromatography (hexane:EtOAc 80:20) to give trifluoro-methanesulfonic acid 5-(3-benzyloxy-phenoxy)-2-formyl-3-methyl-phenyl ester (2.8 g, 93%). $^1$H NMR (400 MHz, CDCl$_3$): δ 10.36 (s, 1H), 7.43-7.32 (m, 6H), 6.90 (dd, J=2.0, 8.4 Hz, 1H), 6.79-6.67 (m, 4H), 5.06 (s, 2H), 2.61 (s, 3H). MS (ESI) m/z=467 [M+H]$^+$.

Step 6: 4-(3-Benzyloxy-phenoxy)-2-methyl-6-(4,4,5,5-tetramethyl-[1,3,2]dioxaborolan-2-yl)-benzaldehyde

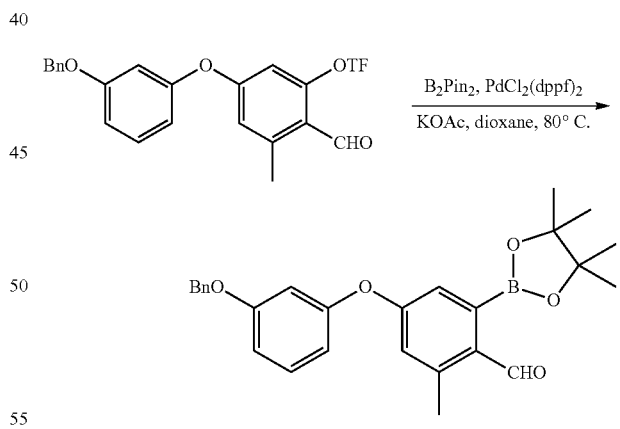

A solution of trifluoro-methanesulfonic acid 5-(3-benzyloxy-phenoxy)-2-formyl-3-methyl-phenyl ester (3.0 g, 6.43 mmol) in dioxane (60 mL) was degassed for 15 minutes with bubbling N$_2$. Bispinacolatodiboron (1.95 g, 7.7 mmol), PdCl$_2$(dppf)$_2$ (0.47 g, 0.64 mmol) and KOAc (1.89 g, 19.2 mmol) were added and the solution stirred at 80° C. for 1 hour. After cooling to room temperature the mixture was filtered through a pad of celite and concentrated in vacuo. The residue was dissolved in EtOAc (20 mL), washed with water (2×10 mL), dried and concentrated in vacuo. The residue was purified by silica gel flash column chromatography (hexane:EtOAc 50:30) to give 4-(3-benzyloxy-phenoxy)-2-methyl-6-(4,4,5,5-tetramethyl-[1,3,2]dioxaborolan-2-yl)-benzaldehyde (1.5 g, 52%). $^1$H NMR (400 MHz, CDCl$_3$): δ 10.38 (s, 1H), 7.43-7.25 (m, 6H), 7.08 (d, J=2.0 Hz, 1H), 6.82-6.62 (m, 4H), 5.04 (s, 2H), 2.63 (s, 3H), 1.40 (s, 12H).

Step 7: [6-(3-Benzyloxy-phenoxy)-1-hydroxy-4-methyl-1,3-dihydro-benzo[c][1,2]oxaborol-3-yl]-acetic acid ethyl ester

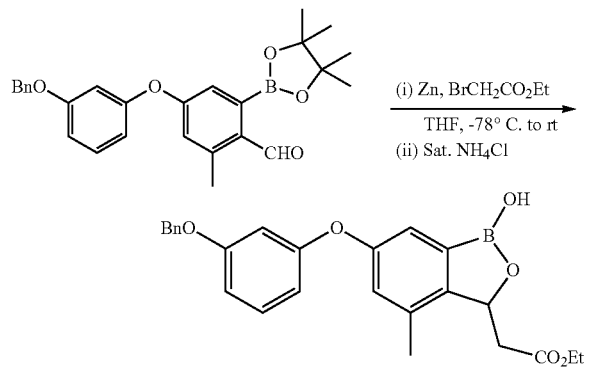

To a suspension of zinc dust (1.03 g, 15.75 mmol) in THF (15 mL) was added trimethylsilyl chloride (1.2 mL, 9.45 mmol) at 40° C. The mixture was heated to 55° C. and stirred for 15 minutes. After cooling down to 37° C., ethyl bromoacetate (1.74 mL, 15.75 mmol) was slowly added to the reaction mixture at 37-40° C. After addition, the resulting mixture was cooled to room temperature over 30 minutes. This solution was added to a solution of 4-(3-benzyloxy-phenoxy)-2-methyl-6-(4,4,5,5-tetramethyl-[1,3,2]dioxaborolan-2-yl)-benzaldehyde (1.4 g, 3.75 mmol) in THF (50 mL) at –78° C. The mixture was allowed to warm to room temperature over 3 hours, quenched with saturated NH$_4$Cl (10 mL) and extracted with EtOAc (2×25 mL). The organic extracts were washed with brine, dried and concentrated in vacuo. The residue was purified by silica gel flash column chromatography (hexane:EtOAc 50:50) to give [6-(3-benzyloxy-phenoxy)-1-hydroxy-4-methyl-1,3-dihydro-benzo[c][1,2]oxaborol-3-yl]-acetic acid ethyl ester (0.93 g, 68%). $^1$H NMR (400 MHz, DMSO): δ 9.22 (s, 1H), 7.41-7.24 (m, 6H), 7.07 (s, 1H), 6.95 (s, 1H), 6.77 (d, J=8.0 Hz, 1H), 6.61 (s, 1H), 6.51 (d, J=6.8 Hz, 1H), 5.48 (d, J=7.2 Hz, 1H), 5.05 (s, 2H), 4.02 (q, J=7.2 Hz, 2H), 3.10 (dd, J=2.4, 15.6 Hz, 1H), 2.30-2.27 (m, 1H), 2.26 (s, 3H), 1.11 (t, J=6.8 Hz, 3H). MS (ESI) m/z=433 [M+H]$^+$.

Step 8: [1-Hydroxy-6-(3-hydroxy-phenoxy)-4-methyl-1,3-dihydro-benzo[c][1,2]oxaborol-3-yl]-acetic acid ethyl ester

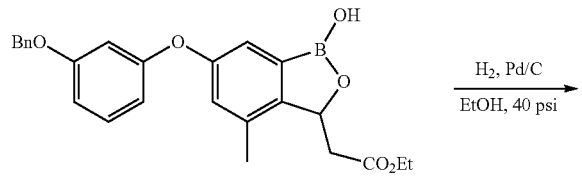

A mixture of [6-(3-benzyloxy-phenoxy)-1-hydroxy-4-methyl-1,3-dihydro-benzo[c][1,2]oxaborol-3-yl]-acetic acid ethyl ester (1.22 g, 2.82 mmol) and 10% Pd/C (1.0 g) in EtOH (20 mL) was hydrogenated at 40 psi for 30 minutes. The mixture was filtered through a pad of celite and concentrated in vacuo. The residue was purified by silica gel flash column chromatography (hexane:EtOAc 50:50) to give [1-hydroxy-6-(3-hydroxy-phenoxy)-4-methyl-1,3-dihydro-benzo[c][1,2]oxaborol-3-yl]-acetic acid ethyl ester (0.65 g, 68%). $^1$H NMR (400 MHz, DMSO): δ 7.13 (t, J=8.4 Hz, 1H), 7.06 (d, J=2.4 Hz, 1H), 6.95 (d, J=1.6 Hz, 1H), 6.50 (dd, J=1.6, 8.0 Hz, 1H), 6.38 (dd, J=1.6, 8.0 Hz, 1H), 6.32 (t, J=2.4 Hz, 1H), 5.48 (dd, J=2.4 Hz, 1H), 4.02 (q, J=7.2 Hz, 2H), 3.09 (dd, J=2.4 Hz, 1H), 2.29-2.23 (m, 1H), 2.26 (s, 3H), 1.12 (t, J=4.4 Hz, 3H). MS (ESI) m/z=341 [M–H]$^-$.

Step 9: {6-[3-(3-tert-Butoxycarbonylamino-propoxy)-phenoxy]-1-hydroxy-4-methyl-1,3-dihydro-benzo[c][1,2]oxaborol-3-yl}-acetic acid ethyl ester

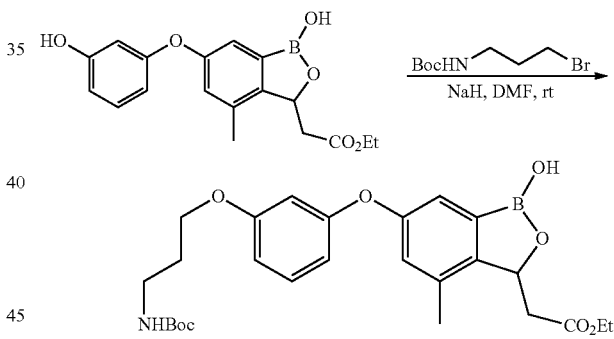

To a solution of [1-hydroxy-6-(3-hydroxy-phenoxy)-4-methyl-1,3-dihydro-benzo[c][1,2]oxaborol-3-yl]-acetic acid ethyl ester (0.53 g, 1.54 mmol) and (3-bromo-propyl)-carbamic acid tert-butyl ester (0.74 g, 3.09 mmol) in DMF (20 mL) at 0° C. was added NaH (0.22 g, 4.64 mmol). The reaction mixture was allowed to warm to room temperature and stirred for 20 hours. Saturated NH$_4$Cl (10 mL) and water (10 mL) were added and the solution acidified to pH~5 with dilute HCl. The mixture was extracted with EtOAc (2×20 mL) and the organic extracts washed with water (10 mL), dried and concentrated in vacuo. The residue was purified by silica gel flash column chromatography (DCM:MeOH 95:5) to give {6-[3-(3-tert-butoxycarbonylamino-propoxy)-phenoxy]-1-hydroxy-4-methyl-1,3-dihydro-benzo[c][1,2]oxaborol-3-yl}-acetic acid ethyl ester (0.52 g, 67%). $^1$H NMR (400 MHz, DMSO): δ 9.18 (s, 1H), 7.24 (t, J=8.0 Hz, 1H), 7.06 (s, 1H), 6.95 (d, J=6.0 Hz, 1H), 6.85 (s, 1H), 6.67 (d, J=8.4 Hz, 1H), 6.51 (d, J=6.0 Hz, 2H), 5.47 (t, J=11.6 Hz, 1H), 4.02 (q, J=7.2 Hz, 2H), 3.93 (t, J=6.0 Hz, 2H), 3.07-3.02

(m, 3H), 2.28-2.27 (m, 1H), 2.26 (s, 3H), 1.77 (t, J=6.4 Hz, 2H), 1.33 (s, 12H), 1.11 (t, J=6.8 Hz, 3H).

Step 10: {6-[3-(3-tert-Butoxycarbonylamino-propoxy)-phenoxy]-1-hydroxy-4-methyl-1,3-dihydro-benzo[c][1,2]oxaborol-3-yl}-acetic acid

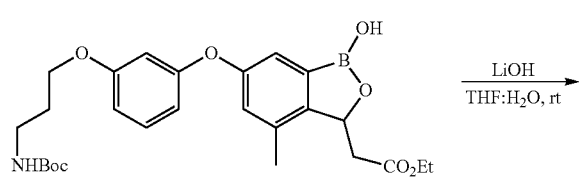

To a solution of {6-[3-(3-tert-butoxycarbonylamino-propoxy)-phenoxy]-1-hydroxy-4-methyl-1,3-dihydro-benzo[c][1,2]oxaborol-3-yl}-acetic acid ethyl ester (0.6 g, 1.2 mmol) in THF:H$_2$O (1:1, 10 mL) at 0° C. was added a solution of LiOH (0.086 g, 3.6 mmol) in water (1 mL). The solution was allowed to warm to room temperature over 3 hours then acidified to pH 2 with 1N HCl at 0° C. and extracted with EtOAc (2×10 mL). The organic extracts were dried and concentrated in vacuo to give crude 6-[3-(3-tert-butoxycarbonylamino-propoxy)-phenoxy]-1-hydroxy-4-methyl-1,3-dihydro-benzo[c][1,2]oxaborol-3-yl}-acetic acid (0.5 g) which was used without further purification MS (ESI) m/z=470 [M−H]⁻.

Step 11: {6-[3-(3-Amino-propoxy)-phenoxy]-1-hydroxy-4-methyl-1,3-dihydro-benzo[c][1,2]oxaborol-3-yl}-acetic acid

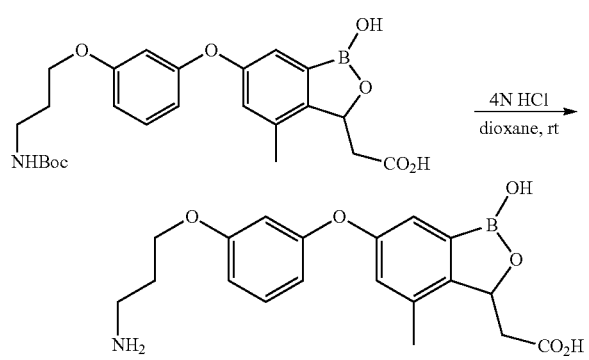

A solution of {6-[3-(3-tert-butoxycarbonylamino-propoxy)-phenoxy]-1-hydroxy-4-methyl-1,3-dihydro-benzo[c][1,2]oxaborol-3-yl}-acetic acid (0.5 g, 1.06 mmol) in 4M HCl in dioxane (5 mL) was stirred for 2 hours at room temperature. The reaction mixture was concentrated in vacuo and the residue purified by preparative HPLC to give {6-[3-(3-amino-propoxy)-phenoxy]-1-hydroxy-4-methyl-1,3-dihydro-benzo[c][1,2]oxaborol-3-yl}-acetic acid (0.18 g, 45%). ¹H NMR (400 MHz, DMSO): δ 8.36 (s, 1H), 7.24 (t, J=8.4 Hz, 1H), 6.99 (s, 1H), 6.85 (s, 1H), 6.66 (d, J=8.0 Hz, 1H), 6.51 (t, J=8.0 Hz, 2.0H), 5.37 (d, J=6.0 Hz, 1H), 3.98 (t, J=5.6 Hz, 2H), 2.85 (d, J=12.0 Hz, 2H), 2.22 (s, 3H), 2.05-1.93 (m, 4H). MS (ESI) m/z=372 [M+H]⁺.

G49: 2-(6-(2-Chloropyridin-4-yloxy)-1-hydroxy-4-methyl-1,3-dihydrobenzo[c][1,2]oxaborol-3-yl)acetic acid

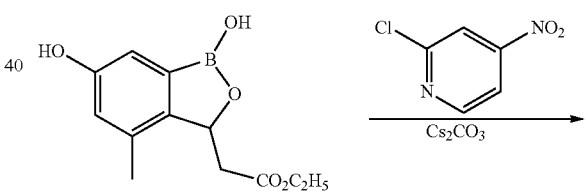

Step 1: Ethyl 2-(6-(2-chloropyridin-4-yloxy)-1-hydroxy-4-methyl-1,3-dihydrobenzo[c][1,2]oxaborol-3-yl)acetate

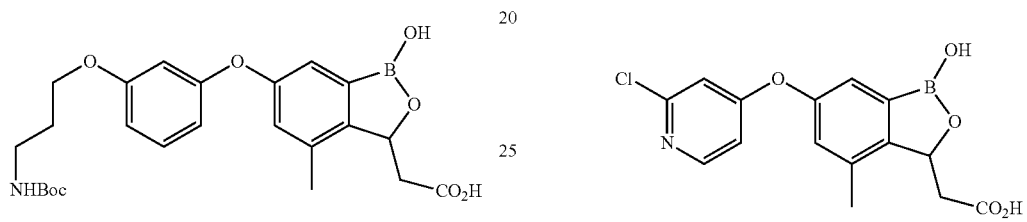

To a mixture of ethyl 2-(1,6-dihydroxy-4-methyl-1,3-dihydrobenzo[c][1,2]oxaborol-3-yl)acetate (0.1 g, 0.4 mmol, 1 eq.) and 2-chloro-4-nitropyridine (158 mg, 1 mmol, 2.5 eq.) in 5 ml DMF was added cesium carbonate (392 mg, 1.2 mmol, 3 eq.). The reaction was stirred at room temperature for three hours. It was then quenched by water, extracted with EtOAc, washed with brine, dried over Na$_2$SO$_4$, and concentrated under reduced pressure. The crude was purified by column chromatography on silica gel (DCM/methanol=39:1 to 19:1) to give desired product as light yellow oil. MS (ESI) m/z=362 [M+H]⁺.

Step 2: 2-(6-(2-Chloropyridin-4-yloxy)-1-hydroxy-4-methyl-1,3-dihydrobenzo[c][1,2]oxaborol-3-yl)acetic acid

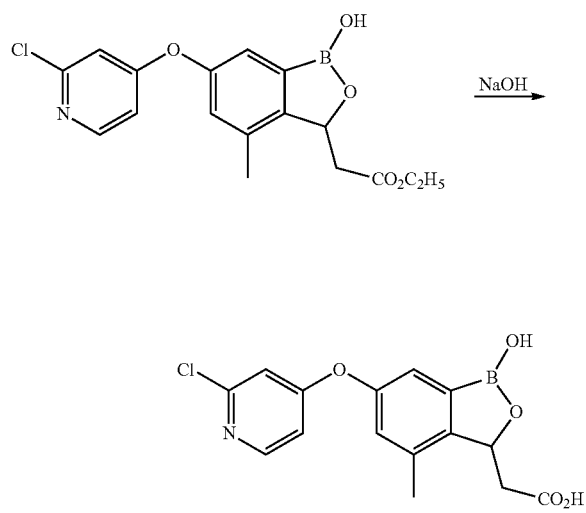

To a solution of ethyl 2-(6-(2-chloropyridin-4-yloxy)-1-hydroxy-4-methyl-1,3-dihydrobenzo[c][1,2]oxaborol-3-yl)acetate in MeOH/THF (6 mL, 1:1) was added aqueous NaOH solution (100 mg in 1.5 mL of water). After stirring at room temperature for two hours, the reaction mixture was evaporated and then acidified to pH 3 using 1 M HCl. This was then extracted with EtOAc, the organic layers were combined, washed by brine and concentrated. HPLC purification gave desired product as a white powder. ¹H NMR (400 MHz, DMSO-$d_6$) δ 9.2 (b, 1H), 8.23 (d, J=6 Hz, 1H), 7.22 (s, 1H), 7.09 (s, 1H), 6.95 (s, 1H), 6.88 (dd, J=6, 2 Hz, 1H), 5.49 (dd, J=9.2, 2.4 Hz, 1H), 3.04 (dd, J=15.6, 2.8 Hz, 1H), 2.28 (s, 3H), 2.13 (dd, J=15.2, 9.2 Hz, 1H). 1 proton assumed to be exchanged with solvents. MS (ESI) m/z=332 [M−H]⁻.

G50: 2-(6-(2-Aminopyridin-4-yloxy)-1-hydroxy-4-methyl-1,3-dihydrobenzo[c][1,2]oxaborol-3-yl)acetic acid

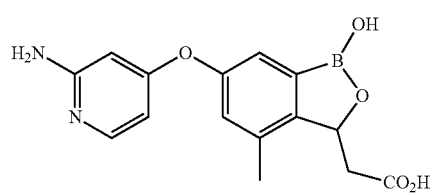 [SMILES: Cc1cc(Oc2ccnc(N)c2)cc2c1C(CC(=O)O)OB2O]

Step 1: Ethyl 2-(1-hydroxy-4-methyl-6-(2-nitropyridin-4-yloxy)-1,3-dihydrobenzo[c][1,2]oxaborol-3-yl)acetate To a mixture of ethyl 2-(1,6-dihydroxy-4-methyl-1,3-dihydrobenzo[c][1,2]oxaborol-3-yl)acetate (2 g, 8 mmol, 1 eq.) and 4-chloro-2-nitropyridine (2.53 g, 16 mmol, 2 eq.) in 50 ml of DMF was added cesium carbonate (7.8 g, 24 mmol, 3 eq.). The reaction was stirred at room temperature overnight. It was then quenched by water, extracted with EtOAc, washed with brine, dried over Na₂SO₄, and concentrated under reduced pressure. The crude was purified by column chromatography on silica gel (DCM/methanol=19:1 to 4:1) to give desired product as light yellow oil. MS (ESI) m/z=743 [2M−H]⁻.

Step 2: Ethyl 2-(6-(2-aminopyridin-4-yloxy)-1-hydroxy-4-methyl-1,3-dihydrobenzo[c][1,2]oxaborol-3-yl)acetate To a solution of ethyl 2-(1-hydroxy-4-methyl-6-(2-nitropyridin-4-yloxy)-1,3-dihydrobenzo[c][1,2]oxaborol-3-yl)acetate in 2M ammonia in ethanol was added 1 ml Raney-Nickel (slurry in water). The mixture was stirred at room

Step 3: 2-(6-(2-Aminopyridin-4-yloxy)-1-hydroxy-4-methyl-1,3-dihydrobenzo[c][1,2]oxaborol-3-yl)acetic acid

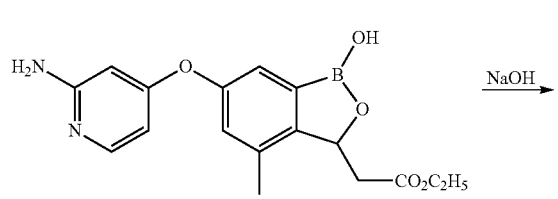

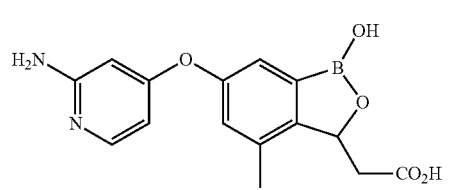

To a solution of ethyl 2-(6-(2-aminopyridin-4-yloxy)-1-hydroxy-4-methyl-1,3-dihydrobenzo[c][1,2]oxaborol-3-yl)acetate in MeOH/THF (8 mL, 1:1) was added aqueous NaOH solution (200 mg in 2 mL of water). After stirring at room temperature for two hours, the reaction mixture was evaporated, acidified to pH 5 using 1 M HCl and then concentrated. HPLC purification gave desired product as a white powder. $^1$H NMR (400 MHz, DMSO-$d_6$) δ 12.3 (b, 1H), 9.30 (b, 1H), 7.87 (d, J=7.2 Hz, 1H), 7.69 (b, 2H), 7.25 (d, J=2 Hz, 1H), 7.13 (d, J=2 Hz, 1H), 6.59 (dd, J=7.2, 2.8 Hz, 1H), 6.00 (d, J=2.4 Hz, 1H), 5.49 (dd, J=9.6, 2.4 Hz, 1H), 3.05 (dd, J=15.6, 2.4 Hz, 1H), 2.28 (s, 3H), 2.08 (dd, J=15.2, 9.6 Hz, 1H). MS (ESI) m/z=313 [M−H]$^+$.

G51: [6-(5-Amino-pyridin-2-yloxy)-1-hydroxy-4-methyl-1,3-dihydro-benzo[c][1,2]oxaborol-3-yl]-acetic acid

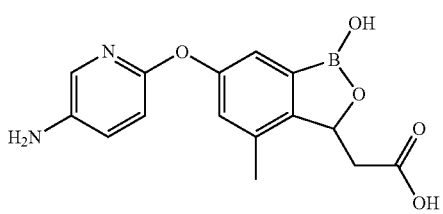 [SMILES: Cc1cc(Oc2ccc(N)cn2)cc2c1C(CC(=O)O)OB2O]

[6-(5-tert-Butoxycarbonylamino-pyridin-2-yloxy)-1-hydroxy-4-methyl-1,3-dihydro-benzo[c][1,2]oxaborol-3-yl]-acetic acid (26 mg) was treated with HCl/dioxane (0.5 mL) at room temperature for 2 h. The reaction was concentrated to dryness. The residue was purified by preparative HPLC to give the title compound (16 mg). $^1$H NMR (300 MHz, CD$_3$OD) δ 7.66 (s, 1H), 7.23 (d, J=7.8 Hz, 1H), 7.00 (s, 1H), 6.96 (s, 1H), 6.78 (d, J=7.8 Hz, 1H), 5.68-5.64 (m, 1H), 3.20-3.14 (m, 1H), 2.36 (s, 3H), 2.34-2.26 (m, 1H). MS calcd for (C$_{15}$H$_{15}$BN$_2$O$_5$+H)$^+$: 315.1. MS found: (M+H)$^+$=315.1.

G52: [1-Hydroxy-4-methyl-6-(pyridin-2-yloxy)-1,3-dihydro-benzo[c][1,2]oxaborol-3-yl]-acetic acid

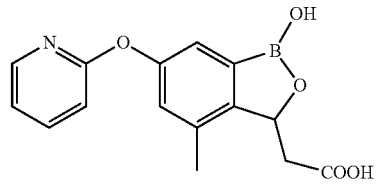 [SMILES: Cc1cc(Oc2ccccn2)cc2c1C(CC(=O)O)OB2O]

Step 1: [1-Hydroxy-4-methyl-6-(1-oxy-pyridin-2-yloxy)-1,3-dihydro-benzo[c][1,2]oxaborol-3-yl]-acetic acid ethyl ester

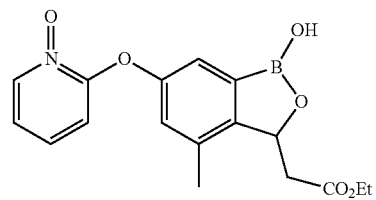 [SMILES: CCOC(=O)CC1OB(O)c2cc(Oc3cccc[n+]3[O-])cc(C)c21]

To a solution of (1,6-dihydroxy-4-methyl-1,3-dihydro-benzo[c][1,2]oxaborol-3-yl)-acetic acid ethyl ester (500 mg, 2 mmol), Cs$_2$CO$_3$ (3.26 g, 10 mmol) and 2-chloro-N-oxide-pyridine (500 mg, 3 mmol) in DMF (5 mL) was heated at 80° C. for 3 h. The reaction mixture was cooled down and acidified to pH 3 with 6N HCl, extracted with ethyl acetate and washed with water and brine. The organic layer was dried over Na$_2$SO$_4$ and concentrated. The residue was purified by column chromatography (silica, Hexanes/EA=8:2, then DCM/MeOH=9:1) affording the title compound (250 mg, 36%) as a light yellow solid. $^1$H NMR (CDCl$_3$) δ 8.39 (m, 1H), 7.58 (s, 1H), 7.28 (m, 1H), 7.01 (m, 1H), 6.90 (s, 1H), 6.81 (m, 1H), 5.58 (dd, 1H), 4.15 (q, 2H), 3.00 (dd, 1H), 2.31 (m, 1H), 2.25 (s, 3H), 1.22 (t, 3H).

Step 2: [1-Hydroxy-4-methyl-6-(pyridin-2-yloxy)-1,3-dihydro-benzo[c][1,2]oxaborol-3-yl]-acetic acid ethyl ester

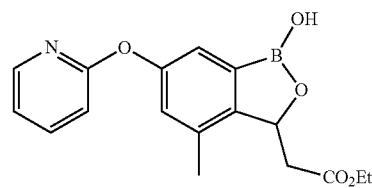 [SMILES: CCOC(=O)CC1OB(O)c2cc(Oc3ccccn3)cc(C)c21]

[1-hydroxy-4-methyl-6-(1-oxy-pyridin-2-yloxy)-1,3-dihydro-benzo[c][1,2]oxaborol-3-yl]-acetic acid ethyl ester (100 mg, 0.73 mmol) was treated with 2M PCl$_3$ in DCM (0.44 mL) and stirred at 40° C. for 30 min. The reaction mixture was concentrated under vacuum and purified by HPLC affording the title compound (75 mg, 79%) as a yellow solid. MS found: (M+H)⁺=328.15.

Step 3: [1-Hydroxy-4-methyl-6-(pyridin-2-yloxy)-1,3-dihydro-benzo[c][1,2]oxaborol-3-yl]-acetic acid

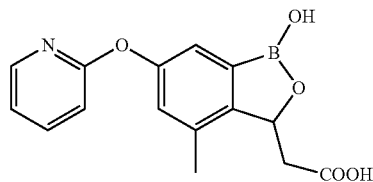 [SMILES: Cc1cc(Oc2ccccn2)cc2c1C(CC(=O)O)OB2O]

To a solution of [1-hydroxy-4-methyl-6-(pyridin-2-yloxy)-1,3-dihydro-benzo[c][1,2]oxaborol-3-yl]-acetic acid ethyl ester (75 mg, 0.23 mmol) in THF (4 mL) was added LiOH (20 mg, 0.48 mmol) in water (2 mL). The mixture was stirred at room temperature for 5 h and acidified by 1N HCl to pH 3. The mixture was concentrated and purified by HPLC affording the title compound (52 mg, 75%) as a white solid. ¹H NMR (DMSO) δ 9.26 (m, 1H), 8.19 (s, 1H), 7.89 (m, 1H), 7.24 (s, 1H), 7.17 (m, 1H), 7.08 (m, 1H), 7.05 (m, 1H), 5.55 (d, 1H), 3.13 (d, 1H), 2.31 (s, 3H), 2.13 (m, 1H). MS found: (M+H)⁺=300.10.

G53: [6-(4-Amino-pyridin-2-yloxy)-1-hydroxy-4-methyl-1,3-dihydro-benzo[c][1,2]oxaborol-3-yl]-acetic acid

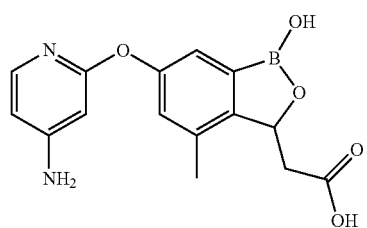 [SMILES: Cc1cc(Oc2cc(N)ccn2)cc2c1C(CC(=O)O)OB2O]

Step 1: [6-(4-Amino-pyridin-2-yloxy)-1-hydroxy-4-methyl-1,3-dihydro-benzo[c][1,2]oxaborol-3-yl]-acetic acid ethyl ester

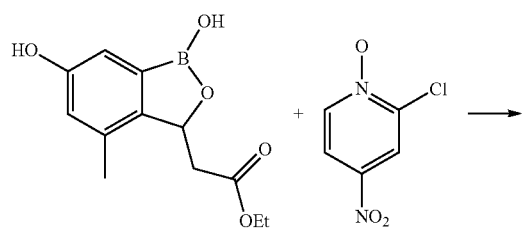

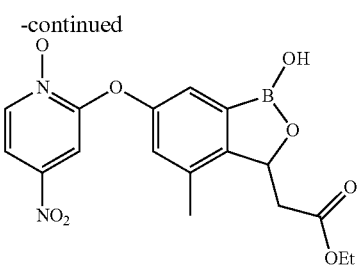

(1,6-dihydroxy-4-methyl-1,3-dihydro-benzo[c][1,2]oxaborol-3-yl)-acetic acid ethyl ester (2 g, 8 mmol), 2-chloro-4-nitro-pyridine oxide (2.2 g, 12 mmol) and Cs₂CO₃ (5.7 g, 18 mmol) were mixed in DMF (50 mL) and stirred at room temperature for 1 h. Water was added and the reaction mixture was adjusted to pH 3. The reaction mixture was extracted with ethyl acetate. The organic layers were concentrated to give a residue. The residue was purified by flash column chromatography (dichloromethane:methanol=15:1) to give the title compound (0.77 g, 29%) as a brown solid. MS found (electrospray): (M+H)⁺=389.1.

Step 2: [1-Oxy-4-methyl-6-(4-nitro-pyridin-2-yloxy)-1,3-dihydro-benzo[c][1,2]oxaborol-3-yl]-acetic acid ethyl ester

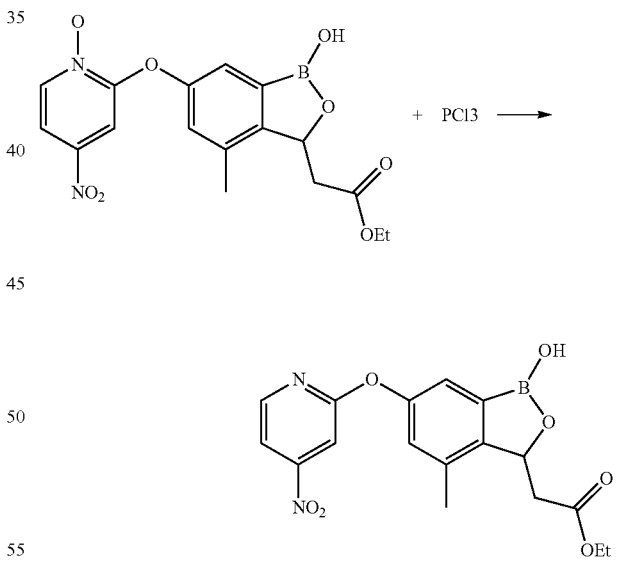

[6-(4-Amino-pyridin-2-yloxy)-1-hydroxy-4-methyl-1,3-dihydro-benzo[c][1,2]oxaborol-3-yl]-acetic acid ethyl ester (0.26 g, 0.68 mmol) was dissolved in dichloromethane (5.3 mL). To this was added PCl₃ (0.38 mL, 0.76 mmol). The reaction was refluxed for 30 min. The reaction mixture was diluted with dichloromethane, extracted with saturate NaHCO₃ and brine. The organic phases were combined and concentrated. The residue was purified by flash column chromatography (ethyl acetate:hexane=3:7 to 2:3) to give the title compound (0.14 g, 60%) as a white solid. MS found (electrospray): (M+H)+=373.1.

Step 3: [6-(4-Amino-pyridin-2-yloxy)-1-hydroxy-4-methyl-1,3-dihydro-benzo[c][1,2]oxaborol-3-yl]-acetic acid ethyl ester

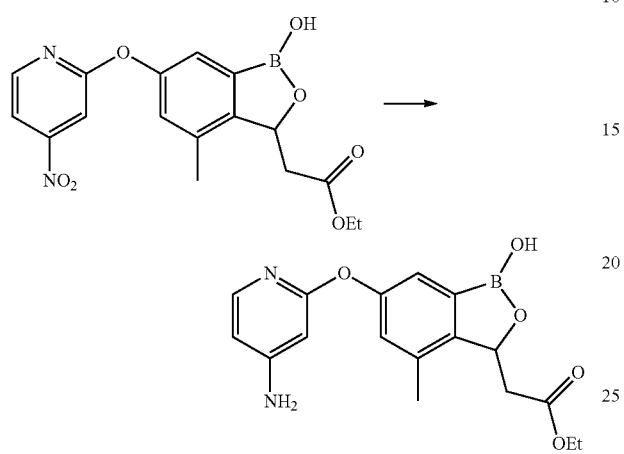

To a solution of [1-oxy-4-methyl-6-(4-nitro-pyridin-2-yloxy)-1,3-dihydro-benzo[c][1,2]oxaborol-3-yl]-acetic acid ethyl ester (0.14 g, 0.37 mmol) in methanol (5.7 mL), was added palladium on carbon (10%, 22 mg) and 3 drops of concentrated aqueous HCl solution. The reaction mixture was stirred under a $H_2$ balloon at room temperature overnight. The solvent was removed to give the title compound (0.13 g, quant.) as a white solid. MS found (electrospray): (M+H)+=343.1.

Step 4: [6-(4-Amino-pyridin-2-yloxy)-1-hydroxy-4-methyl-1,3-dihydro-benzo[c][1,2]oxaborol-3-yl]-acetic acid

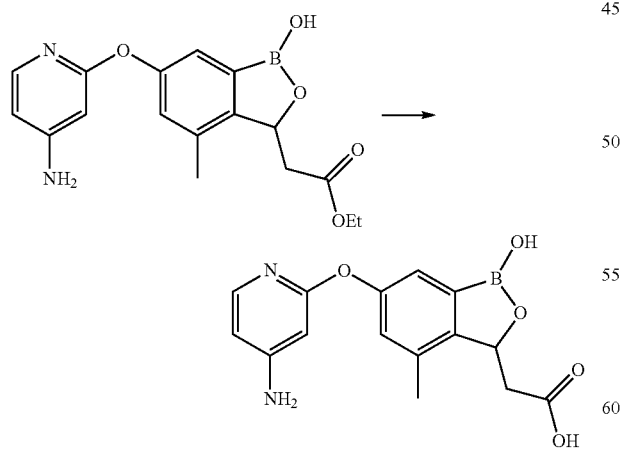

To a solution of [6-(4-amino-pyridin-2-yloxy)-1-hydroxy-4-methyl-1,3-dihydro-benzo[c][1,2]oxaborol-3-yl]-acetic acid ethyl ester (0.13 g, 0.37 mmol in THF (5 mL) and methanol (2 mL) was added lithium hydroxide monohydrate (62 mg, 1.48 mmol) in water (2 mL) at 0° C. The temperature was allowed to warm up to room temperature. The reaction mixture was stirred at room temperature for 4 h. The pH was adjusted to 3 with aqueous HCl (6 N). Prep-HPLC purification (C18 column) gave the title compound (66 mg, 55%) as a white solid. $^1$H NMR (300 MHz, $CD_3OD$) δ 7.68 (1H, d), 7.16 (1H, d), 7.05 (1H, d), 6.44 (1H, dd), 5.88 (1H, s), 5.62 (1H, dd), 3.14 (1H, dd), 2.36 (3H, s), 2.30 (1H, m). MS found (electrospray): (M+H)+=315.1.

G54: 2-(6-(6-Chloropyridin-2-yloxy)-1-hydroxy-4-methyl-1,3-dihydrobenzo[c][1,2]oxaborol-3-yl)acetic acid

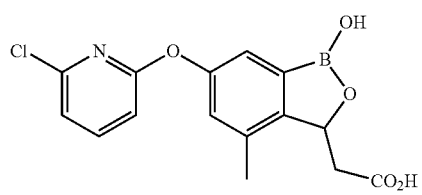 [SMILES: Cc1cc(Oc2cccc(Cl)n2)cc2c1C(CC(=O)O)OB2O]

Step 1: Ethyl 2-(6-(6-chloropyridin-2-yloxy)-1-hydroxy-4-methyl-1,3-dihydrobenzo[c][1,2]oxaborol-3-yl)acetate

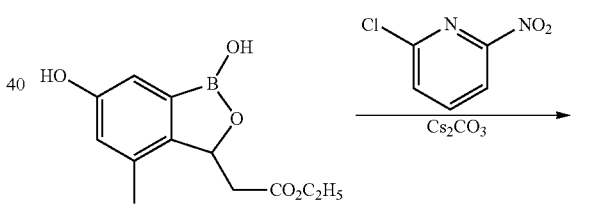

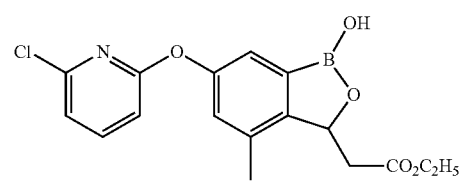

To a mixture of ethyl 2-(1,6-dihydroxy-4-methyl-1,3-dihydrobenzo[c][1,2]oxaborol-3-yl)acetate (0.1 g, 0.4 mmol, 1 eq.) and 2-chloro-6-nitropyridine (158 mg, 1 mmol, 2.5 eq.) in 5 ml DMF was added cesium carbonate (392 mg, 1.2 mmol, 3 eq.). The reaction was stirred at room temperature for three hours. It was then quenched by water, extracted with EtOAc, washed with brine, dried over $Na_2SO_4$, and concentrated under reduced pressure. The crude was purified by column chromatography on silica gel (DCM/methanol=39:1 to 19:1) to give desired product as light yellow oil. MS (ESI) m/z=362 [M+H]⁺.

Step 2: 2-(6-(6-Chloropyridin-2-yloxy)-1-hydroxy-4-methyl-1,3-dihydrobenzo[c][1,2]oxaborol-3-yl)acetic acid

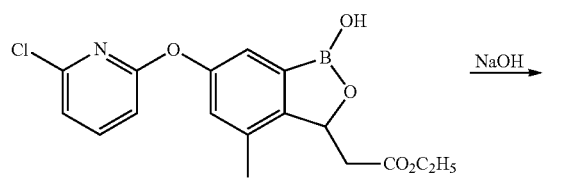

To a solution of ethyl 2-(6-(6-chloropyridin-2-yloxy)-1-hydroxy-4-methyl-1,3-dihydrobenzo[c][1,2]oxaborol-3-yl)acetate in MeOH/THF (6 mL, 1:1) was added aqueous NaOH solution (100 mg in 1.5 mL of water). After stirring at room temperature for two hours, the reaction mixture was evaporated and then acidified to pH 3 using 1 M HCl. This was then extracted with EtOAc, the organic layers were combined, washed by brine and concentrated. HPLC purification gave desired product as a white powder. $^1$H NMR (400 MHz, DMSO-$d_6$) δ 9.2 (b, 1H), 7.90 (t, J=7.6 Hz, 1H), 7.24 (m, 2H), 7.09 (s, 1H), 7.00 (d, J=8.4 Hz, 1H), 5.54 (dd, J=9.6, 2 Hz, 1H), 3.10 (dd, J=15.6, 2.4 Hz, 1H), 2.32 (s, 3H), 2.17 (dd, J=15.6, 9.6 Hz, 1H). 1 proton assumed to be exchanged with solvents. MS (ESI) m/z=332 [M−H]⁺.

G55: 2-(6-(4-Chloropyridin-2-yloxy)-1-hydroxy-4-methyl-1,3-dihydrobenzo[c][1,2]oxaborol-3-yl)acetic acid

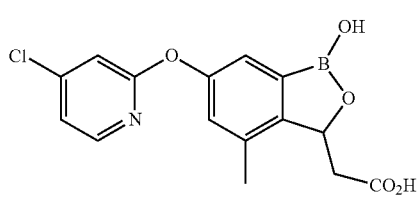 [SMILES: Cc1cc(Oc2cc(Cl)ccn2)cc2c1C(CC(=O)O)OB2O]

Step 1: Ethyl 2-(6-(4-chloropyridin-2-yloxy)-1-hydroxy-4-methyl-1,3-dihydrobenzo[c][1,2]oxaborol-3-yl)acetate

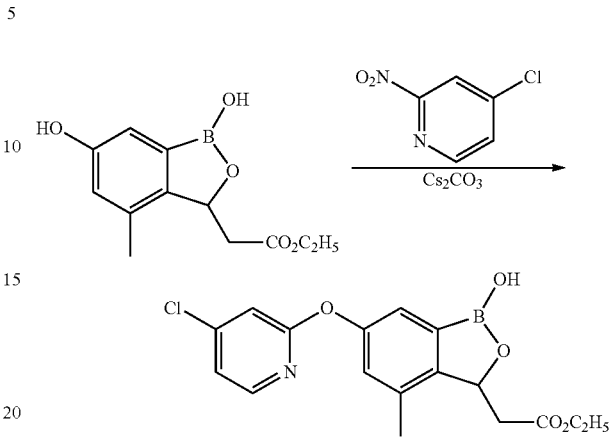

To a mixture of ethyl 2-(1,6-dihydroxy-4-methyl-1,3-dihydrobenzo[c][1,2]oxaborol-3-yl)acetate (2 g, 8 mmol, 1 eq.) and 4-chloro-2-nitropyridine (2.53 g, 16 mmol, 2 eq.) in 50 ml DMF was added cesium carbonate (7.8 g, 24 mmol, 3 eq.). The reaction was stirred at room temperature overnight. It was then quenched by water, extracted with EtOAc, washed with brine, dried over $Na_2SO_4$, and concentrated under reduced pressure. The crude was purified by column chromatography on silica gel (DCM/methanol=19:1 to 4:1) to give desired product as light yellow oil. MS (ESI) m/z=721 [2M−H]⁺.

Step 2: 2-(6-(4-Chloropyridin-2-yloxy)-1-hydroxy-4-methyl-1,3-dihydrobenzo[c][1,2]oxaborol-3-yl)acetic acid

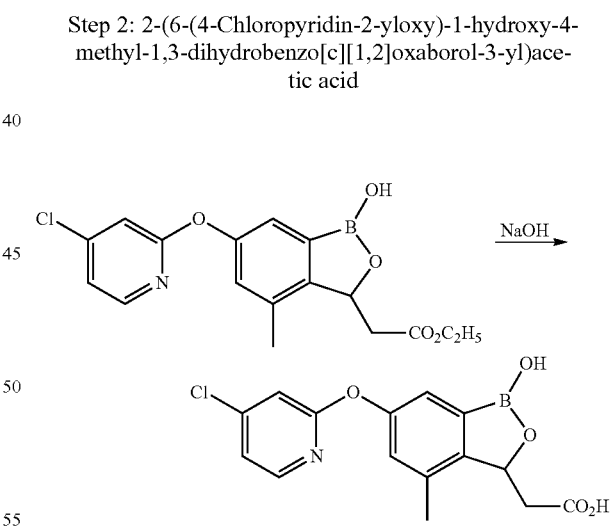

To a solution of ethyl 2-(6-(4-chloropyridin-2-yloxy)-1-hydroxy-4-methyl-1,3-dihydrobenzo[c][1,2]oxaborol-3-yl)acetate in MeOH/THF (8 mL, 1:1) was added aqueous NaOH (200 mg in 2 mL of water). After stirring at room temperature for two hours, the reaction mixture was evaporated and acidified to PH 5 using 1 M HCl and then concentrated. HPLC purification gave desired product as a white powder. $^1$H NMR (400 MHz, DMSO-$d_6$) δ 9.20 (b, 1H), 8.11 (d, J=5.2 Hz, 1H), 7.24 (dd, J=5.6, 2 Hz, 1H), 7.21 (d, m, 2H), 7.05 (d, J=1.6 Hz, 1H), 5.50 (dd, J=9.6, 2.4 Hz, 1H), 3.07 (dd, J=15.6, 2.8 Hz, 1H), 2.28 (s, 3H), 2.12 (dd, J=15.6, 9.6 Hz, 1H). 1 protons assumed to be exchanged with solvents. MS (ESI) m/z=334 [M+H]⁺.

G56: 2-(6-(5-(Aminomethyl)pyridin-2-yloxy)-1-hydroxy-4-methyl-1,3-dihydrobenzo[c][1,2]oxaborol-3-yl)acetic acid

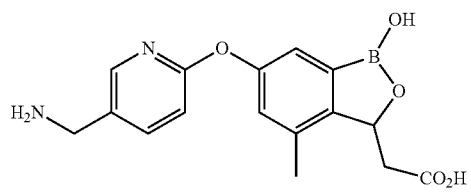 [SMILES: Cc1cc(Oc2ccc(CN)cn2)cc2c1C(CC(=O)O)OB2O]

Step 1: Ethyl 2-(6-(5-cyano-pyridin-2-yloxy)-1-hydroxy-4-methyl-1,3-dihydrobenzo[c][1,2]oxaborol-3-yl)acetate

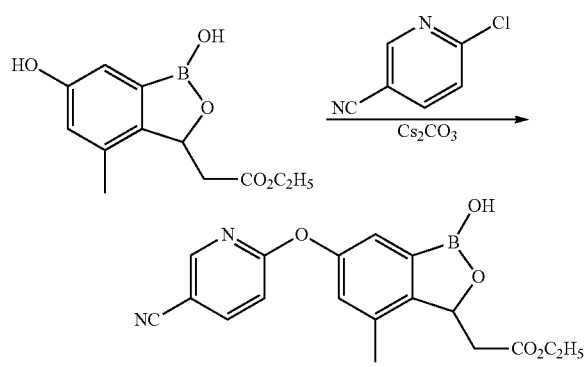

To a mixture of ethyl 2-(1,6-dihydroxy-4-methyl-1,3-dihydrobenzo[c][1,2]oxaborol-3-yl)acetate (2 g, 8 mmol, 1 eq.) and 6-chloronicotinonitrile (2.78 g, 20 mmol, 2.5 eq.) in 50 ml DMF was added cesium carbonate (7.82 mg, 24 mmol, 3 eq.). The reaction was stirred at room temperature overnight. The starting material was gone but no right mass was observed. The reaction was then quenched by water, extracted with EtOAc, washed with brine, dried over Na₂SO₄, and concentrated under reduced pressure. The crude was purified by column chromatography on silica gel (DCM/methanol=39:1 to 19:1) to give colorless oil (2.52 g, yield 89%).

Step 2: Ethyl 2-(6-(5-(aminomethyl)pyridin-2-yloxy)-1-hydroxy-4-methyl-1,3-dihydrobenzo[c][1,2]oxaborol-3-yl)acetate

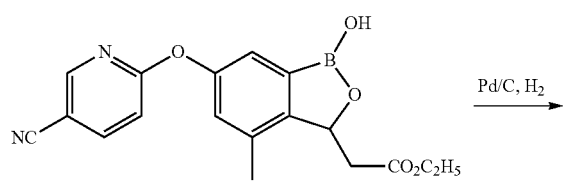

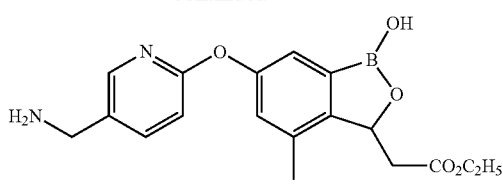

A solution of ethyl 2-(6-(5-cyanopyridin-2-yloxy)-1-hydroxy-4-methyl-1,3-dihydrobenzo[c][1,2]oxaborol-3-yl)acetate (2.5 g, 7.1 mmol) in methanol with couple drops of concentrated HCl was treated with palladium (10% yield wet on charcoal, 530 mg), then hydrogenation with hydrogen balloon overnight. The mixture was filtered through a Celite pad and rinsed with ethyl acetate. The filtrate was concentrated then purified by column chromatography on silica gel (DCM/methanol=19:1 to 9:1) to give product as a white crystal (1.18 g). MS (ESI) m/z=357 [M+H]⁺.

Step 3: 2-(6-(5-(Aminomethyl)pyridin-2-yloxy)-1-hydroxy-4-methyl-1,3-dihydrobenzo[c][1,2]oxaborol-3-yl)acetic acid

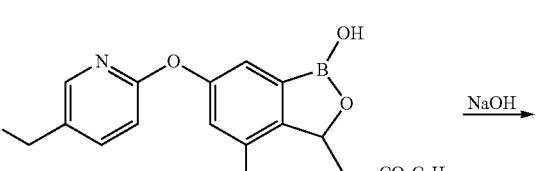

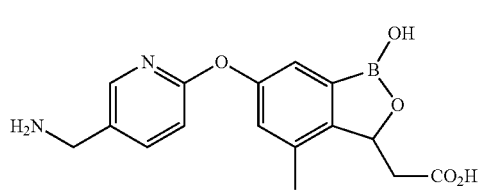

To a solution of ethyl 2-(6-(5-(aminomethyl)pyridin-2-yloxy)-1-hydroxy-4-methyl-1,3-dihydrobenzo[c][1,2]oxaborol-3-yl)acetate (1.18 g, 3.31 mmol) in MeOH/THF (12 mL, 1:1) was added aqueous NaOH solution (250 mg in 3 mL water). After stirring at room temperature for two hours, the reaction mixture was evaporated and then acidified to pH 3 using 1 M HCl. The precipitate was collected and washed with water and dried to give the product as a white solid (0.85 g, yield 78%). No right mass was observed and the structure was confirmed by NMR. ¹H NMR (400 MHz, DMSO-d₆) δ 12.4 (b, 1H), 9.80 (b, 2H), 9.22 (s, 1H), 8.26 (d, J=2 Hz, 1H), 8.07 (m, 1H), 7.21 (d, J=2 Hz, 1H), 7.08 (d, J=8.4 Hz, 1H), 7.01 (m, 1H), 5.51 (dd, J=9.2, 4 Hz, 1H), 4.15 (s, 2H), 3.07 (dd, J=15.6, 2.4 Hz, 1H), 2.28 (s, 3H), 2.12 (dd, J=15.2, 9.6 Hz, 1H).

G57: 2-(6-(5-Carbamoylpyridin-2-yloxy)-1-hydroxy-4-methyl-1,3-dihydrobenzo[c][1,2]oxaborol-3-yl)acetic acid]

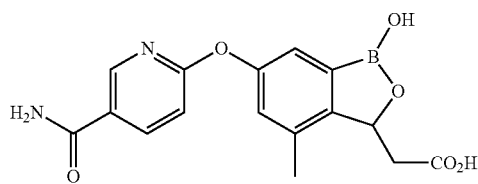 [SMILES: Cc1cc(Oc2ccc(C(N)=O)cn2)cc2c1C(CC(=O)O)OB2O]

Step 1: Ethyl 2-(6-(5-cyanopyridin-2-yloxy)-1-hydroxy-4-methyl-1,3-dihydrobenzo[c][1,2]oxaborol-3-yl)acetate

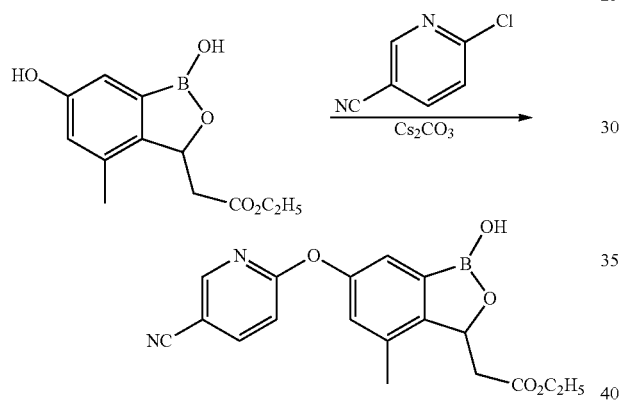

To a mixture of ethyl 2-(1,6-dihydroxy-4-methyl-1,3-dihydrobenzo[c][1,2]oxaborol-3-yl)acetate (2 g, 8 mmol, 1 eq.) and 6-chloronicotinonitrile (2.78 g, 20 mmol, 2.5 eq.) in 50 ml DMF was added cesium carbonate (7.82 g, 24 mmol, 3 eq.). The reaction was stirred at room temperature overnight. The starting material was gone but no right mass was observed. The reaction was then quenched by water, extracted with EtOAc, washed with brine, dried over $Na_2SO_4$, and concentrated under reduced pressure. The crude was purified by column chromatography on silica gel (DCM/methanol=39:1 to 19:1) to give colorless oil (2.52 g, yield 89%).

Step 2: 2-(6-(5-Carbamoylpyridin-2-yloxy)-1-hydroxy-4-methyl-1,3-dihydrobenzo[c][1,2]oxaborol-3-yl)acetic acid

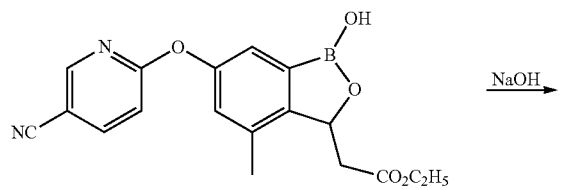

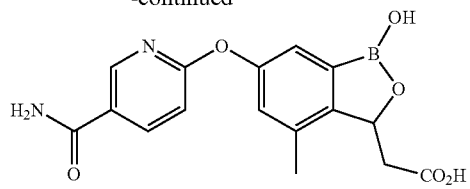

To a solution of ethyl 2-(6-(5-cyanopyridin-2-yloxy)-1-hydroxy-4-methyl-1,3-dihydrobenzo[c][1,2]oxaborol-3-yl)acetate in MeOH/THF (12 mL, 1:1) was added aqueous NaOH solution (250 mg in 3 mL water). After stirring at room temperature for two hours, the reaction mixture was evaporated, acidified to pH 3 with 1 N HCl and then concentrated. HPLC purification gave product as a white powder. $^1$H NMR (400 MHz, DMSO-$d_6$) δ 8.55 (d, J=2 Hz, 1H), 8.20 (dd, J=8.4, 2.4 Hz, 1H), 7.96 (s, 1H), 7.41 (s, 1H), 7.17 (d, J=1.6 Hz, 1H), 7.02 (d, J=8.4 Hz, 1H), 5.46 (dd, J=9.6, 2.4 Hz, 1H), 3.02 (dd, J=15.6, 2.4 Hz, 1H), 2.24 (s, 3H), 2.09 (dd, J=15.2, 9.6 Hz, 1H). 3 protons assumed to be exchanged with solvents. MS (ESI) m/z=341 [M−H]$^+$.

G58: 2-(6-(5-Cyanopyridin-2-yloxy)-1-hydroxy-4-methyl-1,3-dihydrobenzo[c][1,2]oxaborol-3-yl)acetic acid

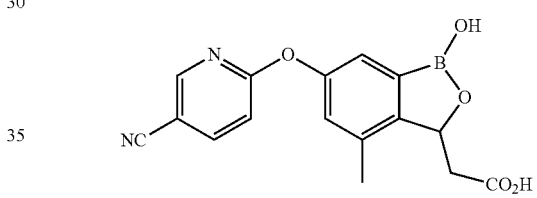

Step 1: Ethyl 2-(6-(5-cyanopyridin-2-yloxy)-1-hydroxy-4-methyl-1,3-dihydrobenzo[c][1,2]oxaborol-3-yl)acetate

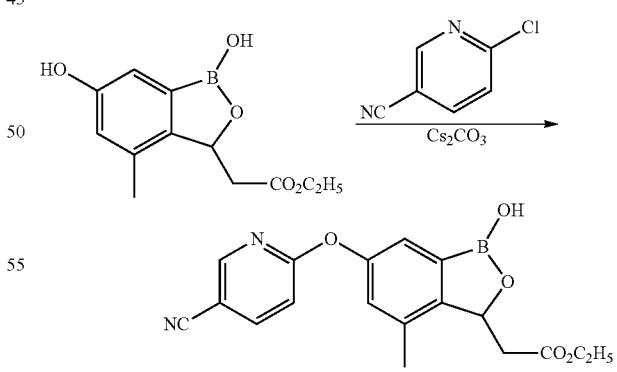

To a mixture of ethyl 2-(1,6-dihydroxy-4-methyl-1,3-dihydrobenzo[c][1,2]oxaborol-3-yl)acetate (2 g, 8 mmol, 1 eq.) and 6-chloronicotinonitrile (2.78 g, 20 mmol, 2.5 eq.) in 50 ml DMF was added cesium carbonate (7.82 g, 24 mmol, 3 eq.). The reaction was stirred at room temperature overnight. The starting material was gone but no right mass was observed. The reaction was then quenched by water, extracted with EtOAc, washed with brine, dried over Na₂SO₄, and concentrated under reduced pressure. The crude was purified by column chromatography on silica gel (DCM/methanol=39:1 to 19:1) to give colorless oil (2.52 g, yield 89%).

Step 2: 2-(6-(5-Cyanopyridin-2-yloxy)-1-hydroxy-4-methyl-1,3-dihydrobenzo[c][1,2]oxaborol-3-yl)acetic acid

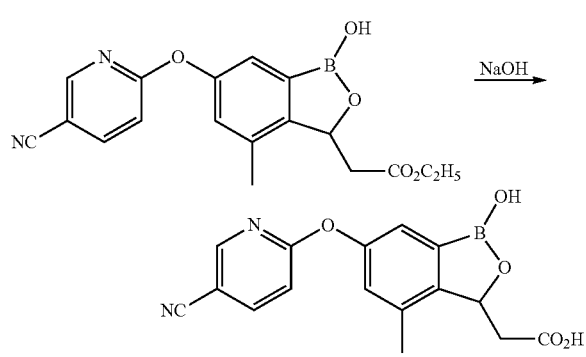

To a solution of ethyl 2-(6-(5-cyanopyridin-2-yloxy)-1-hydroxy-4-methyl-1,3-dihydrobenzo[c][1,2]oxaborol-3-yl)acetate in MeOH/THF (12 mL, 1:1) was added aqueous NaOH solution (250 mg in 3 mL water). After stirring at room temperature for two hours, the reaction mixture was evaporated, acidified to pH 3 with 1 N HCl and then concentrated. HPLC purification gave product as a white powder. ¹H NMR (400 MHz, DMSO-d₆) δ 8.58 (s, 1H), 8.25 (dd, J=8.8, 2.4 Hz, 1H), 7.19 (m, 2H), 7.04 (s, 1H), 5.47 (dd, J=9.6, 2.4 Hz, 1H), 3.03 (dd, J=15.6, 2.4 Hz, 1H), 2.24 (s, 3H), 2.12 (dd, J=15.6, 9.6 Hz, 1H). 2 protons assumed to be exchanged with solvents. MS (ESI) m/z=323 [M−H]⁺.

G59: 2-(6-(4-Cyanopyridin-2-yloxy)-1-hydroxy-4-methyl-1,3-dihydrobenzo[c][1,2]oxaborol-3-yl)acetic acid

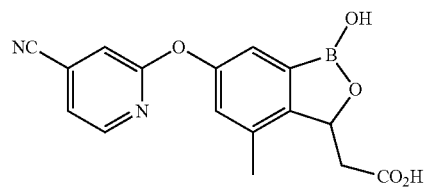 [SMILES: Cc1cc(Oc2cc(C#N)ccn2)cc2c1C(CC(=O)O)OB2O]

Step 1: Ethyl 2-(6-(4-cyanopyridin-2-yloxy)-1-hydroxy-4-methyl-1,3-dihydrobenzo[c][1,2]oxaborol-3-yl)acetate

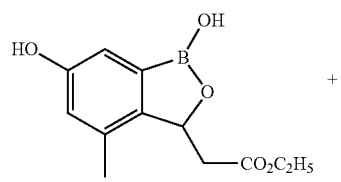

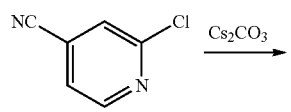

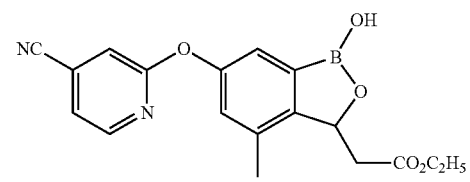

To a mixture of ethyl 2-(1,6-dihydroxy-4-methyl-1,3-dihydrobenzo[c][1,2]oxaborol-3-yl)acetate (2 g, 8 mmol, 1 eq.) and 2-chloroisonicotinonitrile (2.78 g, 20 mmol, 2.5 eq.) in 50 ml DMF was added cesium carbonate (7.82 g, 24 mmol, 3 eq.). The reaction was stirred at room temperature overnight. The starting material was gone but no right mass was observed. The reaction was then quenched by water, extracted with EtOAc, washed with brine, dried over Na₂SO₄, and concentrated under reduced pressure. The crude was purified by column chromatography on silica gel (DCM/methanol=39:1 to 19:1) to give desired product as yellow oil (1.57 g, yield 56%). MS (ESI) m/z=353 [M+H]⁺.

Step 2: 2-(6-(4-Cyanopyridin-2-yloxy)-1-hydroxy-4-methyl-1,3-dihydrobenzo[c][1,2]oxaborol-3-yl)acetic acid

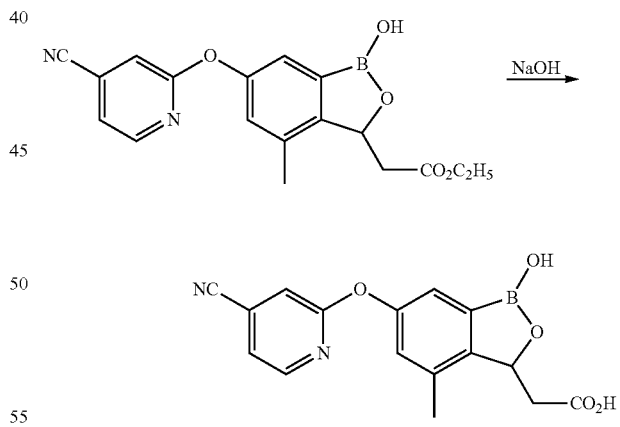

To a solution of ethyl 2-(6-(4-cyanopyridin-2-yloxy)-1-hydroxy-4-methyl-1,3-dihydrobenzo[c][1,2]oxaborol-3-yl)acetate (1.18 g, 3.31 mmol) in MeOH/THF (12 mL, 1:1) was added aqueous NaOH solution (250 mg in 3 mL of water). After stirring at room temperature for two hours, the reaction mixture was evaporated and then acidified to pH 5 using 1 N HCl and then concentrated. HPLC purification gave desired product as a white powder. ¹H NMR (400 MHz, DMSO-d₆) δ 12.2 (b, 1H), 9.24 (b, 1H), 8.30 (d, J=5.2 Hz, 1H), 7.57 (s, 1H), 7.50 (dd, J=5.2, 1.2 Hz, 1H), 7.17 (d, J=2 Hz, 1H), 7.01

(d, J=1.6 Hz, 1H), 5.45 (dd, J=9.6, 2 Hz, 1H), 3.02 (dd, J=15.6, 2.4 Hz, 1H), 2.46 (s, 3H), 2.08 (dd, J=16, 10 Hz, 1H). MS (ESI) m/z=323 [M−H]+.

G60: 2-(3-(Carboxymethyl)-1-hydroxy-4-methyl-1,3-dihydrobenzo[c][1,2]oxaborol-6-yloxy)isonicotinic acid

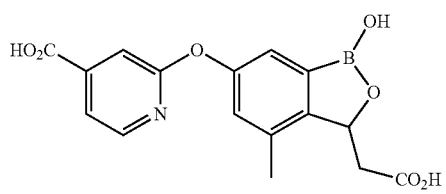 [SMILES: Cc1cc(Oc2cc(C(=O)O)ccn2)cc2c1C(CC(=O)O)OB2O]

Step 1: Ethyl 2-(6-(4-cyanopyridin-2-yloxy)-1-hydroxy-4-methyl-1,3-dihydrobenzo[c][1,2]oxaborol-3-yl)acetate

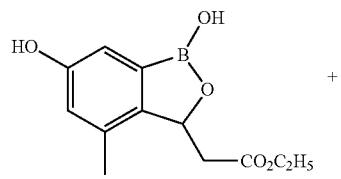

To a mixture of ethyl 2-(1,6-dihydroxy-4-methyl-1,3-dihydrobenzo[c][1,2]oxaborol-3-yl)acetate (2 g, 8 mmol, 1 eq.) and 2-chloroisonicotinonitrile (2.78 g, 20 mmol, 2.5 eq.) in 50 ml DMF was added cesium carbonate (7.82 g, 24 mmol, 3 eq.). The reaction was stirred at room temperature overnight. The starting material was gone but no right mass was observed. The reaction was then quenched by water, extracted with EtOAc, washed with brine, dried over Na₂SO₄, and concentrated under reduced pressure. The crude was purified by column chromatography on silica gel (DCM/methanol=39:1 to 19:1) to give desired product as yellow oil (1.57 g, yield 56%). MS (ESI) m/z=353 [M+H]+.

Step 2: 2-(3-(Carboxymethyl)-1-hydroxy-4-methyl-1,3-dihydrobenzo[c][1,2]oxaborol-6-yloxy)isonicotinic acid

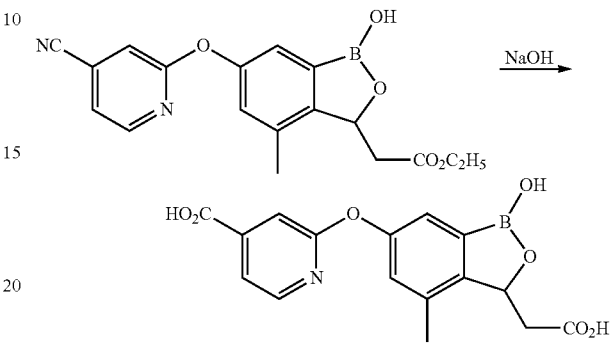

To a solution of ethyl 2-(6-(4-cyanopyridin-2-yloxy)-1-hydroxy-4-methyl-1,3-dihydrobenzo[c][1,2]oxaborol-3-yl)acetate (1.18 g, 3.31 mmol) in MeOH/THF (12 mL, 1:1) was added aqueous NaOH solution (250 mg in 3 mL water). After stirring at room temperature for two hours, the reaction mixture was evaporated and then acidified to pH 5 using 1 N HCl and then concentrated. HPLC purification gave desired product as a white powder. $^1$H NMR (400 MHz, DMSO-d₆) δ 9.20 (b 1H), 8.26 (d, J=5.2 Hz 1H), 7.47 (dd, J=5.2, 1.2 Hz, 1H), 7.29 (s, 1H), 7.17 (s, 1H), 7.02 (s, 1H), 5.46 (dd, J=9.6, 2.4 Hz, 1H), 3.03 (dd, J=16, 2.8 Hz, 1H), 2.24 (s, 3H), 2.08 (dd, J=15.2, 9.6 Hz, 1H). 2 protons assumed to be exchanged with solvents. MS (ESI) m/z=344 [M+H]+.

G61: 2-(6-(4-Carbamoylpyridin-2-yloxy)-1-hydroxy-4-methyl-1,3-dihydrobenzo[c][1,2]oxaborol-3-yl)acetic acid

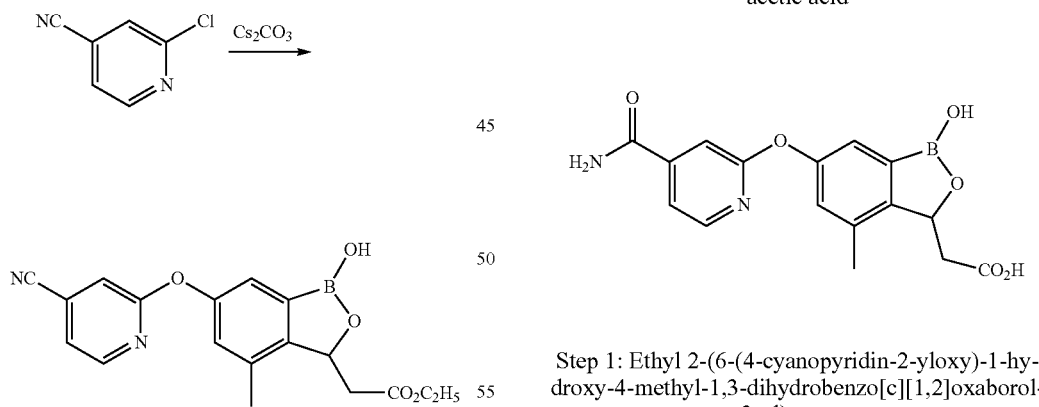

Step 1: Ethyl 2-(6-(4-cyanopyridin-2-yloxy)-1-hydroxy-4-methyl-1,3-dihydrobenzo[c][1,2]oxaborol-3-yl)acetate

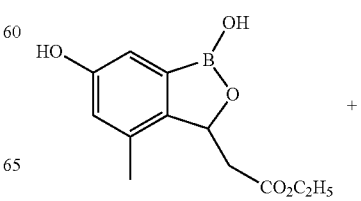

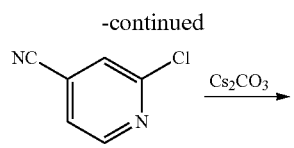

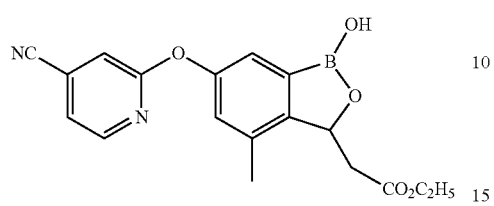

To a mixture of ethyl 2-(1,6-dihydroxy-4-methyl-1,3-dihydrobenzo[c][1,2]oxaborol-3-yl)acetate (2 g, 8 mmol, 1 eq.) and 2-chloroisonicotinonitrile (2.78 g, 20 mmol, 2.5 eq.) in 50 ml DMF was added cesium carbonate (7.82 g, 24 mmol, 3 eq.). The reaction was stirred at room temperature overnight. The starting material was gone but no right mass was observed. The reaction was then quenched by water, extracted with EtOAc, washed with brine, dried over $Na_2SO_4$, and concentrated under reduced pressure. The crude was purified by column chromatography on silica gel (DCM/methanol=39:1 to 19:1) to give desired product as yellow oil (1.57 g, yield 56%). MS (ESI) m/z=353 [M+H]$^+$.

Step 2: 2-(6-(4-Carbamoylpyridin-2-yloxy)-1-hydroxy-4-methyl-1,3-dihydrobenzo[c][1,2]oxaborol-3-yl)acetic acid

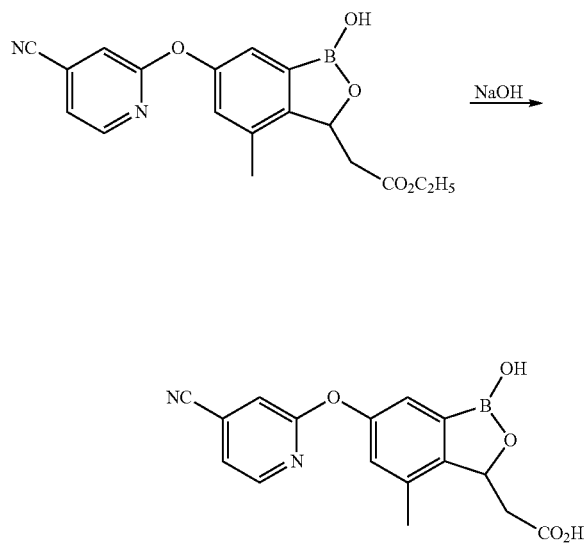

To a solution of ethyl 2-(6-(4-cyanopyridin-2-yloxy)-1-hydroxy-4-methyl-1,3-dihydrobenzo[c][1,2]oxaborol-3-yl)acetate (1.18 g, 3.31 mmol) in MeOH/THF (12 mL, 1:1) was added aqueous NaOH solution (250 mg in 3 mL water). After stirring at room temperature for two hours, the reaction mixture was evaporated and then acidified to pH 5 using 1 N HCl and then concentrated. HPLC purification gave desired product as a white powder. $^1$H NMR (400 MHz, DMSO-$d_6$) δ 12.4 (b, 1H), 9.20 (b, 1H), 8.20 (m, 2H), 7.70 (s, 1H), 7.44 (dd, J=5.6, 1.6 Hz, 1H), 7.33 (s, 1H), 7.15 (d, J=2 Hz, 1H), 7.00 (d, J=2 Hz, 1H), 5.46 (dd, J=9.6, 2.4 Hz, 1H), 3.03 (dd, J=15.6, 2.8 Hz, 1H), 2.44 (s, 3H), 2.08 (dd, J=15.6, 9.6 Hz, 1H). MS (ESI) m/z=343 [M+H]$^+$.

G62: 2-(1-Hydroxy-6-(4-(N-hydroxycarbamimidoyl) pyridin-2-yloxy)-4-methyl-1,3-dihydrobenzo[c][1,2] oxaborol-3-yl)acetic acid

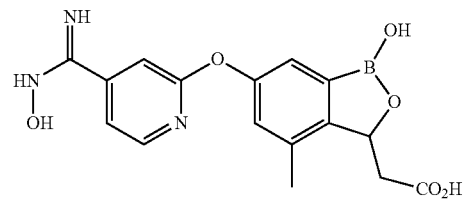 [SMILES: Cc1cc(Oc2cc(C(=N)NO)ccn2)cc2c1C(CC(=O)O)OB2O]

Step 1: Ethyl 2-(6-(4-cyanopyridin-2-yloxy)-1-hydroxy-4-methyl-1,3-dihydrobenzo[c][1,2]oxaborol-3-yl)acetate

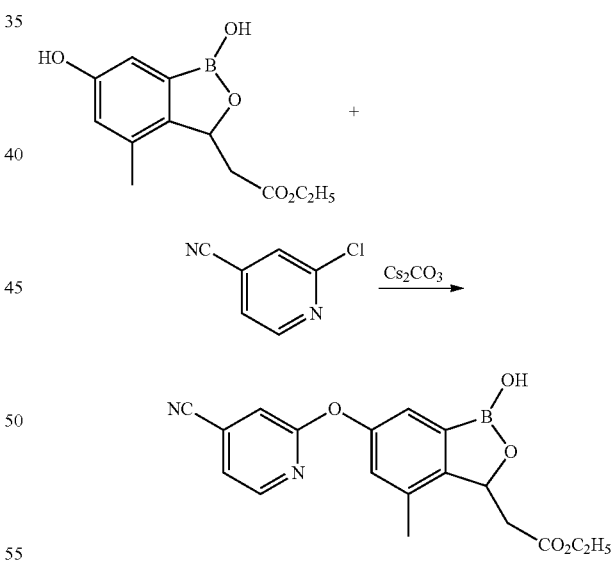

To a mixture of ethyl 2-(1,6-dihydroxy-4-methyl-1,3-dihydrobenzo[c][1,2]oxaborol-3-yl)acetate (2 g, 8 mmol, 1 eq.) and 2-chloroisonicotinonitrile (2.78 g, 20 mmol, 2.5 eq.) in 50 ml DMF was added cesium carbonate (7.82 g, 24 mmol, 3 eq.). The reaction was stirred at room temperature overnight. The starting material was gone but no right mass was observed. The reaction was then quenched by water, extracted with EtOAc, washed with brine, dried over $Na_2SO_4$, and concentrated under reduced pressure. The crude was purified by column chromatography on silica gel (DCM/methanol=39:1 to 19:1) to give desired product as yellow oil (1.57 g, yield 56%). MS (ESI) m/z=353 [M+H]+.

Step 2: 2-(Ethyl 2-(1-hydroxy-6-(4-(N-hydroxycarbamimidoyl)pyridin-2-yloxy)-4-methyl-1,3-dihydrobenzo[c][1,2]oxaborol-3-yl)acetate

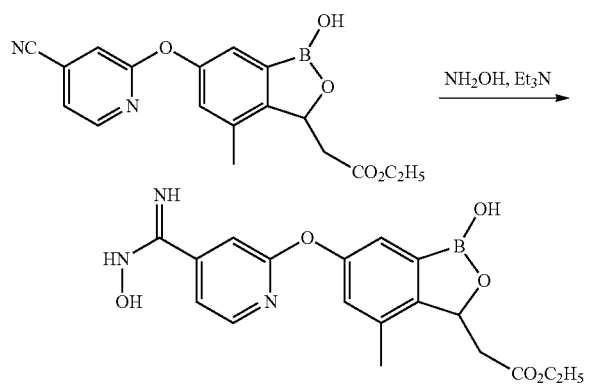

To a solution of ethyl 2-(6-(4-cyanopyridin-2-yloxy)-1-hydroxy-4-methyl-1,3-dihydrobenzo[c][1,2]oxaborol-3-yl) acetate (0.8 g, 2.27 mmol, 1 eq.) and hydroxylamine hydrochloride (0.4 g, 5.68 mmol, 2.5 eq.) in methanl was added triethylamine (1.11 ml, 7.95 mmol, 3.5 eq.). After stirring at room temperature overnight, the starting material was gone but no right mass was observed. The reaction mixture was evaporated under reduced pressure. The residue was dissolved in EtOAc and then washed with water. The organic layers were collected, dried with $Na_2SO_4$ and evaporated to give the crude product as a colorless oil (0.83 g, yield 95%). The crude was used in subsequent steps without further purification.

Step 3: 2-(1-Hydroxy-6-(4-(N-hydroxycarbamimidoyl)pyridin-2-yloxy)-4-methyl-1,3-dihydrobenzo[c][1,2]oxaborol-3-yl)acetic acid

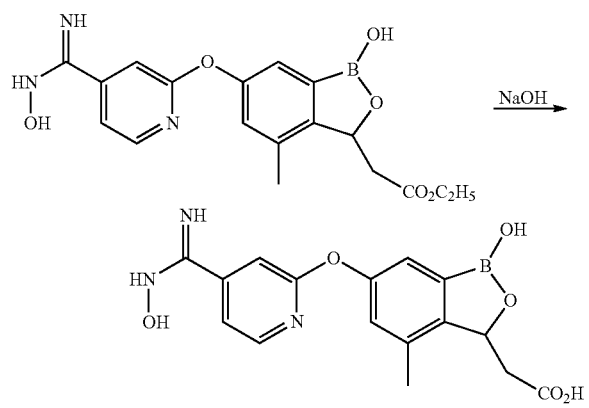

2-(ethyl 2-(1-hydroxy-6-(4-(N-hydroxycarbamimidoyl) pyridin-2-yloxy)-4-methyl-1,3-dihydrobenzo[c][1,2]oxaborol-3-yl)acetate (150 mg) was treated with NaOH solution (200 mg in 10 ml water) for one hour at room temperature. The reaction mixture was acidified to pH 5 with 6 N HCl and then concentrated. HPLC purification gave product as a white solid. $^1$H NMR (400 MHz, DMSO-$d_6$) δ 10.5 (b, 1H), 9.20 (b, 1H), 8.23 (d, J=5.2 Hz, 1H), 7.04 (dd, J=5.2, 1.2 Hz, 1H), 7.34 (s, 1H), 7.23 (s, 1H), 7.06 (d, J=1.6 Hz, 1H), 5.53 (dd, J=9.6, 2.4 Hz, 1H), 3.10 (dd, J=15.6, 2.4 Hz, 1H), 2.50 (s, 3H), 2.28 (dd, J=10, 9.6 Hz, 1H). 3 protons assumed to be exchanged with solvents. MS (ESI) m/z=358 [M+H]+.

G63: 2-(6-(4-(Aminomethyl)pyridin-2-yloxy)-1-hydroxy-4-methyl-1,3-dihydrobenzo[c][1,2]oxaborol-3-yl)acetic acid

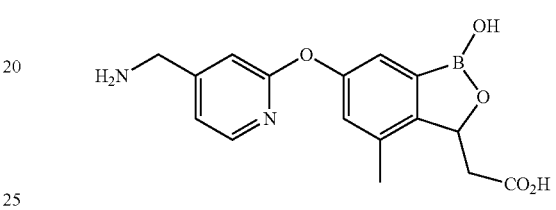

Step 1: Ethyl 2-(6-(4-cyanopyridin-2-yloxy)-1-hydroxy-4-methyl-1,3-dihydrobenzo[c][1,2]oxaborol-3-yl)acetate

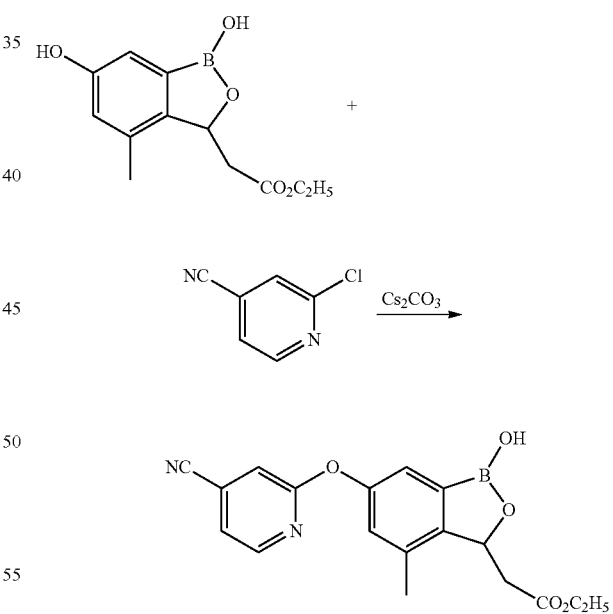

To a mixture of ethyl 2-(1,6-dihydroxy-4-methyl-1,3-dihydrobenzo[c][1,2]oxaborol-3-yl)acetate (2 g, 8 mmol, 1 eq.) and 2-chloroisonicotinonitrile (2.78 g, 20 mmol, 2.5 eq.) in 50 ml DMF was added cesium carbonate (7.82 g, 24 mmol, 3 eq.). The reaction was stirred at room temperature overnight, The reaction was then quenched by water, extracted with EtOAc, washed with brine, dried over $Na_2SO_4$, and concentrated under reduced pressure. The crude was purified by column chromatography on silica gel (DCM/methanol=39:1 to 19:1) to give desired product as yellow oil (1.57 g, yield 56%). MS (ESI) m/z=353 [M+H]+.

Step 2: Ethyl 2-(6-(4-(aminomethyl)pyridin-2-yloxy)-1-hydroxy-4-methyl-1,3-dihydrobenzo[c][1,2]oxaborol-3-yl)acetate

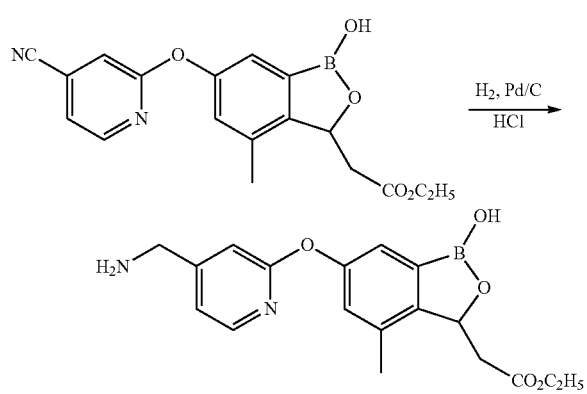

A solution of ethyl 2-(6-(4-cyanopyridin-2-yloxy)-1-hydroxy-4-methyl-1,3-dihydrobenzo[c][1,2]oxaborol-3-yl)acetate (518 mg, 1.47 mmol) in methanol with couple drops of concentrated HCl was treated with palladium (10% yield wet on charcoal, 130 mg), then hydrogenation with hydrogen balloon overnight. The mixture was filtered through a Celite pad and rinsed with ethyl acetate. The filtrate was concentrated and used in subsequent steps without further purification. MS (ESI) m/z=357 [M+H]+.

Step 3: 2-(6-(4-(Aminomethyl)pyridin-2-yloxy)-1-hydroxy-4-methyl-1,3-dihydrobenzo[c][1,2]oxaborol-3-yl)acetic acid

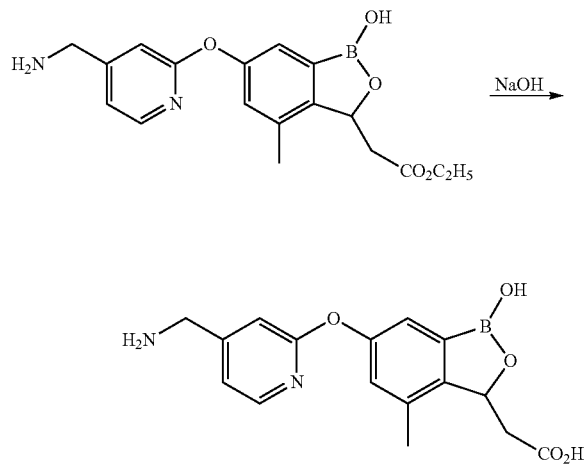

To a solution of crude ethyl 2-(6-(4-(aminomethyl)pyridin-2-yloxy)-1-hydroxy-4-methyl-1,3-dihydrobenzo[c][1,2]oxaborol-3-yl)acetate in MeOH/THF (12 mL, 1:1) was added aqueous NaOH solution (250 mg in 3 mL water). After stirring at room temperature for two hours, the reaction mixture was evaporated, acidified to pH 3 with 1N HCl and then concentrated. HPLC purification gave desired product as a white powder. $^1$H NMR (400 MHz, DMSO-$d_6$) δ 12.4 (b, 1H), 9.20 (b, 1H), 8.33 (b, 2H), 8.18 (d, J=5.2 Hz, 1H), 7.17 (m, 2H), 7.11 (s, 1H), 7.00 (d, J=1.6 Hz, 1H), 5.50 (dd, J=10, 2.8 Hz, 1H), 4.10 (d, J=5.2 Hz, 2H), 3.07 (dd, J=15.2, 2.4 Hz, 1H), 2.29 (s, 3H), 2.12 (dd, J=15.6, 9.6 Hz, 1H). MS (ESI) m/z=329 [M+H]+.

G64: 2-(6-(4-Carbamimidoylpyridin-2-yloxy)-1-hydroxy-4-methyl-1,3-dihydrobenzo[c][1,2]oxaborol-3-yl)acetic acid

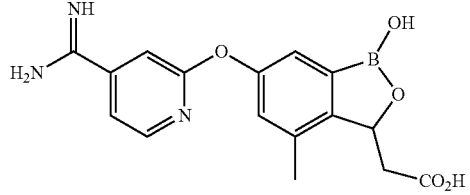 [SMILES: Cc1cc(Oc2cc(C(=N)N)ccn2)cc2c1C(CC(=O)O)OB2O]

Step 1: Ethyl 2-(6-(4-cyanopyridin-2-yloxy)-1-hydroxy-4-methyl-1,3-dihydrobenzo[c][1,2]oxaborol-3-yl)acetate

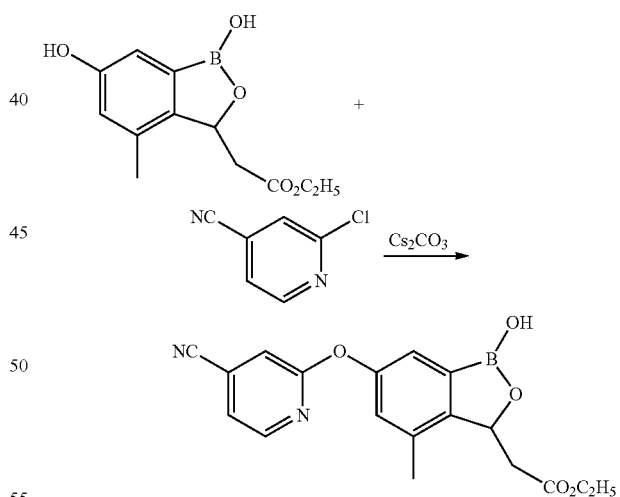

To a mixture of ethyl 2-(1,6-dihydroxy-4-methyl-1,3-dihydrobenzo[c][1,2]oxaborol-3-yl)acetate (2 g, 8 mmol, 1 eq.) and 2-chloroisonicotinonitrile (2.78 g, 20 mmol, 2.5 eq.) in 50 ml DMF was added cesium carbonate (7.82 g, 24 mmol, 3 eq.). The reaction was stirred at room temperature overnight. The starting material was gone but no right mass was observed. The reaction was then quenched by water, extracted with EtOAc, washed with brine, dried over Na$_2$SO$_4$, and concentrated under reduced pressure. The crude was purified by column chromatography on silica gel (DCM/methanol=39:1 to 19:1) to give desired product as yellow oil (1.57 g, yield 56%). MS (ESI) m/z=353 [M+H]⁺.

Step 2: 2-(Ethyl 2-(1-hydroxy-6-(4-(N-hydroxycarbamimidoyl)pyridin-2-yloxy)-4-methyl-1,3-dihydrobenzo[c][1,2]oxaborol-3-yl)acetate

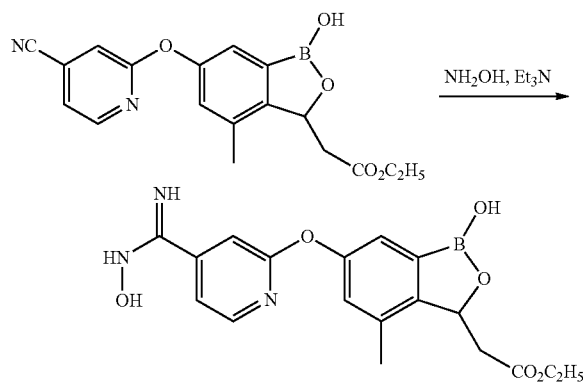

To a solution of ethyl 2-(6-(4-cyanopyridin-2-yloxy)-1-hydroxy-4-methyl-1,3-dihydrobenzo[c][1,2]oxaborol-3-yl) acetate (0.8 g, 2.27 mmol, 1 eq.) and hydroxylamine hydrochloride (0.4 g, 5.68 mmol, 2.5 eq.) in methanl was added triethylamine (1.11 ml, 7.95 mmol, 3.5 eq.). After stirring at room temperature overnight, the starting material was gone but no right mass was observed. The reaction mixture was evaporated under reduced pressure. The residue was dissolved in EtOAc and then washed with water. The organic layers were collected, dried with $Na_2SO_4$ and evaporated to give the crude product as a colorless oil (0.83 g, yield 95%). The crude was used in subsequent steps without further purification.

Step 3: Ethyl 2-(6-(4-carbamimidoylpyridin-2-yloxy)-1-hydroxy-4-methyl-1,3-dihydrobenzo[c][1,2]oxaborol-3-yl)acetate

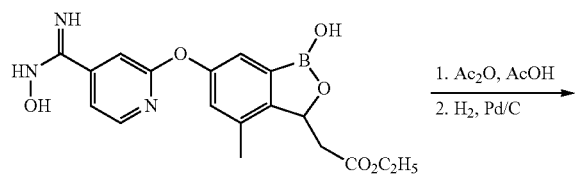

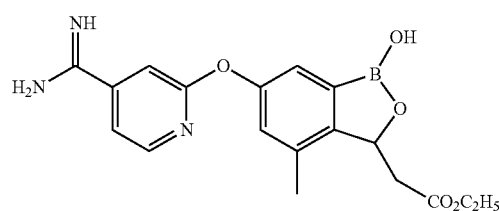

To a solution of 2-(ethyl 2-(1-hydroxy-6-(4-(N-hydroxycarbamimidoyl)pyridin-2-yloxy)-4-methyl-1,3-dihydrobenzo[c][1,2]oxaborol-3-yl)acetate (0.65 g) in 15 ml of acetic acid was added 130 ul of acetic anhydride. After the mixture was stirred at room temperature for one and half hour, it was treated with palladium (10% yield wet on charcoal, 200 mg) and then hydrogenation with hydrogen balloon overnight. The mixture was filtered through a Celite pad and the filtrate was concentrated and dried under hi-Vac to give crude product. MS (ESI) m/z=370 [M+H]⁺.

Step 4: 2-(6-(4-carbamimidoylpyridin-2-yloxy)-1-hydroxy-4-methyl-1,3-dihydrobenzo[c][1,2]oxaborol-3-yl)acetic acid

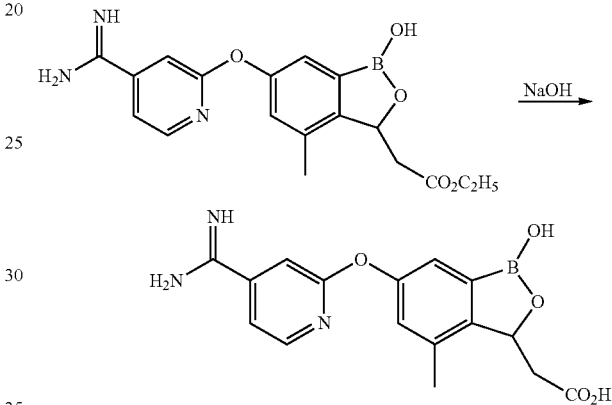

The crude ethyl 2-(6-(4-carbamimidoylpyridin-2-yloxy)-1-hydroxy-4-methyl-1,3-dihydrobenzo[c][1,2]oxaborol-3-yl)acetate was treated with aqueous NaOH solution (500 mg in 20 mL water). After stirring at room temperature for two hours, the reaction mixture was evaporated, acidified with 1N HCl to pH 3 and then concentrated. HPLC purification gave desired product as white solid. ¹H NMR (400 MHz, DMSO-d₆) δ 12.4 (b, 1H), 9.54 (m, 3H), 9.20 (b, 1H), 8.38 (d, J=4.8 Hz, 1H), 7.45 (m, 2H), 7.22 (d, J=4.8 Hz, 1H), 7.05 (d, J=2 Hz, 1H), 5.52 (dd, J=9.6, 2.4 Hz, 1H), 3.09 (dd, J=15.6, 2.4 Hz, 1H), 2.30 (s, 3H), 2.13 (dd, J=15.6, 9.6 Hz, 1H). MS (ESI) m/z=42 [M+H]⁺.

G65: [6-(4-Amino-1-oxy-pyridin-2-yloxy)-1-hydroxy-4-methyl-1,3-dihydro-benzo[c][1,2]oxaborol-3-yl]-acetic acid

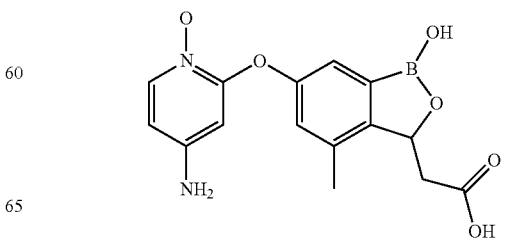

Step 1: [6-(4-Amino-1-oxy-pyridin-2-yloxy)-1-hydroxy-4-methyl-1,3-dihydro-benzo[c][1,2]oxaborol-3-yl]-acetic acid ethyl ester

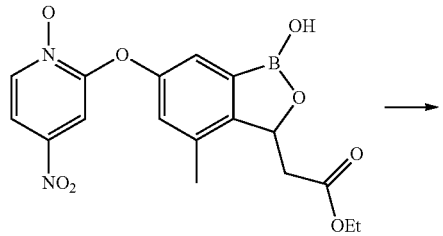

[6-(4-Amino-pyridin-2-yloxy)-1-hydroxy-4-methyl-1,3-dihydro-benzo[c][1,2]oxaborol-3-yl]-acetic acid ethyl ester (255 mg, 0.66 mmol) was dissolved in methanol (10 mL). To this was added palladium on carbon (10%, 38 mg) and 6 drops of concentrated HCl aqueous solution. The reaction mixture was stirred under a $H_2$ balloon overnight. The solvent was removed to give the title compound (235 mg, quant). MS found (electrospray): $(M+H)^+=359.1$.

Step 2: [6-(4-Amino-1-oxy-pyridin-2-yloxy)-1-hydroxy-4-methyl-1,3-dihydro-benzo[c][1,2]oxaborol-3-yl]-acetic acid

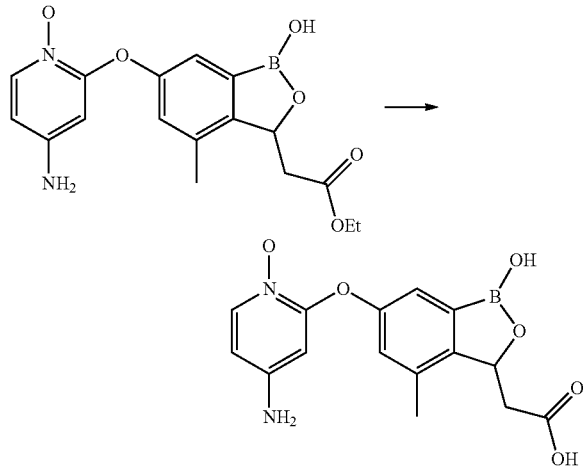

[6-(4-Amino-1-oxy-pyridin-2-yloxy)-1-hydroxy-4-methyl-1,3-dihydro-benzo[c][1,2]oxaborol-3-yl]-acetic acid ethyl ester (235 mg, 0.66 mmol) was dissolved in THF (9 mL) and methanol (3.6 mL). To this was added lithium hydroxide monohydrate (111 mg, 2.64 mmol) in water (3.6 mL) at 0° C. The reaction was allowed to warm up to room temperature and stirred for overnight. The majority of the solvent was removed under reduced pressure. The pH was adjusted to pH 3 with aqueous HCl (6 N). Prep-HPLC purification (C18 column) gave the title compound (66 mg, 55%) as a white solid. $^1$H NMR (300 MHz, $D_2O$) δ 7.62 (1H, d), 6.82 (1H, d), 6.64 (1H, d), 6.30 (1H, dd), 5.84 (1H, s), 5.15 (1H, dd), 2.62 (1H, dd), 2.08 (3H, s), 2.05 (1H, m). MS found (electrospray): $(M+H)^+=331.1$.

G66: 1-Oxy-6-(1-hydroxy-pyridin-2-yloxy)-4-methyl-1,3-dihydro-benzo[c][1,2]oxaborol-3-yl]-acetic acid

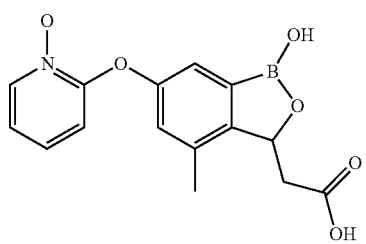

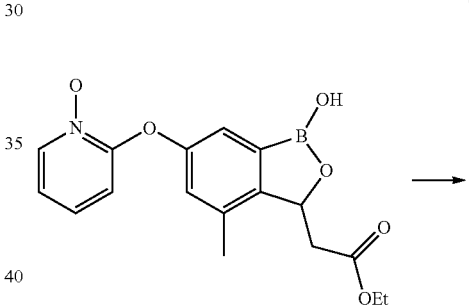

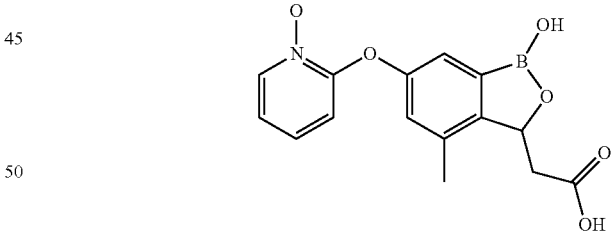

[1-Hydroxy-4-methyl-6-(1-oxy-pyridin-2-yloxy)-1,3-dihydro-benzo[c][1,2]oxaborol-3-yl]-acetic acid ethyl ester (20 mg, 0.06 mmol) was dissolved in THF (0.78 mL). To this was added lithium hydroxide monohydrate (10 mg, 0.23 mmol) in water (0.32 mL) at 0° C. The reaction was allowed to warm up to room temperature and stirred for overnight. The majority of the solvent was removed under reduced pressure. The pH was adjusted to pH 3 with aqueous HCl (6 N). Prep-HPLC purification (C18 column) gave the title compound (17 mg, 93%) as a white solid. $^1$H NMR (300 MHz, $CD_3OD$) δ 8.42 (1H, d), 7.58 (2H, t), 7.30 (2H, t), 7.20 (1H, s), 7.16 (1H, s), 7.05 (1H, d), 5.65 (1H, dd), 3.18 (1H, dd), 2.40 (3H, s), 2.35 (1H, m). MS found (electrospray): (M+H)$^+$=315.1.

G67: [1-Hydroxy-4-methyl-6-(pyrimidin-2-yloxy)-1,3-dihydro-benzo[c][1,2]oxaborol-3-yl]-acetic acid

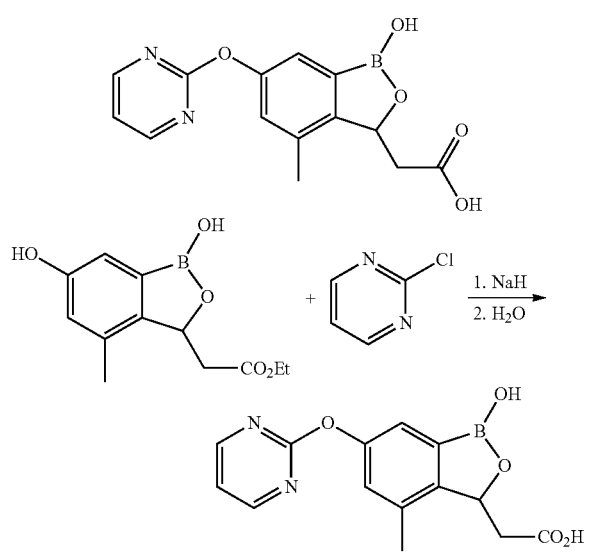

To a solution of (1,6-dihydroxy-4-methyl-1,3-dihydro-benzo[c][1,2]oxaborol-3-yl)-acetic acid ethyl ester (0.5 g, 2.0 mmol) in anhydrous DMF (10 mL) were added NaH (0.240 g, 6.0 mmol, 60% in mineral oil) and 2-chloro-pyrimidine (0.275 g, 2.4 mmol) at 0° C. After stirring at room temperature for 16 hours, the reaction mixture was cooled to 0° C., diluted with water (20 mL) and acidified to pH 2 with dilute hydrochloric acid. The mixture was extracted with ethyl acetate and the organic extract washed with brine, dried over sodium sulfate and concentrated in vacuo. The residue was dissolved in MeOH (10 mL) and aqueous LiOH (1N, 5 mL) was added at 0° C. After stirring at room temperature for 1 hour, the mixture was acidified to pH 3 using dilute hydrochloric acid and concentrated. The residue was purified by silica gel flash column chromatography (DCM/MeOH/AcOH=10:1:trace) to give the product (0.132 g, 22.0%). mp 118-120° C. $^1$HNMR (400 MHz, DMSO-d$_6$) δ 9.22 (s, 1H), 8.65 (d, J=4.68 Hz, 2H), 7.22-7.45 (m, 2H), 7.11 (s, 1H), 5.53 (dd, J=9.51, 1.90 Hz, 1H), 3.10 (dd, J=15.66, 2.49 Hz, 1H), 2.31 (s, 3H), 2.15 (dd, J=15.52, 9.66 Hz, 1H). MS (ESI) m/z=301 [M+H]$^+$.

G68: [4-Ethyl-1-hydroxy-6-(pyrimidin-2-yloxy)-1,3-dihydro-benzo[c][1,2]oxaborol-3-yl]-acetic acid

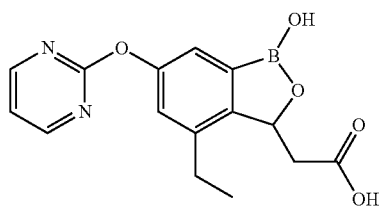 [SMILES: CCc1cc(Oc2ncccn2)cc2c1C(CC(=O)O)OB2O]

Step 1: [4-Ethyl-1-hydroxy-6-(pyrimidin-2-yloxy)-1,3-dihydro-benzo[c][1,2]oxaborol-3-yl]-acetic acid ethyl ester

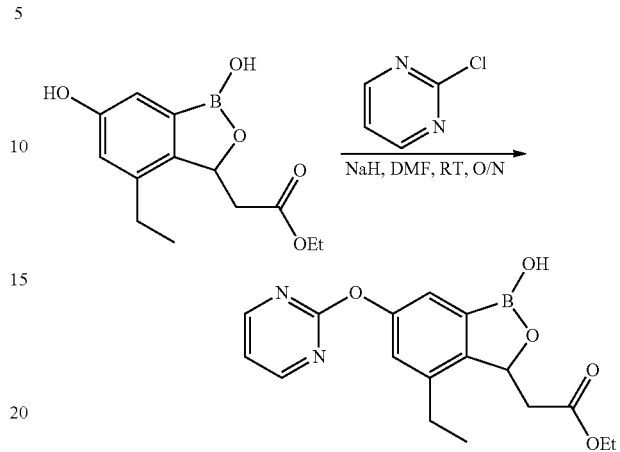

To a solution of 4-ethyl-1,6-dihydroxy-1,3-dihydro-benzo[c][1,2]oxaborol-3-yl)-acetic acid ethyl ester (0.36 g, 1.50 mmol) in DMF (5 mL) was added NaH (0.20 g, 4.50 mmol). The mixture was stirred at room temperature for 10 minutes. 2-Chloropyrimidine (0.43 g, 3.75 mmol) was added and the mixture stirred at room temperature for 48 hours. The reaction mixture was acidified with HCl and concentrated in vacuo. The residue was purified by silica gel flash column chromatography to give [4-ethyl-1-hydroxy-6-(pyrimidin-2-yloxy)-1,3-dihydro-benzo[c][1,2]oxaborol-3-yl]-acetic acid ethyl ester (0.130 g, 25%). $^1$H NMR (400 MHz, MeOD-d$_4$ δ 8.60 (s, 2H), 7.20 (m, 2H), 7.15 (s, 1H), 5.70 (m, 1H), 4.10 (m, 2H), 3.20 (m, 1H), 2.72 (m, 2H), 2.44 (s, 1H), 1.30-1.20 (m, 6H).

Step 2: [4-Ethyl-1-hydroxy-6-(pyrimidin-2-yloxy)-1,3-dihydro-benzo[c][1,2]oxaborol-3-yl]-acetic acid

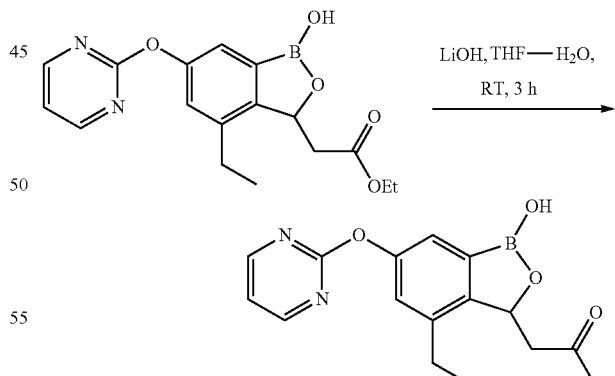

To a solution of [4-ethyl-1-hydroxy-6-(pyrimidin-2-yloxy)-1,3-dihydro-benzo[c][1,2]oxaborol-3-yl]-acetic acid ethyl ester (0.13 g, 0.38 mmol) in THF (8 mL) and H$_2$O (2 mL) was added LiOH (0.091 g) at 0° C. The resulting mixture was stirred at room temperature for 2 hours then cooled to 0° C. and acidified to pH 3 with 6N HCl. The mixture was concentrated in vacuo and the residue purified by preparative HPLC to give [4-ethyl-1-hydroxy-6-(pyrimidin-2-yloxy)-1, 3-dihydro-benzo[c][1,2]oxaborol-3-yl]-acetic acid (0.030 g, 25%). ¹H NMR (400 MHz, DMSO-d₆) δ 9.00 (br s, 1H), 8.63 (s, 1H), 8.62 (s, 1H), 7.25 (s, 1H), 7.24 (s, 1H), 7.23 (s, 1H), 7.10 (s, 1H), 5.51 (m, 1H), 3.01 (m, 1H), 2.61 (m, 2H), 2.14 (m, 1H), 1.17 (m, 3H). MS (ES) m/z: 313 (M−1)⁻. HPLC purity: 99.12% (220 nm), 98.58% (Maxplot).

G69: [6-(2-Dimethylamino-pyrimidin-4-yloxy)-1-hydroxy-4-methyl-1,3-dihydro-benzo[c][1,2]oxaborol-3-yl]-acetic acid

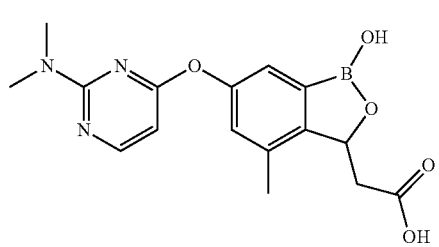 [SMILES: Cc1cc(Oc2ccnc(N(C)C)n2)cc2c1C(CC(=O)O)OB2O]

Step 1: [6-(2-Chloro-pyrimidin-4-yloxy)-1-hydroxy-4-methyl-1,3-dihydro-benzo[c][1,2]oxaborol-3-yl]-acetic acid ethyl ester

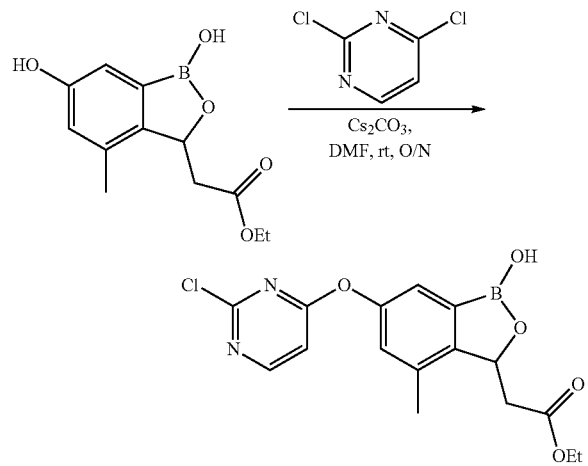

A solution of (1,6-dihydroxy-4-methyl-1,3-dihydro-benzo[c][1,2]oxaborol-3-yl)-acetic acid ethyl ester (3.30 g, 13.20 mmol) in DMF (10 mL) was treated with cesium carbonate (13.30 g, 40.82 mmol) at 0° C. followed by 2,4-dichloropyrimidine (3.90 g, 26.20 mmol). The mixture was stirred at room temperature for 24 hours. The suspension was quenched with ice water, acidified with 2N HCl and extracted with ethyl acetate. The extracts were dried (Na₂SO₄), filtered and concentrated in vacuo. The residue was purified by silica gel flash column chromatography (EtOAc/hexane; 1:1 then MeOH/CH₂Cl₂; 1:99 gradient) to give [6-(2-chloro-pyrimidin-4-yloxy)-1-hydroxy-4-methyl-1,3-dihydro-benzo[c][1,2]oxaborol-3-yl]-acetic acid ethyl ester as a yellow foam (3.00 g, 63%). ¹H NMR (400 MHz, CD₃OD) δ 8.48 (d, J=5.85 Hz, 1H), 7.22 (s, 1H), 7.10 (s, 1H), 6.98 (d, J=5.85 Hz, 1H), 5.65 (dd, J=8.20, 2.73 Hz, 1H), 4.14-4.07 (m, 2H), 3.18 (dd, J=15.22, 2.73 Hz, 1H), 2.52 (dd, J=15.22, 8.20 Hz, 1H), 2.39 (s, 3H), 1.19 (t, J=7.03 Hz, 3H).

Step 2: [6-(2-Dimethylamino-pyrimidin-4-yloxy)-1-hydroxy-4-methyl-1,3-dihydro-benzo[c][1,2]oxaborol-3-yl]-acetic acid ethyl ester

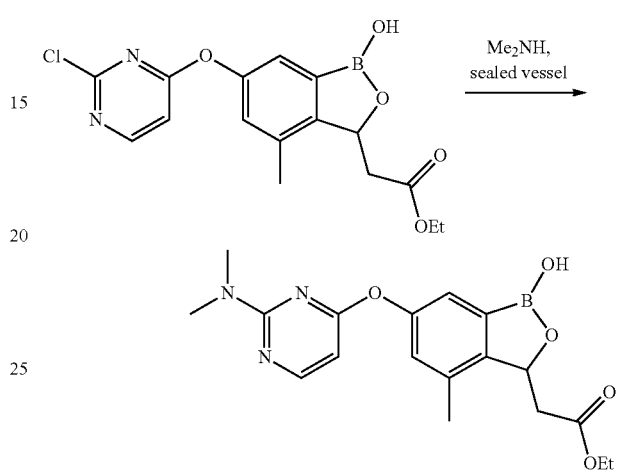

A solution of [6-(2-chloro-pyrimidin-4-yloxy)-1-hydroxy-4-methyl-1,3-dihydro-benzo[c][1,2]oxaborol-3-yl]-acetic acid ethyl ester (impure, 0.42 g, 1.16 mmol) in dimethylamine (2M solution in THF, 5 mL, 10 mmol) was stirred in a sealed tube at room temperature for 3 hours. The mixture was concentrated in vacuo and the residue purified by silica gel flash column chromatography using EtOAc and hexane (1:1) as eluant, followed by MeOH and CH₂Cl₂ (2:98 gradient) and preparative HPLC (CH₃CN/0.1% AcOH in water). The required fraction was lyophilized to give [6-(2-dimethylamino-pyrimidin-4-yloxy)-1-hydroxy-4-methyl-1,3-dihydro-benzo[c][1,2]oxaborol-3-yl]-acetic acid ethyl ester as a light yellow solid (0.094 g, 22%). ¹H NMR (400 MHz, CD₃OD) δ 8.12 (d, J=5.85 Hz, 1H), 7.19 (s, 1H), 7.05 (s, 1H), 6.07 (d, J=5.85 Hz, 1H), 5.68-5.60 (m, 1H), 4.15-4.03 (m, 2H), 3.17 (dd, J=14.38, 2.34 Hz, 1H), 3.00 (s, 6H), 2.47 (dd, J=14.83, 8.20 Hz, 1H), 2.36 (s, 3H), 1.20 (t, J=7.03 Hz, 3H).

Step 3: [6-(2-Dimethylamino-pyrimidin-4-yloxy)-1-hydroxy-4-methyl-1,3-dihydro-benzo[c][1,2]oxaborol-3-yl]-acetic acid

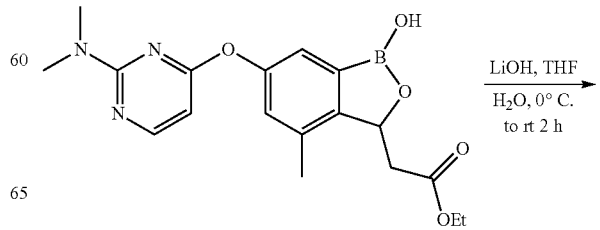

215
-continued

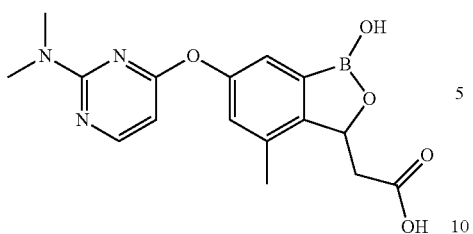

A solution of [6-(2-dimethylamino-pyrimidin-4-yloxy)-1-hydroxy-4-methyl-1,3-dihydro-benzo[c][1,2]oxaborol-3-yl]-acetic acid ethyl ester (0.094 g, 0.25 mmol) in THF (5 mL) was treated with lithium hydroxide (0.029 g, 1.27 mmol) in water (0.5 mL) at 0° C. The solution was stirred at 0° C. to room temperature for 2 hours, then acidified with 2N HCl to pH 2, and concentrated. The residue was purified by silica gel flash column chromatography (AcOH:acetone:hexanes; trace:1:2; then MeOH:CH$_2$Cl$_2$; 5:95) to give [6-(2-dimethylamino-pyrimidin-4-yloxy)-1-hydroxy-4-methyl-1,3-dihydro-benzo[c][1,2]oxaborol-3-yl]-acetic acid as a white solid after lyophilization (0.02 g, 23%). $^1$H NMR (400 MHz, DMSO-d$_6$) δ 8.18 (d, J=5.47 Hz, 1H), 7.24 (s, 1H), 7.07 (s, 1H), 6.01 (d, J=5.47 Hz, 1H), 5.50-5.45 (m, 1H), 3.02 (dd, J=15.63, 2.40 Hz, 1H), 2.96 (s, 6H), 2.28 (s, 3H), 2.11 (dd, J=15.63, 9.38 Hz, 1H). MS (ESI) m/z: 344 [M+1].

G70: {6-[2-(2-Amino-ethylamino)-pyrimidin-4-yloxy]-1-hydroxy-4-methyl-1,3-dihydro-benzo[c][1,2]oxaborol-3-yl}-acetic acid hydrochloride salt

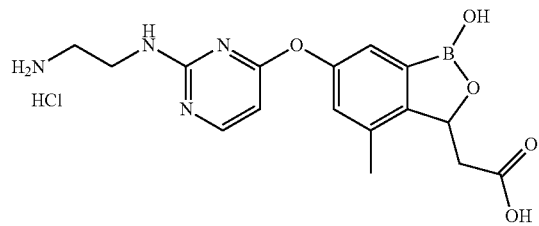 [SMILES: Cl ; Cc1cc(Oc2ccnc(NCCN)n2)cc2c1C(CC(=O)O)OB2O]

Step 1: {6-[2-(2-tert-Butoxycarbonylamino-ethylamino)-pyrimidin-4-yloxy]-1-hydroxy-4-methyl-1,3-dihydro-benzo[c][1,2]oxaborol-3-yl}-acetic acid ethyl ester

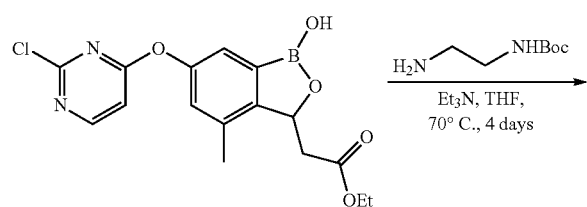

216
-continued

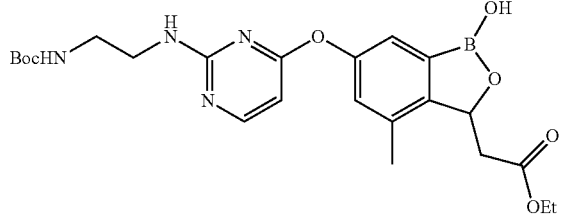

A solution of (1,6-dihydroxy-4-methyl-1,3-dihydro-benzo[c][1,2]oxaborol-3-yl)-acetic acid ethyl ester (0.50 g, 1.38 mmol) in THF (5 mL), was treated with (2-amino-ethyl)-carbamic acid tert-butyl ester (0.54 g, 3.38 mmol) followed by triethylamine (1.20 mL, 8.60 mmol). The mixture was heated at 70° C. in a sealed vessel for 4 days then concentrated in vacuo. The residue was purified by preparative HPLC (CH$_3$CN/H$_2$O) and required fraction was lyophilized to give {6-[2-(2-tert-butoxycarbonylamino-ethylamino)-pyrimidin-4-yloxy]-1-hydroxy-4-methyl-1,3-dihydro-benzo[c][1,2]oxaborol-3-yl}-acetic acid ethyl ester as a light yellow solid (0.35 g, 52%). $^1$H NMR (400 MHz, CD$_3$OD) δ 8.08 (d, J=5.86 Hz, 1H), 7.20 (s, 1H), 7.07 (s, 1H), 6.19 (d, J=5.86 Hz, 1H), 5.70-5.60 (m, 1H), 4.15-4.08 (m, 2H), 3.18 (dd, J=15.24, 3.13 Hz, 1H), 3.12 (br m, 3H), 2.46 (m, 1H), 2.37 (s, 3H), 1.40 (s, 9H), 1.37 (m, 1H), 1.21 (t, J=7.03 Hz, 3H).

Step 2: {6-[2-(2-tert-Butoxycarbonylamino-ethylamino)-pyrimidin-4-yloxy]-1-hydroxy-4-methyl-1,3-dihydro-benzo[c][1,2]oxaborol-3-yl}-acetic acid

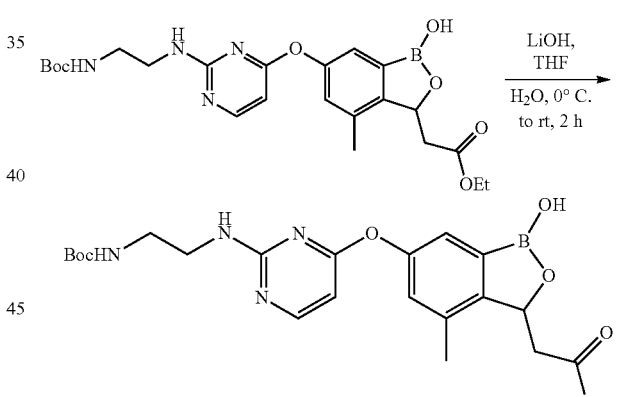

A solution of {6-[2-(2-tert-butoxycarbonylamino-ethylamino)-pyrimidin-4-yloxy]-1-hydroxy-4-methyl-1,3-dihydro-benzo[c][1,2]oxaborol-3-yl}-acetic acid ethyl ester (0.35 g, 0.72 mmol) in THF (5 mL) was treated with lithium hydroxide (0.084 g, 3.60 mmol) in water (5 mL) at 0° C. The mixture was stirred at 0° C. for 1 hour then at room temperature for 1 hour. The mixture was quenched with 2N HCl to pH 2 then concentrated to approximately half of the entire volume. The mixture was diluted with brine and extracted with ethyl acetate. The organic extracts were dried (Na$_2$SO$_4$), filtered and concentrated to give {6-[2-(2-tert-butoxycarbonylamino-ethylamino)-pyrimidin-4-yloxy]-1-hydroxy-4-methyl-1,3-dihydro-benzo[c][1,2]oxaborol-3-yl}-acetic acid, as a light yellow solid (0.18 g) after lyophilization. The aqueous layer was lyophilized, diluted with water (3 mL) and extracted with ethyl acetate. The organic extracts were dried (Na$_2$SO$_4$), filtered and concentrated to a light yellow solid after lyophilization, to give a total of 0.21 g (64%) of product. ¹H NMR (400 MHz, CD₃OD) δ 8.13 (d, J=6.64 Hz, 1H), 7.25 (s, 1H), 7.12 (s, 1H), 6.46 (m, 1H), 5.67 (dd, J=8.21, 2.40 Hz, 1H), 3.17 (dd, J=15.63, 3.13 Hz, 1H), 3.20-3.00 (m, 3H), 2.38 (br s, 4H), 1.40 (br s, 10H).

Step 3: {6-[2-(2-Amino-ethylamino)-pyrimidin-4-yloxy]-1-hydroxy-4-methyl-1,3-dihydro-benzo[c][1,2]oxaborol-3-yl}-acetic acid hydrochloride salt

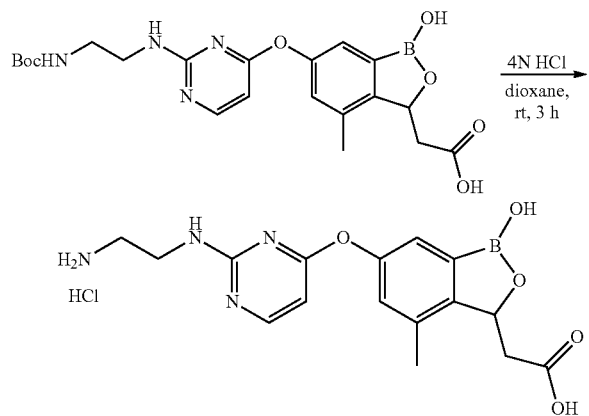

A solution of {6-[2-(2-tert-butoxycarbonylamino-ethylamino)-pyrimidin-4-yloxy]-1-hydroxy-4-methyl-1,3-dihydro-benzo[c][1,2]oxaborol-3-yl}-acetic acid (0.21 g, 0.46 mmol) in dioxane (7 mL) was treated with 4N HCl in dioxane (2 mL) at room temperature. The mixture was stirred for 3 hours at room temperature. The precipitated solid was collected by vacuum filtration, dissolved in water and lyophilized to give {6-[2-(2-amino-ethylamino)-pyrimidin-4-yloxy]-1-hydroxy-4-methyl-1,3-dihydro-benzo[c][1,2]oxaborol-3-yl}-acetic acid hydrochloride salt as a yellow solid (0.142 g, 78%). ¹H NMR (400 MHz, DMSO-d₆) δ 8.57 (br s, 1H), 8.35-8.20 (br m, 1H), 8.02 (br s, 3H), 7.40-7.30 (br m, 1H), 7.15 (br s, 1H), 6.48 (br s, 1H), 5.53 (d, J=9.38 Hz, 1H), 3.36 (br m, 2H), 3.07 (d, J=14.07 Hz, 1H), 2.95-2.70 (m, 2H), 2.30 (s, 3H), 2.14 (m, 1H). MS (ESI) m/z: 357 [M−1]. ¹H NMR (400 MHz, CD₃OD) δ 8.27 (d, J=6.64 Hz, 1H), 7.28 (s, 1H), 7.17 (s, 1H), 6.70 (d, J=6.64 Hz, 1H), 5.68 (dd, J=8.21, 3.13 Hz, 1H), 3.48 (br m, 2H), 3.19 (dd, J=15.63, 2.74 Hz, 1H), 2.98 (br m, 2H), 2.50 (br m, 1H), 2.40 (s, 3H).

G71: {6-[2-(3-Amino-propylamino)-pyrimidin-4-yloxy]-1-hydroxy-4-methyl-1,3-dihydro-benzo[c][1,2]oxaborol-3-yl}-acetic acid hydrochloride salt

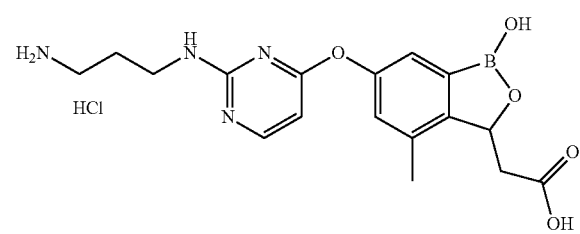 [SMILES: Cc1cc(Oc2ccnc(NCCCN)n2)cc2c1C(CC(=O)O)OB2O ; Cl]

Step 1: {6-[2-(3-tert-Butoxycarbonylamino-propylamino)-pyrimidin-4-yloxy]-1-hydroxy-4-methyl-1,3-dihydro-benzo[c][1,2]oxaborol-3-yl}-acetic acid ethyl ester

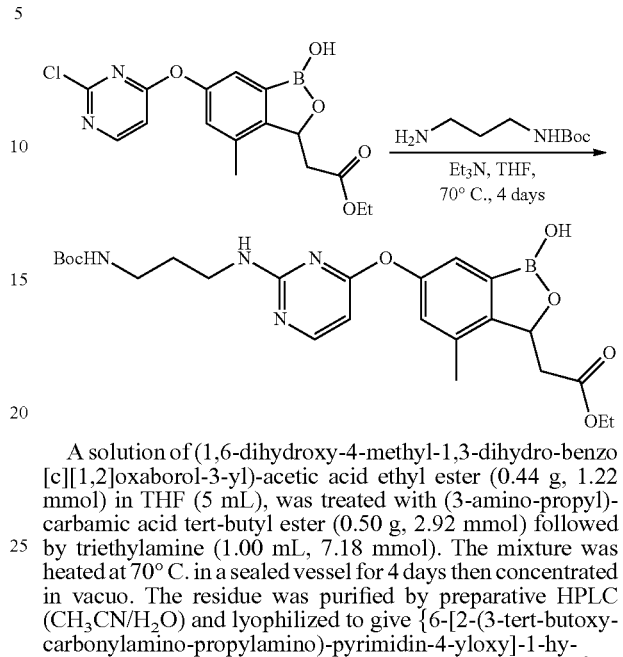

A solution of (1,6-dihydroxy-4-methyl-1,3-dihydro-benzo[c][1,2]oxaborol-3-yl)-acetic acid ethyl ester (0.44 g, 1.22 mmol) in THF (5 mL), was treated with (3-amino-propyl)-carbamic acid tert-butyl ester (0.50 g, 2.92 mmol) followed by triethylamine (1.00 mL, 7.18 mmol). The mixture was heated at 70° C. in a sealed vessel for 4 days then concentrated in vacuo. The residue was purified by preparative HPLC (CH₃CN/H₂O) and lyophilized to give {6-[2-(3-tert-butoxycarbonylamino-propylamino)-pyrimidin-4-yloxy]-1-hydroxy-4-methyl-1,3-dihydro-benzo[c][1,2]oxaborol-3-yl}-acetic acid ethyl ester as a yellow solid (0.39 g, 64%). ¹H NMR (400 MHz, CD₃OD) δ 8.07 (d, J=5.86 Hz, 1H), 7.19 (s, 1H), 7.07 (s, 1H), 6.17 (d, J=5.86 Hz, 1H), 5.65 (dd, J=8.60, 2.35 Hz, 1H), 4.17-4.00 (m, 2H), 3.30-3.12 (br m, 2H), 3.18 (dd, J=15.24, 2.74 Hz, 1H), 3.10-2.94 (br m, 1H), 2.50-2.40 (m, 1H), 2.36 (s, 3H), 1.62-1.55 (br m, 2H), 1.41 (s, 9H), 1.21 (t, J=7.42 Hz, 3H).

Step 2: {6-[2-(3-tert-Butoxycarbonylamino-propylamino)-pyrimidin-4-yloxy]-1-hydroxy-4-methyl-1,3-dihydro-benzo[c][1,2]oxaborol-3-yl}-acetic acid

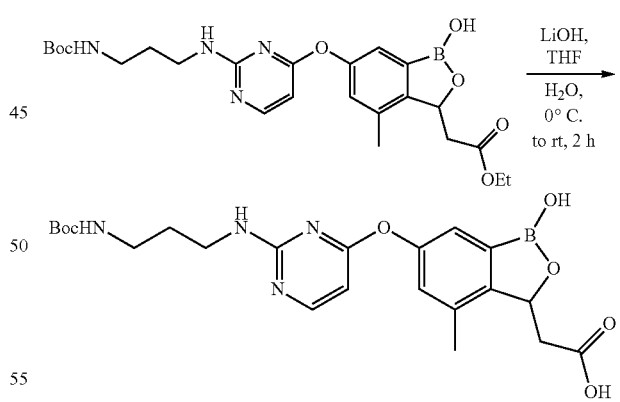

A solution of {6-[2-(3-tert-butoxycarbonylamino-propylamino)-pyrimidin-4-yloxy]-1-hydroxy-4-methyl-1,3-dihydro-benzo[c][1,2]oxaborol-3-yl}-acetic acid ethyl ester (0.39 g, 0.78 mmol) in THF (10 mL) was treated with lithium hydroxide (0.089 g, 3.90 mmol) in water (2 mL) at 0° C. The mixture was stirred at 0° C. for 1 hour, then at room temperature for 1 hour. The mixture was quenched with 2N HCl to pH 2 then concentrated in vacuo. The residue was diluted with brine and extracted with ethyl acetate. The organic extracts were dried (Na₂SO₄), filtered and concentrated to give {6-[2-(3-tert-butoxycarbonylamino-propylamino)-pyrimidin-4-yloxy]-1-hydroxy-4-methyl-1,3-dihydro-benzo[c][1,2]oxaborol-3-yl}-acetic acid as a yellow solid (0.27 g, 74%) after lyophilization. $^1$H NMR (400 MHz, CD$_3$OD) δ8.09 (d, J=6.25 Hz, 1H), 7.22 (s, 1H), 7.10 (s, 1H), 6.32 (m, 1H), 5.67 (d, J=6.25 Hz, 1H), 3.28-3.14 (br m, 2H), 3.17 (dd, J=15.24, 2.35 Hz, 1H), 3.10-2.90 (m, 2H), 2.38 (s, 3H), 2.36-2.25 (m, 1H), 1.70-1.50 (m, 2H), 1.41 (s, 9H).

Step 3: {6-[2-(3-Amino-propylamino)-pyrimidin-4-yloxy]-1-hydroxy-4-methyl-1,3-dihydro-benzo[c][1,2]oxaborol-3-yl}-acetic acid hydrochloride salt

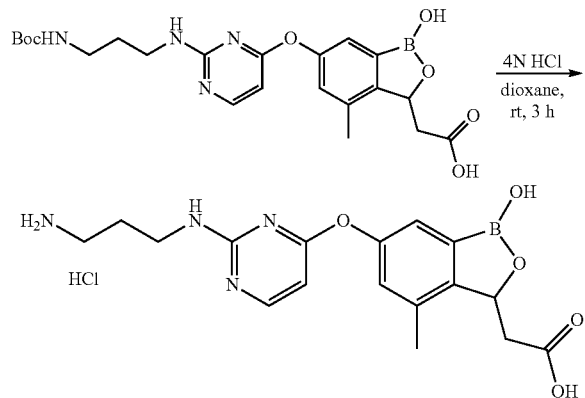

A solution of {6-[2-(3-tert-butoxycarbonylamino-propylamino)-pyrimidin-4-yloxy]-1-hydroxy-4-methyl-1,3-dihydro-benzo[c][1,2]oxaborol-3-yl}-acetic acid (0.27 g, 0.57 mmol) in dioxane (7 mL) was treated with 4N HCl in dioxane (2 mL) at room temperature and stirred for 3 hours at room temperature. The precipitated solid was collected by vacuum filtration, dissolved in water and lyophilized to give {6-[2-(3-amino-propylamino)-pyrimidin-4-yloxy]-1-hydroxy-4-methyl-1,3-dihydro-benzo[c][1,2]oxaborol-3-yl}-acetic acid hydrochloride salt as a yellow solid (0.12 g, 56%). $^1$H NMR (400 MHz, DMSO-d$_6$) δ 8.57 (br s, 1H), 8.37-8.10 (br m, 1H), 7.94 (br m, 3H), 7.50-7.25 (br m, 1H), 7.20-7.05 (br m, 1H), 6.47 (br s, 1H), 5.54 (d, J=9.38 Hz, 1H), 3.36 (br m, 1H), 3.20-3.00 (m, 2H), 2.80 ((m, 1H), 2.67 (m, 1H), 2.33 (s, 3H), 2.20-2.07 (m, 1H), 1.95-1.60 (m, 2H). MS (ESI) m/z: 371 [M−1].

G72: [6-(2-Amino-pyrimidin-4-yloxy)-1-hydroxy-4-methyl-1,3-dihydro-benzo[c][1,2]oxaborol-3-yl]-acetic acid

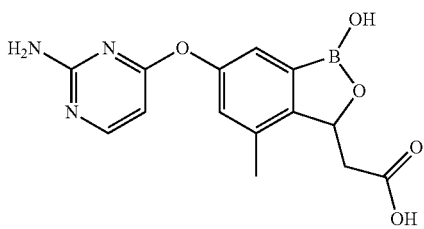 [SMILES: Cc1cc(Oc2ccnc(N)n2)cc2c1C(CC(=O)O)OB2O]

Step 1: {6-[2-(2,5-Dimethoxy-benzylamino)-pyrimidin-4-yloxy]-1-hydroxy-4-methyl-1,3-dihydro-benzo[c][1,2]oxaborol-3-yl}-acetic acid ethyl ester

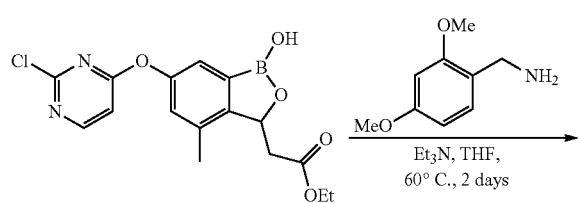

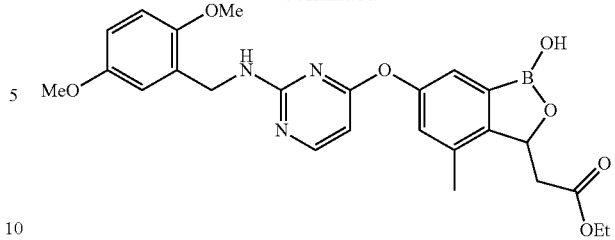

A solution of [6-(2-chloro-pyrimidin-4-yloxy)-1-hydroxy-4-methyl-1,3-dihydro-benzo[c][1,2]oxaborol-3-yl]-acetic acid ethyl ester (0.50 g, 1.38 mmol) in THF (10 mL) was treated with 2,4-dimethoxybenzylamine (0.41 mL, 2.73 mmol) followed by triethylamine (0.77 mL, 5.52 mmol). The mixture was heated at 60° C. in a sealed tube for 2 days. The solid was filtered and the filtrate was concentrated in vacuo. The residue was purified by preparative HPLC (CH$_3$CN/ 0.1% formic acid in water) to give {6-[2-(2,5-dimethoxy-benzylamino)-pyrimidin-4-yloxy]-1-hydroxy-4-methyl-1,3-dihydro-benzo[c][1,2]oxaborol-3-yl}-acetic acid ethyl ester as a light yellow solid (0.35 g, 51%). $^1$H NMR (400 MHz, CD$_3$OD) δ 8.04 (d, J=5.71 Hz, 1H), 7.17 (s, 1H), 7.04 (s, 1H), 6.60-6.22 (m, 3H), 6.14 (d, J=5.71 Hz, 1H), 5.69-5.64 (m, 1H), 4.10-4.00 (m, 4H), 3.78 (s, 3H), 3.75 (s, 3H), 3.16 (dd, J=14.91, 2.86 Hz, 1H), 2.43 (dd, J=14.91, 8.73 Hz, 1H), 2.36 (s, 3H), 1.20 (t, J=7.30 Hz, 3H).

Step 2: {6-[2-(2,5-Dimethoxy-benzylamino)-pyrimidin-4-yloxy]-1-hydroxy-4-methyl-1,3-dihydro-benzo[c][1.2]oxaborol-3-yl}-acetic acid

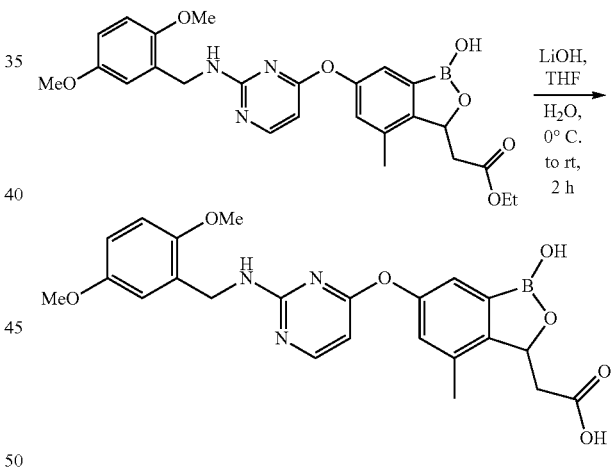

A solution of {6-[2-(2,5-dimethoxy-benzylamino)-pyrimidin-4-yloxy]-1-hydroxy-4-methyl-1,3-dihydro-benzo[c][1,2]oxaborol-3-yl}-acetic acid ethyl ester (0.35 g, 0.71 mmol) in THF (5 mL) was treated with lithium hydroxide (0.081 g, 3.55 mmol) in water (5 mL) at 0° C. The mixture was stirred at 0° C. for 1 hour then at room temperature for 1 hour. The mixture was quenched with 2N HCl to pH 2 then concentrated to approximately ½ the entire volume, diluted with brine and extracted with ethyl acetate. The organic extracts were dried (Na$_2$SO$_4$), filtered and concentrated to give {6-[2-(2,5-dimethoxy-benzylamino)-pyrimidin-4-yloxy]-1-hydroxy-4-methyl-1,3-dihydro-benzo[c][1,2]oxaborol-3-yl}-acetic acid as a yellow solid (0.32 g, 97%). $^1$H NMR (400 MHz, CD$_3$OD) δ8.11 (d, J=6.64 Hz, 1H), 7.25 (s, 1H), 7.13 (s, 1H), 6.60-6.20 (m, 4H), 5.75-5.65 (m, 1H), 4.20-4.10 (m, 2H), 3.80 (s, 3H), 3.76 (s, 3H), 3.21-3.10 (m, 1H), 2.40 (s, 3H), 2.39-2.20 (m, 1H).

Step 3: [6-(2-Amino-pyrimidin-4-yloxy)-1-hydroxy-4-methyl-1,3-dihydro-benzo[c][1,2]oxaborol-3-yl]-acetic acid formic acid salt

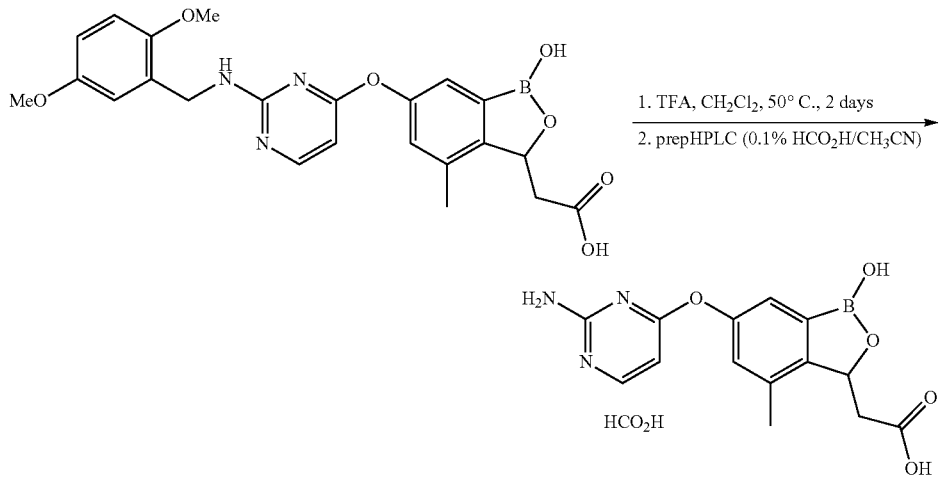

A suspension of {6-[2-(2,5-dimethoxy-benzylamino)-pyrimidin-4-yloxy]-1-hydroxy-4-methyl-1,3-dihydro-benzo[c][1,2]oxaborol-3-yl}-acetic acid (0.32 g, 0.69 mmol) in CH$_2$Cl$_2$ (10 mL) was treated with trifluoroacetic acid (1 mL, 12.98 mmol) and refluxed for 18 hours. A second portion of trifluoroacetic acid was added (1 mL, 12.98 mmol) and the solution was refluxed for another 18 hours. The mixture was concentrated and purified by preparative HPLC (CH$_3$CN/0.1% formic acid in water) to give [6-(2-amino-pyrimidin-4-yloxy)-1-hydroxy-4-methyl-1,3-dihydro-benzo[c][1,2]oxaborol-3-yl]-acetic acid formic acid salt as a white solid (0.10 g, 46%) after lyophilization. $^1$H NMR (400 MHz, DMSO-d δ9.26 (br s, 1H), 8.14 (d, J=6.24 Hz, 1H), 8.11 (s, 1H), 7.24 (d, J=2.34 Hz, 1H), 7.17 (br s, 2H), 7.08 (d, J=2.34 Hz, 1H), 6.26 (d, J=5.86 Hz, 1H), 5.51 (dd, J=9.76, 2.73 Hz, 1H), 3.08 (dd, J=15.61, 2.73 Hz, 1H), 2.29 (d, 3H), 2.10 (dd, J=15.76, 9.76 Hz, 1H). MS (ESI) m/z: 316 [M+1].

G73: [6-(2-Aminomethyl-pyrimidin-4-yloxy)-1-hydroxy-4-methyl-1,3-dihydro-benzo[c][1,2]oxaborol-3-yl)-acetic acid hydrochloride salt

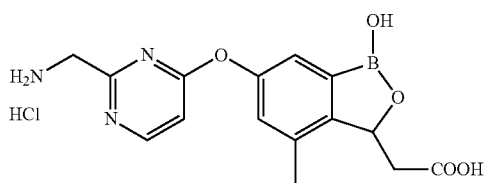 [SMILES: Cl ; Cc1cc(Oc2ccnc(CN)n2)cc2c1C(CC(=O)O)OB2O]

Step 1: [6-(2-Cyano-pyramidin-4-yloxy)-1-Hydroxy-4-methyl-1,3-dihydro-benzo[c][1,2]oxaborol-3-yl)-acetic acid ethyl ester

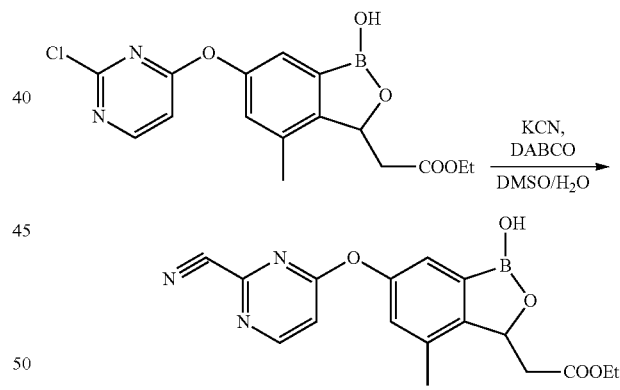

To a solution of [6-(2-chloro-pyramidin-4-yloxy)-1-hydroxy-4-methyl-1,3-dihydro-benzo[c][1,2]oxaborol-3-yl)-acetic acid ethyl ester (0.33 g, 0.91 mmol) in DMSO (2.55 mL) and H$_2$O (0.45 mL) was added 1,4-diazabicyclo[2.2.2]octane (0.2 g 1.86 mmol) and potassium cyanide (0.12 g, 1.86 mmol). The resulting mixture was stirred at room temperature for 1 hour then extracted with EtOAc. The organic extracts were washed with water, brine, dried over Na$_2$SO$_4$, and concentrated in vacuo to give [6-(2-cyano-pyramidin-4-yloxy)-1-hydroxy-4-methyl-1,3-dihydro-benzo[c][1,2]oxaborol-3-yl)-acetic acid ethyl ester (0.3 g, 93%), which was used without further purification. $^1$H NMR (400 MHz, DMSO-d δ 9.33 (s, 1H), 8.85 (d, J=6.0 Hz, 1H), 7.49 (d, J=6.0 Hz, 1H), 7.33 (d, J=2.4 Hz, 1H), 7.19 (d, J=2.0 Hz, 1H), 5.59 (dd, J=8.8, 2.8 Hz, 1H), 4.03 (q, J=6.8 Hz, 2H), 3.17 (dd, J=15.2, 2.8 Hz, 1H), 2.40 (m, 1H), 2.33 (s, 3H), 1.14 (t, J=7.2 Hz, 3H).

Step 2: [6-(2-Aminomethyl-pyramidin-4-yloxy)-1-Hydroxy-4-methyl-1,3-dihydro-benzo[c][1,2]oxaborol-3-yl)-acetic acid ethyl ester

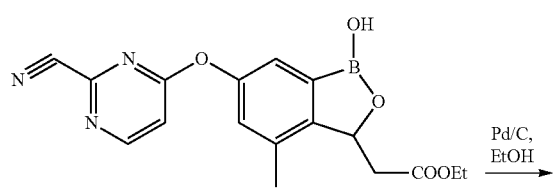

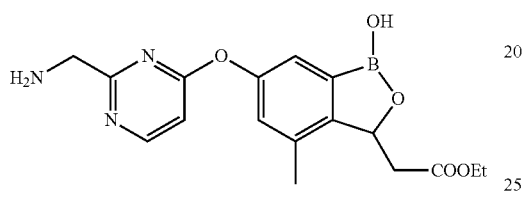

A solution of [6-(2-cyano-pyramidin-4-yloxy)-1-hydroxy-4-methyl-1,3-dihydro-benzo[c][1,2]oxaborol-3-yl)-acetic acid ethyl ester (0.2 g, 0.56 mmol), 10% Pd/C (0.35 g) and 6M HCl (2 drops) in EtOH (40 mL) was hydrogenated at 40 psi for 1 hour. The mixture was filtered through a pad of celite and concentrated in vacuo to give [6-(2-aminomethyl-pyramidin-4-yloxy)-1-hydroxy-4-methyl-1,3-dihydro-benzo[c][1,2]oxaborol-3-yl)-acetic acid ethyl ester (0.15 g, 75%), which was used without further purification. $^1$H NMR (400 MHz, DMSO-d δ9.32 (s, 1H), 8.72 (m, 1H), 8.38 (brs, 2H), 7.38 (s, 1H), 7.17 (s, 1H), 7.00 (m, 1H), 5.58 (m, 1H), 4.18 (s, 2H), 4.03 (m, 2H), 3.18 (m, 1H), 2.38 (m, 4H), 1.14 (m, 3H).

Step 3: [6-(2-Aminomethyl-pyramidin-4-yloxy)-1-hydroxy-4-methyl-1,3-dihydro-benzo[c][1,2]oxaborol-3-yl)-acetic acid hydrochloride salt

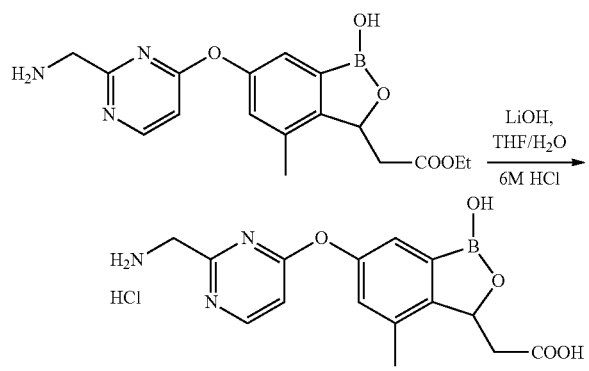

To a solution [6-(2-aminomethyl-pyramidin-4-yloxy)-1-hydroxy-4-methyl-1,3-dihydro-benzo[c][1,2]oxaborol-3-yl)-acetic acid ethyl ester (0.2 g, 0.56 mmol) in THF (10 mL) was added a solution of LiOH (0.067 g, 2.8 mmol) in water (3 mL) at 0° C. The resulting mixture was stirred at room temperature for 2 hours then concentrated in vacuo and purified by preparative HPLC. The residue was acidified with 6M HCl (1 mL) and lyophilized to give [6-(2-aminomethyl-pyramidin-4-yloxy)-1-hydroxy-4-methyl-1,3-dihydro-benzo[c][1,2]oxaborol-3-yl)-acetic acid hydrochloride salt as an off white solid (0.027 g, 13%). $^1$H NMR (400 MHz, DMSO-d δ8.70 (d, J=5.2 Hz, 1H), 8.52 (brs, 2H), 7.45 (s, 1H), 7.14 (s, 1H), 6.98 (d, J=5.2 Hz, 1H), 5.52 (m, 1H), 4.10 (d, J=5.2 Hz, 2H), 3.09 (m, 1H), 2.30 (s, 3H), 2.16 (m, 1H). MS (ESI) m/z: 330 [M+1]$^+$. HPLC purity: 96.21% (Maxplot), 96.45% (220 nm).

G74: [1-Hydroxy-4-methyl-6-(pyrimidin-4-yloxy)-1,3-dihydro-benzo[c][1,2]oxaborol-3-yl]-acetic acid

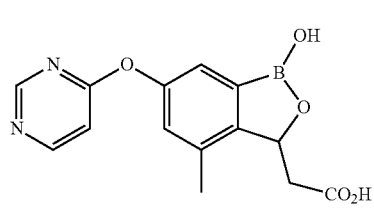 [SMILES: Cc1cc(Oc2ccncn2)cc2c1C(CC(=O)O)OB2O]

Step 1: [1-Hydroxy-4-methyl-6-(pyrimidin-4-yloxy)-1,3-dihydro-benzo[c][1,2]oxaborol-3-yl]-acetic acid ethyl ester

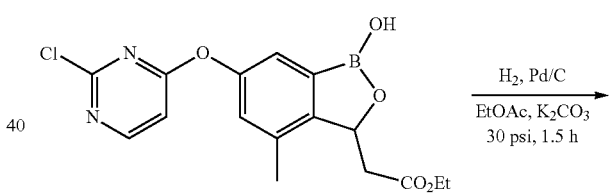

A mixture of [6-(2-chloro-pyrimidin-4-yloxy)-1-hydroxy-4-methyl-1,3-dihydro-benzo[c][1,2]oxaborol-3-yl]-acetic acid ethyl ester (0.5 g, 1.38 mmol), 10% Pd/C (0.45 g) and $K_2CO_3$ (0.38 g, 2.75 mmol) in EtOAc (15 mL) was hydrogenated at 30 psi for 1.5 hours. The mixture was filtered through a pad of celite and concentrated in vacuo. The residue was purified by silica gel flash column chromatography (DCM: MeOH 95:5) to give [1-hydroxy-4-methyl-6-(pyrimidin-4-yloxy)-1,3-dihydro-benzo[c][1,2]oxaborol-3-yl]-acetic acid ethyl ester (0.4 g, 88%). $^1$H NMR (400 MHz, DMSO): δ 9.27 (s, 1H), 8.73 (s, 1H), 8.65 (d, J=5.6 Hz, 1H), 7.26 (d, J=2.0 Hz, 1H), 7.12 (d, J=6.8 Hz, 2H), 5.54 (dd, J=2.4, 9.2 Hz, 1H), 4.04

(q, J=6.8 Hz, 2H), 3.13 (dd, J=2.4, 15.2 Hz, 1H), 2.34-2.27 (m, 1H), 2.30 (s, 3H), 1.13 (t, J=7.2 Hz, 3H). MS (ESI) m/z=329 [M+H]⁺.

Step 2: [1-Hydroxy-4-methyl-6-(pyrimidin-4-yloxy)-1,3-dihydro-benzo[c][1,2]oxaborol-3-yl]-acetic acid

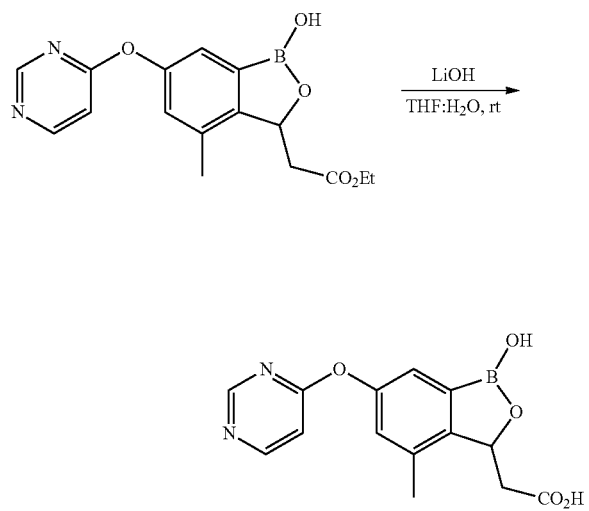

To a solution of [1-hydroxy-4-methyl-6-(pyrimidin-4-yloxy)-1,3-dihydro-benzo[c][1,2]oxaborol-3-yl]-acetic acid ethyl ester (0.4 g, 1.21 mmol) in THF:H₂O (1:1, 10 mL) at 0° C. was added LiOH (0.087 g, 3.65 mmol) in water (1 mL). The solution was allowed to warm to room temperature over 6 hours then acidified to pH 2 with 1N HCl at 0° C. and extracted with EtOAc (2×10 mL). The organic extracts were dried and concentrated in vacuo. The residue was purified by preparative HPLC to give [1-hydroxy-4-methyl-6-(pyrimidin-4-yloxy)-1,3-dihydro-benzo[c][1,2]oxaborol-3-yl]-acetic acid (0.3 g, 82%). ¹H NMR (400 MHz, DMSO): δ 9.25 (s, 1H), 8.73 (s, 1H), 8.65 (d, J=5.6 Hz, 1H), 7.26 (d, J=2.0 Hz, 1H), 7.12 (d, J=7.2 Hz, 2H), 5.51 (dd, J=2.4, 9.6 Hz, 1H), 3.07 (dd, J=2.0, 15.2 Hz, 1H), 2.29 (s, 3H), 2.17-2.11 (m, 1H). MS (ESI) m/z=301 [M+H]⁺.

G75: {6-[2-(3-Amino-propoxy)-pyrimidin-4-yloxy]-1-hydroxy-4-methyl-1,3-dihydro-benzo[c][1,2]oxaborol-3-yl}-acetic acid

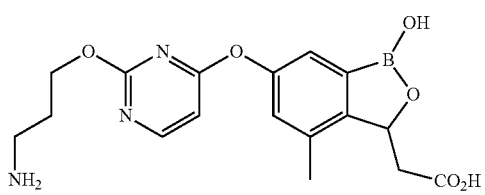 [SMILES: Cc1cc(Oc2ccnc(OCCCN)n2)cc2c1C(CC(=O)O)OB2O]

Step 1: {6-[2-(3-tert-Butoxycarbonylamino-propoxy)-pyrimidin-4-yloxy]-1-hydroxy-4-methyl-1,3-dihydro-benzo[c][1,2]oxaborol-3-yl}-acetic acid ethyl ester

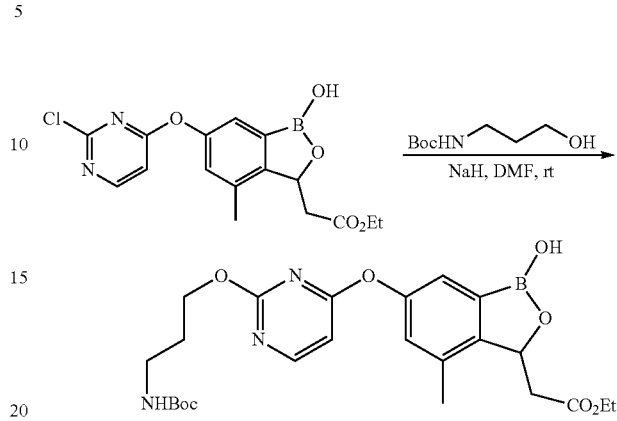

To a solution of [6-(2-chloro-pyrimidin-4-yloxy)-1-hydroxy-4-methyl-1,3-dihydro-benzo[c][1,2]oxaborol-3-yl]-acetic acid ethyl ester (0.5 g, 1.37 mmol) and (3-hydroxypropyl)-carbamic acid tert-butyl ester (0.48 g, 2.75 mmol) in DMF at 0° C. was added NaH (0.2 g, 4.13 mmol). The reaction mixture was allowed to warm to room temperature and stirred for 12 hours. Saturated NH₄Cl (10 mL) was added at 0° C. and the solution acidified to pH~5 with dilute HCl. The mixture was extracted with EtOAc (2×10 mL) and the organic extracts washed with water (10 mL), dried and concentrated in vacuo. The residue was purified by silica gel flash column chromatography (DCM:MeOH 95:5) to give {6-[2-(3-tert-butoxycarbonylamino-propoxy)-pyrimidin-4-yloxy]-1-hydroxy-4-methyl-1,3-dihydro-benzo[c][1,2]oxaborol-3-yl}-acetic acid ethyl ester (0.45 g, 65%). ¹H NMR (400 MHz, DMSO): δ 9.10 (s, 1H), 8.41 (d, J=5.2 Hz, 1H), 8.22 (d, J=5.6 Hz, 1H), 7.24 (s, 1H), 7.09 (s, 1H), 5.51 (d, J=9.6 Hz, 1H), 4.02 (q, J=7.2 Hz, 2H), 3.93 (t, J=6.0 Hz, 2H), 3.07-3.02 (m, 3H), 2.28-2.27 (m, 1H), 2.26 (s, 3H), 1.77 (t, J=6.4 Hz, 2H), 1.33 (s, 12H), 1.11 (t, J=6.8 Hz, 3H). MS (ESI) m/z=502 [M+H]⁺.

Step 2: {6-[2-(3-tert-Butoxycarbonylamino-propoxy)-pyrimidin-4-yloxy]-1-hydroxy-4-methyl-1,3-dihydro-benzo[c][1,2]oxaborol-3-yl}-acetic acid

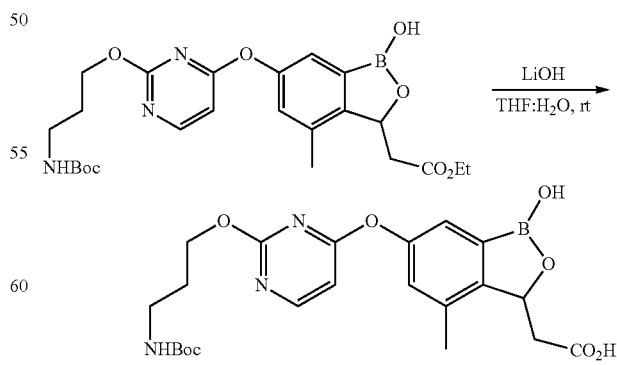

To a solution of {6-[2-(3-tert-butoxycarbonylamino-propoxy)-pyrimidin-4-yloxy]-1-hydroxy-4-methyl-1,3-dihydro-benzo[c][1,2]oxaborol-3-yl}-acetic acid ethyl ester (0.45 g, 0.89 mmol) in THF:H₂O (1:1, 6 mL) at 0° C. was added a solution of LiOH (0.043 g, 1.79 mmol) in water (1 mL). The solution was allowed to warm to room temperature over 3 hours then acidified to pH 4 with 1N HCl and extracted with EtOAc (2×10 mL). The organic extracts were dried and concentrated in vacuo to give crude {6-[2-(3-tert-Butoxycarbonylamino-propoxy)-pyrimidin-4-yloxy]-1-hydroxy-4-methyl-1,3-dihydro-benzo[c][1,2]oxaborol-3-yl}-acetic acid (0.3 g) which was used without further purification. MS (ESI) m/z=472 [M−H]⁻.

Step 3: {6-[2-(3-Amino-propoxy)-pyrimidin-4-yloxy]-1-hydroxy-4-methyl-1,3-dihydro-benzo[c][1,2]oxaborol-3-yl}-acetic acid

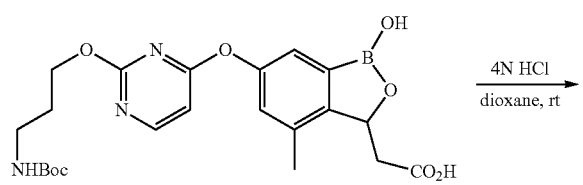

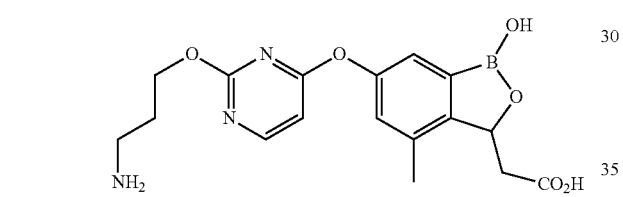

A solution of {6-[2-(3-tert-butoxycarbonylamino-propoxy)-pyrimidin-4-yloxy]-1-hydroxy-4-methyl-1,3-dihydro-benzo[c][1,2]oxaborol-3-yl}-acetic acid (0.3 g, 0.64 mmol) in 4M HCl in dioxane (3 mL) was stirred for 2 hours at room temperature. The reaction mixture was concentrated in vacuo and the residue purified by preparative HPLC to give {6-[2-(3-amino-propoxy)-pyrimidin-4-yloxy]-1-hydroxy-4-methyl-1,3-dihydro-benzo[c][1,2]oxaborol-3-yl}-acetic acid (0.1 g, 42%). ¹H NMR (400 MHz, DMSO): δ 8.46 (d, J=6.0 Hz, 1H), 8.04 (brs, 2H), 7.34 (d, J=2.0 Hz, 1H), 7.12 (d, J=2.0 Hz, 1H), 6.72 (d, J=5.6 Hz, 1H), 5.54 (dd, J=2.0, 9.6 Hz, 1H), 4.28 (t, J=6.0 Hz, 2H), 3.10 (dd, J=2.4 Hz, 15.6 Hz, 1H), 2.88-2.83 (m, 2H), 2.32 (s, 3H), 2.20-2.14 (m, 1H), 2.00-1.97 (m, 2H). MS (ESI) m/z=372 [M−H]⁻.

G76: [6-(6-Cyano-pyrimidin-4-yloxy)-1-hydroxy-4-methyl-1,3-dihydro-benzo[c][1,2]oxaborol-3-yl)-acetic acid

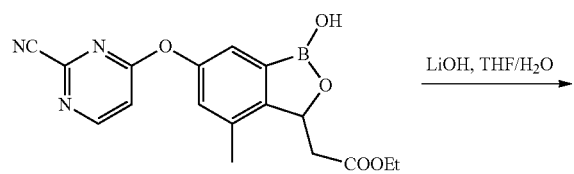

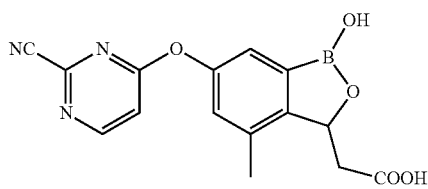

To a solution [6-(6-cyano-pyrimidin-4-yloxy)-1-hydroxy-4-methyl-1,3-dihydro-benzo[c][1,2]oxaborol-3-yl)-acetic acid ethyl ester (0.2 g, 0.556 mmol) in THF (3 mL) was added a solution of LiOH (0.041 g, 1.69 mmol) in water (3 mL) at 0° C. The resulting mixture was stirred at 0° C. for 5 hours, acidified to pH 2 using 6M hydrochloric acid and extracted with EtOAc. The organic extracts were washed with water, brine, dried over Na₂SO₄, and concentrated in vacuo. The residue was purified by preparative HPLC to give [6-(6-cyano-pyrimidin-4-yloxy)-1-hydroxy-4-methyl-1,3-dihydro-benzo[c][1,2]oxaborol-3-yl)-acetic acid as a white solid (0.015 g). ¹H NMR (400 MHz, DMSO-d δ 9.18 (s, 1H), 8.82 (d, J=10.0 Hz, 1H), 7.45 (d, J=6.0 Hz, 1H), 7.30 (s, 1H), 7.16 (s, 1H), 5.51 (m, 1H), 3.07 (m, 1H), 2.31 (s, 3H), 2.16 (m, 1H). MS (ESI) m/z: 324 [M−1]⁻. HPLC purity: 96.94% (Maxplot), 98.24% (220 nm).

G77: 2-(6-(6-Aminopyrimidin-4-yloxy)-1-hydroxy-4-methyl-1,3-dihydrobenzo[c][1,2]oxaborol-3-yl) acetic acid

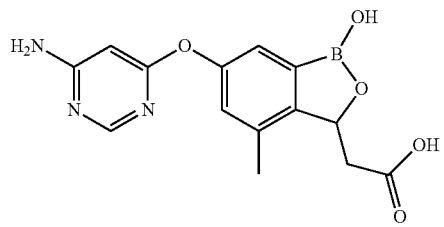 [SMILES: Cc1cc(Oc2cc(N)ncn2)cc2c1C(CC(=O)O)OB2O]

Step 1: Ethyl 2-(6-(6-aminopyrimidin-4-yloxy)-1-hydroxy-4-methyl-1,3-dihydrobenzo[c][1,2]oxaborol-3-yl)acetate

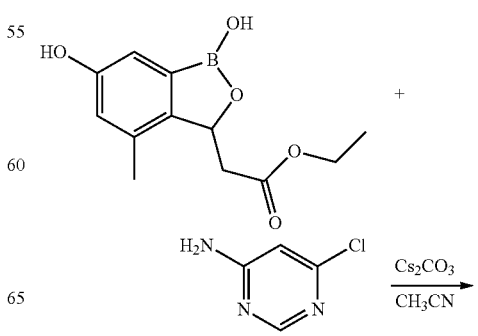

-continued

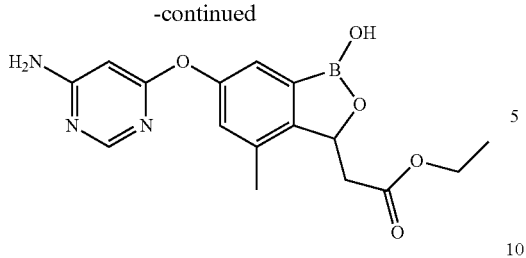

To the mixture of ethyl 2-(1,6-dihydroxy-4-methyl-1,3-dihydrobenzo[c][1,2]oxaborol-3-yl)acetate (1.04 g, 4 mmol) and 4-amino-6-chloropyrimidine (520 mg, 4 mmol) in $CH_3CN$ (20 ml), added $Cs_2CO_3$ (3.9 g, 12 mmol). The mixture was stirred at 50° C. for 24 hours. The result mixture was diluted with EtOAc (200 ml), washed with water and brine, dried over $Na_2SO_4$. Concentrated to give light yellow oil used for next step without further purification. MS (ESI negative): $(M-H)^-=342.1$.

Step 2: 2-(6-(6-Aminopyrimidin-4-yloxy)-1-hydroxy-4-methyl-1,3-dihydrobenzo[c][1,2]oxaborol-3-yl)acetic acid

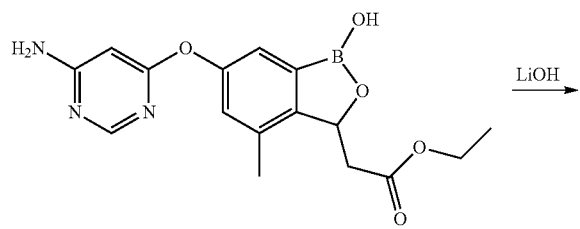

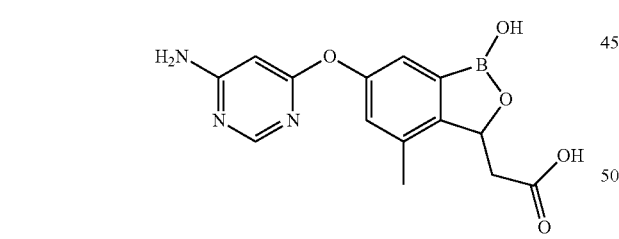

To the solution of crude methyl Ethyl 2-(6-(6-aminopyrimidin-4-yloxy)-1-hydroxy-4-methyl-1,3-dihydrobenzo[c][1,2]oxaborol-3-yl)acetate (105 mg, 0.3 mmol) in MeOH (5 ml), was added LiOH (1N, 1 ml, 1 mmol) at 0° C., then stirred at 40° C. overnight. The reaction mixture was quenched with HCl (1N, 1 ml). Removed solvent, the residue was purified by prep HPLC (SunFire Prep C18 OBD 5 uM 30×50 mm column). Title compound (3 mg) was obtained as light yellow powder. MS calcd for ($C_{14}H_{14}BN_3O_5$): 315.1, MS found (ESI negative): $(M-H)^-=314.1$. $^1H$ NMR (400 MHz, DMSO-$d_6$) δ (ppm): 12.33 (bs, 1H), 9.21 (bs, 1H), 8.01 (s, 1H), 7.20 (s, 1H), 7.04 (s, 1H), 6.92 (s, 1H), 5.71 (s, 1H), 5.50 (dd, J=9.6 Hz, 1H), 3.08 (dd, J=2.4 Hz, 1H), 2.29 (s, 3H), 2.14 (s, 1H).

G78: [1-Hydroxy-4-methyl-6-(pyrazin-2-yloxy)-1,3-dihydro-benzo[c][1,2]oxaborol-3-yl]-acetic acid

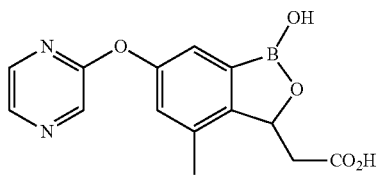 [SMILES: Cc1cc(Oc2cnccn2)cc2c1C(CC(=O)O)OB2O]

Step 1: [1-Hydroxy-4-methyl-6-(pyrazin-2-yloxy)-1,3-dihydro-benzo[c][1,2]oxaborol-3-yl]-acetic acid ethyl ester (G78a)

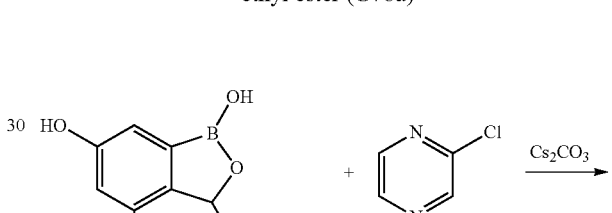

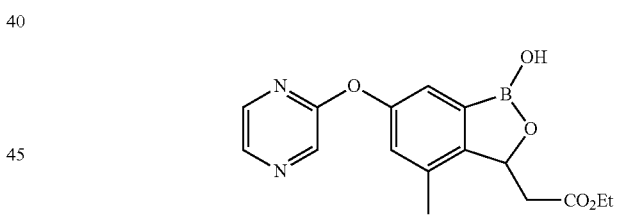

To a solution of (1,6-dihydroxy-4-methyl-1,3-dihydro-benzo[c][1,2]oxaborol-3-yl)acetic acid ethyl ester (0.5 g, 2.0 mmol) in anhydrous DMF (5 mL) were added $Cs_2CO_3$ (1.629 g, 5.0 mmol) and 2-chloro-pyrazine (0.275 g, 2.4 mmol) at room temperature. The reaction mixture was heated to 90° C. for 3 hours then poured into ice-water (10 mL). The mixture was acidified to pH 2 using dilute hydrochloric acid and extracted with ethyl acetate. The organic extracts were dried over sodium sulfate and concentrated in vacuo. The residue was purified by silica gel flash column chromatography (EtOAc/hexane/AcOH=3:2:trace) to give the product as an oil (0.250 g, 38.1%). $^1HNMR$ (400 MHz, DMSO-$d_6$) δ9.22 (s, 1H), 8.53 (d, J=1.17 Hz, 1H), 8.35 (d, J=2.64 Hz, 1H), 8.18 (dd, J=2.78, 1.32 Hz, 1H), 7.25 (d, J=2.05 Hz, 1H), 7.10 (d, J=1.46 Hz, 1H), 5.53 (dd, J=9.08, 2.34 Hz, 1H), 3.94-4.11 (m, 2H), 3.13 (dd, J=15.52, 2.63 Hz, 1H), 2.20-2.40 (m, 4H), 1.06-1.26 (m, 3H). MS (ESI) m/z=329 [M+H]+.

Step 2: [1-Hydroxy-4-methyl-6-(pyrazin-2-yloxy)-1,3-dihydro-benzo[c][1,2]oxaborol-3-yl]-acetic acid

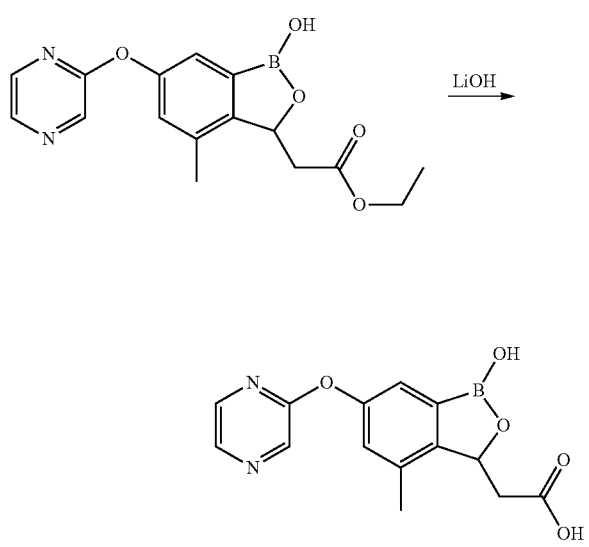

To a solution of [1-hydroxy-4-methyl-6-(pyrazin-2-yloxy)-1,3-dihydro-benzo[c][1,2]-oxaborol-3-yl]-acetic acid ethyl ester (0.250 g, 0.762 mmol) in methanol (5 mL) was added a solution of LiOH (0.091 g, 3.81 mmol) in water (4 mL) at 0° C. The resulting mixture was stirred at 0° C. for 3 hours. The reaction mixture was acidified to pH 2 using 6M HCl and extracted with EtOAc. The organic extracts were washed with brine, dried over sodium sulfate and concentrated in vacuo. The residue was purified by silica gel flash column chromatography (DCM/MeOH/AcOH=20:1:trace) to give pure product as a white powder after lyophilization (0.150 g, 65.6%). mp 156-157° C. $^1$HNMR (400 MHz, DMSO-d6 δ 9.20 (s, 1H), 8.53 (d, J=1.17 Hz, 1H), 8.35 (d, J=2.64 Hz, 1H), 8.19 (dd, J=2.63, 1.46 Hz, 1H), 7.25 (d, J=2.05 Hz, 1H), 7.10 (d, J=1.46 Hz, 1H), 5.51 (dd, J=9.51, 2.20 Hz, 1H), 3.07 (dd, J=15.52, 2.63 Hz, 1H), 2.28 (s, 3H), 2.13 (dd, 1H). MS (ESI) m/z=301 [M+H]+.

G79: (3R)-[1-Hydroxy-4-methyl-6-(pyrazin-2-yloxy)-1,3-dihydro-benzo[c][1,2]-oxaborol-3-yl]-acetic acid ethyl ester

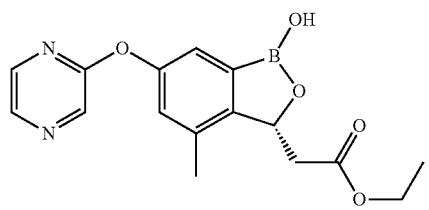 [SMILES: CCOC(=O)C[C@H]1OB(O)c2cc(Oc3cnccn3)cc(C)c21]

G80: (3S)-[1-hydroxy-4-methyl-6-(pyrazin-2-yloxy)-1,3-dihydro-benzo[c][1,2]-oxaborol-3-yl]-acetic acid ethyl ester

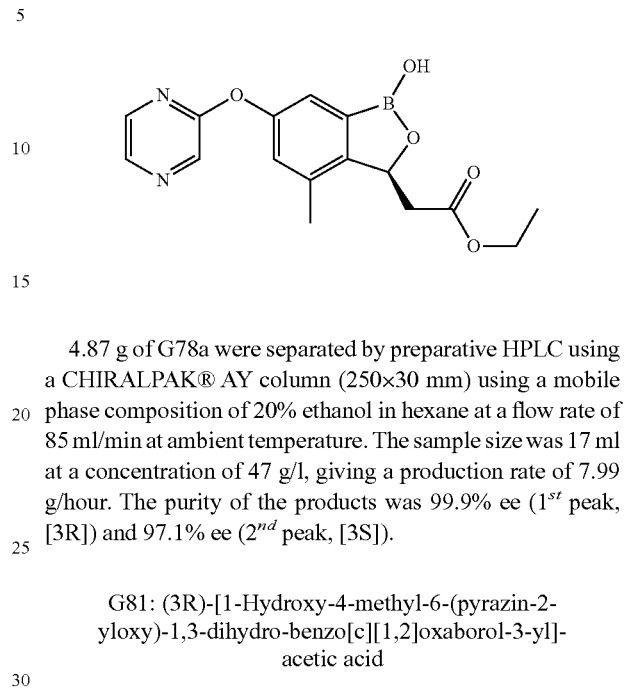

4.87 g of G78a were separated by preparative HPLC using a CHIRALPAK® AY column (250×30 mm) using a mobile phase composition of 20% ethanol in hexane at a flow rate of 85 ml/min at ambient temperature. The sample size was 17 ml at a concentration of 47 g/l, giving a production rate of 7.99 g/hour. The purity of the products was 99.9% ee (1$^{st}$ peak, [3R]) and 97.1% ee (2$^{nd}$ peak, [3S]).

G81: (3R)-[1-Hydroxy-4-methyl-6-(pyrazin-2-yloxy)-1,3-dihydro-benzo[c][1,2]oxaborol-3-yl]-acetic acid

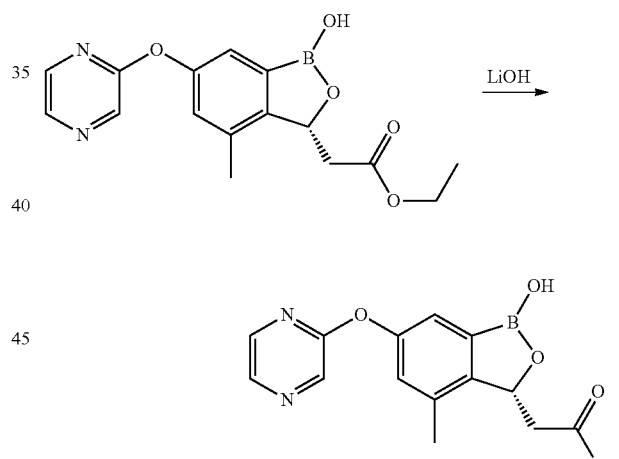

To a solution of (3R)-[1-hydroxy-4-methyl-6-(pyrazin-2-yloxy)-1,3-dihydro-benzo[c][1,2]-oxaborol-3-yl]-acetic acid ethyl ester (0.90 g, 2.74 mmol, 1st peak) in methanol (15 mL) was added a solution of LiOH (0.328 g, 13.7 mmol) in water (12 mL) at 0° C. The resulting mixture was stirred at room temperature for 3 hours then acidified to pH=2 with dilute hydrochloric acid and extracted with EtOAc (2×30 mL). The organic extracts were washed with brine, dried over sodium sulfate and concentrated in vacuo. The residue was purified by silica gel flash column chromatography (DCM/MeOH/AcOH=20:1:trace) to give pure product as a white powder after lyophilization (0.681 g, 82.8%). $^1$HNMR (400 MHz, DMSO-d δ 9.20 (s, 1H), 8.53 (d, J=1.17 Hz, 1H), 8.35 (d, J=2.64 Hz, 1H), 8.19 (dd, J=2.63, 1.46 Hz, 1H), 7.25 (d, J=2.05 Hz, 1H), 7.10 (d, J=1.46 Hz, 1H), 5.51 (dd, J=9.51, 2.20 Hz, 1H), 3.07 (dd, J=15.52, 2.63 Hz, 1H), 2.28 (s, 3H), 2.13 (dd, 1H). MS (ESI) m/z=301 [M+H]+.

G82: (3S)-[1-Hydroxy-4-methyl-6-(pyrazin-2-yloxy)-1,3-dihydro-benzo[c][1,2]oxaborol-3-yl]-acetic acid

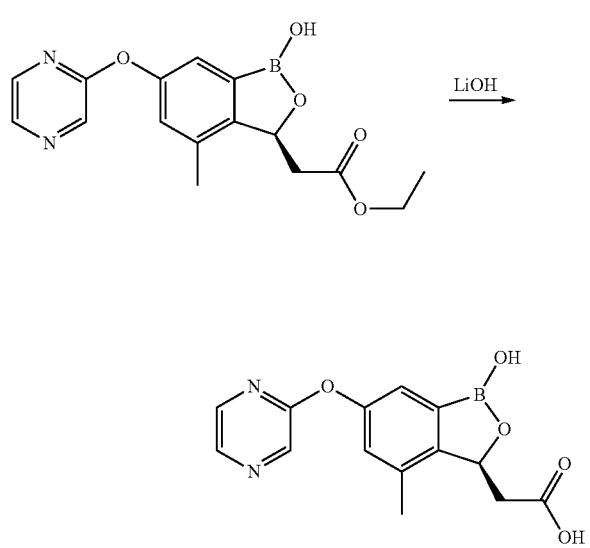

To a solution of 3S-[1-hydroxy-4-methyl-6-(pyrazin-2-yloxy)-1,3-dihydro-benzo[c][1,2]-oxaborol-3-yl]-acetic acid ethyl ester (1.00 g, 3.05 mmol, 2nd peak) in methanol (15 mL) was added a solution of LiOH (0.365 g, 15.2 mmol) in water (12 mL) at 0° C. The resulting mixture was stirred at room temperature for 3 hours then acidified to pH=2 with dilute hydrochloric acid and extracted with EtOAc (2×30 mL). The organic extracts were washed with brine, dried over sodium sulfate and concentrated in vacuo. The residue was purified by silica gel flash column chromatography (DCM/MeOH/AcOH=20:1:trace) to give pure product as a white powder after lyophilization (0.702 g, 76.7%). 1HNMR (400 MHz, DMSO-d6) δ 9.20 (s, 1H), 8.54 (d, J=1.17 Hz, 1H), 8.35 (d, J=2.64 Hz, 1H), 8.20 (dd, J=2.63, 1.46 Hz, 1H), 7.23 (d, J=2.05 Hz, 1H), 7.10 (d, J=1.46 Hz, 1H), 5.51 (dd, J=9.51, 2.20 Hz, 1H), 3.07 (dd, J=15.52, 2.63 Hz, 1H), 2.28 (s, 3H), 2.13 (dd, 1H). MS (ESI) m/z=301 [M+H]+.

G83: [4-Ethyl-1-hydroxy-6-(pyrazin-2-yloxy)-1,3-dihydro-benzo[c][1,2]oxaborol-3-yl]-acetic acid

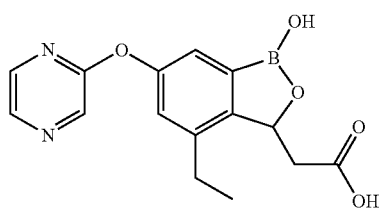 [SMILES: CCc1cc(Oc2cnccn2)cc2c1C(CC(=O)O)OB2O]

Step 1: [4-Ethyl-1-hydroxy-6-(pyrazin-2-yloxy)-1,3-dihydro-benzo[c][1,2]oxaborol-3-yl]-acetic acid ethyl ester

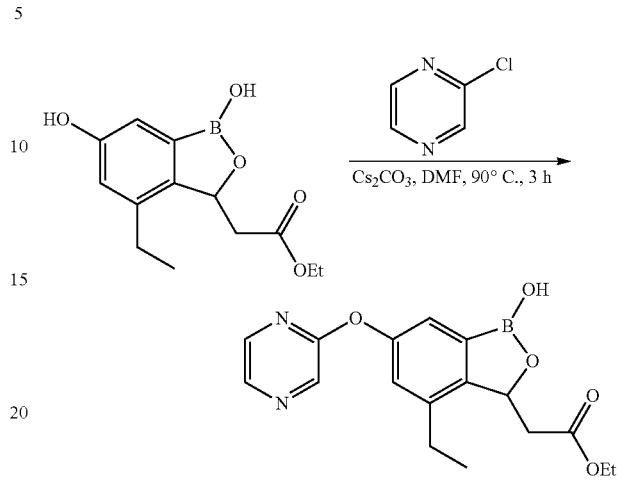

To a mixture of 4-ethyl-1,6-dihydroxy-1,3-dihydro-benzo[c][1,2]oxaborol-3-yl)-acetic acid ethyl ester (0.200 g, 0.75 mmol) in DMF (5 mL) was added Cs2CO3 (0.74 g, 2.25 mmol). The mixture was heated at 90° C. for 3 hours then concentrated in vacuo. The residue was purified by silica gel flash column chromatography to give [4-ethyl-1-hydroxy-6-(pyrazin-2-yloxy)-1,3-dihydro-benzo[c][1,2]oxaborol-3-yl]-acetic acid ethyl ester (0.110 g, 43%). 1H NMR (400 MHz, MeOD-d4) δ 8.40 (s, 1H), 8.27 (s, 1H), 8.10 (s, 1H), 7.20 (s, 1H), 7.10 (s, 1H), 5.65 (m, 1H), 4.10 (m, 2H), 3.13 (m, 1H), 2.68 (m, 2H), 2.44 (m, 1H), 1.27 (m, 6H).

Step 2: [4-Ethyl-1-hydroxy-6-(pyrazin-2-yloxy)-1,3-dihydro-benzo[c][1,2]oxaborol-3-yl]-acetic acid

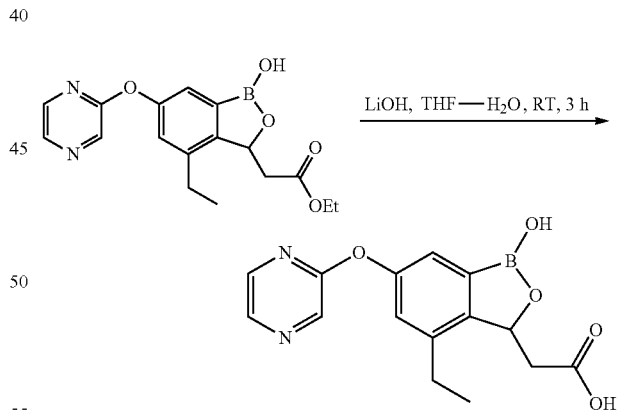

To a solution of [4-ethyl-1-hydroxy-6-(pyrazin-2-yloxy)-1,3-dihydro-benzo[c][1,2]oxaborol-3-yl]-acetic acid ethyl ester (0.11 g, 0.32 mmol) in THF (4 mL) and H2O (2 mL) was added LiOH (0.040 g) at 0° C. The resulting mixture was stirred at room temperature for 2 hours then cooled to 0° C. and acidified to pH 3 with 6N HCl. The mixture was concentrated in vacuo and the residue purified by silica gel flash column chromatography to give [4-ethyl-1-hydroxy-6-(pyrazin-2-yloxy)-1,3-dihydro-benzo[c][1,2]oxaborol-3-yl]-acetic acid (0.080 g, 80%). 1H NMR (400 MHz, DMSO-d6) δ 12.39 (s, 1H), 9.20 (s, 1H), 8.56 (s, 1H), 8.38 (s, 1H), 8.22 (s, 1H), 7.27 (s, 1H), 7.16 (s, 1H), 5.56 (s, 1H), 3.05 (M, 1H), 2.65 (m, 2H), 2.19 (M, 1H), 1.20 (M, 3H). MS (ES) m/z: 315 (M+1)⁺. HPLC purity: 99.19% (220 nm), 98.31% (Max-plot).

G84: 6-(6-Dimethylamino-pyrazin-2-yloxy)-1-hydroxy-4-methyl-1,3-dihydro benzo[c][1,2]oxaborol-3-yl)-acetic acid

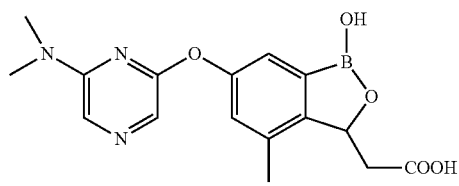 [SMILES: Cc1cc(Oc2cncc(N(C)C)n2)cc2c1C(CC(=O)O)OB2O]

Step 1: 6-(6-Chloro-pyrazin-2-yloxy)-1-hydroxy-4-methyl-1,3-dihydro benzo[c][1,2]oxaborol-3-yl)-acetic acid ethyl ester

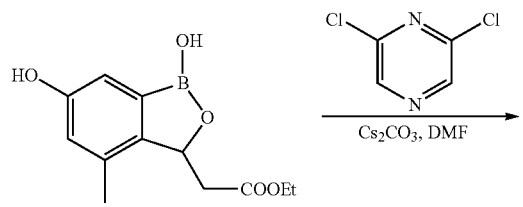

To a solution of (1,6-dihydroxy-4-methyl-1,3-dihydro-benzo[c][1,2]oxaborol-3-yl)-acetic acid ethyl ester (2.0 g, 8.0 mmol) in anhydrous DMF (40 mL) was added cesium carbonate (6.5 g, 20.0 mmol) and 2,6-dichloropyrazine (1.43 g, 9.6 mmol). The resulting mixture was stirred at room temperature for 4 days then quenched with crushed ice. The pH was adjusted to 2 with 6M HCl and the mixture extracted with EtOAc. The organic extracts were washed with water, brine, dried over Na₂SO₄, filtered, and concentrated in vacuo. The residue was purified by silica gel flash column chromatography (0-70% EtOAc in hexane) to give 6-(6-chloro-pyrazin-2-yloxy)-1-hydroxy-4-methyl-1,3-dihydro-benzo[c][1,2]oxaborol-3-yl)-acetic acid ethyl ester (1.9 g, 65.7%). ¹H NMR 400 MHz (DMSO-d₆) δ 9.30 (s, 1H), 8.55 (s, 1H), 8.51 (s, 1H), 7.30 (s, 1H), 7.18 (s, 1H), 5.57 (m, 1H), 4.05 (q, J=7.2, 2H), 3.18 (m, 1H), 2.40 (m, 1H), 2.35 (s, 3H), 1.18 (t, J=6.8 Hz, 3H).

Step 2: 6-(6-Dimethylamino-pyrazin-2-yloxy)-1-hydroxy-4-methyl-1,3-dihydro benzo[c][1,2]oxaborol-3-yl)-acetic acid ethyl ester

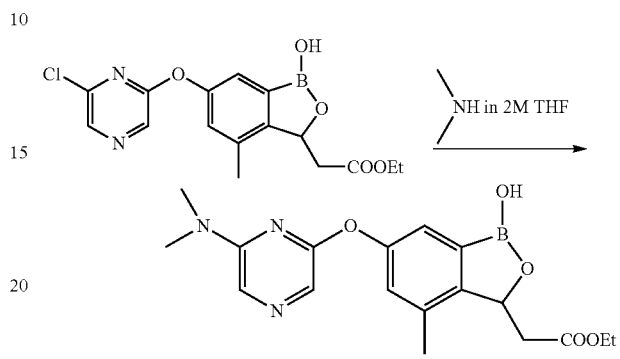

A solution of 6-(6-chloro-pyrazin-2-yloxy)-1-hydroxy-4-methyl-1,3-dihydro-benzo[c][1,2]oxaborol-3-yl)-acetic acid ethyl ester (0.3 g, 0.83 mmol) in 2M dimethylamine in THF (4.14 mL, 8.3 mmol) was heated at 65° C. for 18 hours. The reaction mixture was concentrated in vacuo and the residue purified by Biotage (2% MeOH in DCM) to give 6-(6-dimethylamino-pyrazin-2-yloxy)-1-hydroxy-4-methyl-1,3-dihydro-benzo[c][1,2]oxaborol-3-yl)-acetic acid ethyl ester (0.22 g, 71.6%). ¹H NMR 400 MHz (DMSO-d₆) δ 9.18 (s, 1H), 7.82 (s, 1H), 7.44 (s, 1H), 7.21 (s, 1H), 7.07 (s, 1H), 5.52 (m, 1H), 4.02 (q, J=7.2 Hz, 2H), 3.08 (m, 1H), 2.93 (s, 6H), 2.30 (m, 1H), 2.28 (s, 3H), 1.11 (t, J=6.8 Hz, 3H).

Step 3: 6-(6-Dimethylamino-pyrazin-2-yloxy)-1-hydroxy-4-methyl-1,3-dihydro benzo[c][1,2]oxaborol-3-yl)-acetic acid

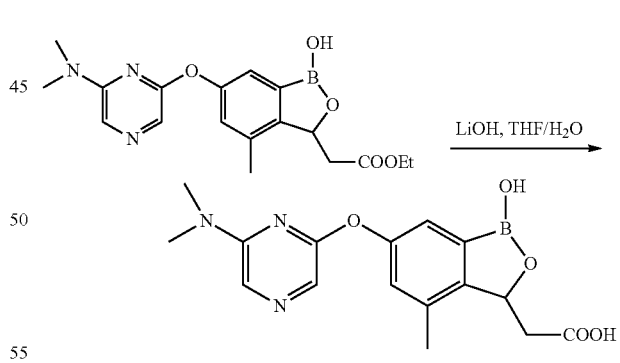

To a solution of 6-(6-dimethylamino-pyrazin-2-yloxy)-1-hydroxy-4-methyl-1,3-dihydro-benzo[c][1,2]oxaborol-3-yl)-acetic acid ethyl ester (0.22 g, 0.60 mmol) in tetrahydrofuran (10 mL) at 0° C. was added a solution of LiOH (0.073 g, 3.03 mmol) in water (5 mL). The solution was allowed to warm to room temperature and stirred for 2 hours then acidified to pH 2 with 6M HCl. The solution was extracted with ethyl acetate (2×50 mL) and the organic extracts were washed with water, brine, dried over sodium sulfate and concentrated in vacuo. The residue was purified by silica gel flash column chromatography (0-6% MeOH in DCM) to give 6-(6-dimethylamino-pyrazin-2-yloxy)-1-hydroxy-4-methyl-1,3-dihydro benzo[c][1,2]oxaborol-3-yl)-acetic acid as a white solid (0.12 g, 58%). mp 224-224.2° C. $^1$H NMR 400 MHz (DMSO-d$_6$) δ 9.15 (s, 1H), 7.84 (s, 1H), 7.45 (s, 1H), 7.23 (s, 1H), 7.09 (s, 1H), 5.50 (m, 1H), 3.08 (m, 1H), 2.95 (s, 6H), 2.29 (s, 3H), 2.13 (m, 1H). MS (ESI) m/z: 311 (M+1)$^+$. HPLC purity: 94.03% (Maxplot), 95.1% (220 nm).

G85: [6-(6-Chloro-pyrazin-2-yloxy)-1-hydroxy-4-methyl-1,3-dihydro-benzo[c][1,2]oxaborol-3-yl)-acetic acid

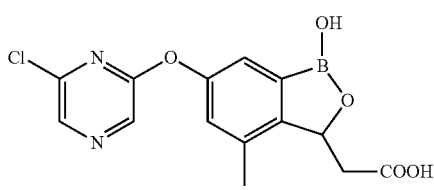 [SMILES: Cc1cc(Oc2cncc(Cl)n2)cc2c1C(CC(=O)O)OB2O]

Step 1: [6-(6-Chloro-pyrazin-2-yloxy)-1-Hydroxy-4-methyl-1,3-dihydro-benzo[c][1,2]oxaborol-3-yl)-acetic acid

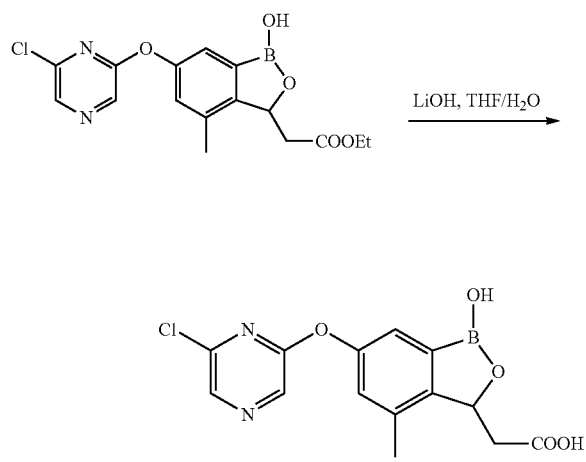

To a solution of [6-(6-chloro-pyrazin-2-yloxy)-1-hydroxy-4-methyl-1,3-dihydro-benzo[c][1,2]oxaborol-3-yl)-acetic acid ethyl ester (0.11 g, 0.30 mmol) in THF (3 mL) was added a solution of LiOH (0.036 g, 1.5 mmol) in water (1 mL) at 0° C. The resulting mixture was stirred at room temperature for 2 hours then acidified to pH 2 using 6M hydrochloric acid and extracted with EtOAc. The organic extracts were washed with water, brine, dried over Na$_2$SO$_4$, and concentrated in vacuo. The residue was purified by preparative HPLC to give [6-(6-chloro-pyrazin-2-yloxy)-1-hydroxy-4-methyl-1,3-dihydro-benzo[c][1,2]oxaborol-3-yl)-acetic acid as an off white solid (0.05 g, 50%). mp 187.2-188° C. $^1$H NMR (400 MHz, DMSO-d δ 12.34 (s, 1H), 9.26 (s, 1H), 8.54 (s, 1H), 8.51 (s, 1H), 7.31 (s, 1H), 7.17 (s, 1H), 5.55 (m, 1H), 3.10 (dd, J=15.60, 2.80 Hz, 1H), 2.32 (s, 3H), 2.16 (m, 1H). MS (ESI) m/z: 333 (M−1)$^−$. HPLC purity: 98.97% (Maxplot), 99.14% (220 nm).

G86: 2-(4-fluoro-1-hydroxy-6-(pyrazin-2-yloxy)-1,3-dihydrobenzo[c][1,2]oxaborol-3-yl)acetic acid

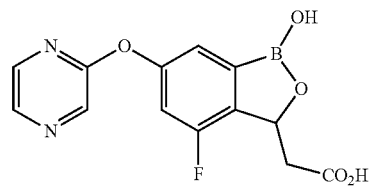 [SMILES: O=C(O)CC1OB(O)c2cc(Oc3cnccn3)cc(F)c21]

Step 1: Ethyl-2-(4-fluoro-1-hydroxy-6-(pyrazin-2-yloxy)-1,3-dihydrobenzo[c][1,2]oxaborol-3-yl)acetate

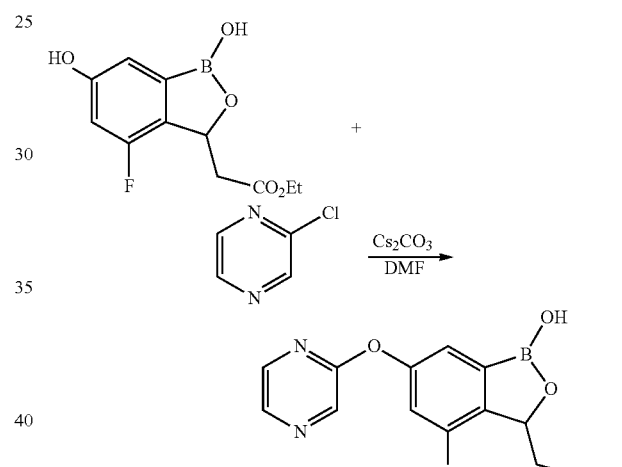

A mixture of ethyl-2-(4-fluoro-1,6-dihydroxy-1,3-dihydrobenzo[c][1,2]oxaborol-3-yl)acetate (0.25 g, 1.0 mmol), cesium carbonate (0.65 g, 2.0 mmol) and 2-chloropyrazine (0.17 g, 1.5 mmol) in DMF (3 mL) was heated to 90° C. for 3 hr. The reaction mixture was concentrated in vacuo and the residue was purified by column chromatography (EtOAc/PE=1/2) on silica gel to give the title compound as a light yellow solid (0.25 g, Yield: 76.7%). MS (ESI) m/z=333 [M+H]$^+$.

Step 2: 2-(4-fluoro-1-hydroxy-6-(pyrazin-2-yloxy)-1,3-dihydrobenzo[c][1,2]oxaborol-3-yl)acetic acid

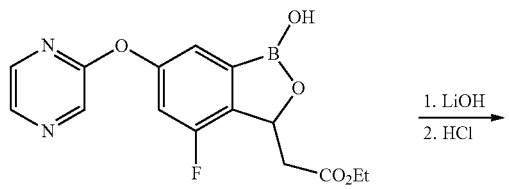

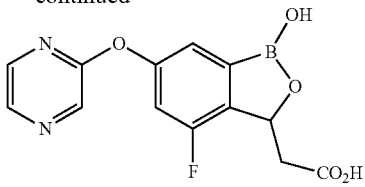

To a solution of ethyl-2-(4-fluoro-1-hydroxy-6-(pyrazin-2-yloxy)-1,3-dihydrobenzo[c][1,2]oxaborol-3-yl)acetate (166 mg, 0.50 mmol) in THF (2 mL) was added dropwise an aqueous solution of lithium hydroxide (102 mg, 2.5 mmol) in water (3 mL) at 0° C. The reaction mixture was stirred at room temperature for 1.5 h and acidified to pH=2 at 0° C. with a diluted HCl solution. The resulting mixture was extracted with ethyl acetate (2×15 mL), the combined organic layers were dried over anhydrous $Na_2SO_4$ and concentrated in vacuo. The residue was purified by HPLC to give the title compound as a white solid (21 mg, Yield: 13.8%). $^1$H NMR (400 MHz, DMSO-d) δ 12.50 (s, 1H), 9.50 (s, 1H), 8.61-8.62 (d, J=2.8 Hz, 1H), 8.42-8.43 (d, J=2.8 Hz, 1H), 8.24-8.25 (m, 1H), 7.31-7.33 (m, 1H), 5.61-5.64 (m, 1H), 2.97-3.02 (m, 1H), 2.37-2.43 (m, 1H). MS (ESI) m/z=305 [M+H]$^+$.

G87: 2-(4-Chloro-1-hydroxy-6-(pyrazin-2-yloxy)-1,3-dihydrobenzo[c][1,2]oxaborol-3-yl)acetic acid

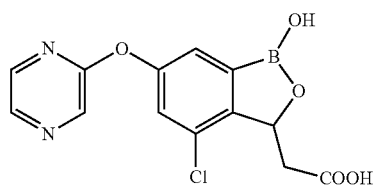 [SMILES: O=C(O)CC1OB(O)c2cc(Oc3cnccn3)cc(Cl)c21]

Step 1: Ethyl 2-(4-chloro-1-hydroxy-6-(pyrazin-2-yloxy)-1,3-dihydrobenzo[c][1,2]oxaborol-3-yl)-acetate

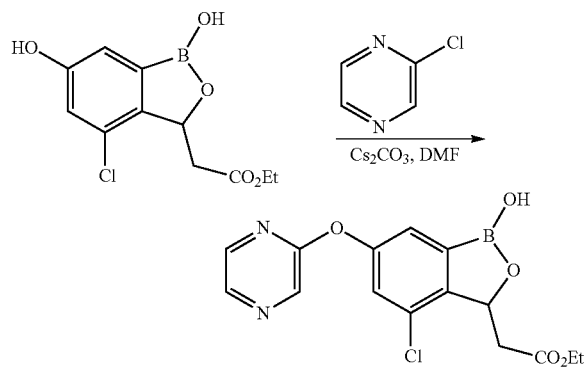

To a solution of ethyl 2-(4-chloro-1,6-dihydroxy-1,3-dihydrobenzo[c][1,2]oxaborol-3-yl)acetate (500 mg, 1.85 mmol) in DMF (5 mL) was added $Cs_2CO_3$ (1.51 g, 4.62 mmol) at room temperature, followed by 2-chloropyrazine (254 mg, 2.22 mL). The resulting mixture was stirred at 90° C. for 40 min. The mixture was poured into ice-water and acidified to pH=2 with diluted hydrochloric acid. The resulting mixture was extracted with EtOAc (2×25 mL), dried over anhydrous $Na_2SO_4$ and concentrated in vacuo. The residue was purified by HPLC to give the product (110 mg, yield: 32%). MS (ESI) m/z=349 [M+H]$^+$.

Step 2: 2-(4-chloro-1-hydroxy-6-(pyrazin-2-yloxy)-1,3-dihydrobenzo[c][1,2]oxaborol-3-yl)acetic acid

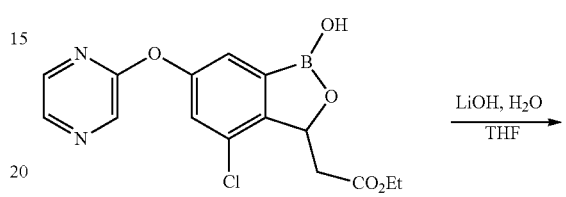

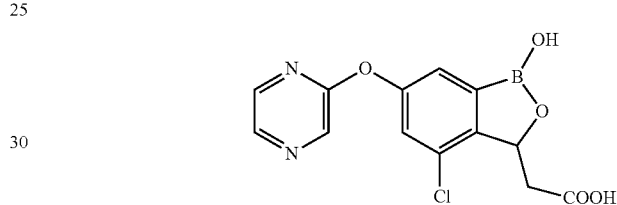

To the solution of ethyl 2-(4-chloro-1-hydroxy-6-(pyrazin-2-yloxy)-1,3-dihydrobenzo[c][1,2]oxaborol-3-yl)acetate (110 mg, 0.316 mmol) in THF (2 mL) was added an aqueous solution of lithium hydroxide (66 mg, 1.58 mmol) in water (1 mL) at 0° C. The resulting mixture was stirred at 0° C. for 2 h, acidified with diluted hydrochloric acid at 0° C. to pH=1~2 and extracted with EtOAc (2×20 mL). The combined organic layers were dried over anhydrous $Na_2SO_4$ and concentrated in vacuo. The residue was purified by prep HPLC to give the title compound as a white powder (66.9 mg, Yield: 83.5%). $^1$H NMR (400 MHz, DMSO-d6)δ 9.51 (s, 1H), 8.61 (s, 1H), 8.43 (s, 1H), 8.24 (s, 1H), 7.53 (s, 1H), 7.47 (s, 1H), 5.53-5.55 (d, J=8.4 Hz, 1H), 3.23-3.36 (d, J=15.6 Hz, 1H), 2.33-2.40 (m, 1H); MS (ESI) m/z=321 [M+H]$^+$.

G88: [6-(6-Aminomethyl-pyrazin-2-yloxy)-1-hydroxy-4-methyl-1,3-dihydro-benzo[c][1,2]oxaborol-3-yl)-acetic acid

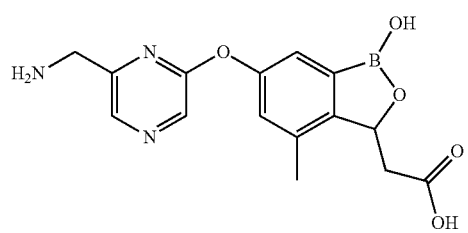 [SMILES: Cc1cc(Oc2cncc(CN)n2)cc2c1C(CC(=O)O)OB2O]

Step 1: [6-(6-Cyano-pyrazin-2-yloxy)-1-hydroxy-4-methyl-1,3-dihydro-benzo[c][1,2]oxaborol-3-yl)-acetic acid ethyl ester

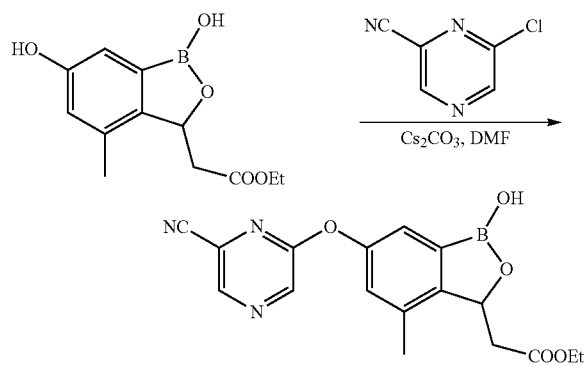

To a solution of (1,6-dihydroxy-4-methyl-1,3-dihydro-benzo[c][1,2]oxaborol-3-yl)-acetic acid ethyl ester (1.6 g, 6.4 mmol) in anhydrous DMF (15 mL) was added cesium carbonate (5.2 g, 16.0 mmol) and 6-chloro-pyrazine-2-carbonitrile (0.89 g, 6.4 mmol). The resulting mixture was stirred at room temperature overnight then quenched with crushed ice. The pH was adjusted to 2 with 6M HCl and the mixture extracted with EtOAc (2×200 mL). The organic extracts were washed with water, brine, dried over $Na_2SO_4$, filtered, and concentrated in vacuo. The residue was purified by silica gel flash column chromatography (0-75% EtOAc in hexane) to give 6-(6-cyano-pyrazin-2-yloxy)-1-hydroxy-4-methyl-1,3-dihydro-benzo[c][1,2]oxaborol-3-yl)-acetic acid ethyl ester (1.6 g, 71%). $^1$H NMR 400 MHz (DMSO-$d_6$) δ 9.30 (s, 1H), 8.93 (s, 1H), 8.90 (s, 1H), 7.33 (s, 1H), 7.18 (s, 1H), 5.58 (m, 1H), 4.05 (q, J=7.2, 2H), 3.17 (m, 1H), 2.40 (m, 1H), 2.33 (s, 3H), 1.13 (t, J=6.8 Hz, 3H).

Step 2: [6-(6-Aminomethyl-pyrazin-2-yloxy)-1-Hydroxy-4-methyl-1,3-dihydro-benzo[c][1,2]oxaborol-3-yl)-acetic acid ethyl ester

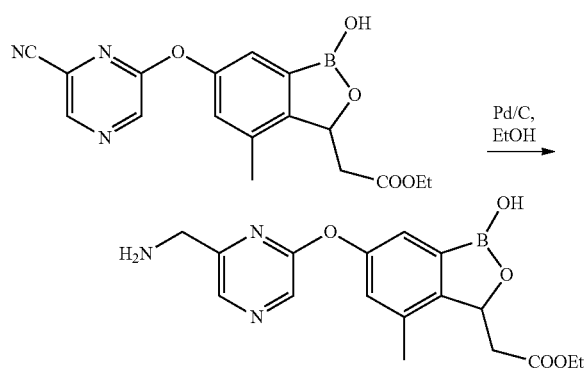

A solution of [6-(6-cyano-pyrazin-2-yloxy)-1-hydroxy-4-methyl-1,3-dihydro-benzo[c][1,2]oxaborol-3-yl)-acetic acid ethyl ester (1.35 g, 3.82 mmol), 10% Pd/C (1.35 g) and 6M HCl (2 drops) in EtOH (60 mL) was hydrogenated at 40 psi for 1 hour. The mixture was filtered through a pad of celite and the filtrate was concentrated in vacuo. The residue was purified by preparative HPLC to give [6-(6-aminomethyl-pyrazin-2-yloxy)-1-hydroxy-4-methyl-1,3-dihydro-benzo[c][1,2]oxaborol-3-yl)-acetic acid ethyl ester (0.16 g, 11.7%). $^1$H NMR (400 MHz, DMSO-d δ 8.42 (s, 1H), 8.32 (s, 1H), 8.25 (s, 1H), 7.30 (s, 1H), 7.17 (s, 1H), 7.00 (m, 1H), 5.58 (m, 1H), 3.80 (s, 2H), 3.18 (m, 1H), 2.38 (m, 4H), 1.17 (m, 3H).

Step 3: [6-(6-Aminomethyl-pyrazin-2-yloxy)-1-Hydroxy-4-methyl-1,3-dihydro-benzo[c][1,2]oxaborol-3-yl)-acetic acid

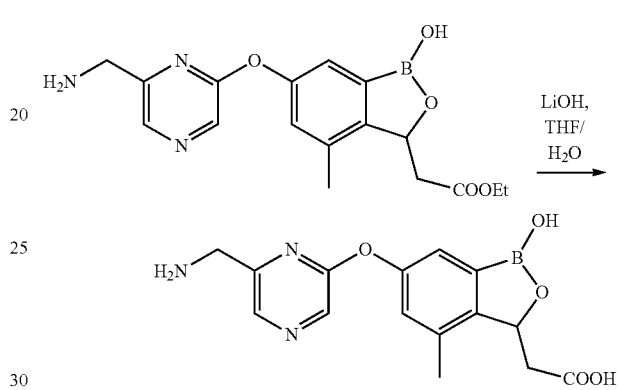

To a solution [6-(6-aminomethyl-pyrazin-2-yloxy)-1-hydroxy-4-methyl-1,3-dihydro-benzo[c][1,2]oxaborol-3-yl)-acetic acid ethyl ester (0.16 g, 0.448 mmol) in THF (3 mL) was added a solution of LiOH (0.054 g, 2.24 mmol) in water (3 mL) at 0° C. The resulting mixture was stirred at room temperature for 3 hours then concentrated in vacuo. The residue was purified by preparative HPLC then lyophilized to give [6-(2-aminomethyl-pyrazin-2-yloxy)-1-hydroxy-4-methyl-1,3-dihydro-benzo[c][1,2]oxaborol-3-yl)-acetic acid as an off white solid (0.025 g, 17%). $^1$H NMR (400 MHz, DMSO-$d_6$δ 8.44 (s, 1H), 8.32 (s, 1H), 8.25 (s, 1H), 7.24 (s, 1H), 7.07 (s, 1H), 5.47 (m, 1H), 3.83 (s, 2H), 3.02 (m, 1H), 2.27 (s, 3H), 2.10 (m, 1H). MS (ESI) m/z: 330 [M+1]$^+$. HPLC purity: 97.03% (Maxplot), 97.23% (220 nm).

G89: [6-(6-Cyano-pyrazin-2-yloxy)-1-hydroxy-4-methyl-1,3-dihydro-benzo[c][1,2]oxaborol-3-yl)-acetic acid and

G90: [6-(6-Carbamoyl-pyrazin-2-yloxy)-1-hydroxy-4-methyl-1,3-dihydro-benzo[c][1,2]oxaborol-3-yl)-acetic acid

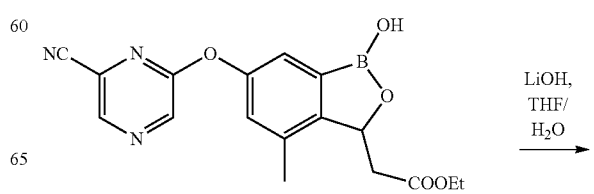

-continued

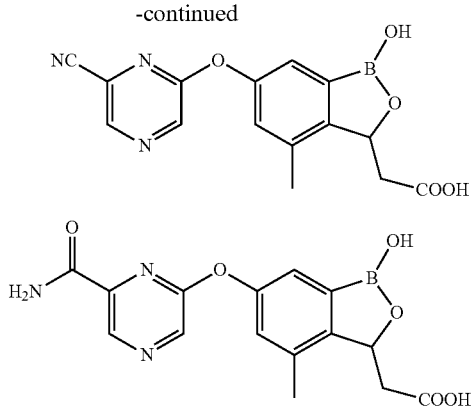

To a solution [6-(6-cyano-pyrazin-2-yloxy)-1-hydroxy-4-methyl-1,3-dihydro-benzo[c][1,2]oxaborol-3-yl)-acetic acid ethyl ester (0.2 g, 0.556 mmol) in THF (3 mL) was added a solution of LiOH (0.041 g, 1.69 mmol) in water (3 mL) at 0° C. The resulting mixture was stirred at 0° C. for 5 hours, acidified to pH 2 using 6M hydrochloric acid and extracted with EtOAc. The organic extracts were washed with water, brine, dried over $Na_2SO_4$, and concentrated in vacuo. The residue was purified by preparative HPLC to give [6-(6-cyano-pyrazin-2-yloxy)-1-hydroxy-4-methyl-1,3-dihydro-benzo[c][1,2]oxaborol-3-yl)-acetic acid as a white solid (0.067 g) and [6-(6-carbamoyl-pyrazin-2-yloxy)-1-hydroxy-4-methyl-1,3-dihydro-benzo[c][1,2]oxaborol-3-yl)-acetic acid as a white solid (0.025 g).

[6-(6-cyano-pyrazin-2-yloxy)-1-hydroxy-4-methyl-1,3-dihydro-benzo[c][1,2]oxaborol-3-yl)-acetic acid $^1$H NMR (400 MHz, DMSO-d δ 9.33 (s, 1H), 8.99 (s, 1H), 8.95 (s, 1H), 7.39 (s, 1H), 7.24 (s, 1H), 5.61 (m, 1H), 3.17 (m, 1H), 2.38 (s, 3H), 2.24 (m, 1H). MS (ESI) m/z: 324 [M−1]$^−$. HPLC purity: 97.70% (Maxplot), 97.94% (220 nm).

[6-(6-carbamoyl-pyrazin-2-yloxy)-1-hydroxy-4-methyl-1,3-dihydro-benzo[c][1,2]oxaborol-3-yl)-acetic acid $^1$H NMR (400 MHz, DMSO-d δ 9.20 (s, 1H), 8.87 (s, 1H), 8.60 (s, 1H), 7.81 (s, 1H), 7.57 (s, 1H), 7.32 (s, 1H), 7.18 (s, 1H), 5.50 (m, 1H), 3.09 (m, 1H), 2.30 (s, 3H), 2.17 (m, 1H). MS (ESI) m/z: 344 [M+1]$^+$. HPLC purity: 98.23% (Maxplot), 98.78% (220 nm).

G91: [6-(3-Aminomethyl-pyrazin-2-yloxy)-1-hydroxy-4-methyl-1,3-dihydro-benzo[c][1,2]oxaborol-3-yl]-acetic acid

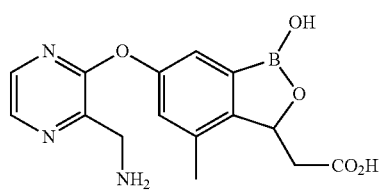 [SMILES: Cc1cc(Oc2nccnc2CN)cc2c1C(CC(=O)O)OB2O]

Step 1: [6-(3-Cyano-pyrazin-2-yloxy)-1-hydroxy-4-methyl-1,3-dihydro-benzo[c][1,2]oxaborol-3-yl]-acetic acid ethyl ester

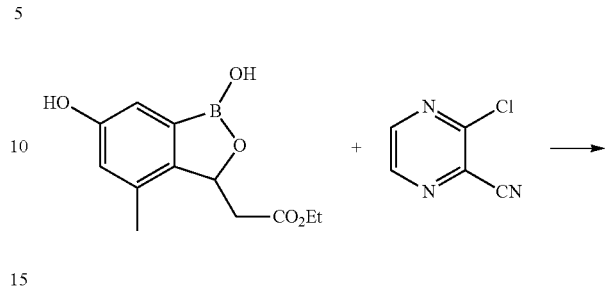

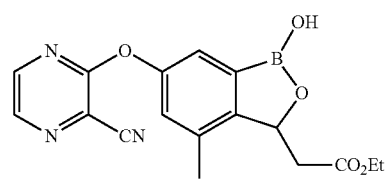

To a solution of ethyl 2-(1,6-dihydroxy-4-methyl-1,3-dihydrobenzo[c][1,2]oxaborol-3-yl)acetate (1.0 g, 4.0 mmol) and 3-chloro-pyrazine-2-carbonitrile (0.84 g, 6.0 mmol) in DMF (24 mL) was added cesium carbonate (2.68 g, 8.8 mmol). The mixture was heated to 80° C. for 2 hrs. The reaction was cooled down, diluted with $H_2O$, acidified to pH 3 with aqueous HCl (1N). The mixture was extracted with ethyl acetate. The organic phase was separated, dried ($Na_2SO_4$), and concentrated. The residue was purified by column chromatography (silica, Hexanes/Ethyl acetate=1:4) affording the title compound (1.30 g, 92%) as a white solid. $^1$H NMR (CDCl$_3$) δ 8.40 (d, 1H), 8.29 (d, 1H), 7.36 (d, 1H), 7.11 (d, 1H), 5.69 (dd, 1H), 4.81 (s, 1H), 4.20 (q, 2H), 3.11 (dd, 1H), 2.44 (dd, 1H), 2.39 (s, 3H), 1.26 (t, 3H). MS found: (M+H)$^+$=354.

Step 2: [6-(3-Aminomethyl-pyrazin-2-yloxy)-1-hydroxy-4-methyl-1,3-dihydro-benzo[c][1,2]oxaborol-3-yl]-acetic acid ethyl ester

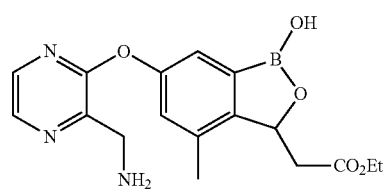 [SMILES: CCOC(=O)CC1OB(O)c2cc(Oc3nccnc3CN)cc(C)c21]

To a solution of [6-(3-cyano-pyrazin-2-yloxy)-1-hydroxy-4-methyl-1,3-dihydro-benzo[c][1,2]oxaborol-3-yl]-acetic acid ethyl ester (200 mg, 0.566 mmol) in MeOH (10 mL) was added Pd/C (20 mg), HCl (conc., 2 drops). The resulting solution was degassed, and reacted under 1-atm H$_2$ balloon for 6 hrs. The mixture was filtrated. The filtration was removed in vacuo to afford the title compound (190 mg, 94%) as a light yellow solid. MS found: (M+H)⁺=358.

Step 3: [6-(3-Aminomethyl-pyrazin-2-yloxy)-1-hydroxy-4-methyl-1,3-dihydro-benzo[c][1,2]oxaborol-3-yl]-acetic acid

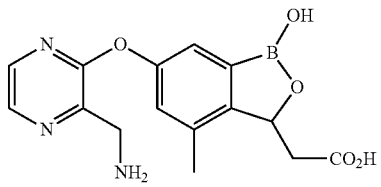 [SMILES: Cc1cc(Oc2nccnc2CN)cc2c1C(CC(=O)O)OB2O]

To a solution of [6-(3-aminomethyl-pyrazin-2-yloxy)-1-hydroxy-4-methyl-1,3-dihydro-benzo[c][1,2]oxaborol-3-yl]-acetic acid ethyl ester (190 mg, 0.532 mmol) in THF (5 mL) and H$_2$O (2 mL) was added LiOH (0.111 g, 2.66 mmol). The resulting solution was stirred at room temperature overnight. The mixture was diluted with H$_2$O and acidified to pH 3 with 1N HCl. The resulting mixture was concentrated and the residue was purified by prep HPLC. The title compound was obtained (100 mg, 57%) as a white solid. ¹H NMR (CD$_3$OD) δ 8.30 (d, 1H), 8.07 (d, 1H), 7.21 (d, 1H), 7.09 (d, 1H), 5.66 (dd, 1H), 4.47 (s, 2H), 3.14 (dd, 1H), 2.37 (s, 3H), 2.30 (dd, 1H). MS calcd for (C$_{15}$H$_{16}$BN$_3$O$_5$+H)⁺: 330. MS found: (M+H)⁺=330.

G92: [6-(3-Cyano-pyrazin-2-yloxy)-1-hydroxy-4-methyl-1,3-dihydro-benzo[c][1,2]oxaborol-3-yl]-acetic acid

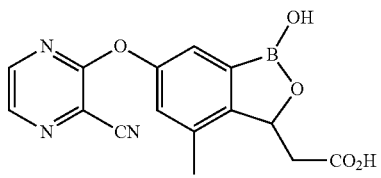 [SMILES: Cc1cc(Oc2nccnc2C#N)cc2c1C(CC(=O)O)OB2O]

To a solution of [6-(3-cyano-pyrazin-2-yloxy)-1-hydroxy-4-methyl-1,3-dihydro-benzo[c][1,2]oxaborol-3-yl]-acetic acid ethyl ester (200 mg, 0.566 mmol) in THF (5 mL) and H$_2$O (2 mL) was added LiOH (0.120 g, 2.83 mmol). The resulting solution was stirred at 0° C. for 2 hrs. The mixture was diluted with H$_2$O and acidified to pH 3 with 1N HCl at 0° C. The resulting mixture was extracted with ethyl acetate. The organic phase was separated, dried (Na$_2$SO$_4$), and concentrated. The title compound was obtained (150 mg, 82%) as a white solid. ¹H NMR (CD$_3$OD) δ 8.42 (d, 1H), 8.38 (d, 1H), 7.32 (d, 1H), 7.18 (d, 1H), 5.65 (dd, 1H), 3.20 (dd, 1H), 2.41 (s, 3H), 2.36 (dd, 1H). MS found: (M+H)⁺: 326.

G93: [6-(5-Cyano-pyrazin-2-yloxy)-1-hydroxy-4-methyl-1,3-dihydro-benzo[c][1,2]oxaborol-3-yl]-acetic acid

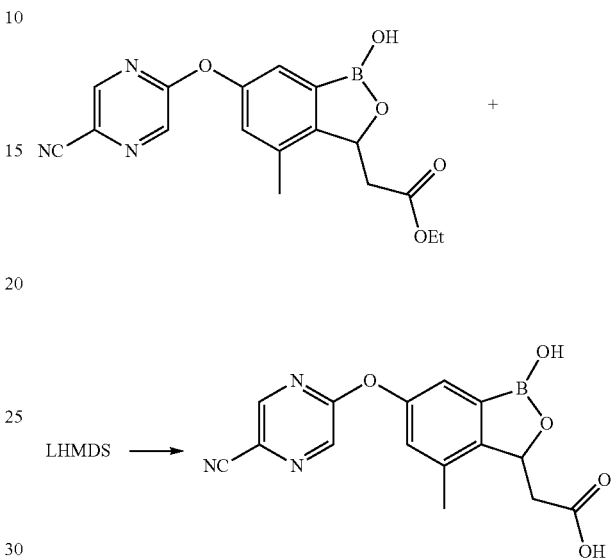

[6-(5-Cyano-pyrazin-2-yloxy)-1-hydroxy-4-methyl-1,3-dihydro-benzo[c][1,2]oxaborol-3-yl]-acetic acid ethyl ester (100 mg, 0.28 mmol) was dissolved in THF (4 mL) and cooled to 0° C. To this was added LHMDS (1M in THF, 0.28 mL, 0.28 mmol) and stirred at 0° C. for 1 h. Another portion of LHMDS (1M in THF, 0.28 mL, 0.28 mmol) was added at 0° C. The reaction was stirred at 0° C. for 2 h and was allowed to warm up to room temperature. The reaction was stirred at room temperature for 6 h. The solvent was removed. Preparative HPLC (C18 column) gave the title compound (33 mg, 36%) as a white solid. MS (ESI) m/z: 326 [M+1]⁺; ¹H NMR (300 MHz, CD$_3$OD) δ 8.56 (1H, s), 8.50 (1H, s), 7.28 (1H, s), 7.15 (1H, s), 5.65 (1H, dd), 3.18 (1H, dd), 2.35 (3H, s), 2.30 (1H, m).

G94: 3-(3-Carboxymethyl-1-hydroxy-4-methyl-1,3-dihydro-benzo[c][1,2]oxaborol-6-yloxy)-pyrazine-2-carboxylic acid

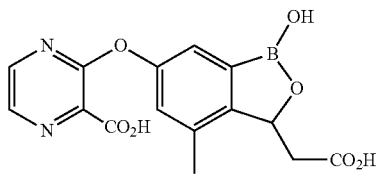 [SMILES: Cc1cc(Oc2nccnc2C(=O)O)cc2c1C(CC(=O)O)OB2O]

To a solution of [6-(3-cyano-pyrazin-2-yloxy)-1-hydroxy-4-methyl-1,3-dihydro-benzo[c][1,2]oxaborol-3-yl]-acetic acid ethyl ester (100 mg, 0.283 mmol) in THF (3 mL) was added NaOH (1N in H$_2$O, 2.0 mL). The resulting solution was stirred at room temperature overnight. The mixture was diluted with H₂O and acidified to pH 3 with 1N HCl at 0° C. The resulting mixture was extracted with ethyl acetate. The organic phase was separated, dried (Na₂SO₄), and concentrated. The crude mixture was purified by prep HPLC to give the title compound (150 mg, 82%) as a white solid. $^1$H NMR (CD₃OD) δ 8.33 (d, 1H), 8.23 (d, 1H), 7.20 (d, 1H), 7.08 (d, 1H), 5.64 (dd, 1H), 3.15 (dd, 1H), 2.34 (s, 3H), 2.26 (dd, 1H). MS found: (M+H)⁺: 345.

G95: [6-(5-Aminomethyl-pyrazin-2-yloxy)-1-hydroxy-4-methyl-1,3-dihydro-benzo[c][1,2]oxaborol-3-yl]-acetic acid

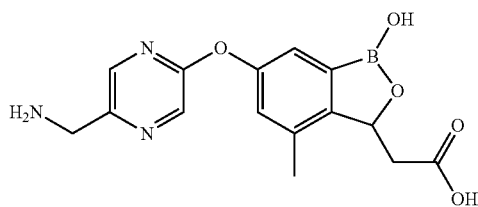 [SMILES: Cc1cc(Oc2cnc(CN)cn2)cc2c1C(CC(=O)O)OB2O]

Step 1: [6-(5-Cyano-pyrazin-2-yloxy)-1-hydroxy-4-methyl-1,3-dihydro-benzo[c][1,2]oxaborol-3-yl]-acetic acid ethyl ester

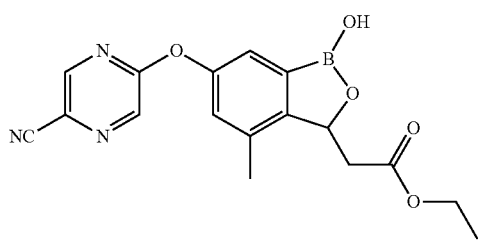 [SMILES: CCOC(=O)CC1OB(O)c2cc(Oc3cnc(C#N)cn3)cc(C)c21]

To a solution of (1,6-dihydroxy-4-methyl-1,3-dihydro-benzo[c][1,2]oxaborol-3-yl)-acetic acid ethyl ester (3.68 g, 20.0 mmol) in THF (60 mL) was treated with NaH (1.20 g, 30.0 mmol) at 0° C. The resulting suspension was stirred at room temperature 15 min and 5-bromo-pyrazine-2-carbonitrile was added. The reaction was stirred at room temperature for 3 h. The suspension was quenched with 1N HCl and extracted with ethyl acetate. The organic phase was separated, dried (Na₂SO₄), and concentrated. The residue was purified by the flash column chromatography (silica, hexanes/ethyl acetate=1:1) to afford the title compound (1.63 g). $^1$H NMR (300 MHz, CD₃OD) δ 8.58 (s, 1H), 8.55 (s, 1H), 7.29 (s, 1H), 7.16 (s, 1H), 5.73-5.69 (m, 1H), 4.16 (q, 2H), 3.27-3.18 (m, 1H), 2.56-2.48 (m, 1H), 2.41 (s, 3H), 1.23 (t, 3H). MS found: (M+H)⁺=354.1.

Step 2: 6-(5-Aminomethyl-pyrazin-2-yloxy)-1-hydroxy-4-methyl-1,3-dihydro-benzo[c][1,2]oxaborol-3-yl]-acetic acid ethyl ester

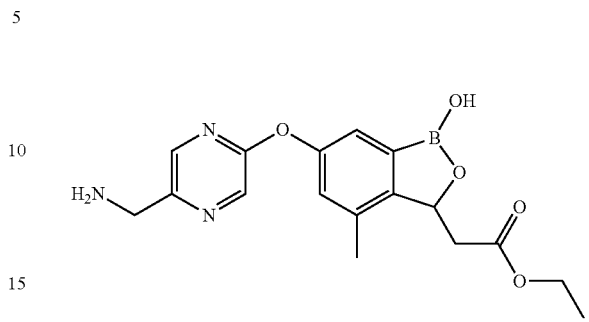

To a mixture of [6-(5-cyano-pyrazin-2-yloxy)-1-hydroxy-4-methyl-1,3-dihydro-benzo[c][1,2]oxaborol-3-yl]-acetic acid ethyl ester (1.63 g) and Pd/C (250 mg) in methanol (80 mL) was degassed 3 times and the suspension was charged with H₂ balloon at room temperature overnight. The reaction mixture was filtered through a pad of Celite and the filtrate was concentrated to dryness, affording the title compound (1.45 g). $^1$H NMR (300 MHz, CD₃OD) δ 8.49 (s, 1H), 8.44 (s, 1H), 8.21 (s, 1H), 7.21 (s, 1H), 7.10 (s, 1H), 5.70-5.66 (m, 1H), 4.29 (s, 2H), 4.19 (q, 2H), 3.22-3.16 (m, 1H), 2.54-2.46 (m, 1H), 2.40 (s, 3H), 1.24 (t, 3H). MS found: (M+H)⁺=358.2.

Step 3: 6-(5-Aminomethyl-pyrazin-2-yloxy)-1-hydroxy-4-methyl-1,3-dihydro-benzo[c][1,2]oxaborol-3-yl]-acetic acid

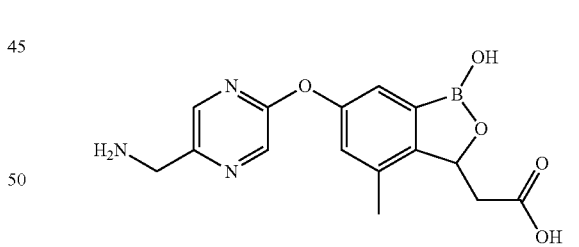

A solution of [6-(5-aminomethyl-pyrazin-2-yloxy)-1-hydroxy-4-methyl-1,3-dihydro-benzo[c][1,2]oxaborol-3-yl]-acetic acid ethyl ester (700 mg, 2.24 mmol) in THF (16 mL) was treated with LiOH (470 mg, 11.2 mmol) in water (8 mL) at room temperature for 2 h. The reaction was concentrated to dryness. The residue was diluted with water and adjusted to pH 3. The mixture was purified by preparative HPLC to give the title compound (250 mg). $^1$H NMR (300 MHz, CD₃OD) δ 8.48 (s, 1H), 8.35 (s, 1H), 8.21 (s, 1H), 7.18 (s, 1H), 7.07 (s, 1H), 5.70-5.63 (m, 1H), 4.29 (s, 2H), 3.18-3.12 (m, 1H), 2.40 (s, 3H), 2.36-2.28 (m, 1H). MS found: (M+H)⁺=330.1.

G96: [6-(5-tert-Butoxycarbonylamino-pyrazin-2-yloxy)-1-hydroxy-4-methyl-1,3-dihydro-benzo[c][1,2]oxaborol-3-yl]-acetic acid

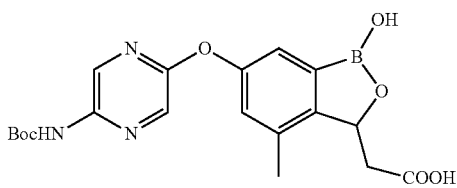 [SMILES: Cc1cc(Oc2cnc(NC(=O)OC(C)(C)C)cn2)cc2c1C(CC(=O)O)OB2O]

Step 1: 5-(3-Ethoxycarbonylmethyl-1-hydroxy-4-methyl-1,3-dihydro-benzo[c][1,2]oxaborol-6-yloxy)-pyrazine-2-carboxylic acid methyl ester

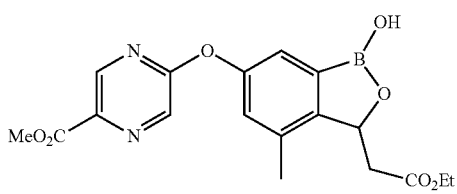 [SMILES: CCOC(=O)CC1OB(O)c2cc(Oc3cnc(C(=O)OC)cn3)cc(C)c21]

To a solution of (1,6-dihydroxy-4-methyl-1,3-dihydro-benzo[c][1,2]oxaborol-3-yl)-acetic acid ethyl ester (2 g, 8 mmol) and methyl 2-chloro-5-pyrazinecarboxylate (1.95 g, 12 mmol) in DMF (40 mL) at 0° C. was added NaH (0.8 g, 20 mmol). The reaction mixture was allowed to warm up to room temperature slowly and heated at 50° C. for 1 h. The reaction mixture was cooled down and acidified to pH 3 with 6N HCl, extracted with ethyl acetate. The organic layer was washed with water and brine, and dried over $Na_2SO_4$ and concentrated. The residue was purified by column chromatography (silica, DCM/MeOH=9:1) affording the title compound (1.9 g, 61%) as a light yellow solid. $^1$H NMR (CDCl$_3$) δ 8.82 (s, 1H), 8.53 (s, 1H), 7.38 (d, 1H), 7.07 (d, 1H), 5.69 (dd, 1H), 4.10 (q, 2H), 4.02 (s, 3H), 3.06 (dd, 1H), 2.43 (m, 1H), 2.39 (s, 3H), 1.23 (t, 3H).

Step 2: 5-(3-Ethoxycarbonylmethyl-1-hydroxy-4-methyl-1,3-dihydro-benzo[c][1,2]oxaborol-6-yloxy)-pyrazine-2-carboxylic acid

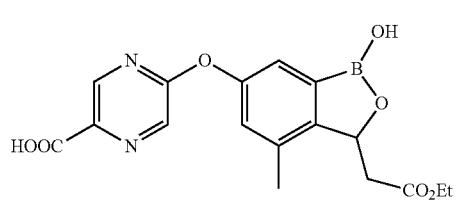 [SMILES: CCOC(=O)CC1OB(O)c2cc(Oc3cnc(C(=O)O)cn3)cc(C)c21]

To a solution of 5-(3-ethoxycarbonylmethyl-1-hydroxy-4-methyl-1,3-dihydro-benzo[c][1,2]oxaborol-6-yloxy)-pyrazine-2-carboxylic acid methyl ester (2.15 g, 11.3 mmol) in THF (42 mL) was added LiOH (0.47 g, 22.6 mmol) in water (21 mL). The mixture was stirred at room temperature for 1 h and acidified by 1N HCl to pH 3. The mixture was extracted by ethyl acetate, and the organic layer was washed with water and brine, dried from $Na_2SO_4$ and concentrated. The residue was purified by column chromatography (silica, DCM/MeOH=9:1) affording the title compound (1.9 g, 92%) as a white solid. $^1$H NMR (CDCl$_3$) δ 8.96 (s, 1H), 8.42 (s, 1H), 7.31 (d, 1H), 7.03 (d, 1H), 5.68 (dd, 1H), 4.10 (q, 2H), 3.11 (dd, 1H), 2.43 (m, 1H), 2.40 (s, 3H), 1.25 (t, 3H).

Step 3: tert-Butoxycarbonylamino-pyrazin-2-yloxy)-1-hydroxy-4-methyl-1,3-dihydro-benzo[c][1,2]oxaborol-3-yl]-acetic acid ethyl ester

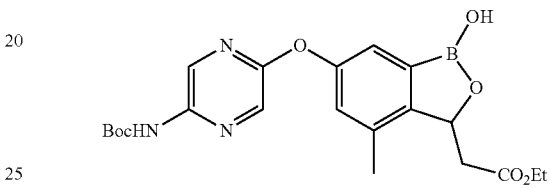

To a solution of 5-(3-ethoxycarbonylmethyl-1-hydroxy-4-methyl-1,3-dihydro-benzo[c][1,2]oxaborol-6-yloxy)-pyrazine-2-carboxylic acid (500 mg, 1.34 mmol) in tBuOH (10 mL) was added diphenylphosphoryl azide (0.35 mL, 1.61 mmol) and triethylamine (0.41 mL, 2.95 mmol). The reaction mixture was heated to 95° C. for 2 h. The solvent was removed under vacuum and the residue was extracted with ethyl acetate, washed with water and brine. The organic portion was dried by $Na_2SO_4$ and concentrated. The residue was purified by column chromatography (silica, DCM/MeOH=20:1) affording the title compound (155 mg, 27%) as a white solid. $^1$H NMR (CDCl$_3$) δ 8.79 (s, 1H), 8.02 (s, 1H), 7.20 (d, 1H), 7.03 (d, 1H), 5.63 (dd, 1H), 4.19 (q, 2H), 3.08 (dd, 1H), 2.42 (m, 1H), 2.38 (s, 3H), 1.57 (s, 9H), 1.26 (t, 3H).

Step 4: [6-(5-tert-Butoxycarbonylamino-pyrazin-2-yloxy)-1-hydroxy-4-methyl-1,3-dihydro-benzo[c][1,2]oxaborol-3-yl]-acetic acid

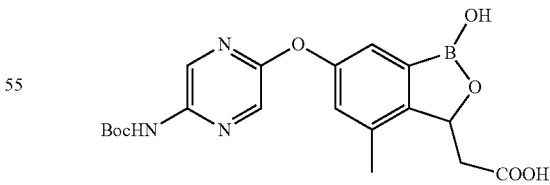

To a solution of tert-butoxycarbonylamino-pyrazin-2-yloxy)-1-hydroxy-4-methyl-1,3-dihydro-benzo[c][1,2]oxaborol-3-yl]-acetic acid ethyl ester (160 mg, 0.36 mmol) in THF (5 mL) was added LiOH (90 mg, 2.16 mmol) in water (2.5 mL). The mixture was stirred at room temperature for 5 h and acidified by 1N HCl to pH 3. The mixture was extracted by ethyl acetate. The organic layer was washed with water and brine, dried over Na₂SO₄ and concentrated. The residue was purified by HPLC affording the title compound (110 mg, 73%) as a white solid. ¹H NMR (CD₃OD) δ 8.26 (s, 1H), 7.61 (s, 1H), 6.74 (d, 1H), 6.60 (d, 1H), 5.22 (dd, 1H), 2.91 (m, 1H), 2.70 (dd, 1H), 1.91 (s, 3H), 1.10 (s, 9H). MS found: $(M+H)^+=416.2$.

G97: [6-(5-Carbamimidoyl-pyrazin-2-yloxy)-1-hydroxy-4-methyl-1,3-dihydro-benzo[c]oxaborol-3-yl]-acetic acid

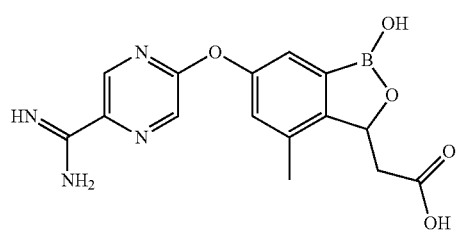 [SMILES: Cc1cc(Oc2cnc(C(=N)N)cn2)cc2c1C(CC(=O)O)OB2O]

Step 1: {1-Hydroxy-6-[5-(N-hydroxycarbamimidoyl)-pyrazin-2-yloxy]-4-methyl-1,3-dihydro-benzo[c][1,2]oxaborol-3-yl}-acetic acid ethyl ester

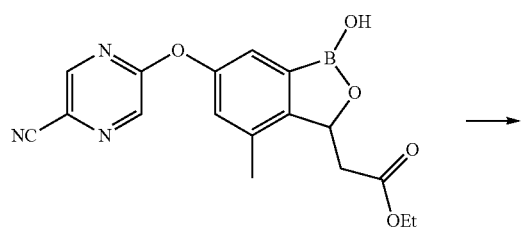

[6-(5-Cyano-pyrazin-2-yloxy)-1-hydroxy-4-methyl-1,3-dihydro-benzo[c][1,2]oxaborol-3-yl]-acetic acid ethyl ester (200 mg, 0.57 mmol) and hydroxylamine hydrochloride (99 mg, 1.4 mmol) were mixed in methanol (5.4 mL). To this was added triethylamine (0.28 mL, 2 mmol). The reaction was stirred at room temperature overnight. The solvent was removed. The residue was dissolved in dichloromethane and washed with water. The organic layer was separated and the solvent was removed to give a residue. The residue was dried under high vacuum to give the title compound (174 mg, 79%) as a white solid. MS found (electrospray): $(M+H)^+=387.1$.

Step 2: [6-(5-Carbamimidoyl-pyrazin-2-yloxy)-1-hydroxy-4-methyl-1,3-dihydro-benzo[c][1,2]oxaborol-3-yl]-acetic acid ethyl ester

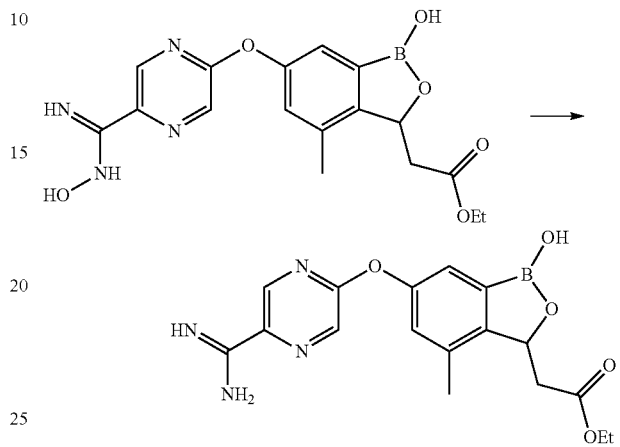

1-Hydroxy-6-[5-(N-hydroxycarbamimidoyl)-pyrazin-2-yloxy]-4-methyl-1,3-dihydro-benzo[c][1,2]oxaborol-3-yl}-acetic acid ethyl ester (80 mg, 0.21 mmol) was dissolved in acetic acid (2 mL) and treated with acetic anhydride (16 uL, 170 mmol) for 90 min. Palladium on carbon (10%, 10 mg) was added and the reaction was stirred under a hydrogen balloon overnight. The reaction was filtered and the solvent was removed to give the title compound (77 mg, quant.) as a yellow solid. MS found (electrospray): $(M+H)^+=371.1$.

Step 3: [6-(5-Carbamimidoyl-pyrazin-2-yloxy)-1-hydroxy-4-methyl-1,3-dihydro-benzo[c]oxaborol-3-yl]-acetic acid

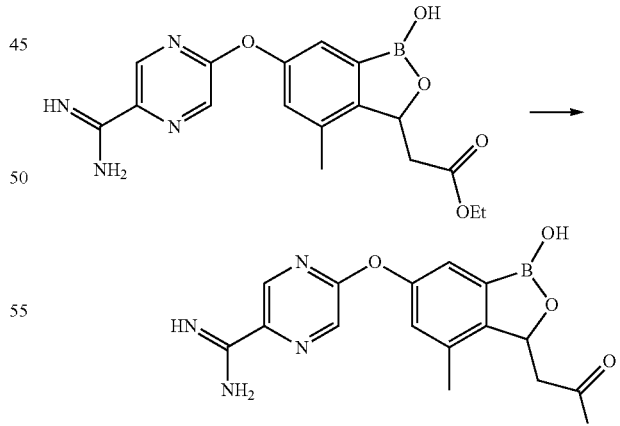

[6-(5-Carbamimidoyl-pyrazin-2-yloxy)-1-hydroxy-4-methyl-1,3-dihydro-benzo[c][1,2]oxaborol-3-yl]-acetic acid ethyl ester (77 mg, 0.21 mmol) was dissolved in THF (3 mL) and methanol (1.2 mL). To this was added lithium hydroxide monohydrate (70 mg, 1.7 mmol) in water (1.2 mL) at 0° C. The reaction was warmed up to room temperature and stirred for 4 h. The reaction mixture was acidified to pH 3 with aqueous HCl (6 N). The solvent was removed. Prep-HPLC separation (C18 column) of the reaction mixture gave the title compound (35 mg, 49%) as a white solid. $^1$H NMR (300 MHz, CD$_3$OD) δ 8.42 (1H, s), 8.20 (1H, s), 6.85 (1H, s), 6.65 (1H, s), 5.18 (1H, dd), 2.64 (1H, dd), 2.16 (3H, s), 2.15 (1H, m). MS found (electrospray): (M+H)$^+$=343.2.

G98: [6-(5-Carbamoyl-pyrazin-2-yloxy)-1-hydroxy-4-methyl-1,3-dihydro-benzo[c][1,2]oxaborol-3-yl]-acetic acid

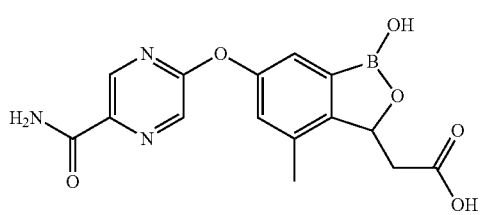 [SMILES: Cc1cc(Oc2cnc(C(N)=O)cn2)cc2c1C(CC(=O)O)OB2O]

Step 1: 5-Bromo-pyrazine-2-carboxylic acid amide

A suspension of 5-bromo-pyrazine-2-carbonitrile (1.84 g, 10.0 mmol) and potassium carbonate (1.38 g, 10.0 mmol) in DMSO/acetone (16 mL, 1:3) was treated with H$_2$O$_2$ (2.42 mL, 25.0 mmol) at 65° C. over 15 min. The reaction was kept stirring at 65° C. 1 h. Water (2 mL) was added at 40° C. and the suspension was cooled to 0° C. The precipitate was filtered to give the title compound as a yellow solid (556 mg). $^1$H NMR (300 MHz, DMSO-d$_6$) δ 9.06 (s, 1H), 8.94 (s, 1H), 8.34 (s, 1H), 7.92 (s, 1H).

Step 2: [6-(5-Carbamoyl-pyrazin-2-yloxy)-1-hydroxy-4-methyl-1,3-dihydro-benzo[c][1,2]oxaborol-3-yl]-acetic acid ethyl ester

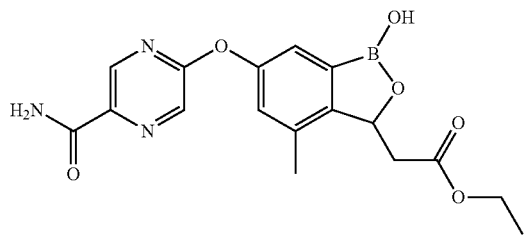 [SMILES: CCOC(=O)CC1OB(O)c2cc(Oc3cnc(C(N)=O)cn3)cc(C)c21]

A suspension of (1,6-dihydroxy-4-methoxymethyl-1,3-dihydro-benzo[c][1,2]oxaborol-3-yl)-acetic acid ethyl ester (150 mg, 0.600 mmol) and Cs$_2$CO$_3$ (430 mg, 1.32 mmol) in DMF (4 mL) was treated with 5-bromo-pyrazine-2-carboxylic acid amide (158 mg, 0.780 mmol) at room temperature and the reaction was heated to 80° C. for 2 h. The reaction mixture was concentrated to dryness. The residue was diluted with water and adjusted to pH 2 with 1N HCl. The aqueous phase was extracted with ethyl acetate. The organic phase was separated, dried (Na$_2$SO$_4$), and concentrated. The residue was purified by the flash column chromatography (silica, hexanes/ethyl acetate=1:2 to DCM/MeOH=10:1) to afford the title compound as a white solid (110 mg). $^1$H NMR (300 MHz, CD$_3$OD) δ 8.90 (s, 1H), 8.34 (s, 1H), 7.48 (s, 1H), 7.35 (s, 1H), 7.08 (s, 1H), 5.70 (s, 1H), 5.69-5.66 (m, 1H), 4.21 (q, 2H), 3.14-3.12 (m, 1H), 2.49-2.41 (m, 1H), 2.37 (s, 3H), 1.26 (t, 1H). MS found: (M+H)$^+$: 372.2.

Step 3: [6-(5-Carbamoyl-pyrazin-2-yloxy)-1-hydroxy-4-methyl-1,3-dihydro-benzo[c][1,2]oxaborol-3-yl]-acetic acid

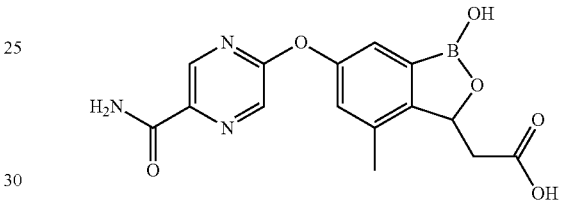

A solution of [6-(5-carbamoyl-pyrazin-2-yloxy)-1-hydroxy-4-methyl-1,3-dihydro-benzo[c][1,2]oxaborol-3-yl]-acetic acid ethyl ester (77 mg, 0.21 mmol) in THF (4 mL) was treated with LiOH (35 mg, 0.84 mmol) in water (4 mL) at room temperature for 1 h. The reaction was concentrated to dryness. The residue was diluted with water and adjusted to pH 3. The mixture was purified by preparative HPLC to give the title compound (38 mg). $^1$H NMR (300 MHz, CD$_3$OD) δ 8.76 (s, 1H), 8.46 (s, 1H), 7.29 (s, 1H), 7.16 (s, 1H), 5.73-5.69 (m, 1H), 3.33-3.18 (m, 1H), 2.42 (s, 3H), 2.38-2.33 (m, 1H). MS found: (M+H)$^+$: 344.1.

G99: [6-(5-Amino-pyrazin-2-yloxy)-1-hydroxy-4-methyl-1,3-dihydro-benzo[c][1,2]oxaborol-3-yl]-acetic acid

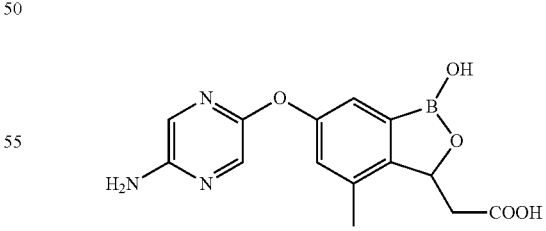

[6-(5-tert-Butoxycarbonylamino-pyrazin-2-yloxy)-1-hydroxy-4-methyl-1,3-dihydro-benzo[c][1,2]oxaborol-3-yl]-acetic acid (70 mg, 0.17 mmol) was treated with 4M HCl in dioxane (1 mL, 4 mmol) and stirred at room temperature for 3 h. The reaction mixture was concentrated under vacuum and purified by HPLC affording the title compound (40 mg, 75%) as a white solid. $^1$H NMR (CD$_3$OD) δ 7.79 (s, 1H), 7.64 (s, 1H), 7.02 (d, 1H), 6.98 (d, 1H), 5.65 (dd, 1H), 3.35 (m, 1H), 3.20 (dd, 1H), 2.36 (s, 3H). MS found: (M+H)⁺: 316.05.

G100: {1-Hydroxy-6-[6-(N-isobutyl-carbamimidoyl)-pyrazin-2-yloxy]-4-methyl-1,3-dihydro-benzo[c][1,2]oxaborol-3-yl}-acetic acid

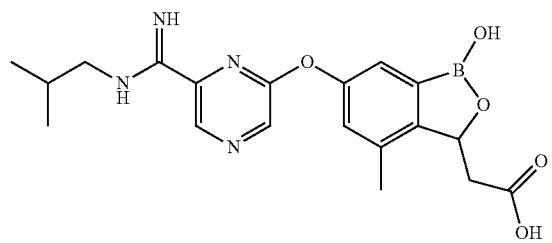

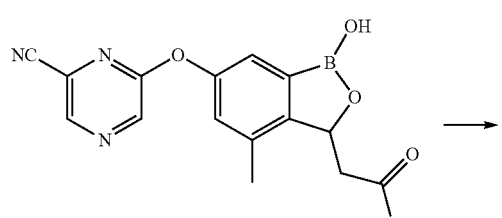

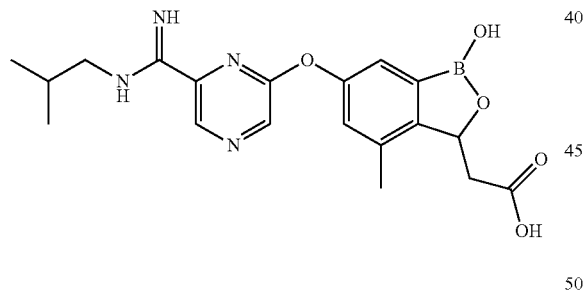

A solution of [6-(6-cyano-pyrazin-2-yloxy)-1-hydroxy-4-methyl-1,3-dihydro-benzo[c][1,2]oxaborol-3-yl]-acetic acid ethyl ester (200 mg, 0.57 mmol) in methanol (4.7 mL) was bubbled through gaseous HCl for 40 minutes at 0° C. The reaction mixture was allowed to warm to room temperature and stirred for 4 h. The solvent was removed under reduced pressure. To the residue was added methanol (2.5 mL) and ammonia solution (28%, 0.27 mL). The reaction mixture was refluxed for overnight. LC-MS showed all material converted to methyl imidate while the ethyl ester group was also hydrolyzed to free acid. The solvent was removed under reduced pressure. Half of the residue (0.28 mmol) was dissolved in methanol (2 mL) and isobutylamine (0.29 mL, 2.9 mmol) was added. The reaction mixture was refluxed overnight. The pH was adjusted to pH 3 with aqueous HCl (6 N). Prep-HPLC separation (C18 column) gave the title compound (11 mg, 10%) as a white solid. ¹H NMR (300 MHz, CD₃OD) δ 8.90 (1H, s), 8.58 (1H, s), 7.25 (1H, s), 7.14 (1H, s), 5.65 (1H, dd), 3.15 (1H, m), 3.02 (2H, m), 2.60 (3H, s), 2.30 (1H, m), 1.78 (1H, m), 0.95 (3H, d), 0.94 (3H, d). MS found (electrospray): (M+H)⁺=399.2.

G101: [1-Hydroxy-6-(6-methoxycarbonimidoyl-pyrazin-2-yloxy)-4-methyl-1,3-dihydro-benzo[c][1,2]oxaborol-3-yl]-acetic acid

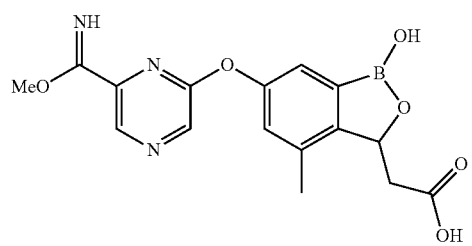

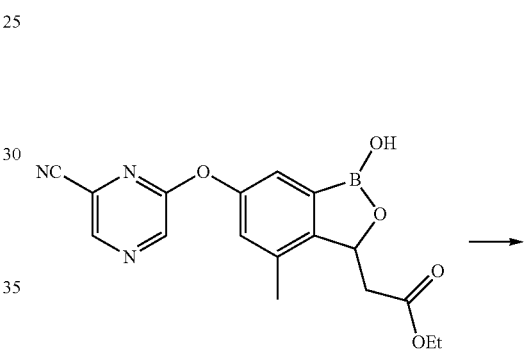

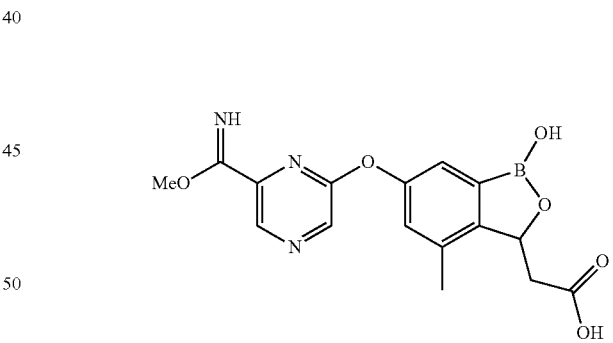

A solution of [6-(6-cyano-pyrazin-2-yloxy)-1-hydroxy-4-methyl-1,3-dihydro-benzo[c][1,2]oxaborol-3-yl]-acetic acid ethyl ester (200 mg, 0.57 mmol) in methanol (4.7 mL) was bubbled through gaseous HCl for 40 minutes at 0° C. The reaction mixture was allowed to warm to room temperature and stirred for 4 h. The solvent was removed under reduced pressure. To the residue was added methanol (2.5 mL) and ammonia solution (28%, 0.27 mL). The reaction mixture was refluxed overnight. Prep-HPLC separation (C18 column) gave the title compound (60 mg, 30%) as a white solid. ¹H NMR (300 MHz, CD₃OD) δ 8.90 (1H, s), 8.58 (1H, s), 7.18

(1H, s), 6.92 (1H, s), 5.58 (1H, dd), 3.65 (3H, s), 3.05 (1H, dd), 2.45 (1H, dd), 2.30 (3H, s). MS found (electrospray): (M+H)+=358.1.

G102: [1-Hydroxy-4-methoxymethyl-6-(pyrazin-2-yloxy)-1,3-dihydro-benzo[c][1,2]oxaborol-3-yl]-acetic acid Step 1: [1-Hydroxy-4-methoxymethyl-6-(pyrazin-2-yloxy)-1,3-dihydro-benzo[c][1,2]oxaborol-3-yl]-acetic acid ethyl ester

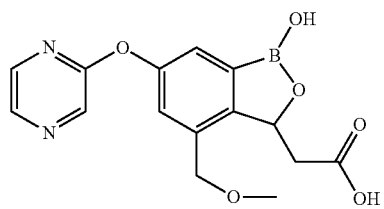 [SMILES: COCc1cc(Oc2cnccn2)cc2c1C(CC(=O)O)OB2O]

To a mixture of (1,6-dihydroxy-4-methoxymethyl-1,3-dihydro-benzo[c][1,2]oxaborol-3-yl)-acetic acid ethyl ester (0.360 g, 1.29 mmol) in DMF (5 mL) was added Cs₂CO₃ (1.26 g, 3.87 mmol). The mixture was heated at 90° C. for 3 hours then concentrated in vacuo. The residue was purified by silica gel flash column chromatography to give [1-hydroxy-4-methoxymethyl-6-(pyrazin-2-yloxy)-1,3-dihydro-benzo[c][1,2]oxaborol-3-yl]-acetic acid ethyl ester (0.200 g, 56%). ¹H NMR (400 MHz, MeOD-d₄) δ 8.41 (s, 1H), 8.22 (s, 1H), 8.10 (s, 1H), 7.30 9s, 1H), 7.20 (s, 1H), 5.58 (m, 1H), 5.55 (m, 2H), 4.10 (m, 2H), 3.40 (s, 3H), 3.20 (m, 1H), 2.45 (m, 1H), 1.20 (m, 3H).

Step 2: [1-Hydroxy-4-methoxymethyl-6-(pyrazin-2-yloxy)-1,3-dihydro-benzoic/[1,2]oxaborol-3-yl]-acetic acid

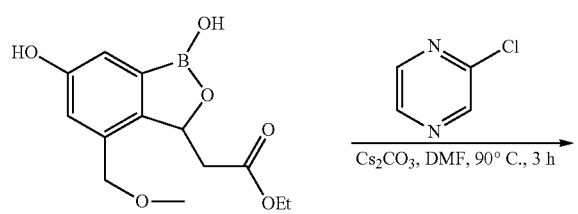

To a solution of [1-hydroxy-4-methoxymethyl-6-(pyrazin-2-yloxy)-1,3-dihydro-benzo[c][1,2]oxaborol-3-yl]-acetic acid ethyl ester (0.20 g, 0.56 mmol) in THF (6 mL) and H₂O (2 mL) was added LiOH (0.110 g) at 0° C. The resulting mixture was stirred at room temperature for 2 hours then cooled to 0° C. and acidified to pH 3 with 6N HCl. The mixture was concentrated in vacuo and the residue purified by silica gel flash column chromatography to give [1-hydroxy-4-methoxymethyl-6-(pyrazin-2-yloxy)-1,3-dihydro-benzo[c][1,2]oxaborol-3-yl]-acetic acid (0.150 g, 81%). ¹H NMR (400 MHz, DMSO-d₆) δ 12.33 (s, 1H), 9.27 (s, 1H), 8.58 (s, 1H), 8.39 (s, 1H), 8.21 (s, 1H), 7.40 (s, 1H), 7.26 (s, 1H), 5.60 (s, 1H), 4.50 (m, 2H), 3.30 (s, 3H), 3.10 (m, 1H), 2.17 (m, 1H). MS (ESI) m/z: 329 [M−1]⁻. HPLC purity: 97.28% (220 nm), 96.84% (Maxplot).

G103: [1-Hydroxy-4-methoxy-6-(pyrazin-2-yloxy)-1,3-dihydro-benzo[c][1,2]oxaborol-3-yl]-acetic acid

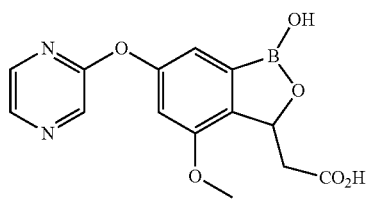 [SMILES: COc1cc(Oc2cnccn2)cc2c1C(CC(=O)O)OB2O]

Step 1: Ethyl-2-(1-hydroxy-4-methoxy-6-(pyrazin-2-yloxy)-1,3-dihydrobenzo[c][1,2]oxaborol-3-yl)acetate

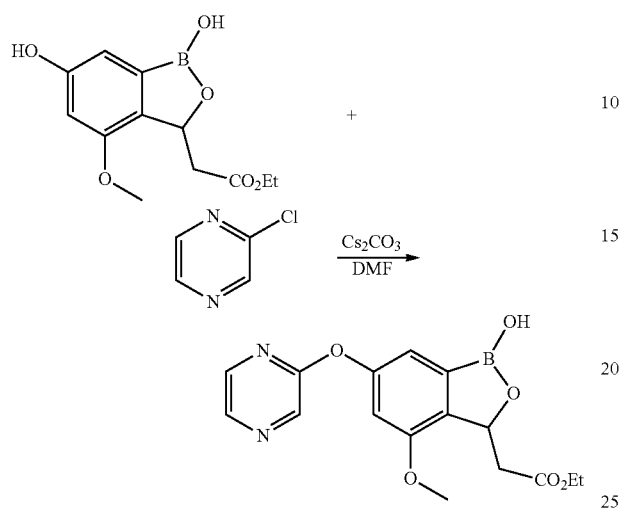

A mixture of ethyl 2-(1,6-dihydroxy-4-methoxy-1,3-dihydrobenzo[c][1,2]oxaborol-3-yl)acetate (0.15 g, 0.56 mmol), cesium carbonate (0.37 g, 1.12 mmol) and 2-chloropyrazine (96 mg, 0.84 mmol) in DMF (2 mL) was heated to 90° C. for 3 hr. The reaction mixture was quenched by saturated aqueous NaHCO$_3$ (20 mL) and extracted with EtOAc (15 mL×2). The combined extracts were dried over anhydrous Na$_2$SO$_4$ and concentrated in vacuo. The residue was purified by column chromatography (EtOAc/PE=1/2) on silica gel to give the title compound as a light yellow solid (156 mg, Y: 81.2%). MS (ESI) m/z=345 [M+H]$^+$.

Step 2: 2-(1-hydroxy-4-methoxy-6-(pyrazin-2-yloxy)-1,3-dihydrobenzo[c][1,2]oxaborol-3-yl)acetic acid

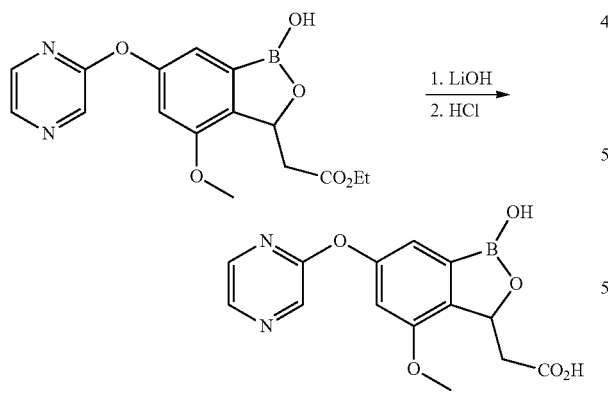

To a solution of ethyl 2-(1-hydroxy-4-methoxy-6-(pyrazin-2-yloxy)-1,3-dihydrobenzo[c][1,2]oxaborol-3-yl) acetate (150 mg, 0.44 mmol) in THF (2 mL) was added an aqueous solution of lithium hydroxide (90 mg, 2.2 mmol) in 3 mL of water at 0° C., The reaction mixture was stirred at room temperature for 1.5 hr and acidified to pH=2 using diluted hydrochloride acid. The resulting mixture was extracted with ethyl acetate (15 mL×2) and combined organic layers were dried over anhydrous Na$_2$SO$_4$ and concentrated in vacuo. The residue was purified by HPLC to give the title compound as a white solid (71 mg, Y: 51.0%). $^1$H NMR (400 MHz, DMSO-d) δ 9.28 (s, 1H), 8.56 (s, 1H), 8.39-8.40 (d, J=2.4 Hz, 1H), 8.24 (s, 1H), 7.00-7.02 (d, J=10.8 Hz, 2H), 5.44-5.46 (m, 1H), 3.81 (s, 3H), 3.13-3.16 (m, 1H), 2.14-2.20 (m, 1H). MS (ESI) m/z=317 [M+H]$^+$.

G104: 2-(1,4-Dihydroxy-6-(pyrazin-2-yloxy)-1,3-dihydrobenzo[c][1,2]oxaborol-3-yl)acetic acid

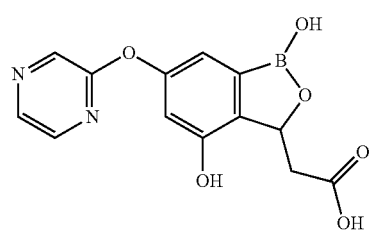 [SMILES: O=C(O)CC1OB(O)c2cc(Oc3cnccn3)cc(O)c21]

Step 1: Ethyl 2-(4-(benzyloxy)-1-hydroxy-6-(pyrazin-2-yloxy)-1,3-dihydrobenzo[c][1,2]-oxaborol-3-yl)acetate

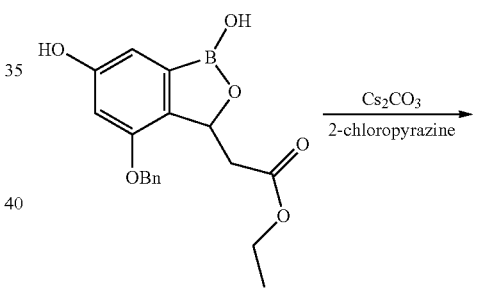

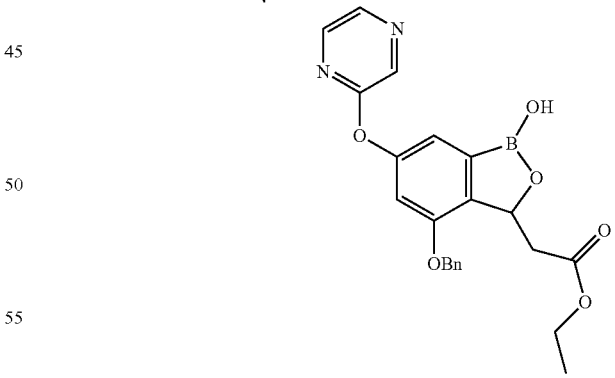

To a mixture of ethyl 2-(4-(benzyloxy)-1,6-dihydroxy-1,3-dihydrobenzo[c][1,2]oxaborol-3-yl)acetate (1.00 g, 2.9 mmol) and anhydrous Cs$_2$CO$_3$ (1.12 g, 5.84 mmol) in DMF (10 mL) was added 2-chloropyrazine (0.40 g, 3.5 mmol). The reaction mixture was stirred at 90° C. for 1 h and quenched by addition of water (15 mL). The resulting mixture was extracted by EtOAc and the combined organic layers were washed with water (20 mL) and brine (25 mL), dried over anhydrous Na₂SO₄ and concentrated in vacuo to give the title compound as a yellow oil (0.74 g, Yield: 61%).

Step 2: Ethyl 2-(1,4-dihydroxy-6-(pyrazin-2-yloxy)-1,3-dihydrobenzo[c][1,2]oxaborol-3-yl)acetate

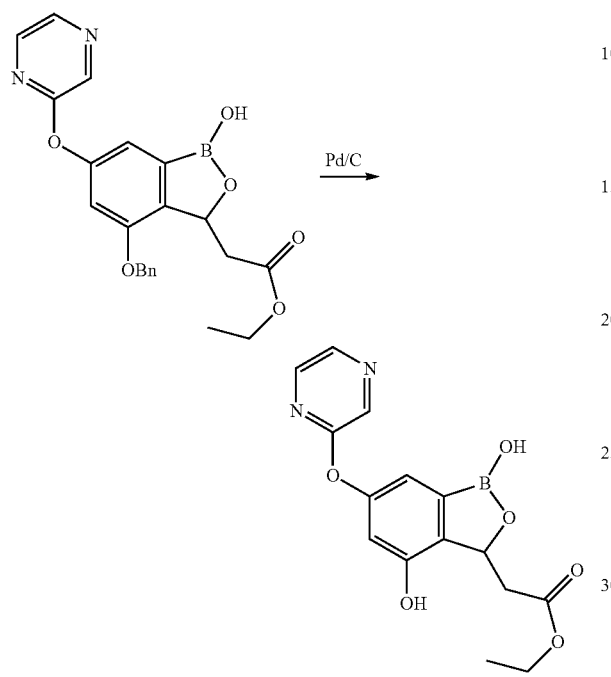

A mixture of ethyl 2-(4-(benzyloxy)-1-hydroxy-6-(pyrazin-2-yloxy)-1,3-dihydrobenzo[c][1,2]-oxaborol-3-yl) acetate (1.61 g, 3.8 mmol) and 10% Pd/C (0.24 g) in EtOH (10 mL) was stirred at room temperature under H₂ atmosphere overnight. The reaction mixture was filtrated through a pad of Celite and the filtrate was concentrated in vacuo to give the title compound (0.71 g, yield: 57%).

Step 3: 2-(1,4-Dihydroxy-6-(pyrazin-2-yloxy)-1,3-dihydrobenzo[c][1,2]oxaborol-3-yl)acetic acid

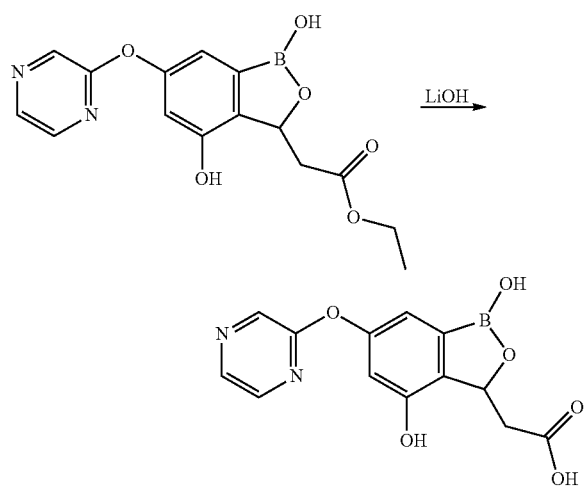

To a solution of ethyl 2-(1,4-dihydroxy-6-(pyrazin-2-yloxy)-1,3-dihydrobenzo[c][1,2]oxaborol-3-yl)acetate (100 mg, 0.31 mmol) in EtOH (5 ml) was added an aqueous solution of lithium hydroxide (26.1 mg, 0.62 mmol) in water (1 mL). The reaction mixture was stirred at room temperature overnight and acidified with 1 N HCl to pH=3. The resulting mixture was extracted with EtOAc (20 mL) and combined organic layers were washed with water (15 mL) and brine (15 mL), dried over anhydrous Na₂SO₄ and concentrated in vacuo. The residue was purified by prep HPLC to give the title compound as a white powder (17 mg, yield: 18%). ¹H NMR (400 MHz, DMSO-d6) δ 12.31 (s, 1H), 10.13 (s, 1H), 9.19 (s, 1H), 8.54 (s, 1H), 8.38 (d, J=2.8 Hz, 1H), 8.24 (d, J=1.2 Hz, 1H), 6.90 (d, J=1.6 Hz, 1H), 5.44 (m, 1H), 3.22 (m, 1H), 2.18-2.11 (m, 1H). MS (ESI) m/z=303 [M+H]⁺.

G105: 2-(4-(Benzyloxy)-1-hydroxy-6-(pyrazin-2-yloxy)-1,3-dihydrobenzo[c][1,2]oxaborol-3-yl) acetic acid

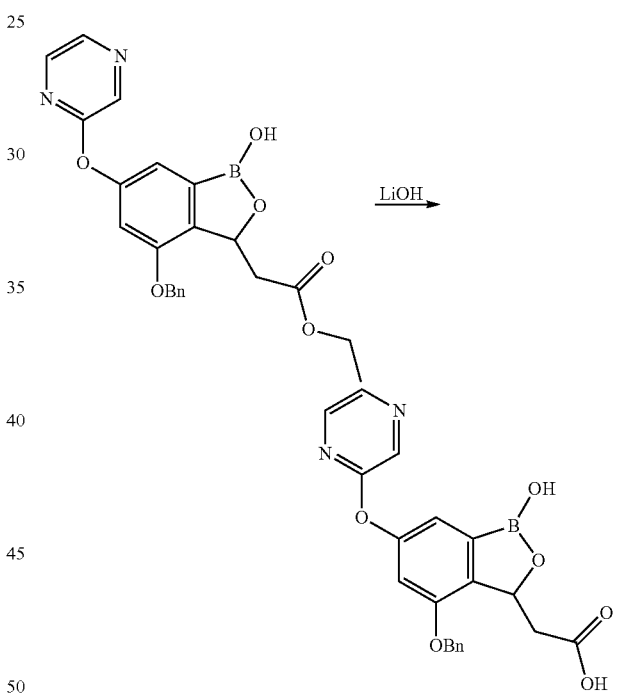

To a solution of ethyl 2-(4-(benzyloxy)-1-hydroxy-6-(pyrazin-2-yloxy)-1,3-dihydrobenzo[c][1,2]oxaborol-3-yl) acetate (100 mg, 0.24 mmol) in EtOH (5 mL) was added an aqueous solution of lithium hydroxide (20.1 mg, 0.48 mmol) in water (1 mL). The reaction mixture was stirred at room temperature overnight and acidified with 1 N HCl to pH=3. The resulting mixture was extracted with EtOAc (15 mL) and combined organic layers were washed with water (10 mL) and brine (10 mL), dried over anhydrous Na₂SO₄ and concentrated in vacuo. The residue was purified by prep HPLC to give the title compound as a white powder (17 mg, yield: 18%). ¹H NMR (400 MHz, DMSO-d6) δ 12.34 (s, 1H), 9.29 (s, 1H), 8.56 (s, 1H), 8.40 (s, 1H), 8.23 (s, 1H), 7.44-7.34 (m, 5H), 7.06 (d, J=19.2 Hz, 2H), 5.50 (d, J=8.8 Hz, 1H), 5.172 (m, 5H), 3.2 (d, J=15.6 Hz, 1H), 2.18-2.11 (m, 1H). MS (ESI) m/z=393 [M+H]⁺.

G106: 2-(1-Hydroxy-4-isopropoxy-6-(pyrazin-2-yloxy)-1,3-dihydrobenzo[c][1,2]-oxaborol-3-yl)acetic acid

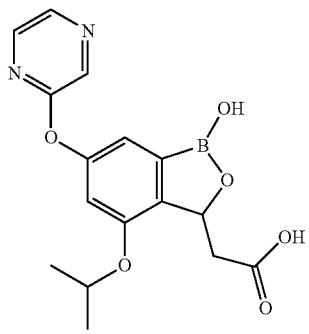 [SMILES: CC(C)Oc1cc(Oc2cnccn2)cc2c1C(CC(=O)O)OB2O]

Step 1: Ethyl-2-(1-hydroxy-4-isopropoxy-6-(pyrazin-2-yloxy)-1,3-dihydrobenzo[c][1,2]oxaborol-3-yl)acetate

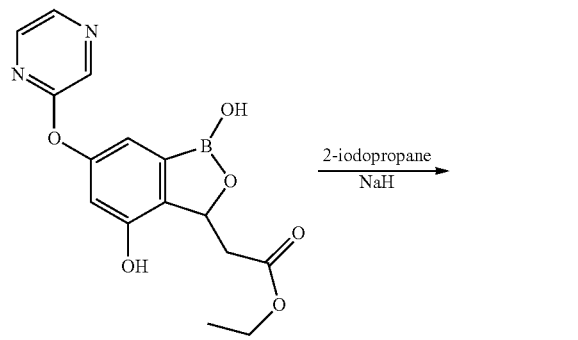

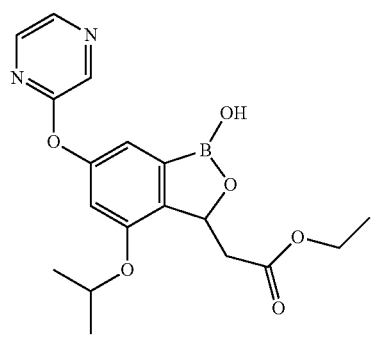

To a mixture of ethyl 2-(1,4-dihydroxy-6-(pyrazin-2-yloxy)-1,3-dihydrobenzo[c][1,2]oxa-borol-3-yl)acetate (100 mg, 0.30 mmol) and 2-iodopropane (154 mg, 0.91 mmol) in DMF (5 mL) was added 60% NaH (4.85 mg, 1.21 mmol) at 0° C. The reaction mixture was stirred at room temperature for 1 h and quenched by slow addition of water (3 mL). The resulting mixture was acidified with 1 N HCl to pH=4 and extracted with EtOAc (2×15 mL). The combined organic layers were washed with water (10 mL) and brine (10 mL), dried over anhydrous Na₂SO₄ and concentrated in vacuo to give the title compound as a yellow oil (96 mg, yield: 86%).

Step 2: 2-(1-Hydroxy-4-isopropoxy-6-(pyrazin-2-yloxy)-1,3-dihydrobenzo[c][1,2]oxaborol-3-yl)acetic acid

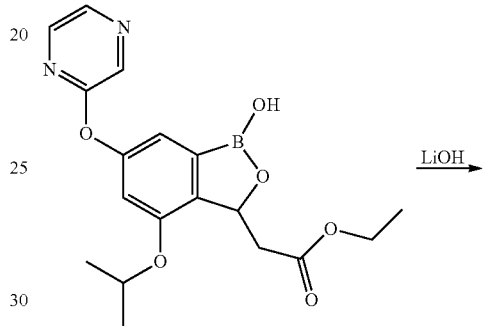

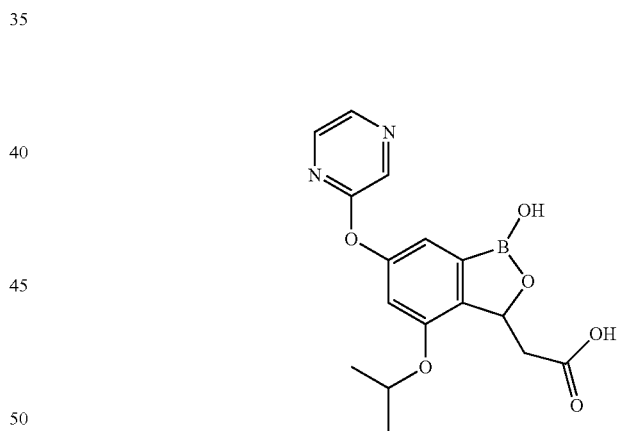

To a solution of ethyl 2-(1-hydroxy-4-isopropoxy-6-(pyrazin-2-yloxy)-1,3-dihydrobenzo[c][1,2]oxaborol-3-yl)acetate (96 mg, 0.26 mmol) in EtOH (4 mL) was added an aqueous solution of lithium hydroxide (21.8 mg, 0.52 mmol) in water (1 mL). The reaction mixture stirred at room temperature overnight and acidified with 1 N HCl to pH=4. The resulting mixture was extracted with EtOAc (15 mL) and combined organic layers were washed with water (10 mL) and brine (10 mL), dried over anhydrous Na₂SO₄ and concentrated in vacuo. The residue was purified by prep HPLC to give the title compound as a white powder (41 mg. Yield: 45%). ¹H NMR (400 MHz, DMSO-d6) δ 12.41-12.12 (m, 1H), 9.25 (s, 1H), 8.55 (d, J=0.8 Hz, 1H), 8.38 (d, J=2.8 Hz, 1H), 8.23 (t, J=1.2 Hz, 1H), 6.99 (s, 1H), 5.42 (m, 1H), 4.67 (m, 1H), 3.18 (m, 1H), 2.19 (m, 1H), 1.27 (m, 6H). MS (ESI) m/z=345 [M+H]$^+$.

G107: [4-Aminomethyl-1-hydroxy-6-(pyrazin-2-yloxy)-1,3-dihydro-benzo[c][1,2]oxaborol-3-yl]-acetic acid

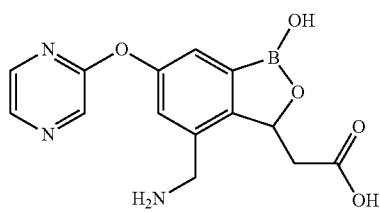 [SMILES: NCc1cc(Oc2cnccn2)cc2c1C(CC(=O)O)OB2O]

To a mixture of [4-azidomethyl-1-hydroxy-6-(pyrazin-2-yloxy)-1,3-dihydro-benzo[c][1,2]oxaborol-3-yl]-acetic acid (100 mg, 0.29 mmol) was treated with PPh$_3$ on resin (140 mg, about 0.42 mmol) in THF/water (5/1 mL). The reaction mixture was stirred at r.t overnight and filtered off. The filtrate was purified by HPLC, yielded 25 mg of the desired product. $^1$H NMR (300 MHz, CD$_3$CN) δ 8.44 (s, 1H), 8.30 (d, 1H), 8.12 (s, 1H), 7.50 (s, 1H), 7.36 (s, 1H), 5.71 (m, 1H), 4.24 (s, 2H), 3.04-3.10 (m, 1H), 2.50-2.58 (m, 1H).

G108: [4-Azidomethyl-1-hydroxy-6-(pyrazin-2-yloxy)-1,3-dihydro-benzo[c][1,2]oxaborol-3-yl]-acetic acid

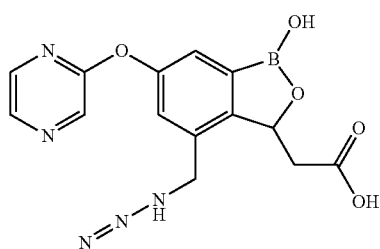 [SMILES: N=NNCc1cc(Oc2cnccn2)cc2c1C(CC(=O)O)OB2O]

Step 1: (4-Bromomethyl-1,6-dihydroxy-1,3-dihydro-benzo[c][1,2]oxaborol-3-yl)-acetic acid ethyl ester

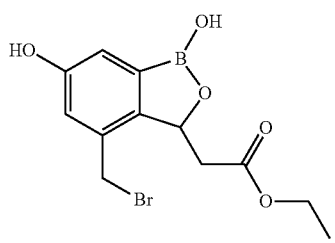

To a solution of [1-hydroxy-4-methoxymethyl-6-(tetrahydro-pyran-2-yloxy)-1,3-dihydro-benzo[c][1,2]oxaborol-3-yl]-acetic acid ethyl ester from step 1.10. (870 mg, 1.37 mmol) in DCM (10 mL) was added boron tribromide (0.46 mL, 3.02 mmol) slowly under −78° C. The reaction mixture was allowed to stir at room temperature for 1 h. Ethanol was added slowly and the solvent was removed under vacuum. The crude product was used for next step without further purification. $^1$H NMR (300 MHz, CD$_3$CN) δ 7.13 (s, 1H), 7.01 (s, 1H), 5.62 (dd, 1H), 4.42-4.63 (dd, 2H), 4.14 (q, 2H), 3.18-3.24 (dd, 1H), 2.40-2.51 (m, 1H), 1.22 (t, 3H).

Step 2: (4-Azidomethyl-1,6-dihydroxy-1,3-dihydro-benzo[c][1,2]oxaborol-3-yl)-acetic acid ethyl ester

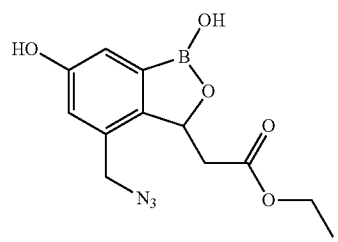 [SMILES: CCOC(=O)CC1OB(O)c2cc(O)cc(CN=[N+]=[N-])c21]

To a crude (4-bromomethyl-1,6-dihydroxy-1,3-dihydro-benzo[c][1,2]oxaborol-3-yl)-acetic acid ethyl ester in CH$_3$CN/H$_2$O (10/2 mL) was added sodium azide (3.1 g, 48 mmol). The solution was stirred overnight at r.t. The crude solution was purified by HPLC, yielded 450 mg of the title compound. $^1$H NMR (300 MHz, CD$_3$CN) δ 7.21 (s, 1H), 6.99 (s, 1H), 5.61 (dd, 1H), 4.31-4.56 (dd, 2H), 4.10 (q, 2H), 3.02-3.14 (dd, 1H), 2.37-2.43 (m, 1H), 1.21 (t, 3H).

Step 3: [4-Azidomethyl-1-hydroxy-6-(pyrazin-2-yloxy)-1,3-dihydro-benzo[c][1,2]oxaborol-3-yl]-acetic acid ethyl ester

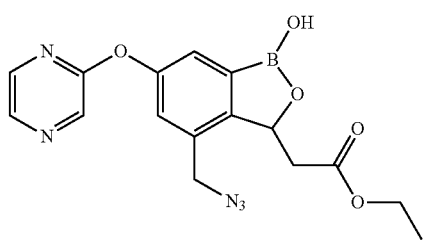 [SMILES: CCOC(=O)CC1OB(O)c2cc(Oc3cnccn3)cc(CN=[N+]=[N-])c21]

To a mixture of (4-azidomethyl-1,6-dihydroxy-1,3-dihydro-benzo[c][1,2]oxaborol-3-yl)-acetic acid ethyl ester (550 mg, 1.89 mmol), 2-chloropyrazine (350 mg, 3.05 mmol), Cs$_2$CO$_3$ (1.34 g, 4.11 mmol) in 5 mL of DMF was heated to 80° C. for 3.5 h. The reaction mixture was adjusted to pH 3 by 1N HCl. The crude product was purified by HPLC to yield 200 mg of the title compound.

Step 4: [4-Azidomethyl-1-hydroxy-6-(pyrazin-2-yloxy)-1,3-dihydro-benzo[c][1,2]oxaborol-3-yl]-acetic acid

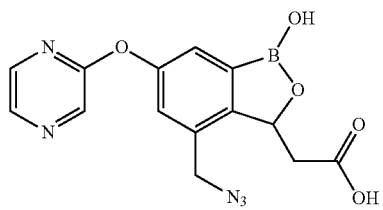 [SMILES: [N-]=[N+]=NCc1cc(Oc2cnccn2)cc2c1C(CC(=O)O)OB2O]

To a mixture of [4-azidomethyl-1-hydroxy-6-(pyrazin-2-yloxy)-1,3-dihydro-benzo[c][1,2]oxaborol-3-yl]-acetic acid ethyl ester (200 mg, 0.54 mmol) was added 1N HCl (5 mL) and AcOH (20 mL). The mixture was heated at 100° C. for 4 h. The acid was removed under vacuum and the crude product was purified by HPLC, yielded 100 mg of desire product. $^1$H NMR (300 MHz, CD$_3$CN) δ 8.59 (s, 1H), 8.44 (s, 1H), 8.23 (s, 1H), 8.20 (s, 1H), 7.59 (s, 1H), 7.43 (s, 1H), 5.81 (dd, 1H), 4.54-4.72 (m, 2H), 3.23-3.29 (m, 2H), 2.49-2.58 (dd, 2H), 2.08 (t, 3H).

G109: [4-(2-Amino-ethoxy)-1-hydroxy-6-(pyrazin-2-yloxy)-1,3-dihydro-benzo[c][1,2]oxaborol-3-yl]-acetic acid

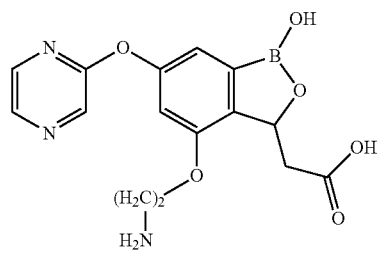

Step 1: [4-(2-tert-Butoxycarbonylamino-ethoxy)-1-hydroxy-6-(pyrazin-2-yloxy)-1,3-dihydro-benzo[c][1,2]oxaborol-3-yl]-acetic acid ethyl ester

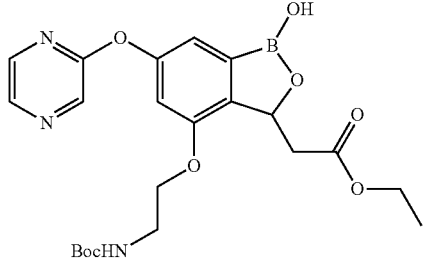 [SMILES: CCOC(=O)CC1OB(O)c2cc(Oc3cnccn3)cc(OCCNC(=O)OC(C)(C)C)c21]

A solution of [1,4-dihydroxy-6-(pyrazin-2-yloxy)-1,3-dihydro-benzo[c][1,2]oxaborol-3-yl]-acetic acid ethyl ester (from Step 7.9, 90 mg, 0.27 mmol) in DMF (10 mL) was treated with (3-bromo-propyl)-carbamic acid tert-butyl ester (92 mg, 0.41 mmol) and potassium carbonate (187 mg, 1.35 mmol) at 50° C. overnight. The reaction was concentrated to dryness. The residue was diluted with MeOH/H$_2$O and the mixture was adjusted pH to 3. The solution was purified by preparative HPLC to afford the title compound as a white solid (53 mg). MS calcd for (C$_{22}$H$_{28}$BN$_3$O$_8$+H-Boc)$^+$: 374.2. MS found: (M+H-Boc)$^+$=374.2.

Step 2: [4-(2-Amino-ethoxy)-1-hydroxy-6-(pyrazin-2-yloxy)-1,3-dihydro-benzo[c][1,2]oxaborol-3-yl]-acetic acid

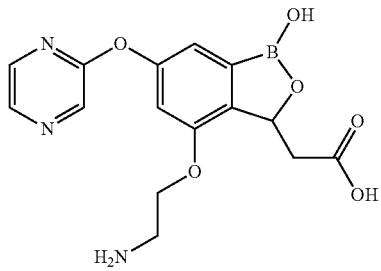 [SMILES: NCCOc1cc(Oc2cnccn2)cc2c1C(CC(=O)O)OB2O]

A solution of [4-(2-tert-butoxycarbonylamino-ethoxy)-1-hydroxy-6-(pyrazin-2-yloxy)-1,3-dihydro-benzo[c][1,2]oxaborol-3-yl]-acetic acid ethyl ester (47 mg) in acetic acid (4 mL) was treated with 1N HCl (1 mL) at 100° C. 2 h. The reaction was concentrated to dryness. The residue was purified by preparative HPLC to give the title compound (22 mg) as a white solid. $^1$H NMR (300 MHz, CD$_3$OD) δ 8.47 (s, 1H), 8.34-8.33 (m, 1H), 8.17-8.15 (m, 1H), 7.08 (d, J=1.8 Hz, 1H), 7.04 (d, J=1.8 Hz, 1H), 5.76-5.72 (m, 1H), 4.35-4.32 (m, 2H), 3.47-3.44 (m, 2H), 3.31-3.25 (m, 1H), 2.57-2.49 (m, 1H). MS calcd for (C$_{15}$H$_{16}$BN$_3$O$_6$+H)$^+$: 346.2. MS found: (M+H)$^+$=346.2.

G110: [4-(3-Amino-propoxy)-1-hydroxy-6-(pyrazin-2-yloxy)-1,3-dihydro-benzo[c][1,2]oxaborol-3-yl]-acetic acid

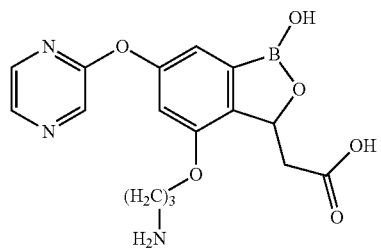

A solution of [4-(3-tert-butoxycarbonylamino-propoxy)-1-hydroxy-6-(pyrazin-2-yloxy)-1,3-dihydro-benzo[c][1,2]oxaborol-3-yl]-acetic acid ethyl ester (81 mg) in acetic acid (4 mL) was treated with 1N HCl (1 mL) at 100° C. for 2 h. The reaction was concentrated to dryness. The residue was purified by preparative HPLC to give the title compound (32 mg) as a white solid. $^1$H NMR (300 MHz, CD$_3$OD) δ 8.42 (s, 1H), 8.31-8.30 (m, 1H), 8.17-8.15 (m, 1H), 6.98 (d, J=1.5 Hz, 1H), 6.90 (d, J=1.5 Hz, 1H), 5.66-5.62 (m, 1H), 4.16 (t, 2H), 3.19 (t, 2H), 3.17-3.09 (m, 1H), 2.47-2.39 (m, 1H), 2.23-2.21 (m, 2H). MS calcd for (C$_{16}$H$_{18}$BN$_3$O$_6$+H)$^+$:360.2. MS found: (M+H)$^+$=360.2.

G111: [4-(3-tert-Butoxycarbonylamino-propoxy)-1-hydroxy-6-(pyrazin-2-yloxy)-1,3-dihydro-benzo[c][1,2]oxaborol-3-yl]-acetic acid

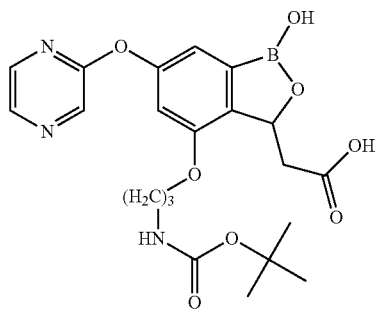

Step 1: 2-Bromo-4,6-dimethoxy-benzaldehyde

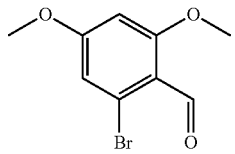

A solution of 1-bromo-3,5-dimethoxybenzene (10.0 g, 46.1 mmol) in DMF (40 mL) was treated with POCl$_3$ (6.32 mL, 69.1 mmol) at 0° C. and heated to 100° C. for 6 h. The reaction was cooled to room temperature and water (40 mL) was added. The resulting mixture was heated to 50° C. 1 h. The reaction was cooled down and extracted with ethyl acetate. The organic layer was separated, dried (Na$_2$SO$_4$), and concentrated. The residue was purified by flash column chromatography (silica, hexanes/ethyl acetate=2:1) to give the title compound (7.26 g, 65%). $^1$H NMR (300 MHz, CDCl$_3$) δ 10.24 (s, 1H), 6.81 (s, 1H), 6.42 (s, 1H), 3.96 (s, 3H), 3.93 (s, 3H).

Step 2: 2-Bromo-4,6-dihydroxy-benzaldehyde

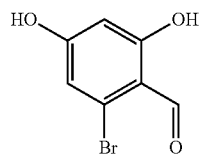

To a solution of 2-bromo-4,6-dimethoxy-benzaldehyde (5.83 g, 23.9 mmol) in dichloromethane (50 mL) was added BBr$_3$ (6.78 mL, 71.7 mmol) at −78° C. The reaction was stirred at room temperature overnight and poured into ice slowly. The resulting mixture was extracted with ethyl acetate. The organic layer was separated, dried (Na$_2$SO$_4$), and concentrated. The residue was purified by flash column chromatography (silica, hexanes/ethyl acetate=2:1) to give the title compound (4.84 g, 94%) as a white solid. $^1$H NMR (300 MHz, CDCl$_3$) δ 12.2 (s, 1H), 11.3 (br, 1H), 10.0 (s, 1H), 6.75 (d, J=2.1 Hz, 1H), 6.33 (d, J=2.1 Hz, 1H).

Step 3: 2-Bromo-6-hydroxy-4-(tetrahydro-pyran-2-yloxy)-benzaldehyde

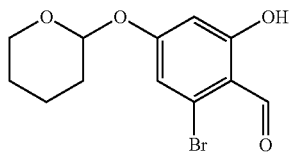 [SMILES: O=Cc1c(O)cc(OC2CCCCO2)cc1Br]

A solution of 2-bromo-4,6-dihydroxy-benzaldehyde (4.69 g, 21.7 mmol) in dichloromethane (100 mL) was treated with DHP (3.94 mL, 43.4 mmol) and PPTS (200 mg) at room temperature for 1 h. The reaction mixture was concentrated to dryness. The residue purified by flash column chromatography (silica, hexanes/ethyl acetate=4:1) to give the title compound (5.96 g, 92%) as a colorless oil. $^1$H NMR (300 MHz, CDCl$_3$) δ 12.2 (s, 1H), 10.1 (s, 1H), 6.88 (d, J=2.1 Hz, 1H), 6.58 (d, J=2.1 Hz, 1H), 5.56 (s, 1H), 3.84-3.81 (m, 1H), 3.68-3.62 (m, 1H), 1.96-1.54 (m, 6H).

Step 4: 2-Benzyloxy-6-bromo-4-(tetrahydro-pyran-2-yloxy)-benzaldehyde

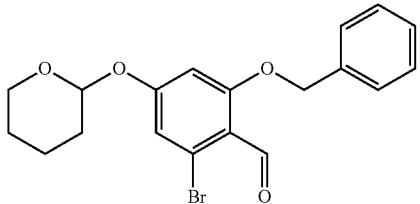 [SMILES: O=Cc1c(Br)cc(OC2CCCCO2)cc1OCc1ccccc1]

To a solution of 2-bromo-6-hydroxy-4-(tetrahydro-pyran-2-yloxy)-benzaldehyde (3.00 g, 10.0 mmol) in DMF (20 mL) was added K$_2$CO$_3$ (2.76 g, 20.0 mmol) followed by benzyl bromide (1.43 mL, 12.0 mmol) at 0° C. The suspension was stirred at room temperature for 1 h. The reaction mixture was diluted with ethyl acetate and washed with brine. The organic layer was separated, dried (Na$_2$SO$_4$), and concentrated. The residue was purified by flash column chromatography (silica, hexanes/ethyl acetate=6:1) to give the title compound (3.79 g, 97%) as a white solid. $^1$H NMR (300 MHz, CDCl$_3$) δ 10.39 (s, 1H), 7.47-7.33 (m, 5H), 6.98 (d, J=2.1 Hz, 1H), 6.70 (d, J=2.1 Hz, 1H), 5.47-5.45 (m, 1H), 5.16 (s, 2H), 3.80-3.78 (m, 1H), 3.66-3.62 (m, 1H), 1.88-1.55 (m, 6H).

Step 5: 2-Benzyloxy-4-(tetrahydro-pyran-2-yloxy)-6-(4,4,5,5-tetramethyl-[1,3,2]dioxaborolan-2-yl)-benzaldehyde

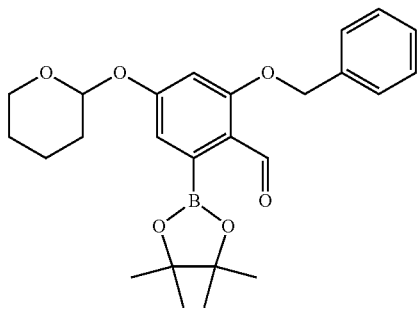 [SMILES: CC1(C)OB(c2cc(OC3CCCCO3)cc(OCc3ccccc3)c2C=O)OC1(C)C]

2-Benzyloxy-6-bromo-4-(tetrahydro-pyran-2-yloxy)benzaldehyde (3.79 g, 9.70 mmol), bis(pinacolato)diboron (2.96 g, 11.6 mmol), potassium acetate (2.86 g, 29.1 mmol), and Pd(dppf)$_2$Cl$_2$ (792 mg, 0.970 mmol) in a round bottle were degassed 3 times. Dioxane (50 mL) was added to the bottle and the suspension was heated to 80° C. for 2 h. The mixture was filtered through a pad of Celite and the filtrate was concentrated to dryness. The residue was purified by the flash column chromatography (silica, hexanes/ethyl acetate=6:1) to afford the title compound (2.41 g, 57%). $^1$H NMR (300 MHz, CDCl$_3$) δ 10.34 (s, 1H), 7.45-7.28 (m, 5H), 6.72-6.68 (m, 2H), 5.47-5.45 (m, 1H), 5.16 (s, 2H), 3.82-3.78 (m, 1H), 3.62-3.59 (m, 1H), 1.88-1.55 (m, 6H), 1.41 (s, 12H).

Step 6: [4-Benzyloxy-1-hydroxy-6-(tetrahydro-pyran-2-yloxy)-1,3-dihydro-benzo[c][1,2]oxaborol-3-yl]-acetic acid ethyl ester

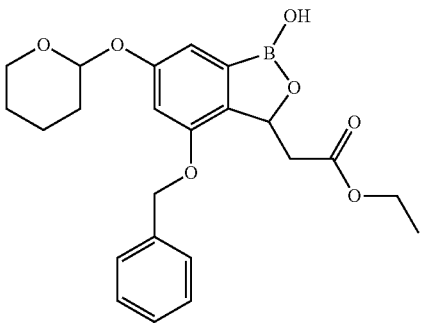 [SMILES: CCOC(=O)CC1OB(O)c2cc(OC3CCCCO3)cc(OCc3ccccc3)c21]

A suspension of Zn (2.91 g, 44.5 mmol) in THF (10 mL) was added TMSCl (0.833 ml, 6.57 mmol) at 40° C. The temperature was increased to 55° C. over 30 min. Then, the temperature was lowered to 37° C. and bromo ethyl acetate (4.55 mL, 41.1 mmol) was added slowly. The resulting solution was stirred for 30 min from 45° C. to room temperature and stood by for 1 h. The top clear layer (3 mL) was added to a solution of 2-benzyloxy-4-(tetrahydro-pyran-2-yloxy)-6-(4,4,5,5-tetramethyl-[1,3,2]dioxaborolan-2-yl)-benzaldehyde (1.50 g, 3.42 mmol) in THF (5 ml) at −78° C. After the addition, the reaction was warmed to 0° C. using an ice bath and stirred at 0° C. 30 min. The reaction mixture was quenched with NH$_4$Cl and extracted with ethyl acetate. The organic phase was separated, dried (Na$_2$SO$_4$), and concentrated. The residue was purified by the flash column chromatography (silica, hexanes/ethyl acetate=3:2) to afford the title compound (1.06 g, 73%). MS calcd for (C$_{23}$H$_{27}$BO$_7$+H)$^+$: 427.2. MS found: (M+H)$^+$=427.2.

Step 7: (4-Benzyloxy-1,6-dihydroxy-1,3-dihydro-benzo[c][1,2]oxaborol-3-yl)-acetic acid ethyl ester

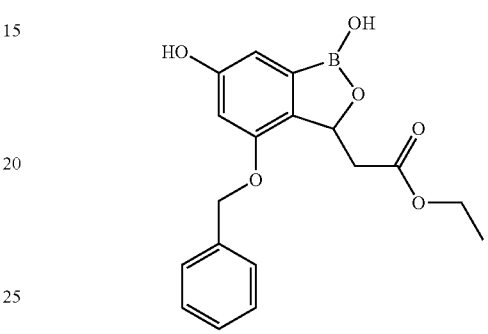

A solution of [4-benzyloxy-1-hydroxy-6-(tetrahydro-pyran-2-yloxy)-1,3-dihydro-benzo[c][1,2]oxaborol-3-yl]-acetic acid ethyl ester (1.00 g, 2.35 mmol) in THF (10 mL) was treated with 6N HCl (0.3 mL) at 0° C. for 2 h. The mixture was diluted with ethyl acetate and washed with brine. The organic phase was separated, dried (Na$_2$SO$_4$), and concentrated. The residue was purified by the flash column chromatography (silica, hexanes/ethyl acetate=2:3) to afford the title compound (710 mg, 89%). $^1$H NMR (300 MHz, CD$_3$OD) δ 7.51-7.38 (m, 5H), 6.64 (s, 1H), 6.61 (s, 1H), 5.58-5.53 (m, 1H), 5.14 (s, 2H), 4.12 (q, 2H), 3.28-3.20 (m, 1H), 2.47-2.43 (m, 1H), 1.22 (t, 3H).

Step 8: [4-Benzyloxy-1-hydroxy-6-(pyrazin-2-yloxy)-1,3-dihydro-benzo[c][1,2]oxaborol-3-yl]-acetic acid ethyl ester

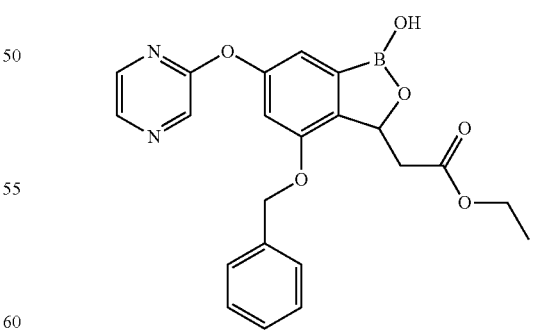

A suspension of (4-benzyloxy-1,6-dihydroxy-1,3-dihydro-benzo[c][1,2]oxaborol-3-yl)-acetic acid ethyl ester (710 mg, 2.08 mmol) and Cs$_2$CO$_3$ (1.36 g, 4.16 mmol) in DMF (10 mL) was treated with 2-chloropyrazine (357 mg, 3.11 mmol) at room temperature and the reaction was heated to 80° C. for 3 h. The reaction mixture was concentrated to dryness. The residue was diluted with water and adjusted pH to 3 by 1N HCl. The aqueous phase was extracted with ethyl acetate. The organic phase was separated, dried (Na$_2$SO$_4$), and concentrated. The residue was purified by preparative HPLC to afford the title compound (410 mg, 50%). MS calcd for (C$_{22}$H$_{21}$BN$_2$O$_6$+H)$^+$: 421.2. MS found: (M+H)$^+$=421.2.

Step 9: [1,4-Dihydroxy-6-(pyrazin-2-yloxy)-1,3-dihydro-benzo[c][1,2]oxaborol-3-yl]-acetic acid ethyl ester

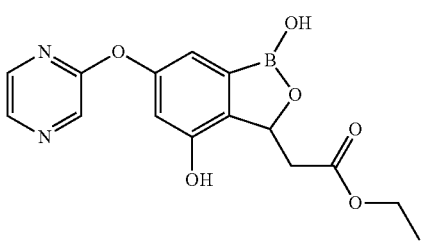 [SMILES: CCOC(=O)CC1OB(O)c2cc(Oc3cnccn3)cc(O)c21]

A solution of [4-benzyloxy-1-hydroxy-6-(pyrazin-2-yloxy)-1,3-dihydro-benzo[c][1,2]oxaborol-3-yl]-acetic acid ethyl ester (410 mg, 0.976 mmol) in THF/EtOH (20 mL, 1:1) was degassed 3 times and Pd/C (40 mg) was added. The suspension was degassed 3 times and charged with H$_2$ at room temperature overnight. The reaction was filtered through a pad of Celite and the filtrate was concentrated to dryness. The residue was purified by preparative HPLC to give the title compound (200 mg, 62%). MS calcd for (C$_{15}$H$_{15}$BN$_2$O$_6$+H)$^+$: 331.1. MS found: (M+H)$^+$=331.1.

Step 10: [4-(3-tert-Butoxycarbonylamino-propoxy)-1-hydroxy-6-(pyrazin-2-yloxy)-1,3-dihydro-benzo[c][1,2]oxaborol-3-yl]-acetic acid ethyl ester

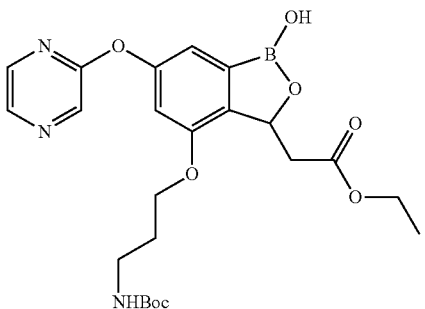 [SMILES: CCOC(=O)CC1OB(O)c2cc(Oc3cnccn3)cc(OCCCNC(=O)OC(C)(C)C)c21]

A solution of [1,4-dihydroxy-6-(pyrazin-2-yloxy)-1,3-dihydro-benzo[c][1,2]oxaborol-3-yl]-acetic acid ethyl ester (100 mg, 0.303 mmol) in DMF (10 mL) was treated with (3-bromo-propyl)-carbamic acid tert-butyl ester (100 mg, 0.454 mmol) and potassium carbonate (209 mg, 1.52 mmol) at 50° C. for 5 h. The reaction was concentrated to dryness. The residue was diluted with MeOH/H$_2$O and the mixture was adjusted pH to 3. The solution was purified by preparative HPLC to afford the title compound as a white solid (88 mg, 60%). MS calcd for (C$_{23}$H$_{30}$BN$_3$O$_8$+H)$^+$: 488.2. MS found: (M+H)$^+$=488.2.

Step 11: [4-(3-tert-Butoxycarbonylamino-propoxy)-1-hydroxy-6-(pyrazin-2-yloxy)-1,3-dihydro-benzo[c][1,2]oxaborol-3-yl]-acetic acid

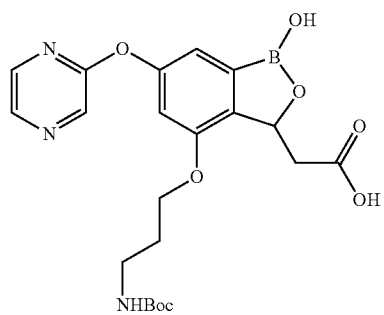 [SMILES: CC(C)(C)OC(=O)NCCCOc1cc(Oc2cnccn2)cc2c1C(CC(=O)O)OB2O]

A solution of [4-(3-tert-butoxycarbonylamino-propoxy)-1-hydroxy-6-(pyrazin-2-yloxy)-1,3-dihydro-benzo[c][1,2]oxaborol-3-yl]-acetic acid ethyl ester (4 mg) in THF/H$_2$O (1 mL, 1:1) was treated with LiOH (1.4 mg) at 0° C. and the reaction was stirred at room temperature for 2 h. The mixture was acidified to pH 3 with 1N HCl and purified by preparative HPLC to give the title compound (1.5 mg) as a white solid. $^1$H NMR (300 MHz, CD$_3$OD) δ 8.40 (s, 1H), 8.28-8.27 (m, 1H), 8.14-8.13 (m, 1H), 6.93 (d, J=1.8 Hz, 1H), 6.87 (d, J=1.8 Hz, 1H), 5.63-5.59 (m, 1H), 4.05 (t, 2H), 3.23-3.20 (m, 2H), 3.18-3.16 (m, 1H), 2.39-2.31 (m, 1H), 1.96 (t, 2H), 1.40 (s, 9H). MS calcd for (C$_{21}$H$_{26}$BN$_3$O$_8$+H-Boc)$^+$: 360.2. MS found: (M+H-Boc)$^+$=360.2.

G112: 2-(4-(2-Ethoxy-2-oxoethoxy)-1-hydroxy-6-(pyrazin-2-yloxy)-1,3-dihydrobenzo[c][1,2]-oxaborol-3-yl)acetic acid

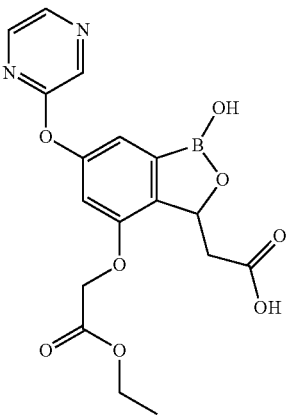 [SMILES: CCOC(=O)COc1cc(Oc2cnccn2)cc2c1C(CC(=O)O)OB2O]

Step 1: Ethyl 2-(4-(cyanomethoxy)-1-hydroxy-6-(pyrazin-2-yloxy)-1,3-dihydrobenzo[c][1,2]ox-aborol-3-yl)acetate

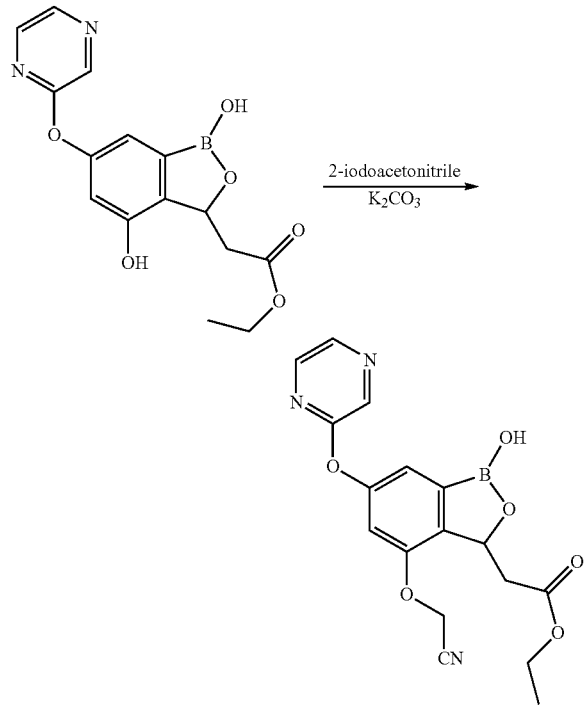

To a mixture of ethyl 2-(4-(cyanomethoxy)-1-hydroxy-6-(pyrazin-2-yloxy)-1,3-dihydrobenzo[c][1,2]oxaborol-3-yl) acetate (100 mg, 0.30 mmol) and anhydrous $K_2CO_3$ (130 mg, 0.91 mmol) in DMF (5 ml) was added 2-iodoacetonitrile (160 mg, 0.91 mmol). The reaction mixture was stirred at room temperature overnight and quenched by water (5 mL). The resulting mixture was acidified with 1 N HCl to pH=4 and extracted with EtOAc. The combined organic layers were washed with water (10 mL) and brine (10 mL), dried over anhydrous $Na_2SO_4$ and concentrated in vacuo to give the title compound (91 mg. Yield: 81%).

Step 2: 2-(4-(2-Ethoxy-2-oxoethoxy)-1-hydroxy-6-(pyrazin-2-yloxy)-1,3-dihydrobenzo[c][1,2]ox-aborol-3-yl)acetic acid

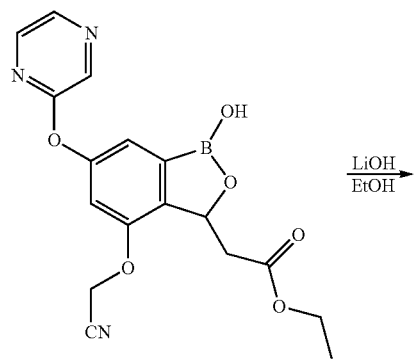

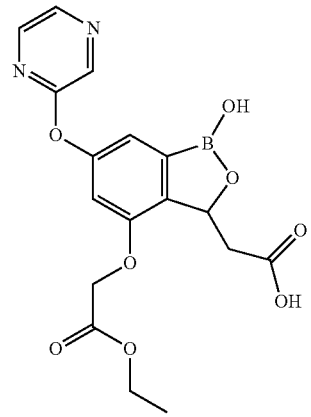

To a solution of ethyl 2-(4-(cyanomethoxy)-1-hydroxy-6-(pyrazin-2-yloxy)-1,3-dihydrobenzo[c][1,2]oxaborol-3-yl) acetate (100 mg, 0.271 mmol) in EtOH (4 mL) was added an aqueous solution of lithium hydroxide (21.9 mg, 0.54 mmol) in water (1 mL). The reaction mixture was stirred at room temperature overnight and acidified with 1N HCl to pH=3. The resulting mixture was extracted with EtOAc (2×20 mL) and the combined organic layers were dried over anhydrous $Na_2SO_4$ and concentrated in vacuo. The residue was purified by prep HPLC to give the title compound as a white powder (30 mg. Yield: 26%). $^1$H NMR (400 MHz, DMSO-d6) δ 12.34 (s, 1H), 9.31 (s, 1H), 8.55 (s, 1H), 8.40 (d, J=2.4 Hz, 1H), 8.23 (t, J=1.2 Hz, 1H), 7.06 (d, J=1.2 Hz, 1H), 7.00 (s, 1H), 5.51 (m, 1H), 4.48 (m, 2H), 4.16 (m, 2H), 3.37 (d, J=2.0 Hz, 1H), 2.21 (m, 1H), 1.16 (m, 3H). MS (ESI) m/z=389 [M+H]$^+$.

G113: 2-(4-(2-Oxyacetic acid)-1-hydroxy-6-(pyrazin-2-yloxy)-1,3-dihydrobenzo[c][1,2]ox-aborol-3-yl)acetic acid

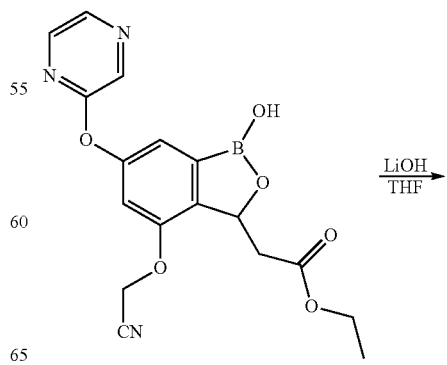

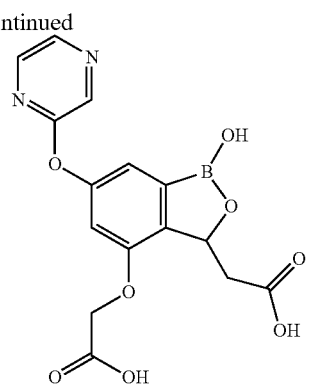

To a solution of ethyl 2-(4-(cyanomethoxy)-1-hydroxy-6-(pyrazin-2-yloxy)-1,3-dihydrobenzo[c][1,2]oxaborol-3-yl)acetate (100 mg, 0.21 mmol) in THF (4 mL) was added an aqueous solution of lithium hydroxide (21.9 mg, 0.54 mmol) in water (1 mL). The reaction mixture was stirred at room temperature for 2 h and acidified with 1N HCl to pH=3. The resulting mixture was extracted with EtOAc (2×20 mL). The combined organic layers were washed with water (10 mL) and brine (10 mL), dried over anhydrous $Na_2SO_4$ and concentrated in vacuo. The residue was purified by prep HPLC to give the title compound as a white powder (42 mg. Yield: 43%). $^1$H NMR (400 MHz, DMSO-d6) δ 9.25 (s, 1H), 8.51 (s, 1H), 8.37 (d, J=2.4 Hz, 1H), 8.22 (s, 1H), 6.86 (s, 1H), 6.62 (s, 1H), 5.39 (t, J=3.6 Hz, 1H), 3.09 (m, 2H), 2.34 (m, 1H). MS (ESI) m/z=361 [M+H]$^+$.

G114: 2-(4-(4-Aminobutoxy)-1-hydroxy-6-(pyrazin-2-yloxy)-1,3-dihydrobenzo[c][1,2]oxaborol-3-yl)acetic acid

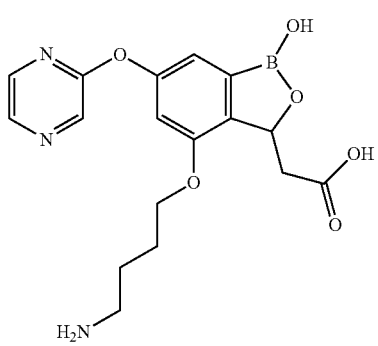 [SMILES: NCCCCOc1cc(Oc2cnccn2)cc2c1C(CC(=O)O)OB2O]

Into a 100-mL round-bottom flask was placed a solution of tert-butyl 2-(4-(4-(tert-butoxycarbonyl)butoxy)-1-hydroxy-6-(pyrazin-2-yloxy)-1,3-dihydrobenzo[c][1,2]oxaborol-3-yl)acetate (1.0 g, 1.32 mmol, 1.00 equiv, 70%) in dichloromethane (30 mL). This was followed by the addition of 2,2,2-trifluoroacetic acid (430 mg, 3.77 mmol, 2.00 equiv) dropwise with stirring at 0° C. The resulting solution was stirred for 10 h at room temperature. The resulting mixture was concentrated under vacuum. The crude product (1 g) was purified by Prep-HPLC with the following conditions: Column, SunFire Prep $C_{18}$, 5 μm, 19×100 mm; Mobile phase, water (with 0.05% TFA) and $CH_3CN$; Gradient, 10% $CH_3CN$ up to 20% $CH_3CN$ in 9 min, up to 100% $CH_3CN$ in 0.1 min, hold at 100% $CH_3CN$ for 1.4 min; Detector, UV 210 nm. This resulted in 40.6 mg (5%) of the target molecule as a white solid. $^1$H NMR (300 MHz, DMSO-d$_6$, ppm); δ 1.664-1.810 (4H, m), 2.154-2.238 (1H, m), 2.846-2.867 (2H, m), 3.120-3.180 (1H, m), 4.036 (2H, t), 5.434-5.475 (1H, m), 7.000-7.021 (2H, m), 7.671 (3H, s), 8.229-8.237 (1H, m), 8.393-8.402 (1H, m), 8.553 (1H, s), 9.298 (1H, s). MS (ESI) m/z: 374 [M-$CF_3COOH$+H]$^+$.

G115: [6-(6-Chloro-pyridazin-3-yloxy)-1-hydroxy-4-methyl-1,3-dihydro-benzo[c][1,2]oxaborol-3-yl]-acetic acid

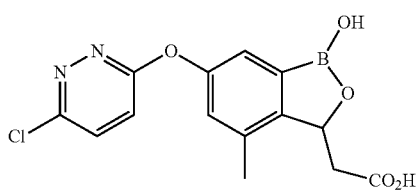 [SMILES: Cc1cc(Oc2ccc(Cl)nn2)cc2c1C(CC(=O)O)OB2O]

Step 1: [6-(6-Chloro-pyridazin-3-yloxy)-1-hydroxy-4-methyl-1,3-dihydro-benzo[c][1,2]oxaborol-3-yl]-acetic acid ethyl ester To a stirred solution of (1,6-dihydroxy-4-methyl-1,3-dihydro-benzo[c][1,2]oxaborol-3-yl)-acetic acid ethyl ester (0.2 g, 0.8 mmol) and 3,6-dichloro-pyridazine (0.24 g, 1.6 mmol) in DMF (15 mL) at 0° C. was added NaH (0.1 g, 2.4 mmol) in portions. The reaction mixture was allowed to warm to room temperature and stirred for 12 hours. Saturated $NH_4Cl$ (10 mL) was added at 0° C. and the solution acidified to pH~4 with dilute HCl. The mixture was extracted with EtOAc (2×10 mL) and the organic extracts washed with water (10 mL), dried and concentrated in vacuo. The residue was purified by silica gel flash column chromatography (DCM:MeOH 95:5) to give [6-(6-chloro-pyridazin-3-yloxy)-1-hydroxy-4-methyl-1,3-dihydro-benzo[c][1,2]oxaborol-3-yl]-acetic acid ethyl ester (0.12 g, 42%). $^1$H NMR (400 MHz, CDCl$_3$): δ 7.49 (d, J=8.8 Hz, 1H), 7.33 (d, J=2.0 Hz, 1H), 7.16 (d, J=9.6 Hz, 1H), 7.11 (s, 1H), 5.66 (dd, J=2.4, 9.6 Hz, 1H), 4.20 (q, J=7.2 Hz, 2H), 3.10 (dd, J=2.0, 15.6 Hz, 1H), 2.44-2.38 (m, 1H), 2.35 (s, 3H), 1.26 (t, J=7.2 Hz, 3H). MS (ESI) m/z=363 [M+H]$^+$.

Step 2: [6-(6-Chloro-pyridazin-3-yloxy)-1-hydroxy-4-methyl-1,3-dihydro-benzo[c][1,2]oxaborol-3-yl]-acetic acid

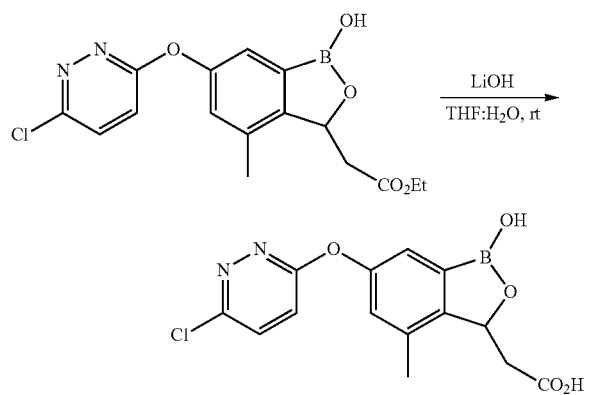

To a solution of [6-(6-chloro-pyridazin-3-yloxy)-1-hydroxy-4-methyl-1,3-dihydro-benzo[c][1,2]oxaborol-3-yl]-acetic acid ethyl ester (0.2 g, 0.55 mmol) in THF:H$_2$O (1:1, 10 mL) at 0° C. was added a solution of LiOH (0.026 g, 1.10 mmol) in water (1 mL). The solution was allowed to warm to room temperature over 3 hours then acidified to pH 2 with 1N HCl (1 mL) at 0° C. and concentrated in vacuo. The residue was purified by preparative HPLC to give [6-(6-chloro-pyridazin-3-yloxy)-1-hydroxy-4-methyl-1,3-dihydro-benzo[c][1,2]oxaborol-3-yl]-acetic acid (0.1 g, 54%). $^1$H NMR (400 MHz, DMSO): δ 9.21 (s, 1H), 7.96 (d, J=9.2 Hz, 1H), 7.60 (d, J=9.2 Hz, 1H), 7.30 (d, J=2.0 Hz, 1H), 7.15 (d, J=1.6 Hz, 1H), 5.52 (dd, J=2.4, 9.2 Hz, 1H), 3.10 (dd, J=2.0, 15.6 Hz, 1H), 2.31 (s, 3H), 2.18-2.12 (m, 1H). MS (ESI) m/z=333 [M−H]$^-$.

G116: [1-Hydroxy-4-methyl-6-(pyridazin-3-yloxy)-1,3-dihydro-benzo[c][1,2]oxaborol-3-yl]-acetic acid

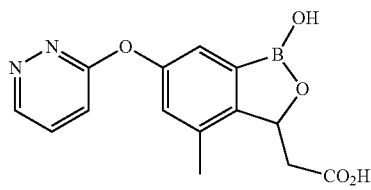 [SMILES: Cc1cc(Oc2cccnn2)cc2c1C(CC(=O)O)OB2O]

Step 1: [1-Hydroxy-4-methyl-6-(pyridazin-3-yloxy)-1,3-dihydro-benzo[c][1,2]oxaborol-3-yl]-acetic acid ethyl ester

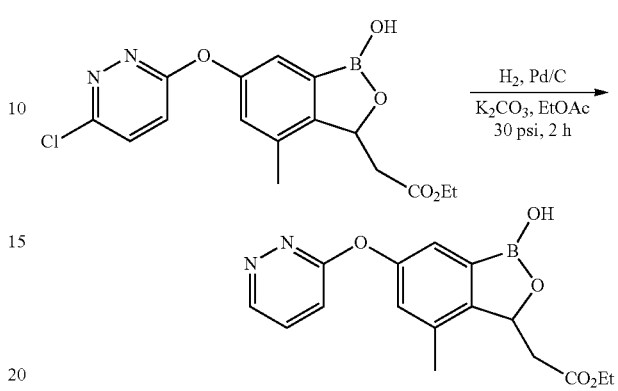

A mixture of [6-(6-Chloro-pyridazin-3-yloxy)-1-hydroxy-4-methyl-1,3-dihydro-benzo[c][1,2]oxaborol-3-yl]-acetic acid ethyl ester (0.5 g, 1.37 mmol), 10% Pd/C (0.45 g) and K$_2$CO$_3$ (0.38 g, 2.75 mmol) in EtOAc (20 mL) was hydrogenated at 30 psi for 2 hours. The mixture was filtered through a pad of celite and concentrated in vacuo. The residue was purified by silica gel flash column chromatography (DCM: MeOH 95:5) to give [1-hydroxy-4-methyl-6-(pyridazin-3-yloxy)-1,3-dihydro-benzo[c][1,2]oxaborol-3-yl]-acetic acid ethyl ester (0.35 g, 77%). $^1$H NMR (400 MHz, DMSO): δ 9.26 (s, 1H), 8.98 (dd, J=1.6, 4.8 Hz, 1H), 7.76-7.73 (m, 1H), 7.44 (dd, J=1.2, 8.8 Hz, 1H), 7.26 (d, J=2.4 Hz, 1H), 7.12 (d, J=1.6 Hz, 1H), 5.53 (dd, J=2.4, 9.2 Hz, 1H), 4.03 (q, J=7.2 Hz, 2H), 3.14 (dd, J=2.8, 15.6 Hz, 1H), 2.33-2.24 (m, 1H), 2.30 (s, 3H), 1.13 (t, J=7.2 Hz, 3H). MS (ESI) m/z=329 [M+H]$^+$.

Step 2: [1-Hydroxy-4-methyl-6-(pyridazin-3-yloxy)-1,3-dihydro-benzo[c][1,2]oxaborol-3-yl]-acetic acid

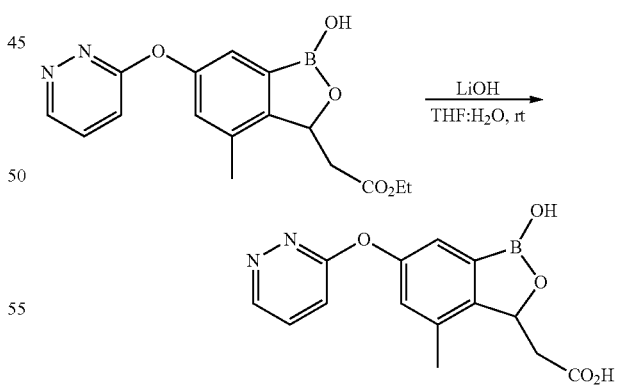

To a solution of [1-hydroxy-4-methyl-6-(pyridazin-3-yloxy)-1,3-dihydro-benzo[c][1,2]oxaborol-3-yl]-acetic acid ethyl ester (0.35 g, 1.06 mmol) in THF:H$_2$O (1:1, 6 mL) at 0° C. was added a solution of LiOH (0.076 g, 3.2 mmol) in water (1 mL). The solution was allowed to warm to room temperature over 3 hours then acidified to pH 2 with 1N HCl and extracted with EtOAc (2×10 mL). The organic extracts were washed with water (10 mL), dried and concentrated in vacuo.

The residue was purified by silica gel flash column chromatography (DCM:MeOH 90:10) to give [1-hydroxy-4-methyl-6-(pyridazin-3-yloxy)-1,3-dihydro-benzo[c][1,2]oxaborol-3-yl]-acetic acid (0.15 g, 47%). $^1$H NMR (400 MHz, DMSO): δ 9.23 (s, 1H), 9.01 (dd, J=1.2, 4.4 Hz, 1H), 7.79-7.76 (m, 1H), 7.47 (dd, J=1.2, 9.2 Hz, 1H), 7.28 (d, J=2.0 Hz, 1H), 7.14 (d, J=2.0 Hz, 1H), 5.54 (dd, J=2.4 Hz, 1H), 3.10 (dd, J=2.4, 15.6 Hz, 1H), 2.32 (s, 3H), 2.19-2.12 (m, 1H). MS (ESI) m/z=299 [M−H]$^−$.

G117: [6-(6-Aminomethyl-pyridazin-3-yloxy)-1-hydroxy-4-methyl-1,3-dihydro-benzo[c][1,2]oxaborol-3-yl]-acetic acid

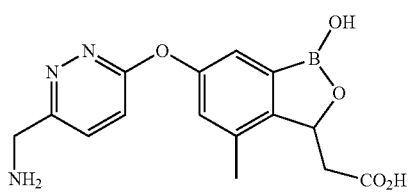 [SMILES: Cc1cc(Oc2ccc(CN)nn2)cc2c1C(CC(=O)O)OB2O]

Step 1: [6-(6-Cyano-pyridazin-3-yloxy)-1-hydroxy-4-methyl-1,3-dihydro-benzo[c][1,2]oxaborol-3-yl]-acetic acid ethyl ester

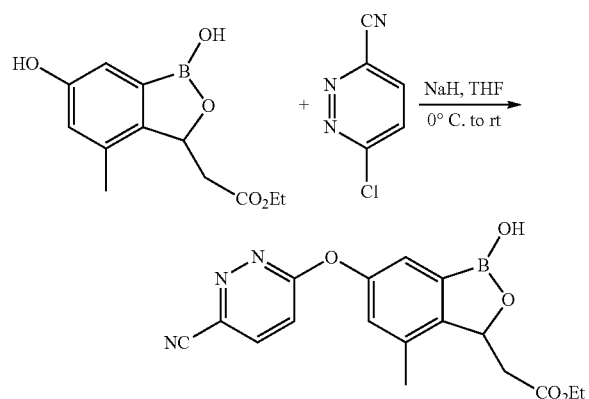

To a stirred solution of (1,6-dihydroxy-4-methyl-1,3-dihydro-benzo[c][1,2]oxaborol-3-yl)-acetic acid ethyl ester (1.0 g, 3.9 mmol) and 6-chloro-pyridazine-3-carbonitrile (1.12 g, 7.9 mmol) in THF (50 mL) at 0° C. was added NaH (0.38 g) in portions. The reaction mixture was allowed to warm to room temperature and stirred for 12 hours. Saturated NH$_4$Cl (10 mL) was added at 0° C. and the solution acidified to pH~4 with 1N HCl. The mixture was extracted with EtOAc (2×15 mL) and the organic extracts washed with water (10 mL), dried and concentrated in vacuo. The residue was purified by silica gel flash column chromatography (DCM:MeOH 95:5) to give [6-(6-cyano-pyridazin-3-yloxy)-1-hydroxy-4-methyl-1,3-dihydro-benzo[c][1,2]oxaborol-3-yl]-acetic acid ethyl ester (0.75 g, 53%). $^1$H NMR (400 MHz, CDCl$_3$): δ 9.27 (s, 1H), 8.36 (d, J=9.2 Hz, 1H), 7.71 (d, J=9.2 Hz, 1H), 7.33 (d, J=2.0 Hz, 1H), 7.18 (d, J=1.6 Hz, 1H), 5.55 (dd, J=2.4, 9.2 Hz, 1H), 4.04 (q, J=6.8 Hz, 2H), 3.14 (dd, J=2.4, 15.6 Hz, 1H), 2.36-2.32 (m, 1H), 2.31 (s, 3H), 1.13 (t, J=6.8 Hz, 3H). MS (ESI) m/z=354 [M+H]$^+$.

Step 2: [6-(6-Aminomethyl-pyridazin-3-yloxy)-1-hydroxy-4-methyl-1,3-dihydro-benzo[c][1,2]oxaborol-3-yl]-acetic acid ethyl ester

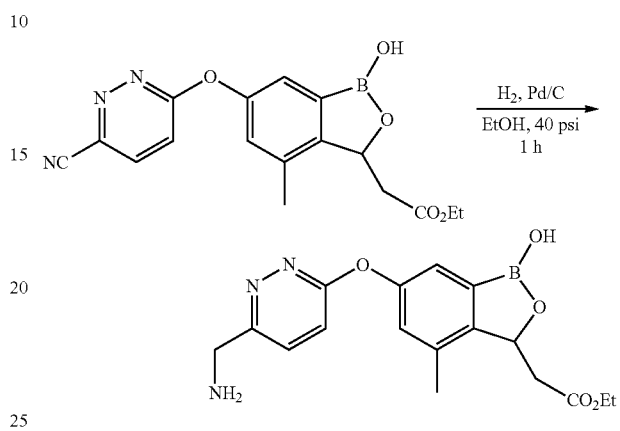

A mixture of [6-(6-cyano-pyridazin-3-yloxy)-1-hydroxy-4-methyl-1,3-dihydro-benzo[c][1,2]oxaborol-3-yl]-acetic acid ethyl ester (0.3 g, 0.85 mmol) and 10% Pd/C (0.35 g) in EtOH (20 mL) was hydrogenated at 40 psi for 1 hour. The mixture was filtered through a pad of celite and concentrated in vacuo to give [6-(6-aminomethyl-pyridazin-3-yloxy)-1-hydroxy-4-methyl-1,3-dihydro-benzo[c][1,2]oxaborol-3-yl]-acetic acid ethyl ester (0.28 g) which was used without further purification. $^1$H NMR (400 MHz, DMSO): δ 9.29 (s, 1H), 7.88 (d, J=8.8 Hz, 1H), 7.51 (d, J=9.6 Hz, 1H), 7.30 (d, J=2.0 Hz, 1H), 7.12 (d, J=1.2 Hz, 1H), 5.55 (dd, J=2.0, 9.2 Hz, 1H), 4.17 (s, 2H), 4.06 (q, J=7.6 Hz, 2H), 3.16 (dd, J=2.4, 15.6 Hz, 1H), 2.35-2.29 (m, 4H), 1.16 (t, J=7.6 Hz, 3H). MS (ESI) m/z=358 [M+H]$^+$.

Step 3: [6-(6-Aminomethyl-pyridazin-3-yloxy)-1-hydroxy-4-methyl-1,3-dihydro-benzo[c][1,2]oxaborol-3-yl]-acetic acid

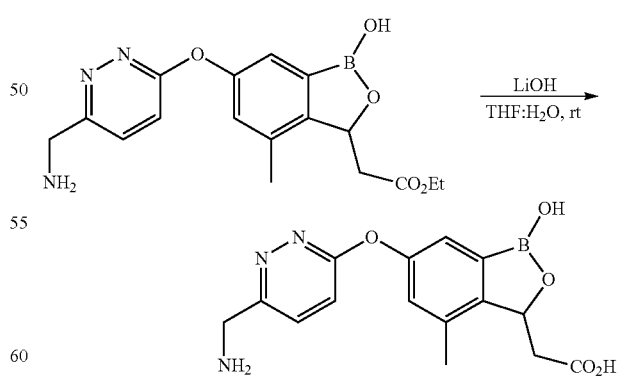

To a solution of [6-(6-aminomethyl-pyridazin-3-yloxy)-1-hydroxy-4-methyl-1,3-dihydro-benzo[c][1,2]oxaborol-3-yl]-acetic acid ethyl ester (0.28 g, 0.78 mmol) in THF:H$_2$O (1:1, 6 mL) at 0° C. was added a solution of LiOH (0.056 g, 2.35 mmol) in water (1 mL). The solution was allowed to warm to room temperature over 3 hours then acidified to pH 2 with 1N HCl at 0° C. and concentrated in vacuo. The residue was purified by preparative HPLC to give [6-(6-aminomethyl-pyridazin-3-yloxy)-1-hydroxy-4-methyl-1,3-dihydro-benzo[c][1,2]oxaborol-3-yl]-acetic acid (0.1 g, 38%). $^1$H NMR (400 MHz, DMSO): δ 8.78 (brs, 2H), 7.93 (d, J=9.2 Hz, 1H), 7.53 (d, J=9.2 Hz, 1H), 7.34 (s, 1H), 7.09 (s, 1H), 5.51 (d, J=8.8 Hz, 1H), 4.27 (d, J=5.2 Hz, 2H), 3.06 (d, J=14.8 Hz, 1H), 2.28 (s, 3H), 2.16-2.10 (m, 1H). MS (ESI) m/z=330 [M+H]$^+$.

G118: [6-(6-Carbamoyl-pyridazin-3-yloxy)-1-hydroxy-4-methyl-1,3-dihydro-benzo[c][1,2]oxaborol-3-yl]-acetic acid

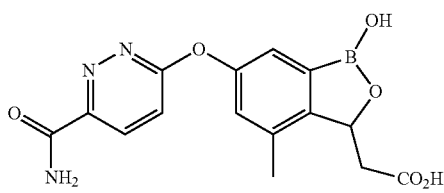 [SMILES: Cc1cc(Oc2ccc(C(N)=O)nn2)cc2c1C(CC(=O)O)OB2O]

G119: [6-(6-Cyano-pyridazin-3-yloxy)-1-hydroxy-4-methyl-1,3-dihydro-benzo[c][1,2]oxaborol-3-yl]-acetic acid

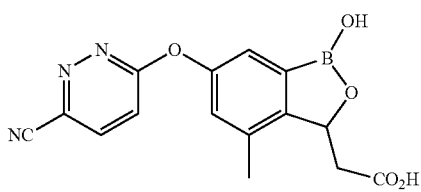

Step 1: [6-(6-Carbamoyl-pyridazin-3-yloxy)-1-hydroxy-4-methyl-1,3-dihydro-benzo[c][1,2]oxaborol-3-yl]-acetic acid and [6-(6-Cyano-pyridazin-3-yloxy)-1-hydroxy-4-methyl-1,3-dihydro-benzo[c][1,2]oxaborol-3-yl]-acetic acid

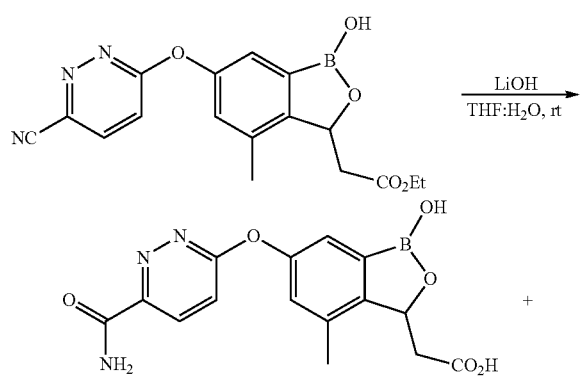

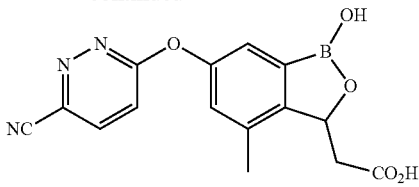 [SMILES: Cc1cc(Oc2ccc(C#N)nn2)cc2c1C(CC(=O)O)OB2O]

To a solution of [6-(6-cyano-pyridazin-3-yloxy)-1-hydroxy-4-methyl-1,3-dihydro-benzo[c][1,2]oxaborol-3-yl]-acetic acid ethyl ester (0.25 g, 0.7 mmol) in THF:H$_2$O (1:1, 6 mL) at 0° C. was added a solution of LiOH (0.025 g, 1.06 ml) in water (1 mL). The solution was stirred at 0° C. for 20 hours then acidified to pH 3 with 1N HCl and extracted with EtOAc (2×10 mL). The organic extracts were dried and concentrated in vacuo. The residue was purified by preparative HPLC to give [6-(6-carbamoyl-pyridazin-3-yloxy)-1-hydroxy-4-methyl-1,3-dihydro-benzo[c][1,2]oxaborol-3-yl]-acetic acid (0.025 g, 11%) and [6-(6-cyano-pyridazin-3-yloxy)-1-hydroxy-4-methyl-1,3-dihydro-benzo[c][1,2]oxaborol-3-yl]-acetic acid (0.058 g, 26%).

[6-(6-carbamoyl-pyridazin-3-yloxy)-1-hydroxy-4-methyl-1,3-dihydro-benzo[c][1,2]oxaborol-3-yl]-acetic acid $^1$H NMR (400 MHz, DMSO): δ 8.33 (brs, 1H), 8.21 (d, J=8.8 Hz, 1H), 7.82 (brs, 1H), 7.56 (d, J=9.2 Hz, 1H), 7.35 (d, J=2.0 Hz, 1H), 7.20 (d, J=1.6 Hz, 1H), 5.54 (dd, J=2.4, 9.6 Hz, 1H), 3.10 (dd, J=2.4, 15.2 Hz, 1H), 2.32 (s, 3H), 2.21-2.15 (m, 1H). MS (ESI) m/z=342 [M−H]$^-$.

[6-(6-cyano-pyridazin-3-yloxy)-1-hydroxy-4-methyl-1,3-dihydro-benzo[c][1,2]oxaborol-3-yl]-acetic acid $^1$H NMR (400 MHz, DMSO): δ 8.36 (d, J=8.8 Hz, 1H), 7.71 (d, J=9.6 Hz, 1H), 7.34 (d, J=2.0 Hz, 1H), 7.18 (d, J=1.6 Hz, 1H), 5.53 (dd, J=2.4, 9.6 Hz, 1H), 3.08 (dd, J=2.8, 15.6 Hz, 1H), 2.31 (s, 3H), 2.19-2.13 (m, 1H). MS (ESI) m/z=324 [M−H]$^-$.

G120: 2-(1-Hydroxy-4-methyl-6-(thiazol-2-yloxy)-1,3-dihydrobenzo[c][1,2]oxaborol-3-yl)acetic acid

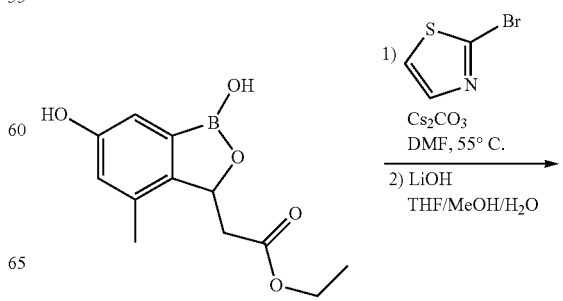

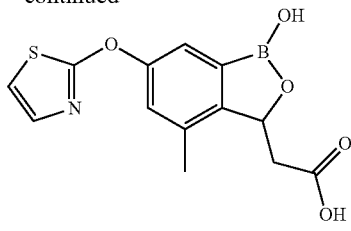

To a solution of ethyl 2-(1,6-dihydroxy-4-methyl-1,3-dihydrobenzo[c][1,2]oxaborol-3-yl)acetate (2.5 g, 10 mmol) in anhydrous DMF (50 mL) was added Cs$_2$CO$_3$ (8.1 g, 24.8 mmol) and 2-bromothiazole (3.28 g, 10 mmol) at 0° C. After stirring for 15 min at room temperature, the resulting mixture was stirred at 55° C. overnight. The reaction quenched by adding cold brine at 0° C. and the mixture was acidified to pH 7 using 1N HCl. The resulting mixture was extract with EtOAc. The extract was washed with brine, dried and concentrated to dryness. The residue was purified by chromatography on silica gel (ethyl acetate/hexanes=0~80%) to give 250 mg of ethyl ester intermediate.

The mixture of the above intermediate (100 mg, 0.3 mmol) and LiOH (36 mg, 1.5 mmol) in THF/MeOH/H$_2$O (3 ml/3 ml/3 ml) was stirred at room temperature for 4 hrs. The reaction mixture was quenched with sat. NH$_4$Cl and extracted with ethyl acetate. The organic layer was washed with H$_2$O and brine, dried and concentrated in reduced pressure to dryness. The crude product was purified by Prep-HPLC to give 35 mg of desired product as white powder. $^1$H NMR (400 MHz, CD$_3$OD) δ 7.30 (d, J=1.6 Hz, 1H), 7.23 (d, J=3.9 Hz, 1H), 7.19 (d, J=1.6 Hz, 1H), 7.05 (d, J=3.9 Hz, 1H), 5.66 (dd, J=9.2, 2.5 Hz, 1H), 3.16 (dd, J=15.5, 2.5 Hz, 1H), 2.38 (s, 3H), and 2.34 (dd, J=9.2, 15.6 Hz, 1H). MS (ESI) m/z=306 [M+H]$^+$.

G121: 2-(1-Hydroxy-4-methyl-6-(5-nitrothiazol-2-yloxy)-1,3-dihydrobenzo[c][1,2]oxaborol-3-yl)acetic acid

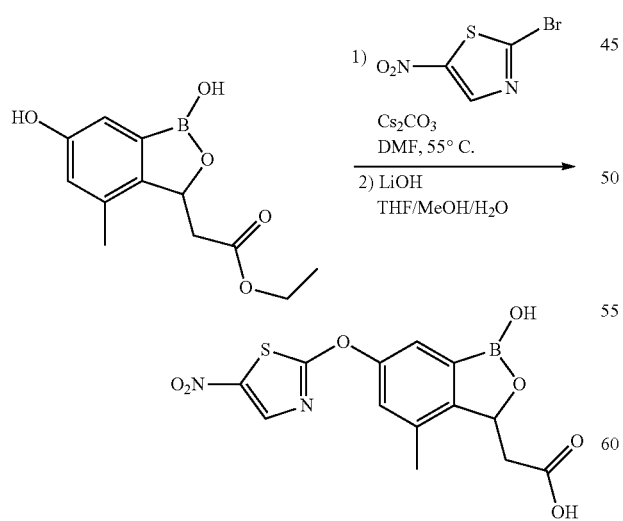

To a solution of ethyl 2-(1,6-dihydroxy-4-methyl-1,3-dihydrobenzo[c][1,2]oxaborol-3-yl)acetate (2.5 g, 10 mmol) in anhydrous DMF (40 mL) was added Cs$_2$CO$_3$ (6.5 g, 20 mmol) and 2-bromo-5-nitrothiazole (2.09 g, 10 mmol) at 0° C. After stirring for 15 min at room temperature, the resulting mixture was stirred at 55° C. overnight. The reaction quenched by adding cold brine at 0° C. and the mixture was acidified to pH 7 using 1N HCl. The resulting mixture was extract with EtOAc. The extract was washed with brine, dried and concentrated to dryness. The residue was purified by chromatography on silica gel (ethyl acetate/hexanes=0~80%) to give 1.6 g of ethyl ester intermediate.

The mixture of the above intermediate (1.14 g, 3 mmol) and LiOH (240 mg, 10 mmol) in THF/MeOH/H$_2$O (10 ml/10 ml/10 ml) was stirred at room temperature for 4 hrs. The reaction mixture was quenched with sat. NH$_4$Cl and extracted with ethyl acetate. The organic layer was washed with H$_2$O and brine, dried and concentrated in reduced pressure to dryness. The crude product was purified by Prep-HPLC to give desired product 620 mg as white powder. $^1$H NMR (400 MHz, DMSO-d$_6$) δ 12.32 (s, 1H), 9.35 (s, 1H), 8.49 (s, 1H), 7.49 (d, J=2.2 Hz, 1H), 7.37 (d, J=2.2 Hz, 1H), 5.55 (dd, J=9.2, 2.5 Hz, 1H), 3.08 (dd, J=15.6, 2.5 Hz, 1H), 2.33 (s, 3H), and 2.20 (dd, J=9.2, 15.6 Hz, 1H). MS (ESI) m/z=379 [M+H]$^+$.

G122: 2-(6-(5-Carbamimidoylthiazol-2-yloxy)-1-hydroxy-4-methyl-1,3-dihydrobenzo[c][1,2]oxaborol-3-yl)acetic acid

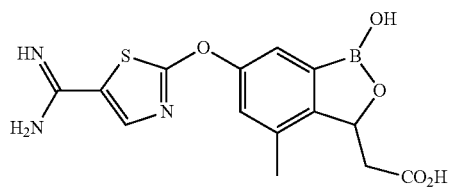 [SMILES: Cc1cc(Oc2ncc(C(=N)N)s2)cc2c1C(CC(=O)O)OB2O]

Step 1: Ethyl 2-(6-(5-cyanothiazol-2-yloxy)-1-hydroxy-4-methyl-1,3-dihydrobenzo[c][1,2]oxaborol-3-yl)acetate

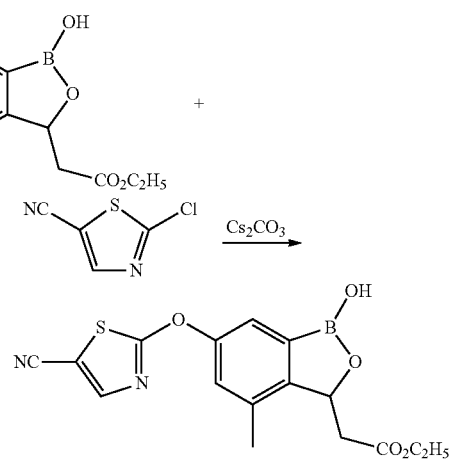

To a mixture of ethyl 2-(1,6-dihydroxy-4-methyl-1,3-dihydrobenzo[c][1,2]oxaborol-3-yl)acetate (3.75 g, 15 mmol, 1 eq.) and 2-chlorothiazole-5-carbonitrile (3.25 g, 22.5 mmol, 1.5 eq.) in 100 ml DMF was added cesium carbonate (14 g, 45 mmol, 3 eq.). The reaction was heated at 70° C. for two hours. It was then quenched by water, extracted with EtOAc, washed with brine, dried over $Na_2SO_4$, and concentrated under reduced pressure. The crude was purified by column chromatography (4.3 g, yield 80%). MS (ESI) m/z=717 $[2M+H]^+$.

Step 2: Ethyl 2-(1-hydroxy-6-(5-(N-hydroxycarbamimidoyl)thiazol-2-yloxy)-4-methyl-1,3-dihydrobenzo[c][1,2]oxaborol-3-yl)acetate

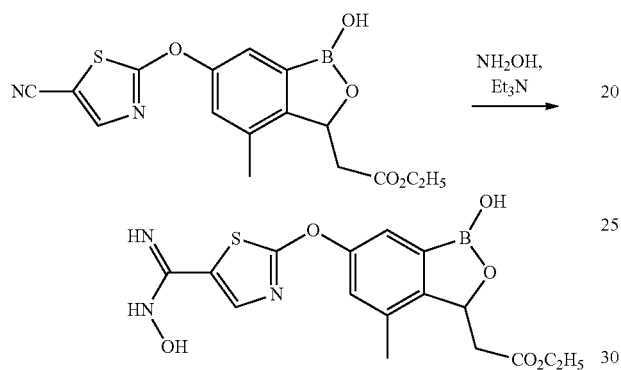

To a solution of ethyl 2-(6-(5-cyanothiazol-2-yloxy)-1-hydroxy-4-methyl-1,3-dihydrobenzo[c][1,2]oxaborol-3-yl)acetate1 (2.5 g, 7 mmol, 1 eq.) and hydroxylamine hydrochloride (1.21 g, 17.4 mmol, 2.5 eq.) in methanl was added triethylamine (3.41 ml, 24.5 mmol, 3.5 eq.). After stirring at room temperature overnight, the starting material was gone but no right mass was observed. The reaction mixture was evaporated under reduced pressure. The residue was dissolved in EtOAc and then washed with water. The organic layers were collected, dried with $Na_2SO_4$ and evaporated to give the crude product as a yellow solid. The crude was used in subsequent steps without further purification.

Step 3: Ethyl 2-(6-(5-carbamimidoylthiazol-2-yloxy)-1-hydroxy-4-methyl-1,3-dihydrobenzo[c][1,2]oxaborol-3-yl)acetate

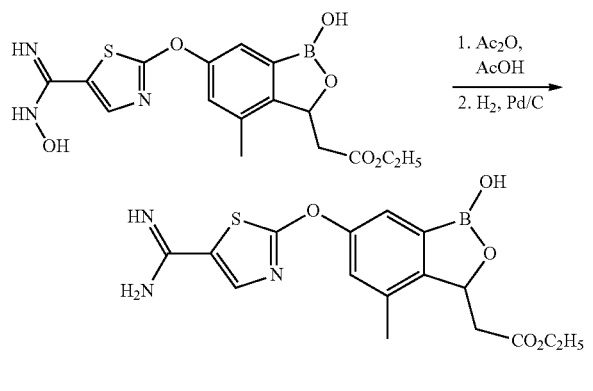

To a solution of crude ethyl 2-(1-hydroxy-6-(5-(N-hydroxycarbamimidoyl)thiazol-2-yloxy)-4-methyl-1,3-dihydrobenzo[c][1,2]oxaborol-3-yl)acetate (6.2 g crude) in 30 ml of acetic acid was added 400 ul of acetic anhydride. After the mixture was stirred at room temperature for one and half hour, it was treated with palladium (10% wet on charcoal, 1.8 g) and then hydrogenation on Parr-shaker for five hours. The mixture was filtered through a Celite pad and the filtrate was concentrated and dried under hi-Vac to give the crude product. The crude was used in subsequent steps without further purification.

Step 4: 2-(6-(5-Carbamimidoylthiazol-2-yloxy)-1-hydroxy-4-methyl-1,3-dihydrobenzo[c][1,2]oxaborol-3-yl)acetic acid

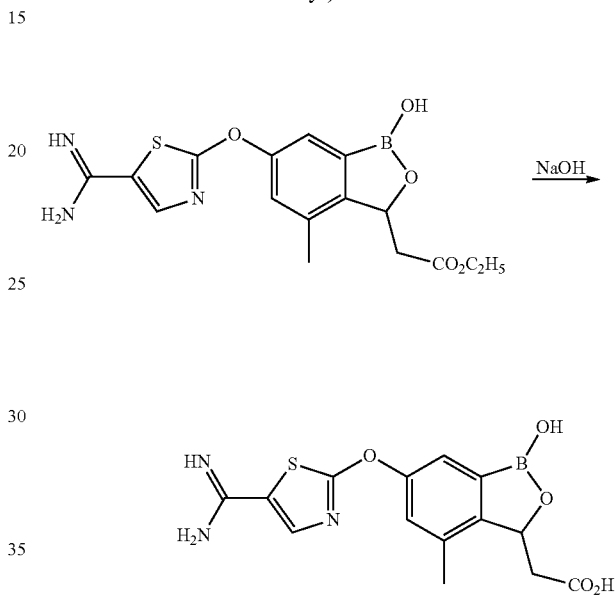

The crude ethyl 2-(6-(5-carbamimidoylthiazol-2-yloxy)-1-hydroxy-4-methyl-1,3-dihydrobenzo[c][1,2]oxaborol-3-yl)acetate in 6 ml methanol was treated with aqueous NaOH solution (500 mg, 6 ml water) for one hour. It was acidified with 1N HCl to pH 5 and then concentrated. HPLC purification gave desired product as white flakes. $^1H$ NMR (400 MHz, DMSO-$d_6$) δ 12.4 (b, 1H), 9.22 (b, 2H), 9.01 (b, 2H), 8.21 (s, 1H), 7.44 (d, J=2 Hz, 1H), 7.32 (d, J=1.6 Hz, 1H), 5.50 (dd, J=9.2, 2.4 Hz, 1H), 3.05 (dd, J=15.6, 2.4 Hz, 1H), 2.28 (s, 3H), 2.12 (dd, J=15.6, 9.6 Hz, 1H). MS (ESI) m/z=348 $[M+H]^+$.

G123: 2-(1-Hydroxy-6-(5-(N-hydroxycarbamimidoyl)thiazol-2-yloxy)-4-methyl-1,3-dihydrobenzo[c][1,2]oxaborol-3-yl)acetic acid

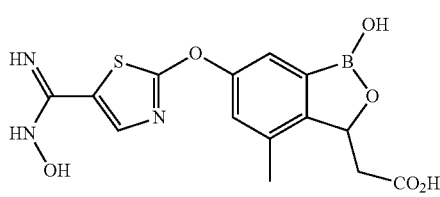 [SMILES: Cc1cc(Oc2ncc(C(=N)NO)s2)cc2c1C(CC(=O)O)OB2O]

Step 1: Ethyl 2-(6-(5-cyanothiazol-2-yloxy)-1-hydroxy-4-methyl-1,3-dihydrobenzo[c][1,2]oxaborol-3-yl)acetate

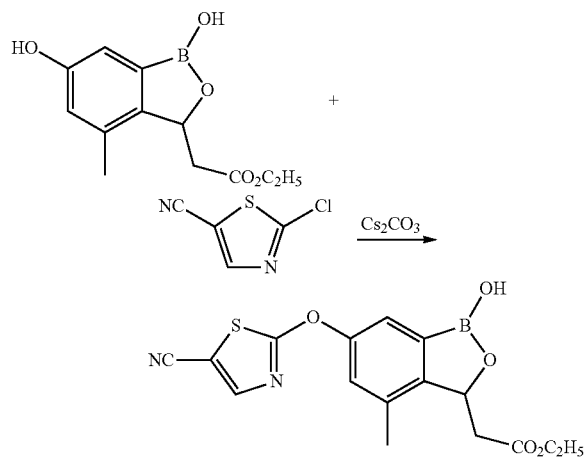

To a mixture of ethyl 2-(1,6-dihydroxy-4-methyl-1,3-dihydrobenzo[c][1,2]oxaborol-3-yl)acetate (3.75 g, 15 mmol, 1 eq.) and 2-chlorothiazole-5-carbonitrile (3.25 g, 22.5 mmol, 1.5 eq.) in 100 ml DMF was added cesium carbonate (14 g, 45 mmol, 3 eq.). The reaction was heated at 70° C. for two hours. It was then quenched by water, extracted with EtOAc, washed with brine, dried over $Na_2SO_4$, and concentrated under reduced pressure. The crude was purified by column chromatography (4.3 g, yield 80%). MS (ESI) m/z=717 [2M+H]$^+$.

Step 2: Ethyl 2-(1-hydroxy-6-(5-(N-hydroxycarbamimidoyl)thiazol-2-yloxy)-4-methyl-1,3-dihydrobenzo[c][1,2]oxaborol-3-yl)acetate

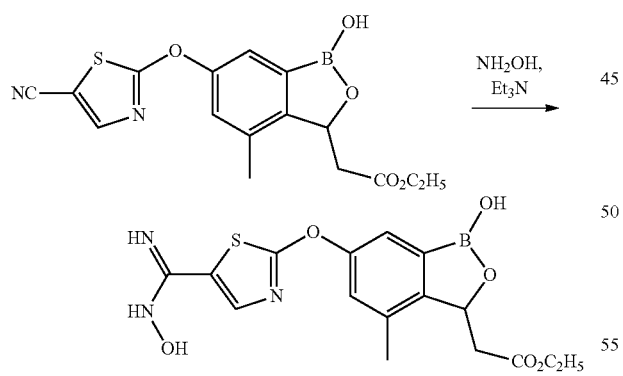

To a solution of ethyl 2-(6-(5-cyanothiazol-2-yloxy)-1-hydroxy-4-methyl-1,3-dihydrobenzo[c][1,2]oxaborol-3-yl)acetate (2.5 g, 7 mmol, 1 eq.) and hydroxylamine hydrochloride (1.21 g, 17.4 mmol, 2.5 eq.) in methanol was added triethylamine (3.41 ml, 24.5 mmol, 3.5 eq.). After stirring at room temperature overnight, the reaction mixture was evaporated under reduced pressure. The residue was dissolved in EtOAc and then washed with water. The organic layers were collected, dried with $Na_2SO_4$ and evaporated to give the crude product as a yellow solid. The crude was used in subsequent steps without further purification.

Step 3: 2-(1-Hydroxy-6-(5-(N-hydroxycarbamimidoyl)thiazol-2-yloxy)-4-methyl-1,3-dihydrobenzo[c][1,2]oxaborol-3-yl)acetic acid

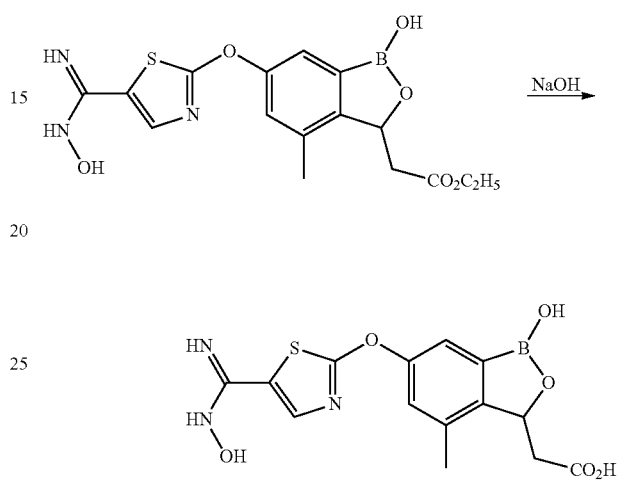

The crude ethyl 2-(1-hydroxy-6-(5-(N-hydroxycarbamimidoyl)thiazol-2-yloxy)-4-methyl-1,3-dihydrobenzo[c][1,2]oxaborol-3-yl)acetate in MeOH/THF (10 mL, 1:1) was added aqueous NaOH solution (200 mg in 3 mL water). After stirring at room temperature for two hours, the reaction mixture was evaporated, acidified with 1N HCl to pH 5 and then concentrated. HPLC purification gave desired product as white solid. $^1$H NMR (400 MHz, DMSO-$d_6$) δ 10.2 (b, 2H), 9.20 (b, 1H), 7.70 (s, 1H), 7.37 (d, J=2 Hz, 1H), 7.22 (d, J=1.6 Hz, 1H), 5.48 (dd, J=9.2, 2 Hz, 1H), 3.02 (dd, J=15.6, 2.4 Hz, 1H), 2.26 (s, 3H), 2.28 (dd, J=15.6, 9.6 Hz, 1H). 2 protons assumed to be exchanged with solvents. MS (ESI) m/z=364 [M+H]$^+$.

G124: 2-(3-Carboxymethyl-1-hydroxy-4-methyl-1,3-dihydro-benzo[c][1,2]oxaborol-6-yloxy)-thiazole-4-carboxylic acid

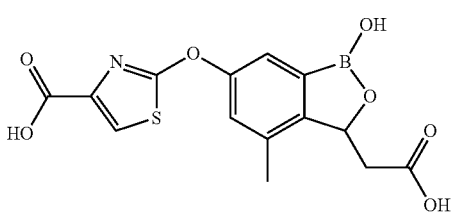 [SMILES: Cc1cc(Oc2nc(C(=O)O)cs2)cc2c1C(CC(=O)O)OB2O]

A solution of 2-(3-ethoxycarbonylmethyl-1-hydroxy-4-methyl-1,3-dihydro-benzo[c][1,2]oxaborol-6-yloxy)-thiazole-4-carboxylic acid methyl ester (500 mg, 1.28 mmol) in THF (30 mL) was treated with LiOH (107 mg, 2.55 mmol) in water (15 mL) at room temperature for 1 h. The reaction was concentrated to dryness. The residue was diluted with water and adjusted to pH 3. The mixture was purified by preparative HPLC to give the title compound (33 mg). $^1$H NMR (300 MHz, CD$_3$OD) δ 7.87 (s, 1H), 7.35 (s, 1H), 7.25 (s, 1H), 5.70-5.66 (m, 1H), 3.27-3.10 (m, 1H), 2.39 (s, 3H), 2.36-2.31 (m, 1H). MS found: (M+H)$^+$: 350.1.

G125: [6-(5-Carbamoyl-thiazol-2-yloxy)-1-hydroxy-4-methyl-1,3-dihydro-benzo[c][1,2]oxaborol-3-yl]-acetic acid

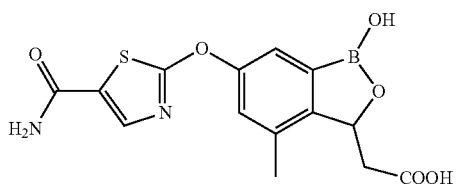 [SMILES: Cc1cc(Oc2ncc(C(N)=O)s2)cc2c1C(CC(=O)O)OB2O]

To a solution of 2-(3-ethoxycarbonylmethyl-1-hydroxy-4-methyl-1,3-dihydro-benzo[c][1,2]oxaborol-6-yloxy)-thiazole-5-carboxylic acid (227 mg, 0.6 mmol) in 4 mL of DCM was added one drop of DMF, 2 mL of oxalyl chloride was added dropwise and stirred for 1 h at room temperature. The reaction mixture was concentrated and dissolved in DCM (2 mL), which was further treated with ammonium hydroxide (5 mL). The reaction mixture was stirred for 1 h and concentrated. The crude product was dissolved in THF (2 mL) and treated with LiOH (90 mg) in water (1 mL). The reaction mixture was stirred for 3 h and concentrated. The crude product was purified by HPLC affording the title compound (63 mg, 30%). $^1$H NMR (DMSO) δ 9.39 (s, 1H), 8.10 (s, 1H), 7.90 (s, 1H), 7.58 (s, 1H), 7.45 (s, 1H), 7.32 (s, 1H), 5.58 (dd, 1H), 3.11 (m, 1H), 2.39 (s, 3H), 2.20 (m, 1H). MS found: (M+H)$^+$=348.95.

G126: (R)-2-(6-(5-carbamoylthiazol-2-yloxy)-1-hydroxy-4-methyl-1,3-dihydrobenzo[c][1,2]oxaborol-3-yl)acetic acid

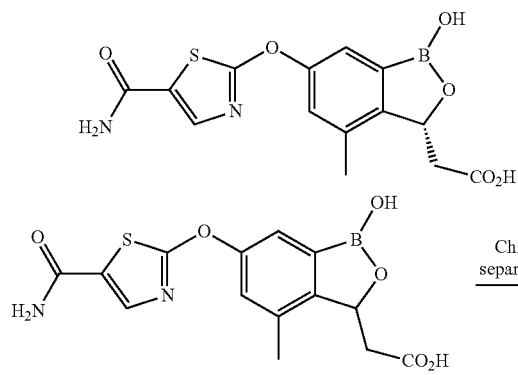

Chiral separation

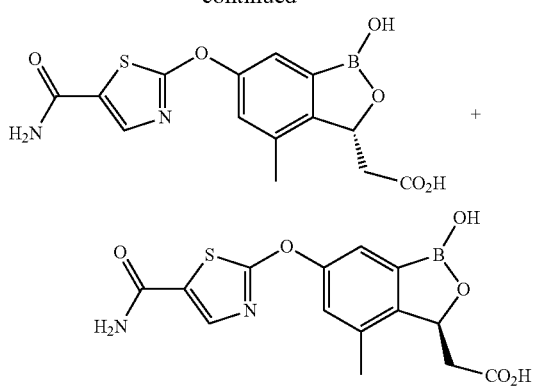

4.29 g of racemate were separated by preparative HPLC using a CHIRALPAK® AZ column afforded 1.78 g of (R)-2-(6-(5-carbamoylthiazol-2-yloxy)-1-hydroxy-4-methyl-1,3-dihydrobenzo[c][1,2]oxaborol-3-yl)acetic acid. The purity of the products was 99.9% ee. $^1$H NMR (DMSO) δ 9.39 (s, 1H), 8.10 (s, 1H), 7.90 (s, 1H), 7.58 (s, 1H), 7.45 (s, 1H), 7.32 (s, 1H), 5.58 (dd, 1H), 3.11 (m, 1H), 2.39 (s, 3H), 2.20 (m, 1H). MS found: (M+H)$^+$=348.95.

G127: (S)-2-(6-(5-carbamoylthiazol-2-yloxy)-1-hydroxy-4-methyl-1,3-dihydrobenzo[c][1,2]oxaborol-3-yl)acetic acid

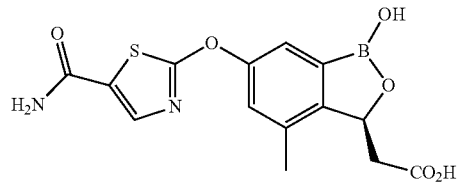 [SMILES: Cc1cc(Oc2ncc(C(N)=O)s2)cc2c1[C@H](CC(=O)O)OB2O]

4.29 g of racemate were separated by preparative HPLC using a CHIRALPAK® AZ column afforded 1.71 g of (S)-2-(6-(5-carbamoylthiazol-2-yloxy)-1-hydroxy-4-methyl-1,3-dihydrobenzo[c][1,2]oxaborol-3-yl)acetic acid. The purity of the products was 99.9% ee. $^1$H NMR (DMSO) δ 9.39 (s, 1H), 8.10 (s, 1H), 7.90 (s, 1H), 7.58 (s, 1H), 7.45 (s, 1H), 7.32 (s, 1H), 5.58 (dd, 1H), 3.11 (m, 1H), 2.39 (s, 3H), 2.20 (m, 1H). MS found: (M+H)$^+$=348.95.

G128: [6-(5-tert-Butoxycarbonylamino-thiazol-2-yloxy)-1-hydroxy-4-methyl-1,3-dihydro-benzo[c][1,2]oxaborol-3-yl]-acetic acid

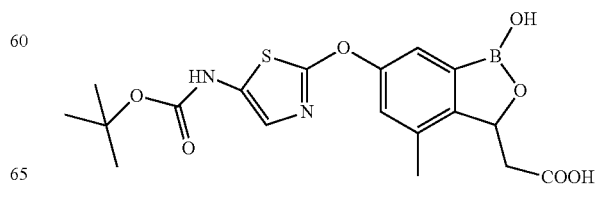

Step 1: 2-(3-Ethoxycarbonylmethyl-1-hydroxy-4-methyl-1,3-dihydro-benzo[c][1,2]oxaborol-6-yloxy)-thiazole-5-carboxylic acid tert-butyl ester

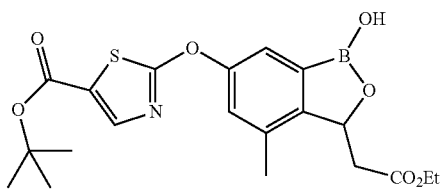 [SMILES: CCOC(=O)CC1OB(O)c2cc(Oc3ncc(C(=O)OC(C)(C)C)s3)cc(C)c21]

To a solution of (1,6-dihydroxy-4-methyl-1,3-dihydro-benzo[c][1,2]oxaborol-3-yl)-acetic acid ethyl ester (2 g, 8 mmol), $Cs_2CO_3$ (7.82 g, 24 mmol) and t-butyl-2-chloro-1,3-thiazole-5-carboxylate (2.64 g, 12 mmol) in DMF (20 mL) was heated at 80° C. for 1 h. The reaction mixture was cooled down and acidified to pH 3 with 6N HCl, extracted with ethyl acetate and washed with water and brine. The organic layer was dried by $Na_2SO_4$ and concentrated. The residue was purified by column chromatography (silica, Hexanes/EA=8:2, then DCM/MeOH=9:1) affording the title compound (3.3 g, 89%) as a light yellow solid. $^1$H NMR (CDCl$_3$) δ 8.01 (s, 1H), 7.46 (d, 1H), 7.18 (d, 1H), 5.68 (dd, 1H), 4.21 (q, 2H), 3.11 (dd, 1H), 2.44 (m, 1H), 2.39 (s, 3H), 1.56 (s, 9H), 1.24 (t, 3H).

Step 2: 2-(3-Ethoxycarbonylmethyl-1-hydroxy-4-methyl-1,3-dihydro-benzo[c][1,2]oxaborol-6-yloxy)-thiazole-5-carboxylic acid

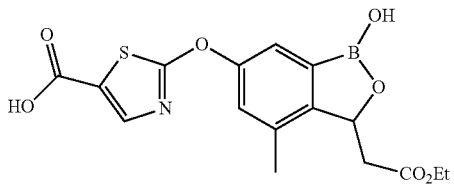 [SMILES: CCOC(=O)CC1OB(O)c2cc(Oc3ncc(C(=O)O)s3)cc(C)c21]

2-(3-Ethoxycarbonylmethyl-1-hydroxy-4-methyl-1,3-dihydro-benzo[c][1,2]oxaborol-6-yloxy)-thiazole-5-carboxylic acid tert-butyl ester (3.3 g, 7.6 mmol) was treated with TFA (40 mL) and stirred at room temperature for overnight. The reaction mixture was concentrated and purified by column chromatography (silica, DCM/MeOH=20:1) affording the title compound (2.5 g, 87%) as a white foam. $^1$H NMR (CDCl$_3$) δ 7.98 (s, 1H), 7.45 (d, 1H), 7.19 (d, 1H), 5.67 (dd, 1H), 4.20 (q, 2H), 3.12 (dd, 1H), 2.43 (m, 1H), 2.39 (s, 3H), 1.56 (s, 9H), 1.24 (t, 3H). MS found: (M+H)$^+$: 378.05.

Step 3: [6-(5-tert-Butoxycarbonylamino-thiazol-2-yloxy)-1-hydroxy-4-methyl-1,3-dihydro-benzo[c][1,2]oxaborol-3-yl]-acetic acid ethyl ester

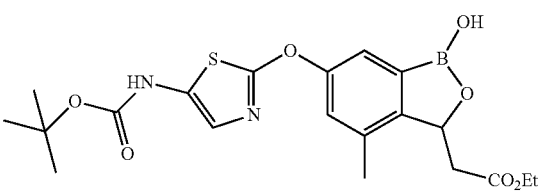 [SMILES: CCOC(=O)CC1OB(O)c2cc(Oc3ncc(NC(=O)OC(C)(C)C)s3)cc(C)c21]

To a solution of 2-(3-ethoxycarbonylmethyl-1-hydroxy-4-methyl-1,3-dihydro-benzo[c][1,2]oxaborol-6-yloxy)-thiazole-5-carboxylic acid (500 mg, 1.33 mmol) in tBuOH (10 mL) was added diphenylphosphoryl azide (0.35 mL, 1.61 mmol) and triethylamine (0.41 mL, 2.95 mmol), the reaction mixture was heated to 95° C. for 1 h. The solvent was removed under vacuum and the residue was extracted with ethyl acetate. The organic portion was washed with water and brine, and dried over $Na_2SO_4$ and concentrated. The residue was purified by column chromatography (silica, DCM/MeOH=20:1) affording the title compound (270 mg, 45%) as a white solid. $^1$H NMR (CDCl$_3$) δ 7.35 (s, 1H), 7.10 (s, 1H), 6.79 (s, 1H), 5.61 (dd, 1H), 4.17 (q, 2H), 3.02 (dd, 1H), 2.37 (m, 1H), 2.30 (s, 3H), 1.48 (s, 9H), 1.23 (t, 3H).

Step 4: [6-(5-tert-Butoxycarbonylamino-thiazol-2-yloxy)-1-hydroxy-4-methyl-1,3-dihydro-benzo[c][1,2]oxaborol-3-yl]-acetic acid

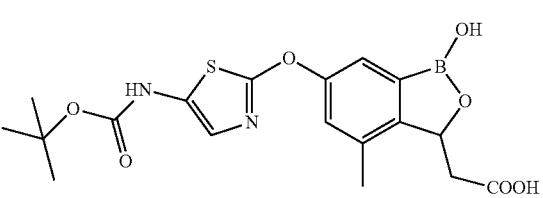 [SMILES: Cc1cc(Oc2ncc(NC(=O)OC(C)(C)C)s2)cc2c1C(CC(=O)O)OB2O]

To a solution of [6-(5-tert-butoxycarbonylamino-thiazol-2-yloxy)-1-hydroxy-4-methyl-1,3-dihydro-benzo[c][1,2]oxaborol-3-yl]-acetic acid ethyl ester (270 mg, 0.6 mmol) in THF (7 mL) was added LiOH (76 mg, 1.8 mmol) in water (3.5 mL). The mixture was stirred at room temperature for 3 h and acidified by 1N HCl to pH 3. The mixture was extracted by ethyl acetate. The organic layer was washed with water and brine, dried over $Na_2SO_4$ and concentrated. The residue was purified by HPLC affording the title compound (100 mg, 40%) as a white solid. $^1$H NMR (CD$_3$OD) δ 7.29 (s, 1H), 7.19

(s, 1H), 6.75 (s, 1H), 5.69 (dd, 1H), 3.19 (m, 1H), 2.40 (s, 3H), 2.35 (m, 1H), 1.52 (s, 9H). MS found: (M+H)+=421.20.

G129: [1-Hydroxy-4-methyl-6-([1,3,4]thiadiazol-2-yloxy)-1,3-dihydro-benzo[c][1,2]oxaborol-3-yl]-acetic acid

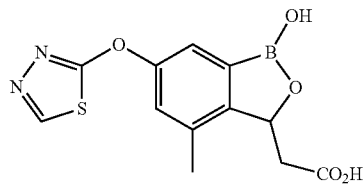

Step 1: [6-(5-Bromo-[1,3,4]thiadiazol-2-yloxy)-1-hydroxy-4-methyl-1,3-dihydro-benzo[c][1,2]oxaborol-3-yl]-acetic acid ethyl ester and [1-Hydroxy-4-methyl-6-(5-nitro-[1,3,4]thiadiazol-2-yloxy)-1,3-dihydro-benzo[c][1,2]oxaborol-3-yl]-acetic acid ethyl ester

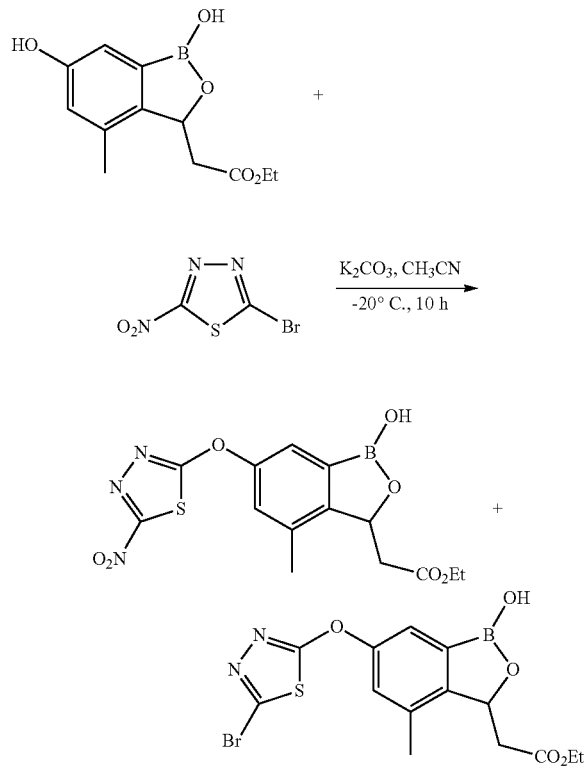

To a solution of (1,6-dihydroxy-4-methyl-1,3-dihydro-benzo[c][1,2]oxaborol-3-yl)-acetic acid ethyl ester (1.5 g, 6.0 mmol) and 2-bromo-5-nitro-[1,3,4]thiadiazole (2.52 g, 12.0 mmol) at −20° C. was added $K_2CO_3$ (1.65 g, 12.0 mmol). The reaction mixture was stirred for 10 hours at −20° C. then concentrated in vacuo. The residue was dissolved in EtOAc (20 mL), washed with water (2×10 mL), dried and concentrated. The residue was purified by silica gel flash column chromatography to give a mixture of products (5:2 nitro:bromide, 1.6 g). This was further purified by preparative HPLC to give [6-(5-bromo-[1,3,4]thiadiazol-2-yloxy)-1-hydroxy-4-methyl-1,3-dihydro-benzo[c][1,2]oxaborol-3-yl]-acetic acid ethyl ester (0.34 g, 14%) and [1-hydroxy-4-methyl-6-(5-nitro-[1,3,4]thiadiazol-2-yloxy)-1,3-dihydro-benzo[c][1,2]oxaborol-3-yl]-acetic acid ethyl ester (0.6 g, 26%).

[6-(5-bromo-[1,3,4]thiadiazol-2-yloxy)-1-hydroxy-4-methyl-1,3-dihydro-benzo[c][1,2]oxaborol-3-yl]-acetic acid ethyl ester $^1$H NMR (400 MHz, CDCl$_3$): δ 9.38 (s, 1H), 7.46 (s, 1H), 7.34 (s, 1H), 5.55 (d, J=8.8 Hz, 1H), 4.02 (q, J=6.8 Hz, 2H), 3.12 (d, J=15.2 Hz, 1H), 2.37-2.33 (m, 1H), 2.31 (s, 3H), 1.11 (t, J=7.2 Hz, 3H). MS (ESI) m/z=411 [M+H]+.

[1-hydroxy-4-methyl-6-(5-nitro-[1,3,4]thiadiazol-2-yloxy)-1,3-dihydro-benzo[c][1,2]oxaborol-3-yl]-acetic acid ethyl ester $^1$H NMR (400 MHz, CDCl$_3$): δ 9.44 (s, 1H), 7.54 (d, J=2.4 Hz, 1H), 7.41 (d, J=2.4 Hz, 1H), 5.58 (dd, J=2.4, 8.8 Hz, 1H), 4.02 (q, J=7.2 Hz, 2H), 3.12 (dd, J=2.8, 12.4 Hz, 1H), 2.42-2.36 (m, 1H), 2.34 (s, 3H), 1.11 (t, J=6.8 Hz, 3H). MS (ESI) m/z=378 [M−H]−.

Step 2: [1-Hydroxy-4-methyl-6-([1,3,4]thiadiazol-2-yloxy)-1,3-dihydro-benzo[c][1,2]oxaborol-3-yl]-acetic acid ethyl ester

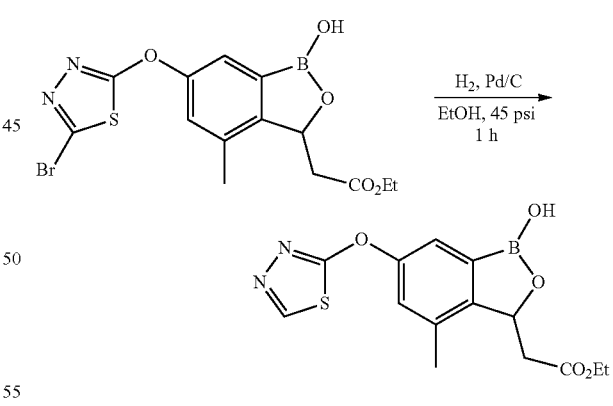

A mixture of [6-(5-bromo-[1,3,4]thiadiazol-2-yloxy)-1-hydroxy-4-methyl-1,3-dihydro-benzo[c][1,2]oxaborol-3-yl]-acetic acid ethyl ester (0.53 g, 1.28 mmol) and Pd/C (0.5 g) in EtOH (15 mL) was hydrogenated at 45 psi for 1 hour. The mixture was filtered through a pad of celite and concentrated in vacuo. The residue was purified by silica gel flash column chromatography (DCM:MeOH 95:5) to give [1-hydroxy-4-methyl-6-([1,3,4]thiadiazol-2-yloxy)-1,3-dihydro-benzo[c][1,2]oxaborol-3-yl]-acetic acid ethyl ester (0.3 g, 70%). $^1$H NMR (400 MHz, DMSO): δ 9.15 (s, 1H), 7.40 (s, 1H), 7.28 (s, 1H), 5.52 (d, J=8.8 Hz, 1H), 4.00 (q, J=7.2 Hz, 2H), 3.10 (dd, J=4.0, 15.6 Hz, 1H), 2.52-2.45 (m, 1H), 2.30 (s, 3H), 1.10 (t, J=6.8 Hz, 3H). MS (ESI) m/z=335 [M+H]⁺.

Step 3: [1-Hydroxy-4-methyl-6-([1,3,4]thiadiazol-2-yloxy)-1,3-dihydro-benzo[c][1,2]oxaborol-3-yl]-acetic acid

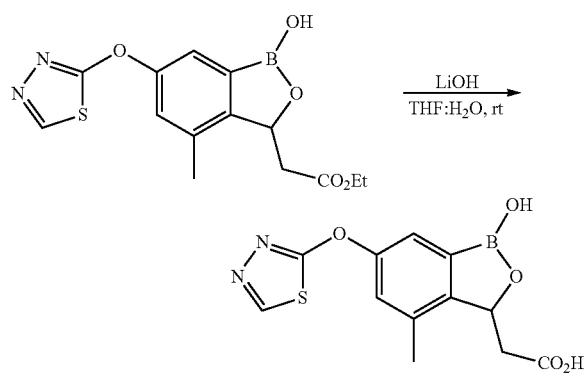

To a solution of [1-hydroxy-4-methyl-6-([1,3,4]thiadiazol-2-yloxy)-1,3-dihydro-benzo[c][1,2]oxaborol-3-yl]-acetic acid ethyl ester (0.17 g, 0.5 mmol) in THF:H₂O (1:1, 10 mL) at 0° C. was added a solution of LiOH (0.024 g, 1.01 mmol) in water (1 mL). The solution was allowed to warm to room temperature over 3 hours then acidified to pH 2 with 1N HCl (1 mL) at 0° C. The mixture was extracted with EtOAc (2×10 mL) and the organic extracts washed with water (10 mL), dried and concentrated in vacuo. The residue was purified by preparative HPLC to give [1-hydroxy-4-methyl-6-([1,3,4]thiadiazol-2-yloxy)-1,3-dihydro-benzo[c][1,2]oxaborol-3-yl]-acetic acid (0.15 g, 96%). $^1$H NMR (400 MHz, DMSO): δ 9.24 (s, 1H), 9.15 (s, 1H), 7.43 (s, 1H), 7.30 (s, 1H), 5.51 (d, J=6.8 Hz, 1H), 3.06 (d, J=15.6 Hz, 1H), 2.30 (s, 3H), 2.18-2.12 (m, 1H). MS (ESI) m/z=305 [M−H]⁻.

G130: [1-Hydroxy-4-methyl-6-(5-nitro-[1,3,4]thiadiazol-2-yloxy)-1,3-dihydro-benzo[c][1,2]oxaborol-3-yl]-acetic acid ethyl ester

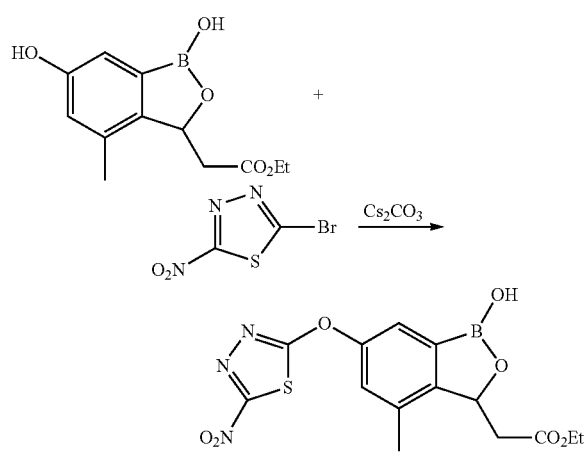

To a solution of (1,6-dihydroxy-4-methyl-1,3-dihydro-benzo[c][1,2]oxaborol-3-yl)-acetic acid ethyl ester (2.55 g, 10.2 mmol) in anhydrous acetonitrile (150 mL) was added 2-bromo-5-nitro-[1,3,4]thiadiazole (3.0 g, 14.3 mmol) at 0° C. The reaction mixture was cooled to −20° C. and K₂CO₃ (9.87 g, 71.4 mmol) was added. After stirring at −20 to −25° C. for 3.5 days, the reaction mixture was acidified to pH 2 with dilute hydrochloric acid at 0° C. and extracted with EtOAc. The organic extracts were washed with brine, dried over sodium sulfate and concentrated in vacuo. The residue was purified by silica gel flash column chromatography (EtOAc/hexanes/AcOH=2:1:trace) followed by recrystallization from methanol to give pure product as a white powder after lyophilization (1.35 g, 34.9%). $^1$HNMR (400 MHz, DMSO-d₆) δ9.41 (s, 1H), 7.54 (d, J=2.34 Hz, 1H), 7.41 (d, J=1.76 Hz, 1H), 5.58 (dd, J=8.64, 2.78 Hz, 1H), 4.02 (q, J=7.22 Hz, 2H), 3.14 (dd, J=15.52, 2.63 Hz, 1H), 2.23-2.43 (m, 4H), 1.12 (t, 3H). MS (ESI) m/z=378 [M−H]⁻.

G131: [6-(5-Amino-[1,3,4]thiadiazol-2-yloxy)-1-hydroxy-4-methyl-1,3-dihydro-benzo[c][1,2]oxaborol-3-yl]-acetic acid

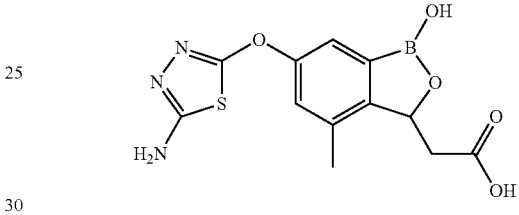

Step 1: [6-(5-Amino-[1,3,4]thiadiazol-2-yloxy)-1-hydroxy-4-methyl-1,3-dihydro-benzo[c][1,2]oxaborol-3-yl]-acetic acid ethyl ester

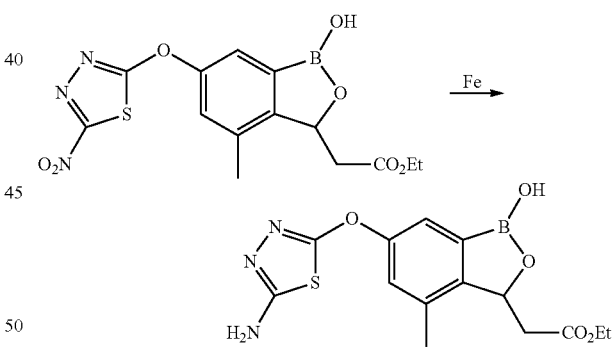

Concentrated HCl (10 drops) and water (12 ml) were added to a mixture of [6-(5-nitro-[1,3,4]thiadiazol-2-yloxy)-1-hydroxy-4-methyl-1,3-dihydro-benzo[c][1,2]oxaborol-3-yl]-acetic acid ethyl ester (0.65 g, 1.71 mmol) and iron powder (0.479 g; 8.55 mmol) in ethanol (30 mL) at room temperature. The resulting mixture was stirred at 85° C. for 1.5 hours, cooled to room temperature and filtered through a pad of celite. The filtrate was evaporated and the residue dissolved in EtOAc (300 mL), washed with brine, dried over Na₂SO₄ and concentrated to give [6-(5-amino-[1,3,4]thiadiazol-2-yloxy)-1-hydroxy-4-methyl-1,3-dihydro-benzo[c][1,2]oxaborol-3-yl]-acetic acid ethyl ester (0.650 g, 100%) which was used without further purification. $^1$HNMR (400 MHz, DMSO-d₆) δ 9.33 (s, 1H), 7.33 (d, J=12.4 Hz, 1H), 7.18 (d, J=16.8 Hz, 1H), 5.51 (d, J=6.0 Hz, 1H), 4.02 (q, J=7.2 Hz, 2H), 3.10 (d, J=14.4 Hz, 1H), 2.33-2.31 (m, 1H), 2.30 (s, 3H), 1.10 (t, J=7.6 Hz, 3H). MS (ESI) m/z=350 [M+H]+.

Step 2: [6-(5-Amino-[1,3,4]thiadiazol-2-yloxy)-1-hydroxy-4-methyl-1,3-dihydro-benzo[c][1,2]oxaborol-3-yl]-acetic acid

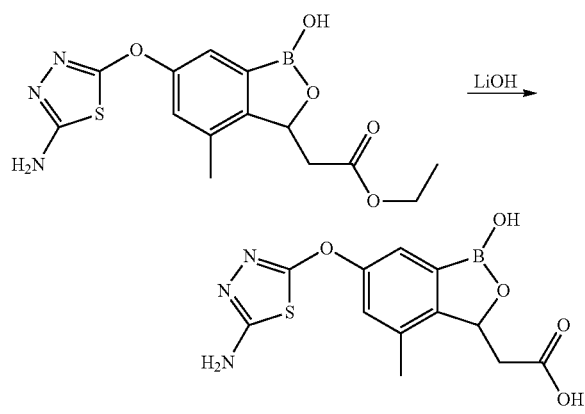

To a solution [6-(5-amino-[1,3,4]thiadiazol-2-yloxy)-1-hydroxy-4-methyl-1,3-dihydro-benzo[c][1,2]oxaborol-3-yl]-acetic acid ethyl ester (0.6 g, 1.72 mmol) in THF (15 mL) and methanol (2 mL) was added a solution of LiOH (0.165 g, 6.87 mmol) in water (15 mL) at 0° C. The resulting mixture was stirred at room temperature for 1.5 hours then acidified to pH=2 with dilute hydrochloric acid at 0° C. After removal of the volatile organics, the residue was neutralized to pH 7 using saturated sodium bicarbonate. The precipitated solid was filtered and stirred with ethyl acetate (20 mL) for 1 hour. The solid was filtered, washed with cold ethyl acetate and water then dried to give the product (0.412 g, 75%). 1HNMR (400 MHz, DMSO-d6) δ9.26 (br. s., 1H), 7.32 (d, J=2.05 Hz, 1H), 7.16 (d, J=1.76 Hz, 1H), 7.05 (s, 2H), 5.48 (dd, J=9.37, 2.05 Hz, 1H), 3.04 (dd, J=15.37, 2.49 Hz, 1H), 2.29 (s, 3H), 2.12 (dd, 1H). MS (ESI) m/z=322 [M+H]+.

G132: (R)-2-(6-(5-Amino-1,3,4-thiadiazol-2-yloxy)-1-hydroxy-4-methyl-1,3-dihydrobenzo[c][1,2]oxaborol-3-yl)acetic acid

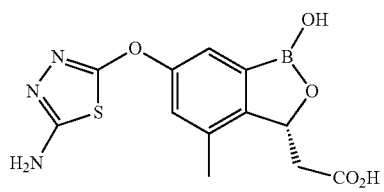 [SMILES: Cc1cc(Oc2nnc(N)s2)cc2c1[C@@H](CC(=O)O)OB2O]

Step 1: 5-Bromo-1,3,4-thiadiazol-2-amine

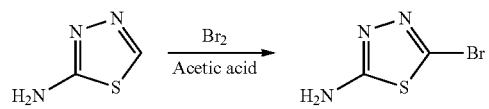

To a solution of 1,3,4-thiadiazol-2-amine (101 g, 1.0 mol) in CH3COOH (400 mL) was slowly added bromine (51 mL, 1.0 mol) at room temperature. The mixture was allowed to react for 5 hrs at 60° C., followed by removal of solvent under reduced pressure. The concentrated residue was neutralized with an aqueous solution of sodium hydrogencarbonate to afford a white solid. The white solid was separated by filtration, washed with water, and dried under vacuum to give the product (144 g, 80% yield). 1H NMR (400 MHz, DMSO-d6) δ 7.50 (2H, s, NH2).

Step 2: 2-Bromo-5-nitro-1,3,4-thiadiazole

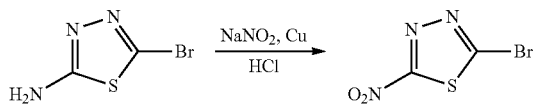

To a stirred solution of NaNO2 (116 g, 1.68 mol) in water (1200 mL) was added copper metal powder (72 g, 1.12 mol) and 1.2 mL conc. HCl. Thereafter, 5-bromo-1,3,4-thiadiazol-2-amine (100 g, 0.56 mol) was warmed to dissolve in 4 M aq. HCl (120 mL) and added potionwise. The mixture was stirred at r.t. for 3 hrs. The precipitated yellow solid was filtered and washed with water. The solid was dissolved in ether, filtered and the filtrate concentrated in vacuo to give 2-bromo-5-nitro-[1,3,4]thiadiazole (57 g, 88% purity in HPLC, 48% yield).

Step 3: Ethyl 2-(1-hydroxy-4-methyl-6-(5-nitro-1,3,4-thiadiazol-2-yloxy)-1,3-dihydrobenzo[c][1,2]oxaborol-3-yl)acetate

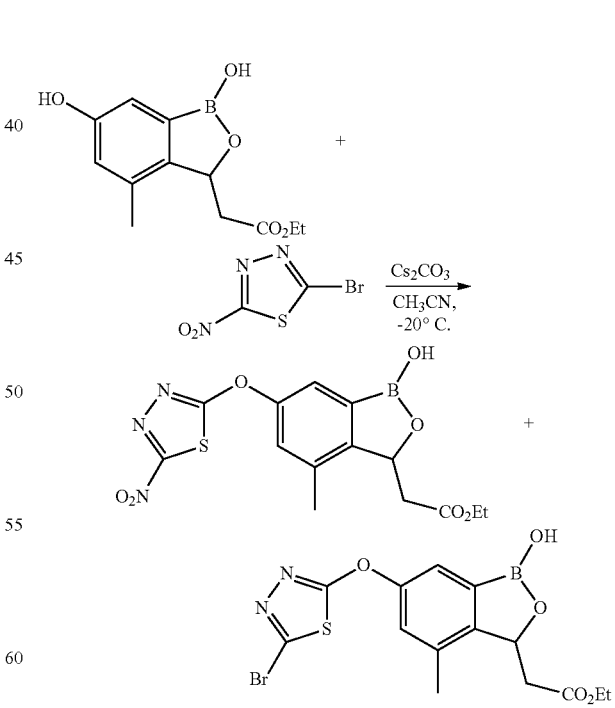

To a stirred solution of ethyl 2-(1,6-dihydroxy-4-methyl-1,3-dihydrobenzo[c][1,2]oxaborol-3-yl)acetate (43 g, 0.17 mol) in anhydrous acetonitrile (2000 mL) at −20° C. was added a solution of 2-bromo-5-nitro-1,3,4-thiadiazole (70 g, 0.33 mol.) in acetonitrile (1000 mL). Then Cs₂CO₃ (166 g, 0.51 mol, 3 eq.) as added portionwise at this temperature. The mixture was stirred at −20 to −30° C. for 20 hrs. Then, the reaction mixture was allowed to warm to r.t. and stirred at this temperature for 15 h. After filtration, the filtrate was concentrated and acidified to pH=2 at 0° C. with diluted hydrochloric acid. The mixture was extracted with EtOAc and the organic extracts were washed with brine, dried over sodium sulfate and concentrated in vacuo The residue was purified by chromatography on silica gel column (petroleum ether/EtOAc/AcOH, gradient elution) to give the ethyl 2-(1-hydroxy-4-methyl-6-(5-nitro-1,3,4-thiadiazol-2-yloxy)-1,3-dihydrobenzo[c][1,2]oxaborol-3-yl)acetate as a yellow solid (23 g, 36% yield).

Step 4: Ethyl 2-(6-(5-amino-1,3,4-thiadiazol-2-yloxy)-1-hydroxy-4-methyl-1,3-dihydrobenzo[c][1,2]oxaborol-3-yl)acetate

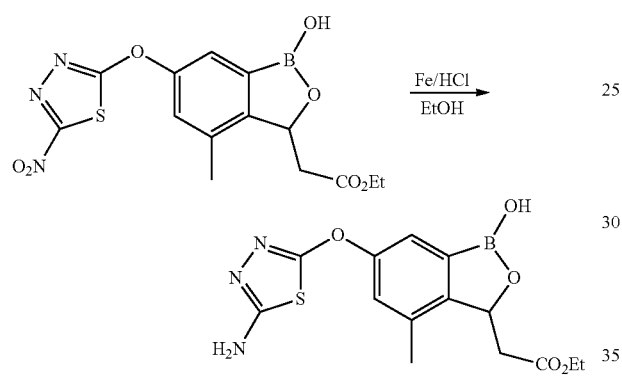

Concentrated aq. HCl (50 mL) and water (1000 mL) were added to a mixture of ethyl 2-(1-hydroxy-4-methyl-6-(5-nitro-1,3,4-thiadiazol-2-yloxy)-1,3-dihydrobenzo[c][1,2]oxaborol-3-yl)acetate (70 g, 0.18 mol) and iron powder (51 g, 0.9 mol) in ethanol (3000 mL) at room temperature. The resulting mixture was stirred at 85° C. for 2 hrs, cooled to room temperature and filtered through a pad of celite. The filtrate was evaporated and the residue dissolved in EtOAc, washed with brine, dried over Na₂SO₄ and concentrated to give compound ethyl 2-(6-(5-amino-1,3,4-thiadiazol-2-yloxy)-1-hydroxy-4-methyl-1,3-dihydrobenzo[c][1,2]oxaborol-3-yl)acetate (40 g, 63% yield) which was used without further purification. $^{1}$H NMR (400 MHz, DMSO-d6) δ 9.30 (1H, s), 7.32 (1H, m), 7.16 (1H, m), 7.15 (2H, s), 5.50 (1H, m), 4.03 (2H, m), 3.08 (1H, m), 2.32 (4H, m), 1.10 (3H, m).

Step 5: (R)-ethyl 2-(6-(5-amino-1,3,4-thiadiazol-2-yloxy)-1-hydroxy-4-methyl-1,3-dihydrobenzo[1,2]oxaborol-3-yl)acetate

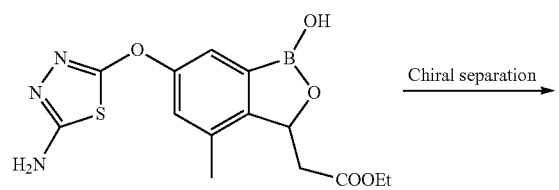

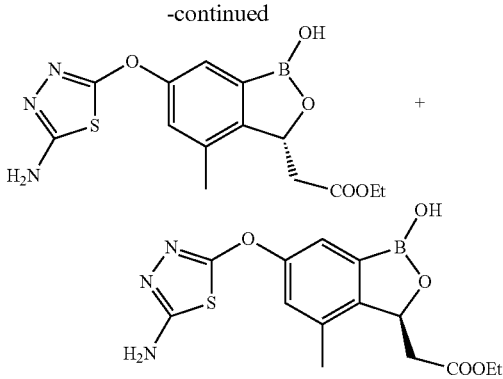

74.0 g of racemic ethyl 2-(6-(5-amino-1,3,4-thiadiazol-2-yloxy)-1-hydroxy-4-methyl-1,3-dihydrobenzo[c][1,2]oxaborol-3-yl)acetate was separated by Chiral column to give, (R)-ethyl 2-(6-(5-amino-1,3,4-thiadiazol-2-yloxy)-1-hydroxy-4-methyl-1,3-dihydrobenzo[c][1,2]oxaborol-3-yl)acetate 30.0 g, Purity: 98%; e.e.: 99%, Yield: 81%) and (R)-ethyl 2-(6-(5-amino-1,3,4-thiadiazol-2-yloxy)-1-hydroxy-4-methyl-1,3-dihydrobenzo[c][1,2]oxaborol-3-yl)acetate (28.3 g, Purity: 98%; e.e.: 99%, Yield: 76.5%). Supercritical Fluid Chromatography (SFC) was used for the analytical and preparative chiral separation. Column: ChiralPak AY-20 um, 300×50 mmI.D. Mobile phase: A for SFC CO₂ and B for Ethanol.

Step 6: (R)-2-(6-(5-Amino-1,3,4-thiadiazol-2-yloxy)-1-hydroxy-4-methyl-1,3-dihydrobenzo[c][1,2]oxaborol-3-yl)acetic acid

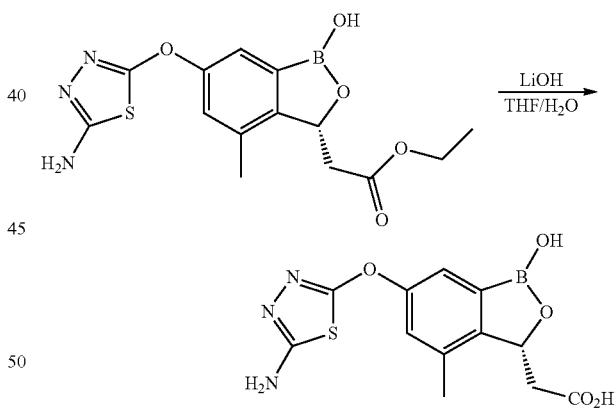

To a solution (R)-ethyl 2-(6-(5-amino-1,3,4-thiadiazol-2-yloxy)-1-hydroxy-4-methyl-1,3-dihydrobenzo[c][1,2]oxaborol-3-yl)acetate (30 g, 86 mmol) in a mixed solution of THF (750 mL) and methanol (100 mL) was added a solution of LiOH.H₂O (12.63 g, 301 mmol) in water (750 mL) at 0° C. The resulting mixture was stirred at room temperature for 2 hrs and then acidified to pH=2 with diluted hydrochloric acid at 0° C. After removal of the volatile organics, the residue was dissolved in EtOAc. The aqueous phase was separated and concentrated in vacuo, and the residue was neutralized to pH=6.5~7.0 using saturated aq. sodium bicarbonate. The precipitated solid was filtered and stirred with EtOAc for 1 hr. The solid was filtered, washed with cold EtOAc and water then dried to give the product (R)-2-(6-(5-amino-1,3,4-thiadiazol-2-yloxy)-1-hydroxy-4-methyl-1,3-dihydrobenzo[c][1,2]oxaborol-3-yl)acetic acid (21 g, 76% yield). $^1$H NMR (400 MHz, DMSO-d6) δ12.31 (1H, s), 9.26 (1H, s), 7.33 (1H, m), 7.16 (1H, m), 7.06 (2H, s), 5.50 (1H, m), 3.03 (1H, m), 2.29 (3H, s), 2.10 (1H, m). ESI-MS m/z 322 (M+H$^+$, positive); $[\alpha]^{25}_D$=−91.395°±0.305° (C=1.0017 g/100 ml diluted with 2M HCl, L=0.5 dm).

G133: (S)-2-(6-(5-amino-1,3,4-thiadiazol-2-yloxy)-1-hydroxy-4-methyl-1,3-dihydrobenzo[c][1,2]oxaborol-3-yl)acetic acid

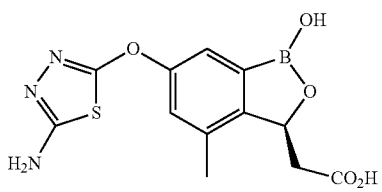 [SMILES: Cc1cc(Oc2nnc(N)s2)cc2c1[C@H](CC(=O)O)OB2O]

Step 1: (S)-Ethyl 2-(6-(5-amino-1,3,4-thiadiazol-2-yloxy)-1-hydroxy-4-methyl-1,3-dihydrobenzo[c][1,2]oxaborol-3-yl)acetate

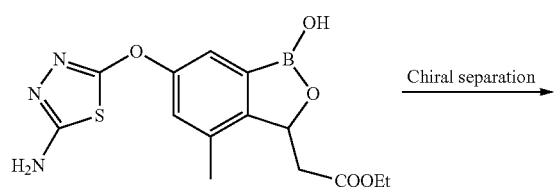

74.0 g of racemic ethyl 2-(6-(5-amino-1,3,4-thiadiazol-2-yloxy)-1-hydroxy-4-methyl-1,3-dihydrobenzo[c][1,2]oxaborol-3-yl)acetate was separated by Chiral column to give, (R)-ethyl 2-(6-(5-amino-1,3,4-thiadiazol-2-yloxy)-1-hydroxy-4-methyl-1,3-dihydrobenzo[c][1,2]oxaborol-3-yl)acetate 30.0 g, Purity: 98%; e.e.: 99%, Yield: 81%) and (R)-ethyl 2-(6-(5-amino-1,3,4-thiadiazol-2-yloxy)-1-hydroxy-4-methyl-1,3-dihydrobenzo[c][1,2]oxaborol-3-yl)acetate (28.3 g, Purity: 98%; e.e.: 99%, Yield: 76.5%). SFC was used for the analytical and preparative chiral separation. Column: ChiralPak AY-20 um, 300×50 mmI.D. Mobile phase: A for SFC $CO_2$ and B for Ethanol.

Step 2: (S)-2-(6-(5-amino-1,3,4-thiadiazol-2-yloxy)-1-hydroxy-4-methyl-1,3-dihydrobenzo[c][1,2]oxaborol-3-yl)acetic acid

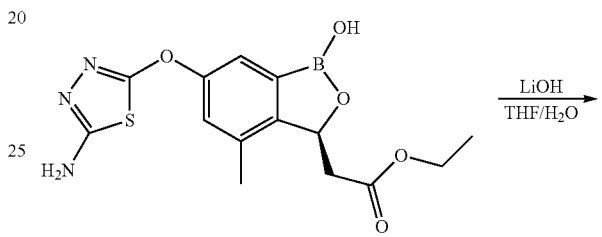

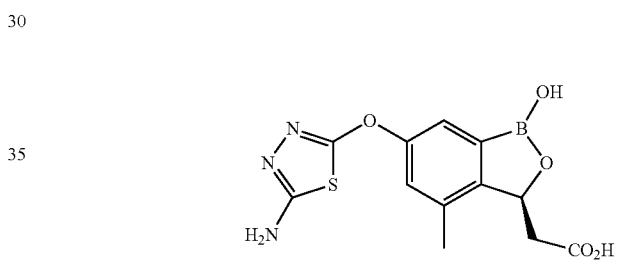

(S)-2-(6-(5-amino-1,3,4-thiadiazol-2-yloxy)-1-hydroxy-4-methyl-1,3-dihydrobenzo[c][1,2]oxaborol-3-yl)acetic acid was obtained using a similar procedure for G129). $^1$H NMR (400 MHz, DMSO-d6) δ 12.29 (1H, s), 9.26 (1H, s), 7.32 (1H, m), 7.16 (1H, m), 7.06 (2H, s), 5.49 (1H, m), 3.03 (1H, m), 2.29 (3H, s), 2.10 (1H, m). ESI-MS m/z 322 (M+H$^+$, positive); $[\alpha]^{25}_D$=−91.395°±0.305° (C=1.0017 g/100 ml diluted with 2M HCl, L=0.5 dm).

G134: 2-(6-(5-Acetamido-1,3,4-thiadiazol-2-yloxy)-1-hydroxy-4-methyl-1,3-dihydrobenzo[c][1,2]oxaborol-3-yl)acetic acid

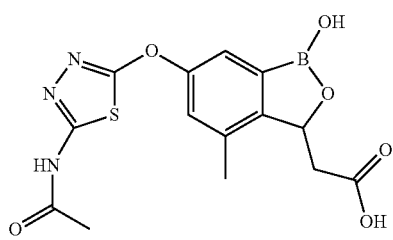 [SMILES: CC(=O)Nc1nnc(Oc2cc(C)c3c(c2)B(O)OC3CC(=O)O)s1]

Step 1: Ethyl 2-(6-(5-acetamido-1,3,4-thiadiazol-2-yloxy)-1-hydroxy-4-methyl-1,3-dihydrobenzo[c][1,2]oxaborol-3-yl)acetate

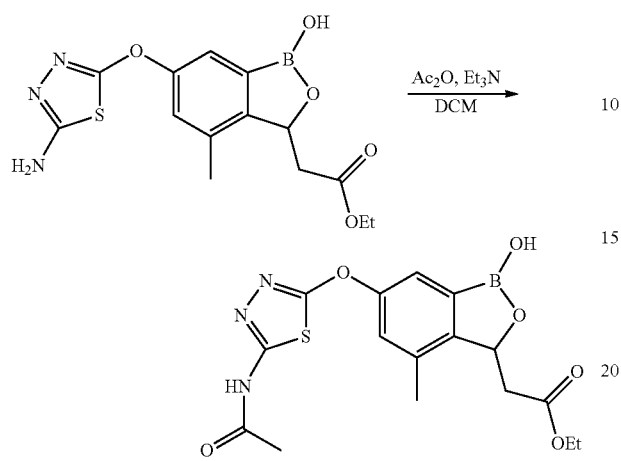

To a solution of ethyl 2-(6-(5-amino-1,3,4-thiadiazol-2-yloxy)-1-hydroxy-4-methyl-1,3-dihydrobenzo[c][1,2]oxaborol-3-yl)acetate (70 mg, 0.2 mmol) in DCM (10 mL) was added Et$_3$N (0.11 ml) and acetic anhydride (0.08 mL). The mixture was stirred at room overnight. The mixture was concentrated and precipitate was filtered and washed with a mixture of hexane and ethyl acetate to afford the product as a light yellow solid (59 mg). $^1$H NMR (DMSO-d6) δ 12.44 (s, 1H), 9.28 (s, 1H), 7.4 (s, 1H), 7.26 (s, 1H), 5.54 (d, 1H), 4.03 (q, H) 3.14 (dd, 1H), 2.48 (d, 1H), 2.35 (s, 3H), 2.13 (s, 3H), 1.11 (t, 3H); MS found: (M+H)$^+$=392.1.

Step 2: 2-(6-(5-Acetamido-1,3,4-thiadiazol-2-yloxy)-1-hydroxy-4-methyl-1,3-dihydrobenzo[c][1,2]oxaborol-3-yl)acetic acid

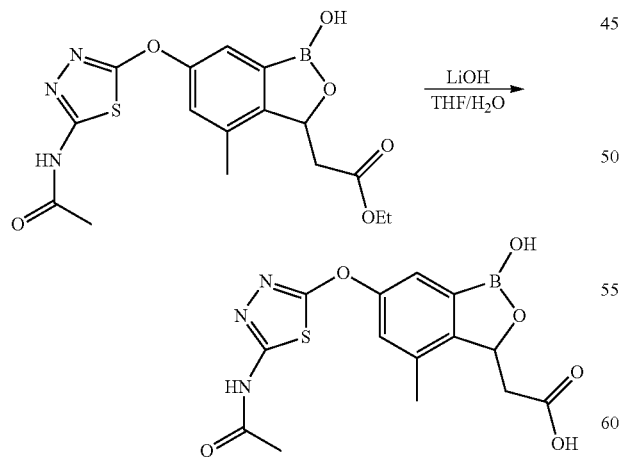

(2-(6-(5-acetamido-1,3,4-thiadiazol-2-yloxy)-1-hydroxy-4-methyl-1,3-dihydrobenzo[c][1,2]oxaborol-3-yl)acetic acid was obtained using a similar procedure for G129. $^1$H NMR (DMSO-d6) δ 12.44 (s, 1H), 12.3 (br, 1H), 9.26 (s, 1H), 7.4 (s, 1H), 7.26 (s, 1H), 5.52 (d, 1H), 3.0 (dd, 1H), 2.48 (d, 1H), 2.35 (s, 3H), 2.13 (s, 3H); MS found: (M+H)$^+$=364.0.

G135: [6-(5-Aminomethyl-[1,3,4]thiadiazol-2-yloxy)-1-hydroxy-4-methyl-1,3-dihydro-benzo[c][1,2]oxaborol-3-yl]-acetic acid

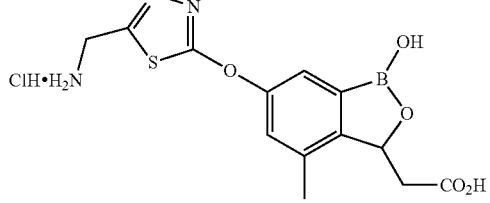

Step 1: 5-Bromo[1,3,4]thiadiazole-2-carbonitrile

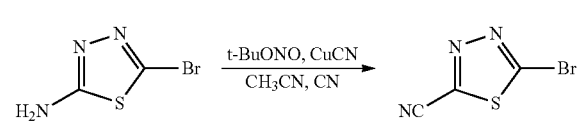

To a suspension of 5-bromo-[1,3,4]thiadiazol-2-ylamine (4 g, 22.2 mmol) in acetonitrile (40 mL) at 0° C. was added CuCN (4 g, 44.4 mmol) and t-BuONO (6 mL, 44.4 mmol). The suspension was stirred for 3 hours then filtered through a pad of Celite and the filtrate was concentrated in vacuo. The residue was purified by silica gel flash column chromatography (3-5% EtOAc/hexane) to give 5-bromo-[1,3,4]thiadiazole-2-carbonitrile (0.62 g, 15%).

Step 2: [6-(5-Cyano[1,3,4]thiadiazol-2-yloxy)-1-hydroxy-4-methyl-1,3-dihydro-benzo[c][1,2]oxaborol-3-yl]-acetic acid ethyl ester

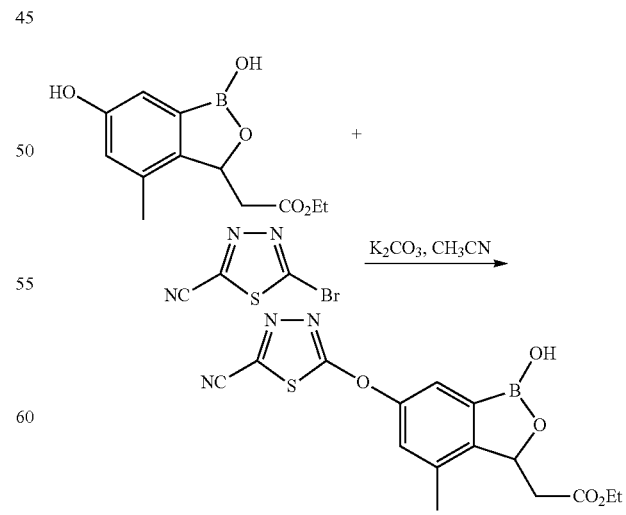

To a solution of (1,6-dihydroxy-4-methyl-1,3-dihydro-benzo[c][1,2]oxaborol-3-yl)-acetic acid ethyl ester (0.44 g, 1.75 mmol) in acetonitrile (30 mL) was added 5-bromo-[1,3,4]thiadiazole-2-carbonitrile (0.6 g, 3.16 mmol) and potassium carbonate (0.73 g, 5.25 mmol). The suspension was heated at 60° C. for 6 hours. The mixture was cooled to 0° C., diluted with water and extracted with EtOAc (2×50 mL). The organic extracts were combined, dried over MgSO$_4$ and concentrated in vacuo. The residue was purified by silica gel flash column chromatography (30-60% EtOAc/hexane) to give [6-(5-cyano-[1,3,4]thiadiazol-2-yloxy)-1-hydroxy-4-methyl-1,3-dihydro-benzo[c][1,2]oxaborol-3-yl]-acetic acid ethyl ester (0.44 g, 72%). $^1$H NMR (400 MHz, DMSO-d$_6$) δ ppm 9.41 (s, 1H), 7.55 (d, J=2.21 Hz, 1H), 7.43 (d, J=1.62 Hz, 1H), 5.59 (dd, J=8.72, 2.73 Hz, 1H), 4.04 (q, J=6.92 Hz, 2H), 3.16 (dd, J=15.56, 2.94 Hz, 1H), 2.37-2.43 (m, 1H), 2.35 (s, 3H), 1.14 (t, J=7.17 Hz, 3H).

Step 3: [6-(5-Aminomethyl-[1,3,4]thiadiazol-2-yloxy)-1-hydroxy-4-methyl-1,3-dihydro-benzo[c][1,2]oxaborol-3-yl]-acetic acid ethyl ester

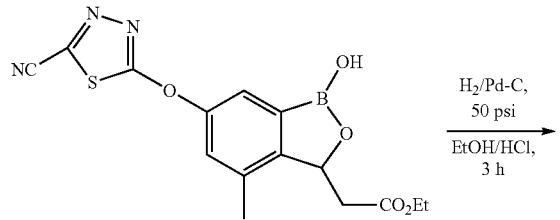

To a solution of [6-(5-cyano-[1,3,4]thiadiazol-2-yloxy)-1-hydroxy-4-methyl-1,3-dihydro-benzo[c][1,2]oxaborol-3-yl]-acetic acid ethyl ester (0.41 g, 1.14 mmol) in ethanol (10 mL) was added 10% Pd/C (0.036 g, 0.34 mmol) and the suspension was hydrogenated at 50 psi for 3 hours. The mixture was filtered through a pad of celite and the filtrate was concentrated in vacuo to give [6-(5-aminomethyl-[1,3,4]thiadiazol-2-yloxy)-1-hydroxy-4-methyl-1,3-dihydro-benzo[c][1,2]oxaborol-3-yl]-acetic acid ethyl ester (0.22 g, 54%). $^1$H NMR (400 MHz, DMSO-d$_6$) δ ppm 9.43 (s, 1H), 8.69 (br. s., 3H), 7.51 (d, J=2.26 Hz, 1H), 7.34 (d, J=1.94 Hz, 1H), 5.58 (dd, J=8.92, 2.55 Hz, 1H), 4.41 (s, 2H), 4.05 (q, J=7.14 Hz, 2H), 3.16 (dd, J=16.72, 1.75 Hz, 1H), 2.35-2.42 (m, 1H), 2.35 (s, 3H), 1.14 (t, J=7.15 Hz, 3H).

Step 4: [6-(5-Aminomethyl-[1,3,4]thiadiazol-2-yloxy)-1-hydroxy-4-methyl-1,3-dihydro-benzo[c][1,2]oxaborol-3-yl]-acetic acid

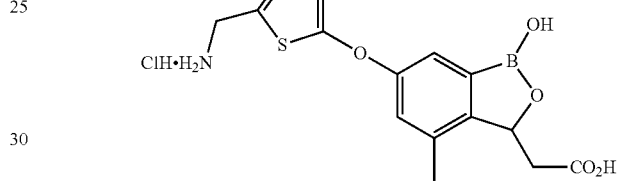

To a solution of [6-(5-aminomethyl-[1,3,4]thiadiazol-2-yloxy)-1-hydroxy-4-methyl-1,3-dihydro-benzo[c][1,2]oxaborol-3-yl]-acetic acid ethyl ester (0.22 g, 0.6 mmol) in tetrahydrofuran (10 mL) at 0° C. was added lithium hydroxide (0.06 g, 2.42 mmol) in water (5 mL). The mixture was stirred at 0° C. for 1.5 hours then acidified to pH=2 with 2N HCl. The mixture was concentrated in vacuo and the residue purified by preparative HPLC to give [6-(5-aminomethyl-[1,3,4]thiadiazol-2-yloxy)-1-hydroxy-4-methyl-1,3-dihydro-benzo[c][1,2]oxaborol-3-yl]-acetic acid (0.015 g, 7%). $^1$H NMR (400 MHz, DMSO-d$_6$) δ ppm 9.37 (s, 1H), 8.58 (br. s., 3H), 7.48 (s, 1H), 7.33 (d, J=1.62 Hz, 1H), 5.56 (dd, J=9.23, 2.52 Hz, 1H), 4.43 (s, 2H), 3.10 (dd, J=15.63, 2.71 Hz, 1H), 2.34 (s, 3H), 2.18 (dd, J=15.44, 9.21 Hz, 1H); MS (ESI) m/z: 336 [M+1]$^+$; HPLC purity: 94.12% (MaxPlot), 96.99% (220 nm).

G136: 2-(6-(5-Amino-1,3,4-thiadiazol-2-yloxy)-4-chloro-1-hydroxy-1,3-dihydrobenzo[c][1,2]oxaborol-3-yl)acetic acid

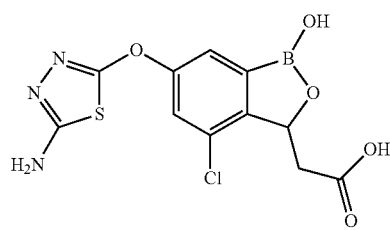 [SMILES: Nc1nnc(Oc2cc(Cl)c3c(c2)B(O)OC3CC(=O)O)s1]

Step 1: Ethyl 2-(4-chloro-1-hydroxy-6-(5-nitro-1,3,4-thiadiazol-2-yloxy)-1,3-dihydro-benzo[c][1,2]oxaborol-3-yl)acetate

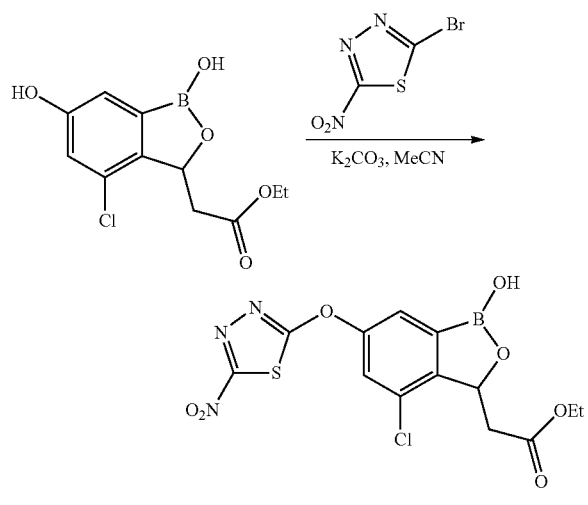

To a solution of ethyl 2-(4-chloro-1-hydroxy-6-isopropoxy-1,3-dihydrobenzo[c][1,2]oxaborol-3-yl)acetate (400 mg, 1.48 mmol) in MeCN (5 mL) was added anhydrous K$_2$CO$_3$ (414 mg, 3 mmol) and the mixture was cooled to −30° C. To this mixture was added 2-bromo-5-nitro-1,3,4-thiadiazole (420 mg, 2 mmol). The reaction mixture was stirred at −30° C. for 5 h. The reaction was quenched by addition of ice and the mixture was extracted with EtOAc (3×5 ml). The combined organic layers were dried over anhydrous Na$_2$SO$_4$ and concentrated in vacuo to give the crude product as a yellow oil (430 mg). MS (ESI) m/z=400 [M+H]$^+$.

Step 2: Ethyl 2-(6-(5-amino-1,3,4-thiadiazol-2-yloxy)-4-chloro-1-hydroxy-1,3-dihydro-benzo[c][1,2]oxaborol-3-yl)acetate

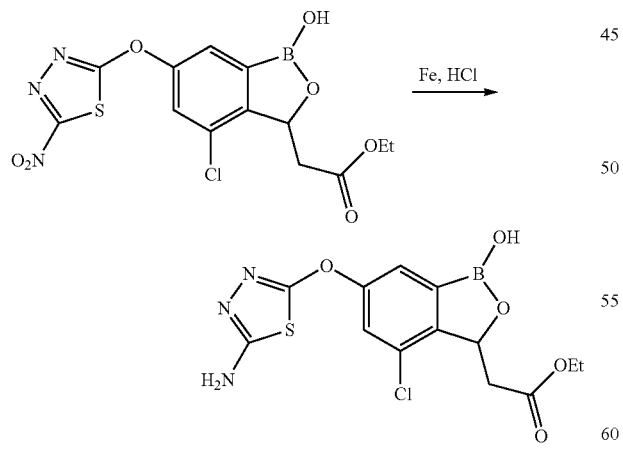

To a solution of ethyl 2-(4-chloro-1-hydroxy-6-(5-nitro-1,3,4-thiadiazol-2-yloxy)-1,3-dihydro-benzo[c][1,2]oxaborol-3-yl)acetate (430 mg, 1.08 mmol) in EtOH (15 mL) and H$_2$O (5 mL) was added 2 drops of conc. HCl and the mixture was heated to reflux for 2 h. Upon cooling, the reaction mixture was filtered and the EtOH was removed under the reduced pressure and the residue was extracted with EtOAc (3×10 ml). The combined organic layers were dried over anhydrous Na$_2$SO$_4$ and concentrated in vacuo to give the crude product as a yellow oil (330 mg). MS (ESI) m/z=370 [M+H]$^+$.

Step 3: 2-(6-(5-Amino-1,3,4-thiadiazol-2-yloxy)-4-chloro-1-hydroxy-1,3-dihydrobenzo[c][1,2]oxaborol-3-yl)acetic acid

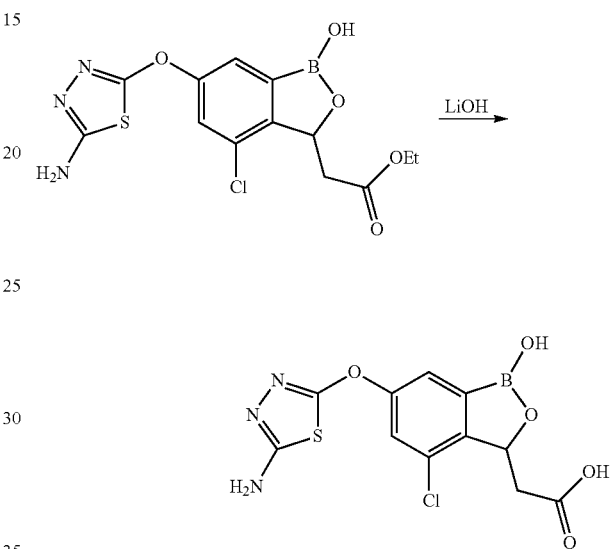

To a solution of ethyl 2-(6-(5-amino-1,3,4-thiadiazol-2-yloxy)-4-chloro-1-hydroxy-1,3-dihydro-benzo[c][1,2]oxaborol-3-yl)acetate (330 mg, 0.89 mmol) in THF (10 mL) and H$_2$O (3 mL) was added LiOH (100 mg, 4.16 mmol). The reaction mixture was stirred at 0° C. for 3 h and acidified with 1N HCl to pH=2-4. The resulting mixture was extracted with EtOAc (2×10 ml). The combined organic layers were dried over anhydrous Na$_2$SO$_4$ and concentrated in vacuo. The residue was purified by prep HPLC to give the title compound as a white powder (15 mg, yield 5%). $^1$H NMR (400 MHz, DMSO-d$_6$) δ 12.45 (s, 1H), 9.57 (s, 1H), 7.56 (m, 2H), 7.20 (s, 2H), 5.51 (m, 1H), 3.22 (m, 1H), 2.32 (s, 3H), 2.36 (m, 1H). MS (ESI) m/z=342 [M+H]$^+$.

G137: 2-(6-(5-Amino-1,3,4-thiadiazol-2-yloxy)-1-hydroxy-4-methyl-1,3-dihydrobenzo[c][1,2]oxaborol-3-yl)propanoic acid

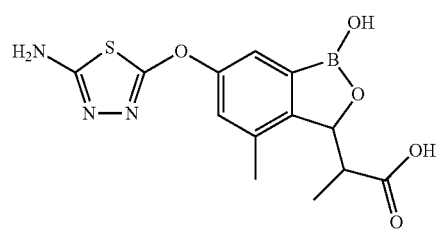

Step 1: 2-Bromo-4,6-dimethoxybenzaldehyde

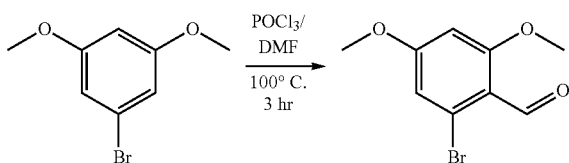

Phosphoryl trichloride (100 g, 657.89 mmol, 4.00 equiv) was added to N,N-dimethylformamide (50 mL) dropwise with stirring at 10-20° C. This was followed by the addition of a solution of 5-methylbenzene-1,3-diol (20 g, 161.29 mmol, 1.00 equiv) in N,N-dimethylformamide (50 mL) dropwise with stirring at 20-30° C. The resulting solution was stirred for 1 h at room temperature, then quenched by the addition of 50 mL of sodium hydroxide (2 M). The pH value of the solution was adjusted to 3-4 with HCl (4 mol/L). The solid was collected by filtration and washed with water, then dried in an oven under reduced pressure. This resulted in 15 g (55%) of 2,4-dihydroxy-6-methylbenzaldehyde as a light yellow solid.

Step 2: 2-Hydroxy-6-methyl-4-(tetrahydro-2H-pyran-2-yloxy)benzaldehyde

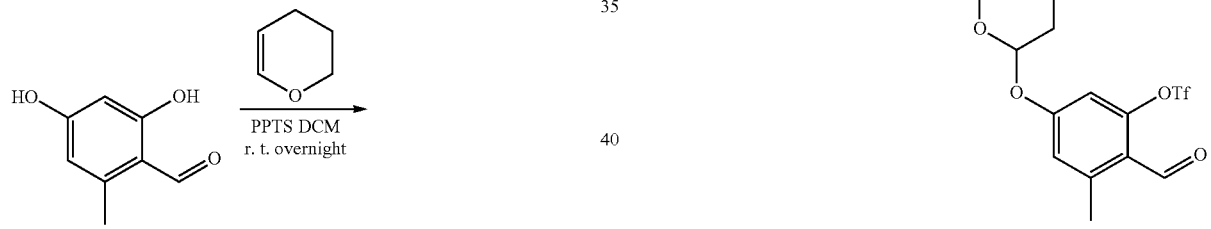

Into a 250-mL round-bottom flask were placed a solution of 2,4-dihydroxy-6-methylbenzaldehyde (2.0 g, 13.16 mmol, 1.00 equiv) in dichloromethane (50 mL), 3,4-dihydro-2H-pyran (1.65 g, 19.64 mmol, 1.49 equiv) and pyridinium p-toluenesulfonate (330 mg, 1.31 mmol, 0.10 equiv). The resulting solution was stirred overnight at room temperature. Then it was diluted with 100 mL of dichloromethane and washed with 3×20 mL of 1 M sodium carbonate solution. The organic layer was dried over anhydrous sodium sulfate and concentrated under vacuum. This resulted in 1.8 g (52%) of 2-hydroxy-6-methyl-4-(tetrahydro-2H-pyran-2-yloxy)benzaldehyde as a yellow oil.

Step 3: 2-Formyl-3-methyl-5-(tetrahydro-2H-pyran-2-yloxy)phenyl trifluoromethanesulfonate

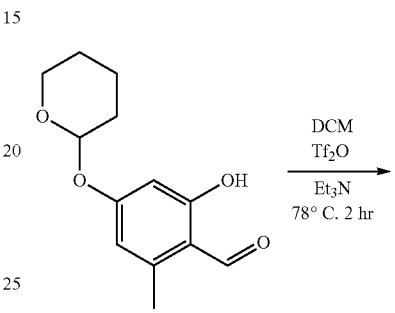

Into a 50-mL 3-necked round-bottom flask, purged and maintained with an inert atmosphere of nitrogen, were placed a solution of 2-hydroxy-6-methyl-4-(tetrahydro-2H-pyran-2-yloxy)benzaldehyde (300 mg, 1.27 mmol, 1.00 equiv) in dichloromethane (20 mL) and triethylamine (510 mg, 5.05 mmol, 3.97 equiv). This was followed by the addition of a solution of Tf$_2$O (720 mg, 2.55 mmol, 2.01 equiv) in dichloromethane (5 mL) dropwise with stirring at −78° C. The resulting solution was stirred for 2 h at −78° C., then quenched by the addition of 5 mL of water. The resulting solution was extracted with 3×30 mL of dichloromethane. The organic layers were combined, washed with 3×10 mL of brine, dried over anhydrous sodium sulfate and concentrated under vacuum. The residue was applied onto a silica gel column and eluted with ethyl acetate/petroleum ether (1:10). This resulted in 110 mg (19%) of 2-formyl-3-methyl-5-(tetrahydro-2H-pyran-2-yloxy)phenyl trifluoromethanesulfonate as a yellow oil.

Step 4: 2-Methyl-4-(tetrahydro-2H-pyran-2-yloxy)-6-(4,4,5,5-tetramethyl-1,3,2-dioxaborolan-2-yl)benzaldehyde

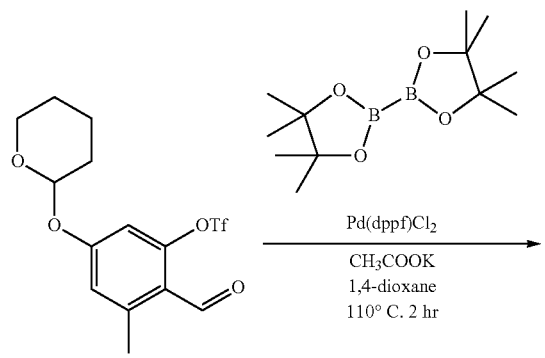

Into a 250-mL round-bottom flask, purged and maintained with an inert atmosphere of nitrogen, were placed a solution of 2-formyl-3-methyl-5-(tetrahydro-2H-pyran-2-yloxy)phenyl trifluoromethanesulfonate (10 g, 27.17 mmol, 1.00 equiv) in 1,4-dioxane (30 mL), 4,4,5,5-tetramethyl-2-(4,4,5,5-tetramethyl-1,3,2-dioxaborolan-2-yl)-1,3,2-dioxaborolane (16 g, 62.99 mmol, 2.00 equiv), CH₃COOK (9.2 g, 93.88 mmol, 3.00 equiv) and Pd(dppf)Cl₂ (4.6 g, 6.28 mmol, 0.10 equiv). The resulting solution was stirred for 2 h at 110° C. in an oil bath. The reaction mixture was cooled and filtered. The filtrate was concentrated under vacuum. The residue was applied onto a silica gel column and eluted with ethyl acetate/petroleum ether (1/50). This resulted in 6 g (51%) of 2-methyl-4-(tetrahydro-2H-pyran-2-yloxy)-6-(4,4,5,5-tetramethyl-1,3,2-dioxaborolan-2-yl)benzaldehyde as a brown oil.

Step 5: Ethyl 2-(1,6-dihydroxy-4-methyl-1,3-dihydrobenzo[c][1,2]oxaborol-3-yl)acrylate

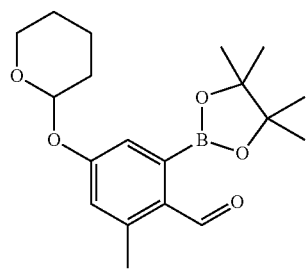

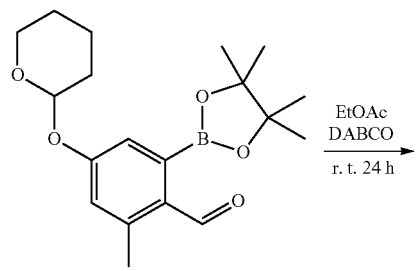

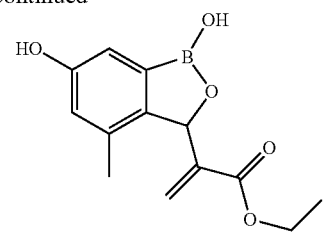

Into a 50-mL round-bottom flask was placed a solution of 2-methyl-4-(tetrahydro-2H-pyran-2-yloxy)-6-(4,4,5,5-tetramethyl-1,3,2-dioxaborolan-2-yl)benzaldehyde (5 g, 14.45 mmol, 1.00 equiv) in ethyl acrylate (10 mL), then added DABCO (2.42 g, 21.61 mmol, 1.50 equiv). The resulting solution was stirred for 24 h at room temperature. The pH value of the solution was adjusted to 3 with HCl (3N) and stirred for 2 h at 30° C. The resulting solution was extracted with 3×50 mL of ethyl acetate. The organic layers were combined, washed with 2×20 mL of brine, dried over anhydrous sodium sulfate and concentrated under vacuum. The residue was applied onto a silica gel column and eluted with ethyl acetate/petroleum ether (1:1). This resulted in 3.0 g (75%) of ethyl 2-(1,6-dihydroxy-4-methyl-1,3-dihydrobenzo[c][1,2]oxaborol-3-yl)acrylate as a white solid.

Step 6: Ethyl 2-(1,6-dihydroxy-4-methyl-1,3-dihydrobenzo[c][1,2]oxaborol-3-yl)propanoate

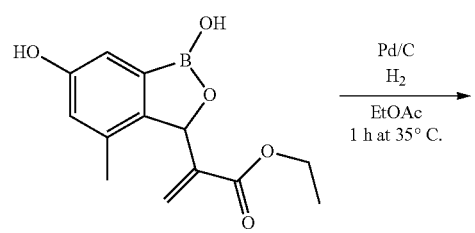

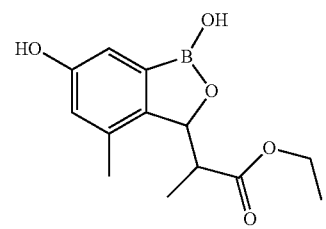

A mixture of ethyl 2-(1,6-dihydroxy-4-methyl-1,3-dihydrobenzo[c][1,2]oxaborol-3-yl)acrylate (1 g, 3.44 mmol, 1.00 equiv, 90%) and Palladium carbon (10%, 300 mg) in ethyl acetate (50 mL) was stirred for 1 h at 35° C. under a hydrogen atmosphere. The solid was filtered out and washed with 2×10 mL of THF. The filtrate was concentrated under vacuum. This resulted in 0.8 g (71%) of ethyl 2-(1,6-dihydroxy-4-methyl-1,3-dihydrobenzo[c][1,2]oxaborol-3-yl)propanoate as a light-brown oil.

Step 7: Ethyl 2-(1-hydroxy-4-methyl-6-(5-nitro-1,3,4-thiadiazol-2-yloxy)-1,3-dihydrobenzo[c][1,2]oxaborol-3-yl)propanoate

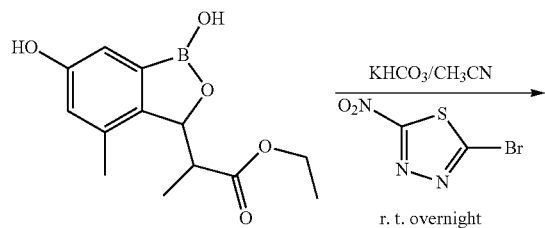

Into a 50-mL round-bottom flask were placed a solution of ethyl 2-(1,6-dihydroxy-4-methyl-1,3-dihydrobenzo[c][1,2]oxaborol-3-yl)propanoate (800 mg, 2.73 mmol, 1.00 equiv, 90%) in CH₃CN (30 mL), KHCO₃ (1.5 g, 15.00 mmol, 5.00 equiv) and 2-bromo-5-nitro-1,3,4-thiadiazole (890 mg, 3.80 mmol, 1.40 equiv, 90%). The resulting mixture was stirred overnight at room temperature. The pH value of the solution was adjusted to 4 with HCl (2 mol/L), then extracted with 4×50 mL of ethyl acetate. The organic layers were combined, washed with 2×50 mL of brine, dried over anhydrous sodium sulfate and concentrated under vacuum. The residue was applied onto a silica gel column and eluted with ethyl acetate/petroleum ether (1:2). This resulted in 0.4 g (22%) of ethyl 2-(1-hydroxy-4-methyl-6-(5-nitro-1,3,4-thiadiazol-2-yloxy)-1,3-dihydrobenzo[c][1,2]oxaborol-3-yl)propanoate as a brown oil.

Step 8: Ethyl 2-(6-(5-amino-1,3,4-thiadiazol-2-yloxy)-1-hydroxy-4-methyl-1,3-dihydrobenzo[c][1,2]oxaborol-3-yl)propanoate

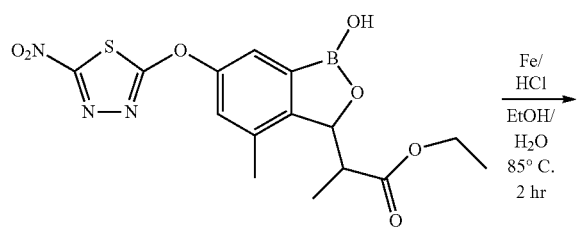

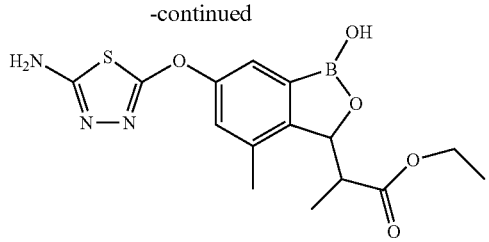

Into a 50-mL round-bottom flask was placed a solution of ethyl 2-(1-hydroxy-4-methyl-6-(5-nitro-1,3,4-thiadiazol-2-yloxy)-1,3-dihydrobenzo[c][1,2]oxaborol-3-yl)propanoate (500 mg, 1.15 mmol, 1.00 equiv, 90%) in ethanol/H₂O (15/5 mL). This was followed by the addition of Fe (280 mg, 5.00 mmol, 4.00 equiv). Then added 2 drops of HCl. The resulting solution was stirred for 2 h at 85° C. The reaction mixture was cooled and filtered. The filtrate was concentrated under vacuum. This resulted in 0.8 g (90%) of ethyl 2-(6-(5-amino-1,3,4-thiadiazol-2-yloxy)-1-hydroxy-4-methyl-1,3-dihydrobenzo[c][1,2]oxaborol-3-yl)propanoate as a brown solid.

Step 9: 2-(6-(5-Amino-1,3,4-thiadiazol-2-yloxy)-1-hydroxy-4-methyl-1,3-dihydrobenzo[c][1,2]oxaborol-3-yl)propanoic acid

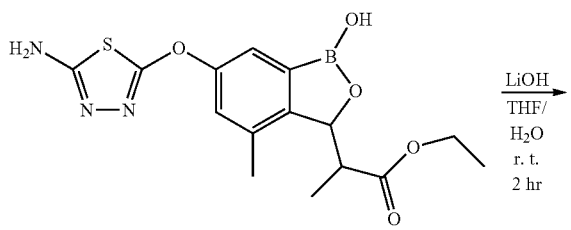

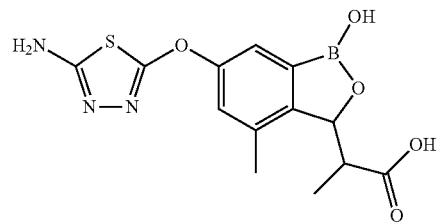 [SMILES: Cc1cc(Oc2nnc(N)s2)cc2c1C(C(C)C(=O)O)OB2O]

Into a 50-mL round-bottom flask was placed a solution of ethyl 2-(6-(5-amino-1,3,4-thiadiazol-2-yloxy)-1-hydroxy-4-methyl-1,3-dihydrobenzo[c][1,2]oxaborol-3-yl)propanoate (500 mg, 1.32 mmol, 1.00 equiv, 96%) in H₂O/THF (10/10 mL), then added lithium hydroxide hydrate (230 mg, 5.48 mmol, 4.00 equiv). The resulting solution was stirred for 2 h at room temperature. The resulting mixture was concentrated under vacuum. The residual solution was adjusted to pH 3 with HCl (1 mol/L) and stirred for 30 min at room temperature. The resulting mixture was concentrated under vacuum. The crude product (200 mg) was purified by Prep-HPLC with the following conditions: Column, Xbridge Prep Phenyl, 5 μm, 19×150 mm; Mobile phase, water (with 0.05% TFA) and CH₃CN; Gradient, 17% CH₃CN up to 30% in 8 min, up to 100% in 1.5 min; Detector, UV 220 & 254 nm. This resulted in 30.2 mg (6%) of 2-(6-(5-amino-1,3,4-thiadiazol-2-yloxy)-1-hydroxy-4-methyl-1,3-dihydrobenzo[c][1,2]oxaborol-3-yl)propanoic acid as a white solid. H-NMR (300 MHz, DMSO-d₆, ppm): δ1.284 (3H, d, J=7.2 Hz), 2.332 (3H, s), 3.120 (2H, m), 5.301 (1H, d, J=2.7 Hz), 7.082-7.141 (3H, m), 7.295 (1H, d, J=2.1 Hz), 9.180 (1H, s). MS (ESI) m/z: 336 [M+H]⁺.

G138: 2-(6-(5-(2-Aminoacetamido)-1,3,4-thiadiazol-2-yloxy)-1-hydroxy-4-methyl-1,3-dihydrobenzo[c][1,2]oxaborol-3-yl)acetic acid

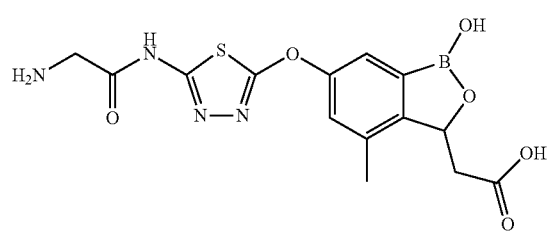 [SMILES: Cc1cc(Oc2nnc(NC(=O)CN)s2)cc2c1C(CC(=O)O)OB2O]

Step 1: Ethyl 2-(6-(5-(2-(tert-butoxycarbonylamino)acetamido)-1,3,4-thiadiazol-2-yloxy)-1-hydroxy-4-methyl-1,3-dihydrobenzo[c][1,2]oxaborol-3-yl)acetate

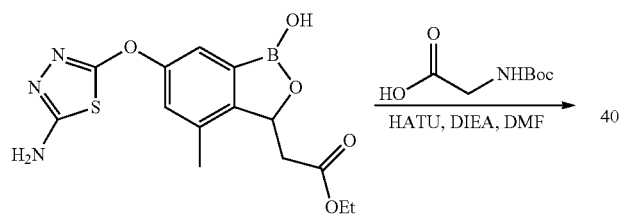

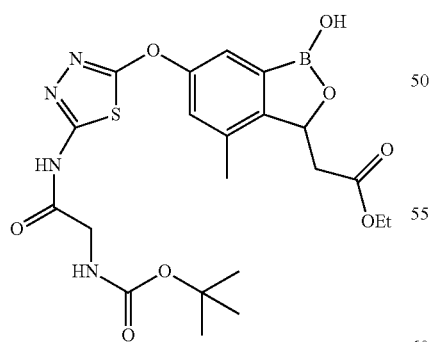

To a solution of N-tert-butoxy carbonyl-glycine (1.05 g, 6 mmol) in DMF (15 mL) was added HATU (2.85 g, 7.5 mmol), ethyl 2-(6-(5-amino-1,3,4-thiadiazol-2-yloxy)-1-hydroxy-4-methyl-1,3-dihydrobenzo[c][1,2]oxaborol-3-yl)acetate (1.74 g, 5 mmol) and DIEA (1.73 mL). The mixture was stirred at room overnight. The mixture was concentrated to afford the target molecule.

Step 2: 2-(6-(5-(2-Aminoacetamido)-1,3,4-thiadiazol-2-yloxy)-1-hydroxy-4-methyl-1,3-dihydrobenzo[c][1,2]oxaborol-3-yl)acetic acid

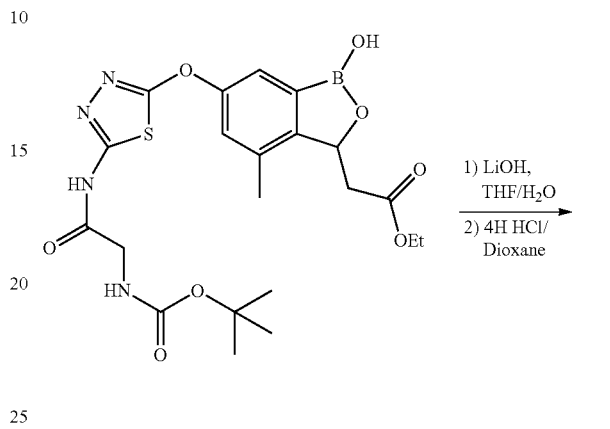

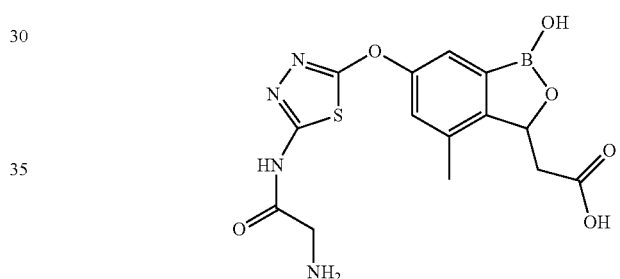

2-(6-(5-(2-Aminoacetamido)-1,3,4-thiadiazol-2-yloxy)-1-hydroxy-4-methyl-1,3-dihydrobenzo[c][1,2]oxaborol-3-yl)acetic acid was obtained using the same procedure for G137. ¹H NMR (DMSO-d₆) δ 12.0 (s, 1H), 9.22 (s, 1H), 9.00 (s, 1H), 6.86 (s, 1H), 6.64 (s, 1H), 5.37 (d, 1H), 2.99 (dd, 1H), 2.17 (s, 3H), 2.02 (dd, 1H); MS found: (M−H)⁻=377.1.

G139: 2-(1-Hydroxy-6-(5-(N-hydroxycarbamimidoyl)-1,3,4-thiadiazol-2-yloxy)-4-methyl-1,3-dihydrobenzo[c][1,2]oxaborol-3-yl)acetic acid

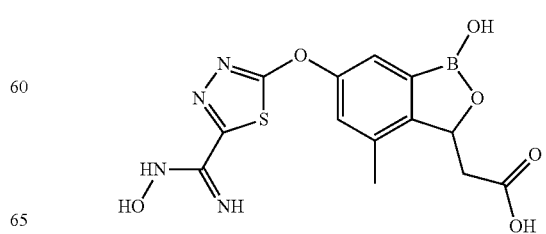

319

G140: 2-(6-(5-Carbamoyl-1,3,4-thiadiazol-2-yloxy)-1-hydroxy-4-methyl-1,3-dihydrobenzo[c][1,2]oxaborol-3-yl)acetic acid

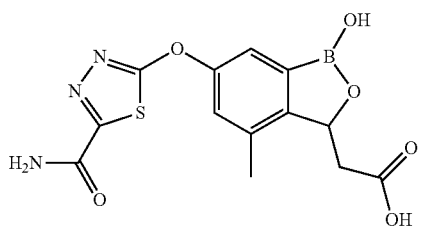 [SMILES: Cc1cc(Oc2nnc(C(N)=O)s2)cc2c1C(CC(=O)O)OB2O]

Step 1: Ethyl 2-(6-(5-carbamoyl-1,3,4-thiadiazol-2-yloxy)-1-hydroxy-4-methyl-1,3-dihydrobenzo[c][1,2]oxaborol-3-yl)acetate

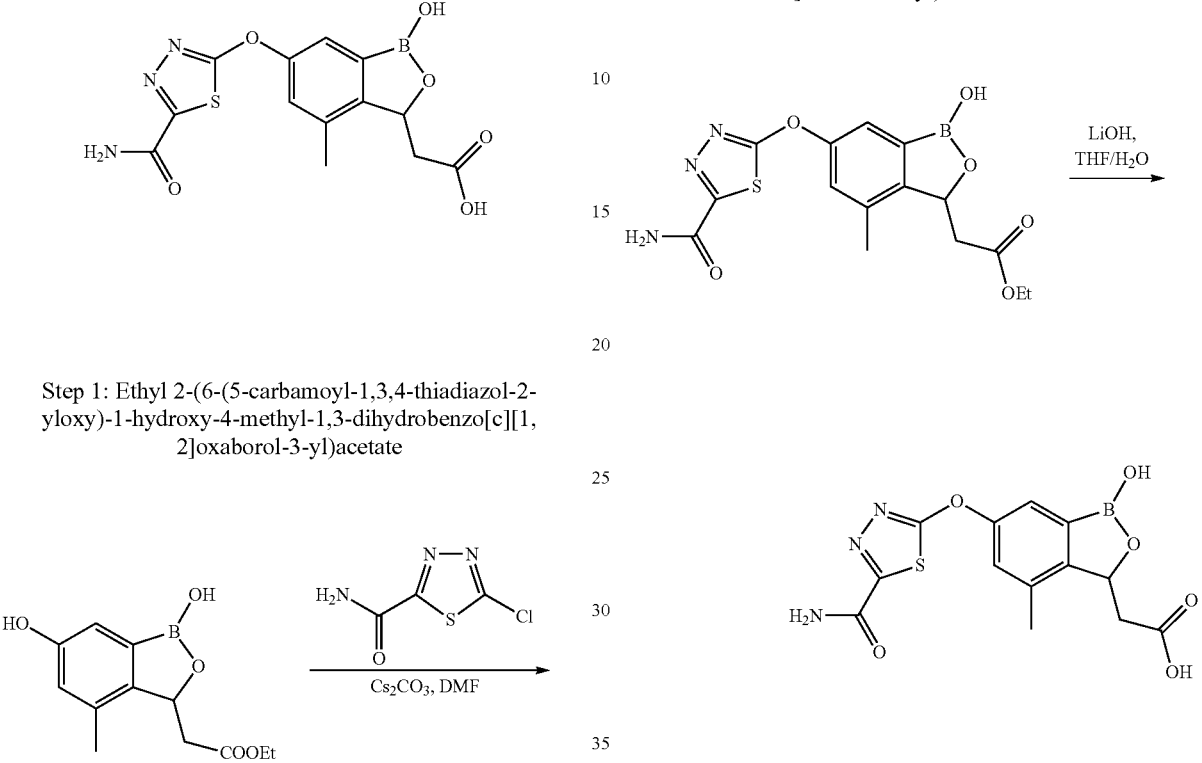

To a solution of (1,6-dihydroxy-4-methyl-1,3-dihydrobenzo[c][1,2]oxaborol-3-yl)-acetic acid ethyl ester (3.2 mmol) in anhydrous DMF (8 mL) was added cesium carbonate (8 mmol) and 5-chloro-1,3,4-thiadiazole-2-carboxamide (3.2 mmol). The resulting mixture was stirred at room temperature overnight then quenched with crushed ice. The pH was adjusted to 2 with 6M HCl and the mixture extracted with EtOAc (2×200 mL). The organic extracts were washed with water, brine, dried over $Na_2SO_4$, filtered, and concentrated in vacuo. The residue was purified by silica gel flash column chromatography (0-75% EtOAc in hexane) to give ethyl 2-(6-

320

(5-carbamoyl-1,3,4-thiadiazol-2-yloxy)-1-hydroxy-4-methyl-1,3-dihydrobenzo[c][1,2]oxaborol-3-yl)acetate.

Step 2: 2-(6-(5-Carbamoyl-1,3,4-thiadiazol-2-yloxy)-1-hydroxy-4-methyl-1,3-dihydrobenzo[c][1,2]oxaborol-3-yl)acetic acid To a solution ethyl 2-(6-(5-carbamoyl-1,3,4-thiadiazol-2-yloxy)-1-hydroxy-4-methyl-1,3-dihydrobenzo[c][1,2]oxaborol-3-yl)acetate (0.448 mmol) in THF (3 mL) was added a solution of LiOH (2.24 mmol) in water (3 mL) at 0° C. The resulting mixture was stirred at room temperature for 3 hours then concentrated in vacuo. The residue was purified by preparative HPLC then lyophilized to give 2-(6-(5-carbamoyl-1,3,4-thiadiazol-2-yloxy)-1-hydroxy-4-methyl-1,3-dihydrobenzo[c][1,2]oxaborol-3-yl)acetic acid as an off white solid (17%). $^1$H NMR (400 MHz, DMSO-$d_6$) δ 12.32 (s, 1H), 9.31 (s, 1H), 8.44 (s, 1H), 8.07 (s, 1H), 7.48 (s, 1H), 7.36 (s, 1H), 5.54 (dd, 1H), 3.07 (dd, 1H), 2.32 (s, 3H), 2.18 (dd, 1H). MS (ESI) m/z: 348.1 [M−1]$^-$.

G141: (R)-2-(6-(1,3,4-Thiadiazol-2-yloxy)-1-hydroxy-4-methyl-1,3-dihydrobenzo[c][1,2]oxaborol-3-yl)acetic acid

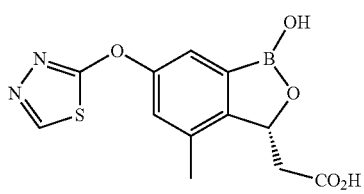 [SMILES: Cc1cc(Oc2nncs2)cc2c1[C@@H](CC(=O)O)OB2O]

G142: (S)-2-(6-(1,3,4-Thiadiazol-2-yloxy)-1-hydroxy-4-methyl-1,3-dihydrobenzo[c][1,2]oxaborol-3-yl)acetic acid

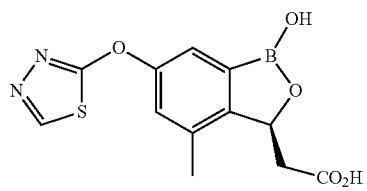 [SMILES: Cc1cc(Oc2nncs2)cc2c1[C@H](CC(=O)O)OB2O]

Step 1: (R)-Ethyl 2-(6-(1,3,4-thiadiazol-2-yloxy)-1-hydroxy-4-methyl-1,3-dihydrobenzo[c][1,2]oxaborol-3-yl)acetate and (S)-ethyl 2-(6-(1,3,4-thiadiazol-2-yloxy)-1-hydroxy-4-methyl-1,3-dihydrobenzo[c][1, 2]oxaborol-3-yl)acetate

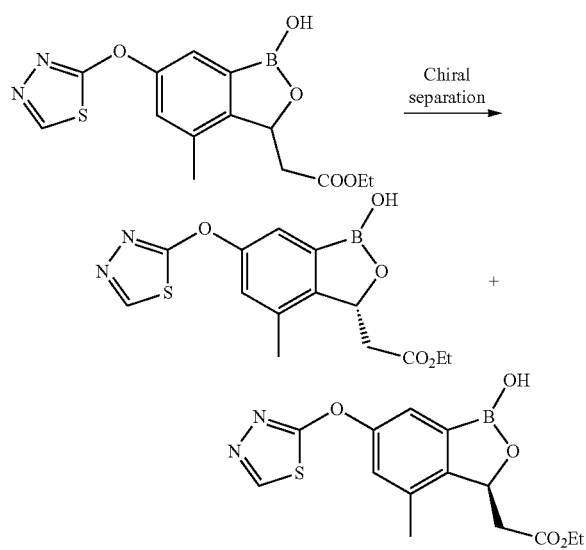

8.0 g of (R,S)-ethyl 2-(6-(1,3,4-thiadiazol-2-yloxy)-1-hydroxy-4-methyl-1,3-dihydrobenzo[c][1,2]oxaborol-3-yl)acetate was separated by Chiral column (CHIRALPAK® AD-H 5 mm, 4.6 mm id×15 cm L) using $CO_2(SCF)/EtOH$ (0.05% TFA) as Mobile Phase to give (R)-ethyl 2-(6-(1,3,4-thiadiazol-2-yloxy)-1-hydroxy-4-methyl-1,3-dihydrobenzo[c][1,2]oxaborol-3-yl)acetate (1.6 g, Purity: 97%; e.e.: 99%, Yield: 20%) and (S)-ethyl 2-(6-(1,3,4-thiadiazol-2-yloxy)-1-hydroxy-4-methyl-1,3-dihydrobenzo[c][1,2]oxaborol-3-yl)acetate (2.7 g, Purity: 96%; e.e.: 95.9%, Yield: 33.8%).

(R)-Ethyl 2-(6-(1,3,4-thiadiazol-2-yloxy)-1-hydroxy-4-methyl-1,3-dihydrobenzo[c][1,2]oxaborol-3-yl)acetate: $^1$H NMR (400 MHz, DMSO-$d_6$) δ 69.16 (s, 1H), 7.45~7.30 (m, 2H), 5.57~5.53 (m, 1H), 4.03~3.99 (m, 2H), 3.15~3.10 (m, 1H), 2.39~2.34 (m, 4H), 1.14~1.09 (m, 3H); ESI-MS m/z 357 (M+Na$^+$, positive); HPLC purity: 97.3% (220 nm), 98.47% (254 nm); Chiral HPLC (analysis) e.e.: 99.52% (220 nm), 100% (254 nm); Rotation $[\alpha]^{25}_D$=+63.416°±0.552°; Detected Conditions: C=0.2092 g/100 ml diluted with ethanol.

(S)-Ethyl 2-(6-(1,3,4-thiadiazol-2-yloxy)-1-hydroxy-4-methyl-1,3-dihydrobenzo[c][1,2]oxaborol-3-yl)acetate: $^1$H NMR (400 MHz, DMSO-$d_6$) δ 9.33 (s, 1H), 9.16 (s, 1H), 7.45~7.31 (m, 2H), 5.56~5.54 (m, 1H), 4.06~4.01 (m, 2H), 3.15~3.11 (m, 1H), 2.39~2.32 (m, 4H), 1.14~1.10 (m, 3H); ESI-MS m/z 357 (M+Na$^+$, positive); HPLC purity: 96.41% (220 nm), 97.78% (254 nm); Chiral HPLC (analysis) e.e.: 95.96% (220 nm), 94.78% (254 nm); Rotation $[\alpha]^{25}_D$=−63.917°±1.636°; Detected Conditions: C=0.1867 g/100 ml diluted with ethanol.

Step 2: (R)-Ethyl 2-(6-(1,3,4-thiadiazol-2-yloxy)-1-hydroxy-4-methyl-1,3-dihydrobenzo[c][1,2]oxaborol-3-yl)acetic acid and (S)-Ethyl 2-(6-(1,3,4-thiadiazol-2-yloxy)-1-hydroxy-4-methyl-1,3-dihydrobenzo[c][1,2]oxaborol-3-yl)acetic acid

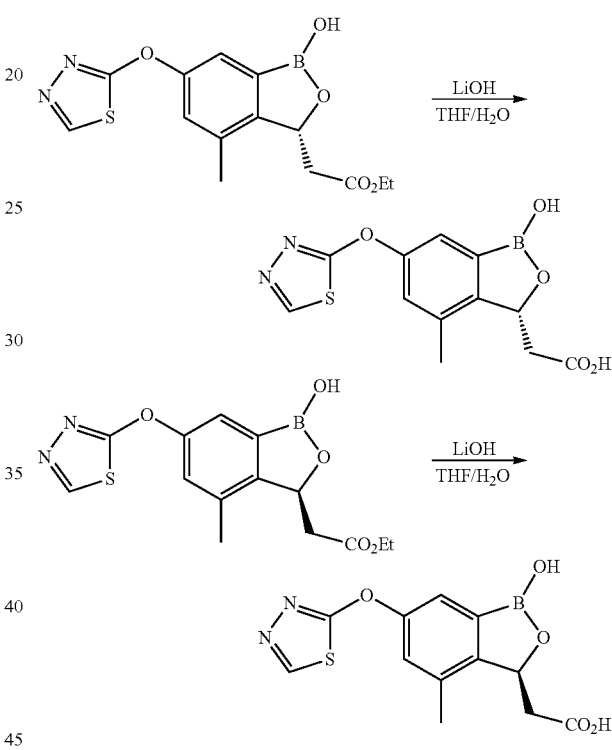

To a solution of (R)-ethyl 2-(6-(1,3,4-thiadiazol-2-yloxy)-1-hydroxy-4-methyl-1,3-dihydrobenzo[c][1,2]oxaborol-3-yl)acetate (0.9 g, 2.69 mmol) in a mixed solution of THF (30 mL) and methanol (4 mL) was added a solution of LiOH. $H_2O$ (0.57 g, 13.5 mmol) in water (30 mL) at 0° C. The resulting mixture was stirred at room temperature for 1.5 hrs and then acidified to pH=2 with diluted hydrochloric acid at 0° C. After removal of the volatile organics, the residue was dissolved in EtOAc. The aqueous phase was dried and concentrated in vacuo to give the products.

(R)-Ethyl 2-(6-(1,3,4-thiadiazol-2-yloxy)-1-hydroxy-4-methyl-1,3-dihydrobenzo[c][1,2]oxaborol-3-yl)acetic acid (0.7 g, 85.4% yield). $^1$H NMR (400 MHz, DMSO-$d_6$) δ 12.30 (1H, s), 9.31 (1H, s), 9.16 (1H, s), 7.45 (1H, s), 7.30 (1H, s), 5.54-5.51 (1H, m), 3.05 (1H, m), 2.32 (3H, s), 2.20-2.13 (1H, m). LC-MS m/z 307 (M+H$^+$, positive); HPLC purity: 98.58% (220 nm), 100% (254 nm); Chiral SFC-MS (analysis) e.e.: 99.08%; Rotation $[\alpha]^{25}_D$=+57.865°±0.658°; Detected Conditions: C=0.4643 g/100 ml diluted with Methanol L=0.5 dm.

(S)-Ethyl 2-(6-(1,3,4-thiadiazol-2-yloxy)-1-hydroxy-4-methyl-1,3-dihydrobenzo[c][1,2]oxaborol-3-yl)acetic acid:

$^1$H NMR (400 MHz, DMSO-d$_6$) δ12.30 (1H, s), 9.27 (1H, s), 9.16 (1H, s), 7.45 (1H, m), 7.30 (1H, m), 5.52 (1H, m), 3.09-3.04 (1H, m), 2.32 (3H, s), 2.20-2.13 (1H, m); LC-MS m/z 307 (M+H$^+$, positive); HPLC purity: 95.32% (220 nm), 97.33% (254 nm); Chiral SFC-MS (analysis) e.e.: 98.62%. Rotation [α]$^{25}_D$=−60.514°±0.580°; Detected Conditions: C=0.5266 g/100 ml diluted with Methanol L=0.5 dm.

G143: 2-(1-Hydroxy-6-(5-(N-hydroxycarbamimidoyl)-1,3,4-thiadiazol-2-yloxy)-4-methyl-1,3-dihydrobenzo[c][1,2]oxaborol-3-yl)acetic acid

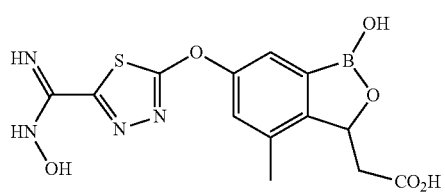

Step 1.1 Ethyl 2-(6-(5-cyano-1,3,4-thiadiazol-2-yloxy)-1-hydroxy-4-methyl-1,3-dihydrobenzo[c][1,2]oxaborol-3-yl)acetate

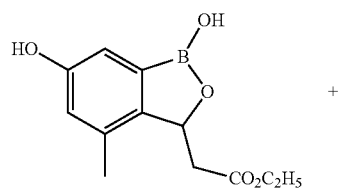

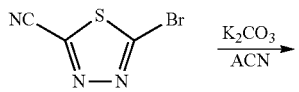

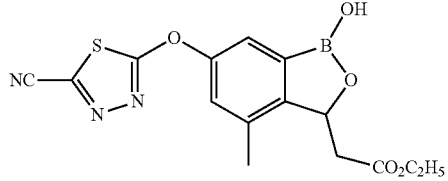

To a mixture of ethyl 2-(1,6-dihydroxy-4-methyl-1,3-dihydrobenzo[c][1,2]oxaborol-3-yl)acetate (1.35 g, 5.4 mmol, 1 eq.) and 5-bromo-1,3,4-thiadiazole-2-carbonitrile (1.54 g, 8.1 mmol, 1.5 eq.) in 50 ml ACN was added potassium carbonate (2.24 g, 16.2 mmol, 3 eq.). The reaction was heated at 60° C. for three hours. The reaction was quenched by water, acidified to pH=3 with 1N HCl and then extracted with EtOAc, washed with brine, dried over Na$_2$SO$_4$, and concentrated under reduced pressure. The crude was purified by column chromatography to give desired product as yellow oil (1.63 g, yield 84%). MS (ESI) m/z=718 [2M+H]$^+$.

Step 1.2 Ethyl 2-(1-hydroxy-6-(5-(N-hydroxycarbamimidoyl)-1,3,4-thiadiazol-2-yloxy)-4-methyl-1,3-dihydrobenzo[c][1,2]oxaborol-3-yl)acetate

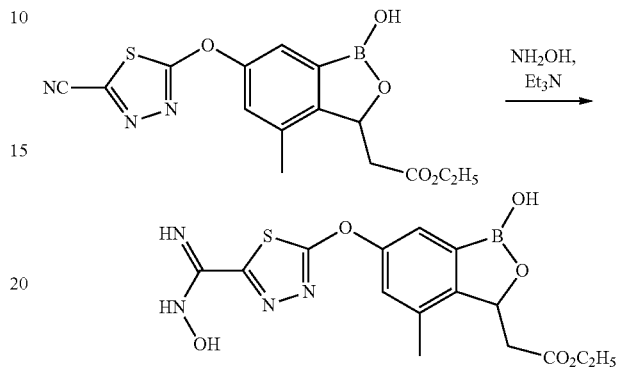

To a solution of ethyl 2-(6-(5-cyano-1,3,4-thiadiazol-2-yloxy)-1-hydroxy-4-methyl-1,3-dihydrobenzo[c][1,2]oxaborol-3-yl)acetate (1.63 g, 4.54 mmol, 1 eq.) and hydroxylamine hydrochloride (0.79 g, 11.35 mmol, 2.5 eq.) in methanol was added triethylamine (2.22 ml, 15.88 mmol, 3.5 eq.). After stirring at room temperature for one hour, the reaction mixture was evaporated under reduced pressure. The residue was dissolved in EtOAc and then washed with water. The organic layers were collected, dried with Na$_2$SO$_4$ and evaporated to give the crude product (1.73 g, yield 97.2%). The crude was used in subsequent steps without further purification.

Step 1.3 2-(1-Hydroxy-6-(5-(N-hydroxycarbamimidoyl)-1,3,4-thiadiazol-2-yloxy)-4-methyl-1,3-dihydrobenzo[c][1,2]oxaborol-3-yl)acetic acid

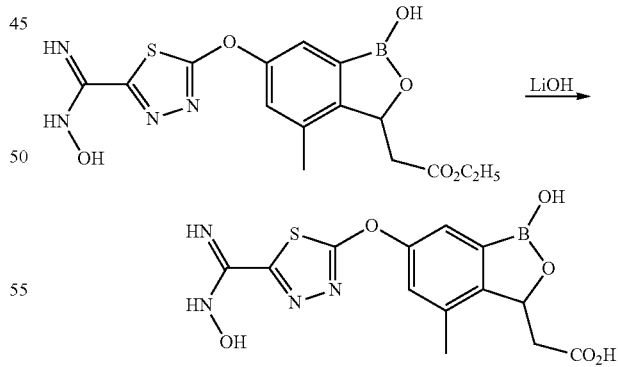

The crude ethyl 2-(1-hydroxy-6-(5-(N-hydroxycarbamimidoyl)-1,3,4-thiadiazol-2-yloxy)-4-methyl-1,3-dihydrobenzo[c][1,2]oxaborol-3-yl)acetate was dissolved in a mixture of THF and MeOH (1:1, 5 ml) and then treated with aqueous LiOH solution (200 mg in 5 mL water). After stirring at room temperature for one hour, the reaction mixture was evaporated, acidified with 1N HCl to pH 3 and then concentrated. HPLC purification gave desired product as white solid.

¹H NMR (400 MHz, DMSO-d₆) δ 12.4 (b, 1H), 10.3 (b, 1H), 9.20 (b, 1H), 7.41 (d, J=2Hz, 1H), 7.28 (d, J=1.6 Hz, 1H), 5.48 (dd, J=9.2, 2 Hz, 1H), 4.07 (b, 2H), 3.00 (dd, J=15.6, 2.4 Hz, 1H), 2.27 (s, 3H), 2.10 (dd, J=15.6, 9.2 Hz, 1H). MS (ESI) m/z=363 [M−H]⁺.

G144: (6-(5-Carbamoyl-1,3,4-thiadiazol-2-yloxy)-1-hydroxy-4-methyl-1,3-dihydrobenzo[c][1,2]oxaborol-3-yl)-methanesulfonic acid

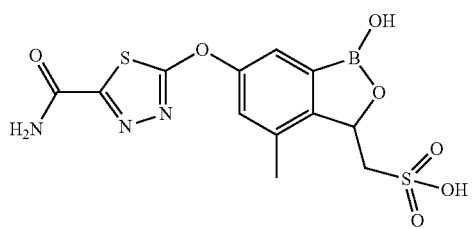 [SMILES: Cc1cc(Oc2nnc(C(N)=O)s2)cc2c1C(CS(=O)(=O)O)OB2O]

Step 2.1 Methyl (1-hydroxy-4-methyl-6-(tetrahydro-2H-pyran-2-yloxy)-1,3-dihydrobenzo[c][1,2]oxaborol-3-yl)methanesulfonate

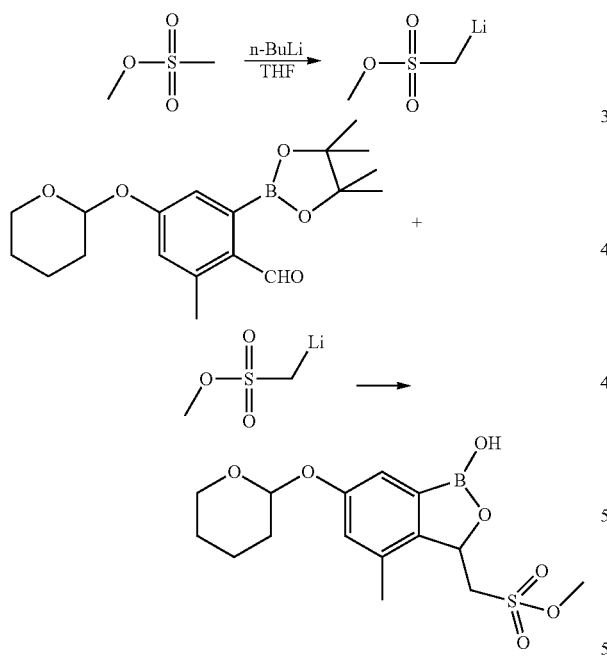

To a cooled (−78° C.) solution of methyl methanesulfonate (1.56 mL, 20 mmol) in 15 ml anhydrous THF was added 1.6 M n-BuLi in hexanes (11.25 ml, 18 mmol) dropwise. The mixture was stirred at −78° C. for 20 minutes, then a solution of 2-methyl-4-(tetrahydro-2H-pyran-2-yloxy)-6-(4,4,5,5-tetramethyl-1,3,2-dioxaborolan-2-yl)benzaldehyde (2.07 g, 6 mmol) in 15 mL THF was added slowly via syringe. After stirring at −78° C. for 10 minutes, the reaction was quenched with saturated ammonium chloride at −78° C. It was then extracted with EtOAc, washed with brine, dried over Na₂SO₄, and concentrated under reduced pressure to give crude product, which was purified by flash column. (1.64 g) MS (ESI) m/z=713 [2M+H]⁺.

Step 2.2 Methyl (1,6-dihydroxy-4-methyl-1,3-dihydrobenzo[c][1,2]oxaborol-3-yl)methanesulfonate

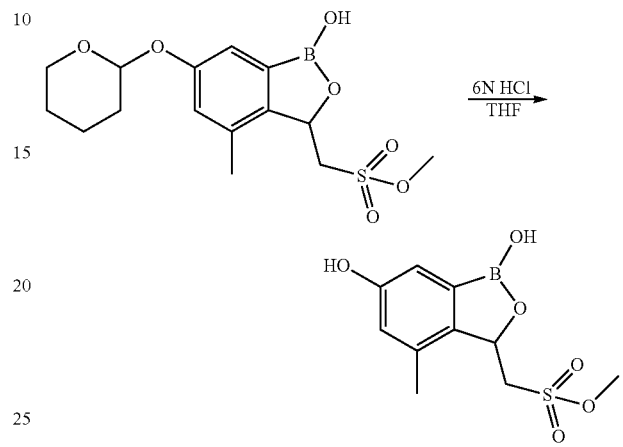

To a solution of methyl (1-hydroxy-4-methyl-6-(tetrahydro-2H-pyran-2-yloxy)-1,3-dihydrobenzo[c][1,2]oxaborol-3-yl)methanesulfonate (1.64 g) in THF cooled at −20° C. was added 6N HCl until pH=1. After the mixture was stirred at −20° C. for 20 minutes, concentrate. The residue was purified by flash chromatography to give desired product as an off-white solid.

Step 2.3 (6-(5-Carbamoyl-1,3,4-thiadiazol-2-yloxy)-1-hydroxy-4-methyl-1,3-dihydrobenzo[c][1,2]oxaborol-3-yl)methanesulfonic acid

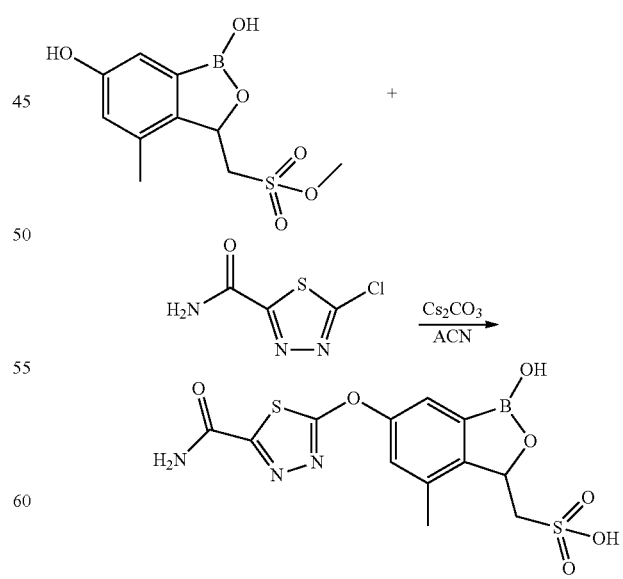

To a mixture of methyl (1,6-dihydroxy-4-methyl-1,3-dihydrobenzo[c][1,2]oxaborol-3-yl)methanesulfonate (0.46 g, 1.71 mmol, 1 eq.) and 5-chloro-1,3,4-thiadiazole-2-carboxamide (0.42 g, 2.56 mmol, 1.5 eq.) in 10 ml DMF was added cesium carbonate (2.22 g, 6.82 mmol, 4 eq.) portionwise. The reaction was stirred at room temperature overnight. It was then quenched by water, extracted with EtOAc. The aqueous layer was collected and prep HPLC gave the product as white flakes. $^1$H NMR (400 MHz, DMSO-$d_6$) δ 8.39 (s, 1H), 8.01 (s, 1H), 7.39 (d, J=2.4 Hz, 1H), 7.27 (d, J=2.4 Hz, 1H), 5.42 (d, 7.6 Hz, 1H), 3.04 (dd, J=14.4, 1.2 Hz, 1H), 2.46 (m, 1H), 2.27 (s, 3H).

G145: [6-(3-Chloro-[1,2,4]thiadiazol-5-yloxy)-1-hydroxy-4-methyl-1,3-dihydro-benzo[c][1,2]oxaborol-3-yl]-acetic acid

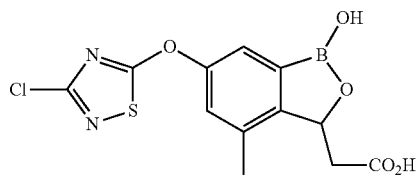 [SMILES: Cc1cc(Oc2nc(Cl)ns2)cc2c1C(CC(=O)O)OB2O]

Step 1: [6-(3-Chloro-[1,2,4]thiadiazol-5-yloxy)-1-hydroxy-4-methyl-1,3-dihydro-benzo[c][1,2]oxaborol-3-yl]-acetic acid ethyl ester

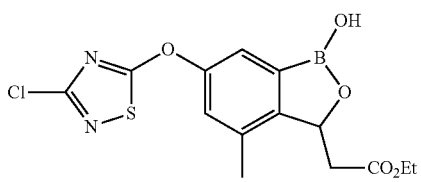 [SMILES: CCOC(=O)CC1OB(O)c2cc(Oc3nc(Cl)ns3)cc(C)c21]

To a solution of (1,6-dihydroxy-4-methyl-1,3-dihydro-benzo[c][1,2]oxaborol-3-yl)-acetic acid ethyl ester (1.0 g, 4.0 mmol) and 3,5-dichloro-1,2,4 thiadiazole (0.45 mL, 4.8 mmol) in DMF (24 mL) was added cesium carbonate (2.61 g, 8 mmol). The mixture was stirred at room temperature overnight. The reaction was diluted with H$_2$O, acidified to pH 3 with aqueous HCl (1N). The mixture was extracted with ethyl acetate. The organic phase was separated, dried (Na$_2$SO$_4$), and concentrated. The residue was purified by column chromatography (silica, Ethyl acetate) affording the title compound (1.25 g, 85%) as a white solid: $^1$H NMR (CDCl$_3$) δ7.48 (d, 1H), 7.19 (d, 1H), 5.68 (dd, 1H), 5.18 (s, 1H), 4.18 (q, 2H), 3.10 (dd, 1H), 2.45 (dd, 1H), 2.39 (s, 3H), 1.25 (t, 3H). MS found: (M+H)$^+$=369.

Step 2: [6-(3-Chloro-[1,2,4]thiadiazol-5-yloxy)-1-hydroxy-4-methyl-1,3-dihydro-benzo[c][1,2]oxaborol-3-yl]-acetic acid

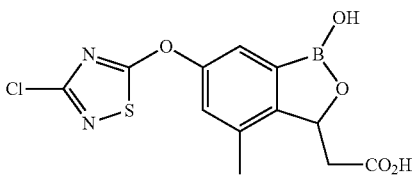 [SMILES: Cc1cc(Oc2nc(Cl)ns2)cc2c1C(CC(=O)O)OB2O]

To a solution of [6-(3-chloro-[1,2,4]thiadiazol-5-yloxy)-1-hydroxy-4-methyl-1,3-dihydro-benzo[c][1,2]oxaborol-3-yl]-acetic acid ethyl ester (135 mg, 0.502 mmol) in THF (5 mL) and H$_2$O (2 mL) was added LiOH (0.105 g, 2.50 mmol). The resulting solution was stirred at room temperature for 2 hrs. The mixture was diluted with H$_2$O and acidified to pH 3 with 1N HCl at 0° C. The resulting mixture was extracted with ethyl acetate. The organic phase was separated, dried (Na$_2$SO$_4$), and concentrated. The crude mixture was purified by prep HPLC to give title compound (20 mg, 18%) as a white solid. $^1$H NMR (CD$_3$OD) δ7.42 (d, 1H), 7.29 (d, 1H), 5.66 (dd, 1H), 3.20 (dd, 1H), 2.40 (s, 3H), 2.36 (dd, 1H). MS found: (M+H)$^+$: 341.

G146: [6-(3-Amino-[1,2,4]thiadiazol-5-yloxy)-1-hydroxy-4-methyl-1,3-dihydro-benzo[c][1,2]oxaborol-3-yl]-acetic acid

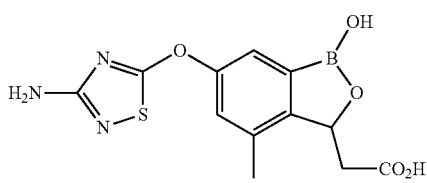

To a solution of [6-(3-chloro-[1,2,4]thiadiazol-5-yloxy)-1-hydroxy-4-methyl-1,3-dihydro-benzo[c][1,2]oxaborol-3-yl]-acetic acid (100 mg, 0.27 mmol) in THF (1.5 mL) was added LHMDS (1M in Hexanes, 0.54 mL, 0.54 mmol). The resulting solution was stirred at room temperature for overnight. LC-MS showed still half starting material left. The mixture was added LHMDS (1M in Hexanes, 0.54 mL, 0.54 mmol) again. After 3 hours, the mixture was diluted with H$_2$O and acidified to pH 3 with 1N HCl at 0° C. The resulting mixture was extracted with ethyl acetate. The organic phase was separated, dried (Na$_2$SO$_4$), and concentrated. The crude mixture was purified by prep HPLC to give title compound (30 mg, 40%) as a white solid. $^1$H NMR (CD$_3$OD) δ7.38 (d, 1H), 7.26 (d, 1H), 5.66 (dd, 1H), 3.16 (dd, 1H), 2.39 (s, 3H), 2.34 (dd, 1H). MS found: (M+H)⁺: 322.

G147: [1-Hydroxy-4-methyl-6-([1,2,4]thiadiazol-5-yloxy)-1,3-dihydro-benzo[c][1,2]oxaborol-3-yl]-acetic acid

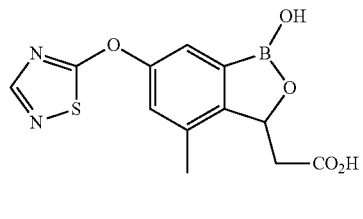

Step 1: [1-Hydroxy-4-methyl-6-([1,2,4]thiadiazol-5-yloxy)-1,3-dihydro-benzo[c][1,2]oxaborol-3-yl]-acetic acid ethyl ester

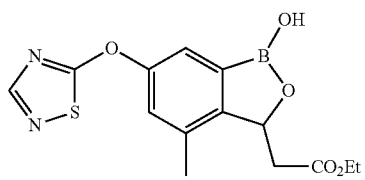 [SMILES: CCOC(=O)CC1OB(O)c2cc(Oc3ncns3)cc(C)c21]

To a solution of [6-(3-chloro-[1,2,4]thiadiazol-5-yloxy)-1-hydroxy-4-methyl-1,3-dihydro-benzo[c][1,2]oxaborol-3-yl]-acetic acid ethyl ester (400 mg, 1.08 mmol) in MeOH (10 mL) was added Pd/C (300 mg, 75%). The resulting solution was degassed, and reacted under H₂ (60 psi) for 2 days. The mixture was filtrated. The filtration was removed in vacuo and purified by column chromatography (silica, DCM/MeOH 4:1) affording the title compound (120 mg, 35%) as a white solid. MS found: (M+H)⁺: 335.

Step 2: [1-Hydroxy-4-methyl-6-([1,2,4]thiadiazol-5-yloxy)-1,3-dihydro-benzo[c][1,2]oxaborol-3-yl]-acetic acid

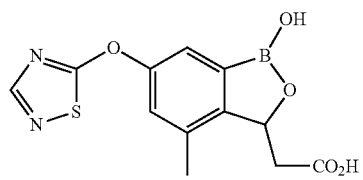 [SMILES: Cc1cc(Oc2ncns2)cc2c1C(CC(=O)O)OB2O]

To a solution of [1-hydroxy-4-methyl-6-([1,2,4]thiadiazol-5-yloxy)-1,3-dihydro-benzo[c][1,2]oxaborol-3-yl]-acetic acid ethyl ester (100 mg, 0.30 mmol) in THF (2.5 mL) and H₂O (1 mL) was added LiOH (0.063 g, 1.50 mmol) at 0° C. The resulting solution was stirred at room temperature for 20 minutes. The mixture was diluted with H₂O and acidified to pH 3 with 1N HCl at 0° C. The resulting mixture was purified by prep HPLC to give the title compound (37 mg, 45%) as a white solid. ¹H NMR (CD₃OD) δ 7.06 (d, 1H), 6.84 (d, 1H), 5.44 (dd, 1H), 3.04 (dd, 1H), 2.30 (s, 3H), 2.18 (dd, 1H). MS found: (M+H)⁺: 307.

G148: Ethyl 2-(1-hydroxy-4-methyl-6-(1-methyl-1H-pyrazol-5-ylsulfonyloxy)-1,3-dihydrobenzo[c][1,2]oxaborol-3-yl)acetate

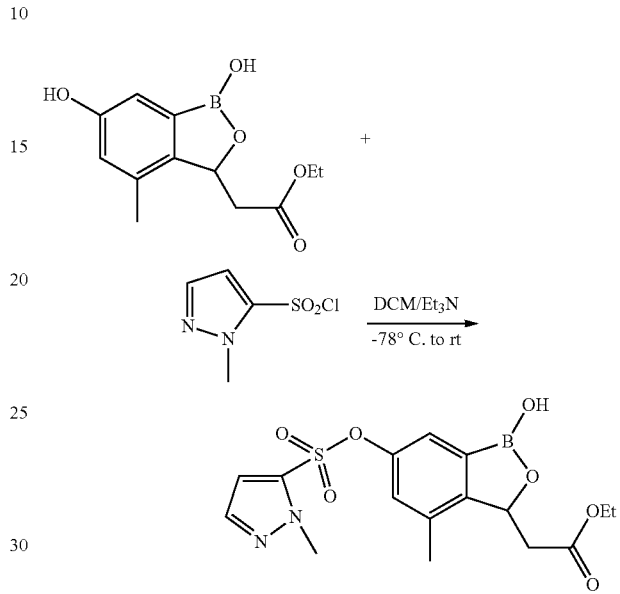

To a solution of ethyl 2-(1,6-dihydroxy-4-methyl-1,3-dihydrobenzo[c][1,2]oxaborol-3-yl)acetate (200 mg, 0.8 mmol) and Et₃N (0.4 ml, 4 mmol) in DCM (8 mL) was added 1-methyl-1H-pyrazole-3-sulfonyl chloride (433 mg, 2.4 mmol) slowly at −78° C. Then stirred at −78° C. to rt overnight. The resulting mixture was concentrated, chromatography on silica gel, (DCM/MeOH 9.5/0.5) to get white solid. Further purification by reverse-phase prep. HPLC to get the title compound colorless oil (64 mg). ¹H NMR (400 MHz, DMSO-d6) δ 9.15 (br, 1H), 8.00 (s, 1H), 7.19 (s, 1H), 6.80 (s, 1H), 6.79 (s, 1H), 5.45 (q, 2H), 4.00 (t, 3H), 2.48 (d, 2H), 2.25 (d, 1H), 2.21 (s, 3H), 1.08 (t, 3H) ppm. MS (ESI) m/z=393.0 [M−H]⁻.

G149: 2-(1-Hydroxy-4-methyl-6-(1-methyl-1H-pyrazol-5-ylsulfonyloxy)-1,3-dihydrobenzo[c][1,2]oxaborol-3-yl)acetic acid

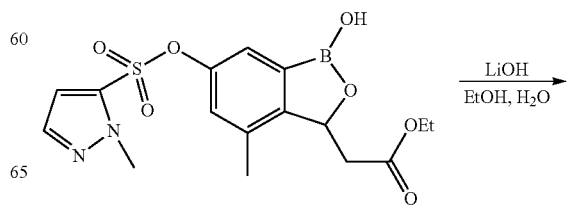

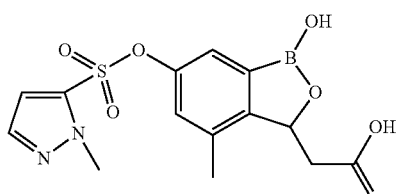

To a solution of ethyl 2-(1-hydroxy-4-methyl-6-(1-methyl-1H-pyrazol-5-ylsulfonyloxy)-1,3-dihydrobenzo[c][1,2]oxaborol-3-yl)acetate (100 mg, 0.25 mmol) in EtOH (4 ml) was added aqueous LiOH (1 ml, 10% aq). The mixture was stirred at 0° C. for 3 h. The reaction was acidified with 1N HCl to pH=2-4, extracted with DCM, washed with brine. The organic layer was dried over Na$_2$SO$_4$ and concentrated. Purify via prep. HPLC to get white solid 72 mg. NMR: $^1$H NMR (DMSO-d6, 400 MHz): δ=12.15 (br, 1H), 9.30 (s, 1H), 8.00 (s, 1H), 7.19 (d, J=2 Hz, 1H), 6.98 (d, J=2 Hz, 1H), 6.80 (d, J=2 Hz, 1H), 5.47 (d, J=6 Hz, 1H), 3.42 (d, J=6 Hz, 1H), 2.25 (s, 3H), 2.12 (d, 1H), 1.03 (s, 3H) ppm. MS (ESI) m/z=365.0 [M−H]$^-$.

G150: Ethyl 2-(6-(4H-1,2,4-triazol-3-ylsulfonyloxy)-1-hydroxy-4-methyl-1,3-dihydrobenzo[c][1,2]oxaborol-3-yl)acetate

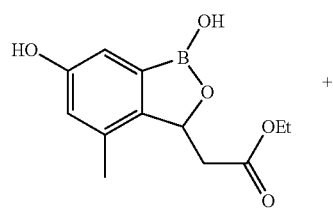

+

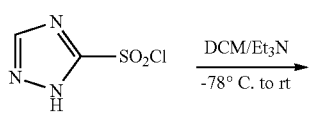

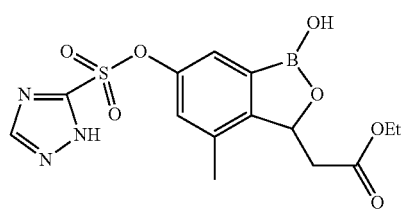

The synthesis of this compound is similar to that described for G148.

G151: 2-(6-(4H-1,2,4-triazol-3-ylsulfonyloxy)-1-hydroxy-4-methyl-1,3-dihydrobenzo[c][1,2]oxaborol-3-yl)acetic acid

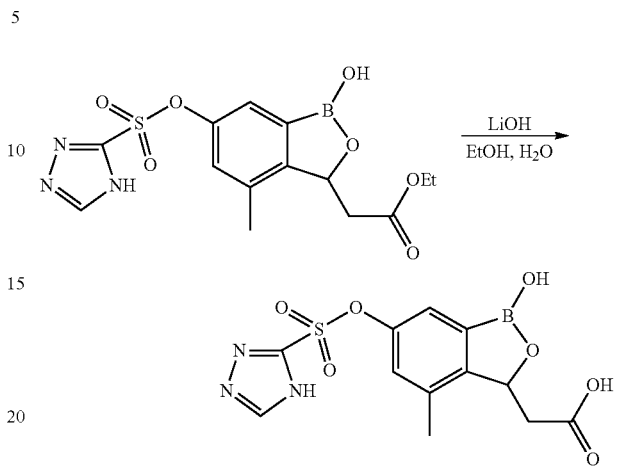

To a solution of ethyl 2-(6-(4H-1,2,4-triazol-3-ylsulfonyloxy)-1-hydroxy-4-methyl-1,3-dihydrobenzo[c][1,2]oxaborol-3-yl)acetate (100 mg, 0.25 mmol) in EtOH (4 ml) was added aqueous LiOH (1 ml, 10% aq). The mixture was stirred at 0° C. for 3 h. The reaction was acidified with 1N HCl to pH=2-4, extracted with DCM, washed with brine. The organic layer was dried over Na$_2$SO$_4$ and concentrated. Purify via prep. HPLC to get white solid 32 mg. NMR: $^1$H NMR (DMSO-d6, 400 MHz): δ=12.3 (br, 1H), 9.15 (br, 1H), 8.99 (s, 1H), 7.20 (d, J=2 Hz, 1H), 7.042 (d, J=2 Hz, 1H), 5.48 (dd, J=2.4, 9.2 Hz, 1H), 3.65 (s, 1H), 3.03 (dd, J=2.8, 16.6 Hz, 1H), 2.14 (s, 3H), and 2.1 (q, 1H) ppm. MS (ESI) m/z=352.0 [M−H]$^-$.

Example 2

Testing of Compounds for the Biochemical and Microbial Inhibition of Beta-Lactamases Biochemical Inhibition of Beta-Lactamases Beta-lactamases CTX-M 9a, KPC-2, SHV-18, TEM-1, TEM-64, AmpC and CMY-2 were used as substrates in in vitro inhibition assays with the compounds of the invention. Beta-lactamases were tested as essentially described by Payne et al., *J. Antimicrob. Chemother.*, 1991; 28: 775-776) with a few modifications. The buffer was 50 mM potassium phosphate pH 7 with 0.2% Triton x-100, and the concentration of nitrocefin was 500 µM for class A β-lactamases and 200 µM for class C β-lactamases. Kinetic data is collected by measuring the rate of change in A$_{486}$ over 30 minutes. The fraction of enzyme inhibited is determined by dividing the reaction rates in the presence of inhibitor by the reaction rate determined in the absence of inhibitor. Dose-response curves are then generated by plotting log [inhibitor] vs. fraction inhibited. IC$_{50}$ values were determined from the dose-response curves by determining the inhibitor concentration required to reduce the maximum inhibitory activity of the compound by 50%. The K$_i$ values were calculated from the IC50 using the K$_m$ for nitrocefin for each enzyme and the following equation $$K_i = \frac{IC_{50}}{1 + \frac{|S|}{K_m}}.$$

AmpC P99 was purchased from Sigma-Aldrich #P4399, TEM-1 was purchased from Invitrogen #PV3575, and CTX-M-9 was obtained from Professor Brian Shoichet of the University of California-San Francisco (Yu Chen, Brian Shoichet, and Richard Bonnet, *J. Am. Chem. Soc.*, 2005, 127 (15): pp 5423-5434).

CMY-2 was synthesized by GenScript and subcloned into pET24b at the NdeI/SalI sites. The DNA sequence of the insert is SEQ ID NO: 1 and is as follows,

CATATGATGAAAAAATCGTTATGCTGCGCTCTGCTGCTGACAGCCTCTT

TCTCCACATTTGCTGCCGCAAAAACAGAACAACAGATTGCCGATATCGT

TAATCGCACCATCACCCCGTTGATGCAGGAGCAGGCTATTCCGGGTATG

GCCGTTGCCGTTATCTACCAGGGAAAACCCTATTATTTCACCTGGGGTA

AAGCCGATATCGCCAATAACCACCCAGTCACGCAGCAAACGCTGTTTGA

GCTAGGATCGGTTAGTAAGACGTTTAACGGCGTGTTGGGCGGCGATGCT

ATCGCCCGCGGCGAAATTAAGCTCAGCGATCCGGTCACGAAATACTGGC

CAGAACTGACAGGCAAACAGTGGCAGGGTATCCGCCTGCTGCACTTAGC

CACCTATACGGCAGGCGGCCTACCGCTGCAGATCCCCGATGACGTTAGG

GATAAAGCCGCATTACTGCATTTTTATCAAAACTGGCAGCCGCAATGGA

CTCCGGGCGCTAAGCGACTTTACGCTAACTCCAGCATTGGTCTGTTTGG

CGCGCTGGCGGTGAAACCCTCAGGAATGAGTTACGAAGAGGCAATGACC

AGACGCGTCCTGCAACCATTAAAACTGGCGCATACCTGGATTACGGTTC

CGCAGAACGAACAAAAAGATTATGCCTGGGGCTATCGCGAAGGGAAGCC

CGTACACGTTTCTCCGGGACAACTTGACGCCGAAGCCTATGCGTGAAA

TCCAGCGTTATTGATATGGCCCGCTGGGTTCAGGCCAACATGGATGCCA

GCCACGTTCAGGAGAAAACGCTCCAGCAGGGCATTGCGCTTGCGCAGTC

TCGCTACTGGCGTATTGGCGATATGTACCAGGGATTAGGCTGGGAGATG

CTGAACTGGCCGCTGAAAGCTGATTCGATCATCAACGGCAGCGACAGCA

AAGTGGCATTGGCAGCGCTTCCCGCCGTTGAGGTAAACCCGCCCGCCCC

CGCAGTGAAAGCCTCATGGGTGCATAAAACGGGCTCCACTGGTGGATTT

GGCAGCTACGTAGCCTTCGTTCCAGAAAAAAACCTTGGCATCGTGATGC

TGGCAAACAAAAGCTATCCTAACCCTGTCCGTGTCGAGGCGGCCTGGCG

CATTCTTGAAAAGCTGCAATAAGTCGAC

KPC-2 was synthesized by GenScript and subcloned into pET24b at the NdeI/SalI sites. The DNA sequence of the insert is SEQ ID NO: 2 and is as follows,

CATATGTCACTGTATCGCCGTCTAGTTCTGCTGTCTTGTCTCTCATGGC

CGCTGGCTGGCTTTTCTGCCACCGCGCTGACCAACCTCGTCGCGGAACC

ATTCGCTAAACTCGAACAGGACTTTGGCGGCTCCATCGGTGTGTACGCG

ATGGATACCGGCTCAGGCGCAACTGTAAGTTACCGCGCTGAGGAGCGCT

TCCCACTGTGCAGCTCATTCAAGGGCTTTCTTGCTGCCGCTGTGCTGGC

TCGCAGCCAGCAGCAGGCCGGCTTGCTGGACACACCCATCCGTTACGGC

AAAAATGCGCTGGTTCCGTGGTCACCCATCTCGGAAAAATATCTGACAA

CAGGCATGACGGTGGCGGAGCTGTCCGCGGCCGCCGTGCAATACAGTGA

TAACGCCGCCGCCAATTTGTTGCTGAAGGAGTTGGGCGGCCCGGCCGGG

CTGACGGCCTTCATGCGCTCTATCGGCGATACCACGTTCCGTCTGGACC

GCTGGGAGCTGGAGCTGAACTCCGCCATCCCAGGCGATGCGCGCGATAC

CTCATCGCCGCGCGCCGTGACGGAAAGCTTACAAAAACTGACACTGGGC

TCTGCACTGGCTGCGCCGCAGCGGCAGCAGTTTGTTGATTGGCTAAAGG

GAAACACGACCGGCAACCACCGCATCCGCGCGGCGGTGCCGGCAGACTG

GGCAGTCGGAGACAAAACCGGAACCTGCGGAGTGTATGGCACGGCAAAT

GACTATGCCGTCGTCTGGCCCACTGGGCGCGCACCTATTGTGTTGGCCG

TCTACACCCGGGCGCCTAACAAGGATGACAAGCACAGCGAGGCCGTCAT

CGCCGCTGCGGCTAGACTCGCGCTCGAGGGATTGGGCGTCAACGGGCAG

TAAGTCGAC

TEM-64 was synthesized by GenScript and subcloned into pET24b at the Nde I/Xho I sites. The DNA sequence of the insert is SEQ ID NO: 3 and is as follows,

CATATGAGTATTCAACATTTCCGTGTCGCCCTTATTCCGTTTTTTGCGG

CATTTTGCCTTCCTGTTTTTGCTCACCCAGAAACGCTGGTGAAAGTAAA

AGATGCTGAAGATCAGTTGGGTGCACGAGTGGGTTACATCGAACTGGAT

CTCAACAGCGGTAAGATCCTTGAGAGTTTTCGCCCGGAAGAACGTTTTC

CAATGATGAGCACTTTTAAAGTTCTGCTGTGTGGCGCGGTATTATCCCG

TGTTGACGCCGGGCAAGAGCAACTCGGTCGCCGCATTCACTATTCTCAG

AATGACTTGGTTAAGTACTCACCAGTCACAGAAAAGCATCTTACGGATG

GCATGACAGTACGCGAATTATGCAGTGCTGCCATTACCATGAGTGATAA

CACTGCGGCCAACTTACTTCTGACAACGATCGGCGGCCCGAAGGAGCTG

ACCGCTTTTTTGCACAACATGGGGGATCATGTAACTCGCCTTGATAGCT

GGGAACCGGAGCTGAATGAAGCCATTCCAAACGACGAGCGTGACACCAC

GACCCCTGCAGCAATGGCAACAACGTTGCGCAAACTGTTAACTGGCGAA

CTGCTTACTCTGGCTTCCCGGCAACAATTAATTGACTGGATGGAGGCGG

ATAAAGTTGCAGGCCCACTTCTGCGCTCGGCCCTTCCGGCTGGCTGGTT

TATTGCTGATAAATCTGGCGCCGGTGAGCGTGGGTCTCGCGGTATCATT

GCAGCACTGGGGCCAGATGGTAAGCCGTCCCGTATCGTAGTTATCTACA

CGACGGGGAGTCAGGCAACTATGGATGAACGAAATCGCCAGATCGCTGA

GATTGGTGCCTCACTGATTAAGCATTGGCTCGAG

SHV-18 was synthesized by GenScript with the CMY-2 leader sequence and subcloned into pET24b at the Nde I/Xho I sites. The DNA sequence of the insert is SEQ ID NO: 4 and is as follows,

```
CATATGATGAAAAAATCGTTATGCTGCGCTCTGCTGCTGACAGCCTCTT
TCTCCACATTTGCTGCCAGCCCGCAGCCGCTTGAGCAAATTAAACTAAG
CGAAAGCCAGCTGTCGGGCAGCGTAGGCATGATAGAAATGGATCTGGCC
AGCGGCCGCACGCTGACCGCCTGGCGCGCCGATGAACGCTTTCCCATGA
TGAGCACCTTTAAAGTAGTGCTCTGCGGCGCAGTGCTGGCGCGGGTGGA
TGCCGGTGACGAACAGCTGGAGCGAAAGATCCACTATCGCCAGCAGGAT
CTGGTGGACTACTCGCCGGTCAGCGAAAAACACCTTGCCGACGGCATGA
CGGTCGGCGAACTCTGTGCCGCCGCCATTACCATGAGCGATAACAGCGC
CGCCAATCTGCTGCTGGCCACCGTCGGCGGCCCCGCAGGATTGACTGCC
TTTTTGCGCCAGATCGGCGACAACGTCACCCGCCTTGACCGCTGGGAAA
CGGAACTGAATGAGGCGCTTCCCGGCGACGCCCGCGACACCACTACCCC
GGCCAGCATGGCCGCGACCCTGCGCAAGCTGCTGACCAGCCAGCGTCTG
AGCGCCCGTTCGCAACGGCAGCTGCTGCAGTGGATGGTGGACGATCGGG
TCGCCGGACCGTTGATCCGCTCCGTGCTGCCGGCGGGCTGGTTTATCGC
CGATAAGACCGGAGCTGCCAAACGGGGTGCGCGCGGGATTGTCGCCCTG
CTTGGCCCGAATAACAAAGCAGAGCGGATTGTGGTGATTTATCTGCGGG
ATACGCCGGCGAGCATGGCCGAGCGAAATCAGCAAATCGCCGGGATCGG
CGCGGCGCTGATCGAGCACTGGCAACGCTAACTCGAG
```

KPC-2, TEM-64, CMY-2, SHV-18 were over-expressed as essentially described for CTX-M-9 (Structure, Function, and Inhibition along the Reaction Coordinate of CTX-M β-Lactamases, Yu Chen, Brian Shoichet, and Richard Bonnet, J. Am. Chem. Soc., 2005, 127 (15), pp 5423-5434). Since β-lactamases are exported to the periplasm the enzymes were obtained by treating the cells with an osmotic shock. Cells were harvested by centrifugation at 4000×g for 20 minutes, the supernatant was discarded and the pellet was resuspended in 30 mM Tris-HCl, 20% sucrose, pH 8.0 (80 ml for each gram of cells wet weight). Then EDTA was added to 1 mM and the cells were incubated for 5-10 minutes at room temperature with shaking. The cells were then centrifuged at 8000×g for 20 minutes at 4° C., the supernatant was removed, and the pellet resuspended in ice-cold 5 mM $MgSO_4$ (80 ml for each gram of cells wet weight). The cells were incubated on ice for 10 minutes and then centrifuged at 8000×g for 20 minutes at 4° C. The supernatant was removed and dialyzed overnight at 4C against 10 mM potassium phosphate pH 6.8, 50% glycerol. These partially purified enzyme preparations were used in for $IC_{50}$ determination.

Biochemical testing results for exemplary compounds of the invention are provided in FIG. 1.

Microbial Inhibition of Beta-Lactamase-Producing Bacteria with a Beta-Lactamase Inhibitor/Beta-Lactam Combination The bacterial activity of the compounds of the invention were screened by measuring the MIC of a β-lactam antibiotic in the presence of 4 μg/mL of compound using the Clinical and Laboratory Standards Institute's microbroth dilution method in cation-adjusted Mueller-Hinton Broth (Methods for dilution Antimicrobial susceptibility tests for bacteria that grow aerobically M7-A7). MICs were obtained utilizing exemplary compounds of the invention in combination with the following antibiotics in the following bacteria containing the following beta-lactamases:

with cefepime in *Enterobacter aerogenes* Entb253 with a CTX-M 8 beta-lactamase;
with cefepime in *Enterobacter cloacae* 01MGH49 with a KPC-2 beta-lactamase;
with cefepime in *Escherichia coli* EC236 with a KPC-3 beta-lactamase;
with cefepime in *Escherichia coli* EC257 with a CTX-M 18 beta-lactamase;
with ceftazidime in *Escherichia coli* EC257 with a CTX-M 18 beta-lactamase;
with ceftazidime in *Escherichia coli* K12 deltalacU169 pSHV18 with a SHV-18 beta-lactamase;
with ceftazidime in *Escherichia coli* K12 deltalacU169 tolC Tn10 mdfA Kan pSHV18 with a SHV-18 beta-lactamase;
with cefepime in *Escherichia coli* with a CTX-M 14 beta-lactamase;
with cefepime in *Escherichia coli* with a CTX-M 14 beta-lactamase;
with cefepime in *Escherichia coli* with a CTX-M 15 beta-lactamase;
with cefepime in *Escherichia coli* with a CTX-M 15 beta-lactamase;
with cefepime in *Escherichia coli* with a CTX-M 9 beta-lactamase;
with cefepime in *Escherichia coli* with a KPC-2 beta-lactamase;
with ceftazidime in *Escherichia coli* with a KPC-2 beta-lactamase;
with cefepime in *Escherichia coli* with a KPC-3 beta-lactamase;
with ceftazidime in *Escherichia coli* with a KPC-3 beta-lactamase;
with cefepime in *Klebsiella oxytoca* ATCC 51983 with a SHV-5 beta-lactamase;
with ceftazidime in *Klebsiella oxytoca* ATCC 51983 with a SHV-5 beta-lactamase;
with cefepime in *Klebsiella pneumoniae* with a KPC-2 beta-lactamase;
with ceftazidime in *Klebsiella pneumoniae* with a KPC-2 beta-lactamase;
with cefepime in *Klebsiella pneumoniae* with a TEM-26 beta-lactamase;
with ceftazidime in *Klebsiella pneumoniae* with a TEM-26 beta-lactamase;
with cefepime in *Klebsiella pneumoniae* ATCC 51503 with a TEM-10 beta-lactamase and a TEM-12 beta-lactamase;
with cefepime in *Klebsiella pneumoniae* ATCC 51504 with a TEM-10 beta-lactamase;
with ceftazidime in *Klebsiella pneumoniae* ATCC 51504 with a TEM-10 beta-lactamase;
with cefepime in *Klebsiella pneumoniae* ATCC 700603 with a SHV-18 beta-lactamase;
with ceftazidime in *Klebsiella pneumoniae* ATCC 700603 with a SHV-18 beta-lactamase;
with cefepime in *Klebsiella pneumoniae* K283 with a CTX-M 14 beta-lactamase;
with cefepime in *Klebsiella pneumoniae* SYN 71 with a KPC-2 beta-lactamase;
with ceftazidime in *Klebsiella pneumoniae* SYN 71 with a KPC-2 beta-lactamase;

with cefepime in *Klebsiella pneumoniae* VII0982 with a CTX-M 2 beta-lactamase;
with cefepime in *Escherichia coli* CUMC247 with a CTX-M 15 beta-lactamase and a OXA-30 beta-lactamase;
with cefepime in *Escherichia coli* with a CTX-M 2 beta-lactamase and a OXA-2 beta-lactamase;
with ceftazidime in *Escherichia coli* with a CTX-M 2 beta-lactamase and a OXA-2 beta-lactamase;
with cefepime in *Escherichia coli* with a SHV-5 beta-lactamase and a OXA-1 beta-lactamase;
with ceftazidime in *Escherichia coli* with a SHV-5 beta-lactamase and a OXA-1 beta-lactamase;
with cefepime in *Escherichia coli* with a TEM-1 beta-lactamase and a OXA-2 beta-lactamase;
with cefepime in *Klebsiella pneumoniae* HUH44 with a CTX-M 15 beta-lactamase and a OXA-30 beta-lactamase;
with ceftazidime in *Enterobacter aerogenes* ATCC 29751 with a AmpC beta-lactamase;
with cefepime in *Enterobacter cloacae* BAA_1143 with a AmpC beta-lactamase;
with cefepime in *Enterobacter cloacae* BAA_1143 with a AmpC beta-lactamase;
with ceftazidime in *Enterobacter cloacae* BAA_1143 with a AmpC beta-lactamase;
with cefepime in *Enterobacter cloacae* P99 with a AmpC beta-lactamase;
with cefepime in *Escherichia coli* K12 deltalacU169 tolC Tn10 mdfA Kan pCMY2 with a CMY-2 beta-lactamase;
with ceftazidime in *Escherichia coli* K12 deltalacU169 tolC Tn10 mdfA Kan pCMY2 with a CMY-2 beta-lactamase;
with cefepime in *Escherichia coli* with a FOX-5 beta-lactamase;
with ceftazidime in *Escherichia coli* with a FOX-5 beta-lactamase;
with cefepime in *Pseudomonas aeruginosa* SYN 228 with a AmpC beta-lactamase;
with ceftazidime in *Pseudomonas aeruginosa* SYN 228 with a AmpC beta-lactamase;
with cefepime in *Klebsiella pneumoniae* CUMCK2 with a CMY-2 beta-lactamase and a CTX-M 14 beta-lactamase To test the synergistic activity, compounds were tested in a modified M7-A7 microbroth method, called a 2-D checkerboard assay. In a 96 well plate, lanes 1-11 contain 2-fold serial dilutions of the test compound usually starting at a concentration 64 µg/mL, while lanes A-G contain 2-fold serial dilutions of β-lactam antibiotic usually starting at a concentration 16 µg/mL. Lane 12 contains no test compound and lane H contains no β-lactam, therefore the dynamic range of the synergistic activity of the test compound can be tested in the presence of the β-lactam.

Microbial testing results for exemplary compounds of the invention are provided in FIG. 1.

Example 3

Antibacterial MIC Testing

All MIC testing of bacteria followed the Clinical and Laboratory Standards Institute (CLSI) guidelines for antimicrobial testing of aerobic bacteria (Methods for Dilution Antimicrobial Susceptibility Tests for Bacteria That Grow Aerobically; Approved Standard—Seventh Edition)(M07-A7) and anaerobic bacteria (Methods for Antimicrobial Susceptibility Testing of Anaerobic Bacteria; Approved Standard—Seventh Edition) (M11-A7). The bacteria against with MIC data for exemplary compounds of the invention are provided in FIG. 1.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound having a structure according to the formula:

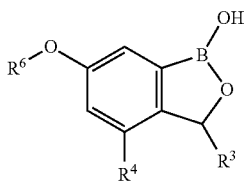

wherein

R$^3$ is —(CH$_2$)$_m$C(O)OR$^{3a}$ wherein m is an integer selected from 1, 2, 3, 4, 5, or 6;

R$^{3a}$ is selected from the group consisting of H, unsubstituted alkyl, and phenyl substituted alkyl;

R$^4$ is selected from the group consisting of unsubstituted alkyl, —OR$^{4b}$, —(CH$_2$)$_n$—O—(CH$_2$)$_p$CH$_3$, and halogen wherein n is an integer selected from 1, 2, 3, 4, 5, or 6;

p is an integer selected from 0, 1, 2, 3, 4, 5, or 6;

R$^{4b}$ is H or substituted or unsubstituted alkyl;

R$^6$ is selected from the group consisting of H, substituted or unsubstituted alkyl, —C(O)OR$^{6a}$, —C(O)NR$^{6a}$R$^{6b}$, —S(O$_2$)R$^{6c}$, and A wherein R$^{6a}$ is H or unsubstituted alkyl R$^{6b}$ is H or unsubstituted alkyl R$^{6c}$ is selected from the group consisting of unsubstituted alkyl, NH$_2$ and heteroaryl, optionally substituted with unsubstituted alkyl A is selected from the group consisting of substituted or unsubstituted cycloalkyl, substituted or unsubstituted heterocycloalkyl, substituted or unsubstituted aryl and substituted or unsubstituted heteroaryl;

or a salt, hydrate or solvate thereof.

2. The compound of claim 1, having a structure according to the formula:

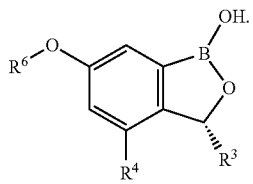

3. The compound of claim 1, wherein said $R^{3a}$ is H.
4. The compound of claim 1, wherein said $R^4$ is selected from unsubstituted $C_1$, $C_2$, $C_3$, $C_4$, $C_5$, or $C_6$ alkyl, or is selected from unsubstituted $C_1$, $C_2$, $C_3$, $C_4$, $C_5$, or $C_6$ alkoxy.
5. The compound of claim 1, wherein said $R^4$ is methyl.
6. The compound of claim 1, wherein said m is an integer selected from 1, 2, 3, or 4.
7. The compound of claim 1, wherein said $R^3$ is —$CH_2C(O)OH$.
8. The compound of claim 1 or 2, wherein said $R^4$ is methyl and $R^3$ is —$CH_2C(O)OH$.
9. The compound of claim 8, wherein said $R^6$ is H.
10. The compound of claim 8, wherein said $R^6$ is selected from unsubstituted $C_1$, $C_2$, or $C_3$ alkyl.
11. The compound of claim 10, wherein said $R^6$ is methyl.
12. The compound of claim 8, wherein said $R^6$ is —$S(O)_2CH_3$.
13. The compound of claim 8, wherein $R^6$ is A and said A is selected from the group consisting of substituted or unsubstituted phenyl, substituted or unsubstituted tetrahydropyran, substituted or unsubstituted pyrimidinyl, substituted or unsubstituted pyrazinyl, substituted or unsubstituted pyridazinyl, substituted or unsubstituted thiazolyl, and substituted or unsubstituted thiadiazolyl.
14. The compound of claim 13, wherein said A is unsubstituted 1,3,4-thiadiazol-2-yl or amino substituted 1,3,4-thiadiazol-2-yl.
15. The compound of claim 13, wherein said A is thiazol-2-yl substituted with carbamoyl or carbamimidoyl.
16. The compound of claim 13, wherein said A is unsubstituted pyrazin-2-yl or pyrazin-2-yl substituted with aminomethyl or carbamimidoyl.
17. The compound of claim 13, wherein said A is pyridin-2-yl substituted with carbamimidoyl.
18. The compound of claim 13, wherein said A is 3-(3-aminopropoxy)phenyl.
19. The compound of claim 7, wherein said $R^6$ is unsubstituted pyrazin-2-yl and $R^4$ is OH or —$O(CH_2)_3NH_2$.
20. A combination comprising:
a) a compound of claim 1, or a pharmaceutically acceptable salt thereof; and
b) at least one therapeutic agent.
21. The combination of claim 20, wherein said at least one therapeutic agent is an antibiotic which comprises a beta-lactam moiety.
22. The combination of claim 20, wherein said at least one therapeutic agent is selected from the group consisting of a penicillin, cephalosporin, cephamycin, monobactam, penem, and carbapenem.
23. A pharmaceutical formulation comprising:
a) a compound of claim 1 or a combination of claim 20, or a pharmaceutically acceptable salt thereof; and
b) a pharmaceutically acceptable excipient.
24. The pharmaceutical formulation of claim 23, wherein said formulation is a unit dosage form.
25. The pharmaceutical formulation of claim 23, wherein said formulation is an oral unit dosage form or a topical unit dosage form.
26. A method of treating a bacterial infection comprising: administering to an animal suffering from said infection an effective amount of a compound of claim 1, or a pharmaceutically-acceptable salt thereof, and an effective amount of an antibiotic, or a pharmaceutically acceptable salt thereof, wherein said antibiotic comprises a β-lactam moiety, thereby treating the bacterial infection.
27. The method of claim 26, wherein a bacteria involved with said infection is resistant to said antibiotic.
28. The method of claim 26, wherein the antibiotic is selected from the group consisting of a penicillin, cephalosporin, cephamycin, monobactam, penem, and carbapenem.
29. The method of claim 26, wherein said animal is a human.
30. The use of a compound of claim 1 or a combination of claim 20, or a pharmaceutically acceptable salt thereof, in the manufacture of a medicament for the treatment and/or prophylaxis of bacterial infection.
31. A method of killing or inhibiting the growth of a bacteria, said method comprising:
contacting said bacteria with an effective amount of the compound of claim 1 or the combination of claim 20, or a pharmaceutically acceptable salt thereof, thereby killing or inhibiting the growth of the bacteria.
32. The method of claim 31, further comprises contacting said bacteria with an effective amount of an antibiotic, or a pharmaceutically acceptable salt thereof, wherein said antibiotic comprises a β-lactam moiety.
33. The method of claim 31, wherein the bacteria is resistant to said antibiotic.
34. A method of inhibiting a β-lactamase, comprising contacting the β-lactamase with an effective amount of the compound of claim 1, or a pharmaceutically acceptable salt thereof, thereby inhibiting the β-lactamase.
35. The method of claim 34, wherein the β-lactamase is selected from the group consisting of a Group 1 β-lactamase, a Group 2 β-lactamase, and a Group 4 β-lactamase.
36. The method of claim 35, wherein said Group 1 β-lactamase is a cephalosporinase.
37. The method of claim 35, wherein said Group 2 β-lactamase is selected from the group consisting of penicillinase, a Group 2b β-lactamase, Group 2be β-lactamase, Group 2br β-lactamase, carbenicillinase, cloxacilanase, cephalosporinase and carbapenamase.
38. The method of claim 35, wherein said Group 4 β-lactamase is a penicillinase.
39. The method of claim 34, wherein the β-lactamase is selected from the group consisting of a class A β-lactamase, a class B β-lactamase, a class C β-lactamase, and a class D β-lactamase.
40. The method of claim 39, wherein the class A β-lactamase is selected from the group consisting of a TEM β-lactamase, SHV β-lactamase, CTX-M β-lactamase and a KPC β-lactamase.
41. The method of claim 39, wherein the class C β-lactamase is a CMY β-lactamase or a AmpC β-lactamase.
42. The method of claim 39, wherein the class D β-lactamase is an OXA β-lactamase.
43. The compound of claim 1, wherein $R^6$ is A and said A is selected from the group consisting of substituted or unsubstituted phenyl, substituted or unsubstituted tetrahydropyran, substituted or unsubstituted pyrimidinyl, substituted or unsubstituted pyrazinyl, substituted or unsubstituted pyridazinyl, substituted or unsubstituted thiazolyl, and substituted or unsubstituted thiadiazolyl.

44. The compound of claim 43, wherein said A is unsubstituted 1,3,4-thiadiazol-2-yl or amino substituted 1,3,4-thiadiazol-2-yl.

45. The compound of claim 43, wherein said A is thiazol-2-yl substituted with carbamoyl or carbamimidoyl.

46. The compound of claim 43, wherein said A is unsubstituted pyrazin-2-yl or pyrazin-2-yl substituted with aminomethyl or carbamimidoyl.

47. The compound of claim 43, wherein said A is pyridin-2-yl substituted with carbamimidoyl.

48. The compound of claim 43, wherein said A is 3-(3-aminopropoxy)phenyl.

49. The compound of claim 1, which is 2-(1-hydroxy-4-methyl-6-(methylsulfonyloxy)-1,3-dihydrobenzo[c][1,2]oxaborol-3-yl)acetic acid, (1,6-dihydroxy-4-methyl-1,3-dihydro-benzo[c][1,2]oxaborol-3-yl)-acetic acid, or (1-hydroxy-6-methoxy-4-methyl-1,3-dihydro-benzo[c][1,2]oxaborol-3-yl)-acetic acid.

50. The compound of claim 1, which is (3R)-(1,6-dihydroxy-4-methyl-1,3-dihydro-benzo[c][1,2]oxaborol-3-yl)-acetic acid or (3R)-(1-hydroxy-6-methoxy-4-methyl-1,3-dihydro-benzo[c][1,2]oxaborol-3-yl)-acetic acid.

51. The compound of claim 1, which is {6-[3-(3-aminopropoxy)-phenoxy]-1-hydroxy-4-methyl-1,3-dihydro-benzo[c][1,2]oxaborol-3-yl}-acetic acid or 2-(6-(4-carbamimidoylpyridin-2-yloxy)-1-hydroxy-4-methyl-1,3-dihydrobenzo[c][1,2]oxaborol-3-yl)acetic acid.

52. The compound of claim 1, which is [1-hydroxy-4-methyl-6-(pyrazin-2-yloxy)-1,3-dihydro-benzo[c][1,2]oxaborol-3-yl]-acetic acid, [6-(6-aminomethyl-pyrazin-2-yloxy)-1-hydroxy-4-methyl-1,3-dihydro-benzo[c][1,2] oxaborol-3-yl)-acetic acid, [6-(5-aminomethyl-pyrazin-2-yloxy)-1-hydroxy-4-methyl-1,3-dihydro-benzo[c][1,2] oxaborol-3-yl]-acetic acid, [6-(5-carbamimidoyl-pyrazin-2-yloxy)-1-hydroxy-4-methyl-1,3-dihyhydro-benzo[c] oxaborol-3-yl)-acetic acid, 2-(1,4-dihydroxy-6-(pyrazin-2-yloxy)-1,3-dihydrobenzo[c][1,2]oxaborol-3-yl)acetic acid, or [4-(3-amino-propoxy)-1-hydroxy-6-(pyrazin-2-yloxy)-1,3-dihydro-benzo[c][1,2]oxaborol-3-yl)-acetic acid.

53. The compound of claim 1, which is (3R)-[1-hydroxy-4-methyl-6-(pyrazin-2-yloxy)-1,3-dihydro-benzo[c][1,2]oxaborol-3-yl)-acetic acid.

54. The compound of claim 1, which is 2-(6-(5-amino-1,3,4-thiadiazol-2-yloxy)-1-hydroxy-4-methyl-1,3-dihydrobenzo[c][1,2]oxaborol-3-yl)propanoic acid, 2-(6-(5-carbamimidoythiazol-2-yloxy)-1-hydroxy-4-methyl-1,3-dihydrobenzo[c][1,2]oxaborol-3-yl)acetic acid or [6-(5-carbamoyl-thiazol-2-yloxy)-1-hydroxy-4-methyl-1,3-dihydro-benzo[c][1,2]oxaborol-3-yl]-acetic acid.

55. The compound of claim 1, which is (R)-2-(6-(5-carbamoylthiazol-2-yloxy)-1-hydroxy-4-methyl-1,3-dihydrobenzo[c][1,2]oxaborol-3-yl)acetic acid.

56. The compound of claim 1, which is [6-(5-amino-[1,3,4]thiadiazol-2-yloxy)-1-hydroxy-4-methyl-1,3-dihydrobenzo[c][1,2oxaborol-3-yl]-acetic acid.

57. The compound of claim 1, which is (R)-2-(6-(5-amino-1,3,4-thiadiazol-2-yloxy)-1-hydroxy-4-methyl-1,3-dihydrobenzo[c][1,2]oxaborol-3-yl)acetic acid.

58. The compound of claim 1, which is [1-hydroxy-4-methyl-6-([1,3,4]thiadiazol-2-yloxy)-1,3-dihydro-benzo[c][1,2]oxaborol-3-yl]-acetic acid.

59. The compound of claim 1, which is (R)-2-(6-(1,3,4-thiadiazol-2-yloxy)-1-hydroxy-4-methyl-1,3-dihydrobenzo[c][1,2]oxaborol-3-yl)acetic acid.

* * * * *

SEQUENCE LISTING

<160> NUMBER OF SEQ ID NOS: 4

<210> SEQ ID NO 1
<211> LENGTH: 1155
<212> TYPE: DNA
<213> ORGANISM: Salmonella enterica

<400> SEQUENCE: 1

```
catatgatga aaaaatcgtt atgctgcgct ctgctgctga cagcctcttt ctccacattt      60
gctgccgcaa aaacagaaca acagattgcc gatatcgtta atcgcaccat cacccgttg     120 atgcaggagc aggctattcc gggtatggcc gttgccgtta tctaccaggg aaaaccctat    180
tatttcacct ggggtaaagc cgatatcgcc aataaccacc cagtcacgca gcaaacgctg    240
tttgagctag gatcggttag taagacgttt aacggcgtgt tgggcggcga tgctatcgcc    300
cgcggcgaaa ttaagctcag cgatccggtc acgaaatact ggccagaact gacaggcaaa    360
cagtggcagg gtatccgcct gctgcactta gccacctata cggcaggcgg cctaccgctg    420
cagatccccg atgacgttag ggataaagcc gcattactgc atttttatca aaactggcag    480
ccgcaatgga ctccgggcgc taagcgactt tacgctaact ccagcattgg tctgtttggc    540
gcgctggcgg tgaaaccctc aggaatgagt tacgaagagg caatgaccag acgcgtcctg    600
```

| | |
|---|---|
| caaccattaa aactggcgca tacctggatt acggttccgc agaacgaaca aaaagattat | 660 |
| gcctggggct atcgcgaagg gaagcccgta cacgtttctc cgggacaact tgacgccgaa | 720 |
| gcctatggcg tgaaatccag cgttattgat atggcccgct gggttcaggc caacatggat | 780 |
| gccagccacg ttcaggagaa aacgctccag cagggcattg cgcttgcgca gtctcgctac | 840 |
| tggcgtattg cgatatgta ccagggatta ggctgggaga tgctgaactg ccgctgaaa | 900 |
| gctgattcga tcatcaacgg cagcgacagc aaagtggcat tggcagcgct tcccgccgtt | 960 |
| gaggtaaacc cgcccgcccc cgcagtgaaa gcctcatggg tgcataaaac gggctccact | 1020 |
| ggtggatttg gcagctacgt agccttcgtt ccagaaaaaa accttggcat cgtgatgctg | 1080 |
| gcaaacaaaa gctatcctaa ccctgtccgt gtcgaggcgg cctggcgcat tcttgaaaag | 1140 |
| ctgcaataag tcgac | 1155 |

<210> SEQ ID NO 2
<211> LENGTH: 891
<212> TYPE: DNA
<213> ORGANISM: Klebsiella pneumoniae

<400> SEQUENCE: 2

| | |
|---|---|
| catatgtcac tgtatcgccg tctagttctg ctgtcttgtc tctcatggcc gctggctggc | 60 |
| ttttctgcca ccgcgctgac caacctcgtc gcggaaccat tcgctaaact cgaacaggac | 120 |
| tttggcggct ccatcggtgt gtacgcgatg gataccggct caggcgcaac tgtaagttac | 180 |
| cgcgctgagg agcgcttccc actgtgcagc tcattcaagg gctttcttgc tgccgctgtg | 240 |
| ctggctcgca gccagcagca ggccggcttg ctggacacac ccatccgtta cggcaaaaat | 300 |
| gcgctggttc cgtggtcacc catctcggaa aaatatctga caacaggcat gacggtggcg | 360 |
| gagctgtccg cggccgccgt gcaatacagt gataacgccg ccgccaattt gttgctgaag | 420 |
| gagttgggcg gccggccgg gctgacggcc ttcatgcgct ctatcggcga taccacgttc | 480 |
| cgtctggacc gctgggagct ggagctgaac tccgccatcc caggcgatgc gcgcgatacc | 540 |
| tcatcgccgc gcgccgtgac ggaaagctta caaaaactga cactgggctc tgcactggct | 600 |
| gcgccgcagc ggcagcagtt tgttgattgg ctaaaggaa acacgaccgg caaccaccgc | 660 |
| atccgcgcgg cggtgccggc agactgggca gtcggagaca aaaccggaac ctgcggagtg | 720 |
| tatggcacgg caaatgacta tgccgtcgtc tggcccactg ggcgcgcacc tattgtgttg | 780 |
| gccgtctaca cccgggcgcc taacaaggat gacaagcaca gcgaggccgt catcgccgct | 840 |
| gcggctagac tcgcgctcga gggattgggc gtcaacgggc agtaagtcga c | 891 |

<210> SEQ ID NO 3
<211> LENGTH: 867
<212> TYPE: DNA
<213> ORGANISM: Klebsiella pneumoniae

<400> SEQUENCE: 3

| | |
|---|---|
| catatgagta ttcaacattt ccgtgtcgcc cttattccgt tttttgcggc atttttgcctt | 60 |
| cctgtttttg ctcacccaga aacgctggtg aaagtaaaag atgctgaaga tcagttgggt | 120 |
| gcacgagtgg gttacatcga actggatctc aacagcggta agatccttga gttttcgc | 180 |
| ccggaagaac gttttccaat gatgagcact tttaaagttc tgctgtgtgg cgcggtatta | 240 |
| tcccgtgttg acgccgggca agagcaactc ggtcgccgca ttcactattc tcagaatgac | 300 |
| ttggttaagt actcaccagt cacagaaaag catcttacgg atggcatgac agtacgcgaa | 360 |
| ttatgcagtg ctgccattac catgagtgat aacactgcgg ccaacttact tctgacaacg | 420 |

-continued

```
atcggcggcc cgaaggagct gaccgctttt ttgcacaaca tggggatca tgtaactcgc    480 cttgatagct gggaaccgga gctgaatgaa gccattccaa acgacgagcg tgacaccacg    540 accccctgcag caatggcaac aacgttgcgc aaactgttaa ctggcgaact gcttactctg   600 gcttccggc aacaattaat tgactggatg gaggcggata agttgcagg cccacttctg     660 cgctcggccc ttccggctgg ctggtttatt gctgataaat ctggcgccgg tgagcgtggg   720
tctcgcggta tcattgcagc actggggcca gatggtaagc cgtcccgtat cgtagttatc   780
tacacgacgg ggagtcaggc aactatggat gaacgaaatc gccagatcgc tgagattggt   840
gcctcactga ttaagcattg gctcgag                                       867
```

<210> SEQ ID NO 4
<211> LENGTH: 870
<212> TYPE: DNA
<213> ORGANISM: Klebsiella pneumoniae

<400> SEQUENCE: 4

```
catatgatga aaaaatcgtt atgctgcgct ctgctgctga cagcctcttt ctccacattt    60
gctgccagcc cgcagccgct tgagcaaatt aaactaagcg aaagccagct gtcgggcagc   120
gtaggcatga tagaaatgga tctggccagc ggccgcacgc tgaccgcctg gcgcgccgat   180
gaacgctttc ccatgatgag caccctttaaa gtagtgctct gcggcgcagt gctggcgcgg   240
gtggatgccg gtgacgaaca gctggagcga aagatccact atcgccagca ggatctggtg   300
gactactcgc cggtcagcga aaacaccctt gccgacggca tgacggtcgg cgaactctgt   360
gccgccgcca ttaccatgag cgataacagc gccgccaatc tgctgctggc caccgtcggc   420
ggccccgcag gattgactgc cttttttgcgc cagatcggcg acaacgtcac ccgccttgac   480
cgctgggaaa cggaactgaa tgaggcgctt cccggcgacg cccgcgacac cactaccccg   540
gccagcatgg ccgcgaccct gcgcaagctg ctgaccagcc agcgtctgag cgcccgttcg   600
caacggcagc tgctgcagtg gatggtggac gatcgggtcg ccggaccgtt gatccgctcc   660
gtgctgccgg cgggctggtt tatcgccgat aagaccggag ctgccaaacg gggtgcgcgc   720
gggattgtcg ccctgcttgg cccgaataac aaagcagagc ggattgtggt gatttatctg   780
cgggatacgc cggcgagcat ggccgagcga aatcagcaaa tcgccgggat cggcgcggcg   840
ctgatcgagc actggcaacg ctaactcgag                                    870
```